US012709637B2

(12) United States Patent
Khalil et al.

(10) Patent No.: US 12,709,637 B2
(45) Date of Patent: Aug. 18, 2026

(54) REGULATED SYNTHETIC GENE ACTIVATION SYSTEMS

(71) Applicant: TRUSTEES OF BOSTON UNIVERSITY, Boston, MA (US)

(72) Inventors: Ahmad S. Khalil, Lexington, MA (US); Kok Ann Gan, Allston, MA (US); Hanrong Ye, Brighton, MA (US); Thea Samuelle Ornstein, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 18/756,596

(22) Filed: Jun. 27, 2024

(65) Prior Publication Data

US 2025/0059243 A1 Feb. 20, 2025

Related U.S. Application Data

(60) Provisional application No. 63/523,569, filed on Jun. 27, 2023.

(51) Int. Cl.

| | |
|---|---|
| ***C12N 15/62*** | (2006.01) |
| ***C07K 14/47*** | (2006.01) |
| ***C12N 15/63*** | (2006.01) |

(52) U.S. Cl.

CPC ........ *C07K 14/4702* (2013.01); *C12N 15/635* (2013.01); *C07K 2319/09* (2013.01); *C07K 2319/50* (2013.01); *C07K 2319/715* (2013.01); *C07K 2319/81* (2013.01); *C07K 2319/95* (2013.01)

(58) Field of Classification Search

None

See application file for complete search history.

(56) References Cited

U.S. PATENT DOCUMENTS

| | | | |
|---|---|---|---|
| 10,138,493 | B2 | 11/2018 | Khalil et al. |
| 11,530,246 | B2 | 12/2022 | Khalil et al. |
| 11,781,149 | B2 | 10/2023 | Khalil et al. |
| 2002/0076762 | A1 | 6/2002 | Yue et al. |
| 2003/0105045 | A1 | 6/2003 | Stanojevic |

FOREIGN PATENT DOCUMENTS

| | | | |
|---|---|---|---|
| WO | 2023023553 | A2 | 2/2023 |

OTHER PUBLICATIONS

Bashor et al. "Complex signal processing in synthetic gene circuits using co-operative regulatory assemblies." Science 364(6440): 593-597 (2019).

Cermakova et al. "A ubiquitous disordered protein interaction module orchestrates transcription elongation." Science 374(6571): 1113-1121 (2021).

Chavez et al. "Highly efficient Cas9-mediated transcriptional programming." Nat Methods 12(4): 326-328 (2015).

Khalil et al. "A Synthetic Biology Framework for Programming Eukaryotic Transcription Functions." Cell 150(3): 647-658 (2012).

Konermann et al. "Genome-scale transcriptional activation by an engineered CRISPR-Cas9 complex." Nature 517 (7536): 583-588 (2015).

Li et al. "Multidimensional control of therapeutic human cell function with synthetic gene circuits." Science 378(6625): 1227-1234 (2022).

Tycko et al. "Development of compact transcriptional effectors using high-throughput measurements in diverse contexts." bioRxiv (May 14, 2023) availble on the world-wide web at https://www.biorxiv.org/content/10.1101/2023.05.12.540558v1.

*Primary Examiner* — Michael D Pak

(74) *Attorney, Agent, or Firm* — Nixon Peabody LLP; Ronald I. Eisenstein; Alissa R. Young

(57) ABSTRACT

The technology described herein is directed to regulated synthetic gene expression systems. In one aspect described herein are synthetic transcription factors (synTFs) comprising a DNA binding domain, a transcriptional activator domain, a transcriptional effector domain (TED), and optionally a regulator protein. In other aspects described herein are gene expression systems comprising said synTFs and methods of treating diseases and disorders using said synTFs.

28 Claims, 28 Drawing Sheets

Specification includes a Sequence Listing.

SEQUENCE LISTING

```
Sequence total quantity: 360
SEQ ID NO: 1            moltype = AA  length = 14
FEATURE                 Location/Qualifiers
source                  1..14
                        mol_type = protein
                        organism = synthetic construct
SEQUENCE: 1
ERPFQCRICM RNFS                                                   14

SEQ ID NO: 2            moltype = AA  length = 4
FEATURE                 Location/Qualifiers
source                  1..4
                        mol_type = protein
                        organism = synthetic construct
SEQUENCE: 2
TGEK                                                              4

SEQ ID NO: 3            moltype = AA  length = 12
FEATURE                 Location/Qualifiers
source                  1..12
                        mol_type = protein
                        organism = synthetic construct
SEQUENCE: 3
PFQCRICMRN FS                                                     12

SEQ ID NO: 4            moltype = AA  length = 818
FEATURE                 Location/Qualifiers
source                  1..818
                        mol_type = protein
                        organism = Homo sapiens
SEQUENCE: 4
MDSEYYSGDQ SDDGGATPVQ DERDSGSDGE DDVNEQHSGS DTGSVERHSE NETSDREDGL  60
PKGHHVTDSE NDEPLNLNAS DSESEELHRQ KDSDSESEER AEPPASDSEN EDVNQHGSDS  120
ESEETRKLPG SDSENEELLN GHASDSENED VGKHPASDSE IEELQKSPAS DSETEDALKP  180
QISDSESEEP PRHQASDSEN EEPPKPRMSD SESEELPKPQ VSDSESEEPP RHQASDSENE  240
ELPKPRISDS ESEDPPRHQA SDSENEELPK PRISDSESED PPRNQASDSE NEELPKPRVS  300
DSESEGPQKG PASDSETEDA SRHKQKPESD DDSDRENKGE DTEMQNDSFH SDSHMDRKKF  360
HSSDSEEEEH KKQKMDSDED EKEGEEEKVA KRKAAVLSDS EDEEKASAKK SRVVSDADDS  420
DSDAVSDKSG KREKTIASDS EEEAGKELSD KKNEEKDLFG SDSESGNEEE NLIADIFGES  480
GDEEEEEFTG FNQEDLEEEK GETQVKEAED SDSDDNIKRG KHMDFLSDFE MMLQRKKSMS  540
GKRRRNRDGG TFISDADDVV SAMIVKMNEA AEEDRQLNNQ KKPALKKLTL LPAVVMHLKK  600
QDLKETFIDS GVMSAIKEWL SPLPDRSLPA LKIREELLKI LQELPSVSQE TLKHSGIGRA  660
VMYLYKHPKE SRSNKDMAGK LINEWSRPIF GLTSNYKGMT REEREQRDLE QMPQRRRMNS  720
TGGQTPRRDL EKVLTGEEKA LRPGDPGFCA RARVPMPSNK DYVVRPKWNV EMESSRPGIL  780
KKGLSRLEKH KRRFAEQKRL SKVHRAVKFS IEGNRMPL                         818

SEQ ID NO: 5            moltype = AA  length = 44
FEATURE                 Location/Qualifiers
```

```
source                  1..44
                        mol_type = protein
                        organism = synthetic construct
SEQUENCE: 5
SDKKNEEKDL FGSDSESGNE EENLIADIFG ESGDEEEEEF TGFN                 44

SEQ ID NO: 6            moltype = AA  length = 5
FEATURE                 Location/Qualifiers
source                  1..5
                        mol_type = protein
                        organism = synthetic construct
SEQUENCE: 6
KDLFG                                                            5

SEQ ID NO: 7            moltype = AA  length = 5
FEATURE                 Location/Qualifiers
source                  1..5
                        mol_type = protein
                        organism = synthetic construct
SEQUENCE: 7
ADIFG                                                            5

SEQ ID NO: 8            moltype = AA  length = 5
FEATURE                 Location/Qualifiers
source                  1..5
                        mol_type = protein
                        organism = synthetic construct
SEQUENCE: 8
EFTGF                                                            5

SEQ ID NO: 9            moltype = AA  length = 44
FEATURE                 Location/Qualifiers
source                  1..44
                        mol_type = protein
                        organism = synthetic construct
SEQUENCE: 9
SDKKNEEKDA AGSDSESGNE EENLIADIFG ESGDEEEEEF TGFN                 44

SEQ ID NO: 10           moltype = AA  length = 44
FEATURE                 Location/Qualifiers
source                  1..44
                        mol_type = protein
                        organism = synthetic construct
SEQUENCE: 10
SDKKNEEKDL FGSDSESGNE EENLIADAAG ESGDEEEEEF TGFN                 44

SEQ ID NO: 11           moltype = AA  length = 44
FEATURE                 Location/Qualifiers
source                  1..44
                        mol_type = protein
                        organism = synthetic construct
SEQUENCE: 11
SDKKNEEKDL FGSDSESGNE EENLIADIFG ESGDEEEEEA TGAN                 44

SEQ ID NO: 12           moltype = AA  length = 5
FEATURE                 Location/Qualifiers
source                  1..5
                        mol_type = protein
                        organism = synthetic construct
SEQUENCE: 12
KDAAG                                                            5

SEQ ID NO: 13           moltype = AA  length = 5
FEATURE                 Location/Qualifiers
source                  1..5
                        mol_type = protein
                        organism = synthetic construct
SEQUENCE: 13
ADAAG                                                            5

SEQ ID NO: 14           moltype = AA  length = 5
FEATURE                 Location/Qualifiers
source                  1..5
                        mol_type = protein
                        organism = synthetic construct
SEQUENCE: 14
EATGA                                                            5

SEQ ID NO: 15           moltype = DNA  length = 714
```

-continued

```
FEATURE               Location/Qualifiers
source                1..714
                      mol_type = other DNA
                      organism = synthetic construct
SEQUENCE: 15
tcagacaaga aaaacgaaga aaaggatttg ttcggaagtg attccgagag cgggaacgaa  60
gaggagaatc tgattgccga catttttggt gagagcggcg atgaggaaga agaagagttc  120
actgggttta atggaagcgg cgatgagttt cccaccatgg tgtttccttc tgggcagatc  180
agccaggcct cggccttggc cccggcccct ccccaagtcc tgccccaggc tccagcccct  240
gcccctgctc cagccatggt atcagctctg gcccaggccc cagcccctgt cccagtccta  300
gccccaggcc ctcctcaggc tgtggcccca cctgcccccca agcccaccca ggctggggaa  360
ggaacgctgt cagaggccct gctgcagctg cagtttgatg atgaagacct gggggccttg  420
cttggcaaca gcacagaccc agctgtgttc acagacctgg catccgtcga caactccgag  480
tttcagcagc tgctgaacca gggcatacct gtggcccccc acacaactga gcccatgctg  540
atggagtacc ctgaggctat aactcgccta gtgacagggg cccagaggcc ccccgaccca  600
gctcctgctc cactgggggc cccggggctc cccaatggcc tcctttcagg agatgaagac  660
ttctcctcca ttgcggacat ggacttctca gccctgctga gtcagatcag ctcc        714

SEQ ID NO: 16         moltype = AA  length = 238
FEATURE               Location/Qualifiers
source                1..238
                      mol_type = protein
                      organism = synthetic construct
SEQUENCE: 16
SDKKNEEKDL FGSDSESGNE EENLIADIFG ESGDEEEEEF TGFNGSGDEF PTMVFPSGQI  60
SQASALAPAP PQVLPQAPAP APAPAMVSAL AQAPAPVPVL APGPPQAVAP PAPKPTQAGE  120
GTLSEALLQL QFDDEDLGAL LGNSTDPAVF TDLASVDNSE FQQLLNQGIP VAPHTTEPML  180
MEYPEAITRL VTGAQRPPDP APAPLGAPGL PNGLLSGDED FSSIADMDFS ALLSQISS    238

SEQ ID NO: 17         moltype = DNA  length = 408
FEATURE               Location/Qualifiers
source                1..408
                      mol_type = other DNA
                      organism = synthetic construct
SEQUENCE: 17
gtaacgccat tttgcaaggc atggaaaaat accaaaccaa gaatagagaa gttcagatca  60
agggcgggta catgaaaata gctaacgttg ggccaaacag gatatctgcg gtgagcagtt  120
tcggccccgg cccggggcca agaacagatg gtcaccgcag tttcggcccc ggcccgaggc  180
caagaacaga tggtccccag atatggccca accctcagca gtttcttaag acccatcaga  240
tgtttccagg ctcccccaag gacctgaaat gaccctgcgc cttatttgaa ttaaccaatc  300
agcctgcttc tcgcttctgt tcgcgcgctt ctgcttcccg agctctataa aagagctcac  360
aacccctcac tcggcgcgcc agtcctccga cagactgagt cgcccggg              408

SEQ ID NO: 18         moltype = DNA  length = 528
FEATURE               Location/Qualifiers
source                1..528
                      mol_type = other DNA
                      organism = synthetic construct
SEQUENCE: 18
tctagacccg gagagcgccc attccagtgt cggatttgca tgcggaactt ttcgagaaga  60
cacggcctgg acagacatac ccgtactcat acaggtgaaa aaccctttca gtgtcggatc  120
tgtatgcgaa atttctccga ccacagcagc ctgaagagac atctacgtac ccacaccggc  180
agccagaagc catttcagtg tcggatctgt atgcggaact tctccgtgag acacaacctg  240
accagacatc tacgtacgca caccggagag aagccattcc aatgccgaat atgcatgcgc  300
aacttcagtg accacagcaa cctgagcaga cacctaaaaa cccacaccgg ttcccagaag  360
ccatttcagt gtcggatctg tatgcggaac ttctcccagc gcagcagcct ggtgagacat  420
ctacgtacgc acaccggaga gaagccattc caatgccgaa tatgcatgcg caacttcagt  480
gagagcggcc acctgaagag acacctgcgt acgcacctga ggggatcc              528

SEQ ID NO: 19         moltype = DNA  length = 711
FEATURE               Location/Qualifiers
source                1..711
                      mol_type = other DNA
                      organism = synthetic construct
SEQUENCE: 19
ggctgcgtgg tcatagtggg caggatcgtc ttgtccggat ccggcactag tgcgcccatc  60
acggcgtacg cccagcagac gagaggcctc ctagggtgta taatcaccag cctgactggc  120
cgggacaaaa accaagtgga gggtgaggtc cagatcgtgt caactgctac ccaaaccttc  180
ctggcaacgt gcatcaatgg ggtatgctgg gcagtctacc acggggccgg aacgaggacc  240
atcgcatcac ccaagggtcc tgtcatccag atgtatacca atgtggacca agaccttgtg  300
ggctggcccg ctcctcaagg ttcccgctca ttgacaccct gtacctgcgg ctcctcggac  360
ctttacctgg tcacgaggca cgccgatgtc attcccgtgc gccggcgagg tgatagcagg  420
ggtagcctgc tttcgccccg gcccatttcc tacttgaaag gctcctcggg gggtccgctg  480
ttgtgccccg cgggacacgc cgtgggccta ttcagggccg cggtgtgcac ccgtggagtg  540
gctaaagcgg tggactttat ccctgtggag aacctagaga caaccatgag atccccggtg  600
ttcacggaca actcctctcc accagcagtc accctgacgc acccaatcac caaaatcgat  660
agggaggttc tctaccagga gttcgatgag atggaagagt gctctcagca c           711

SEQ ID NO: 20         moltype = DNA  length = 132
```

-continued

```
FEATURE                Location/Qualifiers
source                 1..132
                       mol_type = other DNA
                       organism = synthetic construct
SEQUENCE: 20
tcagacaaga aaaacgaaga aaaggatttg ttcggaagtg attccgagag cgggaacgaa  60
gaggagaatc tgattgccga catttttggt gagagcggcg atgaggaaga agaagagttc  120
actgggttta at                                                      132

SEQ ID NO: 21          moltype = DNA  length = 573
FEATURE                Location/Qualifiers
source                 1..573
                       mol_type = other DNA
                       organism = synthetic construct
SEQUENCE: 21
gatgagtttc ccaccatggt gtttccttct gggcagatca gccaggcctc ggccttggcc  60
ccggcccctc cccaagtcct gccccaggct ccagcccctg cccctgctcc agccatggta  120
tcagctctgg cccaggcccc agcccctgtc ccagtcctag ccccaggccc tcctcaggct  180
gtggccccac ctgcccccaa gcccacccag gctggggaag gaacgctgtc agaggccctg  240
ctgcagctgc agtttgatga tgaagacctg gggggccttgc ttggcaacag cacagaccca  300
gctgtgttca cagacctggc atccgtcgac aactccgagt ttcagcagct gctgaaccag  360
ggcatacctg tggcccccca cacaactgag cccatgctga tggagtaccc tgaggctata  420
actcgcctag tgacaggggc ccagaggccc cccgacccag ctcctgctcc actgggggcc  480
ccggggctcc ccaatggcct cctttcagga gatgaagact tctcctccat tgcggacatg  540
gacttctcag ccctgctgag tcagatcagc tcc                               573

SEQ ID NO: 22          moltype = DNA  length = 435
FEATURE                Location/Qualifiers
source                 1..435
                       mol_type = other DNA
                       organism = synthetic construct
SEQUENCE: 22
gagggccaga gcgacgagag agccctgctg gaccagctgc acaccctgct gagcaacacc  60
gacgccaccg gcctggagga gatcgacaga gccctgggca tccccgagct ggtgaaccag  120
ggccaggccc tggagcccaa gcagggagga ggaggtagcg gacacgagaa gttccccagc  180
gacctggacc tggacatgtt caacggcagc ctggagtgcg acatggagag catcatcaga  240
agcgagctga tggacgccga cggcctggac ttcaacttcg acagcggagg aggaggtagc  300
ggattcgtga ccctgaagga cgtgggcatg gacttcaccc tgggcgactg ggagcagctg  360
ggcctggagc agggcgacac cttctgggac accgccctgg acaactgcca ggacctgttc  420
ctgctggacc ccccc                                                   435

SEQ ID NO: 23          moltype = DNA  length = 385
FEATURE                Location/Qualifiers
source                 1..385
                       mol_type = other DNA
                       organism = synthetic construct
SEQUENCE: 23
acgattgagt aacactgtat ctagtctacc tacagggctc ggcgtagccg atgtcgcgcg  60
gatagcgtca acctcttcgg cgtagccgat gtcgcgcaat cagttctccc gaggtcggcg  120
tagccgatgt cgcgcagagc cgtgcttcca atacggcgta gccgatgtcg cgccgggttt  180
cgtaacaatc gcatgaggat tcgcaacgcc ttcggcgtag ccgatgtcgc gctcccgtct  240
cagtaaaggt cggcgtagcc gatgtcgcgc aatcggactg ccttcgtacg gcgtagccga  300
tgtcgcgcgt atcagtcgcc tcggaacggc gtagccgatg tcgcgcattc gtaagaggct  360
cactctccct tacacggagt ggata                                        385

SEQ ID NO: 24          moltype = DNA  length = 25
FEATURE                Location/Qualifiers
source                 1..25
                       mol_type = other DNA
                       organism = synthetic construct
SEQUENCE: 24
tggcccccat tatataccct ctaga                                        25

SEQ ID NO: 25          moltype = DNA  length = 1632
FEATURE                Location/Qualifiers
source                 1..1632
                       mol_type = other DNA
                       organism = synthetic construct
SEQUENCE: 25
gccttaccag tgaccgcctt gctcctgccg ctggccttgc tgctccacgc cgccaggccg  60
gacatccaga tgacacagac tacatcctcc ctgtctgcct ctctgggaga cagagtcacc  120
atcagttgca gggcaagtca ggacattagt aaatatttaa attggtatca gcagaaacca  180
gatggaactg ttaaactcct gatctaccat acatcaagat tacactcagg agtcccatca  240
aggttcagtg gcagtgggtc tggaacagat tattctctca ccattagcaa cctggagcaa  300
gaagatattg ccacttactt ttgccaacag ggtaatacgc ttccgtacac gttcggaggc  360
ggcaccaagc tggagatcac aggtggcggt ggctcgggcg gtggtgggtc gggtggcggc  420
ggatctgagg tgaaactgca ggagtcagga cctggcctgg tggcgccctc acagagcctg  480
tccgtcacat gcactgtctc aggggtctca ttacccgact atggtgtaag ctggattcgc  540
cagcctccac gaaagggtct ggagtggctg ggagtaatat ggggtagtga aaccacatac  600
```

```
tataattcag ctctcaaatc cagactgacc atcatcaagg acaactccaa gagccaagtt  660
ttcttaaaaa tgaacagtct gcaaactgat gacacagcca tttactactg tgccaaacat  720
tattactacg gtggtagcta tgctatggac tactggggcc aaggaacctc agtcaccgtc  780
tcctcagaac aaaaactcat ctcagaagaa gatctgaatg ggccgcaac cacgacgcca  840
gcgccgcgac caccaacacc ggcgcccacc atcgcgttgc agcccctgtc cctgcgccca  900
gaggcgtgcc ggccagcggc ggggggcgca gtgcacacga gggggctgga cttcgcctgt  960
gatttttggg tgctggtggt ggttggtgga gtcctggctt gctatagctt gctagtaaca  1020
gtggccttta ttattttctg ggtgaggagt aagaggagca ggctcctgca cagtgactac  1080
atgaacatga ctccccgccg ccccgggccc acccgcaagc attaccagcc ctatgcccca  1140
ccacgcgact tcgcagccta tcgctccaaa cggggcagaa agaaactcct gtatatattc  1200
aaacaaccat ttatgagacc agtacaaact actcaagagg aagatggctg tagctgccga  1260
tttccagaag aagaagaagg aggatgtgaa ctgagagtga agttcagcag gagcgcagac  1320
gcccccgcgt acaagcaggg ccagaaccag ctctataacg agctcaatct aggacgaaga  1380
gaggagtacg atgttttgga caagagacgt ggccgggacc ctgagatggg gggaaagccg  1440
agaaggaaga accctcagga aggcctgtac aatgaactgc agaaagataa gatggcggag  1500
gcctacagtg agattgggat gaaaggcgag cgccggaggg gcaaggggca cgatggcctt  1560
taccagggtc tcagtacagc caccaaggac acctacgacg cccttcacat gcaggccctg  1620
ccccctcgcg gc                                                     1632

SEQ ID NO: 26          moltype = DNA  length = 711
FEATURE                Location/Qualifiers
source                 1..711
                       mol_type = other DNA
                       organism = synthetic construct
SEQUENCE: 26
ttacttgtac agctcgtcca tgccgccggt ggagtggcgg ccctcggcgc gttcgtactg  60
ttccacgatg gtgtagtcct cgttgtggga ggtgatgtcc aacttgatgt tgacgttgta  120
ggcgccgggc agctgcacgg gcttcttggc cttgtaggtg gtcttgacct cagcgtcgta  180
gtggccgccg tccttcagct tcagcctctg cttgatctcg cccttcaggg cgccgtcctc  240
ggggtacatc cgctcggagg aggcctgcca gcccatggtc ttcttctgca ttacggggcc  300
gtcggagggg aagttggtgc cgcgcagctt caccttgtag atgaactcgc cgtcctgcag  360
ggaggagtcc tgggtcacgg tcaccacgcc gccgtcctcg aagttcatca cgcgctccca  420
cttgaagccc tcggggaagg acagcttcaa gtagtcgggg atgtcggcgg ggtgcttcac  480
gtaggccttg gagccgtaca tgaactgagg ggacaggatg tcccaggcga agggcagggg  540
gccacccttg gtcaccttca gcttggcggt ctgggtgccc tcgtaggggc ggccctcgcc  600
ctcgccctcg atctcgaact cgtggccgtt cacggagccc tccatgtgca ccttgaagcg  660
catgaactcc ttgatgatgg ccatgttatc ctcctcgccc ttgctcacca t           711

SEQ ID NO: 27          moltype = DNA  length = 717
FEATURE                Location/Qualifiers
source                 1..717
                       mol_type = other DNA
                       organism = synthetic construct
SEQUENCE: 27
cttgtacagc tcgtccatgc cgagagtgat cccggcggcg gtcacgaact ccagcaggac  60
catgtgatcg cgcttctcgt tggggtcttt gctcagggcg gactgggtgc tcaggtagtg  120
gttgtcgggc agcagcacgg ggccgtcgcc gatgggggtg ttctgctggt agtggtcggc  180
gagctgcacg ctgccgtcct cgatgttgtg gcggatcttg aagttcgcct tgatgccgtt  240
cttctgcttg tcggccatga tatagacgtt gtggctgttg tagttgtact ccagcttgtg  300
ccccaggatg ttgccgtcct ccttgaagtc gatgcccttc agctcgatgc ggttcaccag  360
ggtgtcgccc tcgaacttca cctcggcgcg ggtcttgtag ttgccgtcgt ccttgaagaa  420
gatggtgcgc tcctggacgt agccttcggg catggcggac ttgaagaagt cgtgctgctt  480
catgtggtcg gggtagcggc tgaagcactg cacgccgtag gtcagggtgg tcacgagggt  540
gggccagggc acgggcagct tgccggtggt gcagatgaac ttcagggtca gcttgccgta  600
ggtggcatcg ccctcgccct cgccagacac gctgaacttg tggccgttta cgtcgccgtc  660
cagctcgacc aggatgggca ccaccccggt gaacagctcc tcgcccttgc tcaccat     717

SEQ ID NO: 28          moltype = DNA  length = 2250
FEATURE                Location/Qualifiers
source                 1..2250
                       mol_type = other DNA
                       organism = synthetic construct
SEQUENCE: 28
tactgtgttc atcatactgt cgaactctac agagcccact atccgagaca cctcgtcaaa  60
ctcctcagga gacatgggga gcaggttgtc tgtggtctga agtctagaag ggtgaacttc  120
agacacagaa atcaactcag tcttgatata tccagttcct ttagggccat caagttccat  180
tggctctggt gcttcctttg gcctggagta atactttcca aaggcatggt ctttgtcaat  240
atttggatac agatacttca ggggattctc aggaatgcac tcgcaagcca tgactttgta  300
attgcgaatg atgtcaggga aagtaacagc agaaagttct ttcttcgtgt agggttcaac  360
cgcatggaag tcaggttcgc ctccgttctg ggaccgctcc acccatgtga atgtgatggc  420
cccttcccgg gagctctcac tgaaccgcag caggaaggtc cccggctgct ggtccttcaa  480
cagggcacgc tctcgctcct tgctgatgaa gcccatgatg cacccatcat tccagagagg  540
gagcaggtgt tttttaatga gttctaggat gctttcaatc caaagccaga agggaaaatt  600
tttatcattt atattttcct tacaaaacct cgtccacgga atgagaccat cggggctggc  660
gttaggacca agaagcttct ctcccaacat gttcagctgg tccacattga gacctctttt  720
ggtgacagaa gaaaactgcc aactcagcac ttctgaaagc tgagcccatc gtgcacatgg  780
tggagtcagg aagaaggaca gattcctggg ttccgccacc agcatgttgt accaaaggat  840
ggaggcccaa ccgctcggga gctggctgac gttggagatc accacaacgg gcagagaggt  900
cgtctcgagg tcaattacca aaccaggctg gcacaattgg gtttcaaaac taagggagtg  960
```

-continued

```
aagctcttca gtaacgatga gaggaccctc attcgttctg gtgccagcat ttttctgttc  1020
tttcaattgc aggtgccgaa attcagccgc cagactgcca ttggtggact cctccatgtt  1080
catcactttt gtgtgcgtgc ccaaaatgtt gaacttccta aatcctttta ctgtatctct  1140
ctcattcaca tctttatcaa ataagacttt gactttcaaa ttataattca gctcttgcaa  1200
tttcaccaac agtctcaact tcacagtgaa ctggacccct gtcttcaaga ccagcggcct  1260
ctgagggtgc gttggcatgc agggctgtct ttccaccaca aacgagctct gaatgagctg  1320
ctggaaaaga ctgaaggtgc ggtcccataa cacttgtttg ttttttgtga tagggtcatg  1380
ttcgtaggtg tatttctgtt ccaattcctc caacttttta agctgctgcc gaacttgctg  1440
cagactctcc gcaactatag tgaaccagtt ctgcagctga tccaagcaag cattgggcgg  1500
ccccccaata caggcgctct gctgtctccg cttccactcc actagttcat cattaatcag  1560
ggcattctgg gtaagttcag tgacattcag caactctatt attttgtgaa ctacttcctt  1620
tctcttattg tcaagcatta aatacatctt cttgagtaac agctgttctt gtttctgatc  1680
actctttgcc acaccattgg tctcgtgttc tctgttctgc aaggttttgc atttgaagtc  1740
atattcatct tgtaaatctt ccaggctctt gatttcatgc tctatacaca taaccttgtc  1800
cttcacattt ctgactttac tgtcaagctc tttctgtttg tctaacatca ctgtgctctg  1860
aatattcccc gactgagcct gattaaatct ctgggcgttt tccagaattt tcctttcttc  1920
cttcagacag ctgtaaatga tcatagacat ctggattggg tcttcctgaa aattatcctg  1980
aagattacgc ttgcttttcc ttatgttatg ctgtagcaag aagttattct ccaaagaaaa  2040
gcgactatat tgatcatcca gctgtgacag gaggtcatga aaacggatgg tggcaaatga  2100
aacatcattg gcagcgtgct cccagtcttg cttttctaac cactgtgcca ggtactgtct  2160
gatttccatg ggaaaactgt catcataaag ctggtgaacc tgctccagga attttgagtc  2220
aagctgctga agttcgtacc actgagacat                                    2250

SEQ ID NO: 29          moltype = DNA  length = 942
FEATURE                Location/Qualifiers
source                 1..942
                       mol_type = other DNA
                       organism = unidentified
SEQUENCE: 29
tctgctggag acatgagagc tgccaacctt tggccaagcc cgctcatgat caaacgctct  60
aagaagaaca gcctggcctt gtccctgacg gccgaccaga tggtcagtgc cttgttggat  120
gctgagcccc ccatactcta ttccgagtat gatcctacca gacccttcag tgaagcttcg  180
atgatgggct tactgaccaa cctggcagac agggagctgg ttcacatgat caactgggcg  240
aagagggtgc caggctttgt ggatttgacc ctccatgatc aggtccacct tctagaatgt  300
gcctggctag agatcctgat gattggtctc gtctggcgct ccatggagca cccagtgaag  360
ctactgtttg ctcctaactt gctcttggac aggaaccagg gaaaatgtgt agagggcatg  420
gtggagatct tcgacatgct gctggctaca tcatctcggt tccgcatgat gaatctgcag  480
ggagaggagt ttgtgtgcct caaatctatt attttgctta attctggagt gtacacattt  540
ctgtccagca ccctgaagtc tctggaagag aaggaccata tccaccgagt cctggacaag  600
atcacagaca ctttgatcca cctgatggcc aaggcaggcc tgaccctgca gcagcagcac  660
cagcggctgg cccagctcct cctcatcctc tcccacatca ggcacatgag taacaaaggc  720
atggagcatc tgtacagcat gaagtgcaag aacgtggtgc ccctctatga cctgctgctg  780
gaggcggcgg acgcccaccg cctacatgcg cccactagcc gtggaggggc atccgtggag  840
gagacggacc aaagccactt ggccactgcg ggctctactt catcgcattc cttgcaaaag  900
tattacatca cgggggaggc agagggtttc cctgccacag ct                      942

SEQ ID NO: 30          moltype = DNA  length = 414
FEATURE                Location/Qualifiers
source                 1..414
                       mol_type = other DNA
                       organism = synthetic construct
SEQUENCE: 30
gcggatcccg cacctacttc aagttctaca aagaaaacac agctacaact ggagcattta  60
cttctggatt tacagatgat tttgaatgga attaataatt acaagaatcc caaactcacc  120
aggatgctca cagcaaagtt ttacatgccc aagaaggcca cagaactgaa acatcttcag  180
tgtctagaag aagaactcaa acctctggag gaagtgctaa atttagctca gagcaaaaac  240
tttcacttcg atcccaggga cgtcgtcagc aatatcaacg tattcgtcct ggaactaaag  300
ggatctgaaa caacattcat gtgtgaatat gctgatgaga cagcaaccat tgtagaattt  360
ctgaacagat ggattacctt ttgtcaaagc atcatctcaa cactaactgg cggc         414

SEQ ID NO: 31          moltype = DNA  length = 385
FEATURE                Location/Qualifiers
source                 1..385
                       mol_type = other DNA
                       organism = synthetic construct
SEQUENCE: 31
tatccactcc gtgtaaggga gagtgagcct cttacgaatc tacggctact tcgacgtctt  60
tccgaggcga ctgataccta cggctacttc gacgtcttac gaaggcagtc cgattctacg  120
gctacttcga cgtctacctt tactgagacg ggactacggc tacttcgacg tctaaggcgt  180
tgcgaatcct catgcgattg ttacgaaacc cgctacggct acttcgacgt cttattggaa  240
gcacggctct ctacggctac ttcgacgtct acctcgggag aactgattct acggctactt  300
cgacgtctaa gaggttgacg ctatccctac ggctacttcg acgtctagcc ctgtaggtag  360
actagataca gtgttactca atcgt                                         385

SEQ ID NO: 32          moltype = DNA  length = 285
FEATURE                Location/Qualifiers
source                 1..285
                       mol_type = other DNA
                       organism = synthetic construct
```

```
SEQUENCE: 32
cgctacaggg cgcgtgggga taccccctag agccccagct ggttctttcc gcctcagaag  60
ccatagagcc caccgcatcc ccagcatgcc tgctattgtc ttcccaatcc tcccccttgc  120
tgtcctgccc caccccaccc cccagaatag aatgacacct actcagacaa tgcgatgcaa  180
tttcctcatt ttattaggaa aggacagtgg gagtggcacc ttccagggtc aaggaaggca  240
cgggggaggg gcaaacaaca gatggctggc aactagaagg cacag                  285

SEQ ID NO: 33           moltype = DNA  length = 528
FEATURE                 Location/Qualifiers
source                  1..528
                        mol_type = other DNA
                        organism = synthetic construct
SEQUENCE: 33
tctagaccag gcgaacgacc gtttcaatgc cggatatgta tgaggaactt ctcccagagg  60
tccagcttgg tacggcacac ccgaacacat acaggagaaa agccattcca atgtcgaatt  120
tgtatgcgca atttttcaga caagtctgtg ttggctcgac acctccgcac acatactggt  180
tcacagaagc cctttcagtg caggatttgt atgcgcaact ttagccaacg ctcatccctg  240
gtaaggcaca ctagaacgca tacaggtgag aagcctttcc agtgtcgcat ctgtatgcgg  300
aacttcagcc agcggaataa cttgggcagg catttgcgaa ctcacaccgg ttctcaaaaa  360
ccttttcagt gccgaatttg tatgcgcaac ttcagcaccc acgccgtatt gacacgacac  420
acgcgcacgc acaccgggga aaaaccgttt caatgtcgaa tctgcatgcg caattttagc  480
gatagaggga acctcactcg acatctgcgc acacacttgc ggggatcc               528

SEQ ID NO: 34           moltype = DNA  length = 584
FEATURE                 Location/Qualifiers
source                  1..584
                        mol_type = other DNA
                        organism = synthetic construct
SEQUENCE: 34
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggagtatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg gtgatgcggt tttggcagta catcaatggg cgtggatagc  420
ggtttgactc acggggattt ccaagtctcc accccattga cgtcaatggg agtttgtttt  480
ggcaccaaaa tcaacgggac tttccaaaat gtcgtaacaa ctccgcccca ttgacgcaaa  540
tgggcggtag gcgtgtacgg tgggaggtct atataagcag agct                   584

SEQ ID NO: 35           moltype = DNA  length = 2544
FEATURE                 Location/Qualifiers
source                  1..2544
                        mol_type = other DNA
                        organism = synthetic construct
SEQUENCE: 35
atgtctctgt ggggtctggt ctccaagatg cccccagaaa aagtgcagcg gctctatgtc  60
gactttcccc aacacctgcg gcatcttctg ggtgactggc tggagagcca gccctgggag  120
ttcctggtcg gctccgacgc cttctgctgc aacttggcta gtgccctact ttcagacact  180
gtccagcacc ttcaggcctc ggtgggagag caggggggagg ggagcaccat cttgcaacac  240
atcagcaccc ttgagagcat atatcagagg gaccccctga agctggtggc cactttcaga  300
caaatacttc aaggagagaa aaaagctgtt atggaacagt tccgccactt gccaatgcct  360
ttccactgga agcaggaaga actcaagttt aagacaggct tgcggaggct gcagcaccga  420
gtaggggaga tccaccttct ccgagaagcc ctgcagaagg gggctgaggc tggccaagtg  480
tctctgcaca gcttgataga aactcctgct aatgggactg ggccaagtga ggccctggcc  540
atgctactgc aggagaccac tggagagcta gaggcagcca aagccctagt gctgaagagg  600
atccagattt ggaaacggca gcagcagctg gcagggaatg gcgcaccgtt tgaggagagc  660
ctggccccac tccaggagag gtgtgaaagc ctggtggaca tttattccca gctacagcag  720
gaggtagggg cggctggtgg ggagcttgag cccaagaccc gggcatcgct gactggccgg  780
ctggatgaag tcctgagaac cctcgtcacc agttgcttcc tggtggagaa gcagcccccc  840
caggtactga agactcagac caagttccag gctggagttc gattcctgtt gggcttgagg  900
ttcctggggg ccccagccaa gcctccgctg gtcagggccg acatggtgac agagaagcag  960
gcgcgggagc tgagtgtgcc tcagggtcct ggggctggag cagaaagcac tggagaaatc  1020
atcaacaaca ctgtgccctt ggagaacagc attcctggga actgctgctc tgccctgttc  1080
aagaacctgc ttctcaagaa gatcaagcgg tgtgagcgga agggcactga gtctgtcaca  1140
gaggagaagt gcgctgtgct cttctctgcc agcttcacac ttggccccgg caaactcccc  1200
atccagctcc aggccctgtc tctgcccctg gtggtcatcg tccatggcaa ccaagacaac  1260
aatgccaaag ccactatcct gtgggacaat gccttctctg agatggaccg cgtgcccttt  1320
gtggtggctg agcgggtgcc ctgggagaag atgtgtgaaa ctctgaacct gaagttcatg  1380
gctgaggtgg ggaccaaccg ggggctgctc ccagagcact tcctcttcct ggcccagaag  1440
atcttcaatg acaacagcct cagtatggag gccttccagc accgttctgt gtcctggtcg  1500
cagttcaaca aggagatcct gctgggccgt ggcttcacct tttggcagtg gtttgatggt  1560
gtcctggacc tcaccaaacg ctgtctccgg agctactggt ctgaccggct gatcattggc  1620
ttcatcagca aacagtacgc tgctagcctt cttctcaatg agcccgacgg aacctttctc  1680
ctccgcttca gcgactcaga gattgggggc atcaccattg cccatgtcat ccggggccag  1740
gatggctctc cacagataga gaacatccag ccattctctg ccaaagacct gtccattcgc  1800
tcactggggg accgaatccg ggatcttgca cagctcaaaa atctctatcc caagaagccc  1860
aaggatgagg ctttccggag ccactacaag cctgaacaga tgggtaagga tggcaggggt  1920
tatgtcccag ctaccatcaa gatgaccgtg gaaagggacc aaccacttcc taccccagag  1980
```

-continued

```
ctccagatgc ctaccatggt gccttcttat gaccttggaa tggcccctga ttcctccatg  2040
agcatgcagc ttggcccaga tatggtgccc caggtgtacc caccacactc tcactccatc  2100
cccccgtatc aaggcctctc cccagaagaa tcagtcaacg tgttgtcagc cttccaggag  2160
cctcacctgc agatgccccc cagcctgggc cagatgagcc tgccctttga ccagcctcac  2220
ccccagggcc tgctgccgtg ccagcctcag gagcatgctg tgtccagccc tgacccccctg  2280
ctctgctcag atgtgaccat ggtggaagac agctgcctga gccagccagt gacagcgttt  2340
cctcagggca cttggattgg tgaagacata ttccctcctc tgctgcctcc cactgaacag  2400
gacctcacta agcttctcct ggaggggcaa ggggagtcgg ggggagggtc cttgggggca  2460
cagcccctcc tgcagccctc ccactatggg caatctggga tctcaatgtc ccacatggac  2520
ctaagggcca accccagttg gtga                                         2544

SEQ ID NO: 36          moltype = AA  length = 176
FEATURE                Location/Qualifiers
source                 1..176
                       mol_type = protein
                       organism = synthetic construct
SEQUENCE: 36
SRPGERPFQC RICMRNFSRR HGLDRHTRTH TGEKPFQCRI CMRNFSDHSS LKRHLRTHTG  60
SQKPFQCRIC MRNFSVRHNL TRHLRTHTGE KPFQCRICMR NFSDHSNLSR HLKTHTGSQK  120
PFQCRICMRN FSQRSSLVRH LRTHTGEKPF QCRICMRNFS ESGHLKRHLR THLRGS      176

SEQ ID NO: 37          moltype = AA  length = 237
FEATURE                Location/Qualifiers
source                 1..237
                       mol_type = protein
                       organism = synthetic construct
SEQUENCE: 37
GCVVIVGRIV LSGSGTSAPI TAYAQQTRGL LGCIITSLTG RDKNQVEGEV QIVSTATQTF  60
LATCINGVCW AVYHGAGTRT IASPKGPVIQ MYTNVDQDLV GWPAPQGSRS LTPCTCGSSD  120
LYLVTRHADV IPVRRRGDSR GSLLSPRPIS YLKGSSGGPL LCPAGHAVGL FRAAVCTRGV  180
AKAVDFIPVE NLETTMRSPV FTDNSSPPAV TLTHPITKID REVLYQEFDE MEECSQH      237

SEQ ID NO: 38          moltype = AA  length = 191
FEATURE                Location/Qualifiers
source                 1..191
                       mol_type = protein
                       organism = Homo sapiens
SEQUENCE: 38
DEFPTMVFPS GQISQASALA PAPPQVLPQA PAPAPAPAMV SALAQAPAPV PVLAPGPPQA  60
VAPPAPKPTQ AGEGTLSEAL LQLQFDDEDL GALLGNSTDP AVFTDLASVD NSEFQQLLNQ  120
GIPVAPHTTE PMLMEYPEAI TRLVTGAQRP PDPAPAPLGA PGLPNGLLSG DEDFSSIADM  180
DFSALLSQIS S                                                       191

SEQ ID NO: 39          moltype = AA  length = 544
FEATURE                Location/Qualifiers
source                 1..544
                       mol_type = protein
                       organism = synthetic construct
SEQUENCE: 39
ALPVTALLLP LALLLHAARP DIQMTQTTSS LSASLGDRVT ISCRASQDIS KYLNWYQQKP  60
DGTVKLLIYH TSRLHSGVPS RFSGSGSGTD YSLTISNLEQ EDIATYFCQQ GNTLPYTFGG  120
GTKLEITGGG GSGGGGSGGG GSEVKLQESG PGLVAPSQSL SVTCTVSGVS LPDYGVSWIR  180
QPPRKGLEWL GVIWGSETTY YNSALKSRLT IIKDNSKSQV FLKMNSLQTD DTAIYYCAKH  240
YYYGGSYAMD YWGQGTSVTV SSEQKLISEE DLNGAATTTP APRPPTPAPT IALQPLSLRP  300
EACRPAAGGA VHTRGLDFAC DFWVLVVVGG VLACYSLLVT VAFIIFWVRS KRSRLLHSDY  360
MNMTPRRPGP TRKHYQPYAP PRDFAAYRSK RGRKKLLYIF KQPFMRPVQT TQEEDGCSCR  420
FPEEEEGGCE LRVKFSRSAD APAYKQGQNQ LYNELNLGRR EEYDVLDKRR GRDPEMGGKP  480
RRKNPQEGLY NELQKDKMAE AYSEIGMKGE RRRGKGHDGL YQGLSTATKD TYDALHMQAL  540
PPRG                                                               544

SEQ ID NO: 40          moltype = AA  length = 237
FEATURE                Location/Qualifiers
source                 1..237
                       mol_type = protein
                       organism = synthetic construct
SEQUENCE: 40
LLVQLVHAAG GVAALGAFVL FHDGVVLVVG GDVQLDVDVV GAGQLHGLLG LVGGLDLSVV  60
VAAVLQLQPL LDLALQGAVL GVHPLGGGLP AHGLLLHYGA VGGEVGAAQL HLVDELAVLQ  120
GGVLGHGHHA AVLEVHHALP LEALGEGQLQ VVGDVGGVLH VGLGAVHELR GQDVPGEGQG  180
ATLGHLQLGG LGALVGAALA LALDLELVAV HGALHVHLEA HELLDDGHVI LLALAHH      237

SEQ ID NO: 41          moltype = AA  length = 239
FEATURE                Location/Qualifiers
source                 1..239
                       mol_type = protein
                       organism = synthetic construct
SEQUENCE: 41
LVQLVHAESD PGGGHELQQD HVIALLVGVF AQGGLGAQVV VVGQQHGAVA DGGVLLVVVG  60
ELHAAVLDVV ADLEVRLDAV LLLVGHDIDV VAVVVVLQLV PQDVAVLLEV DALQLDAVHQ  120
```

```
GVALELHLGA GLVVAVVLEE DGALLDVAFG HGGLEEVVLL HVVGVAAEAL HAVGQGGHEG  180
GPGHGQLAGG ADELQGQLAV GGIALALARH AELVAVYVAV QLDQDGHHPG EQLLALAHH   239

SEQ ID NO: 42          moltype = AA  length = 750
FEATURE                Location/Qualifiers
source                 1..750
                       mol_type = protein
                       organism = synthetic construct
SEQUENCE: 42
MSQWYELQQL DSKFLEQVHQ LYDDSFPMEI RQYLAQWLEK QDWEHAANDV SFATIRFHDL  60
LSQLDDQYSR FSLENNFLLQ HNIRKSKRNL QDNFQEDPIQ MSMIIYSCLK EERKILENAQ  120
RFNQAQSGNI QSTVMLDKQK ELDSKVRNVK DKVMCIEHEI KSLEDLQDEY DFKCKTLQNR  180
EHETNGVAKS DQKQEQLLLK KMYLMLDNKR KEVVHKIIEL LNVTELTQNA LINDELVEWK  240
RRQQSACIGG PPNACLDQLQ NWFTIVAESL QQVRQQLKKL EELEQKYTYE HDPITKNKQV  300
LWDRTFSLFQ QLIQSSFVVE RQPCMPTHPQ RPLVLKTGVQ FTVKLRLLVK LQELNYNLKV  360
KVLFDKDVNE RDTVKGFRKF NILGTHTKVM NMEESTNGSL AAEFRHLQLK EQKNAGTRTN  420
EGPLIVTEEL HSLSFETQLC QPGLVIDLET TSLPVVVISN VSQLPSGWAS ILWYNMLVAE  480
PRNLSFFLTP PCARWAQLSE VLSWQFSSVT KRGLNVDQLN MLGEKLLGPN ASPDGLIPWT  540
RFCKENINDK NFPFWLWIES ILELIKKHLL PLWNDGCIMG FISKERERAL LKDQQPGTFL  600
LRFSESSREG AITFTWVERS QNGGEPDFHA VEPYTKKELS AVTFPDIIRN YKVMACECIP  660
ENPLKYLYPN IDKDHAFGKY YSRPKEAPEP MELDGPKGTG YIKTELISVS EVHPSRLQTT  720
DNLLPMSPEE FDEVSRIVGS VEFDSMMNTV                                  750

SEQ ID NO: 43          moltype = AA  length = 314
FEATURE                Location/Qualifiers
source                 1..314
                       mol_type = protein
                       organism = unidentified
SEQUENCE: 43
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPVK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKG  240
MEHLYSMKCK NVVPLYDLLL EAADAHRLHA PTSRGGASVE ETDQSHLATA GSTSSHSLQK  300
YYITGEAEGF PATA                                                   314

SEQ ID NO: 44          moltype = AA  length = 138
FEATURE                Location/Qualifiers
source                 1..138
                       mol_type = protein
                       organism = synthetic construct
SEQUENCE: 44
ADPAPTSSST KKTQLQLEHL LLDLQMILNG INNYKNPKLT RMLTAKFYMP KKATELKHLQ  60
CLEEELKPLE EVLNLAQSKN FHFDPRDVVS NINVFVLELK GSETTFMCEY ADETATIVEF  120
LNRWITFCQS IISTLTGG                                               138

SEQ ID NO: 45          moltype = AA  length = 176
FEATURE                Location/Qualifiers
source                 1..176
                       mol_type = protein
                       organism = synthetic construct
SEQUENCE: 45
SRPGERPFQC RICMRNFSQR SSLVRHTRTH TGEKPFQCRI CMRNFSDKSV LARHLRTHTG  60
SQKPFQCRIC MRNFSQRSSL VRHTRTHTGE KPFQCRICMR NFSQRNNLGR HLRTHTGSQK  120
PFQCRICMRN FSTHAVLTRH TRTHTGEKPF QCRICMRNFS DRGNLTRHLR THLRGS     176

SEQ ID NO: 46          moltype = AA  length = 847
FEATURE                Location/Qualifiers
source                 1..847
                       mol_type = protein
                       organism = synthetic construct
SEQUENCE: 46
MSLWGLVSKM PPEKVQRLYV DFPQHLRHLL GDWLESQPWE FLVGSDAFCC NLASALLSDT  60
VQHLQASVGE QGEGSTILQH ISTLESIYQR DPLKLVATFR QILQGEKKAV MEQFRHLPMP  120
FHWKQEELKF KTGLRRLQHR VGEIHLLREA LQKGAEAGQV SLHSLIETPA NGTGPSEALA  180
MLLQETTGEL EAAKALVLKR IQIWKRQQQL AGNGAPFEES LAPLQERCES LVDIYSQLQQ  240
EVGAAGGELE PKTRASLTGR LDEVLRTLVT SCFLVEKQPP QVLKTQTKFQ AGVRFLLGLR  300
FLGAPAKPPL VRADMVTEKQ ARELSVPQGP GAGAESTGEI INNTVPLENS IPGNCCSALF  360
KNLLLKKIKR CERKGTESVT EEKCAVLFSA SFTLGPGKLP IQLQALSLPL VVIVHGNQDN  420
NAKATILWDN AFSEMDRVPF VVAERVPWEK MCETLNLKFM AEVGTNRGLL PEHFLFLAQK  480
IFNDNSLSME AFQHRSVSWS QFNKEILLGR GFTFWQWFDG VLDLTKRCLR SYWSDRLIIG  540
FISKQYAASL LLNEPDGTFL LRFSDSEIGG ITIAHVIRGQ DGSPQIENIQ PFSAKDLSIR  600
SLGDRIRDLA QLKNLYPKKP KDEAFRSHYK PEQMGKDGRG YVPATIKMTV ERDQPLPTPE  660
LQMPTMVPSY DLGMAPDSSM SMQLGPDMVP QVYPPHSHSI PPYQGLSPEE SVNVLSAFQE  720
PHLQMPPSLG QMSLPFDQPH PQGLLPCQPQ EHAVSSPDPL LCSDVTMVED SCLSQPVTAF  780
PQGTWIGEDI FPPLLPPTEQ DLTKLLLEGQ GESGGGSLGA QPLLQPSHYG QSGISMSHMD  840
LRANPSW                                                           847

SEQ ID NO: 47          moltype = DNA  length = 309
```

```
FEATURE                 Location/Qualifiers
source                  1..309
                        mol_type = other DNA
                        organism = synthetic construct
SEQUENCE: 47
ggcaaaaaga agcagcacat ctgccacatc cagggctgcg gcaaggtgta cggcgacagg  60
agcaacctga ccaggcacct taggtggcac accggggaga ggcccttcat gtgcacctgg  120
agctactgcg gaaaaaggtt caccatgagc catcacttga gcaggcacaa gaggacccac  180
acaggcgaga agaagttcgc ctgccccgag tgccccaaga ggtttatgag gagcgaccat  240
ctgagcaggc acatcaagac ccaccagaac aagaaaggcg gggcagtgg cgggagcggg  300
cgggccgaa                                                          309

SEQ ID NO: 48           moltype = AA  length = 103
FEATURE                 Location/Qualifiers
source                  1..103
                        mol_type = protein
                        organism = synthetic construct
SEQUENCE: 48
GKKKQHICHI QGCGKVYGDR SNLTRHLRWH TGERPFMCTW SYCGKRFTMS HHLSRHKRTH  60
TGEKKFACPE CPKRFMRSDH LSRHIKTHQN KKGGGSGGSG RAE                    103

SEQ ID NO: 49           moltype = AA  length = 1083
FEATURE                 Location/Qualifiers
source                  1..1083
                        mol_type = protein
                        organism = Homo sapiens
SEQUENCE: 49
MSDSEDSNFS EEEDSERSSD GEEAEVDEER RSAAGSEKEE EPEDEEEEEE EEEYDEEEEE  60
EDDDRPPKKP RHGGFILDEA DVDDEYEDED QWEDGAEDIL EKASNIDNVV LDEDRSGARR  120
LQNLWRDQRE EELGEYYMKK YAKSSVGETV YGGSDELSDD ITQQQLLPGV KDPNLWTVKC  180
KIGEERATAI SLMRKFIAYQ FTDTPLQIKS VVAPEHVKGY IYVEAYKQTH VKQAIEGVGN  240
LRLGYWNQQM VPIKEMTDVL KVVKEVANLK PKSWVRLKRG IYKDDIAQVD YVEPSQNTIS  300
LKMIPRIDYD RIKARMSLKD WFAKRKKFKR PPQRLFDAEK IRSLGGDVAS DGDFLIFEGN  360
RYSRKGFLFK SFAMSAVITE GVKPTLSELE KFEDQPEGID LEVVTESTGK EREHNFQPGD  420
NVEVCEGELI NLQGKILSVD GNKITIMPKH EDLKDMLEFP AQELRKYFKM GDHVKVIAGR  480
FEGDTGLIVR VEENFVILFS DLTMHELKVL PRDLQLCSET ASGVDVGGQH EWGELVQLDP  540
QTVGVIVRLE RETFQVLNMY GKVVTVRHQA VTRKKDNRFA VALDSEQNNI HVKDIVKVID  600
GPHSGREGEI RHLFRSFAFL HCKKLVENGG MFVCKTRHLV LAGGSKPRDV TNFTVGGFAP  660
MSPRISSPMH PSAGGQRGGF GSPGGGSGGM SRGRGRRDNE LIGQTVRISQ GPYKGYIGVV  720
KDATESTARV ELHSTCQTIS VDRQRLTTVG SRRPGGMTST YGRTPMYGSQ TPMYGSGSRT  780
PMYGSQTPLQ DGSRTPHYGS QTPLHDGSRT PAQSGAWDPN NPNTPSRAEE EYEYAFDDEP  840
TPSPQAYGGT PNPQTPGYPD PSSPQVNPQY NPQTPGTPAM YNTDQFSPYA APSPQGSYQP  900
SPSPQSYHQV APSPAGYQNT HSPASYHPTP SPMAYQASPS PSPVGYSPMT PGAPSPGGYN  960
PHTPGSGIEQ NSSDWVTTDI QVKVRDTYLD TQVVGQTGVI RSVTGGMCSV YLKDSEKVVS  1020
ISSEHLEPIT PTKNNKVKVI LGEDREATGV LLSIDGEDGI VRMDLDEQLK ILNLRFLGKL  1080
LEA                                                                1083

SEQ ID NO: 50           moltype = AA  length = 1362
FEATURE                 Location/Qualifiers
source                  1..1362
                        mol_type = protein
                        organism = Homo sapiens
SEQUENCE: 50
MSAESGPGTR LRNLPVMGDG LETSQMSTTQ AQAQPQPANA ASTNPPPPET SNPNKPKRQT  60
NQLQYLLRVV LKTLWKHQFA WPFQQPVDAV KLNLPDYYKI IKTPMDMGTI KKRLENNYYW  120
NAQECIQDFN TMFTNCYIYN KPGDDIVLMA EALEKLFLQK INELPTEETE IMIVQAKGRG  180
RGRKETGTAK PGVSTVPNTT QASTPPQTQT PQPNPPPVQA TPHPFPAVTP DLIVQTPVMT  240
VVPPQPLQTP PPVPPQPQPP PAPAPQPVQS HPPIIAATPQ PVKTKKGVKR KADTTTPTTI  300
DPIHEPPSLP PEPKTTKLGQ RRESSRPVKP PKKDVPDSQQ HPAPEKSSKV SEQLKCCSGI  360
LKEMFAKKHA AYAWPFYKPV DVEALGLHDY CDIIKHPMDM STIKSKLEAR EYRDAQEFGA  420
DVRLMFSNCY KYNPPDHEVV AMARKLQDVF EMRFAKMPDE PEEPVVAVSS PAVPPPTKVV  480
APPSSSDSSS DSSSDSDSST DDSEEERAQR LAELQEQLKA VHEQLAALSQ PQQNKPKKKE  540
KDKKEKKKEK HKRKEEVEEN KKSKAKEPPP KKTKKNNSSN SNVSKKEPAP MKSKPPPTYE  600
SEEEDKCKPM SYEEKRQLSL DINKLPGEKL GRVVHIIQSR EPSLKNSNPD EIEIDFETLK  660
PSTLRELERY VTSCLRKKRK PQAEKVDVIA GSSKMKGFSS SESESSSESS SSDSEDSETE  720
MAPKSKKKGH PGREQKKHHH HHHQQMQQAP APVPQQPPPP PQQPPPPPPP QQQQQPPPPP  780
PPPSMPQQAA PAMKSSPPPF IATQVPVLEP QLPGSVFDPI GHFTQPILHL PQPELPPHLP  840
QPPEHSTPPH LNQHAVVSPP ALHNALPQQP SRPSNRAAAL PPKPARPPAV SPALTQTPLL  900
PQPPMAQPPQ VLLEDEEPPA PPLTSMQMQL YLQQLQKVQP PTPLLPSVKV QSQPPPPLPP  960
PPHPSVQQQL QQQPPPPPPP QPQPPPQQQH QPPPRPVHLQ PMQFSTHIQQ PPPPQGQQPP  1020
HPPPGQQPPP PQPAKPQQVI QHHHSPRHHK SDPYSTGHLR EAPSPLMIHS PQMSQFQSLT  1080
HQSPPQQNVQ PKKQELRAAS VVQPQPLVVV KEEKIHSPII RSEPFSPSLR PEPPKHPESI  1140
KAPVHLPQRP EMKPVDVGRP VIRPPEQNAP PPGAPDKDKQ KQEPKTPVAP KKDLKIKNMG  1200
SWASLVQKHP TTPSSTAKSS SDSFEQFRRA AREKEEREKA LKAQAEHAEK EKERLRQERM  1260
RSREDEDALE QARRAHEEAR RRQEQQQQQR QEQQQQQQQQ AAAVAAAATP QAQSSQPQSM  1320
LDQQRELARK REQERRREA MAATIDMNFQ SDLLSIFEEN LF                      1362

SEQ ID NO: 51           moltype = AA  length = 454
FEATURE                 Location/Qualifiers
```

-continued

```
source                  1..454
                        mol_type = protein
                        organism = Homo sapiens
SEQUENCE: 51
MDFFRVVENQ QPPATMPLNV SFTNRNYDLD YDSVQPYFYC DEEENFYQQQ QQSELQPPAP  60
SEDIWKKFEL LPTPPLSPSR RSGLCSPSYV AVTPFSLRGD NDGGGGSFST ADQLEMVTEL  120
LGGDMVNQSF ICDPDDETFI KNIIIQDCMW SGFSAAAKLV SEKLASYQAA RKDSGSPNPA  180
RGHSVCSTSS LYLQDLSAAA SECIDPSVVF PYPLNDSSSP KSCASQDSSA FSPSSDSLLS  240
STESSPQGSP EPLVLHEETP PTTSSDSEEE QEDEEEIDVV SVEKRQAPGK RSESGSPSAG  300
GHSKPPHSPL VLKRCHVSTH QHNYAAPPST RKDYPAAKRV KLDSVRVLRQ ISNNRKCTSP  360
RSSDTEENVK RRTHNVLERQ RRNELKRSFF ALRDQIPELE NNEKAPKVVI LKKATAYILS  420
VQAEEQKLIS EEDLLRKRRE QLKHKLEQLR NSCA                            454

SEQ ID NO: 52           moltype = AA  length = 529
FEATURE                 Location/Qualifiers
source                  1..529
                        mol_type = protein
                        organism = Homo sapiens
SEQUENCE: 52
MDLPVGPGAA GPSNVPAFLT KLWTLVSDPD TDALICWSPS GNSFHVFDQG QFAKEVLPKY  60
FKHNNMASFV RQLNMYGFRK VVHIEQGGLV KPERDDTEFQ HPCFLRGQEQ LLENIKRKVT  120
SVSTLKSEDI KIRQDSVTKL LTDVQLMKGK QECMDSKLLA MKHENEALWR EVASLRQKHA  180
QQQKVVNKLI QFLISLVQSN RILGVKRKIP LMLNDSGSAH SMPKYSRQFS LEHVHGSGPY  240
SAPSPAYSSS SLYAPDAVAS SGPIISDITE LAPASPMASP GGSIDERPLS SSPLVRVKEE  300
PPSPPQSPRV EEASPGRPSS VDTLLSPTAL IDSILRESEP APASVTALTD ARGHTDTEGR  360
PPSPPPTSTP EKCLSVACLD KNELSDHLDA MDSNLDNLQT MLSSHGFSVD TSALLDLFSP  420
SVTVPDMSLP DLDSSLASIQ ELLSPQEPPR PPEAENSSPD SGKQLVHYTA QPLFLLDPGS  480
VDTGSNDLPV LFELGEGSYF SEGDGFAEDP TISLLTGSEP PKAKDPTVS             529

SEQ ID NO: 53           moltype = AA  length = 777
FEATURE                 Location/Qualifiers
source                  1..777
                        mol_type = protein
                        organism = Homo sapiens
SEQUENCE: 53
MDSKESLTPG REENPSSVLA QERGDVMDFY KTLRGGATVK VSASSPSLAV ASQSDSKQRR  60
LLVDFPKGSV SNAQQPDLSK AVSLSMGLYM GETETKVMGN DLGFPQQGQI SLSSGETDLK  120
LLEESIANLN RSTSVPENPK SSASTAVSAA PTEKEFPKTH SDVSSEQQHL KGQTGTNGGN  180
VKLYTTDQST FDILQDLEFS SGSPGKETNE SPWRSDLLID ENCLLSPLAG EDDSFLLEGN  240
SNEDCKPLIL PDTKPKIKDN GDLVLSSPSN VTLPQVKTEK EDFIELCTPG VIKQEKLGTV  300
YCQASFPGAN IIGNKMSAIS VHGVSTSGGQ MYHYDMNTAS LSQQQDQKPI FNVIPPIPVG  360
SENWNRCQGS GDDNLTSLGT LNFPGRTVFS NGYSSPSMRP DVSSPPSSSS TATTGPPPKL  420
CLVCSDEASG CHYGVLTCGS CKVFFKRAVE GQHNYLCAGR NDCIIDKIRR KNCPACRYRK  480
CLQAGMNLEA RKTKKKIKGI QQATTGVSQE TSENPGNKTI VPATLPQLTP TLVSLLEVIE  540
PEVLYAGYDS SVPDSTWRIM TTLNMLGGRQ VIAAVKWAKA IPGFRNLHLD DQMTLLQYSW  600
MFLMAFALGW RSYRQSSANL LCFAPDLIIN EQRMTLPCMY DQCKHMLYVS SELHRLQVSY  660
EEYLCMKTLL LLSSVPKDGL KSQELFDEIR MTYIKELGKA IVKREGNSSQ NWQRFYQLTK  720
LLDSMHEVVE NLLNYCFQTF LDKTMSIEFP EMLAEIITNQ IPKYSNGNIK KLLFHQK    777

SEQ ID NO: 54           moltype = AA  length = 852
FEATURE                 Location/Qualifiers
source                  1..852
                        mol_type = protein
                        organism = Homo sapiens
SEQUENCE: 54
MAGALAGLAA GLQVPRVAPS PDSDSDTDSE DPSLRRSAGG LLRSQVIHSG HFMVSSPHSD  60
SLPRRRDQEG SVGPSDFGPR SIDPTLTRLF ECLSLAYSGK LVSPKWKNFK GLKLLCRDKI  120
RLNNAIWRAW YIQYVKRRKS PVCGFVTPLQ GPEADAHRKP EAVVLEGNYW KRRIEVVMRE  180
YHKWRIYYKK RLRKPSREDD LLAPKQAEGR WPPPEQWCKQ LFSSVVPVLL GDPEEEPGGR  240
QLLDLNCFLS DISDTLFTMT QSGPSPLQLP PEDAYVGNAD MIQPDLTPLQ PSLDDFMDIS  300
DFFTNSRLPQ PPMPSNFPEP PSFSPVVDSL FSSGTLGPEV PPASSAMTHL SGHSRLQARN  360
SCPGPLDSSA FLSSDFLLPE DPKPRLPPPP VPPPLLHYPP PAKVPGLEPC PPPPFPPMAP  420
PTALLQEEPL FSPRFPFPTV PPAPGVSPLP APAAFPPTPQ SVPSPAPTPF PIELLPLGYS  480
EPAFGPCFSM PRGKPPAPSP RGQKASPPTL APATASPPTT AGSNNPCLTQ LLTAAKPEQA  540
LEPPLVSSTL LRSPGSPQET VPEFPCTFLP PTPAPTPPRP PPGPATLAPS RPLLVPKAER  600
LSPPAPSGSE RRLSGDLSSM PGPGTLSVRV SPPQPILSRG RPDSNKTENR RITHISAEQK  660
RRFNIKLGFD TLHGLVSTLS AQPSLKVSKA TTLQKTAEYI LMLQQERAGL QEEAQQLRDE  720
IEELNAAINL CQQQLPATGV PITHQRFDQM RDMFDDYVRT RTLHNWKFWV FSILIRPLFE  780
SFNGMVSTAS VHTLRQTSLA WLDQYCSLPA LRPTVLNSLR QLGTSTSILT DPGRIPEQAT  840
RAVTEGTLGK PL                                                    852

SEQ ID NO: 55           moltype = AA  length = 525
FEATURE                 Location/Qualifiers
source                  1..525
                        mol_type = protein
                        organism = Homo sapiens
SEQUENCE: 55
MASNDYTQQA TQSYGAYPTQ PGQGYSQQSS QPYGQQSYSG YSQSTDTSGY GQSSYSSYGQ  60
SQNSYGTQST PQGYGSTGGY GSSQSSQSSY GQQSSYPGYG QQPAPSSTSG SYGSSSQSSS  120
```

```
YGQPQSGSYS QQPSYGGQQQ SYGQQQSYNP PQGYGQQNQY NSSSGGGGGG GGGGNYGQDQ  180
SSMSSGGGSG GGYGNQDQSG GGGSGGYGQQ DRGGRGRGGS GGGGGGGGGG YNRSSGGYEP  240
RGRGGGRGGR GGMGGSDRGG FNKFGGPRDQ GSRHDSEQDN SDNNTIFVQG LGENVTIESV  300
ADYFKQIGII KTNKKTGQPM INLYTDRETG KLKGEATVSF DDPPSAKAAI DWFDGKEFSG  360
NPIKVSFATR RADFNRGGGN GRGGRGRGGP MGRGGYGGGG SGGGGRGGFP SGGGGGGGQQ  420
RAGDWKCPNP TCENMNFSWR NECNQCKAPK PDGPGGGPGG SHMGGNYGDD RRGGRGGYDR  480
GGYRGRGGDR GGFRGGRGGG DRGGFGPGKM DSRGEHRQDR RERPY                  525

SEQ ID NO: 56           moltype = AA  length = 655
FEATURE                 Location/Qualifiers
source                  1..655
                        mol_type = protein
                        organism = Homo sapiens
SEQUENCE: 56
MASTDYSTYS QAAAQQGYSA YTAQPTQGYA QTTQAYGQQS YGTYGQPTDV SYTQAQTTAT  60
YGQTAYATSY GQPPTGYTTP TAPQAYSQPV QGYGTGAYDT TTATVTTTQA SYAAQSAYGT  120
QPAYPAYGQQ PAATAPTRPQ DGNKPTETSQ PQSSTGGYNQ PSLGYGQSNY SYPQVPGSYP  180
MQPVTAPPSY PPTSYSSTQP TSYDQSSYSQ QNTYGQPSSY GQQSSYGQQS SYGQQPPTSY  240
PPQTGSYSQA PSQYSQQSSS YGQQSSFRQD HPSSMGVYGQ ESGGFSGPGE NRSMSGPDNR  300
GRGRGGFDRG GMSRGGRGGG RGGMGAGERG GFNKPGGPMD EGPDLDLGPP VDPDEDSDNS  360
AIYVQGLNDS VTLDDLADFF KQCGVVKMNK RTGQPMIHIY LDKETGKPKG DATVSYEDPP  420
TAKAAVEWFD GKDFQGSKLK VSLARKKPPM NSMRGGLPPR EGRGMPPPLR GGPGGPGGPG  480
GPMGRMGGRG GDRGGFPPRG PRGSRGNPSG GGNVQHRAGD WQCPNPGCGN QNFAWRTECN  540
QCKAPKPEGF LPPPFPPPGG DRGRGGPGGM RGGRGGLMDR GGPGGMFRGG RGGDRGGFRG  600
GRGMDRGGFG GGRRGGPGGP PGPLMEQMGG RRGGRGGPGK MDKGEHRQER RDRPY        655

SEQ ID NO: 57           moltype = AA  length = 145
FEATURE                 Location/Qualifiers
source                  1..145
                        mol_type = protein
                        organism = Homo sapiens
SEQUENCE: 57
EGQSDERALL DQLHTLLSNT DATGLEEIDR ALGIPELVNQ GQALEPKQGG GGSGHEKFPS  60
DLDLDMFNGS LECDMESIIR SELMDADGLD FNFDSGGGGS GFVTLKDVGM DFTLGDWEQL  120
GLEQGDTFWD TALDNCQDLF LLDPP                                        145

SEQ ID NO: 58           moltype = AA  length = 551
FEATURE                 Location/Qualifiers
source                  1..551
                        mol_type = protein
                        organism = Homo sapiens
SEQUENCE: 58
MDELFPLIFP AEPAQASGPY VEIIEQPKQR GMRFRYKCEG RSAGSIPGER STDTTKTHPT  60
IKINGYTGPG TVRISLVTKD PPHRPHPHEL VGKDCRDGFY EAELCPDRCI HSFQNLGIQC  120
VKKRDLEQAI SQRIQTNNNP FQVPIEEQRG DYDLNAVRLC FQVTVRDPSG RPLRLPPVLS  180
HPIFDNRAPN TAELKICRVN RNSGSCLGGD EIFLLCDKVQ KEDIEVYFTG PGWEARGSFS  240
QADVHRQVAI VFRTPPYADP SLQAPVRVSM QLRRPSDREL SEPMEFQYLP DTDDRHRIEE  300
KRKRTYETFK SIMKKSPFSG PTDPRPPPRR IAVPSRSSAS VPKPAPQPYP FTSSLSTINY  360
DEFPTMVFPS GQISQASALA PAPPQVLPQA PAPAPAPAMV SALAQAPAPV PVLAPGPPQA  420
VAPPAPKPTQ AGEGTLSEAL LQLQFDDEDL GALLGNSTDP AVFTDLASVD NSEFQQLLNQ  480
GIPVAPHTTE PMLMEYPEAI TRLVTGAQRP PDPAPAPLGA PGLPNGLLSG DEDFSSIADM  540
DFSALLSQIS S                                                       551

SEQ ID NO: 59           moltype = AA  length = 261
FEATURE                 Location/Qualifiers
source                  1..261
                        mol_type = protein
                        organism = Homo sapiens
SEQUENCE: 59
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ VLPQAPAPAP APAMVSALAQ  120
APAPVPVLAP GPPQAVAPPA PKPTQAGEGT LSEALLQLQF DDEDLGALLG NSTDPAVFTD  180
LASVDNSEFQ QLLNQGIPVA PHTTEPMLME YPEAITRLVT GAQRPPDPAP APLGAPGLPN  240
GLLSGDEDFS SIADMDFSAL L                                            261

SEQ ID NO: 60           moltype = AA  length = 112
FEATURE                 Location/Qualifiers
source                  1..112
                        mol_type = protein
                        organism = Homo sapiens
SEQUENCE: 60
SLSEALLQLQ FDDEDLGALL GNSTDPAVFT DLASVDNSEF QQLLNQGIPV APHTTEPMLM  60
EYPEAITRLV TGAQRPPDPA PAPLGAPGLP NGLLSGDEDF SSIADMDFSA LL          112

SEQ ID NO: 61           moltype = AA  length = 162
FEATURE                 Location/Qualifiers
source                  1..162
                        mol_type = protein
                        organism = Homo sapiens
```

```
SEQUENCE: 61
SVLPQAPAPA PAPAMVSALA QAPAPVPVLA PGPPQAVAPP APKPTQAGEG TLSEALLQLQ  60
FDDEDLGALL GNSTDPAVFT DLASVDNSEF QQLLNQGIPV APHTTEPMLM EYPEAITRLV  120
TGAQRPPDPA PAPLGAPGLP NGLLSGDEDF SSIADMDFSA LL                    162

SEQ ID NO: 62          moltype = AA  length = 62
FEATURE                Location/Qualifiers
source                 1..62
                       mol_type = protein
                       organism = Homo sapiens
SEQUENCE: 62
SPHTTEPMLM EYPEAITRLV TGAQRPPDPA PAPLGAPGLP NGLLSGDEDF SSIADMDFSA  60
LL                                                                62

SEQ ID NO: 63          moltype = AA  length = 200
FEATURE                Location/Qualifiers
source                 1..200
                       mol_type = protein
                       organism = Homo sapiens
SEQUENCE: 63
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ VLPQAPAPAP APAMVSALAQ  120
APAPVPVLAP GPPQAVAPPA PKPTQAGEGT LSEALLQLQF DDEDLGALLG NSTDPAVFTD  180
LASVDNSEFQ QLLNQGIPVA                                             200

SEQ ID NO: 64          moltype = AA  length = 150
FEATURE                Location/Qualifiers
source                 1..150
                       mol_type = protein
                       organism = Homo sapiens
SEQUENCE: 64
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ VLPQAPAPAP APAMVSALAQ  120
APAPVPVLAP GPPQAVAPPA PKPTQAGEGT                                  150

SEQ ID NO: 65          moltype = AA  length = 100
FEATURE                Location/Qualifiers
source                 1..100
                       mol_type = protein
                       organism = Homo sapiens
SEQUENCE: 65
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ                       100

SEQ ID NO: 66          moltype = AA  length = 101
FEATURE                Location/Qualifiers
source                 1..101
                       mol_type = protein
                       organism = Homo sapiens
SEQUENCE: 66
SRSSASVPKP APQPYPFTSS LSTINYDEFP TMVFPSGQIS QASALAPAPP QVLPQAPAPA  60
PAPAMVSALA QAPAPVPVLA PGPPQAVAPP APKPTQAGEG T                     101

SEQ ID NO: 67          moltype = AA  length = 119
FEATURE                Location/Qualifiers
source                 1..119
                       mol_type = protein
                       organism = Homo sapiens
SEQUENCE: 67
PTQAGEGTLS EALLQLQFDD EDLGALLGNS TDPAVFTDLA SVDNSEFQQL LNQGIPVAPH  60
TTEPMLMEYP EAITRLVTGA QRPPDPAPAP LGAPGLPNGL LSGDEDFSSI ADMDFSALL   119

SEQ ID NO: 68          moltype = AA  length = 190
FEATURE                Location/Qualifiers
source                 1..190
                       mol_type = protein
                       organism = synthetic construct
SEQUENCE: 68
RDSREGMFLP KPEAGSAISD VFEGREVCQP KRIRPFHPPG SPWANRPLPA SLAPTPTGPV  60
HEPVGSLTPA PVPQPLDPAP AVTPEASHLL EDPDEETSQA VKALREMADT VIPQKEEAAI  120
CGQMDLSHPP PRGHLDELTT TLESMTEDLN LDSPLTPELN EILDTFLNDE CLLHAMHIST  180
GLSIFDTSLF                                                        190

SEQ ID NO: 69          moltype = AA  length = 116
FEATURE                Location/Qualifiers
source                 1..116
                       mol_type = protein
                       organism = synthetic construct
SEQUENCE: 69
```

```
PLDPAPAVTP EASHLLEDPD EETSQAVKAL REMADTVIPQ KEEAAICGQM DLSHPPPRGH  60
LDELTTTLES MTEDLNLDSP LTPELNEILD TFLNDECLLH AMHISTGLSI FDTSLF      116

SEQ ID NO: 70          moltype = AA  length = 66
FEATURE                Location/Qualifiers
source                 1..66
                       mol_type = protein
                       organism = synthetic construct
SEQUENCE: 70
DLSHPPPRGH LDELTTTLES MTEDLNLDSP LTPELNEILD TFLNDECLLH AMHISTGLSI  60
FDTSLF                                                             66

SEQ ID NO: 71          moltype = AA  length = 126
FEATURE                Location/Qualifiers
source                 1..126
                       mol_type = protein
                       organism = synthetic construct
SEQUENCE: 71
SSLAPTPTGP VHEPVGSLTP APVPQPLDPA PAVTPEASHL LEDPDEETSQ AVKALREMAD  60
TVIPQKEEAA ICGQMDLSHP PPRGHLDELT TTLESMTEDL NLDSPLTPEL NEILDTFLND  120
ECLLHA                                                             126

SEQ ID NO: 72          moltype = AA  length = 101
FEATURE                Location/Qualifiers
source                 1..101
                       mol_type = protein
                       organism = synthetic construct
SEQUENCE: 72
PLDPAPAVTP EASHLLEDPD EETSQAVKAL REMADTVIPQ KEEAAICGQM DLSHPPPRGH  60
LDELTTTLES MTEDLNLDSP LTPELNEILD TFLNDECLLH A                      101

SEQ ID NO: 73          moltype = AA  length = 76
FEATURE                Location/Qualifiers
source                 1..76
                       mol_type = protein
                       organism = synthetic construct
SEQUENCE: 73
SVKALREMAD TVIPQKEEAA ICGQMDLSHP PPRGHLDELT TTLESMTEDL NLDSPLTPEL  60
NEILDTFLND ECLLHA                                                  76

SEQ ID NO: 74          moltype = AA  length = 51
FEATURE                Location/Qualifiers
source                 1..51
                       mol_type = protein
                       organism = synthetic construct
SEQUENCE: 74
DLSHPPPRGH LDELTTTLES MTEDLNLDSP LTPELNEILD TFLNDECLLH A           51

SEQ ID NO: 75          moltype = AA  length = 316
FEATURE                Location/Qualifiers
source                 1..316
                       mol_type = protein
                       organism = synthetic construct
SEQUENCE: 75
GRADALDDFD LDMLGSDALD DFDLDMLGSD ALDDFDLDML GSDALDDFDL DMLINSRSSG  60
SPKKKRKVGS GGGSGGSGSV LPQAPAPAPA PAMVSALAQA PAPVPVLAPG PPQAVAPPAP  120
KPTQAGEGTL SEALLQLQFD DEDLGALLGN STDPAVFTDL ASVDNSEFQQ LLNQGIPVAP  180
HTTEPMLMEY PEAITRLVTG AQRPPDPAPA PLGAPGLPNG LLSGDEDFSS IADMDFSALL  240
SGGGSGGSGS DLSHPPPRGH LDELTTTLES MTEDLNLDSP LTPELNEILD TFLNDECLLH  300
AMHISTGLSI FDTSLF                                                  316

SEQ ID NO: 76          moltype = AA  length = 526
FEATURE                Location/Qualifiers
source                 1..526
                       mol_type = protein
                       organism = synthetic construct
SEQUENCE: 76
GRADALDDFD LDMLGSDALD DFDLDMLGSD ALDDFDLDML GSDALDDFDL DMLINSRSSG  60
SPKKKRKVGS QYLPDTDDRH RIEEKRKRTY ETFKSIMKKS PFSGPTDPRP PPRRIAVPSR  120
SSASVPKPAP QPYPFTSSLS TINYDEFPTM VFPSGQISQA SALAPAPPQV LPQAPAPAPA  180
PAMVSALAQA PAPVPVLAPG PPQAVAPPAP KPTQAGEGTL SEALLQLQFD DEDLGALLGN  240
STDPAVFTDL ASVDNSEFQQ LLNQGIPVAP HTTEPMLMEY PEAITRLVTG AQRPPDPAPA  300
PLGAPGLPNG LLSGDEDFSS IADMDFSALL GSGSGSRDSR EGMFLPKPEA GSAISDVFEG  360
REVCQPKRIR PFHPPGSPWA NRPLPASLAP TPTGPVHEPV GSLTPAPVPQ PLDPAPAVTP  420
EASHLLEDPD EETSQAVKAL REMADTVIPQ KEEAAICGQM DLSHPPPRGH LDELTTTLES  480
MTEDLNLDSP LTPELNEILD TFLNDECLLH AMHISTGLSI FDTSLF                 526

SEQ ID NO: 77          moltype = AA  length = 11
FEATURE                Location/Qualifiers
```

-continued source 1..11
mol_type = protein
organism = synthetic construct
SEQUENCE: 77
DALDDFDLDM L 11

SEQ ID NO: 78 moltype = AA length = 53
FEATURE Location/Qualifiers
source 1..53
mol_type = protein
organism = synthetic construct
SEQUENCE: 78
GRADALDDFD LDMLGSDALD DFDLDMLGSD ALDDFDLDML GSDALDDFDL DML 53

SEQ ID NO: 79 moltype = AA length = 2414
FEATURE Location/Qualifiers
source 1..2414
mol_type = protein
organism = Homo sapiens
SEQUENCE: 79
MAENVVEPGP PSAKRPKLSS PALSASASDG TDFGSLFDLE HDLPDELINS TELGLTNGGD 60
INQLQTSLGM VQDAASKHKQ LSELLRSGSS PNLNMGVGGP GQVMASQAQQ SSPGLGLINS 120
MVKSPMTQAG LTSPNMGMGT SGPNQGPTQS TGMMNSPVNQ PAMGMNTGMN AGMNPGMLAA 180
GNGQGIMPNQ VMNGSIGAGR GRQNMQYPNP GMGSAGNLLT EPLQQGSPQM GGQTGLRGPQ 240
PLKMGMMNNP NPYGSPYTQN PGQQIGASGL GLQIQTKTVL SNNLSPFAMD KKAVPGGGMP 300
NMGQQPAPQV QQPGLVTPVA QGMGSGAHTA DPEKRKLIQQ QLVLLLHAHK CQRREQANGE 360
VRQCNLPHCR TMKNVLNHMT HCQSGKSCQV AHCASSRQII SHWKNCTRHD CPVCLPLKNA 420
GDKRNQQPIL TGAPVGLGNP SSLGVGQQSA PNLSTVSQID PSSIERAYAA LGLPYQVNQM 480
PTQPQVQAKN QQNQQPGQSP QGMRPMSNMS ASPMGVNGGV GVQTPSLLSD SMLHSAINSQ 540
NPMMSENASV PSLGPMPTAA QPSTTGIRKQ WHEDITQDLR NHLVHKLVQA IFPTPDPAAL 600
KDRRMENLVA YARKVEGDMY ESANNRAEYY HLLAEKIYKI QKELEEKRRT RLQKQNMLPN 660
AAGMVPVSMN PGPNMGQPQP GMTSNGPLPD PSMIRGSVPN QMMPRITPQS GLNQFGQMSM 720
AQPPIVPRQT PPLQHHGQLA QPGALNPPMG YGPRMQQPSN QGQFLPQTQF PSQGMNVTNI 780
PLAPSSGQAP VSQAQMSSSS CPVNSPIMPP GSQGSHIHCP QLPQPALHQN SPSPVPSRTP 840
TPHHTPPSIG AQQPPATTIP APVPTPPAMP PGPQSQALHP PPRQTPTPPT TQLPQQVQPS 900
LPAAPSADQP QQQPRSQQST AASVPTPTAP LLPPQPATPL SQPAVSIEGQ VSNPPSTSST 960
EVNSQAIAEK QPSQEVKMEA KMEVDQPEPA DTQPEDISES KVEDCKMEST ETEERSTELK 1020
TEIKEEEDQP STSATQSSPA PGQSKKKIFK PEELRQALMP TLEALYRQDP ESLPFRQPVD 1080
PQLLGIPDYF DIVKSPMDLS TIKRKLDTGQ YQEPWQYVDD IWLMFNNAWL YNRKTSRVYK 1140
YCSKLSEVFE QEIDPVMQSL GYCCGRKLEF SPQTLCCYGK QLCTIPRDAT YYSYQNRYHF 1200
CEKCFNEIQG ESVSLGDDPS QPQTTINKEQ FSKRKNDTLD PELFVECTEC GRKMHQICVL 1260
HHEIIWPAGF VCDGCLKKSA RTRKENKFSA KRLPSTRLGT FLENRVNDFL RRQNHPESGE 1320
VTVRVVHASD KTVEVKPGMK ARFVDSGEMA ESFPYRTKAL FAFEEIDGVD LCFFGMHVQE 1380
YGSDCPPPNQ RRVYISYLDS VHFFRPKCLR TAVYHEILIG YLEYVKKLGY TTGHIWACPP 1440
SEGDDYIFHC HPPDQKIPKP KRLQEWYKKM LDKAVSERIV HDYKDIFKQA TEDRLTSAKE 1500
LPYFEGDFWP NVLEESIKEL EQEEEERKRE ENTSNESTDV TKGDSKNAKK KNNKKTSKNK 1560
SSLSRGNKKK PGMPNVSNDL SQKLYATMEK HKEVFFVIRL IAGPAANSLP PIVDPDPLIP 1620
CDLMDGRDAF LTLARDKHLE FSSLRRAQWS TMCMLVELHT QSQDRFVYTC NECKHHVETR 1680
WHCTVCEDYD LCITCYNTKN HDHKMEKLGL GLDDESNNQQ AAATQSPGDS RRLSIQRCIQ 1740
SLVHACQCRN ANCSLPSCQK MKRVVQHTKG CKRKTNGGCP ICKQLIALCC YHAKHCQENK 1800
CPVPFCLNIK QKLRQQQLQH RLQQAQMLRR RMASMQRTGV VGQQQGLPSP TPATPTTPTG 1860
QQPTTPQTPQ PTSQPQPTPP NSMPPYLPRT QAAGPVSQGK AAGQVTPPTP PQTAQPPLPG 1920
PPPAAVEMAM QIQRAAETQR QMAHVQIFQR PIQHQMPPMT PMAPMGMNPP PMTRGPSGHL 1980
EPGMGPTGMQ QQPPWSQGGL PQPQQLQSGM PRPAMMSVAQ HGQPLNMAPQ PGLGQVGISP 2040
LKPGTVSQQA LQNLLRTLRS PSSPLQQQQV LSILHANPQL LAAFIKQRAA KYANSNPQPI 2100
PGQPGMPQGQ PGLQPPTMPG QQGVHSNPAM QNMNPMQAGV QRAGLPQQQP QQQLQPPMGG 2160
MSPQAQQMNM NHNTMPSQFR DILRRQQMMQ QQQQQGAGPG IGPGMANHNQ FQQPQGVGYP 2220
PQQQQRMQHH MQQMQQGNMG QIGQLPQALG AEAGASLQAY QQRLLQQQMG SPVQPNPMSP 2280
QQHMLPNQAQ SPHLQGQQIP NSLSNQVRSP QPVPSPRPQS QPPHSSPSPR MQPQPSPHHV 2340
SPQTSSPHPG LVAAQANPME QGHFASPDQN SMLSQLASNP GMANLHGASA TDLGLSTDNS 2400
DLNSNLSQST LDIH 2414

SEQ ID NO: 80 moltype = AA length = 617
FEATURE Location/Qualifiers
source 1..617
mol_type = protein
organism = Homo sapiens
SEQUENCE: 80
IFKPEELRQA LMPTLEALYR QDPESLPFRQ PVDPQLLGIP DYFDIVKSPM DLSTIKRKLD 60
TGQYQEPWQY VDDIWLMFNN AWLYNRKTSR VYKYCSKLSE VFEQEIDPVM QSLGYCCGRK 120
LEFSPQTLCC YGKQLCTIPR DATYYSYQNR YHFCEKCFNE IQGESVSLGD DPSQPQTTIN 180
KEQFSKRKND TLDPELFVEC TECGRKMHQI CVLHHEIIWP AGFVCDGCLK KSARTRKENK 240
FSAKRLPSTR LGTFLENRVN DFLRRQNHPE SGEVTVRVVH ASDKTVEVKP GMKARFVDSG 300
EMAESFPYRT KALFAFEEID GVDLCFFGMH VQEYGSDCPP PNQRRVYISY LDSVHFFRPK 360
CLRTAVYHEI LIGYLEYVKK LGYTTGHIWA CPPSEGDDYI FHCHPPDQKI PKPKRLQEWY 420
KKMLDKAVSE RIVHDYKDIF KQATEDRLTS AKELPYFEGD FWPNVLEESI KELEQEEEER 480
KREENTSNES TDVTKGDSKN AKKKNNKKTS KNKSSLSRGN KKKPGMPNVS NDLSQKLYAT 540
MEKHKEVFFV IRLIAGPAAN SLPPIVDPDP LIPCDLMDGR DAFLTLARDK HLEFSSLRRA 600
QWSTMCMLVE LHTQSQD 617

```
SEQ ID NO: 81          moltype = AA  length = 308
FEATURE                Location/Qualifiers
source                 1..308
                       mol_type = protein
                       organism = Homo sapiens
SEQUENCE: 81
VNKFLRRQNH PEAGEVFVRV VASSDKTVEV KPGMKSRFVD SGEMSESFPY RTKALFAFEE  60
IDGVDVCFFG MHVQEYGSDC PPPNTRRVYI SYLDSIHFFR PRCLRTAVYH EILIGYLEYV  120
KKLGYVTGHI WACPPSEGDD YIFHCHPPDQ KIPKPKRLQE WYKKMLDKAF AERIIHDYKD  180
IFKQATEDRL TSAKELPYFE GDFWPNVLEE SIKELEQEEE ERKKEESTAA SETTEGSQGD  240
SKNAKKKNNK KTNKNKSSIS RANKKKPSMP NVSNDLSQKL YATMEKHKEV FFVIHLHAGP  300
VINTLPPI                                                          308

SEQ ID NO: 82          moltype = AA  length = 314
FEATURE                Location/Qualifiers
source                 1..314
                       mol_type = protein
                       organism = Drosophila melanogaster
SEQUENCE: 82
VNNFLKKKEA GAGEVHIRVV SSSDKCVEVK PGMRRRFVEQ GEMMNEFPYR AKALFAFEEV  60
DGIDVCFFGM HVQEYGSECP APNTRRVYIA YLDSVHFFRP RQYRTAVYHE ILLGYMDYVK  120
QLGYTMAHIW ACPPSEGDDY IFHCHPTDQK IPKPKRLQEW YKKMLDKGMI ERIIQDYKDI  180
LKQAMEDKLG SAAELPYFEG DFWPNVLEES IKELDQEEEE KRKQAEAAEA AAAANLFSIE  240
ENEVSGDGKK KGQKKAKKSN KSKAAQRKNS KKSNEHQSGN DLSTKIYATM EKHKEVFFVI  300
RLHSAQSAAS LAPI                                                   314

SEQ ID NO: 83          moltype = AA  length = 634
FEATURE                Location/Qualifiers
source                 1..634
                       mol_type = protein
                       organism = Drosophila melanogaster
SEQUENCE: 83
NGKYSDPWEY VDDVWLMFDN AWLYNRKTSR VYRYCTKLSE VFEAEIDPVM QALGYCCGRK  60
YTFNPQVLCC YGKQLCTIPR DAKYYSYQNR YTYCQKCFND IQGDTVTLGD DPLQSQTQIK  120
KDQFKEMKND HLELEPFVNC QECGRKQHQI CVLWLDSIWP GGFVCDNCLK KKNSKRKENK  180
FNAKRLPTTK LGVYIETRVN NFLKKKEAGA GEVHIRVVSS SDKCVEVKPG MRRRFVEQGE  240
MMNEFPYRAK ALFAFEEVDG IDVCFFGMHV QEYGSECPAP NTRRVYIAYL DSVHFFRPRQ  300
YRTAVYHEIL LGYMDYVKQL GYTMAHIWAC PPSEGDDYIF HCHPTDQKIP KPKRLQEWYK  360
KMLDKGMIER IIQDYKDILK QAMEDKLGSA AELPYFEGDF WPNVLEESIK ELDQEEEEKR  420
KQAEAAEAAA AANLFSIEEN EVSGDGKKKG QKKAKKSNKS KAAQRKNSKK SNEHQSGNDL  480
STKIYATMEK HKEVFFVIRL HSAQSAASLA PIQDPDPLLT CDLMDGRDAF LTLARDKHFE  540
FSSLRRAQFS TLSMLYELHN QGQDKFVYTC NHCKTAVETR YHCTVCDDFD LCIVCKEKVG  600
HQHKMEKLGF DIDDGSALAD HKQANPQEAR KQSI                             634

SEQ ID NO: 84          moltype = AA  length = 32
FEATURE                Location/Qualifiers
source                 1..32
                       mol_type = protein
                       organism = synthetic construct
VARIANT                1
                       note = Any amino acid
VARIANT                2
                       note = Any amino acid
VARIANT                3
                       note = Any amino acid
VARIANT                1..3
                       note = This region may encompass 0-3 residues
VARIANT                5
                       note = Any amino acid
VARIANT                6
                       note = Any amino acid
VARIANT                7
                       note = Any amino acid
VARIANT                8
                       note = Any amino acid
VARIANT                9
                       note = Any amino acid
VARIANT                5..9
                       note = This region may encompass 1-5 residues
VARIANT                11
                       note = Any amino acid
VARIANT                12
                       note = Any amino acid
VARIANT                13
                       note = Any amino acid
VARIANT                14
                       note = Any amino acid
VARIANT                15
```

```
                        note = Any amino acid
VARIANT                 16
                        note = Any amino acid
VARIANT                 17
                        note = Any amino acid
VARIANT                 11..17
                        note = This region may encompass 2-7 residues
VARIANT                 18
                        note = Any amino acid
VARIANT                 19
                        note = Any amino acid
VARIANT                 20
                        note = Any amino acid
VARIANT                 21
                        note = Any amino acid
VARIANT                 22
                        note = Any amino acid
VARIANT                 23
                        note = Any amino acid
VARIANT                 24
                        note = Any amino acid
VARIANT                 18..24
                        note = This region may encompass 6-7 residues
VARIANT                 26
                        note = Any amino acid
VARIANT                 27
                        note = Any amino acid
VARIANT                 28
                        note = Any amino acid
VARIANT                 29
                        note = Any amino acid
VARIANT                 30
                        note = Any amino acid
VARIANT                 31
                        note = Any amino acid
VARIANT                 26..31
                        note = This region may encompass 3-6 residues
SEQUENCE: 84
XXXCXXXXXC XXXXXXXXXX XXXXHXXXXX XH                                32

SEQ ID NO: 85           moltype = AA  length = 24
FEATURE                 Location/Qualifiers
source                  1..24
                        mol_type = protein
                        organism = synthetic construct
VARIANT                 1
                        note = Any amino acid
VARIANT                 2
                        note = Any amino acid
VARIANT                 3
                        note = Any amino acid
VARIANT                 5
                        note = Any amino acid
VARIANT                 6
                        note = Any amino acid
VARIANT                 8
                        note = Any amino acid
VARIANT                 9
                        note = Any amino acid
VARIANT                 10
                        note = Any amino acid
VARIANT                 11
                        note = Any amino acid
VARIANT                 12
                        note = Any amino acid
VARIANT                 13
                        note = Any amino acid
VARIANT                 14
                        note = Any amino acid
VARIANT                 15
                        note = Any amino acid
VARIANT                 16
                        note = Any amino acid
VARIANT                 17
                        note = Any amino acid
VARIANT                 18
                        note = Any amino acid
VARIANT                 19
                        note = Any amino acid
```

```
VARIANT              21
                     note = Any amino acid
VARIANT              22
                     note = Any amino acid
VARIANT              23
                     note = Any amino acid
VARIANT              13..19
                     note = This region may encompass 6-7 residues
SEQUENCE: 85
XXXCXXCXXX XXXXXXXXXH XXXH                                        24

SEQ ID NO: 86        moltype = AA  length = 176
FEATURE              Location/Qualifiers
source               1..176
                     mol_type = protein
                     organism = synthetic construct
SEQUENCE: 86
SRPGERPFQC RICMRNFSEE ANLRRHTRTH TGEKPFQCRI CMRNFSDHSS LKRHLRTHTG  60
SQKPFQCRIC MRNFSQSANL LRHTRTHTGE KPFQCRICMR NFSDPSSLKR HLRTHTGSQK  120
PFQCRICMRN FSQQTNLTRH TRTHTGEKPF QCRICMRNFS DATQLVRHLR THLRGS      176

SEQ ID NO: 87        moltype = AA  length = 172
FEATURE              Location/Qualifiers
source               1..172
                     mol_type = protein
                     organism = synthetic construct
VARIANT              17
                     note = Any amino acid
VARIANT              18
                     note = Any amino acid
VARIANT              19
                     note = Any amino acid
VARIANT              20
                     note = Any amino acid
VARIANT              21
                     note = Any amino acid
VARIANT              22
                     note = Any amino acid
VARIANT              23
                     note = Any amino acid
VARIANT              17..23
                     note = This region may encompass 6-7 residues
VARIANT              45
                     note = Any amino acid
VARIANT              46
                     note = Any amino acid
VARIANT              47
                     note = Any amino acid
VARIANT              48
                     note = Any amino acid
VARIANT              49
                     note = Any amino acid
VARIANT              50
                     note = Any amino acid
VARIANT              51
                     note = Any amino acid
VARIANT              45..51
                     note = This region may encompass 6-7 residues
VARIANT              74
                     note = Any amino acid
VARIANT              75
                     note = Any amino acid
VARIANT              76
                     note = Any amino acid
VARIANT              77
                     note = Any amino acid
VARIANT              78
                     note = Any amino acid
VARIANT              79
                     note = Any amino acid
VARIANT              80
                     note = Any amino acid
VARIANT              74..80
                     note = This region may encompass 6-7 residues
VARIANT              102
                     note = Any amino acid
VARIANT              103
                     note = Any amino acid
VARIANT              104
```

-continued

```
                        note = Any amino acid
VARIANT                 105
                        note = Any amino acid
VARIANT                 106
                        note = Any amino acid
VARIANT                 107
                        note = Any amino acid
VARIANT                 108
                        note = Any amino acid
VARIANT                 102..108
                        note = This region may encompass 6-7 residues
VARIANT                 131
                        note = Any amino acid
VARIANT                 132
                        note = Any amino acid
VARIANT                 133
                        note = Any amino acid
VARIANT                 134
                        note = Any amino acid
VARIANT                 135
                        note = Any amino acid
VARIANT                 136
                        note = Any amino acid
VARIANT                 137
                        note = Any amino acid
VARIANT                 131..137
                        note = This region may encompass 6-7 residues
VARIANT                 159
                        note = Any amino acid
VARIANT                 160
                        note = Any amino acid
VARIANT                 161
                        note = Any amino acid
VARIANT                 162
                        note = Any amino acid
VARIANT                 163
                        note = Any amino acid
VARIANT                 164
                        note = Any amino acid
VARIANT                 165
                        note = Any amino acid
VARIANT                 159..165
                        note = This region may encompass 6-7 residues
SEQUENCE: 87
PGERPFQCRI CMRNFSXXXX XXXHTRTHTG EKPFQCRICM RNFSXXXXXX XHLRTHTGSQ  60
KPFQCRICMR NFSXXXXXXX HTRTHTGEKP FQCRICMRNF SXXXXXXXHL RTHTGSQKPF  120
QCRICMRNFS XXXXXXXHTR THTGEKPFQC RICMRNFSXX XXXXXHLRTH LR          172

SEQ ID NO: 88           moltype = AA  length = 176
FEATURE                 Location/Qualifiers
source                  1..176
                        mol_type = protein
                        organism = synthetic construct
VARIANT                 19
                        note = Any amino acid
VARIANT                 20
                        note = Any amino acid
VARIANT                 21
                        note = Any amino acid
VARIANT                 22
                        note = Any amino acid
VARIANT                 23
                        note = Any amino acid
VARIANT                 24
                        note = Any amino acid
VARIANT                 25
                        note = Any amino acid
VARIANT                 47
                        note = Any amino acid
VARIANT                 48
                        note = Any amino acid
VARIANT                 49
                        note = Any amino acid
VARIANT                 50
                        note = Any amino acid
VARIANT                 51
                        note = Any amino acid
VARIANT                 52
                        note = Any amino acid
```

```
VARIANT                 53
                        note = Any amino acid
VARIANT                 76
                        note = Any amino acid
VARIANT                 77
                        note = Any amino acid
VARIANT                 78
                        note = Any amino acid
VARIANT                 79
                        note = Any amino acid
VARIANT                 80
                        note = Any amino acid
VARIANT                 81
                        note = Any amino acid
VARIANT                 82
                        note = Any amino acid
VARIANT                 104
                        note = Any amino acid
VARIANT                 105
                        note = Any amino acid
VARIANT                 106
                        note = Any amino acid
VARIANT                 107
                        note = Any amino acid
VARIANT                 108
                        note = Any amino acid
VARIANT                 109
                        note = Any amino acid
VARIANT                 110
                        note = Any amino acid
VARIANT                 133
                        note = Any amino acid
VARIANT                 134
                        note = Any amino acid
VARIANT                 135
                        note = Any amino acid
VARIANT                 136
                        note = Any amino acid
VARIANT                 137
                        note = Any amino acid
VARIANT                 138
                        note = Any amino acid
VARIANT                 139
                        note = Any amino acid
VARIANT                 161
                        note = Any amino acid
VARIANT                 162
                        note = Any amino acid
VARIANT                 163
                        note = Any amino acid
VARIANT                 164
                        note = Any amino acid
VARIANT                 165
                        note = Any amino acid
VARIANT                 166
                        note = Any amino acid
VARIANT                 167
                        note = Any amino acid
SEQUENCE: 88
SRPGERPFQC RICMRNFSXX XXXXXHTRTH TGEKPFQCRI CMRNFSXXXX XXXHLRTHTG  60
SQKPFQCRIC MRNFSXXXXX XXHTRTHTGE KPFQCRICMR NFSXXXXXXX HLRTHTGSQK  120
PFQCRICMRN FSXXXXXXXH TRTHTGEKPF QCRICMRNFS XXXXXXXHLR THLRGS      176

SEQ ID NO: 89           moltype = AA  length = 172
FEATURE                 Location/Qualifiers
source                  1..172
                        mol_type = protein
                        organism = synthetic construct
VARIANT                 17
                        note = Any amino acid
VARIANT                 18
                        note = Any amino acid
VARIANT                 19
                        note = Any amino acid
VARIANT                 20
                        note = Any amino acid
VARIANT                 21
                        note = Any amino acid
VARIANT                 22
```

-continued

```
                      note = Any amino acid
VARIANT               23
                      note = Any amino acid
VARIANT               45
                      note = Any amino acid
VARIANT               46
                      note = Any amino acid
VARIANT               47
                      note = Any amino acid
VARIANT               48
                      note = Any amino acid
VARIANT               49
                      note = Any amino acid
VARIANT               50
                      note = Any amino acid
VARIANT               51
                      note = Any amino acid
VARIANT               74
                      note = Any amino acid
VARIANT               75
                      note = Any amino acid
VARIANT               76
                      note = Any amino acid
VARIANT               77
                      note = Any amino acid
VARIANT               78
                      note = Any amino acid
VARIANT               79
                      note = Any amino acid
VARIANT               80
                      note = Any amino acid
VARIANT               102
                      note = Any amino acid
VARIANT               103
                      note = Any amino acid
VARIANT               104
                      note = Any amino acid
VARIANT               105
                      note = Any amino acid
VARIANT               106
                      note = Any amino acid
VARIANT               107
                      note = Any amino acid
VARIANT               108
                      note = Any amino acid
VARIANT               131
                      note = Any amino acid
VARIANT               132
                      note = Any amino acid
VARIANT               133
                      note = Any amino acid
VARIANT               134
                      note = Any amino acid
VARIANT               135
                      note = Any amino acid
VARIANT               136
                      note = Any amino acid
VARIANT               137
                      note = Any amino acid
VARIANT               159
                      note = Any amino acid
VARIANT               160
                      note = Any amino acid
VARIANT               161
                      note = Any amino acid
VARIANT               162
                      note = Any amino acid
VARIANT               163
                      note = Any amino acid
VARIANT               164
                      note = Any amino acid
VARIANT               165
                      note = Any amino acid
SEQUENCE: 89
PGERPFQCRI CMRNFSXXXX XXXHTRTHTG EKPFQCRICM RNFSXXXXXX XHLRTHTGSQ  60
KPFQCRICMR NFSXXXXXXX HLRTHTGEKP FQCRICMRNF SXXXXXXXHL KTHTGSQKPF  120
QCRICMRNFS XXXXXXXHLR THTGEKPFQC RICMRNFSXX XXXXXHLRTH LR          172

SEQ ID NO: 90         moltype = AA  length = 176
```

-continued

| FEATURE | Location/Qualifiers |
|---|---|
| source | 1..176<br>mol_type = protein<br>organism = synthetic construct |
| VARIANT | 19<br>note = Any amino acid |
| VARIANT | 20<br>note = Any amino acid |
| VARIANT | 21<br>note = Any amino acid |
| VARIANT | 22<br>note = Any amino acid |
| VARIANT | 23<br>note = Any amino acid |
| VARIANT | 24<br>note = Any amino acid |
| VARIANT | 25<br>note = Any amino acid |
| VARIANT | 47<br>note = Any amino acid |
| VARIANT | 48<br>note = Any amino acid |
| VARIANT | 49<br>note = Any amino acid |
| VARIANT | 50<br>note = Any amino acid |
| VARIANT | 51<br>note = Any amino acid |
| VARIANT | 52<br>note = Any amino acid |
| VARIANT | 53<br>note = Any amino acid |
| VARIANT | 76<br>note = Any amino acid |
| VARIANT | 77<br>note = Any amino acid |
| VARIANT | 78<br>note = Any amino acid |
| VARIANT | 79<br>note = Any amino acid |
| VARIANT | 80<br>note = Any amino acid |
| VARIANT | 81<br>note = Any amino acid |
| VARIANT | 82<br>note = Any amino acid |
| VARIANT | 104<br>note = Any amino acid |
| VARIANT | 105<br>note = Any amino acid |
| VARIANT | 106<br>note = Any amino acid |
| VARIANT | 107<br>note = Any amino acid |
| VARIANT | 108<br>note = Any amino acid |
| VARIANT | 109<br>note = Any amino acid |
| VARIANT | 110<br>note = Any amino acid |
| VARIANT | 133<br>note = Any amino acid |
| VARIANT | 134<br>note = Any amino acid |
| VARIANT | 135<br>note = Any amino acid |
| VARIANT | 136<br>note = Any amino acid |
| VARIANT | 137<br>note = Any amino acid |
| VARIANT | 138<br>note = Any amino acid |
| VARIANT | 139<br>note = Any amino acid |
| VARIANT | 161<br>note = Any amino acid |
| VARIANT | 162<br>note = Any amino acid |
| VARIANT | 163 |

```
                        note = Any amino acid
VARIANT                 164
                        note = Any amino acid
VARIANT                 165
                        note = Any amino acid
VARIANT                 166
                        note = Any amino acid
VARIANT                 167
                        note = Any amino acid
SEQUENCE: 90
SRPGERPFQC RICMRNFSXX XXXXXHTRTH TGEKPFQCRI CMRNFSXXXX XXXHLRTHTG  60
SQKPFQCRIC MRNFSXXXXX XXHLRTHTGE KPFQCRICMR NFSXXXXXXX HLKTHTGSQK  120
PFQCRICMRN FSXXXXXXXH LRTHTGEKPF QCRICMRNFS XXXXXXXHLR THLRGS      176

SEQ ID NO: 91           moltype = DNA  length = 20
FEATURE                 Location/Qualifiers
source                  1..20
                        mol_type = other DNA
                        organism = synthetic construct
SEQUENCE: 91
cgtcgaagtc gaagtcgacc                                              20

SEQ ID NO: 92           moltype = DNA  length = 20
FEATURE                 Location/Qualifiers
source                  1..20
                        mol_type = other DNA
                        organism = synthetic construct
SEQUENCE: 92
ggacgacgtt acggacgtac                                              20

SEQ ID NO: 93           moltype = DNA  length = 20
FEATURE                 Location/Qualifiers
source                  1..20
                        mol_type = other DNA
                        organism = synthetic construct
SEQUENCE: 93
agacgtcgaa gtagccgtag                                              20

SEQ ID NO: 94           moltype = DNA  length = 20
FEATURE                 Location/Qualifiers
source                  1..20
                        mol_type = other DNA
                        organism = synthetic construct
SEQUENCE: 94
ggacgacgcc gatgtagaag                                              20

SEQ ID NO: 95           moltype = DNA  length = 20
FEATURE                 Location/Qualifiers
source                  1..20
                        mol_type = other DNA
                        organism = synthetic construct
SEQUENCE: 95
tgaagcagtc gacgccgaag                                              20

SEQ ID NO: 96           moltype = DNA  length = 20
FEATURE                 Location/Qualifiers
source                  1..20
                        mol_type = other DNA
                        organism = synthetic construct
SEQUENCE: 96
ggacgacgcg gtctaagaag                                              20

SEQ ID NO: 97           moltype = DNA  length = 20
FEATURE                 Location/Qualifiers
source                  1..20
                        mol_type = other DNA
                        organism = synthetic construct
SEQUENCE: 97
cgacgaggtc gcataagtag                                              20

SEQ ID NO: 98           moltype = DNA  length = 20
FEATURE                 Location/Qualifiers
source                  1..20
                        mol_type = other DNA
                        organism = synthetic construct
SEQUENCE: 98
agacgcagta taggtcgaac                                              20

SEQ ID NO: 99           moltype = DNA  length = 20
```

-continued

```
FEATURE                Location/Qualifiers
source                 1..20
                       mol_type = other DNA
                       organism = synthetic construct
SEQUENCE: 99
agacgcagta taggacgacg                                        20

SEQ ID NO: 100         moltype = DNA  length = 20
FEATURE                Location/Qualifiers
source                 1..20
                       mol_type = other DNA
                       organism = synthetic construct
SEQUENCE: 100
cggcgtagcc gatgtcgcgc                                        20

SEQ ID NO: 101         moltype = DNA  length = 20
FEATURE                Location/Qualifiers
source                 1..20
                       mol_type = other DNA
                       organism = synthetic construct
SEQUENCE: 101
ggtcgttgcg gtagtcgaag                                        20

SEQ ID NO: 102         moltype = AA  length = 85
FEATURE                Location/Qualifiers
source                 1..85
                       mol_type = protein
                       organism = synthetic construct
VARIANT                16
                       note = Any amino acid
VARIANT                17
                       note = Any amino acid
VARIANT                18
                       note = Any amino acid
VARIANT                19
                       note = Any amino acid
VARIANT                20
                       note = Any amino acid
VARIANT                21
                       note = Any amino acid
VARIANT                22
                       note = Any amino acid
VARIANT                44
                       note = Any amino acid
VARIANT                45
                       note = Any amino acid
VARIANT                46
                       note = Any amino acid
VARIANT                47
                       note = Any amino acid
VARIANT                48
                       note = Any amino acid
VARIANT                49
                       note = Any amino acid
VARIANT                50
                       note = Any amino acid
VARIANT                72
                       note = Any amino acid
VARIANT                73
                       note = Any amino acid
VARIANT                74
                       note = Any amino acid
VARIANT                75
                       note = Any amino acid
VARIANT                76
                       note = Any amino acid
VARIANT                77
                       note = Any amino acid
VARIANT                78
                       note = Any amino acid
SEQUENCE: 102
GERPFQCRIC MANFSXXXXX XXHTRTHTGE KPFQCRICMA NFSXXXXXXX HLRTHTGEKP  60
FQCRICMANF SXXXXXXXHL KTHLR                                        85

SEQ ID NO: 103         moltype = AA  length = 85
FEATURE                Location/Qualifiers
source                 1..85
                       mol_type = protein
                       organism = synthetic construct
```

```
VARIANT                16
                       note = Any amino acid
VARIANT                17
                       note = Any amino acid
VARIANT                18
                       note = Any amino acid
VARIANT                19
                       note = Any amino acid
VARIANT                20
                       note = Any amino acid
VARIANT                21
                       note = Any amino acid
VARIANT                22
                       note = Any amino acid
VARIANT                44
                       note = Any amino acid
VARIANT                45
                       note = Any amino acid
VARIANT                46
                       note = Any amino acid
VARIANT                47
                       note = Any amino acid
VARIANT                48
                       note = Any amino acid
VARIANT                49
                       note = Any amino acid
VARIANT                50
                       note = Any amino acid
VARIANT                72
                       note = Any amino acid
VARIANT                73
                       note = Any amino acid
VARIANT                74
                       note = Any amino acid
VARIANT                75
                       note = Any amino acid
VARIANT                76
                       note = Any amino acid
VARIANT                77
                       note = Any amino acid
VARIANT                78
                       note = Any amino acid
SEQUENCE: 103
GEAPFQCRIC MANFSXXXXX XXHTRTHTGE KPFQCRICMA NFSXXXXXXX HLRTHTGEKP  60
FQCRICMANF SXXXXXXXHL KTHLR                                        85

SEQ ID NO: 104         moltype = AA  length = 85
FEATURE                Location/Qualifiers
source                 1..85
                       mol_type = protein
                       organism = synthetic construct
SEQUENCE: 104
GERPFQCRIC MANFSGRQAL DRHTRTHTGE KPFQCRICMA NFSDKANLTR HLRTHTGEKP  60
FQCRICMANF SQRNNLGRHL KTHLR                                        85

SEQ ID NO: 105         moltype = AA  length = 85
FEATURE                Location/Qualifiers
source                 1..85
                       mol_type = protein
                       organism = synthetic construct
SEQUENCE: 105
GEAPFQCRIC MANFSRQDRL DRHTRTHTGE KPFQCRICMA NFSQKEHLAG HLRTHTGEKP  60
FQCRICMANF SRRDNLNRHL KTHLR                                        85

SEQ ID NO: 106         moltype = AA  length = 85
FEATURE                Location/Qualifiers
source                 1..85
                       mol_type = protein
                       organism = synthetic construct
SEQUENCE: 106
GERPFQCRIC MANFSRQDRL DRHTRTHTGE KPFQCRICMA NFSQKEHLAG HLRTHTGEKP  60
FQCRICMANF SRRDNLNRHL KTHLR                                        85

SEQ ID NO: 107         moltype = AA  length = 85
FEATURE                Location/Qualifiers
source                 1..85
                       mol_type = protein
                       organism = synthetic construct
SEQUENCE: 107
```

```
GEAPFQCRIC MANFSTGQIL DRHTRTHTGE KPFQCRICMA NFSVAHSLKR HLRTHTGEKP  60
FQCRICMANF SDPSNLRRHL KTHLR                                       85

SEQ ID NO: 108         moltype = AA  length = 85
FEATURE                Location/Qualifiers
source                 1..85
                       mol_type = protein
                       organism = synthetic construct
SEQUENCE: 108
GERPFQCRIC MANFSTGQIL DRHTRTHTGE KPFQCRICMA NFSVAHSLKR HLRTHTGEKP  60
FQCRICMANF SDPSNLRRHL KTHLR                                       85

SEQ ID NO: 109         moltype = AA  length = 85
FEATURE                Location/Qualifiers
source                 1..85
                       mol_type = protein
                       organism = synthetic construct
SEQUENCE: 109
GERPFQCRIC MRNFSRQSNL SRHTRTHTGE KPFQCRICMR NFSRNEHLVL HLRTHTGEKP  60
FQCRICMRNF SQKTGLRVHL KTHLR                                       85

SEQ ID NO: 110         moltype = DNA  length = 11
FEATURE                Location/Qualifiers
source                 1..11
                       mol_type = other DNA
                       organism = synthetic construct
SEQUENCE: 110
cgaagacgct g                                                      11

SEQ ID NO: 111         moltype = DNA  length = 11
FEATURE                Location/Qualifiers
source                 1..11
                       mol_type = other DNA
                       organism = synthetic construct
SEQUENCE: 111
agagtgagga c                                                      11

SEQ ID NO: 112         moltype = DNA  length = 11
FEATURE                Location/Qualifiers
source                 1..11
                       mol_type = other DNA
                       organism = synthetic construct
SEQUENCE: 112
acagtgagga c                                                      11

SEQ ID NO: 113         moltype = DNA  length = 11
FEATURE                Location/Qualifiers
source                 1..11
                       mol_type = other DNA
                       organism = synthetic construct
SEQUENCE: 113
atagtgagga c                                                      11

SEQ ID NO: 114         moltype = DNA  length = 11
FEATURE                Location/Qualifiers
source                 1..11
                       mol_type = other DNA
                       organism = synthetic construct
SEQUENCE: 114
agacgctgct c                                                      11

SEQ ID NO: 115         moltype = DNA  length = 11
FEATURE                Location/Qualifiers
source                 1..11
                       mol_type = other DNA
                       organism = synthetic construct
SEQUENCE: 115
tgacgctgct t                                                      11

SEQ ID NO: 116         moltype = DNA  length = 11
FEATURE                Location/Qualifiers
source                 1..11
                       mol_type = other DNA
                       organism = synthetic construct
SEQUENCE: 116
agacggtgct c                                                      11

SEQ ID NO: 117         moltype = DNA  length = 11
FEATURE                Location/Qualifiers
```

```
source                  1..11
                        mol_type = other DNA
                        organism = synthetic construct
SEQUENCE: 117
acacgctgct c                                                      11

SEQ ID NO: 118          moltype = DNA  length = 11
FEATURE                 Location/Qualifiers
source                  1..11
                        mol_type = other DNA
                        organism = synthetic construct
SEQUENCE: 118
agacgctact c                                                      11

SEQ ID NO: 119          moltype = DNA  length = 11
FEATURE                 Location/Qualifiers
source                  1..11
                        mol_type = other DNA
                        organism = synthetic construct
SEQUENCE: 119
agacgctgct a                                                      11

SEQ ID NO: 120          moltype = DNA  length = 11
FEATURE                 Location/Qualifiers
source                  1..11
                        mol_type = other DNA
                        organism = synthetic construct
SEQUENCE: 120
agactctgct c                                                      11

SEQ ID NO: 121          moltype = DNA  length = 11
FEATURE                 Location/Qualifiers
source                  1..11
                        mol_type = other DNA
                        organism = synthetic construct
SEQUENCE: 121
attatgggag a                                                      11

SEQ ID NO: 122          moltype = AA  length = 7
FEATURE                 Location/Qualifiers
source                  1..7
                        mol_type = protein
                        organism = synthetic construct
SEQUENCE: 122
DEANLRR                                                           7

SEQ ID NO: 123          moltype = AA  length = 7
FEATURE                 Location/Qualifiers
source                  1..7
                        mol_type = protein
                        organism = synthetic construct
SEQUENCE: 123
DPSVLKR                                                           7

SEQ ID NO: 124          moltype = AA  length = 7
FEATURE                 Location/Qualifiers
source                  1..7
                        mol_type = protein
                        organism = synthetic construct
SEQUENCE: 124
QSANLLR                                                           7

SEQ ID NO: 125          moltype = AA  length = 7
FEATURE                 Location/Qualifiers
source                  1..7
                        mol_type = protein
                        organism = synthetic construct
SEQUENCE: 125
DPSSLKR                                                           7

SEQ ID NO: 126          moltype = AA  length = 7
FEATURE                 Location/Qualifiers
source                  1..7
                        mol_type = protein
                        organism = synthetic construct
SEQUENCE: 126
QQTNLTR                                                           7

SEQ ID NO: 127          moltype = AA  length = 7
```

```
FEATURE                 Location/Qualifiers
source                  1..7
                        mol_type = protein
                        organism = synthetic construct
SEQUENCE: 127
DATQLVR                                                                     7

SEQ ID NO: 128          moltype = AA  length = 7
FEATURE                 Location/Qualifiers
source                  1..7
                        mol_type = protein
                        organism = synthetic construct
SEQUENCE: 128
ERRSLAR                                                                     7

SEQ ID NO: 129          moltype = AA  length = 7
FEATURE                 Location/Qualifiers
source                  1..7
                        mol_type = protein
                        organism = synthetic construct
SEQUENCE: 129
EEANLRR                                                                     7

SEQ ID NO: 130          moltype = AA  length = 7
FEATURE                 Location/Qualifiers
source                  1..7
                        mol_type = protein
                        organism = synthetic construct
SEQUENCE: 130
DHSSLKR                                                                     7

SEQ ID NO: 131          moltype = AA  length = 7
FEATURE                 Location/Qualifiers
source                  1..7
                        mol_type = protein
                        organism = synthetic construct
SEQUENCE: 131
QRSSLVR                                                                     7

SEQ ID NO: 132          moltype = AA  length = 7
FEATURE                 Location/Qualifiers
source                  1..7
                        mol_type = protein
                        organism = synthetic construct
SEQUENCE: 132
DMGNLGR                                                                     7

SEQ ID NO: 133          moltype = AA  length = 7
FEATURE                 Location/Qualifiers
source                  1..7
                        mol_type = protein
                        organism = synthetic construct
SEQUENCE: 133
RSHDLTR                                                                     7

SEQ ID NO: 134          moltype = AA  length = 7
FEATURE                 Location/Qualifiers
source                  1..7
                        mol_type = protein
                        organism = synthetic construct
SEQUENCE: 134
HKSSLTR                                                                     7

SEQ ID NO: 135          moltype = AA  length = 7
FEATURE                 Location/Qualifiers
source                  1..7
                        mol_type = protein
                        organism = synthetic construct
SEQUENCE: 135
DSSNLRR                                                                     7

SEQ ID NO: 136          moltype = AA  length = 7
FEATURE                 Location/Qualifiers
source                  1..7
                        mol_type = protein
                        organism = synthetic construct
SEQUENCE: 136
DQGNLIR                                                                     7
```

-continued

```
SEQ ID NO: 137          moltype = AA  length = 7
FEATURE                 Location/Qualifiers
source                  1..7
                        mol_type = protein
                        organism = synthetic construct
SEQUENCE: 137
QKQALTR                                                     7

SEQ ID NO: 138          moltype = AA  length = 7
FEATURE                 Location/Qualifiers
source                  1..7
                        mol_type = protein
                        organism = synthetic construct
SEQUENCE: 138
DRGNLTR                                                     7

SEQ ID NO: 139          moltype = AA  length = 7
FEATURE                 Location/Qualifiers
source                  1..7
                        mol_type = protein
                        organism = synthetic construct
SEQUENCE: 139
RSHDLTV                                                     7

SEQ ID NO: 140          moltype = AA  length = 7
FEATURE                 Location/Qualifiers
source                  1..7
                        mol_type = protein
                        organism = synthetic construct
SEQUENCE: 140
DKSVLAR                                                     7

SEQ ID NO: 141          moltype = AA  length = 7
FEATURE                 Location/Qualifiers
source                  1..7
                        mol_type = protein
                        organism = synthetic construct
SEQUENCE: 141
QTNNLGR                                                     7

SEQ ID NO: 142          moltype = AA  length = 7
FEATURE                 Location/Qualifiers
source                  1..7
                        mol_type = protein
                        organism = synthetic construct
SEQUENCE: 142
THAVLTR                                                     7

SEQ ID NO: 143          moltype = AA  length = 7
FEATURE                 Location/Qualifiers
source                  1..7
                        mol_type = protein
                        organism = synthetic construct
SEQUENCE: 143
TKSLLAR                                                     7

SEQ ID NO: 144          moltype = AA  length = 7
FEATURE                 Location/Qualifiers
source                  1..7
                        mol_type = protein
                        organism = synthetic construct
SEQUENCE: 144
QKQALDR                                                     7

SEQ ID NO: 145          moltype = AA  length = 7
FEATURE                 Location/Qualifiers
source                  1..7
                        mol_type = protein
                        organism = synthetic construct
SEQUENCE: 145
DTSVLNR                                                     7

SEQ ID NO: 146          moltype = AA  length = 7
FEATURE                 Location/Qualifiers
source                  1..7
                        mol_type = protein
                        organism = synthetic construct
SEQUENCE: 146
QGTSLAR                                                     7
```

```
SEQ ID NO: 147          moltype = AA  length = 7
FEATURE                 Location/Qualifiers
source                  1..7
                        mol_type = protein
                        organism = synthetic construct
SEQUENCE: 147
VRHNLTR                                                                  7

SEQ ID NO: 148          moltype = AA  length = 7
FEATURE                 Location/Qualifiers
source                  1..7
                        mol_type = protein
                        organism = synthetic construct
SEQUENCE: 148
EKQNLAR                                                                  7

SEQ ID NO: 149          moltype = AA  length = 7
FEATURE                 Location/Qualifiers
source                  1..7
                        mol_type = protein
                        organism = synthetic construct
SEQUENCE: 149
DPSNLRR                                                                  7

SEQ ID NO: 150          moltype = AA  length = 7
FEATURE                 Location/Qualifiers
source                  1..7
                        mol_type = protein
                        organism = synthetic construct
SEQUENCE: 150
DHSNLSR                                                                  7

SEQ ID NO: 151          moltype = AA  length = 7
FEATURE                 Location/Qualifiers
source                  1..7
                        mol_type = protein
                        organism = synthetic construct
SEQUENCE: 151
QSTSLQR                                                                  7

SEQ ID NO: 152          moltype = AA  length = 7
FEATURE                 Location/Qualifiers
source                  1..7
                        mol_type = protein
                        organism = synthetic construct
SEQUENCE: 152
NMSNLTR                                                                  7

SEQ ID NO: 153          moltype = AA  length = 7
FEATURE                 Location/Qualifiers
source                  1..7
                        mol_type = protein
                        organism = synthetic construct
SEQUENCE: 153
DRSVLRR                                                                  7

SEQ ID NO: 154          moltype = AA  length = 7
FEATURE                 Location/Qualifiers
source                  1..7
                        mol_type = protein
                        organism = synthetic construct
SEQUENCE: 154
LQENLTR                                                                  7

SEQ ID NO: 155          moltype = AA  length = 7
FEATURE                 Location/Qualifiers
source                  1..7
                        mol_type = protein
                        organism = synthetic construct
SEQUENCE: 155
DRSSLRR                                                                  7

SEQ ID NO: 156          moltype = AA  length = 7
FEATURE                 Location/Qualifiers
source                  1..7
                        mol_type = protein
                        organism = synthetic construct
SEQUENCE: 156
```

-continued

```
QSGTLHR                                                     7

SEQ ID NO: 157          moltype = AA  length = 7
FEATURE                 Location/Qualifiers
source                  1..7
                        mol_type = protein
                        organism = synthetic construct
SEQUENCE: 157
QLANLAR                                                     7

SEQ ID NO: 158          moltype = AA  length = 7
FEATURE                 Location/Qualifiers
source                  1..7
                        mol_type = protein
                        organism = synthetic construct
SEQUENCE: 158
DQTTLRR                                                     7

SEQ ID NO: 159          moltype = AA  length = 7
FEATURE                 Location/Qualifiers
source                  1..7
                        mol_type = protein
                        organism = synthetic construct
SEQUENCE: 159
DPSNLAR                                                     7

SEQ ID NO: 160          moltype = AA  length = 7
FEATURE                 Location/Qualifiers
source                  1..7
                        mol_type = protein
                        organism = synthetic construct
SEQUENCE: 160
QGGNLAL                                                     7

SEQ ID NO: 161          moltype = AA  length = 7
FEATURE                 Location/Qualifiers
source                  1..7
                        mol_type = protein
                        organism = synthetic construct
SEQUENCE: 161
RADMLRR                                                     7

SEQ ID NO: 162          moltype = AA  length = 7
FEATURE                 Location/Qualifiers
source                  1..7
                        mol_type = protein
                        organism = synthetic construct
SEQUENCE: 162
QKANLGV                                                     7

SEQ ID NO: 163          moltype = AA  length = 7
FEATURE                 Location/Qualifiers
source                  1..7
                        mol_type = protein
                        organism = synthetic construct
SEQUENCE: 163
RLDMLAR                                                     7

SEQ ID NO: 164          moltype = AA  length = 7
FEATURE                 Location/Qualifiers
source                  1..7
                        mol_type = protein
                        organism = synthetic construct
SEQUENCE: 164
QRGNLNM                                                     7

SEQ ID NO: 165          moltype = AA  length = 7
FEATURE                 Location/Qualifiers
source                  1..7
                        mol_type = protein
                        organism = synthetic construct
SEQUENCE: 165
RPQELRR                                                     7

SEQ ID NO: 166          moltype = AA  length = 7
FEATURE                 Location/Qualifiers
source                  1..7
                        mol_type = protein
                        organism = synthetic construct
```

-continued

```
SEQUENCE: 166
RQDNLGR                                                              7

SEQ ID NO: 167          moltype = AA  length = 7
FEATURE                 Location/Qualifiers
source                  1..7
                        mol_type = protein
                        organism = synthetic construct
SEQUENCE: 167
DGGNLGR                                                              7

SEQ ID NO: 168          moltype = AA  length = 7
FEATURE                 Location/Qualifiers
source                  1..7
                        mol_type = protein
                        organism = synthetic construct
SEQUENCE: 168
QQGNLQL                                                              7

SEQ ID NO: 169          moltype = AA  length = 7
FEATURE                 Location/Qualifiers
source                  1..7
                        mol_type = protein
                        organism = synthetic construct
SEQUENCE: 169
RRQELTR                                                              7

SEQ ID NO: 170          moltype = AA  length = 7
FEATURE                 Location/Qualifiers
source                  1..7
                        mol_type = protein
                        organism = synthetic construct
SEQUENCE: 170
QASNLTR                                                              7

SEQ ID NO: 171          moltype = AA  length = 7
FEATURE                 Location/Qualifiers
source                  1..7
                        mol_type = protein
                        organism = synthetic construct
SEQUENCE: 171
RAHNLLL                                                              7

SEQ ID NO: 172          moltype = AA  length = 7
FEATURE                 Location/Qualifiers
source                  1..7
                        mol_type = protein
                        organism = synthetic construct
SEQUENCE: 172
QSTTLKR                                                              7

SEQ ID NO: 173          moltype = AA  length = 7
FEATURE                 Location/Qualifiers
source                  1..7
                        mol_type = protein
                        organism = synthetic construct
SEQUENCE: 173
QGTTLKR                                                              7

SEQ ID NO: 174          moltype = AA  length = 7
FEATURE                 Location/Qualifiers
source                  1..7
                        mol_type = protein
                        organism = synthetic construct
SEQUENCE: 174
QRSNLAR                                                              7

SEQ ID NO: 175          moltype = AA  length = 7
FEATURE                 Location/Qualifiers
source                  1..7
                        mol_type = protein
                        organism = synthetic construct
SEQUENCE: 175
RRHGLDR                                                              7

SEQ ID NO: 176          moltype = AA  length = 7
FEATURE                 Location/Qualifiers
source                  1..7
                        mol_type = protein
```

```
                         organism = synthetic construct
SEQUENCE: 176
ESGHLKR                                                          7

SEQ ID NO: 177           moltype = AA  length = 7
FEATURE                  Location/Qualifiers
source                   1..7
                         mol_type = protein
                         organism = synthetic construct
SEQUENCE: 177
QLSNLTR                                                          7

SEQ ID NO: 178           moltype = AA  length = 7
FEATURE                  Location/Qualifiers
source                   1..7
                         mol_type = protein
                         organism = synthetic construct
SEQUENCE: 178
DRSSLKR                                                          7

SEQ ID NO: 179           moltype = AA  length = 7
FEATURE                  Location/Qualifiers
source                   1..7
                         mol_type = protein
                         organism = synthetic construct
SEQUENCE: 179
VRHSLTR                                                          7

SEQ ID NO: 180           moltype = AA  length = 7
FEATURE                  Location/Qualifiers
source                   1..7
                         mol_type = protein
                         organism = synthetic construct
SEQUENCE: 180
ESGALRR                                                          7

SEQ ID NO: 181           moltype = AA  length = 7
FEATURE                  Location/Qualifiers
source                   1..7
                         mol_type = protein
                         organism = synthetic construct
SEQUENCE: 181
QRNNLGR                                                          7

SEQ ID NO: 182           moltype = AA  length = 189
FEATURE                  Location/Qualifiers
source                   1..189
                         mol_type = protein
                         organism = Hepacivirus hominis
SEQUENCE: 182
APITAYAQQT RGLLGCIITS LTGRDKNQVE GEVQIVSTAT QTFLATCING VCWAVYHGAG  60
TRTIASPKGP VIQMYTNVDQ DLVGWPAPQG SRSLTPCTCG SSDLYLVTRH ADVIPVRRRG  120
DSRGSLLSPR PISYLKGSSG GPLLCPAGHA VGLFRAAVCT RGVAKAVDFI PVENLETTMR  180
SPVFTDNSS                                                          189

SEQ ID NO: 183           moltype = AA  length = 186
FEATURE                  Location/Qualifiers
source                   1..186
                         mol_type = protein
                         organism = Hepacivirus hominis
SEQUENCE: 183
APITAYAQQT RGLLGCIITS LTGRDKNQVE GEVQIVSTAT QTFLATCING VCWAVYHGAG  60
TRTIASPKGP VIQMYTNVDQ DLVGWPAPQG SRSLTPCTCG SSDLYLVTRH ADVIPVRRRG  120
DSRGSLLSPR PISYLKGSSG GPLLCPAGHA VGLFRAAVCT RGVAKAVDFI PVENLETTMR  180
SPVFTD                                                             186

SEQ ID NO: 184           moltype = AA  length = 180
FEATURE                  Location/Qualifiers
source                   1..180
                         mol_type = protein
                         organism = Hepacivirus hominis
SEQUENCE: 184
APITAYAQQT RGLLGCIITS LTGRDKNQVE GEVQIVSTAT QTFLATCING VCWTVYHGAG  60
TRTIASPKGP VIQMYTNVDQ DLVGWPAPQG SRSLTPCTCG SSDLYLVTRH ADVIPVRRRG  120
DSRGSLLSPR PISYLKGSSG GPLLCPAGHA VGLFRAAVCT RGVAKAVDFI PVENLETTMR  180

SEQ ID NO: 185           moltype = AA  length = 180
FEATURE                  Location/Qualifiers
source                   1..180
```

```
                          mol_type = protein
                          organism = Hepacivirus hominis
SEQUENCE: 185
APITAYSQQT RGLLGCIITS LTGRDKNQVE GEVQVVSTAT QSFLATCVNG VCWTVYHGAG  60
SKTLAGPKGP ITQMYTNVDQ DLVGWQAPPG ARSLTPCTCG SSDLYLVTRH ADVIPVRRRG  120
DSRGSLLSPR PVSYLKGSSG GPLLCPSGHA VGIFRAAVCT RGVAKAVDFV PVESMETTMR  180

SEQ ID NO: 186            moltype = AA  length = 180
FEATURE                   Location/Qualifiers
source                    1..180
                          mol_type = protein
                          organism = Hepacivirus hominis
SEQUENCE: 186
APITAYAQQT RGLLGTIVVS MTGRDKTEQA GEIQVLSTVT QSFLGTSISG VLWTVYHGAG  60
NKTLAGSRGP VTQMYSSAEG DLVGWPSPPG TKSLEPCTCG AVDLYLVTRN ADVIPARRRG  120
DKRGALLSPR PLSTLKGSSG GPVLCPRGHA VGVFRAAVCS RGVAKSIDFI PVETLDIVTR  180

SEQ ID NO: 187            moltype = AA  length = 180
FEATURE                   Location/Qualifiers
source                    1..180
                          mol_type = protein
                          organism = Hepacivirus hominis
SEQUENCE: 187
APITAYAQQT RGLLGTIVTS LTGRDKNVVT GEVQVLSTAT QTFLGTTVGG VIWTVYHGAG  60
SRTLAGAKHP ALQMYTNVDQ DLVGWPAPPG AKSLEPCACG SSDLYLVTRD ADVIPARRRG  120
DSTASLLSPR PLACLKGSSG GPVMCPSGHV AGIFRAAVCT RGVAKSLQFI PVETLSTQAR  180

SEQ ID NO: 188            moltype = AA  length = 180
FEATURE                   Location/Qualifiers
source                    1..180
                          mol_type = protein
                          organism = Hepacivirus hominis
SEQUENCE: 188
APITAYAQQT RGLFSTIVTS LTGRDTNENC GEVQVLSTAT QSFLGTAVNG VMWTVYHGAG  60
AKTISGPKGP VNQMYTNVDQ DLVGWPAPPG VRSLAPCTCG SADLYLVTRH ADVIPVRRRG  120
DTRGALLSPR PISILKGSSG GPLLCPMGHR AGIFRAAVCT RGVAKAVDFV PVESLETTMR  180

SEQ ID NO: 189            moltype = AA  length = 180
FEATURE                   Location/Qualifiers
source                    1..180
                          mol_type = protein
                          organism = Hepacivirus hominis
SEQUENCE: 189
APITAYAQQT RGVLGAIVLS LTGRDKNEAE GEVQFLSTAT QTFLGICING VMWTLFHGAG  60
SKTLAGPKGP VVQMYTNVDK DLVGWPSPPG KGSLTRCTCG SADLYLVTRH ADVIPARRRG  120
DTRASLLSPR PISYLKGSSG GPIMCPSGHV VGVFRAAVCT RGVAKALEFV PVENLETTMR  180

SEQ ID NO: 190            moltype = AA  length = 180
FEATURE                   Location/Qualifiers
source                    1..180
                          mol_type = protein
                          organism = Hepacivirus hominis
SEQUENCE: 190
APITAYAQQT RGLVGTIVTS LTGRDKNEAE GEVQVVSTAT QSFLATTING VLWTVYHGAG  60
SKNLAGPKGP VCQMYTNVDQ DLVGWPAPLG ARSLAPCTCG SSDLYLVTRG ADVIPARRRG  120
DTRAALLSPR PISTLKGSSG GPLMCPSGHV VGLFRAAVCT RGVAKALDFI PVENMDTTMR  180

SEQ ID NO: 191            moltype = AA  length = 180
FEATURE                   Location/Qualifiers
source                    1..180
                          mol_type = protein
                          organism = Hepacivirus hominis
SEQUENCE: 191
APISAYAQQT RGLISTLVVS LTGRDKNETA GEVQVLSTST QTFLGTNVGG VMWGPYHGAG  60
TRTVAGRGGP VLQMYTSVSD DLVGWPAPPG SKSLEPCSCG SADLYLVTRN ADVLPLRRKG  120
DGTASLLSPR PVSSLKGSSG GPVLCPQSHC VGIFRAAVCT RGVAKAVQFV PIEKMQVAQR  180

SEQ ID NO: 192            moltype = AA  length = 180
FEATURE                   Location/Qualifiers
source                    1..180
                          mol_type = protein
                          organism = Hepacivirus hominis
SEQUENCE: 192
APITAYAQQT RGLLGCIITS LTGRDKNQVE GEVQIVSTAT QTFLATCING VCWTVYHGAG  60
TRTIASPKGP VIQMYTNVDQ DLVGWPAPQG SRSLTPCTCG SSDLYLVTRH ADVIPVRRRG  120
DSRGSLLSPR PISYLKGSSG GPLLCPAGHA VGLFRAAVCT RGVTKAVDFI PVENLETTMR  180

SEQ ID NO: 193            moltype = AA  length = 180
FEATURE                   Location/Qualifiers
```

```
source                  1..180
                        mol_type = protein
                        organism = Hepacivirus hominis
SEQUENCE: 193
APITAYSQQT RGLLGCIITS LTGRDKNQVE GEVQVVSTAT QSFLATCVNG VCWTVYHGAG  60
SKTLAAPKGP ITQMYTNVDQ DLVGWPKPPG ARSLTPCTCG SSDLYLVTRH ADVIPVRRRG  120
DSRGSLLSPR PVSYLKGSSG GPLLCPFGHA VGIFRAAVCT RGVAKAVDFV PVESMETTMR  180

SEQ ID NO: 194          moltype = AA  length = 180
FEATURE                 Location/Qualifiers
source                  1..180
                        mol_type = protein
                        organism = Hepacivirus hominis
SEQUENCE: 194
APITAYAQQT RGLLGTIVVS MTGRDKTEQA GEIQVLSTVT QSFLGTTISG VLWTVYHGAG  60
NKTLAGSRGP VTQMYSSAEG DLVGWPSPPG TKSLEPCTCG AVDLYLVTRN ADVIPARRRG  120
DKRGALLSPR PLSTLKGSSG GPVLCPRGHA VGVFRAAVCS RGVAKSIDFI PVETLDIVTR  180

SEQ ID NO: 195          moltype = AA  length = 182
FEATURE                 Location/Qualifiers
source                  1..182
                        mol_type = protein
                        organism = Hepacivirus hominis
SEQUENCE: 195
APITAYTQQT RGLLGAIVVS LTGRDKNEQA GQVQVLSSVT QTFLGTSISG VLWTVYHGAG  60
NKTLAGPKGP VTQMYTSAEG DLVGWPSPPG TKSLDPCTCG AVDLYLVTRN ADVIPVRRKD  120
DRRGALLSPR PLSTLKGSSG GPVLCSRGHA VGLFRAAVSY NTFGVAKSID FIPVESLDVA  180
TR                                                                 182

SEQ ID NO: 196          moltype = AA  length = 180
FEATURE                 Location/Qualifiers
source                  1..180
                        mol_type = protein
                        organism = Hepacivirus hominis
SEQUENCE: 196
APITAYAQQT RGLLGTIVTS LTGRDKNVVT GEVQVLSTAT QTFLGTTVGG VIWTVYHGAG  60
SRTLAGAKHP ALQMYTNVDQ DLVGWPAPPG AKSLEPCACG SSDLYLVTRD ADVIPARRRG  120
DSTASLLSPR PLACLKGSSG GPVMCPSGHV AGIFRAAVCT RGVAKSLQFI PVETLSTQAR  180

SEQ ID NO: 197          moltype = AA  length = 186
FEATURE                 Location/Qualifiers
source                  1..186
                        mol_type = protein
                        organism = synthetic construct
SEQUENCE: 197
APITAYAQQT RGLLGCIITS LTGRDKNQVE GEVQIMSTAT QTFLATCING VCWAVYHGAG  60
TRTIASPKGP VIQMYTNVDQ DLVGWPAPQG SRSLTPCTCG SSDLYLVTRH ADVIPVRRRG  120
DGRGSLLSPR PISYLKGSSG GPLLCPAGHA VGLFRAAVCT RGVAKAVDFI PVENLETTMR  180
SPVFTD                                                             186

SEQ ID NO: 198          moltype = AA  length = 186
FEATURE                 Location/Qualifiers
source                  1..186
                        mol_type = protein
                        organism = synthetic construct
SEQUENCE: 198
APITAYAQQT RGLLGCIITS LTGRDKNQVE GEVQIVSTAT QTLLATCING VCWAVYHGAG  60
TRTIASPKGP VIQMYTNVDK DLVGWPAPQG SRSLTPCTCG SSDLYLVTRH ADVIPVRRRG  120
DRRGSLLSPR PISYLKGSSG GPLLCPAGHA VGLFRAAVCT RGVAKAVYFI PVENLETTMR  180
SPVFTD                                                             186

SEQ ID NO: 199          moltype = AA  length = 13
FEATURE                 Location/Qualifiers
source                  1..13
                        mol_type = protein
                        organism = synthetic construct
SEQUENCE: 199
GCVVIVGRIV LSG                                                     13

SEQ ID NO: 200          moltype = AA  length = 45
FEATURE                 Location/Qualifiers
source                  1..45
                        mol_type = protein
                        organism = synthetic construct
SEQUENCE: 200
STWVLVGGVL AALAAYCLST GCVVIVGRIV LSGKPAIIPD REVLY                  45

SEQ ID NO: 201          moltype = AA  length = 51
FEATURE                 Location/Qualifiers
```

```
source                  1..51
                        mol_type = protein
                        organism = synthetic construct
SEQUENCE: 201
STWVLVGGVL AALAAYCLST GCVVIVGRIV LSGKPAGSSG SSIIPDREVL Y          51

SEQ ID NO: 202          moltype = AA  length = 63
FEATURE                 Location/Qualifiers
source                  1..63
                        mol_type = protein
                        organism = synthetic construct
SEQUENCE: 202
IDTKYIMTCM SADLEVVTST WVLVGGVLAA LAAYCLSTGC VVIVGRIVLS GKPAIIPDRE  60
VLY                                                               63

SEQ ID NO: 203          moltype = AA  length = 12
FEATURE                 Location/Qualifiers
source                  1..12
                        mol_type = protein
                        organism = synthetic construct
SEQUENCE: 203
GSVVIVGRII LS                                                     12

SEQ ID NO: 204          moltype = AA  length = 14
FEATURE                 Location/Qualifiers
source                  1..14
                        mol_type = protein
                        organism = Hepacivirus hominis
SEQUENCE: 204
GCVVIVGRIV LSGK                                                   14

SEQ ID NO: 205          moltype = AA  length = 14
FEATURE                 Location/Qualifiers
source                  1..14
                        mol_type = protein
                        organism = Hepacivirus hominis
SEQUENCE: 205
GCVCIIGRLH INQR                                                   14

SEQ ID NO: 206          moltype = AA  length = 14
FEATURE                 Location/Qualifiers
source                  1..14
                        mol_type = protein
                        organism = Hepacivirus hominis
SEQUENCE: 206
GCVVIVGHIE LEGK                                                   14

SEQ ID NO: 207          moltype = AA  length = 14
FEATURE                 Location/Qualifiers
source                  1..14
                        mol_type = protein
                        organism = Hepacivirus hominis
SEQUENCE: 207
GSVVIVGRVV LSGQ                                                   14

SEQ ID NO: 208          moltype = AA  length = 14
FEATURE                 Location/Qualifiers
source                  1..14
                        mol_type = protein
                        organism = Hepacivirus hominis
SEQUENCE: 208
GSVAIVGRII LSGR                                                   14

SEQ ID NO: 209          moltype = AA  length = 14
FEATURE                 Location/Qualifiers
source                  1..14
                        mol_type = protein
                        organism = Hepacivirus hominis
SEQUENCE: 209
GCVVICGRIV TSGK                                                   14

SEQ ID NO: 210          moltype = AA  length = 14
FEATURE                 Location/Qualifiers
source                  1..14
                        mol_type = protein
                        organism = Hepacivirus hominis
SEQUENCE: 210
GSVVVVGRVV LGSN                                                   14
```

```
SEQ ID NO: 211          moltype = AA  length = 54
FEATURE                 Location/Qualifiers
source                  1..54
                        mol_type = protein
                        organism = Hepacivirus hominis
SEQUENCE: 211
STWVLVGGVL AALAAYCLST GCVVIVGRIV LSGKPAIIPD REVLYQEFDE MEEC        54

SEQ ID NO: 212          moltype = AA  length = 54
FEATURE                 Location/Qualifiers
source                  1..54
                        mol_type = protein
                        organism = Hepacivirus hominis
SEQUENCE: 212
STWVLVGGVL AALAAYCLST GCVVIVGRVV LSGKPAIIPD REVLYREFDE MEEC        54

SEQ ID NO: 213          moltype = AA  length = 54
FEATURE                 Location/Qualifiers
source                  1..54
                        mol_type = protein
                        organism = Hepacivirus hominis
SEQUENCE: 213
STWVLVGGVL AALAAYCLST GCVVIVGRIV LSGRPAIIPD REVLYREFDE MEEC        54

SEQ ID NO: 214          moltype = AA  length = 54
FEATURE                 Location/Qualifiers
source                  1..54
                        mol_type = protein
                        organism = Hepacivirus hominis
SEQUENCE: 214
STWVLVGGVL AALAAYCLTT GSVVIVGRII LSGRPAIVPD RELLYQEFDE MEEC        54

SEQ ID NO: 215          moltype = AA  length = 54
FEATURE                 Location/Qualifiers
source                  1..54
                        mol_type = protein
                        organism = Hepacivirus hominis
SEQUENCE: 215
STWVLVGGVL AALAAYCLTT GSVVIVGRII LSGRPAIIPD RELLYQEFDE MEEC        54

SEQ ID NO: 216          moltype = AA  length = 54
FEATURE                 Location/Qualifiers
source                  1..54
                        mol_type = protein
                        organism = Hepacivirus hominis
SEQUENCE: 216
STWVLVGGVL AALAAYCLTT GSVVIVGRII LSGKPAVVPD RELLYQEFDE MEEC        54

SEQ ID NO: 217          moltype = AA  length = 54
FEATURE                 Location/Qualifiers
source                  1..54
                        mol_type = protein
                        organism = Hepacivirus hominis
SEQUENCE: 217
STWVLVGGVL AALAAYCLTT GSVVIVGRII LSGRPAVIPD RELLYREFDE MEEC        54

SEQ ID NO: 218          moltype = AA  length = 54
FEATURE                 Location/Qualifiers
source                  1..54
                        mol_type = protein
                        organism = Hepacivirus hominis
SEQUENCE: 218
STWVLAGGVL AAVAAYCLAT GCVCIIGRLH VNQRAVVAPD KEVLYEAFDE MEEC        54

SEQ ID NO: 219          moltype = AA  length = 54
FEATURE                 Location/Qualifiers
source                  1..54
                        mol_type = protein
                        organism = Hepacivirus hominis
SEQUENCE: 219
STWVLAGGVL AAVAAYCLAT GCVSIIGRLH INGRAVVAPD KEVLYEAFDE MEEC        54

SEQ ID NO: 220          moltype = AA  length = 54
FEATURE                 Location/Qualifiers
source                  1..54
                        mol_type = protein
                        organism = Hepacivirus hominis
SEQUENCE: 220
SSWVLAGGVL AAVAAYCLAT GCISIIGRLH LNDRVVVAPD KEILYEAFDE MEEC        54
```

```
SEQ ID NO: 221          moltype = AA  length = 54
FEATURE                 Location/Qualifiers
source                  1..54
                        mol_type = protein
                        organism = Hepacivirus hominis
SEQUENCE: 221
STWVLAGGVL AAVAAYCLAT GCVSIIGRLH LNDQVVVTPD KEILYEAFDE MEEC        54

SEQ ID NO: 222          moltype = AA  length = 54
FEATURE                 Location/Qualifiers
source                  1..54
                        mol_type = protein
                        organism = Hepacivirus hominis
SEQUENCE: 222
STWVLLGGVL AALAAYCLSV GCVVIVGHIE LEGKPALVPD KEVLYQQYDE MEEC        54

SEQ ID NO: 223          moltype = AA  length = 54
FEATURE                 Location/Qualifiers
source                  1..54
                        mol_type = protein
                        organism = Hepacivirus hominis
SEQUENCE: 223
STWVLLGGVL AAVAAYCLSV GCVVIVGHIE LGGKPALVPD KEVLYQQYDE MEEC        54

SEQ ID NO: 224          moltype = AA  length = 4
FEATURE                 Location/Qualifiers
source                  1..4
                        mol_type = protein
                        organism = synthetic construct
SEQUENCE: 224
SGTS                                                               4

SEQ ID NO: 225          moltype = AA  length = 4
FEATURE                 Location/Qualifiers
source                  1..4
                        mol_type = protein
                        organism = synthetic construct
SEQUENCE: 225
GSGS                                                               4

SEQ ID NO: 226          moltype = AA  length = 10
FEATURE                 Location/Qualifiers
source                  1..10
                        mol_type = protein
                        organism = synthetic construct
SEQUENCE: 226
EDVVCCHSIY                                                         10

SEQ ID NO: 227          moltype = AA  length = 14
FEATURE                 Location/Qualifiers
source                  1..14
                        mol_type = protein
                        organism = synthetic construct
SEQUENCE: 227
LYQEFDEMEE CSQH                                                    14

SEQ ID NO: 228          moltype = AA  length = 10
FEATURE                 Location/Qualifiers
source                  1..10
                        mol_type = protein
                        organism = synthetic construct
SEQUENCE: 228
DEMEECSQHL                                                         10

SEQ ID NO: 229          moltype = AA  length = 13
FEATURE                 Location/Qualifiers
source                  1..13
                        mol_type = protein
                        organism = synthetic construct
SEQUENCE: 229
QEFEDVVPCS MGS                                                     13

SEQ ID NO: 230          moltype = AA  length = 9
FEATURE                 Location/Qualifiers
source                  1..9
                        mol_type = protein
                        organism = synthetic construct
SEQUENCE: 230
```

```
EDVVCCHSI                                                       9

SEQ ID NO: 231          moltype = AA  length = 9
FEATURE                 Location/Qualifiers
source                  1..9
                        mol_type = protein
                        organism = synthetic construct
SEQUENCE: 231
DEMEECSQH                                                       9

SEQ ID NO: 232          moltype = AA  length = 20
FEATURE                 Location/Qualifiers
source                  1..20
                        mol_type = protein
                        organism = synthetic construct
SEQUENCE: 232
CMSADLEVVT STWVLVGGVL                                           20

SEQ ID NO: 233          moltype = AA  length = 20
FEATURE                 Location/Qualifiers
source                  1..20
                        mol_type = protein
                        organism = synthetic construct
SEQUENCE: 233
CMSADLEVVT STWVLVGGVL                                           20

SEQ ID NO: 234          moltype = AA  length = 20
FEATURE                 Location/Qualifiers
source                  1..20
                        mol_type = protein
                        organism = synthetic construct
SEQUENCE: 234
CMQADLEVMT STWVLAGGVL                                           20

SEQ ID NO: 235          moltype = AA  length = 20
FEATURE                 Location/Qualifiers
source                  1..20
                        mol_type = protein
                        organism = synthetic construct
SEQUENCE: 235
CMQADLEIMT SSWVLAGGVL                                           20

SEQ ID NO: 236          moltype = AA  length = 20
FEATURE                 Location/Qualifiers
source                  1..20
                        mol_type = protein
                        organism = synthetic construct
SEQUENCE: 236
CMSADLEVTT STWVLLGGVL                                           20

SEQ ID NO: 237          moltype = AA  length = 20
FEATURE                 Location/Qualifiers
source                  1..20
                        mol_type = protein
                        organism = synthetic construct
SEQUENCE: 237
YQEFDEMEEC SQHLPYIEQG                                           20

SEQ ID NO: 238          moltype = AA  length = 20
FEATURE                 Location/Qualifiers
source                  1..20
                        mol_type = protein
                        organism = synthetic construct
SEQUENCE: 238
YQEFDEMEEC ASHLPYIEQG                                           20

SEQ ID NO: 239          moltype = AA  length = 20
FEATURE                 Location/Qualifiers
source                  1..20
                        mol_type = protein
                        organism = synthetic construct
SEQUENCE: 239
YEAFDEMEEC ASRAALIEEG                                           20

SEQ ID NO: 240          moltype = AA  length = 20
FEATURE                 Location/Qualifiers
source                  1..20
                        mol_type = protein
                        organism = synthetic construct
```

```
SEQUENCE: 240
YEAFDEMEEC ASKAALIEEG                                              20

SEQ ID NO: 241          moltype = AA  length = 20
FEATURE                 Location/Qualifiers
source                  1..20
                        mol_type = protein
                        organism = synthetic construct
SEQUENCE: 241
YQQYDEMEEC SQAAPYIEQA                                              20

SEQ ID NO: 242          moltype = AA  length = 20
FEATURE                 Location/Qualifiers
source                  1..20
                        mol_type = protein
                        organism = synthetic construct
SEQUENCE: 242
WISSECTTPC SGSWLRDVWD                                              20

SEQ ID NO: 243          moltype = AA  length = 20
FEATURE                 Location/Qualifiers
source                  1..20
                        mol_type = protein
                        organism = synthetic construct
SEQUENCE: 243
WINEDCSTPC SGSWLRDVWD                                              20

SEQ ID NO: 244          moltype = AA  length = 20
FEATURE                 Location/Qualifiers
source                  1..20
                        mol_type = protein
                        organism = synthetic construct
SEQUENCE: 244
WITEDCPIPC SGSWLRDVWD                                              20

SEQ ID NO: 245          moltype = AA  length = 20
FEATURE                 Location/Qualifiers
source                  1..20
                        mol_type = protein
                        organism = synthetic construct
SEQUENCE: 245
WITEDCPVPC SGSWLQDIWD                                              20

SEQ ID NO: 246          moltype = AA  length = 20
FEATURE                 Location/Qualifiers
source                  1..20
                        mol_type = protein
                        organism = synthetic construct
SEQUENCE: 246
WINEDYPSPC SDDWLRTIWD                                              20

SEQ ID NO: 247          moltype = AA  length = 20
FEATURE                 Location/Qualifiers
source                  1..20
                        mol_type = protein
                        organism = synthetic construct
SEQUENCE: 247
GADTEDVVCC SMSYSWTGAL                                              20

SEQ ID NO: 248          moltype = AA  length = 20
FEATURE                 Location/Qualifiers
source                  1..20
                        mol_type = protein
                        organism = synthetic construct
SEQUENCE: 248
EEASEDVVCC SMSYTWTGAL                                              20

SEQ ID NO: 249          moltype = AA  length = 20
FEATURE                 Location/Qualifiers
source                  1..20
                        mol_type = protein
                        organism = synthetic construct
SEQUENCE: 249
SEEDDSVVCC SMSYSWTGAL                                              20

SEQ ID NO: 250          moltype = AA  length = 20
FEATURE                 Location/Qualifiers
source                  1..20
                        mol_type = protein
```

```
                        organism = synthetic construct
SEQUENCE: 250
SDQEDSVICC SMSYSWTGAL                                                20

SEQ ID NO: 251          moltype = AA  length = 20
FEATURE                 Location/Qualifiers
source                  1..20
                        mol_type = protein
                        organism = synthetic construct
SEQUENCE: 251
DSEEQSVVCC SMSYSWTGAL                                                20

SEQ ID NO: 252          moltype = AA  length = 8
FEATURE                 Location/Qualifiers
source                  1..8
                        mol_type = protein
                        organism = synthetic construct
SEQUENCE: 252
HSIYGKKK                                                             8

SEQ ID NO: 253          moltype = AA  length = 241
FEATURE                 Location/Qualifiers
source                  1..241
                        mol_type = protein
                        organism = synthetic construct
SEQUENCE: 253
GKKKGDIDTY RYIGSSGTGC VVIVGRIVLS GSGTSAPITA YAQQTRGLLG CIITSLTGRD  60
KNQVEGEVQI VSTATQTFLA TCINGVCWAV YHGAGTRTIA SPKGPVIQMY TNVDQDLVGW  120
PAPQGSRSLT PCTCGSSDLY LVTRHADVIP VRRRGDSRGS LLSPRPISYL KGSSGGPLLC  180
PAGHAVGLFR AAVCTRGVAK AVDFIPVENL ETTMRSPVFT DNSSPPAVTL THPITKIDRE  240
V                                                                    241

SEQ ID NO: 254          moltype = AA  length = 265
FEATURE                 Location/Qualifiers
source                  1..265
                        mol_type = protein
                        organism = synthetic construct
SEQUENCE: 254
EDVVCCHSIY GKKKGDIDTY RYIGSSGTGC VVIVGRIVLS GSGTSAPITA YAQQTRGLLG  60
CIITSLTGRD KNQVEGEVQI VSTATQTFLA TCINGVCWAV YHGAGTRTIA SPKGPVIQMY  120
TNVDQDLVGW PAPQGSRSLT PCTCGSSDLY LVTRHADVIP VRRRGDSRGS LLSPRPISYL  180
KGSSGGPLLC PAGHAVGLFR AAVCTRGVAK AVDFIPVENL ETTMRSPVFT DNSSPPAVTL  240
THPITKIDRE VLYQEFDEME ECSQH                                          265

SEQ ID NO: 255          moltype = AA  length = 33
FEATURE                 Location/Qualifiers
source                  1..33
                        mol_type = protein
                        organism = synthetic construct
SEQUENCE: 255
NSSPPAVTLT HPITKIDTKY IMTCMSADLE VVT                                 33

SEQ ID NO: 256          moltype = AA  length = 15
FEATURE                 Location/Qualifiers
source                  1..15
                        mol_type = protein
                        organism = synthetic construct
SEQUENCE: 256
NSSPPAVTLT HPITK                                                     15

SEQ ID NO: 257          moltype = AA  length = 11
FEATURE                 Location/Qualifiers
source                  1..11
                        mol_type = protein
                        organism = synthetic construct
SEQUENCE: 257
NSSPPAVTLT H                                                         11

SEQ ID NO: 258          moltype = AA  length = 221
FEATURE                 Location/Qualifiers
source                  1..221
                        mol_type = protein
                        organism = synthetic construct
SEQUENCE: 258
TGCVVIVGRI VLSGSGTSAP ITAYAQQTRG LLGCIITSLT GRDKNQVEGE VQIVSTATQT  60
FLATCINGVC WAVYHGAGTR TIASPKGPVI QMYTNVDQDL VGWPAPQGSR SLTPCTCGSS  120
DLYLVTRHAD VIPVRRRGDS RGSLLSPRPI SYLKGSSGGP LLCPAGHAVG LFRAAVCTRG  180
VAKAVDFIPV ENLETTMRSP VFTDNSSPPA VTLTHGGSGG S                        221
```

```
SEQ ID NO: 259          moltype = AA  length = 221
FEATURE                 Location/Qualifiers
source                  1..221
                        mol_type = protein
                        organism = synthetic construct
SEQUENCE: 259
TGCVVIVGRI VLSGSGTSAP ITAYAQQTRG LLGCIITSLT GRDKNQVEGE VQIMSTATQT  60
FLATCINGVC WAVYHGAGTR TIASPKGPVI QMYTNVDQDL VGWPAPQGSR SLTPCTCGSS  120
DLYLVTRHAD VIPVRRRGDG RGSLLSPRPI SYLKGSSGGP LLCPAGHAVG LFRAAVCTRG  180
VAKAVDFIPV ENLETTMRSP VFTDNSSPPA VTLTHGGSGG S                     221

SEQ ID NO: 260          moltype = AA  length = 221
FEATURE                 Location/Qualifiers
source                  1..221
                        mol_type = protein
                        organism = synthetic construct
SEQUENCE: 260
TGCVVIVGRI VLSGSGTSAP ITAYAQQTRG LLGCIITSLT GRDKNQVEGE VQIVSTATQT  60
LLATCINGVC WAVYHGAGTR TIASPKGPVI QMYTNVDKDL VGWPAPQGSR SLTPCTCGSS  120
DLYLVTRHAD VIPVRRRGDR RGSLLSPRPI SYLKGSSGGP LLCPAGHAVG LFRAAVCTRG  180
VAKAVYFIPV ENLETTMRSP VFTDNSSPPA VTLTHGGSGG S                     221

SEQ ID NO: 261          moltype = AA  length = 182
FEATURE                 Location/Qualifiers
source                  1..182
                        mol_type = protein
                        organism = synthetic construct
SEQUENCE: 261
MAPITAYAQQ TRGLLGCIIT SLTGRDKNQV EGEVQIVSTA AQTFLATCIN GVCWTVYHGA  60
GTRTIASPKG PVIQMYTNVD KDLVGWPAPQ GSRSLTPCTC GSSDLYLVTR HADVIPVRRR  120
GDSRGSLLSP RPISYLKGSS GGPLLCPAGH AVGIFRAAVC TRGVAKAVDF IPVESLETTM  180
RS                                                                182

SEQ ID NO: 262          moltype = AA  length = 195
FEATURE                 Location/Qualifiers
source                  1..195
                        mol_type = protein
                        organism = synthetic construct
SEQUENCE: 262
MKKKGSVVIV GRIVLNGAYA QQTRGLLGCI ITSLTGRDKN QVEGEVQIVS TAAQTFLATC  60
INGVCWTVYH GAGTRTIASP KGPVIQMYTN VDKDLVGWPA PQGSRSLTPC TCGSSDLYLV  120
TRHADVIPVR RRGDSRGSLL SPRPISYLKG SSGGPLLCPA GHAVGIFRAA VCTRGVAKAV  180
DFIPVESLET TMRSP                                                  195

SEQ ID NO: 263          moltype = AA  length = 195
FEATURE                 Location/Qualifiers
source                  1..195
                        mol_type = protein
                        organism = synthetic construct
SEQUENCE: 263
MKKKGSVVIV GRIVLNGAYA QQTRGEEGCQ ETSQTGRDKN QVEGEVQIVS TAAQTFLATC  60
INGVCWTVYH GAGTRTIASP KGPVIQMYTN VDKDLVGWPA PQGSRSLTPC TCGSSDLYLV  120
TRHADVIPVR RRGDSRGSLL SPRPISYLKG SSGGPLLCPA GHAVGIFRAA VCTRGVAKAV  180
DFIPVESLET TMRSP                                                  195

SEQ ID NO: 264          moltype = AA  length = 197
FEATURE                 Location/Qualifiers
source                  1..197
                        mol_type = protein
                        organism = synthetic construct
SEQUENCE: 264
MKKKGSVVIV GRINLSGDTA YAQQTRGEEG CQETSQTGRD KNQVEGEVQI VSTAAQTFLA  60
TCINGVCWTV YHGAGTRTIA SPKGPVIQMY TNVDKDLVGW PAPQGSRSLT PCTCGSSDLY  120
LVTRHADVIP VRRRGDSRGS LLSPRPISYL KGSSGGPLLC PAGHAVGIFR AAVCTRGVAK  180
AVDFIPVESL ETTMRSP                                                197

SEQ ID NO: 265          moltype = AA  length = 197
FEATURE                 Location/Qualifiers
source                  1..197
                        mol_type = protein
                        organism = synthetic construct
SEQUENCE: 265
MKKKGSVVIV GRINLSGDTA YAQQTRGEEG CQETSQTGRD KNQVEGEVQI VSTATQTFLA  60
TCINGVCWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVCTRGVAK  180
AVDFIPVESL ETTMRSP                                                197

SEQ ID NO: 266          moltype = AA  length = 197
FEATURE                 Location/Qualifiers
```

```
source                1..197
                      mol_type = protein
                      organism = synthetic construct
SEQUENCE: 266
MKKKGSVVIV GRINLSGDTA YAQQTRGEEG CQETSQTGRD KNQVEGEVQI VSTATQTFLA  60
TSINGVLWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVSTRGVAK  180
AVDFIPVESL ETTMRSP                                                197

SEQ ID NO: 267        moltype = AA  length = 197
FEATURE               Location/Qualifiers
source                1..197
                      mol_type = protein
                      organism = synthetic construct
SEQUENCE: 267
MKKKGSVVIV GRINLSGDTA YAQQTRGEQG CQKTSHTGRD KNQVEGEVQI VSTATQTFLA  60
TSINGVLWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVSTRGVAK  180
AVDFIPVESL ETTMRSP                                                197

SEQ ID NO: 268        moltype = AA  length = 197
FEATURE               Location/Qualifiers
source                1..197
                      mol_type = protein
                      organism = synthetic construct
SEQUENCE: 268
MKKKGSVVIV GRINLSGDTA YAQQTRGEQG TQKTSHTGRD KNQVEGEVQI VSTATQTFLA  60
TSINGVLWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVSTRGVAK  180
AVDFIPVESL ETTMRSP                                                197

SEQ ID NO: 269        moltype = AA  length = 196
FEATURE               Location/Qualifiers
source                1..196
                      mol_type = protein
                      organism = synthetic construct
SEQUENCE: 269
KKKGSVVIVG RINLSGDTAY AQQTRGEEGC QETSQTGRDK NQVEGEVQIV STATQTFLAT  60
SINGVLWTVY HGAGTRTIAS PKGPVTQMYT NVDKDLVGWQ APQGSRSLTP CTCGSSDLYL  120
VTRHADVIPV RRRGDSRGSL LSPRPISYLK GSAGGPLLCP AGHAVGIFRA AVSTRGVAKA  180
VDFIPVESLE TTMRSP                                                 196

SEQ ID NO: 270        moltype = AA  length = 158
FEATURE               Location/Qualifiers
source                1..158
                      mol_type = protein
                      organism = synthetic construct
SEQUENCE: 270
ISLIAALAVD YVIGMENAMP WNLPADLAWF KRNTLNKPVI MGRHTWESIG RPLPGRKNII  60
LSSQPSTDDR VTWVKSVDEA IAACGDVPEI MVIGGGRVIE QFLPKAQKLY LTHIDAEVEG  120
DTHFPDYEPD DWESVFSEFH DADAQNSHSY CFEILERR                          158

SEQ ID NO: 271        moltype = AA  length = 107
FEATURE               Location/Qualifiers
source                1..107
                      mol_type = protein
                      organism = synthetic construct
SEQUENCE: 271
GVQVETISPG DGRTFPKRGQ TCVVHYTGML EDGKKFDSSR DRNKPFKFML GKQEVIRGWE  60
EGVAQMSVGQ RAKLTISPDY AYGATGHPGI IPPHATLVFD VELLKLE                107

SEQ ID NO: 272        moltype = AA  length = 19
FEATURE               Location/Qualifiers
source                1..19
                      mol_type = protein
                      organism = synthetic construct
SEQUENCE: 272
TRGVEEVAEG VVLLRRRGN                                              19

SEQ ID NO: 273        moltype = AA  length = 229
FEATURE               Location/Qualifiers
source                1..229
                      mol_type = protein
                      organism = Arabidopsis thaliana
SEQUENCE: 273
MMGSVELNLR ETELCLGLPG GDTVAPVTGN KRGFSETVDL KLNLNNEPAN KEGSTTHDVV  60
TFDSKEKSAC PKDPAKPPAK AQVVGWPPVR SYRKNVMVSC QKSSGGPEAA AFVKVSMDGA  120
PYLRKIDLRM YKSYDELSNA LSNMFSSFTM GKHGGEEGMI DFMNERKLMD LVNSWDYVPS  180
YEDKDGDWML VGDVPWPMFV DTCKRLRLMK GSDAIGLAPR AMEKCKSRA              229
```

```
SEQ ID NO: 274          moltype = AA  length = 68
FEATURE                 Location/Qualifiers
source                  1..68
                        mol_type = protein
                        organism = Arabidopsis thaliana
SEQUENCE: 274
KEKSACPKDP AKPPAKAQVV GWPPVRSYRK NVMVSCQKSS GGPEAAAFVK VSMDGAPYLR  60
KIDLRMYK                                                           68

SEQ ID NO: 275          moltype = AA  length = 42
FEATURE                 Location/Qualifiers
source                  1..42
                        mol_type = protein
                        organism = synthetic construct
SEQUENCE: 275
PITKIDTKYI MTCMSADLEV VTSTWVLVGG VLAALAAYCL ST                     42

SEQ ID NO: 276          moltype = AA  length = 304
FEATURE                 Location/Qualifiers
source                  1..304
                        mol_type = protein
                        organism = synthetic construct
SEQUENCE: 276
DEMEECSQHL PGAGSSGDIM DYKDDDDKGS SGTGSGSGTS APITAYAQQT RGLLGCIITS  60
LTGRDKNQVE GEVQIVSTAT QTFLATCING VCWAVYHGAG TRTIASPKGP VIQMYTNVDQ  120
DLVGWPAPQG SRSLTPCTCG SSDLYLVTRH ADVIPVRRRG DSRGSLLSPR PISYLKGSSG  180
GPLLCPAGHA VGLFRAAVCT RGVAKAVDFI PVENLETTMR SPVFTDNSSP PAVTLTHPIT  240
KIDTKYIMTC MSADLEVVTS TWVLVGGVLA ALAAYCLSTG CVVIVGRIVL SGKPAIIPDR  300
EVLY                                                               304

SEQ ID NO: 277          moltype = AA  length = 304
FEATURE                 Location/Qualifiers
source                  1..304
                        mol_type = protein
                        organism = synthetic construct
SEQUENCE: 277
DEMEECSQHL PGAGSSGDIM DYKDDDDKGS SGTGSGSGTS APITAYAQQT RGLLGCIITS  60
LTGRDKNQVE GEVQIMSTAT QTFLATCING VCWAVYHGAG TRTIASPKGP VIQMYTNVDQ  120
DLVGWPAPQG SRSLTPCTCG SSDLYLVTRH ADVIPVRRRG DGRGSLLSPR PISYLKGSSG  180
GPLLCPAGHA VGLFRAAVCT RGVAKAVDFI PVENLETTMR SPVFTDNSSP PAVTLTHPIT  240
KIDTKYIMTC MSADLEVVTS TWVLVGGVLA ALAAYCLSTG CVVIVGRIVL SGKPAIIPDR  300
EVLY                                                               304

SEQ ID NO: 278          moltype = AA  length = 304
FEATURE                 Location/Qualifiers
source                  1..304
                        mol_type = protein
                        organism = synthetic construct
SEQUENCE: 278
DEMEECSQHL PGAGSSGDIM DYKDDDDKGS SGTGSGSGTS APITAYAQQT RGLLGCIITS  60
LTGRDKNQVE GEVQIVSTAT QTLLATCING VCWAVYHGAG TRTIASPKGP VIQMYTNVDK  120
DLVGWPAPQG SRSLTPCTCG SSDLYLVTRH ADVIPVRRRG DRRGSLLSPR PISYLKGSSG  180
GPLLCPAGHA VGLFRAAVCT RGVAKAVYFI PVENLETTMR SPVFTDNSSP PAVTLTHPIT  240
KIDTKYIMTC MSADLEVVTS TWVLVGGVLA ALAAYCLSTG CVVIVGRIVL SGKPAIIPDR  300
EVLY                                                               304

SEQ ID NO: 279          moltype = AA  length = 297
FEATURE                 Location/Qualifiers
source                  1..297
                        mol_type = protein
                        organism = synthetic construct
SEQUENCE: 279
DYKDDDDKGS SGTGSGSGTS APITAYAQQT RGLLGCIITS LTGRDKNQVE GEVQIVSTAT  60
QTFLATCING VCWAVYHGAG TRTIASPKGP VIQMYTNVDQ DLVGWPAPQG SRSLTPCTCG  120
SSDLYLVTRH ADVIPVRRRG DSRGSLLSPR PISYLKGSSG GPLLCPAGHA VGLFRAAVCT  180
RGVAKAVDFI PVENLETTMR SPVFTDNSSP PAVTLTHPIT KIDTKYIMTC MSADLEVVTS  240
TWVLVGGVLA ALAAYCLSTG CVVIVGRIVL SGKPAIIPDR EVLYQEFEDV VPCSMGS     297

SEQ ID NO: 280          moltype = AA  length = 303
FEATURE                 Location/Qualifiers
source                  1..303
                        mol_type = protein
                        organism = synthetic construct
SEQUENCE: 280
DYKDDDDKGS SGTGSGSGTS APITAYAQQT RGLLGCIITS LTGRDKNQVE GEVQIVSTAT  60
QTFLATCING VCWAVYHGAG TRTIASPKGP VIQMYTNVDQ DLVGWPAPQG SRSLTPCTCG  120
SSDLYLVTRH ADVIPVRRRG DSRGSLLSPR PISYLKGSSG GPLLCPAGHA VGLFRAAVCT  180
RGVAKAVDFI PVENLETTMR SPVFTDNSSP PAVTLTHPIT KIDTKYIMTC MSADLEVVTS  240
```

```
TWVLVGGVLA ALAAYCLSTG CVVIVGRIVL SGKPAGSSGS SIIPDREVLY QEFEDVVPCS  300
MGS                                                                303

SEQ ID NO: 281          moltype = AA  length = 297
FEATURE                 Location/Qualifiers
source                  1..297
                        mol_type = protein
                        organism = synthetic construct
SEQUENCE: 281
DYKDDDDKGS SGTGSGSGTS APITAYAQQT RGLLGCIITS LTGRDKNQVE GEVQIMSTAT  60
QTFLATCING VCWAVYHGAG TRTIASPKGP VIQMYTNVDQ DLVGWPAPQG SRSLTPCTCG  120
SSDLYLVTRH ADVIPVRRRG DGRGSLLSPR PISYLKGSSG GPLLCPAGHA VGLFRAAVCT  180
RGVAKAVDFI PVENLETTMR SPVFTDNSSP PAVTLTHPIT KIDTKYIMTC MSADLEVVTS  240
TWVLVGGVLA ALAAYCLSTG CVVIVGRIVL SGKPAIIPDR EVLYQEFEDV VPCSMGS     297

SEQ ID NO: 282          moltype = AA  length = 303
FEATURE                 Location/Qualifiers
source                  1..303
                        mol_type = protein
                        organism = synthetic construct
SEQUENCE: 282
DYKDDDDKGS SGTGSGSGTS APITAYAQQT RGLLGCIITS LTGRDKNQVE GEVQIMSTAT  60
QTFLATCING VCWAVYHGAG TRTIASPKGP VIQMYTNVDQ DLVGWPAPQG SRSLTPCTCG  120
SSDLYLVTRH ADVIPVRRRG DGRGSLLSPR PISYLKGSSG GPLLCPAGHA VGLFRAAVCT  180
RGVAKAVDFI PVENLETTMR SPVFTDNSSP PAVTLTHPIT KIDTKYIMTC MSADLEVVTS  240
TWVLVGGVLA ALAAYCLSTG CVVIVGRIVL SGKPAGSSGS SIIPDREVLY QEFEDVVPCS  300
MGS                                                                303

SEQ ID NO: 283          moltype = AA  length = 297
FEATURE                 Location/Qualifiers
source                  1..297
                        mol_type = protein
                        organism = synthetic construct
SEQUENCE: 283
DYKDDDDKGS SGTGSGSGTS APITAYAQQT RGLLGCIITS LTGRDKNQVE GEVQIVSTAT  60
QTLLATCING VCWAVYHGAG TRTIASPKGP VIQMYTNVDK DLVGWPAPQG SRSLTPCTCG  120
SSDLYLVTRH ADVIPVRRRG DRRGSLLSPR PISYLKGSSG GPLLCPAGHA VGLFRAAVCT  180
RGVAKAVYFI PVENLETTMR SPVFTDNSSP PAVTLTHPIT KIDTKYIMTC MSADLEVVTS  240
TWVLVGGVLA ALAAYCLSTG CVVIVGRIVL SGKPAIIPDR EVLYQEFEDV VPCSMGS     297

SEQ ID NO: 284          moltype = AA  length = 303
FEATURE                 Location/Qualifiers
source                  1..303
                        mol_type = protein
                        organism = synthetic construct
SEQUENCE: 284
DYKDDDDKGS SGTGSGSGTS APITAYAQQT RGLLGCIITS LTGRDKNQVE GEVQIVSTAT  60
QTLLATCING VCWAVYHGAG TRTIASPKGP VIQMYTNVDK DLVGWPAPQG SRSLTPCTCG  120
SSDLYLVTRH ADVIPVRRRG DRRGSLLSPR PISYLKGSSG GPLLCPAGHA VGLFRAAVCT  180
RGVAKAVYFI PVENLETTMR SPVFTDNSSP PAVTLTHPIT KIDTKYIMTC MSADLEVVTS  240
TWVLVGGVLA ALAAYCLSTG CVVIVGRIVL SGKPAGSSGS SIIPDREVLY QEFEDVVPCS  300
MGS                                                                303

SEQ ID NO: 285          moltype = AA  length = 6
FEATURE                 Location/Qualifiers
source                  1..6
                        mol_type = protein
                        organism = synthetic construct
SEQUENCE: 285
GSSGSS                                                             6

SEQ ID NO: 286          moltype = AA  length = 298
FEATURE                 Location/Qualifiers
source                  1..298
                        mol_type = protein
                        organism = synthetic construct
SEQUENCE: 286
VPLYGFTSIC GRRPEMEAAV STIPRFLQSS SGSMLDGRFD PQSAAHFFGV YDGHGGSQVA  60
NYCRERMHLA LAEEIAKEKP MLCDGDTWLE KWKKALFNSF LRVDSEIESV APETVGSTSV  120
VAVVFPSHIF VANCGDSRAV LCRGKTALPL SVDHKPDRED EAARIEAAGG KVIQWNGARV  180
FGVLAMSRSI GDRYLKPSII PDPEVTAVKR VKEDDCLILA SDGVWDVMTD EEACEMARKR  240
ILLWHKKNAV AGDASLLADE RRKEGKDPAA MSAAEYLSKL AIQRGSKDNI SVVVVDLK    298

SEQ ID NO: 287          moltype = AA  length = 305
FEATURE                 Location/Qualifiers
source                  1..305
                        mol_type = protein
                        organism = synthetic construct
SEQUENCE: 287
```

-continued

```
PLYGFTSICG RRPEMEDAVS TIPRFLQSSS GSMLDGRFDP QSAAHFFGVY DGHGGSQVAN  60
YCRERMHLAL AEEIAKEKPM LCDGDTWLEK WKKALFNSFL RVDSEIGSVA PETVGSTSVV  120
AVVFPSHIFV ANCGDSRAVL CRGKTALPLS VDHKPDREDE AARIEAAGGK VIQWNGARVF  180
GVLAMSRSIG DRYLKPSIIP DPEVTAVKRV KEDDCLILAS DGVWDVMTDE EACEMARKRI  240
LLWHKKNAVA GDASLLADER RKEGKDPAAM SAAEYLSKLA IQRGSKDNIS VVVVDLKDYK  300
DDDDK                                                            305

SEQ ID NO: 288         moltype = AA  length = 177
FEATURE                Location/Qualifiers
source                 1..177
                       mol_type = protein
                       organism = synthetic construct
SEQUENCE: 288
TQDEFTQLSQ SIAEFHTYQL GNGRCSSLLA QRIHAPPETV WSVVRRFDRP QIYKHFIKSC  60
NVSEDFEMRV GCTRDVNVIS GLPANTSRER LDLLDDDRRV TGFSITGGEH RLRNYKSVTT  120
VHRFEKEEEE ERIWTVVLES YVVDVPEGNS EEDTRLFADT VIRLNLQKLA SITEAMN     177

SEQ ID NO: 289         moltype = AA  length = 188
FEATURE                Location/Qualifiers
source                 1..188
                       mol_type = protein
                       organism = synthetic construct
SEQUENCE: 289
APTQDEFTQL SQSIAEFHTY QLGNGRCSSL LAQRIHAPPE TVWSVVRRFD RPQIYKHFIK  60
SCNVSEDFEM RVGCTRDVNV ISGLPANTSR ERLDLLDDDR RVTGFSITGG EHRLRNYKSV  120
TTVHRFEKEE EEERIWTVVL ESYVVDVPEG NSEEDTRLFA DTVIRLNLQK LASITEAMNY  180
PYDVPDYA                                                         188

SEQ ID NO: 290         moltype = AA  length = 109
FEATURE                Location/Qualifiers
source                 1..109
                       mol_type = protein
                       organism = synthetic construct
SEQUENCE: 290
SRGVQVETIS PGDGRTFPKR GQTCVVHYTG MLEDGKKFDS SRDRNKPFKF MLGKQEVIRG  60
WEEGVAQMSV GQRAKLTISP DYAYGATGHP GIIPPHATLV FDVELLKLE            109

SEQ ID NO: 291         moltype = AA  length = 92
FEATURE                Location/Qualifiers
source                 1..92
                       mol_type = protein
                       organism = synthetic construct
SEQUENCE: 291
ILWHEMWHEG LEEASRLYFG ERNVKGMFEV LEPLHAMMER GPQTLKETSF NQAYGRDLME  60
AQEWCRKYMK SGNVKDLLQA WDLYYHVFRR IS                              92

SEQ ID NO: 292         moltype = AA  length = 92
FEATURE                Location/Qualifiers
source                 1..92
                       mol_type = protein
                       organism = synthetic construct
SEQUENCE: 292
MKRDHHHHHH QDKKTMMMNE EDDGNGMDEL LAVLGYKVRS SEMADVAQKL EQLEVMMSNV  60
QEDDLSQLAT ETVHYNPAEL YTWLDSMLTD LN                              92

SEQ ID NO: 293         moltype = AA  length = 345
FEATURE                Location/Qualifiers
source                 1..345
                       mol_type = protein
                       organism = synthetic construct
SEQUENCE: 293
MAASDEVNLI ESRTVVPLNT WVLISNFKVA YNILRRPDGT FNRHLAEYLD RKVTANANPV  60
DGVFSFDVLI DRRINLLSRV YRPAYADQEQ PPSILDLEKP VDGDIVPVIL FFHGGSFAHS  120
SANSAIYDTL CRRLVGLCKC VVVSVNYRRA PENPYPCAYD DGWIALNWVN SRSWLKSKKD  180
SKVHIFLAGD SSGGNIAHNV ALRAGESGID VLGNILLNPM FGGNERTESE KSLDGKYFVT  240
VRDRDWYWKA FLPEGEDREH PACNPFSPRG KSLEGVSFPK SLVVVAGLDL IRDWQLAYAE  300
GLKKAGQEVK LMHLEKATVG FYLLPNNNHF HNVMDEISAF VNAEC                345

SEQ ID NO: 294         moltype = AA  length = 150
FEATURE                Location/Qualifiers
source                 1..150
                       mol_type = protein
                       organism = synthetic construct
SEQUENCE: 294
HTLYAPGGYD IMGYLDQIGN RPNPQVELGP VDTSCALILC DLKQKDTPIV YASEAFLYMT  60
GYSNAEVLGR NCRFLQSPDG MVKPKSTRKY VDSNTINTMR KAIDRNAEVQ VEVVNFKKNG  120
QRFVNFLTMI PVRDETGEYR YSMGFQCETE                                 150

SEQ ID NO: 295         moltype = AA  length = 150
```

-continued

```
FEATURE               Location/Qualifiers
source                1..150
                      mol_type = protein
                      organism = synthetic construct
SEQUENCE: 295
HTLYAPGGYD IMGYLRQIRN RPNPQVELGP VDTSCALILC DLKQKDTPIV YASEAFLYMT  60
GYSNAEVLGR NCRFLQSPDG MVKPKSTRKY VDSNTINTMR KAIDRNAEVQ VEVVNFKKNG  120
QRFVNFLTMI PVRDETGEYR YSMGFQCETE                                   150

SEQ ID NO: 296        moltype = AA  length = 171
FEATURE               Location/Qualifiers
source                1..171
                      mol_type = protein
                      organism = synthetic construct
SEQUENCE: 296
MNGAIGGDLL LNFPDMSVLE RQRAHLKYLN PTFDSPLAGF FADSSMITGG EMDSYLSTAG  60
LNLPMMYGET TVEGDSRLSI SPETTLGTGN FKKRKFDTET KDCNEKKKKM TMNRDDLVEE  120
GEEEKSKITE QNNGSTKSIK KMKHKAKKEE NNFSNDSSKV TKELEKTDYI H           171

SEQ ID NO: 297        moltype = AA  length = 612
FEATURE               Location/Qualifiers
source                1..612
                      mol_type = protein
                      organism = synthetic construct
SEQUENCE: 297
MKMDKKTIVW FRRDLRIEDN PALAAAAHEG SVFPVFIWCP EEEGQFYPGR ASRWWMKQSL  60
AHLSQSLKAL GSDLTLIKTH NTISAILDCI RVTGATKVVF NHLYDPVSLV RDHTVKEKLV  120
ERGISVQSYN GDLLYEPWEI YCEKGKPFTS FNSYWKKCLD MSIESVMLPP PWRLMPITAA  180
AEAIWACSIE ELGLENEAEK PSNALLTRAW SPGWSNADKL LNEFIEKQLI DYAKNSKKVV  240
GNSTSLLSPY LHFGEISVRH VFQCARMKQI IWARDKNSEG EESADLFLRG IGLREYSRYI  300
CFNFPFTHEQ SLLSHLRFFP WDADVDKFKA WRQGRTGYPL VDAGMRELWA TGWMHNRIRV  360
IVSSFAVKFL LLPWKWGMKY FWDTLLDADL ECDILGWQYI SGSIPDGHEL DRLDNPALQG  420
AKYDPEGEYI RQWLPELARL PTEWIHHPWD APLTVLKASG VELGTNYAKP IVDIDTAREL  480
LAKAISRTRE AQIMIGAAPD EIVADSFEAL GANTIKEPGL CPSVSSNDQQ VPSAVRYNGS  540
KRVKPEEEEE RDMKKSRGFD ERELFSTAES SSSSSVFFVS QSCSLASEGK NLEGIQDSSD  600
QITTSLGKNG CK                                                      612

SEQ ID NO: 298        moltype = AA  length = 224
FEATURE               Location/Qualifiers
source                1..224
                      mol_type = protein
                      organism = synthetic construct
SEQUENCE: 298
MSVIKPDMKI KLRMEGAVNG HPFAIEGVGL GKPFEGKQSM DLKVKEGGPL PFAYDILTTV  60
FCYGNRVFAK YPENIVDYFK QSFPEGYSWE RSMNYEDGGI CNATNDITLD GDCYIYEIRF  120
DGVNFPANGP VMQKRTVKWE PSTEKLYVRD GVLKGDVNMA LSLEGGGHYR CDFKTTYKAK  180
KVVQLPDYHF VDHHIEIKSH DKDYSNVNLH EHAEAHSELP RQAK                   224

SEQ ID NO: 299        moltype = AA  length = 224
FEATURE               Location/Qualifiers
source                1..224
                      mol_type = protein
                      organism = synthetic construct
SEQUENCE: 299
MSVIKPDMKI KLRMEGAVNG HPFAIEGVGL GKPFEGKQSM DLKVKEGGPL PFAYDILTTV  60
FCYGNRVFAK YPENIVDYFK QSFPEGYSWE RSMNYEDGGI CNATNDITLD GDCYIYEIRF  120
DGVNFPANGP VMQKRTVKWE PSTENLYVRD GVLKGDVNMA LSLEGGGHYR CDFKTTYKAK  180
KVVQLPDYHF VDHHIEIKSH DKDYSNVNLH EHAEAHSELP RQAK                   224

SEQ ID NO: 300        moltype = AA  length = 224
FEATURE               Location/Qualifiers
source                1..224
                      mol_type = protein
                      organism = synthetic construct
SEQUENCE: 300
MSVIKPDMKI KLRMEGAVNG HPFAIEGVGL GKPFEGKQSM DLKVKEGGPL PFAYDILTMA  60
FCYGNRVFAK YPENIVDYFK QSFPEGYSWE RSMHYEDGGS CNATNDITLD GDCYIYEIRF  120
DGVNFPANGP VMQKRTVKWE RSTENLYVRD GVLKSDGNYA LSLEGGGHYR CDFKTTYKAK  180
KVVQLPDYHS VDHHIEIKSH DKDYSNVNLH EHAEAHSELP RQAN                   224

SEQ ID NO: 301        moltype = AA  length = 236
FEATURE               Location/Qualifiers
source                1..236
                      mol_type = protein
                      organism = synthetic construct
SEQUENCE: 301
MVSKGEENNM AIIKEFMRFK VHMEGSVNGH EFEIEGEGEG RPYEAFQTAK LKVTKGGPLP  60
FAWDILSPQF MYGSKVYIKH PADIPDYFKL SFPEGFRWER VMNFEDGGII HVNQDSSLQD  120
GVFIYKVKLR GTNFPSDGPV MQKKTMGWEA SEERMYPEDG AHKAEIKKRL KLKDGGHYAA  180
```

```
EVKTTYKAKK PVQLPGAYIV DIKLDIVSHN EDYTIVEQYE RAEGRHSTGG MDELYK      236

SEQ ID NO: 302          moltype = AA  length = 595
FEATURE                 Location/Qualifiers
source                  1..595
                        mol_type = protein
                        organism = Homo sapiens
SEQUENCE: 302
MTMTLHTKAS GMALLHQIQG NELEPLNRPQ LKIPLERPLG EVYLDSSKPA VYNYPEGAAY  60
EFNAAAAANA QVYGQTGLPY GPGSEAAAFG SNGLGGFPPL NSVSPSPLML LHPPPQLSPF  120
LQPHGQQVPY YLENEPSGYT VREAGPPAFY RPNSDNRRQG GRERLASTND KGSMAMESAK  180
ETRYCAVCND YASGYHYGVW SCEGCKAFFK RSIQGHNDYM CPATNQCTID KNRRKSCQAC  240
RLRKCYEVGM MKGGIRKDRR GGRMLKHKRQ RDDGEGRGEV GSAGDMRAAN LWPSPLMIKR  300
SKKNSLALSL TADQMVSALL DAEPPILYSE YDPTRPFSEA SMMGLLTNLA DRELVHMINW  360
AKRVPGFVDL TLHDQVHLLE CAWLEILMIG LVWRSMEHPG KLLFAPNLLL DRNQGKCVEG  420
MVEIFDMLLA TSSRFRMMNL QGEEFVCLKS IILLNSGVYT FLSSTLKSLE EKDHIHRVLD  480
KITDTLIHLM AKAGLTLQQQ HQRLAQLLLI LSHIRHMSNK GMEHLYSMKC KNVVPLYDLL  540
LEMLDAHRLH APTSRGGASV EETDQSHLAT AGSTSSHSLQ KYYITGEAEG FPATV       595

SEQ ID NO: 303          moltype = AA  length = 222
FEATURE                 Location/Qualifiers
source                  1..222
                        mol_type = protein
                        organism = synthetic construct
SEQUENCE: 303
MAEEFVTLKD VGMDFTLGDW EQLGLEQGDT FWDTALDNCQ DLFLLDPPRP NLTSHPDGSE  60
DLEPLAGGSP EATSMAEEFV TLKDVGMDFT LGDWEQLGLE QGDTFWDTAL DNCQDLFLLD  120
PPRPNLTSHP DGSEDLEPLA GGSPEATSMA EEFVTLKDVG MDFTLGDWEQ LGLEQGDTFW  180
DTALDNCQDL FLLDPPRPNL TSHPDGSEDL EPLAGGSPEA TS                    222

SEQ ID NO: 304          moltype = AA  length = 314
FEATURE                 Location/Qualifiers
source                  1..314
                        mol_type = protein
                        organism = synthetic construct
SEQUENCE: 304
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPGK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKR  240
MEHLYSMKCK NVVPLYDLLL EMLDAHRLHA PTSRGGASVE ETDQSHLATA GSTSSHSLQK  300
YYITGEAEGF PATV                                                    314

SEQ ID NO: 305          moltype = AA  length = 314
FEATURE                 Location/Qualifiers
source                  1..314
                        mol_type = protein
                        organism = synthetic construct
SEQUENCE: 305
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPGK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKG  240
MEHLYSMKCK NVVPLYDLLL EAADAHRLHA PTSRGGASVE ETDQSHLATA GSTSSHSLQK  300
YYITGEAEGF PATA                                                    314

SEQ ID NO: 306          moltype = AA  length = 314
FEATURE                 Location/Qualifiers
source                  1..314
                        mol_type = protein
                        organism = synthetic construct
SEQUENCE: 306
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPVK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKG  240
MEHLYSMKCK NVVPLYDAAL EMLDAHRLHA PTSRGGASVE ETDQSHLATA GSTSSHSLQK  300
YYITGEAEGF PATV                                                    314

SEQ ID NO: 307          moltype = AA  length = 306
FEATURE                 Location/Qualifiers
source                  1..306
                        mol_type = protein
                        organism = synthetic construct
SEQUENCE: 307
PPQIEEACEL PECQVDAGNK VCNLQCNNHA CGWDGGDCSL NFNDPWKNCT QSLQCWKYFS  60
DGHCDSQCNS AGCLFDGFDC QLTEGQCNPL YDQYCKDHFS DGHCDQGCNS AECEWDGLDC  120
AEHVPERLAA GTLVLVVLLP PDQLRNNSFH FLRELSHVLH TNVVFKRDAQ GQQMIFPYYG  180
HEEELRKHPI KRSTVGWATS SLLPGTSGGR QRRELDPMDI RGSIVYLEID NRQCVQSSSQ  240
```

```
CFQSATDVAA FLGALASLGS LNIPYKIEAV KSEPVEPPLP SQLHLMYVAA AAFVLLFFVG  300
CGVLLS                                                             306

SEQ ID NO: 308          moltype = AA  length = 358
FEATURE                 Location/Qualifiers
source                  1..358
                        mol_type = protein
                        organism = synthetic construct
SEQUENCE: 308
PCVGSNPCYN QGTCEPTSEN PFYRCLCPAK FNGLLCHILD YSFTGGAGRD IPPPQIEEAC  60
ELPECQVDAG NKVCNLQCNN HACGWDGGDC SLNFNDPWKN CTQSLQCWKY FSDGHCDSQC  120
NSAGCLFDGF DCQLTEGQCN PLYDQYCKDH FSDGHCDQGC NSAECEWDGL DCAEHVPERL  180
AAGTLVLVVL LPPDQLRNNS FHFLRELSHV LHTNVVFKRD AQGQQMIFPY YGHEEELRKH  240
PIKRSTVGWA TSSLLPGTSG GRQRRELDPM DIRGSIVYLE IDNRQCVQSS SQCFQSATDV  300
AAFLGALASL GSLNIPYKIE AVKSEPVEPP LPSQLHLMYV AAAAFVLLFF VGCGVLLS    358

SEQ ID NO: 309          moltype = AA  length = 4
FEATURE                 Location/Qualifiers
source                  1..4
                        mol_type = protein
                        organism = synthetic construct
SEQUENCE: 309
PGER                                                               4

SEQ ID NO: 310          moltype = AA  length = 5
FEATURE                 Location/Qualifiers
source                  1..5
                        mol_type = protein
                        organism = synthetic construct
SEQUENCE: 310
TGSQK                                                              5

SEQ ID NO: 311          moltype = AA  length = 5
FEATURE                 Location/Qualifiers
source                  1..5
                        mol_type = protein
                        organism = synthetic construct
SEQUENCE: 311
TGEKP                                                              5

SEQ ID NO: 312          moltype = AA  length = 4
FEATURE                 Location/Qualifiers
source                  1..4
                        mol_type = protein
                        organism = synthetic construct
SEQUENCE: 312
THLR                                                               4

SEQ ID NO: 313          moltype = AA  length = 7
FEATURE                 Location/Qualifiers
source                  1..7
                        mol_type = protein
                        organism = synthetic construct
SEQUENCE: 313
TGGGEKP                                                            7

SEQ ID NO: 314          moltype = AA  length = 55
FEATURE                 Location/Qualifiers
source                  1..55
                        mol_type = protein
                        organism = synthetic construct
SEQUENCE: 314
FHYDRNNIAV GADESVVKEA HREVINSSTE GLLLNIDKDI RKILSGYIVE IEDTE       55

SEQ ID NO: 315          moltype = AA  length = 7
FEATURE                 Location/Qualifiers
source                  1..7
                        mol_type = protein
                        organism = synthetic construct
SEQUENCE: 315
VEIEDTE                                                            7

SEQ ID NO: 316          moltype = AA  length = 18
FEATURE                 Location/Qualifiers
source                  1..18
                        mol_type = protein
                        organism = synthetic construct
SEQUENCE: 316
KDIRKILSGY IVEIEDTE                                                18
```

```
SEQ ID NO: 317          moltype = AA  length = 28
FEATURE                 Location/Qualifiers
source                  1..28
                        mol_type = protein
                        organism = synthetic construct
SEQUENCE: 317
STEGLLLNID KDIRKILSGY IVEIEDTE                                28

SEQ ID NO: 318          moltype = AA  length = 14
FEATURE                 Location/Qualifiers
source                  1..14
                        mol_type = protein
                        organism = synthetic construct
SEQUENCE: 318
EVKQENRLLN ESES                                               14

SEQ ID NO: 319          moltype = AA  length = 46
FEATURE                 Location/Qualifiers
source                  1..46
                        mol_type = protein
                        organism = synthetic construct
SEQUENCE: 319
VGADESVVKE AHREVINSST EGLLLNIDKD IRKILSGYIV EIEDTE            46

SEQ ID NO: 320          moltype = AA  length = 5
FEATURE                 Location/Qualifiers
source                  1..5
                        mol_type = protein
                        organism = synthetic construct
SEQUENCE: 320
GGSGG                                                         5

SEQ ID NO: 321          moltype = AA  length = 5
FEATURE                 Location/Qualifiers
source                  1..5
                        mol_type = protein
                        organism = synthetic construct
SEQUENCE: 321
GGGSG                                                         5

SEQ ID NO: 322          moltype = AA  length = 5
FEATURE                 Location/Qualifiers
source                  1..5
                        mol_type = protein
                        organism = synthetic construct
SEQUENCE: 322
CVRGS                                                         5

SEQ ID NO: 323          moltype = AA  length = 6
FEATURE                 Location/Qualifiers
source                  1..6
                        mol_type = protein
                        organism = synthetic construct
SEQUENCE: 323
GGGGSG                                                        6

SEQ ID NO: 324          moltype = AA  length = 9
FEATURE                 Location/Qualifiers
source                  1..9
                        mol_type = protein
                        organism = synthetic construct
SEQUENCE: 324
GGSGSGSAC                                                     9

SEQ ID NO: 325          moltype = AA  length = 9
FEATURE                 Location/Qualifiers
source                  1..9
                        mol_type = protein
                        organism = synthetic construct
SEQUENCE: 325
LEGGGGSGG                                                     9

SEQ ID NO: 326          moltype = AA  length = 8
FEATURE                 Location/Qualifiers
source                  1..8
                        mol_type = protein
                        organism = synthetic construct
SEQUENCE: 326
```

```
GGGGSGGT                                                        8

SEQ ID NO: 327          moltype = AA  length = 11
FEATURE                 Location/Qualifiers
source                  1..11
                        mol_type = protein
                        organism = synthetic construct
SEQUENCE: 327
SGGGSGGSGS S                                                    11

SEQ ID NO: 328          moltype = AA  length = 10
FEATURE                 Location/Qualifiers
source                  1..10
                        mol_type = protein
                        organism = synthetic construct
SEQUENCE: 328
PGAGSSGDIM                                                      10

SEQ ID NO: 329          moltype = AA  length = 12
FEATURE                 Location/Qualifiers
source                  1..12
                        mol_type = protein
                        organism = synthetic construct
SEQUENCE: 329
GSSGTGSGSG TS                                                   12

SEQ ID NO: 330          moltype = AA  length = 6
FEATURE                 Location/Qualifiers
source                  1..6
                        mol_type = protein
                        organism = synthetic construct
SEQUENCE: 330
GGSGGS                                                          6

SEQ ID NO: 331          moltype = AA  length = 24
FEATURE                 Location/Qualifiers
source                  1..24
                        mol_type = protein
                        organism = synthetic construct
SEQUENCE: 331
GGSGGSGGSG GSGGSGGSGG SGGS                                      24

SEQ ID NO: 332          moltype = AA  length = 40
FEATURE                 Location/Qualifiers
source                  1..40
                        mol_type = protein
                        organism = synthetic construct
SEQUENCE: 332
GGGGSGGGGS GGGGSGGGGS GGGGSGGGGS GGGGSGGGGS                     40

SEQ ID NO: 333          moltype = AA  length = 5
FEATURE                 Location/Qualifiers
source                  1..5
                        mol_type = protein
                        organism = synthetic construct
SEQUENCE: 333
GGGGS                                                           5

SEQ ID NO: 334          moltype = AA  length = 6
FEATURE                 Location/Qualifiers
source                  1..6
                        mol_type = protein
                        organism = synthetic construct
SEQUENCE: 334
GGSGGS                                                          6

SEQ ID NO: 335          moltype = AA  length = 16
FEATURE                 Location/Qualifiers
source                  1..16
                        mol_type = protein
                        organism = synthetic construct
SEQUENCE: 335
GSGSGSGSGS GSGSGS                                               16

SEQ ID NO: 336          moltype = AA  length = 5
FEATURE                 Location/Qualifiers
source                  1..5
                        mol_type = protein
                        organism = synthetic construct
```

```
SEQUENCE: 336
TGSKP                                                                5

SEQ ID NO: 337          moltype = AA  length = 5
FEATURE                 Location/Qualifiers
source                  1..5
                        mol_type = protein
                        organism = synthetic construct
SEQUENCE: 337
TGQKP                                                                5

SEQ ID NO: 338          moltype = AA  length = 5
FEATURE                 Location/Qualifiers
source                  1..5
                        mol_type = protein
                        organism = synthetic construct
SEQUENCE: 338
TGGKP                                                                5

SEQ ID NO: 339          moltype = AA  length = 6
FEATURE                 Location/Qualifiers
source                  1..6
                        mol_type = protein
                        organism = synthetic construct
SEQUENCE: 339
TGSQKP                                                               6

SEQ ID NO: 340          moltype = AA  length = 21
FEATURE                 Location/Qualifiers
source                  1..21
                        mol_type = protein
                        organism = synthetic construct
VARIANT                 1..3
                        note = May be absent
SEQUENCE: 340
GSGEGRGSLL TCGDVEENPG P                                              21

SEQ ID NO: 341          moltype = AA  length = 22
FEATURE                 Location/Qualifiers
source                  1..22
                        mol_type = protein
                        organism = synthetic construct
VARIANT                 1..3
                        note = May be absent
SEQUENCE: 341
GSGATNFSLL KQAGDVEENP GP                                             22

SEQ ID NO: 342          moltype = AA  length = 23
FEATURE                 Location/Qualifiers
source                  1..23
                        mol_type = protein
                        organism = synthetic construct
VARIANT                 1..3
                        note = May be absent
SEQUENCE: 342
GSGQCTNYAL LKLAGDVESN PGP                                            23

SEQ ID NO: 343          moltype = AA  length = 25
FEATURE                 Location/Qualifiers
source                  1..25
                        mol_type = protein
                        organism = synthetic construct
VARIANT                 1..3
                        note = May be absent
SEQUENCE: 343
GSGVKQTLNF DLLKLAGDVE SNPGP                                          25

SEQ ID NO: 344          moltype = AA  length = 7
FEATURE                 Location/Qualifiers
source                  1..7
                        mol_type = protein
                        organism = synthetic construct
SEQUENCE: 344
PKKKRKV                                                              7

SEQ ID NO: 345          moltype = AA  length = 39
FEATURE                 Location/Qualifiers
source                  1..39
                        mol_type = protein
```

```
                         organism = synthetic construct
SEQUENCE: 345
DYKDHDGDYK DHDIDYKDDD DKMAPKKKRK VGIHGVPGG                         39

SEQ ID NO: 346           moltype = AA  length = 6
FEATURE                  Location/Qualifiers
source                   1..6
                         mol_type = protein
                         organism = synthetic construct
SEQUENCE: 346
DTYRYI                                                             6

SEQ ID NO: 347           moltype = AA  length = 9
FEATURE                  Location/Qualifiers
source                   1..9
                         mol_type = protein
                         organism = synthetic construct
SEQUENCE: 347
YPYDVPDYA                                                          9

SEQ ID NO: 348           moltype = AA  length = 8
FEATURE                  Location/Qualifiers
source                   1..8
                         mol_type = protein
                         organism = synthetic construct
SEQUENCE: 348
DYKDDDDK                                                           8

SEQ ID NO: 349           moltype = AA  length = 235
FEATURE                  Location/Qualifiers
source                   1..235
                         mol_type = protein
                         organism = unidentified
SEQUENCE: 349
VSKGEEDNMA IIKEFMRFKV HMEGSVNGHE FEIEGEGEGR PYEGTQTAKL KVTKGGPLPF  60
AWDILSPQFM YGSKAYVKHP ADIPDYLKLS FPEGFKWERV MNFEDGGVVT VTQDSSLQDG  120
EFIYKVKLRG TNFPSDGPVM QKKTMGWQAS SERMYPEDGA LKGEIKQRLK LKDGGHYDAE  180
VKTTYKAKKP VQLPGAYNVN IKLDITSHNE DYTIVEQYER AEGRHSTGGM DELYK       235

SEQ ID NO: 350           moltype = AA  length = 335
FEATURE                  Location/Qualifiers
source                   1..335
                         mol_type = protein
                         organism = synthetic construct
SEQUENCE: 350
RKVCNGIGIG EFKDSLSINA TNIKHFKNCT SISGDLHILP VAFRGDSFTH TPPLDPQELD  60
ILKTVKEITG FLLIQAWPEN RTDLHAFENL EIIRGRTKQH GQFSLAVVSL NITSLGLRSL  120
KEISDGDVII SGNKNLCYAN TINWKKLFGT SGQKTKIISN RGENSCKATG QVCHALCSPE  180
GCWGPEPRDC VSCRNVSRGR ECVDKCNLLE GEPREFVENS ECIQCHPECL PQAMNITCTG  240
RGPDNCIQCA HYIDGPHCVK TCPAGVMGEN NTLVWKYADA GHVCHLCHPN CTYGCTGPGL  300
EGCPTNGPKI PSIATGMVGA LLLLLVVALG IGLFM                             335

SEQ ID NO: 351           moltype = DNA  length = 666
FEATURE                  Location/Qualifiers
source                   1..666
                         mol_type = other DNA
                         organism = synthetic construct
SEQUENCE: 351
atggcggaag agtttgtaac gctcaaggat gtaggaatgg attttacatt gggtgactgg  60
gaacagcttg gtttggaaca gggtgatacg ttctgggata ctgcattgga taactgccaa  120
gatctgttcc tgctggatcc cccgaggcca aatcttacct cacatcccga tggcagtgag  180
gatcttgaac ctctggcagg aggaagtccc gaagcaacta gtatggcaga agaatttgtg  240
acattgaagg acgtgggaat ggactttaca ttgggggact gggaacaatt gggtcttgag  300
cagggtgata cattttggga cacagctctc gacaattgcc aagatctttt cttgctggat  360
ccaccccgcc ctaacctgac atcacatcca gacggtagcg aggatttgga acccctggcc  420
ggaggtagtc ctgaggcaac ctccatggcg gaggaatttg tgactctgaa ggatgtaggg  480
atggacttca cgctcggaga ttgggagcag ctcggattgg agcaaggtga cacattctgg  540
gacaccgcac ttgacaactg ccaagatctt tttcttctcg acccaccgcg gccgaacttg  600
actagccacc ccgatggctc tgaagatctt gaaccactcg ccgggggatc acctgaagcc  660
acgagc                                                             666

SEQ ID NO: 352           moltype = AA  length = 6
FEATURE                  Location/Qualifiers
source                   1..6
                         mol_type = protein
                         organism = synthetic construct
SEQUENCE: 352
DDIVPC                                                             6
```

```
SEQ ID NO: 353          moltype = AA  length = 6
FEATURE                 Location/Qualifiers
source                  1..6
                        mol_type = protein
                        organism = synthetic construct
SITE                    1
                        note = Acetylated residue
SEQUENCE: 353
DEMEEC                                                          6

SEQ ID NO: 354          moltype = AA  length = 6
FEATURE                 Location/Qualifiers
source                  1..6
                        mol_type = protein
                        organism = synthetic construct
SITE                    1
                        note = Acetylated residue
SEQUENCE: 354
DEMEFC                                                          6

SEQ ID NO: 355          moltype = AA  length = 21
FEATURE                 Location/Qualifiers
source                  1..21
                        mol_type = protein
                        organism = synthetic construct
SEQUENCE: 355
GELDELVYLL DGPGYDPIHS D                                         21

SEQ ID NO: 356          moltype = AA  length = 4
FEATURE                 Location/Qualifiers
source                  1..4
                        mol_type = protein
                        organism = synthetic construct
SEQUENCE: 356
CCHH                                                            4

SEQ ID NO: 357          moltype = AA  length = 10
FEATURE                 Location/Qualifiers
source                  1..10
                        mol_type = protein
                        organism = synthetic construct
SEQUENCE: 357
GGGGSGGGGS                                                      10

SEQ ID NO: 358          moltype = AA  length = 24
FEATURE                 Location/Qualifiers
source                  1..24
                        mol_type = protein
                        organism = synthetic construct
VARIANT                 1..24
                        note = This sequence may encompass 1-8 GGS repeating units
SEQUENCE: 358
GGSGGSGGSG GSGGSGGSGG SGGS                                      24

SEQ ID NO: 359          moltype = AA  length = 40
FEATURE                 Location/Qualifiers
source                  1..40
                        mol_type = protein
                        organism = synthetic construct
VARIANT                 1..40
                        note = This sequence may encompass 1-8 GGGGS repeating units
SEQUENCE: 359
GGGGSGGGGS GGGGSGGGGS GGGGSGGGGS GGGGSGGGGS                     40

SEQ ID NO: 360          moltype = AA  length = 16
FEATURE                 Location/Qualifiers
source                  1..16
                        mol_type = protein
                        organism = synthetic construct
VARIANT                 1..16
                        note = This sequence may encompass 1-8 GS repeating units
SEQUENCE: 360
GSGSGSGSGS GSGSGS                                               16
```

REGULATED SYNTHETIC GENE ACTIVATION SYSTEMS

CROSS-REFERENCE TO RELATED APPLICATIONS

This application claims benefit under 35 U.S.C. § 119(e) of U.S. Provisional Application No. 63/523,569 filed Jun. 27, 2023, the contents of which are incorporated herein by reference in their entirety.

GOVERNMENT SUPPORT

This invention was made with government support under contract No. R01EB029483 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on Sep. 23, 2024, is named 701586-000114USPT_SL.xml and is 469,842 bytes in size.

TECHNICAL FIELD

The technology described herein relates to regulated synthetic gene activation systems, including humanized hybrid transcription activator domains (hhTADs) and constructs comprising them.

BACKGROUND

Cells function as intricate information processors, capable of sensing a wide range of environmental cues, carrying out elaborate calculations, and generating numerous outcomes, such as gene expression, signal molecule release, morphological alterations, and cell growth. Additionally, various cell types have developed unique abilities to adapt to diverse environments and execute specific functions. These characteristics position cells as prime candidates for intelligent therapeutics that offer improved safety and effectiveness. In fact, several cell types have been explored for the creation of cell therapies, encompassing bacteria and stem cell treatments.

Cell-based therapies offer numerous benefits, including maintaining persistence in patients for extended disease management, involving endogenous cells in a unified response, and applying synthetic biology to achieve precise control over their functions. The capabilities of engineered cell systems have advanced in several areas, such as identifying and targeting cancer cells, regulating the spatiotemporal activity of therapies in response to drugs or antigens, and guiding stem cells to differentiate into intricate tissues. Specifically, human immune cells have emerged as one of the most crucial cell types for developing therapeutics, especially in the context of cancer treatment.

There is however a need to simultaneously tackle safety and efficacy challenges to develop efficient immune cell therapies. This can be achieved via enhancing precision and control. Synthetic biology, which centers on the predictable reprogramming of living cells, holds great potential in this area. More specifically, mammalian synthetic biology is devoted to creating tools and innovative gene circuits to regulate and reprogram diverse functions in mammalian cells.

A key aspect of synthetic biology is the engineering of new biological functions through the identification, analysis, and repurposing of molecular components. The components can then be used to attain the capability to predict and generate a desired output level for any given input. There is great need to manage simple inputs, such as small molecules, which in turn govern more intricate outputs, for example, to regulate immune responses to specific cancer antigens in engineered T cells.

SUMMARY

The technology described herein is directed to compositions and methods to control gene expression. In general, the technology described herein relates to constructs comprising a transcriptional effector domain (TED) in combination with a transcriptional activator (TA) domain. The TED increases the transcriptional activation of the TA compared to a construct with the TA but lacking the TED. The TED can be derived from a human protein, such as the TIMs domain of human IWS1. Use of constructs comprising such human domains allows for clinical use, without concern for foreign immune-activation, such as can occur with non-human (e.g., virally derived) constructs. The TEDs described herein can function in both dual vector and single vector systems. The TEDs described herein can drive more robust expression of a large payload compared a construct not comprising the TED (see e.g., FIG. 15).

In some aspects, described herein are synthetic transcription factors (synTFs) comprising the TED and TA, which further comprise a regulator protein (RP), where the regulator protein regulates the activity of the synTF. In particular, the synTFs according to the methods, systems and compositions as disclosed herein comprise (i) a DNA binding domain (DBD) which binds to a target nucleic acid sequence (or target DNA binding motif (DBM)) located 3' of a promoter that is operatively linked to the nucleic acid of a gene of interest (GOI) to be expressed, (ii) an effector domain (ED) (e.g., TA and TED) and a regulator protein (RP), where the regulator protein controls the coupling of the DNA binding domain (DBD) with the effector domain (ED), or controls the cellular localization of the ED, such that when the ED and DBD are attached and/or located in the nucleus, the ED can function to recruit translation machinery to the promoter to regulate gene expression of a gene of interest. In some embodiments, the ED can be a transcriptional activator (TA) in combination with a transcriptional effector domain (TED), thereby turning on gene expression when the ED is present at the transcription start site of a gene of interest.

In some embodiments of the systems, compositions and methods as disclosed herein, the regulator protein of the SynTF is selected from a protease, a pair of inducible proximity domains (IPDs) or a translocation domain (i.e., a cytosolic sequestering protein), each of which are described herein and in more detail below.

In some embodiments of the systems, compositions and methods as disclosed herein, the synTF comprises a regulator protein that is a self-cleaving protease, for example, one exemplary protease is NS3. SynTFs comprising self-cleaving proteases can also be referred to herein as "repressible proteases SynTF". In such embodiments of the systems, compositions and methods disclosed herein, the DBD is directly linked or indirectly linked (or coupled) to the effector domain, and the protease regulator protein (typically located between the DBD and ED) controls the coupling of the DBD to the ED. In such an embodiment, in the presence of an agent which inhibits the regulator protein (e.g., NS3 protein), the DBD and ED remain coupled or intact (either directly or indirectly) and the effector domain can control gene expression from the promoter (i.e., turning on gene expression of the gene of interest (GOI) if the ED is a TA). In such an embodiment, in the absence of an agent which inhibits the regulator protein (e.g., NS3 protein), the linkage between the DBD and ED is broken or cleaved, and therefore the ED is not brought into proximity of the transcription start site of the gene (or the ED dissociates from the start site), and therefore the TA can no longer initiate gene expression of the GOI.

In another embodiment of the systems, compositions and methods as disclosed herein, the synTF comprises a regulator protein that is a pair of inducer proximity domains (referred to as an "IPD pair") which is located between the DBD and ED, where each domain of the IPD come together in the presence of an inducer agent, and therefore linking the DBD and ED and controlling gene expression. SynTFs comprising an IPD pair can also be referred to herein as a "heterodimerization domain SynTF". For example, in such embodiments, where the regulator protein is an IPD pair, each domain of the IPD pair is attached to either the DBD or the ED, such that in the presence of an inducer agent, each domain of the IPD bind to the inducer agent, thereby indirectly coupling the DBD with the ED, such that when the DBD binds to a promoter region, the ED can control gene expression from the promoter (i.e., turning on gene expression if the ED is a TA). In alternative embodiments where the RP is an IPD pair, in the absence of the inducer agent, the DBD and ED remain uncoupled, and therefore the ED is not in a position to regulate gene transcription from the transcription start site at the GOI. Exemplary IPD pairs and their inducing agents are disclosed herein.

In some embodiments of the systems, compositions and methods as disclosed herein, the synTF comprises a regulator protein that is a translocation domain. In some embodiments, a translocation domain is a cytosolic sequestering protein, for example, one exemplary cytosolic sequestering protein is ERT2 and variants thereof. SynTFs comprising a translocation domain, e.g., a cytosolic sequestering protein can also be referred to herein as "Translocation Domain SynTF". In such embodiments of the systems, compositions and methods disclosed herein, the DBD is directly linked or indirectly linked (or coupled) to the effector domain, and the translocation domain, e.g., a cytosolic sequestering protein regulator protein (which can be attached to either the ED, or DBD or located between the DBD and ED) controls the cellular localization of the synTF comprising the DBD-ED. In such an embodiment, in the absence of a ligand that binds to the cytosolic sequestering protein, the cytosolic sequestering protein sequesters the ED and coupled DBD in the cytosol, and therefore the ED is not brought into proximity of the transcription start site of the gene (or the ED dissociates from the start site), and therefore the TA can no longer initiate gene expression of the GOI. In contrast, in the presence of a ligand that binds to the cytosolic sequestering protein, the cytosolic sequestering protein is inhibited, allowing the DBD-ED of the synTF to translocate from the cytosol to the nucleus where the DBD can bind to the DNA binding motif (DBM) and the effector domain (ED) can control gene expression from the promoter (i.e., turning on gene expression of the gene of interest (GOI) if the ED is a TA).

Another aspect of the systems, compositions and methods as disclosed herein are synTFs comprising a small-molecule assisted shutoff (SMASh) domain, which can also be referred to herein as an "induced degradation domain." In general, SMASh domains function to target the polypeptide that is attached to the SMASh domain for degradation. In some embodiments, the SMASh domain is attached to a synTF comprising a regulator protein that is an inducer proximity domain pair (IPD) or a cytosolic sequestering protein. In alternative embodiments, the regulator protein can be a SMASh domain (i.e., the SMASh domain replaces a self-cleaving protease regulator protein in the synTF).

In all aspects of the methods, systems and compositions disclosed herein, a SMASh domain comprises a self-cleaving protease and a degron domain. In some embodiments, the self-cleaving protease is a NS3 protease or variant thereof as disclosed herein. In some embodiments, the self-cleaving protease of the SMASh domain comprises: an NS3 protease domain, a partial NS3 helical domain, and NS4A domain, and can be fused to the N-terminal or C-terminal of a synTF described herein. Without being limited to theory and by way of explanation only, when a SMASh domain is attached to a synTF as disclosed herein, and when there is an inhibitor of the SMASh domain self-cleaving protease present, both the SMASh domain and the attached synTF are targeted for degradation. This is referred to as "SynTF-degradation" and results in the synTF being "SynTF-OFF"—that is because the synTF is degraded, the synTF cannot bind to the DBM, or regulate the expression of the gene of interest, regardless of the type of effector domain present in the synTF. Conversely, when an inhibitor of the self-cleaving protease is absent, the self-cleaving protease cleaves (or uncouples) the SMASh domain from the synTF, and only the SMASh domain is targeted for degradation, and the activity of the released synTF is regulated by way of the regulator protein. As such, when a SMASh domain is attached to the synTF, in the absence of the protease inhibitor, it is referred to "SMASh-degradation" and results in the synTF being "SynTF-ON" permitting the synTF to be regulated by the regulator protein, and gene expression can occur when the ED is a transcription activator. Accordingly, the presence of a SMASh domain attached to the synTF enables a second level of control for the expression of the GOI in addition to the regulator protein.

In some embodiments, the SMASh domain by itself serves as the regulator protein of a synTF (i.e., SMASh domain replaces a self-cleaving protease regulator protein), and is referred to as an Induced Degradation Domain SynTF. In such embodiments, where the SMASh domain serves as the regulator protein, the SMASh domain can be attached to either the ED or the DBD of the synTF, and in the absence of a NS3 protease inhibitor, the NS3 protease is active and the SMASh domain uncouples from the synTF, thereby resulting in only the SMASh domain being targeted for degradation, and the synTF comprising the DBD and the coupled ED enabling to control gene expression from the promoter (i.e., the DBD binds to the DBM, bringing the ED in close proximity to the promoter and turning on gene expression of the GOI if the ED is a TA). In such an embodiment, in the absence of an agent which inhibits the regulator protein (e.g., NS3 protein), the linkage between the DBD and ED is broken or cleaved, and therefore the ED is not brought into proximity of the transcription start site of the gene (or the ED dissociates from the start site), and therefore the TA can no longer initiate gene expression of the GOI.

In some embodiments, where the SMASh domain is attached to translocation domain synTF (e.g., where the regulator protein is a sequestering protein), or a heterodimerization domain synTF (i.e., where the regulator protein is pair of inducible proximity domains (IPD pair)), the SMASH domain can be referred to as a "SMASh tag" and can be attached to the C-terminal or N-terminal of a synTF. By way of an example only, a C-terminal SMASh tag attached to the C-terminal of an ED or regulator protein of a synTF can comprise in the following N-terminal to C-terminal order: a NS3 cleavage site, at least one linker, a NS3 domain, a NS3 partial helicase, a NS4A domain, wherein the SMASh tag is fused to the C-terminus of the effector domain of the synTF. In some embodiments and by way of an example only, where a SMASh tag is fused to the N-terminus of a synTF (referred to herein as a "N-terminal SMASh tag"), the SMASh tag comprises in a N-terminal to C-terminal order: at least one Linker, a NS3 domain, a NS3 partial helicase, a NS4 domain, and a NS3 cleavage site, wherein the SMASh tag is fused to the N-terminus of the synTF.

Another aspect of the technology disclosed herein relates to a system for controlling gene expression of a gene of interest (GOI), where the system comprises a synTF described herein and a nucleic acid construct comprising the elements that the synTF binds to regulate gene expression. In particular, in some aspects, the system comprising (i) at least one synthetic transcription factor (synTF) as disclosed herein, and (ii) at least a nucleic acid construct, where the synTF comprises at least one DNA binding domain (DBD), a transcriptional effector domain (ED) (e.g., TA and TED), and at least one regulator protein (RP), and where the ED is directly or indirectly coupled or linked to the DBD, and where the coupling is regulated by the at least one RP, or wherein the cellular localization of the ED linked to the DBD is regulated by the at least one RP, and where the at least one RP is regulated by an RP inducer, where the DBD can bind to a target DNA binding motif (DBM) located upstream of a promoter operatively linked to a gene, and where the nucleic acid construct comprises (i) at least one target DNA binding motif (DBM) comprising a target nucleic acid for binding of the at least one DBD of the synTF, and (ii) a promoter sequence located 3' of the at least one DBM, and (iii) a gene of interest (GOI) operatively linked to the promoter sequence. In some embodiments where the regulator protein of the synTFs regulates the coupling of the ED to the DBD (e.g., protease domain synTF or induced proximity domain synTFs), in the presence of the RP inducer, the coupling of the ED to the DBD of the synTF is maintained, permitting the ED to be in proximity to the promoter sequence when the DBD binds to the DNA binding motif (DBM), where the ED controls the expression of the gene of interest ("ED-on"). In embodiments where the ED is a transcriptional activator (TA), it results in turning on gene expression ("TA-on" (expression)). In contrast, where the RP inducer is absent, the coupling of the ED to the DBD of the synTF is severed, preventing the ED from being in proximity to the promoter sequence when the DBD binds to the DNA binding motif (DBM), preventing gene expression of the gene of interest ("ED-off"). In embodiments where the ED is a transcriptional activator (TA), it results in turning off the gene expression ("TA-off" (no expression)).

In embodiments where the regulator protein of the synTF regulates the cellular localization of the synTF (DBD and linked ED), when an RP inducer is present, the ED coupled to the DBD of the synTF is not sequestered in the cytosol, permitting the DBD to bind to the DNA binding motif (DBM) and permitting the transcriptional effector domain (ED) to be in proximity to the promoter sequence to control the expression of the gene of interest ("ED-on"). In embodiments where the ED is a transcriptional activator (TA), it results in turning on gene expression ("TA-on" (expression)).

Moreover, when the RP inducer is absent, the ED coupled to the DBD of the synTF is sequestered in the cytosol, preventing the DBD of the synTF from binding to the DBM, and preventing the effector domain (ED) from being in proximity to the promoter sequence, preventing expression of the gene of interest ("ED-off"). In embodiments where the ED is a transcriptional activator (TA), it results in turning off the gene expression ("TA-off" (no expression)).

TABLE 2 table summarizing the influence of the presence or absence of regulator protein inducers on ultimate expression of the gene of interest.

| SynTF | RP inducer → effect on the SynTF binding to the DBM | Effector domain | Gene expression ON or OFF |
|---|---|---|---|
| Protease domain | Present → ED-On | TA → "TA-on" | ON |
| syn TF | Absent → ED-Off | TA → "TA-off" | OFF |
| Induced proximity | Present → ED-On | TA → "TA-on" | ON |
| domain synTF | Absent → ED-Off | TA → "TA-off" | OFF |
| Translocation domain | Present > ED-On | TA → "TA-on" | ON |
| syn TF | Absent → ED-Off | TA → "TA-off" | OFF |
| Induced degradation | Present → ED-Off, Syn-degradation | TA → "TA-off" | OFF |
| domain synTF | Absent → ED-On, SMASh degradation | TA → "TA-on" | ON |

Accordingly, whether gene expression of the GOI occurs is dependent on 3 levels of control, including but not limited to; (i) the type of regulator protein in the synTF, (ii) the presence or absence of a regulator protein inducer (RP inducer), and (iii) the type of effector domain (e.g., presence or absence of TED in combination with the TA).

Moreover, in some embodiments, the system for controlling gene expression can be configured for an additional level of control for the gene expression, depending on whether there is a SMASh domain attached to the synTF, as disclosed herein. For example, attachment of a SMASh domain to a synTF will result in the following outcomes: if an inhibitor to the SMASh protease is present, the SMASh protease activity is inhibited, resulting in the synTF being degraded ("Syn-degradation") and preventing the DBD of the synTF binding to the DBM and controlling the expression of the gene of interest ("synTF-degradation"; TA-off (no expression). In alternative embodiments, if an inhibitor to the SMASh protease is absent, the SMASh protease is active and self cleaves/uncouples from the synTF, resulting the SMASh domain being targeted for degradation and allowing the DBD of the synTF to bind to the DBM and the ED of synTF to control the expression of the gene of interest ("SMASh-degradation", TA-on (yes-expression)).

Other aspects of the technology described herein relate to a cell comprising the nucleic acid sequences as disclosed herein for binding of the synTF to regulate the expression of the gene of interest, and also a nucleic acid encoding the synthetic transcription factor. In some embodiments, the nucleic acid sequences are on separate constructs, and in some embodiments, they are the same construct, as disclosed herein and referred to as a "single vector".

Other embodiments will become readily apparent from the disclosure. Aspects of the present invention teach certain benefits in construction and use which give rise to the exemplary advantages described below.

Other features and advantages of aspects of the present invention will become apparent from the following more detailed description, taken in conjunction with the accompanying drawings, which illustrate, by way of example, the principles of aspects of the invention.

Accordingly, in one aspect described herein is a synthetic transcription factor (synTF) comprising: (a) at least one DNA binding domain (DBD), (b) a transcriptional activator domain (TA), (c) a transcriptional effector domain (TED), and (d) at least one regulator protein (RP), and wherein the TED increases the transcriptional activation of the synTF compared to an otherwise identical synTF lacking the TED, wherein the TA is directly or indirectly coupled to the DBD, and wherein the coupling is regulated by the at least one RP, or wherein cellular localization of the TA is regulated by the at least one RP.

In some embodiments of any of the aspects, the TED comprises an elongation domain, an activator domain, or a domain with pioneer ability.

In some embodiments of any of the aspects, the elongation domain is derived from a polypeptide selected from the group consisting of: Interacts with Suppressor Of Ty 6 (Spt6) Homolog (IWS1); Suppressor Of Ty 5 (Spt5) Homolog (SUPT5H); Bromodomain-containing protein 4 (BRD4); and cellular Myelocytomatosis (cMyc).

In some embodiments of any of the aspects, the elongation domain is derived from IWS1.

In some embodiments of any of the aspects, the elongation domain is derived from human IWS1.

In some embodiments of any of the aspects, the elongation domain comprises at least one TFIIS N-terminal domains (TND)-interacting motif (TIM) domain of IWS1.

In some embodiments of any of the aspects, the elongation domain comprises at least one TIM1, TIM2, and/or TIM3 domain from IWS1.

In some embodiments of any of the aspects, the elongation domain comprises one of SEQ ID NOs: 5-9 or an amino acid sequence with at least 80% sequence identity to one of SEQ ID NOs: 5-9.

In some embodiments of any of the aspects, the activator domain is derived from a polypeptide selected from the group consisting of: Heat Shock Factor 1 (HSF1), Glucocorticoid Receptor (GR), and MLX interacting protein like (MLXIPL).

In some embodiments of any of the aspects, the domain with pioneer ability is derived from a polypeptide selected from the group consisting of Fused in Sarcoma (FUS) and Ewing Sarcoma Breakpoint Region (EWSR).

In some embodiments of any of the aspects, the TA is selected from the group consisting of: p65; Rta; miniVPR; full VPR; VP16; VP64; NFZ; 3Z; p300; p300 HAT Core; and a CBP HAT domain; or a variant thereof.

In some embodiments of any of the aspects, the TA is p65, or a variant thereof.

In some embodiments of any of the aspects, the p65 comprises one of SEQ ID NOs: 38, 58-67 or an amino acid sequence with at least 80% sequence identity to one of SEQ ID NOs: 38, 58-67.

In some embodiments of any of the aspects, the at least one DBD is an engineered zinc finger (ZF)-binding domain.

In some embodiments of any of the aspects, the engineered ZF-binding domain comprises 2 or more ZF motifs.

In some embodiments of any of the aspects, the engineered ZF-binding domain comprises 3, 4, 5, 6, 7, 8, 9, 10, 11, 12, 13, 14, 15, 16, 17, 18, or more ZF motifs arranged adjacent to each other in tandem to form a ZF array (ZFA).

In some embodiments of any of the aspects, the engineered ZF binding domain comprises a sequence selected from the group consisting of: ZF 1-1, ZF 1-2, ZF 1-3, ZF 1-4, ZF 1-5, ZF 1-6, ZF 1-7, ZF 1-8, ZF 2-1, ZF 2-2, ZF 2-3, ZF 2-4, ZF 2-5, ZF 2-6, ZF 2-7, ZF 2-8, ZF 3-1, ZF 3-2, ZF 3-3, ZF 3-4, ZF 3-5, ZF 3-6, ZF 3-7, ZF 3-8, ZF 4-1, ZF 4-2, ZF 4-3, ZF 4-4, ZF 4-5, ZF 4-6, ZF 4-7, ZF 4-8, ZF 5-1, ZF 5-2, ZF 5-3, ZF 5-4, ZF 5-5, ZF 5-6, ZF 5-7, ZF 5-8, ZF 6-1, ZF 6-2, ZF 6-3, ZF 6-4, ZF 6-5, ZF 6-6, ZF 6-7, ZF 6-8, ZF 7-1, ZF 7-2, ZF 7-3, ZF 7-4, ZF 7-5, ZF 7-6, ZF 7-7, ZF 7-8, ZF 8-1, ZF 8-2, ZF 8-3, ZF 8-4, ZF 9-1, ZF 9-2, ZF 9-3, ZF 9-4, ZF 10-1, and ZF 11-1.

In some embodiments of any of the aspects, the engineered ZF-binding domain comprises one of SEQ ID NO: 36 (ZF10-1), SEQ ID NO: 45 (ZF3-5), or SEQ ID NO: 86 (ZF1-3).

In some embodiments of any of the aspects, the engineered ZF-binding domain comprises ZF 10-1.

In some embodiments of any of the aspects, the engineered ZF-binding domain specifically binds to a nucleic acid with a sequence comprising at least one of SEQ ID NO: 100 (ZF10 binding site (BS)), SEQ ID NO: 93 (ZF3 BS), or SEQ ID NO: 91 (ZF1 BS).

In some embodiments of any of the aspects, the engineered ZF-binding domain comprises SEQ ID NO: 48 and specifically binds endogenous VEGF gene (VEGF ZF).

In some embodiments of any of the aspects, the at least one RP comprises a polypeptide selected from the group consisting of: a repressible protease; a pair of induced proximity domains (IPD pair); a cytosolic sequestering protein; and combinations thereof.

In some embodiments of any of the aspects, the at least one RP comprises a repressible protease.

In some embodiments of any of the aspects, the at least one RP comprises a NS3 protease protein.

In some embodiments of any of the aspects, the at least one RP comprises the amino acid sequence of SEQ ID NOs: 182-198, or a homologue with at least 80% sequence identity to one of SEQ ID NOs: 182-198.

In some embodiments of any of the aspects, in the presence of a protease inhibitor, or an inhibitor of NS3, the protease protein is inhibited, thereby maintaining the coupling of the DBD to the TA.

In some embodiments of any of the aspects, in the absence of a protease inhibitor, or an inhibitor of NS3, the protease protein is active, and the TA is excised from the DBD, thereby uncoupling the DBD and the TA.

In some embodiments of any of the aspects, the inhibitor of NS3 is selected from the group consisting of: grazoprevir (GRZ/GZV), danoprevir, simeprevir, asunaprevir, ciluprevir, boceprevir, sovaprevir, paritaprevir, ombitasvir, paritaprevir, ritonavir, dasabuvir, and telaprevir.

In some embodiments of any of the aspects, the at least one RP is a pair of induced proximity domains (IPD pair), wherein the IPD pair comprises: a first induced proximity domain ($IPD^A$) and at least a second complementary IPD ($IPD^B$), wherein in the presence of an inducer agent or signal, the $IPD^A$ and $IPD^B$ specifically bind together resulting in the coupling of the TA to the DBD, and wherein in the absence of an inducer agent or signal, the TA is uncoupled from the DBD.

In some embodiments of any of the aspects, the IPD pair comprises: (a) a $IPD^A$ comprising a GID1 domain or a fragment thereof, and a $IPD^B$ comprising a GAI domain, wherein the GID1 domain and GAI domain bind to the inducer agent Gibberellin Ester (GIB); (b) a $IPD^A$ comprising a FKBP domain or a fragment thereof, and a $IPD^B$ comprising a FRB domain, wherein the FKBP domain and FRB domain bind to the inducer agent Rapalog (RAP); (c) a $IPD^A$ comprising a PYL domain or a fragment thereof, and a $IPD^B$ comprising an ABI domain, wherein the PYL domain and ABI domain bind to the inducer agent Abscisic acid (ABA); and/or (d) a $IPD^A$ comprising a Light-inducible dimerization domain (LIDD), wherein a LIDD dimerizes with a complementary LIDD ($IPD^B$) upon exposure to a light inducer signal of an appropriate wavelength.

In some embodiments of any of the aspects, the LIDD is nMag, Calcium And Integrin-Binding Protein 1 truncation (CIBN), or a photochromic protein domain; wherein nMag can dimerize with a complementary LIDD pMag upon exposure to a blue light inducer signal; or wherein CIBN can dimerize with a complementary cryptochrome 2 (CRY2) upon exposure to a blue inducer light signal; or wherein the photochromic protein domains can dimerize upon exposure to a blue inducer light signal.

In some embodiments of any of the aspects, the light inducer signal is a pulse light signal.

In some embodiments of any of the aspects, the at least one RP comprises a cytosolic sequestering protein.

In some embodiments of any of the aspects, the cytosolic sequestering protein comprises a ligand binding domain (LBD), wherein in the presence of a ligand to which the LBD binds, sequestering of the synTF to the cytosol is inhibited.

In some embodiments of any of the aspects, the cytosolic sequestering protein comprises a LBD and a nuclear localization signal (NLS); wherein in the absence of a ligand to which the LBD binds, the NLS is inhibited thereby preventing translocation of the synTF to the nucleus; and wherein in the presence of the ligand, the NLS is exposed permitting translocation of the synTF to the nucleus.

In some embodiments of any of the aspects, the cytosolic sequestering protein comprises at least a portion of an estrogen receptor (ER).

In some embodiments of any of the aspects, the cytosolic sequestering protein comprises an estrogen ligand binding domain (ERT) or a variant thereof, selected from the group consisting of: SEQ ID NO: 43 (ERT2), SEQ ID NO: 304, and SEQ ID NO: 305 (ERT3).

In some embodiments of any of the aspects, the ERT binds to one or more ligands selected from the group consisting of: tamoxifen, 4-hydroxytamoxifen (4OHT), endoxifen, and Fulvestrant; wherein binding of the ligand to the ERT exposes the NLS and results in nuclear translocation of the ERT.

In some embodiments of any of the aspects, the cytosolic sequestering protein comprises a transmembrane receptor sequestering protein.

In some embodiments of any of the aspects, the NS3 protease protein is part of a Small molecule-Assisted Shutoff (SMASh) domain, wherein the SMASh domain comprises the NS3 protease protein, a partial protease helical domain and a NS4A domain.

In some embodiments of any of the aspects, the synTF further comprises a Small molecule-Assisted Shutoff (SMASh) domain, wherein the SMASh domain is a N-terminal or C-terminal SMASh domain comprising a repressible protease, a partial protease helical domain and a cofactor domain.

In some embodiments of any of the aspects, the SMASh domain is a C-terminal SMASh domain comprising, in N-terminal to C-terminal order: a NS3 cleavage site, at least one linker, a NS3 domain, a NS3 partial helicase, and a NS4A domain, wherein the SMASh domain is fused to the C-terminus of the synTF.

In some embodiments of any of the aspects, the SMASh domain is a N-terminal SMASh domain comprising in N-terminal to C-terminal order: at least one Linker, a NS3 domain, a NS3 partial helicase, a NS4 domain, and a NS3 cleavage site, wherein the SMASh domain is fused to the N-terminus of the synTF.

In some embodiments of any of the aspects, in the absence of an inhibitor for the NS3 protease, the NS3 protease is active and self cleaves/uncouples from the synTF, thereby resulting in the SMASh domain targeted for degradation ("SMASh-degradation", synTF-on/TA-on), and wherein in the presence of an inhibitor for the NS3 protease, NS3 protease activity is inhibited thereby resulting in the SMASh-comprising synTF targeted for degradation ("synTF-degradation", synTF-OFF/TA-off").

In some embodiments of any of the aspects, the inhibitor for the NS3 protease is selected from the group consisting of: grazoprevir (GRZ/GZV), danoprevir, simeprevir, asunaprevir, ciluprevir, boceprevir, sovaprevir, paritaprevir, ombitasvir, paritaprevir, ritonavir, dasabuvir, and telaprevir.

In some embodiments of any of the aspects, the synTF comprises a SMASh domain and a cytosolic sequestering protein.

In some embodiments of any of the aspects, the synTF is active in the presence of the ligand for the cytosolic sequestering protein and in the absence of the inhibitor for the NS3 protease; and wherein the synTF is inactive in the absence of the ligand for the cytosolic sequestering protein and/or in the presence of the inhibitor for the NS3 protease.

In some embodiments of any of the aspects, the synTF further comprises a linker peptide, wherein the linker peptide can be positioned anywhere from: between the DBD and the RP; between the RP and TA; between the DBD and TA; between the TED and TA; between the TED and DBD; between the TED and RP; within the DBD, TA, TED, or regulator protein; or any combination thereof.

In some embodiments of any of the aspects, the DBD, TA, TED, and/or RP are human domains or humanized domains.

In some embodiments of any of the aspects, the DBD, TA, TED, and RP are human domains or humanized domains.

In one aspect described herein is a synthetic transcription factor (synTF) comprising: (a) at least one DNA binding domain (DBD), (b) a transcriptional activator domain (TA), and (c) a transcriptional effector domain (TED), wherein the TED increases the transcriptional activation of the synTF compared to an otherwise identical synTF lacking the TED.

In one aspect described herein is a hybrid transcription activator domain (hTAD), comprising: (a) a transcriptional activator domain (TA), and (b) a transcriptional effector domain (TED), wherein the TED increases the transcriptional activation of the TA compared to an otherwise identical hTAD lacking the TED.

In some embodiments of any of the aspects, the TA and/or TED are human domains or humanized domains.

In one aspect described herein is a synthetic transcription factor (synTF) comprising an hTAD as described herein and at least one DNA binding domain (DBD).

In some embodiments of any of the aspects, the synTF further comprises at least one regulator protein (RP).

In one aspect described herein is a humanized hybrid transcription activator domain (hhTAD), comprising: (a) a transcriptional activator domain (TA), and (b) a transcriptional effector domain (TED), wherein the TED increases the transcriptional activation of the TA compared to an otherwise identical hhTAD lacking the TED; and wherein the TA and TED are human domains or humanized domains.

In one aspect described herein is a synthetic transcription factor (synTF) comprising an hhTAD as described herein and at least one DNA binding domain (DBD).

In some embodiments of any of the aspects, the synTF further comprises at least one regulator protein (RP).

In one aspect described herein is a system for controlling gene expression, comprising: (a) at least one synthetic transcription factor (synTF) as described herein, wherein the at least one DBD of the synTF can bind to a target DNA binding motif (DBM) located upstream of a promoter operatively linked to a gene; and (b) a nucleic acid construct comprising: (i) at least one target DNA binding motif (DBM) comprising a target nucleic acid for binding of the at least one DBD of the synTF; (ii) a promoter sequence located 3' of the at least one DBM; and (iii) a gene of interest operatively linked to the promoter sequence.

In some embodiments of any of the aspects, the synTF comprises at least one RP regulated by an RP inducer.

In some embodiments of any of the aspects, the coupling of the TA to the DBD is regulated by the at least one RP.

In some embodiments of any of the aspects, the RP comprises a repressible protease or an IPD pair.

In some embodiments of any of the aspects, in the presence of the RP inducer, the coupling of the TA to the DBD of the synTF is maintained, permitting the TA to be in proximity to the promoter sequence when the DBD binds to the DBM, and wherein the TA turns on expression of the gene of interest ("TA-on").

In some embodiments of any of the aspects, in the absence of the RP inducer, the coupling of the TA to the DBD of the synTF is severed, preventing the TA from being in proximity to the promoter sequence when the DBD binds to the DBM, preventing expression of the gene of interest ("TA-off").

In some embodiments of any of the aspects, cellular localization of the TA linked to the DBD is regulated by the at least one RP.

In some embodiments of any of the aspects, the RP comprises a cytosolic sequestering protein.

In some embodiments of any of the aspects, in the presence of the RP inducer, the TA coupled to the DBD of the synTF is not sequestered in the cytosol, permitting the DBD to bind to the DNA binding motif (DBM) and permitting the TA domain to be in proximity to the promoter sequence to thereby turn on expression of the gene of interest ("TA-on").

In some embodiments of any of the aspects, in the absence of the RP inducer, the TA coupled to the DBD of the synTF is sequestered in the cytosol, preventing the DBD from binding to the DBM, and preventing the TA domain from being in proximity to the promoter sequence, thereby preventing expression of the gene of interest ("TA-off").

In some embodiments of any of the aspects, the at least one synTF further comprises a N-terminal or C-terminal Small molecule-Assisted Shutoff (SMASh) domain, wherein SMASh domain comprises a self-cleaving SMASh protease, a partial protease helical domain and a cofactor domain.

In some embodiments of any of the aspects, in the presence of an inhibitor to the SMASh protease, the SMASh protease activity is inhibited, resulting in the synTF being degraded and preventing the DBD of the synTF binding to the DBM and controlling the expression of the gene of interest ("synTF-degradation"; TA-off (no expression)).

In some embodiments of any of the aspects, in the absence of an inhibitor to the SMASh protease, the SMASh protease is active and self cleaves/uncouples from the synTF, resulting the SMASh domain being targeted for degradation and allowing the DBD of the synTF to bind to the DBM and the TA of synTF to control the expression of the gene of interest ("SMASh-degradation, TA-on (yes-expression)).

In some embodiments of any of the aspects, the promoter is selected from the group consisting of: miniCMV promoter, miniTK promoter, ybTATA promoter, minSV40 promoter, CMV53 promoter, pJB42CAT5 promoter, MLP promoter, TATA promoter, pSFFV promoter, CMV promoter, pUb/UbC promoter, EF1a promoter, PGK/pGK promoter, CAG/CAGG promoter, SV40 promoter, and beta actin/ACTB promoter.

In one aspect described herein is a system comprising: (a) a first nucleic acid sequence comprising at least one target DNA binding motif (DBM) comprising a target nucleic acid for binding of at least one DBD of a synTF, a promoter sequence located 3' of the at least one DBM, and a nucleic acid encoding a gene of interest (GOI) operatively linked to the promoter sequence; and (b) a second nucleic acid sequence comprising a nucleic acid encoding a synthetic transcription factor (synTF) according to any one of the embodiments described herein, operatively linked to an inducible or constitutive promoter.

In some embodiments of any of the aspects, the promoter sequence operatively linked to the GOI is selected from the group consisting of: miniCMV promoter, miniTK promoter, ybTATA promoter, minSV40 promoter, CMV53 promoter, pJB42CAT5 promoter, MLP promoter, and TATA promoter.

In some embodiments of any of the aspects, the promoter sequence operatively linked to the nucleic acid encoding the synTF is selected from the group consisting of pSFFV promoter, CMV promoter, pUb/UbC promoter, EF1a promoter, PGK/pGK promoter, CAG/CAGG promoter, SV40 promoter, and beta actin/ACTB promoter.

In one aspect described herein is a polynucleotide encoding a synTF as described herein; a hTAD as described herein; a hhTAD as described herein; or a system as described herein; or portion thereof.

In one aspect described herein is a nucleic acid construct, comprising in the 5' to 3' direction: (a) a nucleic acid sequence encoding a gene of interest (GOI) in the inverse orientation, (b) a first promoter sequence in the inverse orientation and operatively linked to the nucleic acid encoding the GOI, (c) a nucleic acid sequence comprising at least one target DNA binding motif (DBM) comprising a target nucleic acid for binding of at least one DBD of a synthetic transcription factor (synTF), wherein binding of the DBD places a TA of the synTF in the proximity of the promoter sequence operatively linked to the GOI, (d) a second promoter sequence, and (e) a nucleic acid sequence encoding the synTF, operatively linked to the second promoter sequence, wherein the encoded synTF comprises at least one DBD that binds to the at least one DBM of the nucleic acid sequence of (c).

In some embodiments of any of the aspects, the promoter sequence operatively linked to the GOI is selected from the group consisting of: miniCMV promoter, miniTK promoter, ybTATA promoter, minSV40 promoter, CMV53 promoter, pJB42CAT5 promoter, MLP promoter, and TATA promoter.

In some embodiments of any of the aspects, the promoter sequence operatively linked to the nucleic acid encoding the synTF is selected from the group consisting of a pSFFV promoter, CMV promoter, pUb/UbC promoter, EF1a promoter, PGK/pGK promoter, CAG/CAGG promoter, SV40 promoter, and beta actin/ACTB promoter.

In one aspect described herein is a vector comprising a system as described herein; a polynucleotide as described herein; or a nucleic acid construct as described herein; or portion thereof.

In some embodiments of any of the aspects, the vector is a lentiviral vector.

In one aspect described herein is a cell comprising a synTF as described herein; a hTAD as described herein; a hhTAD as described herein; a system as described herein; a polynucleotide as described herein; a nucleic acid construct as described herein; or a vector as described herein; or portion thereof.

In some embodiments of any of the aspects, the cell is an immune cell.

In some embodiments of any of the aspects, the immune cell is selected from the group consisting of: a CD4+ T cell, a CD8+ T cell, a Treg, an NK cell, a monocyte, and a macrophage.

In one aspect described herein is a composition comprising a synTF as described herein; a hTAD as described herein; a hhTAD as described herein; a system as described herein; a polynucleotide as described herein; a nucleic acid construct as described herein; a vector as described herein; a cell as described herein; or portion thereof.

In one aspect described herein is a pharmaceutical composition comprising a synTF as described herein; a hTAD as described herein; a hhTAD as described herein; a system as described herein; a polynucleotide as described herein; a nucleic acid construct as described herein; a vector as described herein; a cell as described herein; or portion thereof; and a pharmaceutically acceptable carrier.

In one aspect described herein is a method of regulating the activity of a synTF, comprising the steps of: (a) providing a population of cells as described herein; and (b) contacting the population of cells with an effective amount of at least one RP inducer.

In one aspect described herein is a method of regulating the expression of a gene of interest, comprising the steps of: (a) providing a population of cells as described herein; and (b) contacting the population of cells with an effective amount of at least one RP inducer.

In one aspect described herein is a method of treating a subject in need of a cell-based therapy, comprising the steps of: (a) administering to the subject a population of cells as described herein; and (b) administering to the subject an effective amount of at least one RP inducer.

In some embodiments of any of the aspects, the population of cells comprises immune cells.

In some embodiments of any of the aspects, the population of immune cells comprises CD4+ T cells, CD8+ T cells, Tregs, NK cells, monocytes, or macrophages.

In some embodiments of any of the aspects, the at least one RP inducer is administered at the same time the population of cells is administered.

In some embodiments of any of the aspects, the at least one RP inducer is administered after the population of cells is administered.

BRIEF DESCRIPTION OF THE DRAWINGS

(FIG. 1A) Construction of TED integrated-synZiFTRs. A set consisting of 10 effector domains (Fused in Sarcoma (FUS), Ewing Sarcoma Breakpoint Region (EWSR), Heat Shock Factor 1 (HSF1), Glucocorticoid Receptor (GR), MLX interacting protein like (MLXIPL), Kow5 domain of Suppressor Of Ty 5 (Spt5) Homolog (SUPT5H), Interacts with Suppressor Of Ty 6 (Spt6) Homolog (IWS1), Bromodomain-containing protein 4 (BRD4), cellular Myelocytomatosis (cMyc), enhanced green fluorescent protein (eGFP)) was inserted into a lentiviral backbone between the ZF10 DNA binding domain and the p65 human transcription domain. This set included domains that have been identified as intrinsically disordered domains with pioneer ability ("txn. (transcription) pioneer factors" FUS, EWSR), activator domains (ADs; "txn. activation factors (Weak) HSF1, GR, MLXIPL), elongation domains (EDs; "txn. Elongation factors" Kow5, IWS1, BRD4, cMyc), and EGFP as control. (FIG. 1B) Overview of genetic circuits used to evaluate candidate TEDs in Jurkat cells. Responsive promoters and synZiFTRs were integrated into Jurkat T cells in an equal ratio using lentiviral co-transduction. mCherry was measured by flow cytometry 3 days following Dox-induction. (FIG. 1C) 5 TED integrated-synZiFTRs activated stronger gene expression compared to synZiFTR. TEDs were inserted into a lentiviral backbone between the ZF10 DNA binding domain and the p65 human transcription domain. Bars represent median fluorescence intensity (MFI) values for three measurements±standard deviation (SD). Selected domain yielding highest enrichment of mCherry fluorescent output is highlighted in gray. Statistics represent two-tailed Student's t test; **$P<0.0001$. PhPGK, human phosphoglycerate kinase 1 promoter; TRE3G, tetracycline-responsive promoter; pybTATA, synthetic YB_TATA promoter; p65, amino acids 361 to 551; FUS, amino acids 2-214; EWSR1, amino acids 47-267; HSF1, amino acids 406-529; GR, amino acids 187-244; MLXIP, amino acids 318-370; Kow5 (SUPT5H), amino acids 698-765; TIMs (IWS1), amino acids 449-492; BRD4, amino acids 1308-1362; cMyc, amino acids 1-70. (FIG. 1D) Evaluation of TIMs integrated-synZiFTR order variants. TIMs were inserted into a lentiviral backbone containing the ZF10 DNA binding domain and the p65 human transcription domain at different locations. Experiments were conducted via same circuit design in FIG. 1B. Bars represent median fluorescence intensity (MFI) values for three measurements±SD. Statistics represent two-tailed Student's t test; $P<0.0001$. (FIG. 1E) Evaluation of transcription synergy. Comparing min. synZiFTR2.0 mCherry fluorescent output with min. synZiFTR+ZF10-TIMs. Experiments were conducted via same circuit design in FIG. 1B. Bars represent median fluorescence intensity (MFI) values for three measurements±SD. Statistics represent two-tailed Student's t test; **$P<0.0001$.

(FIG. 2A) Integrating TIMs into orthogonal gene switches regulated by clinically relevant small molecules. Design of GZV- and 4OHT-distinct synZiFTR2.0s. Grazoprevir (GZV), and 4-hydroxytamoxifen/tamoxifen (4OHT/TMX). NS3, hepatitis C virus NS3 protease domain; ERT2, human estrogen receptor T2 mutant domain. (FIG. 2B) synZiFTR2.0 evaluation gene circuit. Jurkat T cells were co-transduced with reporter, synZiFTR2.0 and synZiFTR expression lentiviral vectors in an equal ratio. mCherry fluorescence was measured by flow cytometry 3 days following induction by small molecules at indicated concentrations. (FIG. 2C) GZV-synZiFTR2.0 switches permit stronger inducible gene expression in Jurkat T cells. TIMs was inserted into various locations of the GZV-synZiFTR. Selected design(s) designated as GZV-synZiFTR2.0 is highlighted in gray. Bars represent median values for three measurements±SD. Statistics represent two-tailed Student's t test; **$P<0.0001$. Histograms show absolute levels and mean fold activation for one representative measurement (insets). Points represent median values for three measurements±SD. pSFFV, Spleen Focus-Forming Virus promoter. (FIG. 2D) 4OHT-synZiFTR2.0 switches permit stronger inducible gene expression in Jurkat T cells. TIMs were inserted into various locations of the 4OHT-synZiFTR. Selected design(s) designated as 4OHT-synZiFTR2.0 is highlighted in gray. Bars represent median values for three measurements±SD. Statistics represent two-tailed Student's t test; P<0.0001. Histograms show absolute levels and mean fold activation for one representative measurement (insets). Points represent median values for three measurements±SD. Statistics represent two-tailed Student's t test; P<0.0001. (FIG. 2E) Double TIMs integrated GZV- and 4OHT-SynZiFTR2.0 further enhanced gene expression in Jurkat T cells. Two TIMs domains were inserted into selected designs of both GZV- and 4OHT-SynZiFTR. Selected design(s) with 2 TIMs domains is highlighted in gray. Bars represent median values for three measurements±SD. Statistics represent two-tailed Student's t test; **P<0.0001. Comparison of GZV-SynZiFTR vs. GZV-SynZiFTR2.0, for all genes.

(FIG. 3A) Comparing heterodimers' circuit output. Circuit output of reconstituted of split min. synZiFTR is measured in Jurkat T cells via a mammalian-two-hybrid circuit. Responsive promoters, input 1, and input 2 were integrated into Jurkat T cells in an equal ratio using lentiviral co-transduction. mCherry was measured by flow cytometry 3 days following Dox-induction. Selected heterodimer is highlighted in gray. Bars represent median fluorescence intensity (MFI) values for three measurements±SD. Selected heterodimer yielding highest mCherry fluorescent output is highlighted in gray. Statistics represent two-tailed Student's t test; **P<0.0001. (FIG. 3B) Characterizing ZF affinity variant. Min. synZiFTR with non-modified ZF (domain 1: SEQ ID NO: 1, ERPFQCRICMRNFS; SEQ ID NO: 2, TGEK; domains 2-6: SEQ ID NO: 3, PFQCRICMRNFS) or ZFs with 3R2A (see e.g., 3 asterisks, bottom row, indicating arginine (R) to alanine (A) mutations in ZF domains 1, 3, and 6), 5R2A (see e.g., 5 asterisks, middle row, indicating arginine (R) to alanine (A) mutations in ZF domains 1, 3, 4, and 6), and 7R2A mutants (see e.g., 7 asterisks, top row, indicating arginine (R) to alanine (A) mutations in ZF domains 1-6) were expressed in Jurkat T cells. Responsive promoters and synZiFTRs were integrated into Jurkat T cells in an equal ratio using lentiviral co-transduction. mCherry was measured by flow cytometry 3 days following Dox-induction. Points represent median fluorescence intensity (MFI) values for three measurements±SD. Statistics represent two-tailed Student's t test; P<0.0001. (FIG. 3C) Characterizing transcription output via scaffold mediated cooperativity. Min. synZiFTRs with ZF carrying 7R2A mutations regulated mCherry expression in the presence of a $n_c$=2 scaffold in Jurkat T cells. Responsive promoters, input 1, and input 2 were integrated into Jurkat T cells in an equal ratio using lentiviral co-transduction. mCherry was measured by flow cytometry 3 days following Dox-induction. Bars represent median fluorescence intensity (MFI) values for three measurements±SD. Selected heterodimer yielding highest mCherry fluorescent output is highlighted in gray. Statistics represent two-tailed Student's t test; P<0.0001; P<0.01. (FIG. 3D) Characterizing transcription output of split minimal synZiFTR2.0. Circuit output of reconstituted of split min. synZiFTR2.0 was measured in Jurkat T cells via a mammalian-two-hybrid circuit. Responsive promoters, input 1, and input 2 were integrated into Jurkat T cells in an equal ratio using lentiviral co-transduction. mCherry was measured by flow cytometry 3 days following Dox-induction. Bars represent median fluorescence intensity (MFI) values for three measurements±SD. Selected heterodimer yielding highest mCherry fluorescent output is highlighted in gray. Statistics represent two-tailed Student's t test; ****P<0.0001.

(FIG. 4A) IWS1 mutants affecting TIMs employed in this study. WT TIMs domain in GZV-synZiFTR2.0 were replaced by TIMs structural mutant variants (see e.g., SEQ ID NOs: 5-14). The amino acid sequence of the TIMs domain is shown (see e.g., SEQ ID NO: 5). The boxes highlight each of the 3 TIM amino acid sequences (see e.g., SEQ ID NOs: 6-8) and the mutants respectively (see e.g., SEQ ID NOs: 12-14). Different TIM mutations caused loss of interactions with various transcription elongation factors (Transcription factor IIS (TFIIS) and Elongin A (EloA) for the TIM1 mutant; Protein Phosphatase 1 Nuclear Targeting Subunit (PP1-PNUTs) for the TIM2 mutant; lens epithelium-derived growth factor (LEDGF) and H3K36me2/3 binding protein HDGFL2 (HRP2) for the TIM3 mutant). Figure discloses SEQ ID NOS 5-6, 12, 6, 6-7, 7, 13, 7-8, 8, 8, and 14, respectively, in order of appearance. (FIG. 4B) Evaluating loss of function TIMs mutations. GZV-synZiFTR2.04 distinct mutant variants of TIMs were expressed in Jurkat T cells. The circuit outputs were compared to GZV-synZiFTR2.0 carrying WT TIMs. Jurkat T cells were co-transduced with reporter, synZiFTR2.0 and synZiFTR expression lentiviral vectors in an equal ratio. mCherry fluorescence was measured by flow cytometry 3 days after induction by small molecules at the indicated concentrations. Bars represent mean values for three measurements±SD. Statistics represent two-tailed Student's t test; ****P<0.0001.

FIG. 5A is a schematic showing that the IWS1 TIMs domain can be incorporated into synTF constructs to increase transcriptional activation. FIG. 5B is a schematic showing small-molecule-regulated synTFs. FIG. 5C is a schematic showing an exemplary grazoprevir-regulated synTF comprising an NS3 domain. FIG. 5D is a schematic showing an exemplary tamoxifen-regulated synTF comprising an ERT2 domain.

FIG. 6A is a schematic and bar graph showing that the IWS1 TIMs domain increases transcriptional activation in an NS3-comprising synTF in the presence of grazoprevir. FIG. 6B is a schematic and bar graph showing that the IWS1 TIMs domain increases transcriptional activation in an ERT2-comprising synTF in the presence of 4OHT.

FIG. 8A: a single copy of TIMs domain was placed on N or C terminus of p65 in synZiFTR, and N terminally fused TIMs enhanced synZiFTR activity more. FIG. 8B: fusing two copies of TIMs on N terminus of p65 drives higher output than fusing a single copy of TIMs at the same loci.

FIG. 9A: a single copy of TIMs domain was placed on N or C terminus of p65 in synZiFTR, and N terminally fused TIMs enhanced synZiFTR activity with less increase in the basal induction (no drug added). FIG. 9B: fusing two copies of TIMs on N terminus of p65 drove higher output than fusing a single copy of TIMs at the same loci.

DETAILED DESCRIPTION

Figure 1A:
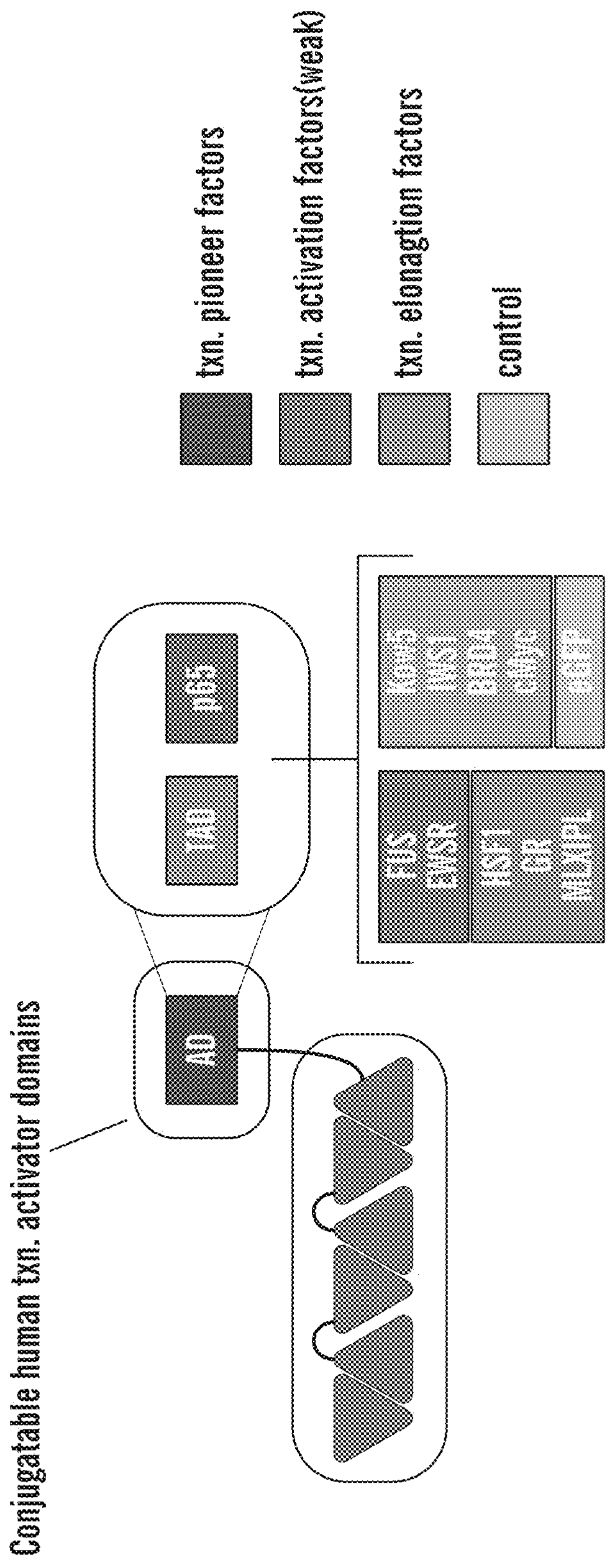
FIG. 1A-1E. Screen of Transcription Effector Domains (TEDs).
Figure 1B:
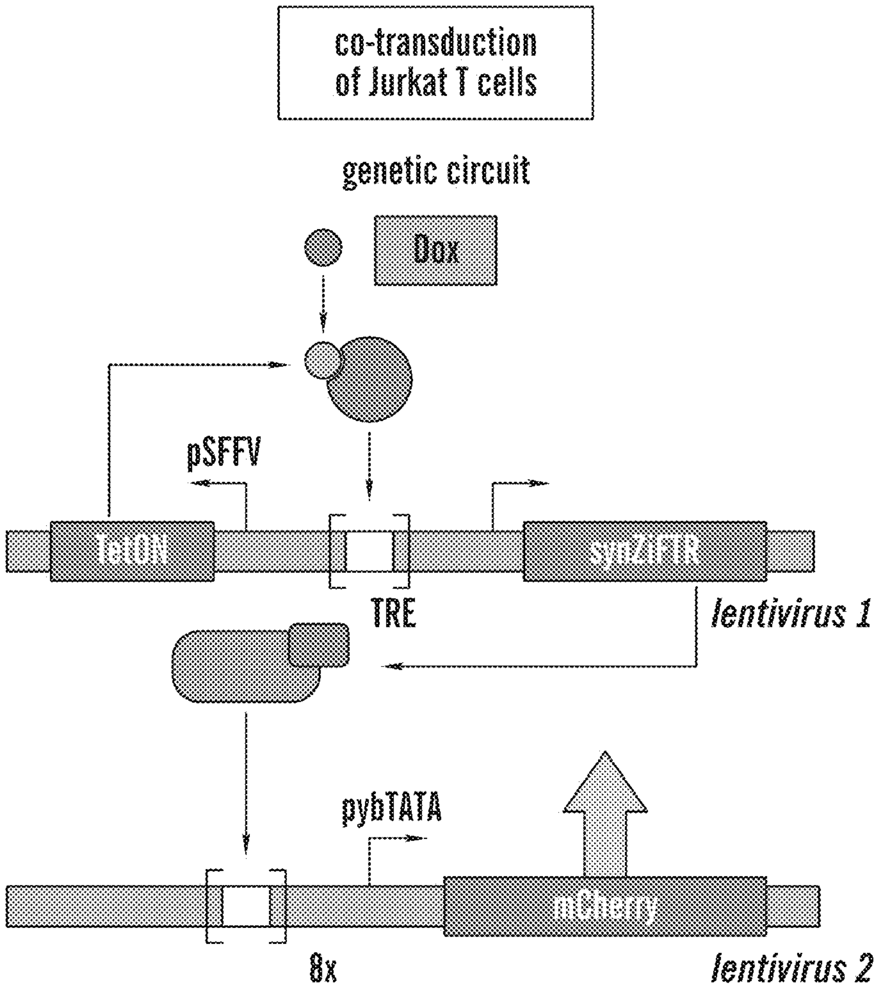

Described herein are synTFs for use in the methods and compositions as disclosed herein, where the synTFs comprise (i) a DNA binding domain (DBD) which binds to a target nucleic acid sequence (or target DNA binding motif (DBM)), (ii) a transcriptional effector domain (TED), (iii) a transcriptional activation (TA) domain, and (iv) optionally a regulator protein (RP).

In one aspect, described herein is a synthetic transcription factor (synTF) comprising: (a) at least one DNA binding domain (DBD), (b) a transcriptional activator (TA) domain, (c) a transcriptional effector domain (TED), and (d) at least one regulator protein (RP). In some embodiments, the synTF comprises the DBD, TA, TED, and RP domains in a N-terminal to C-terminal order (or 5' to 3' order in a corresponding nucleic acid) selected from Table 3.

TABLE 3

Exemplary SynTF domain orders. The first number corresponds to the position of the DBD, the second number corresponds to the position of the TA, the third number corresponds to the position of the TED, and the fourth number corresponds to the position of the RP. For examples, 1, 2, 3, 4 indicates that the DBD in the first (N-terminal) position, the TA in the second position, the TED in the third position, and the RP in the fourth position (C-terminal).

| DBD, TA, TED, RP | | | |
|---|---|---|---|
| 1, 2, 3, 4 | 3, 2, 4, 1 | 4, 1, 3, 2 | 2, 1, 4, 3 |
| 2, 1, 3, 4 | 2, 3, 4, 1 | 1, 4, 3, 2 | 1, 2, 4, 3 |
| 3, 1, 2, 4 | 4, 3, 2, 1 | 3, 4, 1, 2 | 4, 2, 1, 3 |
| 1, 3, 2, 4 | 3, 4, 2, 1 | 4, 3, 1, 2 | 2, 4, 1, 3 |
| 2, 3, 1, 4 | 2, 4, 3, 1 | 1, 3, 4, 2 | 1, 4, 2, 3 |
| 3, 2, 1, 4 | 4, 2, 3, 1 | 3, 1, 4, 2 | 4, 1, 2, 3 |

In another aspect, described herein is a synthetic transcription factor (synTF) comprising: (a) at least one DNA binding domain (DBD), (b) a transcriptional activator (TA) domain, and (c) a transcriptional effector domain (TED). In some embodiments, the synTF comprises the DBD, TA, and TED domains in a N-terminal to C-terminal order (or 5' to 3' order in a corresponding nucleic acid) selected from Table 4.

TABLE 4

Exemplary SynTF domain orders. The first number corresponds to the position of the DBD, the second number corresponds to the position of the TA, and the third number corresponds to the position of the TED. For examples, 1, 2, 3 indicates that the DBD in the first (N-terminal) position, the TA in the second position, and the TED in the third position (C-terminal).

| DBD, TA, TED |
|---|
| 1, 2, 3 |
| 2, 1, 3 |
| 3, 1, 2 |
| 1, 3, 2 |
| 2, 3, 1 |
| 3, 2, 1 |

In one aspect, described herein is a hybrid transcription activator domain (hTAD), comprising: (a) a transcriptional activator (TA) domain, and (b) a transcriptional effector domain (TED). In some embodiments, the TA is N terminal to the TED. In some embodiments, the TA is C terminal to the TED.

In another aspect, described herein is a humanized hybrid transcription activator domain (hhTAD), comprising: (a) a transcriptional activator (TA) domain, and (b) a transcriptional effector domain (TED), wherein the TA and TED are human domains or humanized domains. In some embodiments, the hhTAD comprises SEQ ID NO: 16 or an amino acid sequence with at least 60%, at least 65%, at least 70%, at least 75%, at least 80%, at least 85%, at least 90%, at least 95%, at least 96%, at least 97%, at least 98%, or at least 99% sequence identity to SEQ ID NO: 16, which maintains the same function (e.g., increased transcriptional activation, compared to a construct lacking the TED).

The TED increases the transcriptional activation of the TA compared to a construct comprising the TA and lacking the TED. As a non-limiting example, the TED increases the transcriptional activation of the TA by at least about 10%, at least about 20%, or at least about 30%, or at least about 40%, or at least about 50%, or at least about 60%, or at least about 70%, or at least about 80%, or at least about 90% or up to and including a 100% increase or any increase between 10%-100%, or at least about a 2-fold, or at least about a 3-fold, or at least about a 4-fold, or at least about a 5-fold or at least about a 10-fold increase, or any increase between 2-fold and 10-fold or greater as compared to a construct comprising the TA and lacking the TED.

The TED can be derived from a human protein, such as the TIMs domain of human IWS1. In some embodiments, at least one, at least two, at least three, at least four, or more of the domains in the construct (e.g., DBD, TA, TED, and/or RP) are human or humanized. Use of constructs comprising such human or humanized domains allows for clinical use, without concern for foreign immune-activation, such as can occur with non-human (e.g., virally derived) constructs.

Figure 12:
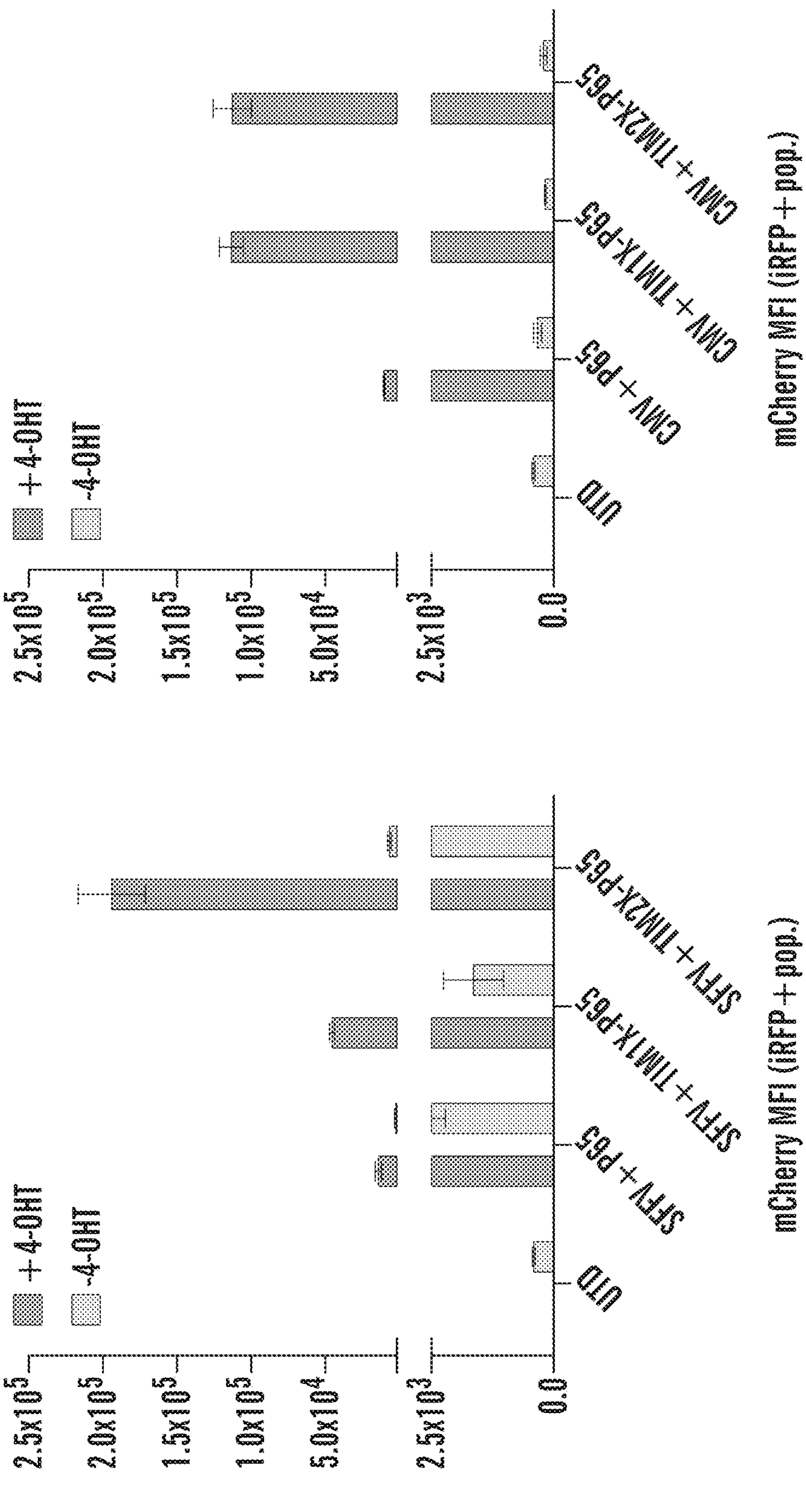
FIG. 12 shows testing of single lentiviral vectors for 4OHT inducible systems driving mCherry reporter in HEK cells (benchmarked against the original (1.0) synZiFTR).
Figure 15:
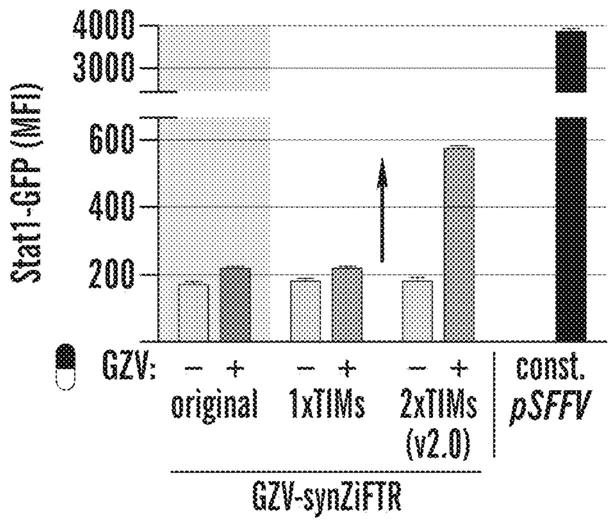
FIG. 15 shows testing of dual lentiviral vectors for GZV inducible systems driving GFP-STAT1 protein in THP1 monocytes.
Figure 16:
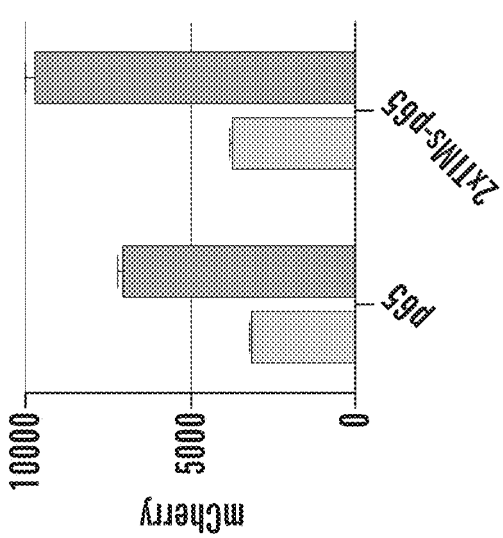
FIG. 16 shows testing of single lentiviral vectors for GZV inducible systems driving GFP-STAT1 in THP1 monocytes.

The TEDs described herein can function in both dual vector and single vector systems (see e.g., FIG. 12, FIG. 16 for exemplary single vector systems). The TEDs described herein can drive more robust expression of a large payload compared a construct not comprising the TED (see e.g., FIG. 15). As a non-limiting example, a synTF comprising at least one TED as described herein can increase complete transcription of a nucleic acid that is at least 1000 nucleotides long, at least 1100 nucleotides long, at least 1200 nucleotides long, at least 1300 nucleotides long, at least 1400 nucleotides long, at least 1500 nucleotides long, at least 1600 nucleotides long, at least 1700 nucleotides long, at least 1800 nucleotides long, at least 1900 nucleotides long, at least 2000 nucleotides long, at least 2100 nucleotides long, at least 2200 nucleotides long, at least 2300 nucleotides long, at least 2400 nucleotides long, at least 2500 nucleotides long, at least 2600 nucleotides long, at least 2700 nucleotides long, at least 2800 nucleotides long, at least 2900 nucleotides long, at least 3000 nucleotides long, at least 3100 nucleotides long, at least 3200 nucleotides long, at least 3300 nucleotides long, at least 3400 nucleotides long, at least 3500 nucleotides long, at least 3600 nucleotides long, at least 3700 nucleotides long, at least 3800 nucleotides long, at least 3900 nucleotides long, at least 4000 nucleotides long, at least 4100 nucleotides long, at least 4200 nucleotides long, at least 4300 nucleotides long, at least 4400 nucleotides long, at least 4500 nucleotides long, at least 4600 nucleotides long, at least 4700 nucleotides long, at least 4800 nucleotides long, at least 4900 nucleotides long, at least 5000 nucleotides long, or more (see e.g., SEQ ID NO: 27-28, Example 7.8, FIG. 15, SEQ ID NO: 35).

In embodiments comprising a regulator protein, the regulator protein can control the coupling or linkage of the DNA binding domain (DBD) with the TA (such coupling can also be referred to as a "mediator domain"), or can control the cellular localization of the TA, such that when the TA and DBD are attached and/or located in the nucleus, the TA can function to recruit translation machinery to the promoter to increase gene expression of a gene of interest.

In some embodiments of any of the aspects, regulator proteins can be activated or inhibited by a variety of inputs, non-limiting examples of which include: inducers (e.g., small molecules), light-inducible control (e.g., dimerization, assembly, localization), temperature, pH, phosphorylation, oxygen, lipid, magnetic, electric, spatial mechanisms (e.g., intracellular and/or extracellular; e.g., synthetic receptors and/or soluble factors), endogenous ligands (e.g., biomarkers), cell-cycle state, native signaling pathways, or disease and/or pathogenic states (e.g., aggregation, infection).

In some embodiments of the systems, compositions and methods as disclosed herein, the regulator protein of the SynTF is selected from a protease, a pair of inducible proximity domains (IPDs), a translocation domain (i.e., a cytosolic sequestering protein), or an induced degradation domain, each of which are described herein and in more detail below.

Described herein are four general frameworks of inducible or drug-controllable synthetic transcription factors comprising the TA and TED: (1) a synTF comprising a repressible protease, referred to as a repressible protease synTF; (2) a synTF comprising induced proximity domains, referred to as a induced proximity domain SynTF; (3) a synTF system comprising a cytosolic sequestering domain, referred to as a cytosolic sequestering synTF; and (4) a synTF comprising an induced degradation domain referred to as an induced degradation domain synTF. Also described herein are polynucleotides and vector encoding said synTF polypeptides, cells expressing said synTF polypeptides, pharmaceutical compositions comprising said synTF polypeptides, and methods of using said synTF polypeptides.

Described herein is a class of engineered transcription factor proteins (synTFs) and corresponding responsive artificial engineered promoters capable of precisely controlling gene expression in a wide range of eukaryotic cells and organisms, including mammalian cells. These synTFs are specifically designed to have reduced or minimal binding potential in the host genome (i.e., "orthogonal" activity to the host genome). The synTF proteins described herein can comprise a DNA binding domain (DBD) which are based on engineered zinc finger (ZF) arrays that are designed to target and bind specific 18-20 nucleotide sequences that are distant and different from the host genome sequences, when the synTF proteins are used in the selected hosts. This strategy limits non-specific interactions of the synTF proteins with the host's genome; such non-specific interactions are not ideal and therefore, are not desired.

The synTFs described herein are designed, in some aspects, according to the following parameters: (1) targetable DNA sequences (also known as ZF binding sites) are identified for the ZF arrays that are specifically designed to have reduced binding potential in a host genome; (2) ZF arrays are designed and assembled; (3) synTFs are designed by coupling engineered (i.e., covalently linked) ZF arrays to the transcriptional activator (TA) domain and transcriptional effector domain (TED); (4) corresponding responsive promoters are designed by placing instances of the targetable DNA sequences (i.e., ZF binding sites) upstream of constitutive promoters. The targetable DNA sequences are operably linked to the promoters such that the occupancy of synTFs on the targetable DNA sequences regulates the activity of the promoter in gene expression. The combination of a synTF and a targetable DNA sequence-promoter forms a unique expression system that is artificial, scalable, and regulatable, for the expressions of desired genes placed within the expression systems, with no or minimal effects on the expression of endogenous genes, meaning no or minimal off-site gene regulation of endogenous genes.

The synTFs described herein have reduced or minimal functional binding potential in the host genome, which provides, in part, advantages of no or minimal off-site DNA targeting by the synTFs. In addition, the synthetic ZF-based proteins (synTFs) described herein are derived from mammalian or human protein scaffolds, conferring minimal degree of immunogenicity over other prokaryotically-derived domains. In contrast to other classes of programmable DNA-targeting domains, these zinc-finger-based regulatory proteins are considerably smaller (~4-5×) than TALE and dCas9 proteins, less repetitive than TALE repeat proteins, and are not as constrained by lentiviral packaging limits, permitting convenient packaging in lentiviral delivery constructs and affording space for other desirable control elements.

I. Synthetic Transcription Factor Domains

In multiple aspects described herein are constructs, including synTF polypeptides or synTF polypeptide systems, which comprise at least one of the following domains: transcriptional activator domain; a transcriptional effector domain (TED); a DNA-binding domain; at least one (e.g., 1, 2, 3, 4, 5, or more) regulator protein(s) selected from the group consisting of: repressible protease, induced proximity domain, cytosolic sequestration domain, and/or an induced degradation domain (e.g., SMASh domain); at least one linker peptide, at least one detectable marker, and/or self-cleaving peptide, or any combination thereof.

In some embodiments of any of the aspects, a synTF polypeptide or a synTF polypeptide system collectively (i.e., the first polypeptide and/or the second polypeptide) comprises at least the following: a transcriptional activator (TA) domain, a transcriptional effector domain (TED), a DNA-binding domain, and at least one (e.g., 1, 2, 3, 4, 5, or more) regulator protein(s) selected from the group consisting of: repressible protease, induced proximity domain, cytosolic sequestration domain, and/or induced degradation domain. In some embodiments of any of the aspects, a synTF polypeptide or system further comprises at least one linker peptide, and/or at least one detectable marker, and/or at least one self-cleaving peptide, or any combination thereof. Specific synTFs described herein are not to be construed as limitations. For example, the following combinations are contemplated herein (see e.g., Table 5) below.

TABLE 5

Exemplary Combinations of Domains in a synTF Polypeptide or synTF Polypeptide System. Each exemplary synTF polypeptide shown in Table 5 also comprises a transcriptional activator (TA) domain, a transcriptional effector domain (TED), and a DNA-binding domain. The domains can be in any order. "PRO" indicates repressible protease. "IPD" indicates induced proximity domain. "CS" indicates cytosolic sequestering domain. "DD" indicates induced degron domain. "LP" indicates linker peptide. "DM" indicates detectable marker. "SP" indicates self-cleaving peptide.

| PRO | IPD | CS | DD | LP | DM | SP | PRO | IPD | CS | DD | LP | DM | SP |
|---|---|---|---|---|---|---|---|---|---|---|---|---|---|
| | | | | | | | | | | | X | | |
| X | | | | | | | X | | | | X | | |
| | X | | | | | | | X | | | X | | |
| X | X | | | | | | X | X | | | X | | |
| | | X | | | | | | | X | | X | | |
| X | | X | | | | | X | | X | | X | | |
| | X | X | | | | | | X | X | | X | | |
| X | X | X | | | | | X | X | X | | X | | |
| | | | X | | | | | | | X | X | | |
| X | | | X | | | | X | | | X | X | | |
| | X | | X | | | | | X | | X | X | | |
| X | X | | X | | | | X | X | | X | X | | |
| | | X | X | | | | | | X | X | X | | |
| X | | X | X | | | | X | | X | X | X | | |
| | X | X | X | | | | | X | X | X | X | | |
| X | X | X | X | | | | X | X | X | X | X | | |
| | | | | | X | | X | | | X | | | X |
| X | | | | | X | | | X | | X | | | X |
| | X | | | | X | | X | X | | X | | | X |
| X | X | | | | X | | | | X | X | | | X |
| | | X | | | X | | X | | X | X | | | X |
| X | | X | | | X | | | X | X | X | | | X |
| | X | X | | | X | | X | X | X | X | | | X |
| X | X | X | | | X | | | | | | X | | X |
| | | | X | | X | | X | | | | X | | X |
| X | | | X | | X | | | X | | | X | | X |
| | X | | X | | X | | X | X | | | X | | X |
| X | X | | X | | X | | | | X | | X | | X |
| | | X | X | | X | | X | | X | | X | | X |
| X | | X | X | | X | | | X | X | | X | | X |
| | X | X | X | | X | | X | X | X | | X | | X |
| X | X | X | X | | X | | | | | X | X | | X |
| | | | | X | X | | X | | | X | X | | X |
| X | | | | X | X | | | X | | X | X | | X |
| | X | | | X | X | | X | X | | X | X | | X |
| X | X | | | X | X | | | | X | X | X | | X |
| | | X | | X | X | | X | | X | X | X | | X |
| X | | X | | X | X | | | X | X | X | X | | X |
| | X | X | | X | X | | X | X | X | X | X | | X |
| X | X | X | | X | X | | | | | | | X | X |
| | | | X | X | X | | X | | | | | X | X |
| X | | | X | X | X | | | X | | | | X | X |
| | X | | X | X | X | | X | X | | | | X | X |
| X | X | | X | X | X | | | | X | | | X | X |
| | | X | X | X | X | | X | | X | | | X | X |
| X | | X | X | X | X | | | X | X | | | X | X |

TABLE 5-continued

Exemplary Combinations of Domains in a synTF Polypeptide or synTF Polypeptide System. Each exemplary synTF polypeptide shown in Table 5 also comprises a transcriptional activator (TA) domain, a transcriptional effector domain (TED), and a DNA-binding domain. The domains can be in any order. "PRO" indicates repressible protease. "IPD" indicates induced proximity domain. "CS" indicates cytosolic sequestering domain. "DD" indicates induced degron domain. "LP" indicates linker peptide. "DM" indicates detectable marker. "SP" indicates self-cleaving peptide.

| PRO | IPD | CS | DD | LP | DM | SP | PRO | IPD | CS | DD | LP | DM | SP |
|---|---|---|---|---|---|---|---|---|---|---|---|---|---|
| | X | X | X | X | X | | X | X | X | | | X | X |
| X | X | X | X | X | X | | | | | X | | X | X |
| | | | | | | X | X | | | X | | X | X |
| X | | | | | | X | | X | | X | | X | X |
| | X | | | | | X | X | X | | X | | X | X |
| X | X | | | | | X | | | X | X | | X | X |
| | | X | | | | X | X | | X | X | | X | X |
| X | | X | | | | X | | X | X | X | | X | X |
| | X | X | | | | X | X | X | X | X | | X | X |
| X | X | X | | | | X | | | | X | X | X | X |
| | | | X | | | X | X | | | X | X | X | X |
| | X | | | X | X | X | X | | | X | X | X | X |
| X | X | | | X | X | X | | X | | X | X | X | X |
| | | X | | X | X | X | X | X | | X | X | X | X |
| X | | X | | X | X | X | | | X | X | X | X | X |
| | X | X | | X | X | X | X | | X | X | X | X | X |
| X | X | X | | X | X | X | | X | X | X | X | X | X |
| | | | X | X | X | X | X | X | X | X | X | X | X |

In some embodiments, a synTF or synTF system as described herein comprises a DBD, a TA, a TED, at least one ligand binding domain (LBD) and at least one ligand specific for the LBD. In some embodiments, the DBD, TA, TED, LBD, and ligand domains can be comprised by two separate polypeptides. In some embodiments, the DBD and TA are in separate polypeptides, such that the system is active only when both polypeptides are expressed. In some embodiments, a synTF or synTF system as described herein comprises a DBD, a TA, a TED, at least one PDZ, and at least one ligand specific for the PDZ domain (see e.g., Example 4, FIG. 3A-3D). As a non-limiting example, in one aspect described herein is a synTF system comprising: (a) a first polypeptide comprising: (i) a DBD, (ii) a TED, and (iii) an LBD; and (b) a second polypeptide comprising: (i) a ligand specific for the LBD, and (ii) a TA. Non-limiting examples of PDZs and PDZ-specific ligands are provided in U.S. Pat. No. 11,781,149 B2, the contents of which are incorporated herein by reference in their entirety.

Transcriptional Effector Domain (TED)

In multiple aspects, described herein are constructs, including synTFs, comprising at least one Transcriptional Effector Domain (TED). As used herein, the term "Transcriptional Effector Domain (TED)" refers to a domain that increases the transcriptional activity of a transcriptional activator (TA) domain, compared to a construct comprising the TA but lacking the TED. In some embodiments, the TED comprises an elongation domain, an activator domain, and/or a domain with pioneer ability.

In some embodiments of any of the aspects, a synTF polypeptide as described herein (or a synTF polypeptide system collectively) comprises 1, 2, 3, 4, 5, or more TED(s). In some embodiments of any of the aspects, the synTF polypeptide or system comprises one TED. In some embodiments of any of the aspects, the synTF polypeptide or system comprises two TEDs. In embodiments comprising multiple TEDs, the multiple TEDs can be different individual TEDs or multiple copies of the same TED, or a combination of the foregoing.

In some embodiments, the TED comprises an elongation domain. As used herein, the term "elongation domain" refers to a polypeptide that promotes elongation of the transcript by a polymerase, e.g., by decreasing transcriptional pausing and/or polymerase backtracking, arrest, and/or termination (see e.g., Section 3.1.1.3 of Example 3). In some embodiments, the TED comprises an elongation domain derived from a polypeptide selected from the group consisting of: Interacts with Suppressor Of Ty 6 (Spt6) Homolog (IWS1); Suppressor Of Ty 5 (Spt5) Homolog (SUPT5H); Bromodomain-containing protein 4 (BRD4); and cellular Myelocytomatosis (cMyc).

In some embodiments, the TED comprises an elongation domain derived from IWS1. In some embodiments, the TED comprises an elongation domain derived from mammalian IWS1. In some embodiments, the TED comprises an elongation domain derived from human IWS1 (see e.g., SEQ ID NO: 4). In some embodiments, the TED comprises amino acids 449-492, 450-492, 451-492, 452-492, 453-492, 454-492, 455-492, 456-492, 449-491, 450-491, 451-491, 452-491, 453-491, 454-491, 455-491, or 456-491 of IWS1 in SEQ ID NO: 4.

```
IWS1, NCBI reference NP_001397852.1,
818 amino acids (aa)
                                     SEQ ID NO: 4
MDSEYYSGDQSDDGGATPVQDERDSGSDGEDDVNEQHSGSDTGSVE

RHSENETSDREDGLPKGHHVTDSENDEPLNLNASDSESEELHRQK

DSDSESEERAEPPASDSENEDVNQHGSDSESEETRKLPGSDSENE

ELLNGHASDSENEDVGKHPASDSEIEELQKSPASDSETEDALKPQ

ISDSESEEPPRHQASDSENEEPPKPRMSDSESEELPKPQVSDSES

EEPPRHQASDSENEELPKPRISDSESEDPPRHQASDSENEELPKP

RISDSESEDPPRNQASDSENEELPKPRVSDSESEGPQKGPASDSE
```

-continued

TEDASRHKQKPESDDDSDRENKGEDTEMQNDSFHSDSHMDRKKFH

SSDSEEEEHKKQKMDSDEDEKEGEEEKVAKRKAAVLSDSEDEEKA

SAKKSRVVSDADDSDSDAVSDKSGKREKTIASDSEEEAGKELSDK

KNEEKDLFGSDSESGNEEENLIADIFGESGDEEEEEFTGFNQEDL

EEEKGETQVKEAEDSDSDDNIKRGKHMDFLSDFEMMLQRKKSMSG

KRRRNRDGGTFISDADDVVSAMIVKMNEAAEEDRQLNNQKKPALK

KLTLLPAVVMHLKKQDLKETFIDSGVMSAIKEWLSPLPDRSLPAL

KIREELLKILQELPSVSQETLKHSGIGRAVMYLYKHPKESRSNKD

MAGKLINEWSRPIFGLTSNYKGMTREEREQRDLEQMPQRRRMNST

GGQTPRRDLEKVLTGEEKALRPGDPGFCARARVPMPSNKDYVVRP

KWNVEMESSRPGILKKGLSRLEKHKRRFAEQKRLSKVHRAVKFSI

EGNRMPL,

In some embodiments, the elongation domain comprises at least one TFIIS N-terminal domains (TND)-interacting motif (TIM) domain of IWS1 (see e.g., SEQ ID NOs: 5-9). IWS1 is a transcription elongation factor, which directly interacts with RNA polymerase II (RNAPII) and is phosphorylated at casein kinase II (CKII) sites. The human IWS1 homolog physically interacts with protein arginine methyltransferase 5 (PRMT5). IWS1 also recruits a SET2 histone methyltransferase (Huntingtin-interacting protein HYPB, also known as SETD2) to RNAPII during transcription elongation and is involved in H3K36 trimethylation.

In some embodiments, the elongation domain comprises at least one TIM1, TIM2, and/or TIM3 domain from IWS1. In some embodiments, the elongation domain comprises at least one TIM1. In some embodiments, the elongation domain comprises at least one TIM2. In some embodiments, the elongation domain comprises at least one TIM3. In some embodiments, the elongation domain comprises at least one TIM1 and at least one TIM2. In some embodiments, the elongation domain comprises at least one TIM1 and at least one TIM3. In some embodiments, the elongation domain comprises at least one TIM2 and at least one TIM3. In some embodiments, the elongation domain comprises at least one TIM1, at least one TIM2, and at least one TIM3 domain from IWS1.

In some embodiments, the elongation domain comprises at least one of SEQ ID NOs: 5-9 or an amino acid sequence with at least 60%, at least 65%, at least 70%, at least 75%, at least 80%, at least 85%, at least 90%, at least 95%, at least 96%, at least 97%, at least 98%, or at least 99% sequence identity to one of SEQ ID NOs: 5-9, which maintains the same function (e.g., increased transcriptional activity of the synTF).

SEQ ID NO: 5, amino acids 449-492 of IWS1, IWS1 TIMs domain (see e.g., SEQ ID NO: 4), TIM1 bolded (see e.g., SEQ ID NO: 6), TIM2 italicized (see e.g., SEQ ID NO: 7), TIM3 bolded and italicized (see e.g., SEQ ID NO: 8), 44 amino acids (aa):

SDKKNEEKDLFGSDSESGNEEEN*LIADIFG*ESGDEEEE*EFTGF*N.

SEQ ID NO: 6, TIM1: KDLFG.

SEQ ID NO: 7, TIM2: ADIFG.

SEQ ID NO: 8, TIM3: EFTGF.

In some embodiments, the elongation domain comprises at least one (e.g., 1, 2, 3) mutation(s) in a TIM domain. In some embodiments, the elongation domain comprises at least one of SEQ ID NOs: 9-14 or an amino acid sequence with at least 60%, at least 65%, at least 70%, at least 75%, at least 80%, at least 85%, at least 90%, at least 95%, at least 96%, at least 97%, at least 98%, or at least 99% sequence identity to one of SEQ ID NOs: 9-14, which maintains the same function (e.g., increased transcriptional activity of the synTF).

SEQ ID NO: 9,
amino acids 449-492 of IWS, mutant 1
(M1; L458A and F459A: bolded;
TIM1 mutant; see e.g., SEQ ID NO: 12):
SDKKNEEKDAAGSDSESGNEEENLIADIFGESGDEEEEEFTGFN.

SEQ ID NO: 10,
amino acids 449-492 of IWS, mutant 2
(M2; 1476A and F477A: bolded;
TIM2 mutant; see e.g., SEQ ID NO: 13):
SDKKNEEKDLFGSDSESGNEEENLIADAAGESGDEEEEEFTGFN.

SEQ ID NO: 11,
amino acids 449-492 of IWS, mutant 3
(M3; F488A and F491A: bolded;
TIM3 mutant; see e.g., SEQ ID NO: 14):
SDKKNEEKDLFGSDSESGNEEEN*LIADIF*GESGDEEEEEATGAN.

SEQ ID NO: 12, TIM1 mutant: KDAAG.

SEQ ID NO: 13, TIM2 mutant: ADAAG.

SEQ ID NO: 14, TIM3 mutant: EATGA.

In some embodiments, the elongation domain is derived from Suppressor Of Ty 5 (Spt5) Homolog (SUPT5H). In some embodiments, the elongation domain is the Kow5 domain of SUPT5H. In some embodiments, the elongation domain comprises approximately amino acids 698-765 of SUPT5H (see e.g., SEQ ID NO: 49). In some embodiments, the elongation domain is derived from Bromodomain-containing protein 4 (BRD4). In some embodiments, the elongation domain comprises approximately amino acids 1308-1362 of BRD4 (see e.g., SEQ ID NO: 50). In some embodiments, the elongation domain is derived from cellular Myelocytomatosis (cMyc). In some embodiments, the elongation domain comprises approximately amino acids 1-70 of cMyc (see e.g., SEQ ID NO: 51).

SEQ ID NO: 49, human Suppressor Of Ty 5 (Spt5)
Homolog (SUPT5H), DSIF elongation
factor subunit, NCBI Reference
Sequence: NP_001124297.1, 1083 aa
MSDSEDSNFSEEEDSERSSDGEEAEVDEERRSAAGSEKEEEPEDE

EEEEEEEEYDEEEEEEDDDRPPKKPRHGGFILDEADVDDEYEDED

QWEDGAEDILEKASNIDNVVLDEDRSGARRLQNLWRDQREEELGE

YYMKKYAKSSVGETVYGGSDELSDDITQQQLLPGVKDPNLWTVKC

KIGEERATAISLMRKFIAYQFTDTPLQIKSVVAPEHVKGYIYVEA

YKQTHVKQAIEGVGNLRLGYWNQQMVPIKEMTDVLKVVKEVANLK

PKSWVRLKRGIYKDDIAQVDYVEPSQNTISLKMIPRIDYDRIKAR

MSLKDWFAKRKKFKRPPQRLFDAEKIRSLGGDVASDGDFLIFEGN

RYSRKGFLFKSFAMSAVITEGVKPTLSELEKFEDQPEGIDLEVVT

ESTGKEREHNFQPGDNVEVCEGELINLQGKILSVDGNKITIMPKH

EDLKDMLEFPAQELRKYFKMGDHVKVIAGRFEGDTGLIVRVEENF

VILFSDLTMHELKVLPRDLQLCSETASGVDVGGQHEWGELVQLDP

-continued

QTVGVIVRLERETFQVLNMYGKVVTVRHQAVTRKKDNRFAVALDS

EQNNIHVKDIVKVIDGPHSGREGEIRHLFRSFAFLHCKKLVENGG

MFVCKTRHLVLAGGSKPRDVTNFTVGGFAPMSPRISSPMHPSAGG

QRGGFGSPGGGSGGMSRGRGRRDNELIGQTVRISQGPYKGYIGVV

KDATESTARVELHSTCQTISVDRQRLTTVGSRRPGGMTSTYGRTP

MYGSQTPMYGSGSRTPMYGSQTPLQDGSRTPHYGSQTPLHDGSRT

PAQSGAWDPNNPNTPSRAEEEYEYAFDDEPTPSPQAYGGTPNPQT

PGYPDPSSPQVNPQYNPQTPGTPAMYNTDQFSPYAAPSPQGSYQP

SPSPQSYHQVAPSPAGYQNTHSPASYHPTPSPMAYQASPSPSPVG

YSPMTPGAPSPGGYNPHTPGSGIEQNSSDWVTTDIQVKVRDTYLD

TQVVGQTGVIRSVTGGMCSVYLKDSEKVVSISSEHLEPITPTKNN

KVKVILGEDREATGVLLSIDGEDGIVRMDLDEQLKILNLRFLGKL

LEA,

SEQ ID NO: 50,
human Bromodomain-containing protein 4 (BRD4), NCBI Reference Sequence: NP_001366220.1, 1362 aa,
MSAESGPGTRLRNLPVMGDGLETSQMSTTQAQAQPQPANAASTNP

PPPETSNPNKPKRQTNQLQYLLRVVLKTLWKHQFAWPFQQPVDAV

KLNLPDYYKIIKTPMDMGTIKKRLENNYYWNAQECIQDFNTMFTN

CYIYNKPGDDIVLMAEALEKLFLQKINELPTEETEIMIVQAKGRG

RGRKETGTAKPGVSTVPNTTQASTPPQTQTPQPNPPPVQATPHPF

PAVTPDLIVQTPVMTVVPPQPLQTPPPVPPQPQPPPAPAPQPVQS

HPPIIAATPQPVKTKKGVKRKADTTTPTTIDPIHEPPSLPPEPKT

TKLGQRRESSRPVKPPKKDVPDSQQHPAPEKSSKVSEQLKCCSGI

LKEMFAKKHAAYAWPFYKPVDVEALGLHDYCDIIKHPMDMSTIKS

KLEAREYRDAQEFGADVRLMFSNCYKYNPPDHEVVAMARKLQDVF

EMRFAKMPDEPEEPVVAVSSPAVPPPTKVVAPPSSSDSSSDSSSD

SDSSTDDSEEERAQRLAELQEQLKAVHEQLAALSQPQQNKPKKKE

KDKKEKKKEKHKRKEEVEENKKSKAKEPPPKKTKKNNSSNSNVSK

KEPAPMKSKPPPTYESEEEDKCKPMSYEEKRQLSLDINKLPGEKL

GRVVHIIQSREPSLKNSNPDEIEIDFETLKPSTLRELERYVTSCL

RKKRKPQAEKVDVIAGSSKMKGFSSSESESSSESSSSDSEDSETE

MAPKSKKKGHPGREQKKHHHHHHQQMQQAPAPVPQQPPPPPQQPP

PPPPPQQQQQPPPPPPPPSMPQQAAPAMKSSPPPFIATQVPVLEP

QLPGSVFDPIGHFTQPILHLPQPELPPHLPQPPEHSTPPHLNQHA

VVSPPALHNALPQQPSRPSNRAAALPPKPARPPAVSPALTQTPLL

PQPPMAQPPQVLLEDEEPPAPPLTSMQMQLYLQQLQKVQPPTPLL

PSVKVQSQPPPPLPPPPHPSVQQQLQQQPPPPPPPQPQPPPQQQH

QPPPRPVHLQPMQFSTHIQQPPPPQGQQPPHPPPGQQPPPPQPAK

PQQVIQHHHSPRHHKSDPYSTGHLREAPSPLMIHSPQMSQFQSLT

HQSPPQQNVQPKKQELRAASVVQPQPLVVVKEEKIHSPIIRSEPF

SPSLRPEPPKHPESIKAPVHLPQRPEMKPVDVGRPVIRPPEQNAP

-continued

PPGAPDKDKQKQEPKTPVAPKKDLKIKNMGSWASLVQKHPTTPSS

TAKSSSDSFEQFRRAAREKEEREKALKAQAEHAEKEKERLRQERM

RSREDEDALEQARRAHEEARRRQEQQQQQRQEQQQQQQQQAAAVA

AAATPQAQSSQPQSMLDQQRELARKREQERRRREAMAATIDMNFQ

SDLLSIFEENLF

SEQ ID NO: 51,
cellular Myelocytomatosis (cMyc), human MYC proto-oncogene, bHLH transcription factor, UNIPROT reference number P01106-2, 454 aa
MDFFRVVENQQPPATMPLNVSFTNRNYDLDYDSVQPYFYCDEEEN

FYQQQQQSELQPPAPSEDIWKKFELLPTPPLSPSRRSGLCSPSYV

AVTPFSLRGDNDGGGGSFSTADQLEMVTELLGGDMVNQSFICDPD

DETFIKNIIIQDCMWSGFSAAAKLVSEKLASYQAARKDSGSPNPA

RGHSVCSTSSLYLQDLSAAASECIDPSVVFPYPLNDSSSPKSCAS

QDSSAFSPSSDSLLSSTESSPQGSPEPLVLHEETPPTTSSDSEEE

QEDEEEIDVVSVEKRQAPGKRSESGSPSAGGHSKPPHSPLVLKRC

HVSTHQHNYAAPPSTRKDYPAAKRVKLDSVRVLRQISNNRKCTSP

RSSDTEENVKRRTHNVLERQRRNELKRSFFALRDQIPELENNEKA

PKVVILKKATAYILSVQAEEQKLISEEDLLRKRREQLKHKLEQLR

NSCA

In some embodiments, the TED comprises an activator domain. As used herein, the term "activator domain" refers to a polypeptide that is involved in positive transcription regulation (see e.g., Section 3.1.1.2 of Example 3). In some embodiments, the TED comprises an activator domain derived from a polypeptide selected from the group consisting of: Heat Shock Factor 1 (HSF1), Glucocorticoid Receptor (GR), and MLX interacting protein like (MLXIPL).

In some embodiments, the activator domain is derived from Heat Shock Factor 1 (HSF1). In some embodiments, the activator domain comprises approximately amino acids 406-529 of HSF (see e.g., SEQ ID NO: 52). In some embodiments, the activator domain is derived from Glucocorticoid Receptor (GR). In some embodiments, the activator domain comprises approximately amino acids 187-244 of GR (see e.g., SEQ ID NO: 53). In some embodiments, the activator domain is derived from MLX interacting protein like (MLXIPL). In some embodiments, the activator domain comprises approximately amino acids 318-370 of MLXIPL (see e.g., SEQ ID NO: 54).

SEQ ID NO: 52,
human Heat Shock Factor 1 (HSF1), NCBI Reference Sequence: NP_005517.1, 529 aa
MDLPVGPGAAGPSNVPAFLTKLWTLVSDPDTDALICWSPSGNSFH

VFDQGQFAKEVLPKYFKHNNMASFVRQLNMYGFRKVVHIEQGGLV

KPERDDTEFQHPCFLRGQEQLLENIKRKVTSVSTLKSEDIKIRQD

SVTKLLTDVQLMKGKQECMDSKLLAMKHENEALWREVASLRQKHA

QQQKVVNKLIQFLISLVQSNRILGVKRKIPLMLNDSGSAHSMPKY

SRQFSLEHVHGSGPYSAPSPAYSSSSLYAPDAVASSGPIISDITE

LAPASPMASPGGSIDERPLSSSPLVRVKEEPPSPPQSPRVEEASP

-continued

GRPSSVDTLLSPTALIDSILRESEPAPASVTALTDARGHTDTEGR

PPSPPPTSTPEKCLSVACLDKNELSDHLDAMDSNLDNLQTMLSSH

GFSVDTSALLDLFSPSVTVPDMSLPDLDSSLASIQELLSPQEPPR

PPEAENSSPDSGKQLVHYTAQPLFLLDPGSVDTGSNDLPVLFELG

EGSYFSEGDGFAEDPTISLLTGSEPPKAKDPTVS

SEQ ID NO: 53,
human Glucocorticoid Receptor (GR),
also referred to as Nuclear Receptor
Subfamily 3 Group C Member 1 (NR3C1), NCBI
Reference Sequence: NP_000167.1, 777 aa
MDSKESLTPGREENPSSVLAQERGDVMDFYKTLRGGATVKVSASS

PSLAVASQSDSKQRRLLVDFPKGSVSNAQQPDLSKAVSLSMGLYM

GETETKVMGNDLGFPQQGQISLSSGETDLKLLEESIANLNRSTSV

PENPKSSASTAVSAAPTEKEFPKTHSDVSSEQQHLKGQTGTNGGN

VKLYTTDQSTFDILQDLEFSSGSPGKETNESPWRSDLLIDENCLL

SPLAGEDDSFLLEGNSNEDCKPLILPDTKPKIKDNGDLVLSSPSN

VTLPQVKTEKEDFIELCTPGVIKQEKLGTVYCQASFPGANIIGNK

MSAISVHGVSTSGGQMYHYDMNTASLSQQQDQKPIFNVIPPIPVG

SENWNRCQGSGDDNLTSLGTLNFPGRTVFSNGYSSPSMRPDVSSP

PSSSSTATTGPPPKLCLVCSDEASGCHYGVLTCGSCKVFFKRAVE

GQHNYLCAGRNDCIIDKIRRKNCPACRYRKCLQAGMNLEARKTKK

KIKGIQQATTGVSQETSENPGNKTIVPATLPQLTPTLVSLLEVIE

PEVLYAGYDSSVPDSTWRIMTTLNMLGGRQVIAAVKWAKAIPGFR

NLHLDDQMTLLQYSWMFLMAFALGWRSYRQSSANLLCFAPDLIIN

EQRMTLPCMYDQCKHMLYVSSELHRLQVSYEEYLCMKTLLLLSSV

PKDGLKSQELFDEIRMTYIKELGKAIVKREGNSSQNWQRFYQLTK

LLDSMHEVVENLLNYCFQTFLDKTMSIEFPEMLAEIITNQIPKYS

NGNIKKLLFHQK

SEQ ID NO: 54, human MLX interacting protein
like (MLXIPL), NCBI Reference Sequence:
NP_116569.1 852 aa
MAGALAGLAAGLQVPRVAPSPDSDSDTDSEDPSLRRSAGGLLRSQ

VIHSGHFMVSSPHSDSLPRRRDQEGSVGPSDFGPRSIDPTLTRLF

ECLSLAYSGKLVSPKWKNFKGLKLLCRDKIRLNNAIWRAWYIQYV

KRRKSPVCGFVTPLQGPEADAHRKPEAVVLEGNYWKRRIEVVMRE

YHKWRIYYKKRLRKPSREDDLLAPKQAEGRWPPPEQWCKQLFSSV

VPVLLGDPEEEPGGRQLLDLNCFLSDISDTLFTMTQSGPSPLQLP

PEDAYVGNADMIQPDLTPLQPSLDDFMDISDFFTNSRLPQPPMPS

NFPEPPSFSPVVDSLFSSGTLGPEVPPASSAMTHLSGHSRLQARN

SCPGPLDSSAFLSSDFLLPEDPKPRLPPPPVPPPLLHYPPPAKVP

GLEPCPPPPFPPMAPPTALLQEEPLFSPRFPFPTVPPAPGVSPLP

APAAFPPTPQSVPSPAPTPFPIELLPLGYSEPAFGPCFSMPRGKP

PAPSPRGQKASPPTLAPATASPPTTAGSNNPCLTQLLTAAKPEQA

LEPPLVSSTLLRSPGSPQETVPEFPCTFLPPTPAPTPPRPPPGPA

-continued

TLAPSRPLLVPKAERLSPPAPSGSERRLSGDLSSMPGPGTLSVRV

SPPQPILSRGRPDSNKTENRRITHISAEQKRRFNIKLGFDTLHGL

VSTLSAQPSLKVSKATTLQKTAEYILMLQQERAGLQEEAQQLRDE

IEELNAAINLCQQQLPATGVPITHQRFDQMRDMFDDYVRTRTLHN

WKFWVFSILIRPLFESFNGMVSTASVHTLRQTSLAWLDQYCSLPA

LRPTVLNSLRQLGTSTSILTDPGRIPEQATRAVTEGTLGKPL,

In some embodiments, the TED comprises a domain with pioneer ability. As used herein, the term "domain with pioneer ability" refers to a polypeptide that has the ability to access DNA in compacted heterochromatin (see e.g., Section 3.1.1.1 of Example 3). In some embodiments, the TED comprises a domain with pioneer ability derived from a polypeptide selected from the group consisting of: Fused in Sarcoma (FUS) and Ewing Sarcoma Breakpoint Region (EWSR).

In some embodiments, the domain with pioneer ability is derived from Fused in Sarcoma (FUS). In some embodiments, the domain with pioneer ability comprises approximately amino acids 2-214 of FUS (see e.g., SEQ ID NO: 55). In some embodiments, the domain with pioneer ability is derived from Ewing Sarcoma Breakpoint Region (EWSR). In some embodiments, the domain with pioneer ability comprises approximately amino acids 47-267 of EWSR (see e.g., SEQ ID NO: 56).

SEQ ID NO: 55, human Fused in Sarcoma (FUS),
NP_001164105.1, 525 aa
MASNDYTQQATQSYGAYPTQPGQGYSQQSSQPYGQQSYSGYSQST

DTSGYGQSSYSSYGQSQNSYGTQSTPQGYGSTGGYGSSQSSQSSY

GQQSSYPGYGQQPAPSSTSGSYGSSSQSSSYGQPQSGSYSQQPSY

GGQQQSYGQQQSYNPPQGYGQQNQYNSSSGGGGGGGGGGNYGQDQ

SSMSSGGGSGGGYGNQDQSGGGGSGGYGQQDRGGRGRGGSGGGGG

GGGGGYNRSSGGYEPRGRGGGRGGRGGMGGSDRGGFNKFGGPRDQ

GSRHDSEQDNSDNNTIFVQGLGENVTIESVADYFKQIGIIKTNKK

TGQPMINLYTDRETGKLKGEATVSFDDPPSAKAAIDWFDGKEFSG

NPIKVSFATRRADFNRGGGNGRGGRGRGGPMGRGGYGGGGSGGGG

RGGFPSGGGGGGGQQRAGDWKCPNPTCENMNFSWRNECNQCKAPK

PDGPGGGPGGSHMGGNYGDDRRGGRGGYDRGGYRGRGGDRGGFRG

GRGGGDRGGFGPGKMDSRGEHRQDRRERPY

SEQ ID NO: 56, human Ewing Sarcoma Breakpoint
Region (EWSR), NCBI Reference
Sequence: NP_001156757.1, 655 aa
MASTDYSTYSQAAAQQGYSAYTAQPTQGYAQTTQAYGQQSYGTYG

QPTDVSYTQAQTTATYGQTAYATSYGQPPTGYTTPTAPQAYSQPV

QGYGTGAYDTTTATVTTTQASYAAQSAYGTQPAYPAYGQQPAATA

PTRPQDGNKPTETSQPQSSTGGYNQPSLGYGQSNYSYPQVPGSYP

MQPVTAPPSYPPTSYSSTQPTSYDQSSYSQQNTYGQPSSYGQQSS

YGQQSSYGQQPPTSYPPQTGSYSQAPSQYSQQSSSYGQQSSFRQD

HPSSMGVYGQESGGFSGPGENRSMSGPDNRGRGRGGFDRGGMSRG

GRGGGRGGMGAGERGGFNKPGGPMDEGPDLDLGPPVDPDEDSDNS

-continued

AIYVQGLNDSVTLDDLADFFKQCGVVKMNKRTGQPMIHIYLDKET

GKPKGDATVSYEDPPTAKAAVEWFDGKDFQGSKLKVSLARKKPPM

NSMRGGLPPREGRGMPPPLRGGPGGPGGPGGPMGRMGGRGGDRGG

FPPRGPRGSRGNPSGGGNVQHRAGDWQCPNPGCGNQNFAWRTECN

QCKAPKPEGFLPPPFPPPGGDRGRGGPGGMRGGRGGLMDRGGPGG

MFRGGRGGDRGGFRGGRGMDRGGFGGGRRGGPGGPPGPLMEQMGG

RRGGRGGPGKMDKGEHRQERRDRPY,

In some embodiments, the TED comprises an elongation domain and an activator domain. In some embodiments, the TED comprises an elongation domain and a domain with pioneer ability. In some embodiments, the TED comprises an activator domain and a domain with pioneer ability. In some embodiments, the TED comprises an elongation domain, an activator domain, and a domain with pioneer ability.

Transcriptional Activator (TA) Domain

Described herein are synTFs comprising a transcription activator (or activating) domain (TA). For example, the transcriptional effector domain is selected from the group consisting of a Herpes Simplex Virus Protein 16 (VP16) activation domain; an activation domain consisting of four tandem copies of VP16, a VP64 activation domain; a p65 activation domain of NFkB or functional fragment thereof; an Epstein-Barr virus R transactivator (Rta) activation domain or functional fragment thereof; a tripartite activator consisting of the VP64, the p65, and the Rta activation domains, wherein the tripartite activator is known as a VPR activation domain; a miniVPR (or "minVPR"); NFZ; 3Z; a histone acetyltransferase (HAT) core domain of the human E1A-associated protein p300, known as a p300 HAT core activation domain; a CBP HAT domain. In some embodiments, the transcriptional activator domain is selected from VPR (VP64-p65-Rta), VP64, p65, Rta, minVPR, NFZ, and 3Z.

In some embodiments of any of the aspects, a synTF polypeptide as described herein (or a synTF polypeptide system collectively) comprises 1, 2, 3, 4, 5, or more transcriptional activator domain(s). In some embodiments of any of the aspects, the synTF polypeptide or system comprises one transcriptional activator domain. In embodiments comprising multiple transcriptional activator domains, the multiple transcriptional activator domains can be different individual transcriptional activator domains or multiple copies of the same transcriptional activator domain, or a combination of the foregoing.

As used herein, the term "transcriptional activator" domain refers to an effector that increases gene expression. In some embodiments of any of the aspects, the TA is selected from the group consisting of: p65; Rta; miniVPR; full VPR; VP16; VP64; NFZ; 3Z; p300; p300 HAT Core; and a CBP HAT domain. See e.g., U.S. Pat. Nos. 10,138,493; 10,590,182; Khalil et al., Cell Volume 150, Issue 3, 3 Aug. 2012, Pages 647-658; Vora et al., Rational design of a compact CRISPR-Cas9 activator for AAV-mediated delivery, bioRxiv 2018 doi.org/10.1101/298620; Chavez et al., Nat Methods. 2015 April, 12(4): 326-328; Park et al., Cell. 2019 Jan. 10, 176(1-2):227-238, e20; Hilton et al., Nature Biotechnology volume 33, pages 510-517(2015); Sajwan et al., Sci Rep. 2019; 9: 18104; the contents of each of which are incorporated herein by reference in their entireties.

In some embodiments of any of the aspects, the TA is p65, or a functional fragment thereof. Transcription factor p65 also known as nuclear factor NF-kappa-B p65 subunit is a protein that in humans is encoded by the RELA gene. In some embodiments of any of the aspects, p65 comprises SEQ ID NO: 38 or a protein having at least 85% sequence identity to SEQ ID NO: 38. In some embodiments of any of the aspects, p65 comprises SEQ ID NO: 58 or a protein having at least 85% sequence identity to SEQ ID NO: 58. In some embodiments of any of the aspects, p65 comprises SEQ ID NO: 59 or a portion of SEQ ID NO: 59, e.g., residues 150-261, 100-261, 200-261, 1-200, 1-50, 1-100, or 50-100 of SEQ ID NO: 59. In some embodiments of any of the aspects, p65 comprises one of SEQ ID NOs: 38, 58-67 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 38, 58-67 that maintains its function. In some embodiments of any of the aspects, p65 comprises SEQ ID NO: 61 (p65 100-261) or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 61 that maintains the same function.

SEQ ID NO: 38, (p65 amino acids 361-551 of NFKB) Activation Domain (191 aa)
DEFPTMVFPSGQISQASALAPAPPQVLPQAPAPAPAPAMVSALAQ

APAPVPVLAPGPPQAVAPPAPKPTQAGEGTLSEALLQLQFDDEDL

GALLGNSTDPAVFTDLASVDNSEFQQLLNQGIPVAPHTTEPMLME

YPEAITRLVTGAQRPPDPAPAPLGAPGLPNGLLSGDEDFSSIADM

DFSALLSQISS

SEQ ID NO: 58,
p65 (full sequence, 551 aa),
transcription factor p65 isoform 1 [*Homo sapiens*], NCBI Reference Sequence: NP_068810.3
MDELFPLIFPAEPAQASGPYVEIIEQPKQRGMRFRYKCEGRSAGS

IPGERSTDTTKTHPTIKINGYTGPGTVRISLVTKDPPHRPHPHEL

VGKDCRDGFYEAELCPDRCIHSFQNLGIQCVKKRDLEQAISQRIQ

TNNNPFQVPIEEQRGDYDLNAVRLCFQVTVRDPSGRPLRLPPVLS

HPIFDNRAPNTAELKICRVNRNSGSCLGGDEIFLLCDKVQKEDIE

VYFTGPGWEARGSFSQADVHRQVAIVFRTPPYADPSLQAPVRVSM

QLRRPSDRELSEPMEFQYLPDTDDRHRIEEKRKRTYETFKSIMKK

SPFSGPTDPRPPPRRIAVPSRSSASVPKPAPQPYPFTSSLSTINY

DEFPTMVFPSGQISQASALAPAPPQVLPQAPAPAPAPAMVSALAQ

APAPVPVLAPGPPQAVAPPAPKPTQAGEGTLSEALLQLQFDDEDL

GALLGNSTDPAVFTDLASVDNSEFQQLLNQGIPVAPHTTEPMLME

YPEAITRLVTGAQRPPDPAPAPLGAPGLPNGLLSGDEDFSSIADM

DFSALLSQISS

SEQ ID NO: 59,
p65 1-261 (261 aa)
SQYLPDTDDRHRIEEKRKRTYETFKSIMKKSPFSGPTDPRPPPRR

IAVPSRSSASVPKPAPQPYPFTSSLSTINYDEFPTMVFPSGQISQ

-continued

ASALAPAPPQVLPQAPAPAPAPAMVSALAQAPAPVPVLAPGPPQA

VAPPAPKPTQAGEGTLSEALLQLQFDDEDLGALLGNSTDPAVFTD

LASVDNSEFQQLLNQGIPVAPHTTEPMLMEYPEAITRLVTGAQRP

PDPAPAPLGAPGLPNGLLSGDEDFSSIADMDFSALL

SEQ ID NO: 60,
p65 150-261 (112 aa)
SLSEALLQLQFDDEDLGALLGNSTDPAVFTDLASVDNSEFQQLLN

QGIPVAPHTTEPMLMEYPEAITRLVTGAQRPPDPAPAPLGAPGLP

NGLLSGDEDFSSIADMDFSALL

SEQ ID NO: 61,
p65 100-261 (162 aa)
SVLPQAPAPAPAPAMVSALAQAPAPVPVLAPGPPQAVAPPAPKPT

QAGEGTLSEALLQLQFDDEDLGALLGNSTDPAVFTDLASVDNSEF

QQLLNQGIPVAPHTTEPMLMEYPEAITRLVTGAQRPPDPAPAPLG

APGLPNGLLSGDEDFSSIADMDFSALL

SEQ ID NO: 62,
p65 200-261 (62 aa)
SPHTTEPMLMEYPEAITRLVTGAQRPPDPAPAPLGAPGLPNGLLS

GDEDFSSIADMDFSALL,

SEQ ID NO: 63,
p65 1-200 (200 aa)
SQYLPDTDDRHRIEEKRKRTYETFKSIMKKSPFSGPTDPRPPPRR

IAVPSRSSASVPKPAPQPYPFTSSLSTINYDEFPTMVFPSGQISQ

ASALAPAPPQVLPQAPAPAPAPAMVSALAQAPAPVPVLAPGPPQA

VAPPAPKPTQAGEGTLSEALLQLQFDDEDLGALLGNSTDPAVFTD

LASVDNSEFQQLLNQGIPVA

SEQ ID NO: 64,
p65 1-150 (150 aa)
SQYLPDTDDRHRIEEKRKRTYETFKSIMKKSPFSGPTDPRPPPRR

IAVPSRSSASVPKPAPQPYPFTSSLSTINYDEFPTMVFPSGQISQ

ASALAPAPPQVLPQAPAPAPAPAMVSALAQAPAPVPVLAPGPPQA

VAPPAPKPTQAGEGT

SEQ ID NO: 65,
p65 1-100 (100 aa)
SQYLPDTDDRHRIEEKRKRTYETFKSIMKKSPFSGPTDPRPPPRR

IAVPSRSSASVPKPAPQPYPFTSSLSTINYDEFPTMVFPSGQISQ

ASALAPAPPQ

SEQ ID NO: 66,
p65 50-150 (101 aa)
SRSSASVPKPAPQPYPFTSSLSTINYDEFPTMVFPSGQISQASAL

APAPPQVLPQAPAPAPAPAMVSALAQAPAPVPVLAPGPPQAVAPP

APKPTQAGEGT

SEQ ID NO: 67,
p65 143-261 (119 aa)
PTQAGEGTLSEALLQLQFDDEDLGALLGNSTDPAVFTDLASVDNS

EFQQLLNQGIPVAPHTTEPMLMEYPEAITRLVTGAQRPPDPAPAP

LGAPGLPNGLLSGDEDFSSIADMDFSALL

In some embodiments of any of the aspects, the TA is Rta, or a functional fragment thereof. Rta is an Epstein-Barr virus R transactivator (Rta) activation domain. In some embodiments of any of the aspects, Rta comprises SEQ ID NO: 68 or a protein having at least 85% sequence identity to SEQ ID NO: 68. In some embodiments of any of the aspects, Rta comprises a portion of SEQ ID NO: 68, e.g., residues 75-190, 125-190, 50-175, 75-175, 100-175, or 125-175 of SEQ ID NO: 68. In some embodiments of any of the aspects, Rta comprises one of SEQ ID NOs: 68-74 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 68-74 that maintains its function. In some embodiments of any of the aspects, Rta comprises SEQ ID NO: 70 (Rta 125-190) or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 70 that maintains the same function.

Rta (full sequence, 1-190; 190 aa)
SEQ ID NO: 68
RDSREGMFLPKPEAGSAISDVFEGREVCQPKRIRPFHPPGSPWAN

RPLPASLAPTPTGPVHEPVGSLTPAPVPQPLDPAPAVTPEASHLL

EDPDEETSQAVKALREMADTVIPQKEEAAICGQMDLSHPPPRGHL

DELTTTLESMTEDLNLDSPLTPELNEILDTFLNDECLLHAMHIST

GLSIFDTSLF,

Rta (75-190; 116 aa)
SEQ ID NO: 69
PLDPAPAVTPEASHLLEDPDEETSQAVKALREMADTVIPQKEEAA

ICGQMDLSHPPPRGHLDELTTTLESMTEDLNLDSPLTPELNEILD

TFLNDECLLHAMHISTGLSIFDTSLF,

Rta (125-190; 66 aa)
SEQ ID NO: 70
DLSHPPPRGHLDELTTTLESMTEDLNLDSPLTPELNEILDTFLND

ECLLHAMHISTGLSIFDTSLF,

Rta (50-175; 126 aa)
SEQ ID NO: 71
SSLAPTPTGPVHEPVGSLTPAPVPQPLDPAPAVTPEASHLLEDPD

EETSQAVKALREMADTVIPQKEEAAICGQMDLSHPPPRGHLDELT

TTLESMTEDLNLDSPLTPELNEILDTFLNDECLLHA,

Rta (75-175; 101 aa)
SEQ ID NO: 72
PLDPAPAVTPEASHLLEDPDEETSQAVKALREMADTVIPQKEEAA

ICGQMDLSHPPPRGHLDELTTTLESMTEDLNLDSPLTPELNEILD

TFLNDECLLHA,

Rta (100-175; 76 aa)
SEQ ID NO: 73
SVKALREMADTVIPQKEEAAICGQMDLSHPPPRGHLDELTTTLES

MTEDLNLDSPLTPELNEILDTFLNDECLLHA,

Rta (125-175; 51 aa)
SEQ ID NO: 74
DLSHPPPRGHLDELTTTLESMTEDLNLDSPLTPELNEILDTFLND

ECLLHA,

In some embodiments of any of the aspects, the TA is VPR, or a functional fragment thereof. VPR is a tripartite activator consisting of the VP64, the p65, and the Rta activation domains. In some embodiments of any of the aspects, VPR comprises VP64 (e.g., SEQ ID NO: 78), p65

(e.g., any one of SEQ ID NOs: 38, 58 to 67 or a polypeptide with at least 85% sequence identity to any one of SEQ ID NOs: 38, 58 to 67 that maintains the same function), and Rta (e.g., any one of SEQ ID NOs: 68-74 or a polypeptide with at least 85% sequence identity to any one of SEQ ID NOs: 68-74 that maintains the same function). In some embodiments of any of the aspects, VPR comprises one of SEQ ID NOs: 75, 76, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 75 or 76, that maintains its function.

SEQ ID NO: 75, miniVPR, comprising the p65 (100-261 aa; SEQ ID NO: 61) truncation and the RTA (125-190 aa; SEQ ID NO: 70) truncation;
bold text indicates VP64 (SEQ ID NO: 78);
italicized text indicates SV40 NLS;
bold italicized text indicates p65 (100-261 aa; SEQ ID NO: 61); double underlined text indicates RTA (125-190 aa; SEQ ID NO: 70).

GRADALDDFDLDMLGSDALDDFDLDMLGSDALDDFDLDMLGSDAL

DDFDLDMLINSRSSGS*PKKKRKV*GSGGGSGGSGS*VLPQAPAPAPA*

*PAMVSALAQAPAPVPVLAPGPPQAVAPPAPKPTQAGEGTLSEALL*

*QLQFDDEDLGALLGNSTDPAVFTDLASVDNSEFQQLLNQGIPVAP*

*HTTEPMLMEYPEAITRLVTGAQRPPDPAPAPLGAPGLPNGLLSGD*

*EDFSSIADMDFSALL*SGGGSGGSGSDLSHPPPRGHLDELTTTLES

MTEDLNLDSPLTPELNEILDTFLNDECLLHAMHISTGLSIFDTSL

F

SEQ ID NO: 76, full VPR; bold text indicates VP64 (SEQ ID NO: 78); italicized text indicates SV40 NLS; bold italicized text indicates p65 (SEQ ID NO: 59); double underlined text indicates RTA (SEQ ID NO: 68).

GRADALDDFDLDMLGSDALDDFDLDMLGSDALDDFDLDMLGSDAL

DDFDLDMLINSRSSGS*PKKKRKV**GSQYLPDTDDRHRIEEKRKRTY*

*ETFKSIMKKSPFSGPTDPRPPPRRIAVPSRSSASVPKPAPQPYPF*

*TSSLSTINYDEFPTMVFPSGQISQASALAPAPPQVLPQAPAPAPA*

PAMVSALAQAPAPVPVLAPGPPQAVAPPAPKPTQAGEGTLSEALL

*QLQFDDEDLGALLGNSTDPAVFTDLASVDNSEFQQLLNQGIPVAP*

*HTTEPMLMEYPEAITRLVTGAQRPPDPAPAPLGAPGLPNGLLSGD*

*EDFSSIADMDFSALL*GSGSGSRDSREGMFLPKPEAGSAISDVFEG

REVCQPKRIRPFHPPGSPWANRPLPASLAPTPTGPVHEPVGSLTP

APVPQPLDPAPAVTPEASHLLEDPDEETSQAVKALREMADTVIPQ

KEEAAICGQMDLSHPPPRGHLDELTTTLESMTEDLNLDSPLTPEL

NEILDTFLNDECLLHAMHISTGLSIFDTSLE

In some embodiments of any of the aspects, the TA comprises the Herpes Simplex Virus Protein 16 (VP16) activation domain. In some embodiments of any of the aspects, the TA comprises the VP64 activation domain, which comprises four tandem copies of VP16. In some embodiments of any of the aspects, the TA comprises one of SEQ ID NOs: 77, 78, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 77 or 78, that maintains its function.

VP16 (11 aa)

SEQ ID NO: 77

DALDDFDLDML,

VP64 (53 aa), with the VP16 domain indicated by bold text,

SEQ ID NO: 78

GRADALDDFDLDMLGSDALDDFDLDMLGSDALDDFDLDMLGSDALDDFD

LDML,

In some embodiments of any of the aspects, the TA comprises NFZ or a functional fragment thereof. In some embodiments of any of the aspects, NFZ comprises SEQ ID NO: 57 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 57 that maintains the same function.

In some embodiments of any of the aspects, the TA comprises 3Z or a functional fragment thereof. In some embodiments of any of the aspects, 3Z comprises SEQ ID NO: 303 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 303 that maintains the same function.

In some embodiments of any of the aspects, the TA comprises p300 or a functional fragment thereof. The adenovirus E1A-associated cellular p300 transcriptional co-activator protein functions as histone acetyltransferase that regulates transcription via chromatin remodeling. In some embodiments of any of the aspects, p300 comprises SEQ ID NO: 79 or a protein having at least 85% sequence identity to SEQ ID NO: 79. In some embodiments of any of the aspects, p300 comprises a portion of SEQ ID NO: 79, e.g., residues 1048-1664 of SEQ ID NO: 79. In some embodiments of any of the aspects, the TA comprises the p300 HAT Core activation domain. In some embodiments of any of the aspects, p300 comprises SEQ ID NO: 80 or a protein having at least 85% sequence identity to SEQ ID NO: 80. In some embodiments of any of the aspects, the TA comprises one of SEQ ID NOs: 79, 80, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 79 or 80, that maintains its function.

human acetyltransferase p300 (2414 aa), bold text indicates the core activation domain

SEQ ID NO: 79

MAENVVEPGPPSAKRPKLSSPALSASASDGTDFGSLFDLEHDLPDELINSTELGLINGGDINQLQT

SLGMVQDAASKHKQLSELLRSGSSPNLNMGVGGPGQVMASQAQQSSPGLGLINSMVKSPMTQA

GLTSPNMGMGTSGPNQGPTQSTGMMNSPVNQPAMGMNTGMNAGMNPGMLAAGNGQGIMPN

-continued

QVMNGSIGAGRGRQNMQYPNPGMGSAGNLLTEPLQQGSPQMGGQTGLRGPQPLKMGMMNNP

NPYGSPYTQNPGQQIGASGLGLQIQTKTVLSNNLSPFAMDKKAVPGGGMPNMGQQPAPQVQQP

GLVTPVAQGMGSGAHTADPEKRKLIQQQLVLLLHAHKCQRREQANGEVRQCNLPHCRTMKNV

LNHMTHCQSGKSCQVAHCASSRQIISHWKNCTRHDCPVCLPLKNAGDKRNQQPILTGAPVGLG

NPSSLGVGQQSAPNLSTVSQIDPSSIERAYAALGLPYQVNQMPTQPQVQAKNQQNQQPGQSPQG

MRPMSNMSASPMGVNGGVGVQTPSLLSDSMLHSAINSQNPMMSENASVPSLGPMPTAAQPSTT

GIRKQWHEDITQDLRNHLVHKLVQAIFPTPDPAALKDRRMENLVAYARKVEGDMYESANNRAE

YYHLLAEKIYKIQKELEEKRRTRLQKQNMLPNAAGMVPVSMNPGPNMGQPQPGMTSNGPLPDP

SMIRGSVPNQMMPRITPQSGLNQFGQMSMAQPPIVPRQTPPLQHHGQLAQPGALNPPMGYGPRM

QQPSNQGQFLPQTQFPSQGMNVTNIPLAPSSGQAPVSQAQMSSSSCPVNSPIMPPGSQGSHIHCPQ

LPQPALHQNSPSPVPSRTPTPHHTPPSIGAQQPPATTIPAPVPTPPAMPPGPQSQALHPPPRQTPTPP

TTQLPQQVQPSLPAAPSADQPQQQPRSQQSTAASVPTPTAPLLPPQPATPLSQPAVSIEGQVSNPPS

TSSTEVNSQAIAEKQPSQEVKMEAKMEVDQPEPADTQPEDISESKVEDCKMESTETEERSTELKT

EIKEEEDQPSTSATQSSPAPGQSKKKIFKPEELRQALMPTLEALYRQDPESLPFRQPVDPQLLG

IPDYFDIVKSPMDLSTIKRKLDTGQYQEPWQYVDDIWLMFNNAWLYNRKTSRVYKYCSKL

SEVFEQEIDPVMQSLGYCCGRKLEFSPQTLCCYGKQLCTIPRDATYYSYQNRYHFCEKCFN

EIQGESVSLGDDPSQPQTTINKEQFSKRKNDTLDPELFVECTECGRKMHQICVLHHEIIWPA

GFVCDGCLKKSARTRKENKFSAKRLPSTRLGTFLENRVNDFLRRQNHPESGEVTVRVVHAS

DKTVEVKPGMKARFVDSGEMAESFPYRTKALFAFEEIDGVDLCFFGMHVQEYGSDCPPPN

QRRVYISYLDSVHFFRPKCLRTAVYHEILIGYLEYVKKLGYTTGHIWACPPSEGDDYIFHCH

PPDQKIPKPKRLQEWYKKMLDKAVSERIVHDYKDIFKQATEDRLTSAKELPYFEGDFWPN

VLEESIKELEQEEEERKREENTSNESTDVTKGDSKNAKKKNNKKTSKNKSSLSRGNKKKPG

MPNVSNDLSQKLYATMEKHKEVFFVIRLIAGPAANSLPPIVDPDPLIPCDLMDGRDAFLTLA

RDKHLEFSSLRRAQWSTMCMLVELHTQSQDRFVYTCNECKHHVETRWHCTVCEDYDLCITC

YNTKNHDHKMEKLGLGLDDESNNQQAAATQSPGDSRRLSIQRCIQSLVHACQCRNANCSLPSCQ

KMKRVVQHTKGCKRKTNGGCPICKQLIALCCYHAKHCQENKCPVPFCLNIKQKLRQQQLQHRL

QQAQMLRRRMASMQRTGVVGQQQGLPSPTPATPTTPTGQQPTTPQTPQPTSQPQPTPPNSMPPY

LPRTQAAGPVSQGKAAGQVTPPTPPQTAQPPLPGPPPAAVEMAMQIQRAAETQRQMAHVQIFQR

PIQHQMPPMTPMAPMGMNPPPMTRGPSGHLEPGMGPTGMQQQPPWSQGGLPQPQQLQSGMPR

PAMMSVAQHGQPLNMAPQPGLGQVGISPLKPGTVSQQALQNLLRTLRSPSSPLQQQQVLSILHA

NPQLLAAFIKQRAAKYANSNPQPIPGQPGMPQGQPGLQPPTMPGQQGVHSNPAMQNMNPMQA

GVQRAGLPQQQPQQQLQPPMGGMSPQAQQMNMNHNTMPSQFRDILRRQQMMQQQQQGAGP

GIGPGMANHNQFQQPQGVGYPPQQQQRMQHHMQQMQQGNMGQIGQLPQALGAEAGASLQAY

QQRLLQQQMGSPVQPNPMSPQQHMLPNQAQSPHLQGQQIPNSLSNQVRSPQPVPSPRPQSQPPHS

SPSPRMQPQPSPHHVSPQTSSPHPGLVAAQANPMEQGHFASPDQNSMLSQLASNPGMANLHGAS

ATDLGLSTDNSDLNSNLSQSTLDIH, p300 HAT Core activation domain (617 aa)

SEQ ID NO: 80

IFKPEELRQALMPTLEALYRQDPESLPFRQPVDPQLLGIPDYFDIVKSPMDLSTIKRKLDTGQYQE

PWQYVDDIWLMFNNAWLYNRKTSRVYKYCSKLSEVFEQEIDPVMQSLGYCCGRKLEFSPQTLC

CYGKQLCTIPRDATYYSYQNRYHFCEKCFNEIQGESVSLGDDPSQPQTTINKEQFSKRKNDTLDP

-continued

ELFVECTECGRKMHQICVLHHEIIWPAGFVCDGCLKKSARTRKENKFSAKRLPSTRLGTFLENRV

NDFLRRQNHPESGEVTVRVVHASDKTVEVKPGMKARFVDSGEMAESFPYRTKALFAFEEIDGV

DLCFFGMHVQEYGSDCPPPNQRRVYISYLDSVHFFRPKCLRTAVYHEILIGYLEYVKKLGYTTG

HIWACPPSEGDDYIFHCHPPDQKIPKPKRLQEWYKKMLDKAVSERIVHDYKDIFKQATEDRLTS

AKELPYFEGDFWPNVLEESIKELEQEEEERKREENTSNESTDVTKGDSKNAKKKNNKKTSKNKS

SLSRGNKKKPGMPNVSNDLSQKLYATMEKHKEVFFVIRLIAGPAANSLPPIVDPDPLIPCDLMDG

RDAFLTLARDKHLEFSSLRRAQWSTMCMLVELHTQSQD,

In some embodiments of any of the aspects, the TA comprises CBP or a functional fragment thereof. CBP (CREB (Cyclic AMP-Responsive Element-Binding Protein) Binding Protein; CREBBP) is involved in the transcriptional coactivation of many different transcription factors and has intrinsic histone acetyltransferase activity. In some embodiments of any of the aspects, CBP is derived from *Homo sapiens, Drosophila melanogaster*, or any other organism expressing a homologous CBP protein. In some embodiments of any of the aspects, the TA comprises the CBP HAT Core activation domain. In some embodiments of any of the aspects, the TA comprises one of SEQ ID NOs: 81-83, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 81-83, that maintains its function.

*Homo sapiens* CBP, histone acetyltransferase (HAT)-domain; residues 1342-1649 of CREB-binding protein isoform a [*Homo sapiens*], NCBI Reference Sequence: NP_004371.2; residues 1304-1611 of CREB-binding protein isoform b [*Homo sapiens*], NCBI Reference Sequence: NP_001073315.1.

SEQ ID NO: 81

VNKFLRRQNHPEAGEVFVRVVASSDKTVEVKPGMKSRFVDSGEMSESFPYRTKALFAFEEIDGV

DVCFFGMHVQEYGSDCPPPNTRRVYISYLDSIHFFRPRCLRTAVYHEILIGYLEYVKKLGYVTGHI

WACPPSEGDDYIFHCHPPDQKIPKPKRLQEWYKKMLDKAFAERIIHDYKDIFKQATEDRLTSAKE

LPYFEGDFWPNVLEESIKELEQEEEERKKEESTAASETTEGSQGDSKNAKKKNNKKTNKNKSSIS

RANKKKPSMPNVSNDLSQKLYATMEKHKEVFFVIHLHAGPVINTLPPI, residues 1954-2267 of nejire, isoform E [*Drosophila melanogaster*], NCBI Reference Sequence: NP_001259387.1, HAT_KAT11, Histone acetylation protein

SEQ ID NO: 82

VNNFLKKKEAGAGEVHIRVVSSSDKCVEVKPGMRRRFVEQGEMMNEFPYRAKALFAFEEVDGI

DVCFFGMHVQEYGSECPAPNTRRVYIAYLDSVHFFRPRQYRTAVYHEILLGYMDYVKQLGYTM

AHIWACPPSEGDDYIFHCHPTDQKIPKPKRLQEWYKKMLDKGMIERIIQDYKDILKQAMEDKLG

SAAELPYFEGDFWPNVLEESIKELDQEEEEKRKQAEAAEAAAAANLFSIEENEVSGDGKKKGQK

KAKKSNKSKAAQRKNSKKSNEHQSGNDLSTKIYATMEKHKEVFFVIRLHSAQSAASLAPI, aa 1696-2329 from *Drosophila* CBP (nejire), NCBI Reference Sequence: NP_001259387.1, including the bromodomain, PHD domain, and HAT domain

SEQ ID NO: 83

NGKYSDPWEYVDDVWLMFDNAWLYNRKTSRVYRYCTKLSEVFEAEIDPVMQALGYCCGRKY

TFNPQVLCCYGKQLCTIPRDAKYYSYQNRYTYCQKCFNDIQGDTVTLGDDPLQSQTQIKKDQFK

EMKNDHLELEPFVNCQECGRKQHQICVLWLDSIWPGGFVCDNCLKKKNSKRKENKFNAKRLPT

TKLGVYIETRVNNFLKKKEAGAGEVHIRVVSSSDKCVEVKPGMRRRFVEQGEMMNEFPYRAKA

LFAFEEVDGIDVCFFGMHVQEYGSECPAPNTRRVYIAYLDSVHFFRPRQYRTAVYHEILLGYMD

YVKQLGYTMAHIWACPPSEGDDYIFHCHPTDQKIPKPKRLQEWYKKMLDKGMIERIIQDYKDIL

KQAMEDKLGSAAELPYFEGDFWPNVLEESIKELDQEEEEKRKQAEAAEAAAAANLFSIEENEVS

GDGKKKGQKKAKKSNKSKAAQRKNSKKSNEHQSGNDLSTKIYATMEKHKEVFFVIRLHSAQSA

-continued

ASLAPIQDPDPLLTCDLMDGRDAFLTLARDKHFEFSSLRRAQFSTLSMLYELHNQGQDKFVYTC

NHCKTAVETRYHCTVCDDFDLCIVCKEKVGHQHKMEKLGFDIDDGSALADHKQANPQEARKQ

SI.,

In another embodiment of any aspect described herein, in the synTF described or the ZF-containing fusion protein described herein, the transcriptional effector domain comprises an epigenetic effector domain. For example, at least one ZF protein domain is fused to one or more chromatin regulating enzymes that (1) catalyze chemical modifications of DNA or histone residues (e.g. DNA methyltransferases, histone methyltransferases, histone acetyltransferases) or (2) remove chemical modifications (e.g. DNA demethylases, DNA di-oxygenases, DNA hydroxylases, histone demethylases, histone deacetylases). One example is CBP/p300 histone acetyltransferase, which is typically associated with transcriptional activation through the interactions with multiple transcription factors. Related epigenetic effector domains associated with the deposition of biochemical marks on DNA or histone residue(s) include HAT1, GCN5, PCAF, MLL, SET, DOT1, SUV39H, G9a, KAT2A/B and EZH1/2. Related epigenetic effector domains associated with the removal of biochemical marks from DNA or histone residue(s) include TET1/2, SIRT family, LSD1, and KDM family.

DNA-Binding Domain

Described herein are synTFs comprising at least one DNA-binding domain (DBD). In some embodiments of any of the aspects, a synTF polypeptide as described herein (or a synTF polypeptide system collectively) comprises 1, 2, 3, 4, 5, or more DBD(s). In some embodiments of any of the aspects, the synTF polypeptide or system comprises one DBD. In embodiments comprising multiple DBDs, the multiple DBDs can be different individual DBDs or multiple copies of the same DBDs, or a combination of the foregoing.

In some embodiments of any of the aspects, the at least one DBD is an engineered zinc finger (ZF) binding domain. A zinc finger (ZF) is a finger-shaped fold in a protein that permits it to interact with nucleic acid sequences such as DNA and RNA. Such a fold is well known in the art. The fold is created by the binding of specific amino acids in the protein to a zinc atom. Zinc-finger containing proteins (also known as ZF proteins) can regulate the expression of genes as well as nucleic acid recognition, reverse transcription and virus assembly.

A ZF is a relatively small polypeptide domain comprising approximately 30 amino acids, which folds to form an α-helix adjacent an antiparallel β-sheet (known as a ββα-fold). The fold is stabilized by the co-ordination of a zinc ion between four largely invariant (depending on zinc finger framework type) Cys and/or His residues, as described further below. Natural zinc finger domains have been well studied and described in the literature, see for example, Miller et al., (1985) EMBO J. 4: 1609-1614; Berg (1988) Proc. Natl. Acad. Sci. USA 85: 99-102; and Lee et al., (1989) Science 245: 635-637. A ZF domain recognizes and binds to a nucleic acid triplet, or an overlapping quadruplet (as explained below), in a double-stranded DNA target sequence. However, ZFs are also known to bind RNA and proteins (Clemens, K. R. et al. (1993) Science 260: 530-533; Bogenhagen, D. F. (1993) Mol. Cell. Biol. 13: 5149-5158; Searles, M. A. et al. (2000) J. Mol. Biol. 301: 47-60; Mackay, J. P. & Crossley, M. (1998) Trends Biochem. Sci. 23: 1-4).

In one embodiment, as used herein, the term "zinc finger" (ZF) or "zinc finger motif" (ZF motif) or "zinc finger domain" (ZF domain) refers to an individual "finger", which comprises a beta-beta-alpha (ββα)-protein fold stabilized by a zinc ion as described elsewhere herein. The Zn-coordinated ββα protein fold produces a finger-like protrusion, a "finger." Each ZF motif typically includes approximately 30 amino acids. The term "motif" as used herein refers to a structural motif. The ZF motif is a supersecondary structure having the ββα-fold that stabilized by a zinc ion.

In one embodiment, the term "ZF motif" according to its ordinary usage in the art, refers to a discrete continuous part of the amino acid sequence of a polypeptide that can be equated with a particular function. ZF motifs are largely structurally independent and may retain their structure and function in different environments. Because the ZF motifs are structurally and functionally independent, the motifs also qualify as domains, thus are often referred as ZF domains. Therefore, ZF domains are protein motifs that contain multiple finger-like protrusions that make tandem contacts with their target molecule. Typically, a ZF domain binds a triplet or (overlapping) quadruplet nucleotide sequence. Adjacent ZF domains arranged in tandem are joined together by linker sequences to form an array. A ZF peptide typically contains a ZF array and is composed of a plurality of "ZF domains", which in combination do not exist in nature. Therefore, they are considered to be artificial or synthetic ZF peptides or proteins.

$C_2H_2$ zinc fingers ($C_2H_2$-ZFs) are the most prevalent type of vertebrate DNA-binding domain, and typically appear in tandem arrays (ZFAs), with sequential $C_2H_2$-ZFs each contacting three (or more) sequential bases. $C_2H_2$-ZFs can be assembled in a modular fashion. Given a set of modules with defined three-base specificities, modular assembly also presents a way to construct artificial proteins with specific DNA-binding preferences.

ZF-containing proteins generally contain strings or chains of ZF motifs, forming an array of ZF (ZFA). Thus, a natural ZF protein may include 2 or more ZF, i.e., a ZFA consisting of 2 or more ZF motifs, which may be directly adjacent one another (i.e. separated by a short (canonical) linker sequence), or may be separated by longer, flexible or structured polypeptide sequences. Directly adjacent ZF domains are expected to bind to contiguous nucleic acid sequences, i.e. to adjacent trinucleotides/triplets. In some cases cross-binding may also occur between adjacent ZF and their respective target triplets, which helps to strengthen or enhance the recognition of the target sequence, and leads to the binding of overlapping quadruplet sequences (Isalan et al., (1997) Proc. Natl. Acad. Sci. USA, 94: 5617-5621). By comparison, distant ZF domains within the same protein may recognize (or bind to) non-contiguous nucleic acid sequences or even to different molecules (e.g. protein rather than nucleic acid).

Engineered ZF-containing proteins are chimeric proteins composed of a DNA-binding zinc finger protein domain (ZF protein domain) and another domain through which the protein exerts its effect (effector domain). The effector domain may be a transcriptional activator, a methylation domain or a nuclease. DNA-binding ZF protein domain would contain engineered zinc finger arrays (ZFAs). See e.g., Khalil et al., Cell Volume 150, Issue 3, 3 Aug. 2012, Pages 647-658; U.S. Pat. No. 10,138,493; US Patent Application US20200002710A1; the contents of each of which are incorporated herein by reference in their entireties.

Engineered ZF-containing proteins are non-natural and suitably contain 3 or more, for example, 4, 5, 6, 8, 9, 10, 11, 12, 13, 14, 15, 16, 17, 18 or more (e.g., up to approximately 30 or 32) ZF motifs arranged adjacent one another in tandem, forming arrays of ZF motifs or ZFA. Particularly ZF-containing synTF proteins (ZF-containing synTF fusion protein, or simply synTF) of the disclosure include at least 3 ZF, at least 4 ZF motifs, at least 5 ZF motifs, or at least 6 ZF motifs, at least 7 ZF motifs, at least 8 ZF motifs, at least 9 ZF motifs, at least 10 ZF motifs, at least 11 or at least 12 ZF motifs; and in some cases at least 18 ZF motifs. In other embodiments, the ZF synTF contains up to 6, 7, 8, 10, 11, 12, 16, 17, 18, 22, 23, 24, 28, 29, 30, 34, 35, 36, 40, 41, 42, 46, 47, 48, 54, 55, 56, 58, 59, or 60 ZF motifs. In some embodiments, the ZF array comprises 1 or more ZF motif. The ZF-containing synTF of the disclosure bind to contiguous orthogonal target nucleic acid binding sites. That is, the ZFs or ZFAs comprising in the ZF domain of the fusion protein binds orthogonal target nucleic acid sequences.

In one embodiment, as used herein, an "engineered synthetic transcription factor" or "engineered synTF" or "synTF" refers to an engineered ZF-containing chimeric protein having at least one of the following characteristics and may have more than one: bind target orthogonal specific DNA sequences and have, for example, reduced or minimal functional binding potential in a host eukaryotic genome; are derived from mammalian protein scaffolds, conferring minimal degree of immunogenicity over other prokaryotically-derived domains; and can be packaged in viral delivery systems, such as lentiviral delivery constructs.

In another embodiment, as used herein, the term "engineered synthetic transcription factor" or "engineered synTF," abbreviated as "synTF" or "ZF synTF," refers to an engineered ZF containing synthetic transcription factor that is a polypeptide, in other words, a ZF-containing synthetic transcription factor protein. These synTFs contain ZF arrays (ZFA) therein for binding to specific target nucleic acid sequences. The synTF is a chimeric, fusion protein that comprises a DNA-binding, ZF-containing protein domain and an effector domain through which the synTF exerts its effect on gene expression. These synTFs can modulate gene expression, wherein the modulation is by increasing or decreasing the expression of a gene that is operably linked to a promoter that is also operably linked to the specific target nucleic acid sequence to which the DNA-binding, ZF-containing protein domain of the synTF binds.

As used herein, the term "ZF array," abbreviated as "ZFA" refers to an array, or a string, or a chain of ZF motifs arranged in tandem. A ZFA can have six ZF motifs (a 6-finger ZFA), seven ZF motifs (a 7-finger ZFA), or eight ZF motifs (an 8-finger ZFA).

As used herein, the term "engineered responsive/response promoter," "engineered promoter," or "engineered responsive/response promoter element" refers is a nucleic acid construct containing a promoter sequence that has at least one orthogonal DNA target sequence operably linked upstream of the promoter sequence such that the orthogonal DNA target sequence confer a responsive property to the promoter when the orthogonal DNA target sequence is bound by its respective transcription factor, the responsive property being whether gene transcription initiation from that promoter is enhanced when the upstream nearby orthogonal DNA target sequences are bound by a ZF-containing synthetic transcription factor. There may be more than one orthogonal DNA target sequence operably linked upstream of the promoter sequence. When there is one orthogonal DNA target sequence, the promoter is referred to a "1×" promoter, where the "1×" refers to the number of orthogonal DNA target sequence present in the promoter construct. For example, a 4× responsive promoter would be identified as having four orthogonal DNA target sequences in the engineered response promoter construct, and the four orthogonal DNA target sequences are upstream of the promoter sequence.

The ZF protein domain is modular in design, with zinc finger arrays (ZFA) as the main components, and each ZFA is made of 6-8 ZF motifs. The ZF protein domain comprises at least one ZFA and can contain as many as up to ten ZFA. The ZF protein domain can have one and up to ten ZFA.

The design of the synTF or any engineered fusion protein described herein is also modular, meaning the synTF is made up of modules of ZF domains (ZFA) and modules of effector domains/protein interaction domains/ligand binding domains/dimerization domains, the individual modules are covalently conjugated together as described herein, and the individual modules function independently of each other. The number of ZFA can range from one, two, three, four, five, six, seven, eight, nine, and up to ten. When there are two or more ZFA, the ZFAs are covalently conjugated to each other in tandem, e.g., by a L1 peptide linker, in an $NH_2$— to COOH— terminus arrangement to form an array of ZFA. The ZFAs, as a whole, forms the ZF protein domain, is covalently linked to the N-terminus or the C-terminus of the effector domain or the regulator protein. When there are two or more ZFAs present in the ZF protein domain of a synTF or a ZF containing fusion protein described herein, the ZFAs can be the same, or different.

Each modular ZFA in the ZF protein domain of a synTF disclosed herein or a ZF containing fusion protein described herein is comprised of six to eight ZF motifs. For example, a single ZFA having seven ZF motifs is referred to as a seven-finger ZFA. The ZF motif is a small protein structural motif consisting of an α helix and an antiparallel β sheet (αββ) and is characterized by the coordination of one zinc ion by two histidine residues and two cysteine residues in the motif in order to stabilize the finger-like protrusion fold, the "finger". The ZF motif in the ZF protein domain of a synTF disclosed herein is a $Cys_2His_2$ zinc finger motif (SEQ ID NO: 356). In one embodiment, the ZF motif comprises, consisting essentially of, or consisting of a peptide of formula 1: $[X_{0-3}CX_{1-5}CX_{2-7}$-(helix)-$HX_{3-6}H]$ (SEQ ID NO: 84) wherein X is any amino acid, the subscript numbers indicate the possible number of amino acid residues, C is cysteine, H is histidine, and (helix) is a-six (or seven) contiguous amino acid residue peptide that forms a short alpha helix. The helix is variable. This short alpha helix forms one facet of the finger formed by the coordination of the zinc ion by two histidine residues and two cysteine residues in the ZF motif. For each ZFA, the six to eight ZF motifs therein are linked to each other, $NH_2$— to COOH— terminus by a peptide linker having about four to six amino acid residues to form an array of ZF motifs or ZF. The finger-like protrusion fold of each ZF motif interacts with and binds nucleic acid sequence. Approximately a peptide sequence for two ZF motif interacts with and binds a ~six-base pair (bp) nucleic acid sequence. The multiple ZF motifs in a ZFA form finger-like protrusions that would make contact with an orthogonal target DNA sequence. Hence, for example, a ZFA with six ZF motifs or finger-like protrusions (a six-finger ZFA) interacts with and binds a ~18-20 bp nucleic acid sequence, and an eight-finger ZFA would bind a ~24-26 bp nucleic acid sequence. Accordingly, in one embodiment, the ZFA in the ZF protein domain of a synTF comprises, consists essentially of, or consists of a sequence: N'-[(formula 1)-$L_2$]$_{6-8}$-C', where the subscript 6-8 indicates the number of ZF motifs, the $L_2$ is a linker peptide having 4-6 amino acid residues, and the N'- and C'- indicates the N-terminus and C-terminus respectively of the peptide sequence. For example, for a ZFA consists essentially of six ZF motifs, the sequence is N'-[(formula 1)-$L_2$]-[(formula 1)-$L_2$]-[(formula 1)-$L_2$]-[(formula 1)-$L_2$]-[(formula 1)-$L_2$]-[(formula 1)-$L_2$]-C', and a ZFA consists essentially of eight ZF motifs, the sequence is N'-[(formula 1)-$L_2$]-[(formula 1)-$L_2$]-[(formula 1)-$L_2$]-[(formula 1)-$L_2$]-[(formula 1)-$L_2$]-[(formula 1)-$L_2$]-[(formula 1)-$L_2$]-[(formula 1)-$L_2$]-C'.

SEQ ID NO: 84: XXXCXXXXXCXXXXXXXXHXXXXXXH

In another embodiment of any aspect described herein, the ZF motif comprises a peptide of formula 2: [$X_3CX_2CX_5$-(helix)-$HX_3H$] (SEQ ID NO: 85) wherein X is any amino acid, the subscript numbers indicate the possible number of amino acid residues, C is cysteine, H is histidine, and (helix) is a-six (or seven) contiguous amino acid residue peptide that forms a short alpha helix. Accordingly, in one embodiment, the ZFA in the ZF protein domain of a synTF comprises, consists essentially of, or consists of a sequence: N'-[(formula 2)-$L_2$]$_{6-8}$-C', where the subscript 6-8 indicates the number of ZF motifs, the $L_2$ is a linker peptide having 4-6 amino acid residues, and the N'- and C'- indicates the N-terminus and C-terminus respectively of the peptide sequence. For example, for a ZFA consists essentially of six ZF motifs, the sequence is N'-[(formula 2)-$L_2$]-[(formula 2)-$L_2$]-[(formula 2)-$L_2$]-[(formula 2)-$L_2$]-[(formula 2)-$L_2$]-[(formula 2)-$L_2$]-C' and a ZFA consists essentially of eight ZF motifs, the sequence is N'-[(formula 2)-$L_2$]-[(formula 2)-$L_2$]-[(formula 2)-$L_2$]-[(formula 2)-$L_2$]-[(formula 2)-$L_2$]-[(formula 2)-$L_2$]-[(formula 2)-$L_2$]-[(formula 2)-$L_2$]-C'.

SEQ ID NO: 85: XXXCXXCXXXXXXXXXXXXHXXXH

In one embodiment of any aspect described herein, for a single ZFA is the ZF protein domain of a synTF disclosed herein, the ZFA in the ZF protein domain comprises, consists essentially of, or consists of a sequence: N'-PGERPFQCRICMRNFS-(Helix 1)-HTRTHTGEKPFQCRICMRNFS-(Helix 2)-HLRTHTGSQKPFQCRICMRNFS-(Helix 3)-HTRTHTGEKPFQCRICMRNFS-(Helix 4)-HLRTHTGSQKPFQCRICMRNFS-(Helix 5)-HTRTHTGEKPFQCRICMRNFS-(Helix 6)-HLRTHLR-C' (SEQ ID NO: 87), wherein the (Helix) is a-six (or seven) contiguous amino acid residue peptide that forms a short alpha helix and can also be represented as plain text "xxxxxxx".

Zinc Finger Domain scaffold; italicized double underlined text indicates the restriction sites; plain text "xxxxxxx" indicates six ZF helices, e.g., from N terminus to C terminus: helix 1, helix 2, helix 3, helix 4, helix 5, and helix 6

SEQ ID NO: 88

*GS*PGERPFQCRICMRNFSxxxxxxxHTRTHTGEKPFQCRICMRNFSxxxxxxxHLRTHTGSQKPFQCRI

CMRNFSxxxxxxxHTRTHTGEKPFQCRICMRNFSxxxxxxxHLRTHTGSQKPFQCRICMRNFSXXXXXXX

HTRTHTGEKPFQCRICMRNFSxxxxxxxHLRTHLR*GS*,

Zinc Finger Domain scaffold, wherein [Helix 1], [Helix 2], [Helix 3], [Helix 4], [Helix 5], and [Helix 6] can also be represented as plain text "xxxxxxx"

SEQ ID NO: 89

PGERPFQCRICMRNFS [Helix1] HTRTHTGEKPFQCRICMRNFS [Helix 2]

HLRTHTGSQKPFQCRICMRNFS [Helix 3] HLRTHTGEKPFQCRICMRNFS [Helix 4]

HLKTHTGSQKPFQCRICMRNFS [Helix 5] HLRTHTGEKPFQCRICMRNFS [Helix 6]

HLRTHLR,

Zinc Finger Domain scaffold; italicized double underlined text indicates the restriction sites; plain text "xxxxxxx" indicates six ZF helices, e.g., from N terminus to C terminus: helix 1, helix 2, helix 3, helix 4, helix 5, and helix 6

SEQ ID NO: 90

*GS*PGERPFQCRICMRNFSxxxxxxxHTRTHTGEKPFQCRICMRNFSxxxxxxxHLRTHTGSQKPFQCRI

CMRNFSxxxxxxxHLRTHTGEKPFQCRICMRNFSxxxxxxxHLKTHTGSQKPFQCRICMRNFSXXXXXXX

HLRTHTGEKPFQCRICMRNFSxxxxxxxHLRTHLR*GS*,

In some embodiments of any of the aspects, the zinc finger scaffold comprises one of SEQ ID NOs: 84-90 or an amino acid sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 84-90 that maintains the same function.

In one embodiment, all six of the helix 1, 2, 3, 4, 5 and 6 are distinct and different from each other. In another embodiment, all six of the helix 1, 2, 3, 4, 5 and 6 are identical to each other. Alternatively, at least two of the six helices are identical and the same with each other. In other embodiments, at least three of the six helices in a ZFA are identical and the same with each other, at least four of the six helices in a ZFA are identical and the same with each other, or at least five of the six helices in a ZFA are identical and the same with each other.

In some embodiments of any aspect described herein, the helices of the six to eight ZF motifs of an individual ZFA disclosed herein are selected from the six-amino acid (or seven-amino acid) residue peptide sequences disclosed in one of the following Groups 1-11 (e.g., SEQ ID NOs: 122-181). In some embodiments, at least four of the ZF motifs in an individual ZFA disclosed herein are selected from the six-amino acid (or seven-amino acid) residue peptide sequences disclosed in one of the following Groups 1-11. In other embodiments, all of the ZF motifs, i.e. the six, seven or eight ZF motifs in an individual ZFA disclosed herein, are selected from the six (or seven) amino acid residue peptide sequences disclosed in one of the following Groups 1-11. In any individual ZFA, the helix selected for a single ZF comprising the ZFA can be repeated twice or more in the ZFA. This means that for any given single ZFA, at least four or all the helices in the ZFA are selected from the same group disclosed herein. For example, wherein a ZFA consists essentially of six ZF motifs, that means there are six alpha helices. All the 6-8 helices (Helix 1; Helix 2; Helix 3; Helix 4; Helix 5; Helix 6; Helix 7; Helix 8) of the ZFs in an individual ZFA is selected from one of the following group 1-11, for example, all six helices are selected from group 2. That is, all the helices for all the ZF comprising a single ZFA come from the same group. Alternatively, at least four of the six helices are selected from the same group, a group selected from group 1-11. For example, four of the six helices are selected from group 5, and the remainder two helices of the six-ZF motif ZFA are selected from the other groups 1-4, 6-11, or can be any other helices that would form a short alpha helix. The other remaining helices making up the ZFA can be those that are known in the art.

TABLE 6

| Groups 1-4 helices | | | | | | | |
|---|---|---|---|---|---|---|---|
| Group 1 | SEQ ID NO: | Group 2 | SEQ ID NO: | Group 3 | SEQ ID NO: | Group 4 | SEQ ID NO: |
| DEANLRR | 122 | QRSSLVR | 131 | QRSSLVR | 131 | QQTNLTR | 126 |
| DPSVLKR | 123 | DMGNLGR | 132 | DKSVLAR | 140 | QGTSLAR | 146 |
| QSANLLR | 124 | RSHDLTR | 133 | QTNNLGR | 141 | VRHNLTR | 147 |
| DPSSLKR | 125 | HKSSLTR | 134 | THAVLTR | 142 | DKSVLAR | 140 |
| QQTNLTR | 126 | DSSNLRR | 135 | DRGNLTR | 138 | DSSNLRR | 135 |
| DATQLVR | 127 | DQGNLIR | 136 | TKSLLAR | 143 | DQGNLIR | 136 |
| ERRSLAR | 128 | QKQALTR | 137 | QKQALDR | 144 | EKQNLAR | 148 |
| EEANLRR | 129 | DRGNLTR | 138 | DTSVLNR | 145 | DPSNLRR | 149 |
| DHSSLKR | 130 | RSHDLTV | 139 | QRNNLGR | 181 | DHSNLSR | 150 |

TABLE 6-continued

| Groups 1-4 helices | | | | | | | |
|---|---|---|---|---|---|---|---|
| Group 1 | SEQ ID NO: | Group 2 | SEQ ID NO: | Group 3 | SEQ ID NO: | Group 4 | SEQ ID NO: |
| | | | | | | QSTSLQR | 151 |

TABLE 7

| Groups 5-7 helices | | | | | |
|---|---|---|---|---|---|
| Group 5 | SEQ ID NO: | Group 6 | SEQ ID NO: | Group 7 | SEQ ID NO: |
| NMSNLTR | 152 | QQTNLTR | 126 | QRSSLVR | 131 |
| DRSVLRR | 153 | QGGNLAL | 160 | QRGNLNM | 164 |
| LQENLTR | 154 | DHSSLKR | 130 | RPQELRR | 165 |
| DRSSLRR | 155 | RADMLRR | 161 | DHSSLKR | 130 |
| QSGTLHR | 156 | DSSNLRR | 135 | RQDNLGR | 166 |
| QLANLAR | 157 | DQGNLIR | 136 | DGGNLGR | 167 |
| DQTTLRR | 158 | EKQNLAR | 148 | QQGNLQL | 168 |
| DPSNLAR | 159 | DPSNLRR | 149 | RRQELTR | 169 |
| | | QKANLGV | 162 | DPSNLRR | 149 |
| | | RLDMLAR | 163 | | |

TABLE 8

| Groups 8-11 helices | | | | | | | |
|---|---|---|---|---|---|---|---|
| Group 8 | SEQ ID NO: | Group 9 | SEQ ID NO: | Group 10 | SEQ ID NO: | Group 11 | SEQ ID NO: |
| QASNLTR | 170 | DSSNLRR | 135 | RRHGLDR | 175 | QLSNLTR | 177 |
| DHSSLKR | 130 | DQGNLIR | 136 | DHSSLKR | 130 | DRSSLKR | 178 |
| RAHNLLL | 171 | RAHNLLL | 171 | VRHNLTR | 147 | QRSSLVR | 131 |
| QRSSLVR | 131 | QRSSLVR | 131 | DHSNLSR | 150 | RLDMLAR | 163 |
| QSTTLKR | 172 | QSTTLKR | 172 | QRSSLVR | 131 | VRHSLTR | 179 |
| DPSNLRR | 149 | DPSNLRR | 149 | ESGHLKR | 176 | ESGALRR | 180 |
| QGTTLKR | 173 | EKQNLAR | 148 | | | | |
| QRSNLAR | 174 | DSSNLRR | 135 | | | | |

Non-limiting examples of the combinations and arrangements of six helices in a single ZFA where the helices are selected from Group 1 and where the motifs are in an $NH_2$— to COOH— terminus arrangement, (Group 1 ZFA helix combo), are as follows:

ZF 1-1:
N'-DEANLRR, DPSVLKR, QSANLLR, DPSSLKR, QQTNLTR, DATQLVR-C'
(SEQ ID NOS 122, 123, 124, 125, 126, and 127, respectively, in order of appearance)

-continued

```
ZF 1-2:
N'-DEANLRR, DPSVLKR, QSANLLR, DPSSLKR, QQTNLTR, ERRSLAR-C'
(SEQ ID NOS 122, 123, 124, 125, 126, and 128, respectively,
in order of appearance)

ZF 1-3:
N'-EEANLRR, DHSSLKR, QSANLLR, DPSSLKR QQTNLTR, DATQLVR-C'
(SEQ ID NOS 129, 130, 124, 125, 126, and 127, respectively,
in order of appearance)

ZF 1-4:
N'-EEANLRR, DHSSLKR, QSANLLR, DPSSLKR QQTNLTR, ERRSLAR-C'
(SEQ ID NOS 129, 130, 124, 125, 126, and 128, respectively,
in order of appearance)

ZF 1-5:
N'-DEANLRR, DPSVLKR, QQTNLTR, ERRSLAR QQTNLTR, DATQLVR-C'
(SEQ ID NOS 122, 123, 126, 128, 126, and 127, respectively,
in order of appearance)

ZF 1-6:
N'-DEANLRR, DPSVLKR, QQTNLTR, ERRSLAR QQTNLTR, ERRSLAR-C'
(SEQ ID NOS 122, 123, 126, 128, 126, and 128, respectively,
in order of appearance)

ZF 1-7:
N'-EEANLRR, DHSSLKR, QQTNLTR, ERRSLAR QQTNLTR, DATQLVR-C'
(SEQ ID NOS 129, 130, 126, 128, 126, and 127, respectively,
in order of appearance)

ZF 1-8:
N'-EEANLRR, DHSSLKR, QQTNLTR, ERRSLAR QQTNLTR, ERRSLAR-C'
(SEQ ID NOS 129, 130, 126, 128, 126, and 128, respectively,
in order of appearance)
```

Non-limiting examples of the combinations and arrangements of six helices in a single six-finger ZFA where the helices are selected from Group 2 and where the motifs are in an $NH_2$— to COOH— terminus arrangement, (Group 2 ZFA helix combo), are as follows:

```
ZF 2-1:
N'-QRSSLVR, DMGNLGR, RSHDLTR, HKSSLTR, DSSNLRR, DOGNLIR-C'
(SEQ ID NOS 131, 132, 133, 134, 135, and 136, respectively,
in order of appearance)

ZF 2-2:
N'-QKQALTR, DRGNLTR, RSHDLTR, HKSSLTR, DSSNLRR, DQGNLIR-C'
(SEQ ID NOS 137, 138, 133, 134, 135, and 136, respectively,
in order of appearance)

ZF 2-3:
N'-QRSSLVR, DMGNLGR, RSHDLTV, HKSSLTR, DSSNLRR, DQGNLIR-C'
(SEQ ID NOS 131, 132, 139, 134, 135, and 136, respectively,
in order of appearance)

ZF 2-4:
N'-QKQALTR, DRGNLTR, RSHDLTV, HKSSLTR, DSSNLRR, DQGNLIR-C'
(SEQ ID NOS 137, 138, 139, 134, 135, and 136, respectively,
in order of appearance)

ZF 2-5:
N'-QRSSLVR, DMGNLGR, RSHDLTR, HKSSLTR, EKQNLAR, DPSNLRR-C'
(SEQ ID NOS 131, 132, 133, 134, 148, and 149, respectively,
in order of appearance)

ZF 2-6:
N'-QKQALTR, DRGNLTR, RSHDLTR, HKSSLTR, EKQNLAR, DPSNLRR-C'
(SEQ ID NOS 137, 138, 133, 134, 148, and 149, respectively,
in order of appearance)
```

-continued

```
ZF 2-7:
N'-QRSSLVR, DMGNLGR, RSHDLTV, HKSSLTR, EKQNLAR, DPSNLRR-C'
(SEQ ID NOS 131, 132, 139, 134, 148, and 149, respectively,
in order of appearance)

ZF 2-8:
N'-QKQALTR, DRGNLTR, RSHDLTV, HKSSLTR, EKQNLAR, DPSNLRR-C'
(SEQ ID NOS 137, 138, 139, 134, 148, and 149, respectively,
in order of appearance)
```

Non-limiting examples of the combinations and arrangements of six helices in a single six-finger ZFA where the helices are selected from Group 3 and where the motifs are in an $NH_2$— to COOH— terminus arrangement, (Group 3 ZFA helix combo), are as follows:

```
ZF 3-1:
N'-QRSSLVR, DKSVLAR, QRSSLVR, QTNNLGR, THAVLTR, DRGNLTR-C'
(SEQ ID NOS 131, 140, 131, 141, 142, and 138, respectively,
in order of appearance)

ZF 3-2:
N'-QRSSLVR, DKSVLAR, QRSSLVR, QTNNLGR, TKSLLAR, DRGNLTR-C'
(SEQ ID NOS 131, 140, 131, 141, 143, and 138, respectively,
in order of appearance)

ZF 3-3:
N'-QKQALDR, DTSVLNR, QRSSLVR, QTNNLGR, THAVLTR, DRGNLTR-C'
(SEQ ID NOS 144, 145, 131, 141, 142, and 138, respectively,
in order of appearance)

ZF 3-4:
N'-QKQALDR, DTSVLNR, QRSSLVR, QTNNLGR, TKSLLAR, DRGNLTR-C'
(SEQ ID NOS 144, 145, 131, 141, 143, and 138, respectively,
in order of appearance)

ZF 3-5:
N'-QRSSLVR, DKSVLAR, QRSSLVR, QTNNLGR, THAVLTR, DRGNLTR-C'
(SEQ ID NOS 131, 140, 131, 141, 142, and 138, respectively,
in order of appearance)

ZF 3-6:
N'-QRSSLVR, DKSVLAR, QRSSLVR, QTNNLGR, TKSLLAR, DRGNLTR-C'
(SEQ ID NOS 131, 140, 131, 141, 143, and 138, respectively,
in order of appearance)

ZF 3-7:
N'-QKQALDR, DTSVLNR, QRSSLVR, QTNNLGR, THAVLTR, DRGNLTR-C'
(SEQ ID NOS 144, 145, 131, 141, 142, and 138, respectively,
in order of appearance)

ZF 3-8:
N'-QKQALDR, DTSVLNR, QRSSLVR, QTNNLGR, TKSLLAR, DRGNLTR-C'
(SEQ ID NOS 144, 145, 131, 141, 143, and 138, respectively,
in order of appearance)
```

In some embodiments of any of the aspects, QRNNLGR (SEQ ID NO: 181) is used in place of QTNNLGR (SEQ ID NO: 141). Non-limiting examples of the combinations and arrangements of six helices in a single six-finger ZFA where the helices are selected from Group 3 and where the motifs are in an $NH_2$— to COOH— terminus arrangement, (Group 3 ZFA helix combo), are as follows:

```
ZF 3-1:
N'-QRSSLVR, DKSVLAR, QRSSLVR, QRNNLGR, THAVLTR, DRGNLTR-C'
(SEQ ID NOS 131, 140, 131, 181, 142, and 138, respectively,
in order of appearance)

ZF 3-2:
N'-QRSSLVR, DKSVLAR, QRSSLVR, QRNNLGR, TKSLLAR, DRGNLTR-C'
(SEQ ID NOS 131, 140, 131, 181, 143, and 138, respectively,
in order of appearance)
```

-continued

ZF 3-3:
N'-QKQALDR, DTSVLNR, QRSSLVR, QRNNLGR, THAVLTR, DRGNLTR-C'
(SEQ ID NOS 144, 145, 131, 181, 142, and 138, respectively, in order of appearance)

ZF 3-4:
N'-QKQALDR, DTSVLNR, QRSSLVR, QRNNLGR, TKSLLAR, DRGNLTR-C'
(SEQ ID NOS 144, 145, 131, 181, 143, and 138, respectively, in order of appearance)

ZF 3-5:
N'-QRSSLVR, DKSVLAR, QRSSLVR, QRNNLGR, THAVLTR, DRGNLTR-C'
(SEQ ID NOS 131, 140, 131, 181, 142, and 138, respectively, in order of appearance)

ZF 3-6:
N'-QRSSLVR, DKSVLAR, QRSSLVR, QRNNLGR, TKSLLAR, DRGNLTR-C'
(SEQ ID NOS 131, 140, 131, 181, 143, and 138, respectively, in order of appearance)

ZF 3-7:
N'-QKQALDR, DTSVLNR, QRSSLVR, QRNNLGR, THAVLTR, DRGNLTR-C'
(SEQ ID NOS 144, 145, 131, 181, 142, and 138, respectively, in order of appearance)

ZF 3-8:
N'-QKQALDR, DTSVLNR, QRSSLVR, QRNNLGR, TKSLLAR, DRGNLTR-C'
(SEQ ID NOS 144, 145, 131, 181, 143, and 138, respectively, in order of appearance)

Non-limiting examples of the combinations and arrangements of six helices in a single six-finger ZFA where the helices are selected from Group 4 and where the motifs are in an $NH_2$— to COOH— terminus arrangement, (Group 4 ZFA helix combo), are as follows:

ZF 4-1:
N'-QQTNLTR, QGTSLAR, VRHNLTR, DKSVLAR, DSSNLRR, DOGNLIR-C'
(SEQ ID NOS 126, 146, 147, 140, 135, and 136, respectively, in order of appearance)

ZF 4-2:
N'-QQTNLTR, QGTSLAR, VRHNLTR, DKSVLAR, EKQNLAR, DPSNLRR-C'
(SEQ ID NOS 126, 146, 147, 140, 148, and 149, respectively, in order of appearance)

ZF 4-3:
N'-QQTNLTR, QGTSLAR, VRHNLTR, DHSNLSR, DSSNLRR, DQGNLIR-C'
(SEQ ID NOS 126, 146, 147, 150, 135, and 136, respectively, in order of appearance)

ZF 4-4:
N'-QQTNLTR, QGTSLAR, VRHNLTR, DHSNLSR, EKQNLAR, DPSNLRR-C'
(SEQ ID NOS 126, 146, 147, 150, 148, and 149, respectively, in order of appearance)

ZF 4-5:
N'-QQTNLTR, QSTSLQR, VRHNLTR, DKSVLAR, DSSNLRR, DQGNLIR-C'
(SEQ ID NOS 126, 151, 147, 140, 135, and 136, respectively, in order of appearance)

ZF 4-6:
N'-QQTNLTR, QSTSLQR, VRHNLTR, DKSVLAR, EKQNLAR, DPSNLRR-C'
(SEQ ID NOS 126, 151, 147, 140, 148, and 149, respectively, in order of appearance)

ZF 4-7:
N'-QQTNLTR, QSTSLQR, VRHNLTR, DHSNLSR, DSSNLRR, DQGNLIR-C'
(SEQ ID NOS 126, 151, 147, 150, 135, and 136, respectively, in order of appearance)

ZF 4-8:
N'-QQTNLTR, QSTSLQR, VRHNLTR, DHSNLSR, EKQNLAR, DPSNLRR-C'
(SEQ ID NOS 126, 151, 147, 150, 148, and 149, respectively, in order of appearance)

Non-limiting examples of the combinations and arrangements of six helices in a single six-finger ZFA where the helices are selected from Group 5 and where the motifs are in an $NH_2$— to COOH— terminus arrangement, (Group 5 ZFA helix combo), are as follows:

```
ZF 5-1:
N'-NMSNLTR, DRSVLRR, LQENLTR, DRSSLRR, QSGTLHR, QSGTLHR-C'
(SEQ ID NOS 152, 153, 154, 155, 156, and 156, respectively,
in order of appearance)

ZF 5-2:
N'-QLANLAR, DQTTLRR, LQENLTR, DRSSLRR, QSGTLHR, QSGTLHR-C'
(SEQ ID NOS 157, 158, 154, 155, 156, and 156, respectively,
in order of appearance)

ZF 5-3:
N'-NMSNLTR, DRSVLRR, DPSNLAR, DRSSLRR, QSGTLHR, QSGTLHR-C'
(SEQ ID NOS 152, 153, 159, 155, 156, and 156, respectively,
in order of appearance)

ZF 5-4:
N'-QLANLAR, DQTTLRR, DPSNLAR, DRSSLRR, QSGTLHR, QSGTLHR-C'
(SEQ ID NOS 157, 158, 159, 155, 156, and 156, respectively,
in order of appearance)

ZF 5-5:
N'-NMSNLTR, DRSVLRR, LQENLTR, DRSSLRR, QSGTLHR, QSGTLHR-C'
(SEQ ID NOS 152, 153, 154, 155, 156, and 156, respectively,
in order of appearance)

ZF 5-6:
N'-QLANLAR, DQTTLRR, LQENLTR, DRSSLRR, QSGTLHR, QSGTLHR-C'
(SEQ ID NOS 157, 158, 154, 155, 156, and 156, respectively,
in order of appearance)

ZF 5-7:
N'-NMSNLTR, DRSVLRR, DPSNLAR, DRSSLRR, QSGTLHR, QSGTLHR-C'
(SEQ ID NOS 152, 153, 159, 155, 156, and 156, respectively,
in order of appearance)

ZF 5-8:
N'-QLANLAR, DQTTLRR, DPSNLAR, DRSSLRR, QSGTLHR, QSGTLHR-C'
(SEQ ID NOS 157, 158, 159, 155, 156, and 156, respectively,
in order of appearance)
```

Non-limiting examples of the combinations and arrangements of six helices in a single six-finger ZFA where the helices are selected from Group 6 and where the motifs are in an $NH_2$— to COOH— terminus arrangement, (Group 6 ZFA helix combo), are as follows:

```
N'-QQTNLTR, QGGNLAL, DHSSLKR,
RADMLRR, DSSNLRR, DQGNLIR-C'
(SEQ ID NOS 126, 160, 130, 161, 135, and
136, respectively, in order of appearance)

N'-QQTNLTR, QGGNLAL, DHSSLKR,
RADMLRR, EKQNLAR, DPSNLRR-C'
(SEQ ID NOS 126, 160, 130, 161, 148, and
149, respectively, in order of appearance)

N'-QQTNLTR, QKANLGV, DHSSLKR,
RADMLRR, DSSNLRR, DQGNLIR-C'
(SEQ ID NOS 126, 162, 130, 161, 135, and
136, respectively, in order of appearance)

N'-QQTNLTR, QKANLGV, DHSSLKR,
RADMLRR, EKQNLAR, DPSNLRR-C'
(SEQ ID NOS 126, 162, 130, 161, 148, and
149, respectively, in order of appearance)

N'-QQTNLTR, QGGNLAL, DHSSLKR,
RLDMLAR, DSSNLRR, DQGNLIR-C'
(SEQ ID NOS 126, 160, 130, 163, 135, and
136, respectively, in order of appearance)
```

-continued

```
N'-QQTNLTR, QGGNLAL, DHSSLKR,
RLDMLAR, EKQNLAR, DPSNLRR-C'
(SEQ ID NOS 126, 160, 130, 163, 148, and
149, respectively, in order of appearance)

N'-QQTNLTR, QKANLGV, DHSSLKR,
RLDMLAR, DSSNLRR, DQGNLIR-C'
(SEQ ID NOS 126, 162, 130, 163, 135, and
136, respectively, in order of appearance)

N'-QQTNLTR, QKANLGV, DHSSLKR,
RLDMLAR,EKQNLAR, DPSNLRR-C'
(SEQ ID NOS 126, 162, 130, 163, 148, and
149, respectively, in order of appearance)
```

Non-limiting examples of the combinations and arrangements of six helices in a single six-finger ZFA where the helices are selected from Group 7 and where the motifs are in an $NH_2$— to COOH— terminus arrangement, (Group 7 ZFA helix combo), are as follows:

```
N'-QRSSLVR, QRGNLNM, RPQELRR, DHSSLKR,
RQDNLGR, DGGNLGR-C'
(SEQ ID NOS 131, 164, 165, 130, 166, and
167, respectively, in order of appearance)

N'-QRSSLVR, QQGNLQL, RPQELRR, DHSSLKR,
RQDNLGR, DGGNLGR-C'
(SEQ ID NOS 131, 168, 165, 130, 166, and
167, respectively, in order of appearance)
```

-continued

```
N'-QRSSLVR, QRGNLNM, RRQELTR, DHSSLKR,

RQDNLGR, DGGNLGR-C'
(SEQ ID NOS 131, 164, 169, 130, 166, and
167, respectively, in order of appearance)

N'-QRSSLVR, QQGNLQL, RRQELTR, DHSSLKR,

RQDNLGR, DGGNLGR-C'
(SEQ ID NOS 131, 168, 169, 130, 166, and
167, respectively, in order of appearance)

N'-QRSSLVR, QRGNLNM, RPQELRR, DHSSLKR,

RODNLGR, DPSNLRR-C'
(SEQ ID NOS 131, 164, 165, 130, 166, and
149, respectively, in order of appearance)

N'-QRSSLVR, QQGNLQL, RPQELRR, DHSSLKR,

RQDNLGR, DPSNLRR-C'
(SEQ ID NOS 131, 168, 165, 130, 166, and
149, respectively, in order of appearance)

N'-QRSSLVR, QRGNLNM, RRQELTR, DHSSLKR,

RQDNLGR, DPSNLRR-C'
(SEQ ID NOS 131, 164, 169, 130, 166, and
149, respectively, in order of appearance)

N'-QRSSLVR, QQGNLQL, RRQELTR, DHSSLKR,

RQDNLGR, DPSNLRR-C'
(SEQ ID NOS 131, 168, 169, 130, 166, and
149, respectively, in order of appearance)
```

Non-limiting examples of the combinations and arrangements of six helices in a single six-finger ZFA where the helices are selected from Group 8 and where the motifs are in an $NH_2$— to COOH— terminus arrangement, (Group 8 ZFA helix combo), are as follows:

```
N'-QASNLTR, DHSSLKR, RAHNLLL, QRSSLVR,

QSTTLKR, DPSNLRR-C'
(SEQ ID NOS 170, 130, 171, 131, 172, and
149, respectively, in order of appearance)

N'-QASNLTR, DHSSLKR, RAHNLLL, QRSSLVR,

QGTTLKR, DPSNLRR-C'
(SEQ ID NOS 170, 130, 171, 131, 173, and
149, respectively, in order of appearance)

N'-QRSNLAR, DHSSLKR, RAHNLLL, QRSSLVR,

QSTTLKR, DPSNLRR-C'
(SEQ ID NOS 174, 130, 171, 131, 172, and
149, respectively, in order of appearance)

N'-QRSNLAR, DHSSLKR, RAHNLLL, QRSSLVR,

QGTTLKR, DPSNLRR-C'
(SEQ ID NOS 174, 130, 171, 131, 173, and
149, respectively, in order of appearance)
```

Non-limiting examples of the combinations and arrangements of six helices in a single six-finger ZFA where the helices are selected from Group 9 and where the motifs are in an $NH_2$— to COOH— terminus arrangement, (Group 9 ZFA helix combo), are as follows:

```
N'-DSSNLRR, DQGNLIR, RAHNLLL, QRSSLVR,

QSTTLKR, DPSNLRR-C'
(SEQ ID NOS 135, 136, 171, 131, 172, and
149, respectively, in order of appearance)

N'-EKQNLAR, DPSNLRR, RAHNLLL, QRSSLVR,

QSTTLKR, DPSNLRR-C'
(SEQ ID NOS 148, 149, 171, 131, 172, and
149, respectively, in order of appearance)

N'-DSSNLRR, DQGNLIR, RAHNLLL, QRSSLVR,

QGTTLKR, DPSNLRR-C'
(SEQ ID NOS 135, 136, 171, 131, 173, and
149, respectively, in order of appearance)

N'-EKQNLAR, DPSNLRR, RAHNLLL, QRSSLVR,

QGTTLKR, DPSNLRR-C'
(SEQ ID NOS 148, 149, 171, 131, 173, and
149, respectively, in order of appearance)
```

A non-limiting example of the combination and arrangement of six helices in a single six-finger ZFA where the helices are selected from Group 10 and where the motif are in an $NH_2$— to COOH— terminus arrangement, (Group 10 ZFA helix combo), is as follows:

```
ZF 10-1:
N'-RRHGLDR, DHSSLKR, VRHNLTR, DHSNLSR,

QRSSLVR, ESGHLKR-C'
(SEQ ID NOS 175, 130, 147, 150, 131, and
176, respectively, in order of appearance)
```

A non-limiting example of the combination and arrangement of six helices in a single six-finger ZFA where the helices are selected from Group 11 and where the motif are in an $NH_2$— to COOH— terminus arrangement, (Group 11 ZFA helix combo), is as follows:

```
ZF 11-1:
N'-QLSNLTR, DRSSLKR, QRSSLVR, RLDMLAR,

VRHSLTR, ESGALRR-C'
(SEQ ID NOS 177, 178, 131, 163, 179, and
180, respectively, in order of appearance)
```

Accordingly, provided herein, in some aspects, are engineered synTF or ZF-containing fusion proteins described herein comprising a ZF protein domain, an effector domain, and a regulator protein, wherein the ZF protein domain comprises at least one ZFA having the ZFA helix combo selected from one of the ZFA helix combo Groups 1-11 disclosed herein. Where there are two or more ZFAs, (i.e., a ZF array) in the ZF protein domain, each ZFAs in the domain has a ZFA helix combo selected from one of the ZFA helix combo Groups 1-11 disclosed herein, and the selected ZFA helix combo groups can be different or duplicated for the each ZFAs in the ZF protein domain of the synTF. For example, when a synTF comprises a ZF protein domain consisting essentially of three ZFAs (ZFA-1-ZFA-2-ZFA-3 in a three-ZFA array) and an effector domain, ZFA-1 has a ZFA helix combo selected from the Group 1 ZFA helix combo, ZFA-2 has a ZFA helix combo selected from the Group 5 ZFA helix combo, and ZFA-3 has a ZFA helix combo selected from the Group 7 ZFA helix combo. In other embodiments, the selected ZFA helix combo groups can be duplicated or triplicated for the ZF array in the synTF. For example, in a three-ZFA array-containing ZF protein domain of a synTF, two of the ZFAs comprises ZFA helix combo selected from the same ZFA helix combo group, e.g., Group 2, and the third ZFA has a ZFA helix combo selected from a different ZFA helix combo group, e.g., Group 4. The two ZFAs having ZFA helix combos selected from the same Group 2 ZFA helix combo can have different or the same actual combination and arrangement of the helices ZFAs. For example, when the synTF comprises of a ZF protein domain consisting essentially of five ZFAs (ZFA-1-ZFA-2-ZFA-3-ZFA-4-ZFA-5 in a five-ZFA array) and an effector domain, ZFA-1 has a ZFA helix combo selected from the Group 1 ZFA helix combo, ZFA-2 has a ZFA helix combo selected from the Group 5 ZFA helix combo, ZFA-3 has a ZFA helix combo also selected from the Group 1 ZFA helix combo, ZFA-4 has a ZFA helix combo selected from the Group 4 ZFA helix combo, and ZFA-5 has a ZFA helix combo selected from the Group 2 ZFA helix combo. While ZFA-1 and ZFA-3 both have ZFA helix combo selected from the Group 1 ZFA helix combo, the actual combination and arrangement of the helices within ZFA-1 and ZFA-3 can be different or the same. For example, ZFA-1 and ZFA-3 have the ZFA helix combo ZF 1-1 and ZF 1-5 respectively, or both ZFA-1 and ZFA-3 have the ZFA helix combo ZF 1-1.

In other aspects, provided herein are engineered synTF or a ZF-containing fusion protein described herein comprising a ZF protein domain and an effector domain, or comprising a ZF protein domain, an effector domain, and a ligand binding domain, or comprising a ZF protein domain and a ligand binding domain or a dimerization domain, wherein the ZF protein domain comprises at least one ZFA having a ZFA helix combo selected from the group consisting of ZF 1-1, ZF 1-2, ZF 1-3, ZF 1-4, ZF 1-5, ZF 1-6, ZF 1-7, ZF 1-8, ZF 2-1, ZF 2-2, ZF 2-3, ZF 2-4, ZF 2-5, ZF 2-6, ZF 2-7, ZF 2- 8, ZF 3-1, ZF 3-2, ZF 3-3, ZF 3-4, ZF 3-5, ZF 3-6, ZF 3-7, ZF 3-8, ZF 4-1, ZF 4-2, ZF 4-3, ZF 4-4, ZF 4- 5, ZF 4-6, ZF 4-7, ZF 4-8, ZF 5-1, ZF 5-2, ZF 5-3, ZF 5-4, ZF 5-5, ZF 5-6, ZF 5-7, ZF 5-8, ZF 6-1, ZF 6- 2, ZF 6-3, ZF 6-4, ZF 6-5, ZF 6-6, ZF 6-7, ZF 6-8, ZF 7-1, ZF 7-2, ZF 7-3, ZF 7-4, ZF 7-5, ZF 7-6, ZF 7- 7, ZF 7-8, ZF 8-1, ZF 8-2, ZF 8-3, ZF 8-4, ZF 9-1, ZF 9-2, ZF 9-3, ZF 9-4, ZF 10-1, and ZF 11-1 disclosed herein.

In some embodiments of any of the aspects, the ZF protein domain comprises at least one ZFA having a ZFA helix combo selected from the group consisting of ZF1-3, ZF2-6, ZF3-5, ZF4-8, ZF5-7, ZF6-4, ZF7-3, ZF8-1, ZF9-2, ZF10-1, and ZF11-1, which are also referred to herein as ZF1, ZF2, ZF3, ZF4, ZF5, ZF6, ZF7, ZF8, ZF9, ZF10, and ZF11, respectively.

In some embodiments of any aspect described herein, in the synTF described or any ZF-containing fusion protein described herein, the individual ZFA therein described are specifically designed to bind orthogonal target DNA sequences (also referred to herein as DNA binding motifs) such as the following:

```
Target 1:
                                  (SEQ ID NO: 91)
5' C GTC GAA GTC GAA GTC GAC C 3'

Target 2:
                                  (SEQ ID NO: 92)
5' G GAC GAC GTT ACG GAC GTA C 3'

Target 3:
                                  (SEQ ID NO: 93)
5' A GAC GTC GAA GTA GCC GTA G 3'
```

-continued

```
Target 4:
                                  (SEQ ID NO: 94)
5' G GAC GAC GCC GAT GTA GAA G 3'

Target 5:
                                  (SEQ ID NO: 95)
5' T GAA GCA GTC GAC GCC GAA G 3'

Target 6:
                                  (SEQ ID NO: 96)
5' G GAC GAC GCG GTC TAA GAA G 3'

Target 7:
                                  (SEQ ID NO: 97)
5' C GAC GAG GTC GCA TAA GTA G 3'

Target 8:
                                  (SEQ ID NO: 98)
5' A GAC GCA GTA TAG GTC GAA C 3'

Target 9:
                                  (SEQ ID NO: 99)
5' A GAC GCA GTA TAG GAC GAC G 3'

Target 10:
                                 (SEQ ID NO: 100)
5' C GGC GTA GCC GAT GTC GCG C 3'

Target 11:
                                 (SEQ ID NO: 101)
5' G GTC GTT GCG GTA GTC GAA G 3'
```

In some embodiments of any of the aspects, the ZF binding domain specifically binds to a sequence comprising at least one of SEQ ID NOs: 91-101 or to a nucleic acid sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 91-101 that maintains the same function.

In some embodiments of any of the aspects, ZF 1-1, ZF 1-2, ZF 1-3, ZF 1-4, ZF 1-5, ZF 1-6, ZF 1-7, and ZF 1-8 bind to Target 1. In some embodiments of any of the aspects, ZF 2-1, ZF 2-2, ZF 2-3, ZF 2-4, ZF 2-5, ZF 2-6, ZF 2-7, and ZF 2-8 bind to Target 2. In some embodiments of any of the aspects, ZF 3-1, ZF 3-2, ZF 3-3, ZF 3-4, ZF 3-5, ZF 3-6, ZF 3-7, and ZF 3-8 bind to Target 3. In some embodiments of any of the aspects, ZF 4-1, ZF 4-2, ZF 4-3, ZF 4-4, ZF 4-5, ZF 4-6, ZF 4-7, ZF 4-8 bind to Target 4. In some embodiments of any of the aspects, ZF 5-1, ZF 5-2, ZF 5-3, ZF 5-4, ZF 5-5, ZF 5-6, ZF 5-7, and ZF 5-8 bind to Target 5. In some embodiments of any of the aspects, ZF 6-1, ZF 6-2, ZF 6-3, ZF 6-4, ZF 6-5, ZF 6-6, ZF 6-7, and ZF 6-8 bind to Target 6. In some embodiments of any of the aspects, ZF 7-1, ZF 7-2, ZF 7-3, ZF 7-4, ZF 7-5, ZF 7-6, ZF 7-7, and ZF 7-8 bind to Target 7. In some embodiments of any of the aspects, ZF 8-1, ZF 8-2, ZF 8-3, and ZF 8-4 bind to Target 8. In some embodiments of any of the aspects, ZF 9-1, ZF 9-2, ZF 9-3, and ZF 9-4 bind to Target 9. In some embodiments of any of the aspects, ZF10-1 binds to Target 10. In some embodiments of any of the aspects, ZF11-1 binds to Target 11.

In one embodiment of any aspect described herein, provided herein is a ZFA that comprises, consists of, or consist essentially of a sequence: N'-[(formula 1)-$L_2$]$_{6-8}$-C' or a sequence N'-[(formula 2)-$L_2$]$_{6-8}$-C' that targets a target DNA sequence selected from Target 1-11, wherein the formula 1 is [$X_{0-3}CX_{1-5}CX_{2-7}$-(helix)-$HX_{3-6}H$] (SEQ ID NO: 84) and the formula 2 is [$X_3CX_2CX_5$-(helix)-$HX_3H$] (SEQ ID NO: 85).

In other aspects, provided herein are engineered synTF or the ZF containing fusion protein described herein comprising a ZF protein domain and an effector domain, or comprising a ZF protein domain, an effector domain, and a ligand binding domain, or comprising a ZF protein domain and a ligand binding domain or a dimerization domain, wherein the ZF protein domain comprises at least one ZFA, wherein the an least ZFA comprises, consists of, or consist essentially of a sequence: N'-[(formula 1)-$L_2$]$_{6-8}$-C' or a sequence N'-[(formula 2)-$L_2$]$_{6-8}$-C', and wherein the ZFA(s) therein targets a target DNA sequence selected from Target 1-11, wherein the formula 1 is [$X_{0-3}CX_{1-5}CX_{2-7}$-(helix)-$HX_3$-6H] (SEQ ID NO: 84) and the formula 2 is [$X_3CX_2CX_5$-(helix)-$HX_3H$] (SEQ ID NO: 85).

In some embodiments of any of the aspects, the ZF binding domain comprises one of SEQ ID NOs: 36, 45, 86, or an amino acid sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 36, 45, 86 that maintains the same function.

SEQ ID NO: 86, Sequence of ZF1-3 (ZF1)
SRPGERPFQCRICMRNFSEEANLRRHTRTHTGEKPFQCRICMRNF

SDHSSLKRHLRTHTGSQKPFQCRICMRNFSQSANLLRHTRTHTGE

KPFQCRICMRNFSDPSSLKRHLRTHTGSQKPFQCRICMRNFSQQT

NLTRHTRTHTGEKPFQCRICMRNFSDATQLVRHLRTHLRGS

SEQ ID NO: 45, Sequence of ZF3-5 (ZF3)
SRPGERPFQCRICMRNFSQRSSLVRHTRTHTGEKPFQCRICMRNF

SDKSVLARHLRTHTGSQKPFQCRICMRNFSQRSSLVRHTRTHTGE

KPFQCRICMRNFSQRNNLGRHLRTHTGSQKPFQCRICMRNFSTHA

VLTRHTRTHTGEKPFQCRICMRNFSDRGNLTRHLRTHLRGS

SEQ ID NO: 36, Sequence of ZF10-1 (ZF10)
SRPGERPFQCRICMRNFSRRHGLDRHTRTHTGEKPFQCRICMRNF

SDHSSLKRHLRTHTGSQKPFQCRICMRNFSVRHNLTRHLRTHTGE

KPFQCRICMRNFSDHSNLSRHLKTHTGSQKPFQCRICMRNFSQRS

SLVRHLRTHTGEKPFQCRICMRNFSESGHLKRHLRTHLRGS

In some embodiments of any of the aspects, the DBD comprises a 3-unit ZF protein. In some embodiments of any of the aspects, the 3-unit ZF protein comprises one of SEQ ID NOs: 102-109 or an amino acid sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 102-109 that maintains the same function.

SEQ ID NO: 102 high affinity scaffold
(bolded letter shows mutated residue, and
plain text "xxxxxx" indicates three ZF
helices, e.g., from N terminus to C terminus:
helix 1, helix 2, helix 3, respectively)
GERPFQCRICMANFSxxxxxxxHTRTHTGEKPFQCRICMANFS xxxxxxxHLRTHTGEKPFQCRICMANFSxxxxxxxHLKTHLR SEQ ID NO: 103 low affinity scaffold
(bolded letter shows mutated residue,
and bold italic text indicates
helices 1, 2, and 3 respectively)
GEAPFQCRICMANFSxxxxxxxHTRTHTGEKPFQCRICMANFSx xxxxxxHLRTHTGEKPFQCRICMANFSxxxxxxxHLKTHLR In some embodiments of any of the aspects, the at least one DBD is selected from the group consisting of: 13-6, 14-3, 21-16, 36-4, 37-12, 42-10, 43-8, 54-8, 55-1, 62-1, 92-1, 93-10, 97-4, 129-3, 150-4, 151-1, 158-2, 172-5, and 173-3; see e.g., Khalil et al., Cell Volume 150, Issue 3, 3 Aug. 2012, Pages 647-658; U.S. Pat. No. 10,138,493; US Patent Application US20200002710A1; the contents of each of which are incorporated herein by reference in their entireties. In some embodiments of any of the aspects, the at least one DBD is selected from one or more of any of: 36-4 (SEQ ID NO: 104), 43-8 (SEQ ID NO: 105 or 106), 42-10 (SEQ ID NO: 107-108), 97-4 (SEQ ID NO: 109).

SEQ ID NO: 104, 36-4 (bold italic text
indicates helices 1, 2, and 3 respectively)
GERPFQCRICMANFS*GRQALDR*HTRTHTGEKPFQCRICMANFS*D*

*KANLTR*HLRTHTGEKPFQCRICMANFS*QRNNLGR*HLKTHLR

SEQ ID NO: 105 43-8 low affinity
(bolded letter shows mutated residue,
and bold italic text indicates helices
1, 2, and 3 respectively)
GEAPFQCRICMANFS*RQDRLDR*HTRTHTGEKPFQCRICMANFS

*QKEHLAG*HLRTHTGEKPFQCRICMANFS*RRDNLNR*HLKTHLR

SEQ ID NO: 106 43-8 high affinity
(bolded letter shows mutated residue,
and bold italic text indicates
helices 1, 2, and 3 respectively)
GERPFQCRICMANFS*RQDRLDR*HTRTHTGEKPFQCRICMANFS

*QKEHLAG*HLRTHTGEKPFQCRICMANFS*RRDNLNR*HLKTHLR

SEQ ID NO: 107 42-10 low affinity
(bolded letter shows mutated residue,
and bold italic text indicates
helices 1, 2, and 3 respectively)
GEAPFQCRICMANFS*TGQILDR*HTRTHTGEKPFQCRICMANFS

*VAHSLKR*HLRTHTGEKPFQCRICMANFS*DPSNLRR*HLKTHLR

SEQ ID NO: 108 42-10 high affinity
(bolded letter shows mutated residue,
and bold italic text indicates helices
1, 2, and 3 respectively)
GERPFQCRICMANFS*TGQILDR*HTRTHTGEKPFQCRICMANFS

*VAHSLKR*HLRTHTGEKPFQCRICMANFS*DPSNLRR*HLKTHLR

SEQ ID NO: 109, 97-4
(bold italic text indicates helices
1, 2, and 3 respectively)
GERPFQCRICMRNFS*RQSNLSR*HTRTHTGEKPFQCRICMRNFS

*RNEHLVL*HLRTHTGEKPFQCRICMRNFS*QKTGLRV*HLKTHLR

In some embodiments of any of the aspects, the DBD binds to DNA binding motifs (DBM) comprising any of: SEQ ID NOs: 110-121.

SEQ ID NO: 110 is an exemplary DBM (DNA binding
motif) nucleic acid sequence for 36-4:
c GAA GAC GCT g.

SEQ ID NO: 111-SEQ ID NO: 113 are exemplary DBM
affinity variant nucleic acid sequences for 43-8.
Bold text indicates residues mutated from the WT
sequence.
SEQ ID NO: 111 is 43-8 DBM1-
aGAGTGAGGAc.

SEQ ID NO: 112 is 43-8 DBM2-
aCAGTGAGGAc.

SEQ ID NO: 113 is 43-8 DBM3-
aTAGTGAGGAc.

-continued

SEQ ID NOS 114-120 are exemplary DBM affinity variant nucleic acid sequences for 42-10. Bold text indicates residues mutated from the WT sequence.

SEQ ID NO: 114 is 42-10 DBM1-
aGACGCTGCTc.

SEQ ID NO: 115 is 42-10 DBM2-
tGACGCTGCTt.

SEQ ID NO: 116 is 42-10 DBM3-
aGACGGTGCTc.

SEQ ID NO: 117 is 42-10 DBM4-
aCACGCTGCTc.

SEQ ID NO: 118 is 42-10 DBM5-
aGACGCTACTc.

SEQ ID NO: 119 is 42-10 DBM6-
aGACGCTGCTa.

SEQ ID NO: 120 is 42-10 DBM7-
aGACTCTGCTc.

SEQ ID NO: 121 is an exemplary DBM (DNA binding motif) nucleic acid sequence for 97-4:
a TTA TGG GAG a.

In some embodiments, the engineered ZF-binding domain binds to an endogenous gene, such as an endogenous promoter. As a non-limiting example, the engineered ZF-binding domain binds to endogenous VEGF gene (VEGF ZF), such as the endogenous promoter of the human VEGF gene. In some embodiments, the engineered ZF-binding domain comprises SEQ ID NO: 48 or amino acid sequence with at least at least 60%, at least 65%, at least 70%, at least 75%, at least 80%, at least 85%, at least 90%, at least 95%, at least 96%, at least 97%, at least 98%, or at least 99% sequence identity to SEQ ID NO: 48, which maintains its function (e.g., binding to the endogenous VEGF gene).

Repressible Protease Domain

In some embodiments of any of the aspects, a synTF as described herein comprises a regulator protein, wherein the regulator protein is a repressible protease domain (referred to herein as PRO or RPD). As used herein, the term "repressible protease" refers to a protease that can be inactivated by the presence or absence of a specific agent (e.g., that specifically binds to the protease). In some embodiments, a repressible protease is active (e.g., cleaves a protease cleavage site) in the absence of the specific agent and is inactive (e.g., does not cleave a protease cleavage site) in the presence of the specific agent. In some embodiments, the specific agent is a protease inhibitor. In some embodiments, the protease inhibitor specifically inhibits a given repressible protease as described herein.

In some embodiments of any of the aspects, a synTF polypeptide as described herein (or a synTF polypeptide system collectively) comprises 1, 2, 3, 4, 5, or more repressible protease(s). In some embodiments of any of the aspects, the synTF polypeptide or system comprises one repressible protease. In embodiments comprising multiple repressible proteases, the multiple repressible proteases can be different individual repressible proteases or multiple copies of the same repressible protease, or a combination of the foregoing.

Non-limiting examples of repressible proteases include hepatitis C virus proteases (e.g., NS3 and NS2-3); HIV1 protease; coronavirus (main) protease; Tobacco etch virus (TEV) protease; signal peptidase; proprotein convertases of the subtilisin/kexin family (furin, PCI, PC2, PC4, PACE4, PC5, PC); proprotein convertases cleaving at hydrophobic residues (e.g., Leu, Phe, Val, or Met); proprotein convertases cleaving at small amino acid residues such as Ala or Thr; proopiomelanocortin converting enzyme (PCE); chromaffin granule aspartic protease (CGAP); prohormone thiol protease; carboxypeptidases (e.g., carboxypeptidase E/H, carboxypeptidase D and carboxypeptidase Z); aminopeptidases (e.g., arginine aminopeptidase, lysine aminopeptidase, aminopeptidase B); prolyl endopeptidase; aminopeptidase N; insulin degrading enzyme; calpain; high molecular weight protease; and, caspases 1, 2, 3, 4, 5, 6, 7, 8, and 9. Other proteases include, but are not limited to, aminopeptidase N; puromycin sensitive aminopeptidase; angiotensin converting enzyme; pyroglutamyl peptidase II; dipeptidyl peptidase IV; N-arginine dibasic convertase; endopeptidase 24.15; endopeptidase 24.16; amyloid precursor protein secretases alpha, beta and gamma; angiotensin converting enzyme secretase; TGF alpha secretase; T F alpha secretase; FAS ligand secretase; TNF receptor-I and -II secretases; CD30 secretase; KL1 and KL2 secretases; IL6 receptor secretase; CD43, CD44 secretase; CD 16-1 and CD 16-11 secretases; L-selectin secretase; Folate receptor secretase; MMP 1, 2, 3, 7, 8, 9, 10, 11, 12, 13, 14, and 15; urokinase plasminogen activator; tissue plasminogen activator; plasmin; thrombin; BMP-1 (procollagen C-peptidase); ADAM 1, 2, 3, 4, 5, 6, 7, 8, 9, 10, and 11; and, granzymes A, B, C, D, E, F, G, and H. For a discussion of proteases, see, e.g., V. Y. H. Hook, Proteolytic and cellular mechanisms in prohormone and proprotein processing, RG Landes Company, Austin, Tex., USA (1998); N. M. Hooper et al., Biochem. J. 321: 265-279 (1997); Z. Werb, Cell 9 1: 439-442 (1997); T. G. Wolfsberg et al., J. Cell Biol. 131: 275-278 (1995); K. Murakami and J. D. Etlinger, Biochem. Biophys. Res. Comm. 146: 1249-1259 (1987); T. Berg et al., Biochem. J. 307: 313-326 (1995); M. J. Smyth and J. A. Trapani, Immunology Today 16: 202-206 (1995); R. V. Talanian et al., J. Biol. Chem. 272: 9677-9682 (1997); and N. A. Thomberry et al., J. Biol. Chem. 272: 17907-1791 1 (1997); International Patent Application WO2019118518; Rajakuberan et al., Methods Mol Biol. 2012; 903:393-405; Gao et al. Science 21 Sep. 2018: Vol. 361, Issue 6408, pp. 1252-1258; Tague et al., Nat Methods. 2018 July; 15(7):519-522; Lin et al. PNAS Jun. 3, 2008 105 (22) 7744-7749; U.S. patent application Ser. No. 16/832,751 filed Mar. 27, 2020; the contents of each of which are incorporated herein by reference in their entireties.

In some embodiments of any of the aspects, the repressible protease is hepatitis C virus (HCV) nonstructural protein 3 (NS3). NS3, also known as p-70, is a viral nonstructural protein that is a 70 kDa cleavage product of the hepatitis C virus polyprotein. The 631-residue HCV NS3 protein is a dual-function protein, containing the trypsin/chymotrypsin-like serine protease in the N-terminal region and a helicase and nucleoside triphosphatase in the C-terminal region. The minimal sequences required for a functional serine protease activity comprise the N-terminal 180 amino acids of the NS3 protein, which can also be referred to as "NS3a". Deletion of up to 14 residues from the N terminus of the NS3 protein is tolerated while maintaining the serine protease activity. Accordingly, the repressible proteases described herein comprise at the least residues 14-180 of the wildtype NS3 protein.

HCV has at least seven genotypes, labeled 1 through 7, which can also be further designated with "a" and "b" subtypes. Accordingly, the repressible protease can be an HCV genotype 1 NS3, an HCV genotype 1a NS3, an HCV genotype 1b NS3, an HCV genotype 2 NS3, an HCV genotype 2a NS3, an HCV genotype 2b NS3, an HCV genotype 3 NS3, an HCV genotype 3a NS3, an HCV genotype 3b NS3, an HCV genotype 4 NS3, an HCV genotype 4a NS3, an HCV genotype 4b NS3, an HCV genotype 5 NS3, an HCV genotype 5a NS3, an HCV genotype 5b NS3, an HCV genotype 6 NS3, an HCV genotype 6a NS3, an HCV genotype 6b NS3, an HCV genotype 7 NS3, an HCV genotype 7a NS3, or an HCV genotype 7b NS3. In some embodiments of any of the aspects, the repressible protease can be any known HCV NS3 genotype, variant, or mutant, e.g., that maintains the same function. In some embodiments of any of the aspects, the NS3 sequence comprises residues 1-180 of the NS3 protein from HCV-H, HCV-1, HCV-J1, HCV-BK, HCV-JK1, HCV-J4, HCV-J, HCV-J6, C14112, HCV-J8, D14114, HCV-Nz11, or HCV-K3a (see e.g., Chao Lin, Chapter 6: HCV NS3-4A Serine Protease, Hepatitis C Viruses: Genomes and Molecular Biology, Editor: Tan S L, Norfolk (UK): Horizon Bioscience, 2006; the content of which is incorporated herein by reference in its entirety). In some embodiments of any of the aspects, the repressible protease is a chimera of 2, 3, 4, 5, or more different NS3 genotypes, variants, or mutants as described herein, such that the protease maintains its cleavage and/or binding functions.

In some embodiments of any of the aspects, the repressible protease of a synTF polypeptide as described herein comprises SEQ ID NOs: 182-198 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 182-198 that maintains the same function.

In some embodiments of any of the aspects, the repressible protease of a synTF polypeptide as described herein does not comprise at most the first (i.e., N-terminal) residues of SEQ ID NOs: 182-198. In some embodiments of any of the aspects, the repressible protease of a synTF polypeptide as described herein comprises residues 1-180, 2-180, 3-180, 4-180, 5-180, 6-180, 7-180, 8-180, 9-180, 10-180, 11-180, 12-180, 13-180, 14-180, 15-180, 16-180, 17-180, 18-180, 19-180, 20-180, 21-180, 22-180, 23-180, 24-180, 25-180, 26-180, 27-180, 28-180, 29-180, or 30-180 of SEQ ID NOs: 182-198.

SEQ ID NO: 182, NS3
(genotype 1A), 189 aa; bold text indicates His-57 of the catalytic triad; italicized double underlined text indicates Asp-81 of the catalytic triad; bold italicized indicates Ser-139 of the catalytic triad; double underlined text indicates Asp-168.
APITAYAQQTRGLLGCIITSLTGRDKNQVEGEVQIVSTATQTFL

ATCINGVCWAVYHGAGTRTIASPKGPVIQMYTNVDQ*D*LVGWPA

PQGSRSLTPCTCGSSDLYLVTRHADVIPVRRRGDSRGSLLSPR

PISYLKGS*S*GGPLLCPAGHAVGLFRAAVCTRGVAKAV*D*FIPVE

NLETTMRSPVFTDNSS

SEQ ID NO: 183, NS3 protease domain
(genotype 1A)
APITAYAQQTRGLLGCIITSLTGRDKNQVEGEVQIVSTATQTFLA

TCINGVCWAVYHGAGTRTIASPKGPVIQMYTNVDQDLVGWPAPQG

SRSLTPCTCGSSDLYLVTRHADVIPVRRRGDSRGSLLSPRPISYL

-continued

KGSSGGPLLCPAGHAVGLFRAAVCTRGVAKAVDFIPVENLETTMR

SPVFTD

SEQ ID NO: 184, NS3
(genotype 1A), 180 aa
(see e.g., residues 1027-1206 of Hepatitis C virus genotype 1 polyprotein,
NCBI Reference Sequence: NP_671491.1).
APITAYAQQTRGLLGCIITSLTGRDKNQVEGEVQIVSTATQTFLA

TCINGVCWTVYHGAGTRTIASPKGPVIQMYTNVDQDLVGWPAPQG

SRSLTPCTCGSSDLYLVTRHADVIPVRRRGDSRGSLLSPRPISYL

KGSSGGPLLCPAGHAVGLFRAAVCTRGVAKAVDFIPVENLETTMR

SEQ ID NO: 185, NS3 (genotype 1B), 180 aa
(see e.g., residues 1-180 Chain A, Ns3 Protease, PDB: 4K8B_A)
APITAYSQQTRGLLGCIITSLTGRDKNQVEGEVQVVSTATQSFLA

TCVNGVCWTVYHGAGSKTLAGPKGPITQMYTNVDQDLVGWQAPPG

ARSLTPCTCGSSDLYLVTRHADVIPVRRRGDSRGSLLSPRPVSYL

KGSSGGPLLCPSGHAVGIFRAAVCTRGVAKAVDFVPVESMETTMR

SEQ ID NO: 186, NS3 (genotype 2), 180 aa
(see e.g., residues 1031-1210 of Hepatitis C virus genotype 2 polyprotein, NCBI Reference Sequence: YP_001469630.1)
APITAYAQQTRGLLGTIVVSMTGRDKTEQAGEIQVLSTVTQSFLG

TSISGVLWTVYHGAGNKTLAGSRGPVTQMYSSAEGDLVGWPSPPG

TKSLEPCTCGAVDLYLVTRNADVIPARRRGDKRGALLSPRPLSTL

KGSSGGPVLCPRGHAVGVFRAAVCSRGVAKSIDFIPVETLDIVTR

SEQ ID NO: 187, NS3 (genotype 3), 180 aa
(see e.g., residues 1033-1212 of Hepatitis C virus genotype 3 polyprotein, NCBI Reference Sequence: YP_001469631.1)
APITAYAQQTRGLLGTIVTSLTGRDKNVVTGEVQVLSTATQTFLG

TTVGGVIWTVYHGAGSRTLAGAKHPALQMYTNVDQDLVGWPAPPG

AKSLEPCACGSSDLYLVTRDADVIPARRRGDSTASLLSPRPLACL

KGSSGGPVMCPSGHVAGIFRAAVCTRGVAKSLQFIPVETLSTQAR

SEQ ID NO: 188, NS3 (genotype 4), 180 aa
(see e.g., residues 1027-1206 of Hepatitis C virus genotype 4 polyprotein, NCBI Reference Sequence: YP_001469632.1)
APITAYAQQTRGLFSTIVTSLTGRDTNENCGEVQVLSTATQSFLG

TAVNGVMWTVYHGAGAKTISGPKGPVNQMYTNVDQDLVGWPAPPG

VRSLAPCTCGSADLYLVTRHADVIPVRRRGDTRGALLSPRPISIL

KGSSGGPLLCPMGHRAGIFRAAVCTRGVAKAVDFVPVESLETTMR

SEQ ID NO: 189, NS3
(genotype 5), 180 aa
(see e.g., residues 1028-1207 of Hepatitis C virus genotype 5 polyprotein, NCBI Reference Sequence: YP_001469633.1)
APITAYAQQTRGVLGAIVLSLTGRDKNEAEGEVQFLSTATQTFLG

ICINGVMWTLFHGAGSKTLAGPKGPVVQMYTNVDKDLVGWPSPPG

KGSLTRCTCGSADLYLVTRHADVIPARRRGDTRASLLSPRPISYL

KGSSGGPIMCPSGHVVGVFRAAVCTRGVAKALEFVPVENLETTMR

-continued

SEQ ID NO: 190, NS3
(genotype 6), 180 aa
(see e.g., residues 1032-1211 of Hepatitis C virus genotype 6 polyprotein, NCBI Reference Sequence: YP_001469634.1)
APITAYAQQTRGLVGTIVTSLTGRDKNEAEGEVQVVSTATQSFLA

TTINGVLWTVYHGAGSKNLAGPKGPVCQMYTNVDQDLVGWPAPLG

ARSLAPCTCGSSDLYLVTRGADVIPARRRGDTRAALLSPRPISTL

KGSSGGPLMCPSGHVVGLFRAAVCTRGVAKALDFIPVENMDTTMR

SEQ ID NO: 191, NS3
(genotype 7), 180 aa
(see e.g., residues 1031-1210 of Hepatitis C virus genotype 7 polyprotein, NCBI Reference Sequence: YP_009272536.1)
APISAYAQQTRGLISTLVVSLTGRDKNETAGEVQVLSTSTQTFLG

TNVGGVMWGPYHGAGTRTVAGRGGPVLQMYTSVSDDLVGWPAPPG

SKSLEPCSCGSADLYLVTRNADVLPLRRKGDGTASLLSPRPVSSL

KGSSGGPVLCPQSHCVGIFRAAVCTRGVAKAVQFVPIEKMQVAQR

SEQ ID NO: 192, NS3 genotype 1a
(HCV-H), 180 aa
APITAYAQQTRGLLGCIITSLTGRDKNQVEGEVQIVSTATQTFLA

TCINGVCWTVYHGAGTRTIASPKGPVIQMYTNVDQDLVGWPAPQG

SRSLTPCTCGSSDLYLVTRHADVIPVRRRGDSRGSLLSPRPISYL

KGSSGGPLLCPAGHAVGLFRAAVCTRGVTKAVDFIPVENLETTMR

SEQ ID NO: 193, NS3 genotype 1b
(HCV-BK), 180 aa
APITAYSQQTRGLLGCIITSLTGRDKNQVEGEVQVVSTATQSFLA

TCVNGVCWTVYHGAGSKTLAAPKGPITQMYTNVDQDLVGWPKPPG

ARSLTPCTCGSSDLYLVTRHADVIPVRRRGDSRGSLLSPRPVSYL

KGSSGGPLLCPFGHAVGIFRAAVCTRGVAKAVDFVPVESMETTMR

SEQ ID NO: 194, NS3 genotype 2a
(HCV-J6), 180 aa
APITAYAQQTRGLLGTIVVSMTGRDKTEQAGEIQVLSTVTQSFLG

TTISGVLWTVYHGAGNKTLAGSRGPVTQMYSSAEGDLVGWPSPPG

TKSLEPCTCGAVDLYLVTRNADVIPARRRGDKRGALLSPRPLSTL

KGSSGGPVLCPRGHAVGVFRAAVCSRGVAKSIDFIPVETLDIVTR

SEQ ID NO: 195, NS3 genotype 2b
(HCV-J8), 180 aa
APITAYTQQTRGLLGAIVVSLTGRDKNEQAGQVQVLSSVTQTFLG

TSISGVLWTVYHGAGNKTLAGPKGPVTQMYTSAEGDLVGWPSPPG

TKSLDPCTCGAVDLYLVTRNADVIPVRRKDDRRGALLSPRPLSTL

KGSSGGPVLCSRGHAVGLFRAAVsynTFGVAKSIDFIPVESLDVA

TR

SEQ ID NO: 196, NS3 genotype 3a
(HCV-Nz11), 180 aa
APITAYAQQTRGLLGTIVTSLTGRDKNVVTGEVQVLSTATQTFLG

TTVGGVIWTVYHGAGSRTLAGAKHPALQMYTNVDQDLVGWPAPPG

AKSLEPCACGSSDLYLVTRDADVIPARRRGDSTASLLSPRPLACL

KGSSGGPVMCPSGHVAGIFRAAVCTRGVAKSLQFIPVETLSTQAR

In some embodiments of any of the aspects, a repressible protease as described herein is resistant to 1, 2, 3, 4, 5, or more different protease inhibitors as described herein. Non-limiting examples of NS3 amino acid substitutions conferring resistance to HCV NS3 protease inhibitors include: V36L (e.g., genotype 1b), V36M (e.g., genotype 2a), T54S (e.g., genotype 1b), Y56F (e.g., genotype 1b), Q80L (e.g., genotype 1b), Q80R (e.g., genotype 1b), Q80K (e.g., genotype 1a, 1b, 6a), Y1321 (e.g., genotype 1b), A156S (e.g., genotype 2a), A156G, A156T, A156V, D168A (e.g., genotype 1b), 1170V (e.g., genotype 1b), S20N, R26K, Q28R, A39T, Q41R, I71V, Q80R, Q86R, P89L, P89S, S101N, A111S, P115S, S122R, R155Q, L144F, A150V, R155W, V158L, D168A, D168G, D168H, D168N, D168V, D168E, D168Y, E176K, T178S, M179I, M179V, and M179T. See e.g., Sun et al., Gene Expr. 2018, 18(1): 63-69; Kliemann et al., World J Gastroenterol. 2016 Oct. 28, 22(40): 8910-8917; U.S. Pat. Nos. 7,208,309; 7,494,660; the contents of each of which are incorporated herein by reference in their entireties.

In some embodiments of any of the aspects, a synTF polypeptide as described herein comprises an NS3 protease comprising at least one resistance mutation as described herein or any combination thereof. In some embodiments of any of the aspects, a synTF polypeptide as described herein comprises an NS3 protease that is resistant to one protease inhibitor but responsive to at least one other protease inhibitor. In some embodiments of any of the aspects, a synTF system comprises: (a) a first synTF polypeptide comprising a repressible protease (e.g., NS3) that is resistant to a first protease inhibitor and that is susceptible to a second protease inhibitor; and (b) a second synTF polypeptide comprising a repressible protease (e.g., NS3) that is susceptible to a first protease inhibitor and that is resistant to a second protease inhibitor. Accordingly, presence of the first protease inhibitor can modulate the activity of the second synTF polypeptide but not the first synTF polypeptide, while the presence of the second protease inhibitor can modulate the activity of the first synTF polypeptide but not the second synTF polypeptide.

In some embodiments of any of the aspects, a repressible protease as described herein is sensitive to 1, 2, 3, 4, 5, or more different protease inhibitors as described herein. In some embodiments of any of the aspects, the NS3 protease comprises at least one of the following mutations: V36M, T54A, S122G, F43L, Q80K, S122R, D168Y, or any combination thereof. In some embodiments of any of the aspects, the NS3 protease comprises at least one of the following mutations: V36M, T54A, S122G, or any combination thereof; such a protease is also referred to herein as $NS3^{AI}$, as these mutations increase its sensitivity to asunaprevir (see e.g., SEQ ID NO: 197). In some embodiments of any of the aspects, the NS3 protease comprises at least one of the following mutations: F43L, Q80K, S122R, D168Y, or any combination thereof; such a protease is also referred to herein as $NS3^{TI}$, as these mutations increase its sensitivity to telaprevir (see e.g., SEQ ID NO: 198). See e.g., WO2019023164; Jacobs et al., StaPLs: versatile genetically encoded modules for engineering drug-inducible proteins, Nat Methods. 2018 July; 15(7): 523-526; the contents of each of each are incorporated herein by reference in their entireties.

SEQ ID NO: 197, $NS3^{AI}$; the V36M, T54A, S122G mutations are shown in bold double underlined text, respectively
APITAYAQQTRGLLGCIITSLTGRDKNQVEGEVQIMSTATQTFLAT

CINGVCWAVYHGAGTRTIASPKGPVIQMYTNVDQDLVGWPAPQGSR

-continued

SLTPCTCGSSDLYLVTRHADVIPVRRRGDGRGSLLSPRPISYLKGS

SGGPLLCPAGHAVGLFRAAVCTRGVAKAVDFIPVENLETTMRSPVF

TD

SEQ ID NO: 198, $NS3^{H}$; the F43L, Q80K, S122R, D168Y mutations are shown in bold double underlined text, respectively
APITAYAQQTRGLLGCIITSLTGRDKNQVEGEVQIVSTATQTLLAT

CINGVCWAVYHGAGTRTIASPKGPVIQMYTNVDKDLVGWPAPQGSR

SLTPCTCGSSDLYLVTRHADVIPVRRRGDRRGSLLSPRPISYLKGS

SGGPLLCPAGHAVGLFRAAVCTRGVAKAVYFIPVENLETTMRSPVF

TD

In some embodiments of any of the aspects, the polypeptide further comprising a cofactor for the repressible protease. As used herein the term "cofactor for the repressible protease" refers to a molecule that increases the activity of the repressible protease. In some embodiments of any of the aspects, a synTF polypeptide as described herein comprises 1, 2, 3, 4, 5, or more cofactors for the repressible protease. In some embodiments of any of the aspects, the synTF polypeptide comprises one cofactor for each repressible protease. In embodiments comprising multiple cofactors for the repressible protease, the multiple cofactors for the repressible protease can be different individual cofactors or multiple copies of the same cofactor, or a combination of the foregoing.

In some embodiments of any of the aspects, the cofactor is an HSV NS4A domain, and the repressible protease is HSV NS3. The nonstructural protein 4a (NS4A) is the smallest of the nonstructural HCV proteins. The NS4A protein has multiple functions in the HCV life cycle, including (1) anchoring the NS3-4A complex to the outer leaflet of the endoplasmic reticulum and mitochondrial outer membrane, (2) serving as a cofactor for the NS3A serine protease, (3) augmenting NS3A helicase activity, and (4) regulating NS5A hyperphosphorylation and viral replication. The interactions between NS4A and NS4B control genome replication and between NS3 and NS4A play a role in virus assembly.

In some embodiments of any of the aspects, a synTF polypeptide as described herein comprises the portion of the NS4a polypeptide that serves as a cofactor for NS3. Deletion analysis has shown that the central region (approximately residues 21 to 34) of the 54-residue NS4A protein is essential and sufficient for the cofactor function of the NS3 serine protease. Accordingly, in some embodiments of any of the aspects, the repressible protease cofactor comprises a 14-residue region of the wildtype NS4A protein.

In some embodiments of any of the aspects, the cofactor for the repressible protease can be an HCV genotype 1 NS4A, an HCV genotype 1a NS4A, an HCV genotype 1b NS4A, an HCV genotype 2 NS4A, an HCV genotype 2a NS4A, an HCV genotype 2b NS4A, an HCV genotype 3 NS4A, an HCV genotype 3a NS4A, an HCV genotype 3b NS4A, an HCV genotype 4 NS4A, an HCV genotype 4a NS4A, an HCV genotype 4b NS4A, an HCV genotype 5 NS4A, an HCV genotype 5a NS4A, an HCV genotype 5b NS4A, an HCV genotype 6 NS4A, an HCV genotype 6a NS4A, an HCV genotype 6b NS4A, an HCV genotype 7 NS4A, an HCV genotype 7a NS4A, or an HCV genotype 7b NS4A. In some embodiments of any of the aspects, the cofactor for the repressible protease can be any known NS4A genotype, variant, or mutant, e.g., that maintains the same function. In some embodiments of any of the aspects, the NS4A sequence comprises residues 21-31 of the NS4A protein from HCV-H, HCV-1, HCV-J1, HCV-BK, HCV-JK1, HCV-J4, HCV-J, HCV-J6, C14112, HCV-J8, D14114, HCV-Nz11, or HCV-K3a (see e.g., Chao Lin 2006 supra; see e.g., Table 9).

In some embodiments of any of the aspects, the cofactor for a repressible protease of a synTF polypeptide as described herein comprises SEQ ID NOs: 199-223, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 199-223 that maintains the same functions as one of SEQ ID NOs: 48, 98, 137-156. In some embodiments of any of the aspects, the cofactor for a repressible protease of a synTF polypeptide as described herein comprises SEQ ID NOs: 199-223, or an amino acid sequence that is at least 95% identical to the sequence of one of SEQ ID NOs: 199-223 that maintains the same function.

In some embodiments of any of the aspects, the cofactor for the repressible protease of a synTF polypeptide as described herein comprises residues 1-14, 1-13, 1-12, 1-11, 1-10, 2-14, 2-13, 2-12, 2-11, 2-10, 3-14, 3-13, 3-12, 3-11, 3-10, 4-14, 4-13, 4-12, 4-11, or 4-10 of any of SEQ ID NOs: 199-223.

SEQ ID NO: 199, NS4A (genotype 1A), 13 aa,
GCVVIVGRIVLSG

SEQ ID NO: 200, NS4A domain
(genotype 1a)
STWVLVGGVLAALAAYCLSTGCVVIVGRIVLSGKPA

IIPDREVLY

SEQ ID NO: 201, NS4
(with L6 linker in bold text)
STWVLVGGVLAALAAYCLSTGCVVIVGRIVLSGKPA

GSSGSSIIPDREVLY

SEQ ID NO: 202, NS4A domain,
IDTKYIMTCMSADLEVVTSTWVLVGGVLAALAAYCL

STGCVVIVGRIVLSGKPAIIPDREVLY

SEQ ID NO: 203, NS4A
(genotype 1B), 12 aa, GSVVIVGRIILS;
see e.g., Chain C,
Nonstructural Protein, PDB: 4K8B_C.

SEQ ID NO: 204, NS4A (genotype 1), 14 aa
(see e.g., residues 1678-1691 of
Hepatitis C virus genotype 1 polyprotein,
NCBI Reference Sequence: NP_671491.1):
GCVVIVGRIVLSGK SEQ ID NO: 205, NS4A
(genotype 2), 14 aa
(see e.g., residues 1682-1695 of Hepatitis C
virus genotype 2 polyprotein, NCBI Reference
Sequence: YP_001469630.1): GCVCIIGRLHINQR SEQ ID NO: 206, NS4A
(genotype 3), 14 aa
(see e.g., residues 1684-1697 of Hepatitis C
virus genotype 3 polyprotein, NCBI Reference
Sequence: YP_001469631.1): GCVVIVGHIELEGK -continued SEQ ID NO: 207, NS4A (genotype 4), 14 aa (see e.g., residues 1678-1691 of Hepatitis C virus genotype 4 polyprotein, NCBI Reference Sequence: YP_001469632.1): GSVVIVGRVVLSGQ SEQ ID NO: 208, NS4A (genotype 5), 14 aa (see e.g., residues 1679-1692 of Hepatitis C virus genotype 5 polyprotein, NCBI Reference Sequence: YP_001469633.1): GSVAIVGRIILSGR SEQ ID NO: 209, NS4A (genotype 6), 14 aa (see e.g., residues 1683-1696 of Hepatitis C virus genotype 6 polyprotein, NCBI Reference Sequence: YP_001469634.1): GCVVICGRIVTSGK SEQ ID NO: 210, NS4A (genotype 7), 14 aa (see e.g., residues 1682-1695 of Hepatitis C virus genotype 7 polyprotein, NCBI Reference Sequence: YP_009272536.1): GSVVVVGRVVLGSN In some embodiments of any of the aspects, the NS4A sequence is selected from Table 9. In one embodiment, the NS4A comprises residues 21-31 of SEQ ID NO: 211-223 or a sequence that is at least 70% identical.

TABLE 9

Exemplary NS4A sequences (see e.g., Chao Lin 2006 supra). Residues 21-31 are bolded.

| SEQ ID NO | Genotype (strain) | Sequence |
|---|---|---|
| 211 | 1a (HCV-H) | STWVL VGGVL AALAA YCLST **GCVVI VGRIV LS**GKP AIIPD REVLY QEFDE MEEC |
| 212 | 1a (HCV-1) | STWVL VGGVL AALAA YCLST **GCVVI VGRVV LS**GKP AIIPD REVLY REFDE MEEC |
| 213 | 1a (HCV-J1) | STWVL VGGVL AALAA YCLST **GCVVI VGRIV LS**GRP AIIPD REVLY REFDE MEEC |
| 214 | 1b (HCV-BK) | STWVL VGGVL AALAA YCLTT **GSVVI VGRII LS**GRP AIVPD RELLY QEFDE MEEC |
| 215 | 1b (HCV-JK1) | STWVL VGGVL AALAA YCLTT **GSVVI VGRII LS**GRP AIIPD RELLY QEFDE MEEC |
| 216 | 1b (HCV-J4) | STWVL VGGVL AALAA YCLTT **GSVVI VGRII LS**GKP AVVPD RELLY QEFDE MEEC |
| 217 | 1b (HCV-J) | STWVL VGGVL AALAA YCLTT **GSVVI VGRII LS**GRP AVIPD RELLY REFDE MEEC |
| 218 | 2a (HCV-J6) | STWVL AGGVL AAVAA YCLAT **GCVCI IGRLH VN**QRA VVAPD KEVLY EAFDE MEEC |
| 219 | 2a (D14112) | STWVL AGGVL AAVAA YCLAT **GCVSI IGRLH IN**GRA VVAPD KEVLY EAFDE MEEC |
| 220 | 2b (HCV-J8) | SSWVL AGGVL AAVAA YCLAT **GCISI IGRLH LN**DRV VVAPD KEILY EAFDE MEEC |
| 221 | 2b (D14114) | STWVL AGGVL AAVAA YCLAT **GCVSI IGRLH LN**DQV VVTPD KEILY EAFDE MEEC |
| 222 | 3a (HCV-Nz11) | STWVL LGGVL AALAA YCLSV **GCVVI VGHIE LE**GKP ALVPD KEVLY QQYDE MEEC |
| 223 | 3a (HCV-K3a) | STWVL LGGVL AAVAA YCLSV **GCVVI VGHIE LG**GKP ALVPD KEVLY QQYDE MEEC |

In some embodiments of any of the aspects, a synTF polypeptide as described herein can comprise any combination of NS3 and NS4A genotypes, variants, or mutants as described herein. In one embodiment, the NS3 and NS4A are selected from the same genotype as each other. In some embodiments of any of the aspects, the NS3 is genotype 1a and the NS4A is genotype 1b. In some embodiments of any of the aspects, the NS3 is genotype 1b and the NS4A is genotype 1a.

In some embodiments of any of the aspects, a synTF polypeptide as described herein comprises an HSV NS4A domain adjacent to the NS3 repressible protease. In some embodiments of any of the aspects, the NS4A domain is N-terminal of the NS3 repressible protease. In some embodiments of any of the aspects, the NS4A domain is C-terminal of the NS3 repressible protease. In some embodiments of any of the aspects, the synTF polypeptide comprises a peptide linker between the NS4A domain and the NS3 repressible protease. Non-limiting examples of linker (e.g., between the NS4A domain and the NS3 repressible protease) include: SGTS (SEQ ID NO: 224) and GSGS (SEQ ID NO: 225).

In some embodiments of any of the aspects, any two domains as described herein in a synTF polypeptide can be joined into a single polypeptide by positioning a peptide linker, e.g., a flexible linker between them. As used herein "peptide linker" refers to an oligo- or polypeptide region from about 2 to 100 amino acids in length, which links together any of the sequences of the polypeptides as described herein. In some embodiment, linkers can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable.

Described herein are synTF polypeptides comprising protease cleavage sites. As used herein, the term "protease cleavage site" refers to a specific sequence or sequence motif recognized by and cleaved by the repressible protease. A cleavage site for a protease includes the specific amino acid sequence or motif recognized by the protease during proteolytic cleavage and typically includes the surrounding one to six amino acids on either side of the scissile bond, which bind to the active site of the protease and are used for recognition as a substrate. In some embodiments of any of the aspects, the protease cleavage site can be any site specifically bound by and cleaved by the repressible protease. In some embodiments of any of the aspects, a synTF polypeptide as described herein (or the synTF polypeptide system collectively) comprises 1, 2, 3, 4, 5, or more protease cleavage sites. In some embodiments of any of the aspects, the synTF polypeptide comprises two protease cleavage sites. In embodiments comprising multiple protease cleavage sites, the multiple protease cleavage sites can be different individual protease cleavage sites or multiple copies of the same protease cleavage sites, or a combination of the foregoing.

As a non-limiting example, during HCV replication, the NS3-4A serine protease is responsible for the proteolytic cleavage at four junctions of the HCV polyprotein precursor: NS3/NS4A (self-cleavage), NS4A/NS4B, NS4B/NS5A, and NS5A/NS5B. Accordingly, the protease cleavage site of a synTF polypeptide as described herein can be a NS3/NS4A cleavage site, a NS4A/NS4B cleavage site, a NS4B/NS5A cleavage site, or a NS5A/NS5B cleavage site. The protease cleavage site can be a protease cleavage sites from HCV genotype 1, genotype 1a, genotype 1b, genotype 2, genotype 2a, genotype 2b, genotype 3, genotype 3a, genotype 3b, genotype 4, genotype 4a, genotype 4b, genotype 5, genotype 5a, genotype 5b, genotype 6, genotype 6a, genotype 6b, genotype 7, genotype 7a, or genotype 7b. In some embodiments of any of the aspects, the protease cleavage site can be any known NS3/NS4A protease cleavage site or variant or mutant thereof, e.g., that maintains the same function. In some embodiments of any of the aspects, the NS4A sequence comprises residues 21-31 of the NS4A protein from HCV-H, HCV-1, HCV-J1, HCV-BK, HCV-JK1, HCV-J4, HCV-J, HCV-J6, C14112, HCV-J8, D14114, HCV-Nz11, or HCV-K3a (see e.g., Chao Lin 2006 supra).

In some embodiments of any of the aspects, the protease cleavage site of a synTF polypeptide as described herein comprises SEQ ID NOs: 226-251, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 226-251 that maintains the same function.

In some embodiments of any of the aspects, the protease cleavage site of a synTF polypeptide as described herein comprises residues 1-20, 1-19, 1-18, 1-17, 1-16, 1-15, 2-20, 2-19, 2-18, 2-17, 2-16, 2-15, 3-20, 3-19, 3-18, 3-17, 3-16, 3-15, 4-20, 4-19, 4-18, 4-17, 4-16, 4-15, 5-20, 5-19, 5-18, 5-17, 5-16, or 5-15, of any of SEQ ID NOs: 226-251.

SEQ ID NO: 226
NS5A/5B cut site (CC), 10 aa, EDVVCCHSIY,

SEQ ID NO: 227
NS4A/4B cut site (CS), 14 aa, LYQEFDEMEECSQH,

SEQ ID NO: 228
N3 cleavage site (NS4A/4B cut site), DEMEECSQHL,

SEQ ID NO: 229
QEFEDVVPCSMGS,

SEQ ID NO: 230
NS5A/5B cut site, EDVVCCHSI,

SEQ ID NO: 231
NS4A/4B cut site, DEMEECSQH,

TABLE 10

Exemplary NS3/NS4A protease cleavage sites (see e.g., Chao Lin 2006 supra).

| Cleavage Site Type | SEQ ID NO | Genotype (Strain) | Sequence (cleavage site shown with space) |
|---|---|---|---|
| NS3/NS4A | 232 | 1a (HCV-H) | CMSADLEVVT STWVLVGGVL |
| | 233 | 1b (HCV-BK) | CMSADLEVVT STWVLVGGVL |
| | 234 | 2a (HCV-J6) | CMQADLEVMT STWVLAGGVL |
| | 235 | 2b (HCV-J8) | CMQADLEIMT SSWVLAGGVL |
| | 236 | 3a (HCV-Nz11) | CMSADLEVTT STWVLLGGVL |
| NS4A/NS4B | 237 | 1a (HCV-H) | YQEFDEMEEC SQHLPYIEQG |
| | 238 | 1b (HCV-BK) | YQEFDEMEEC ASHLPYIEQG |
| | 239 | 2a (HCV-J6) | YEAFDEMEEC ASRAALIEEG |
| | 240 | 2b (HCV-J8) | YEAFDEMEEC ASKAALIEEG |
| | 241 | 3a (HCV-Nz11) | YQQYDEMEEC SQAAPYIEQA |
| NS4B/NS5A | 242 | 1a (HCV-H) | WISSECTTPC SGSWLRDVWD |
| | 243 | 1b (HCV-BK) | WINEDCSTPC SGSWLRDVWD |
| | 244 | 2a (HCV-J6) | WITEDCPIPC SGSWLRDVWD |
| | 245 | 2b (HCV-J8) | WITEDCPVPC SGSWLQDIWD |
| | 246 | 3a (HCV-Nz11) | WINEDYPSPC SDDWLRTIWD |

TABLE 10-continued

Exemplary NS3/NS4A protease cleavage sites (see e.g., Chao Lin 2006 supra).

| Cleavage Site Type | SEQ ID NO | Genotype (Strain) | Sequence (cleavage site shown with space) |
|---|---|---|---|
| NS5A/NS5B | 247 | 1a (HCV-H) | GADTEDVVCC SMSYSWTGAL |
| | 248 | 1b (HCV-BK) | EEASEDVVCC SMSYTWTGAL |
| | 249 | 2a (HCV-J6) | SEEDDSVVCC SMSYSWTGAL |
| | 250 | 2b (HCV-J8) | SDQEDSVICC SMSYSWTGAL |
| | 251 | 3a (HCV-Nz11) | DSEEQSVVCC SMSYSWTGAL |

In some embodiments of any of the aspects, a synTF polypeptide as described herein comprises two protease cleavage sites, with one N-terminal of the NS3-NS4A complex, and the other C-terminal of the NS3-NS4A complex (see e.g., Table 11). In some embodiments of any of the aspects, the two protease cleavage sites can be the same cleavage sites or different cleavage sites.

TABLE 11

Exemplary Protease Cleavage Site Combinations. "N" indicates N-terminal of the NS3-NS4A complex. "C" indicates C-terminal of the NS3-NS4A complex. "3/4A" indicates the NS3/NS4A cleavage site. "4A/4B" indicates the NS4A/NS4B cleavage site. "4B/5A" indicates the NS4B/NS5A cleavage site. "5A/5B" indicates the NS5A/NS5B cleavage site.

| N | 3/4A | | | | 4A/4B | | | |
|---|---|---|---|---|---|---|---|---|
| C | 3/4A | 4A/4B | 4B/5A | 5A/5B | 3/4A | 4A/4B | 4B/5A | 5A/5B |
| N | 4B/5A | | | | 5A/5B | | | |
| C | 3/4A | 4A/4B | 4B/5A | 5A/5B | 3/4A | 4A/4B | 4B/5A | 5A/5B |

In some embodiments of any of the aspects, a synTF polypeptide as described herein comprise any known genotypes, variants, or mutants of NS3/NS4A, NS4A/NS4B, NS4B/NS5A, and NS5A/NS5B cleavage sites. In one embodiment, the two protease cleavage sites are selected from the same genotype as each other.

In some embodiments of any of the aspects, the protease cleavage site is located or engineered such that, when the synTF cleaves itself using the repressible protease in the absence of a protease inhibitor, the resulting amino acid at the N-terminus of the newly cleaved polypeptide(s) causes the polypeptide(s) to degrade at a faster rate and have a shorter half-life compared to other cleaved polypeptides. According to the N-end rule, newly cleaved polypeptides comprising the amino acid His, Tyr, Gln, Asp, Asn, Phe, Leu, Trp, Lys, or Arg at the N-terminus exhibit a high degradation rate and a short half-life (e.g., 10 minutes or less in yeast; 1-5.5 hours in mammalian reticulocytes). Comparatively, newly cleaved polypeptides comprising the amino acid Val, Met, Gly, Pro, Ala, Ser, Thr, Cys, Ile, or Glu at the N-terminus exhibit a lower degradation rate and a longer half-life (e.g., 30 minutes or more in yeast; 1-100 hours in mammalian reticulocytes). See e.g., Gonda et al., Universality and Structure of the N-end Rule, The Journal of Biological Chemistry, Vol. 264 (28), pp. 16700-16712, 1989, the content of which is incorporated herein by reference in its entirety. Accordingly, in some embodiments of any of the aspects, the resulting amino acid at the N-terminus of a newly cleaved synTF polypeptide as described herein is His, Tyr, Gln, Asp, Asn, Phe, Leu, Trp, Lys, or Arg. In some embodiments of any of the aspects, the resulting amino acid at the N-terminus of the newly cleaved synTF polypeptide as described herein is not Val, Met, Gly, Pro, Ala, Ser, Thr, Cys, Ile, or Glu.

In some embodiments of any of the aspects, the N-terminus of a newly cleaved synTF polypeptide as described herein comprises SEQ ID NO: 252 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 252 that maintains a His or another highly degraded amino acid at the N-terminus. SEQ ID NO: 252, N-end rule, 8 aa, HSIYGKKK.

In some embodiments of any of the aspects, a synTF polypeptide as described herein comprises a repressible protease that is catalytically active. For HCV NS3, the catalytic triad comprises His-57, Asp-81, and Ser-139. In regard to a repressible protease, "catalytically active" refers to the ability to cleave at a protease cleavage site. In some embodiments of any of the aspects, the catalytically active repressible protease can be any repressible protease as described further herein that maintains the catalytic triad, i.e., comprises no non-synonymous substitutions at His-57, Asp-81, and/or Ser-139.

In some embodiments of any of the aspects, the synTF comprises SEQ ID NO: 37 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 37, which maintains its function.

In some embodiments of any of the aspects, the synTF comprises NS3 protease domain, NS4A and/or at least one protease cleavage site. In some embodiments of any of the aspects, the synTF comprises SEQ ID NOs: 253 or 254 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 253 or 254.

NS3 domain, comprising: a portion of the N-end rule (bold text), AU1 tag (*italicized double underlined text*), NS4A (*bold italicized text*), and NS3 protease (italicized text):, SEQ ID NO: 253
GKKKGDI*DTYRYI* GSSGT*GCVVIVGRIVLSG* SGTS*APITAYAQQTRGLLGCIITSLTGRDKNQVEGEVQ*

*IVSTATQTFLATCINGVCWAVYHGAGTRTIASPKGPVIQMYTNVDQDLVGWPAPQGSRSLTPCTCGSSD*

*LYLVTRHADVIPVRRRGDSRGSLLSPRPISYLKGSSGGPLLCPAGHAVGLFRAAVCTRGVAKAVDFIPVE*

*NLETTMRSPVFTDNSS*PPAVTLTHPITKIDREV

NS3 domain, comprising: NS3 cleavage sites (double underlined text), N-end rule (bold text), AU1 tag (italicized text), NS4A (*bold italicized text*), and NS3 protease (*italicized double underlined text*):, SEQ ID NO: 254
EDVVCCHSIYEDVVCCHSIY GKKKGDI*DTYRYI* GSSGT*GCVVIVGRIVLSG* SGTS*APITAYAQQTR*

*GLLGCIITSLTGRDKNQVEGEVQIVSTATQTFLATCINGVCWAVYHGAGTRTIASPKGPVIQMYTNVDQD*

*LVGWPAPQGSRSLTPCTCGSSDLYLVTRHADVIPVRRRGDSRGSLLSPRPISYLKGSSGGPLLCPAGHAV*

*GLFRAAVCTRGVAKAVDFIPVENLETTMRSPVFTDNSS*PPAVTLTHPITKIDREVLYQEFDEMEECSQH

In some embodiments of any of the aspects, the synTF comprises a stabilizable polypeptide linkage (StaPL) domain. In some embodiments of any of the aspects, the StaPL domain comprises NS4A, the NS3 protease domain, and a portion of the NS3 helicase domain. In some embodiments of any of the aspects, the partial NS3 helicase domain comprises SEQ ID NOs: 255-257, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 255-257.

NS3 Partial Helicase Domain,
SEQ ID NO: 255
NSSPPAVTLTHPITKIDTKYIMTCMSADLEVVT,

NS3 Partial Helicase Domain,
]SEQ ID NO: 256
NSSPPAVTLTHPITK,

NS3 partial helicase domain,
SEQ ID NO: 257
NSSPPAVTLTH,

In some embodiments of any of the aspects, the StaPL domain further comprises a protease cleavage site at the N terminus, e.g., selected from EDVVCCHSI (SEQ ID NO: 230) or DEMEECSQH (SEQ ID NO: 231), directly linked or indirectly linked through a peptide linker. In some embodiments of any of the aspects, the StaPL domain comprises one of SEQ ID NOs: 258-260, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 258-260.

StaPL domain, comprising: NS4A (*bold italicized text*), and NS3 protease (italicized text); linkers ( ); NS3 helicase (*bold italicized double underlined text*), SEQ ID NO: 258
T*GCVVIVGRIVLSG*SGTS SGTS*APITAYAQQTRGLLGCIITSLTGRDKNQVEGEVQIVSTATQTFLATCINGVC*

*WAVYHGAGTRTIASPKGPVIQMYTNVDQDLVGWPAPQGSRSLTPCTCGSSDLYLVTRHADVIPVRRRG*

*DSRGSLLSPRPISYLKGSSGGPLLCPAGHAVGLFRAAVCTRGVAKAVDFIPVENLETTMRSPVFTD**NSSP*

*PAVTLTH*

In some embodiments of any of the aspects, StaPL domain comprises a repressible protease that comprises at least one mutation that increases its sensitivity to at least one protease inhibitor. In some embodiments of any of the aspects, the NS3 protease (e.g., of the StaPL domain) comprises at least one of the following mutations: V36M, T54A, S122G, F43L, Q80K, S122R, D168Y, or any combination thereof. In some embodiments of any of the aspects, the NS3 protease (e.g., of the StaPL domain) comprises at least one of the following mutations: V36M, T54A, S122G, or any combination thereof; such a StaPL is also referred to herein as $StaPL^{AI}$, as these mutations increase its sensitivity to asunaprevir (see e.g., SEQ ID NO: 197, 259). In some embodiments of any of the aspects, the NS3 protease (e.g., of the StaPL domain) comprises at least one of the following mutations: F43L, Q80K, S122R, D168Y, or any combination thereof; such a protease is also referred to herein as $StaPL^{TI}$, as these mutations increase its sensitivity to telaprevir (see e.g., SEQ ID NO: 198, 260).

StaPL$^{AI}$ domain, comprising: NS4A (*bold italicized text*), and NS3 protease (italicized text); linkers (double underlined text); NS3 helicase (*bold italicized double underlined text*); the V36M, T54A, S122G mutations are shown in bold double underlined text, respectively.

SEQ ID NO: 259

*TGCVVIVGRIVLSG*SGTS *APITAYAQQTRGLLGCIITSLTGRDKNQVEGEVQIMSTATQTFLATCINGVC*

*WAVYHGAGTRTIASPKGPVIQMYTNVDQDLVGWPAPQGSRSLTPCTCGSSDLYLVTRHADVIPVRRRG*

*DGRGSLLSPRPISYLKGSSGGPLLCPAGHAVGLFRAAVCTRGVAKAVDFIPVENLETTMRSPVFTDNSS*

*PPAVTLTH*GGSGGS

StaPL$^{TI}$ domain, comprising: NS4A (bold italicized text), and NS3 protease (italicized text); linkers (*bold italicized double underlined text*); NS3 helicase (bold italicized double underlined text); the F43L, Q80K, S122R, D168Y mutations are shown in bold double underlined text, respectively.

SEQ ID NO: 260

*TGCVVIVGRIVLSG*SGTS *APITAYAQQTRGLLGCIITSLTGRDKNQVEGEVQIVSTATQTL LATCINGVC*

*WAVYHGAGTRTIASPKGPVIQMYTNVDK DLVGWPAPQGSRSLTPCTCGSSDLYLVTRHADVIPVRRRG*

*DR RGSLLSPRPISYLKGSSGGPLLCPAGHAVGLFRAAVCTRGVAKAVY FIPVENLETTMRSPVFTDNSS*

*PPAVTLTH*GGSGGS

In some embodiments of any of the aspects, the synTF comprises a TimeSTAMP domain (a time-specific tag for the age measurement of proteins). In some embodiments of any of the aspects, the TimeSTAMP comprises a repressible protease, at least one protease cleavage site, and a detectable marker. The detectable marker is removed from the synTF immediately after translation by the activity of the repressible protease until the time a protease inhibitor is added, after which newly synthesized synTF polypeptides retain their markers. TimeSTAMP allows for time-specific tagging of the age measurement of proteins, and allows sensitive and nonperturbative visualization and quantification of newly synthesized proteins of interest with exceptionally tight temporal control.

In some embodiments of any of the aspects, the repressible protease exhibits increased solubility compared to the wild-type protease. As a non-limiting example, the NS3 protease can comprise at least one of the following mutations or any combination thereof: Leu13 is substituted to Glu; Leu14 is substituted to Glu; Ile17 is substituted to Gln; Ile18 is substituted to Glu; and/or Leu21 is substituted to Gln. In some embodiments of any of the aspects, a synTF polypeptide as described herein comprises a repressible protease comprising SEQ ID NOs: 261-269, or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 261-269 that maintains the same functions (e.g., serine protease; increased solubility) as SEQ ID NOs: 261-269; see e.g., U.S. Pat. No. 6,333,186 and US Patent Publication US20020106642, the contents of each are incorporated herein by reference in their entireties.

soluble NS3, 182 aa

SEQ ID NO: 261

MAPITAYAQQTRGLLGCIITSLTGRDKNQVEGEVQIVSTAAQTFLATCINGVCWTVYHGAGTRTI

ASPKGPVIQMYTNVDKDLVGWPAPQGSRSLTPCTCGSSDLYLVTRHADVIPVRRRGDSRGSLLSP

RPISYLKGSSGGPLLCPAGHAVGIFRAAVCTRGVAKAVDFIPVESLETTMRS, soluble NS3/NS4A, 195 aa

SEQ ID NO: 262

MKKKGSVVIVGRIVLNGAYAQQTRGLLGCIITSLTGRDKNQVEGEVQIVSTAAQTFLATCINGVC

WTVYHGAGTRTIASPKGPVIQMYTNVDKDLVGWPAPQGSRSLTPCTCGSSDLYLVTRHADVIPV

RRRGDSRGSLLSPRPISYLKGSSGGPLLCPAGHAVGIFRAAVCTRGVAKAVDFIPVESLETTMRSP, soluble NS3/NS4A, 195 aa

SEQ ID NO: 263

MKKKGSVVIVGRIVLNGAYAQQTRGEEGCQETSQTGRDKNQVEGEVQIVSTAAQTFLATCINGV

CWTVYHGAGTRTIASPKGPVIQMYTNVDKDLVGWPAPQGSRSLTPCTCGSSDLYLVTRHADVIP

VRRRGDSRGSLLSPRPISYLKGSSGGPLLCPAGHAVGIFRAAVCTRGVAKAVDFIPVESLETTMRS

P,

-continued soluble NS3/NS4A, 197 aa

SEQ ID NO: 264

MKKKGSVVIVGRINLSGDTAYAQQTRGEEGCQETSQTGRDKNQVEGEVQIVSTAAQTFLATCIN

GVCWTVYHGAGTRTIASPKGPVIQMYTNVDKDLVGWPAPQGSRSLTPCTCGSSDLYLVTRHAD

VIPVRRRGDSRGSLLSPRPISYLKGSSGGPLLCPAGHAVGIFRAAVCTRGVAKAVDFIPVESLETT

MRSP, soluble NS3/NS4A, 197 aa

SEQ ID NO: 265

MKKKGSVVIVGRINLSGDTAYAQQTRGEEGCQETSQTGRDKNQVEGEVQIVSTATQTFLATCIN

GVCWTVYHGAGTRTIASPKGPVTQMYTNVDKDLVGWQAPQGSRSLTPCTCGSSDLYLVTRHA

DVIPVRRRGDSRGSLLSPRPISYLKGSSGGPLLCPAGHAVGIFRAAVCTRGVAKAVDFIPVESLET

TMRSP, soluble NS3/NS4A, 197 aa

SEQ ID NO: 266

MKKKGSVVIVGRINLSGDTAYAQQTRGEEGCQETSQTGRDKNQVEGEVQIVSTATQTFLATSIN

GVLWTVYHGAGTRTIASPKGPVTQMYTNVDKDLVGWQAPQGSRSLTPCTCGSSDLYLVTRHAD

VIPVRRRGDSRGSLLSPRPISYLKGSSGGPLLCPAGHAVGIFRAAVSTRGVAKAVDFIPVESLETT

MRSP, soluble NS3/NS4A, 197 aa

SEQ ID NO: 267

MKKKGSVVIVGRINLSGDTAYAQQTRGEQGCQKTSHTGRDKNQVEGEVQIVSTATQTFLATSIN

GVLWTVYHGAGTRTIASPKGPVTQMYTNVDKDLVGWQAPQGSRSLTPCTCGSSDLYLVTRHAD

VIPVRRRGDSRGSLLSPRPISYLKGSSGGPLLCPAGHAVGIFRAAVSTRGVAKAVDFIPVESLETT

MRSP, soluble NS3/NS4A, 197 aa

SEQ ID NO: 268

MKKKGSVVIVGRINLSGDTAYAQQTRGEQGTQKTSHTGRDKNQVEGEVQIVSTATQTFLATSIN

GVLWTVYHGAGTRTIASPKGPVTQMYTNVDKDLVGWQAPQGSRSLTPCTCGSSDLYLVTRHAD

VIPVRRRGDSRGSLLSPRPISYLKGSSGGPLLCPAGHAVGIFRAAVSTRGVAKAVDFIPVESLETT

MRSP,

NS3aH1, soluble NS3/NS4A (S139A), 196 aa

SEQ ID NO: 269

KKKGSVVIVGRINLSGDTAYAQQTRGEEGCQETSQTGRDKNQVEGEVQIVSTATQTFLATSINGV

LWTVYHGAGTRTIASPKGPVTQMYTNVDKDLVGWQAPQGSRSLTPCTCGSSDLYLVTRHADVI

PVRRRGDSRGSLLSPRPISYLKGSAGGPLLCPAGHAVGIFRAAVSTRGVAKAVDFIPVESLETTMR

SP,

In some embodiments of any of the aspects, the repressible protease comprises mutations to increase binding affinity for a specific ligand. As a non-limiting example, NS3aH1 (e.g., SEQ ID NO: 269) comprises four mutations needed for interaction with the ANR peptide (e.g., SEQ ID NO: 355, GELDELVYLLDGPGYDPIHSD): A7S, E13L, I35V and T42S. Accordingly, in some embodiments of any of the aspects, a repressible protease as described herein comprises at least one of the following mutations: A7S, E13L, I35V and T42S, or any combination thereof.

In some embodiments of any of the aspects, a synTF polypeptide as described herein is in combination with a protease inhibitor. As used herein, "in combination with" refers to two or more substances being present in the same formulation in any molecular or physical arrangement, e.g., in an admixture, in a solution, in a mixture, in a suspension, in a colloid, in an emulsion. The formulation can be a homogeneous or heterogeneous mixture. In some embodiments of any of the aspects, the active compound(s) can be comprised by a superstructure, e.g., nanoparticles, liposomes, vectors, cells, scaffolds, or the like, said superstructure is which in solution, mixture, admixture, suspension, etc., with the synTF polypeptide or synTF polypeptide system. In some embodiments of any of the aspects, the synTF polypeptide is bound to a protease inhibitor bound to the repressible protease. In some embodiments of any of the aspects, the synTF polypeptide is bound specifically to a protease inhibitor bound to the repressible protease.

In some embodiments of any of the aspects, the synTF polypeptide is in combination with 1, 2, 3, 4, 5, or more protease inhibitors. In some embodiments of any of the aspects, the synTF polypeptide is in combination with one protease inhibitor. In embodiments comprising multiple protease inhibitors, the multiple protease inhibitors can be different individual protease inhibitors or multiple copies of the same protease inhibitor, or a combination of the foregoing.

In some embodiments of any of the aspects, the protease inhibitor is grazoprevir (abbreviated as GZV or GZP; see e.g., PubChem CID: 44603531). In some embodiments of any of the aspects, the protease inhibitor is danoprevir (DNV; see e.g., PubChem CID: 11285588). In some embodiments of any of the aspects, the protease inhibitor is an approved NS3 protease inhibitor, such as but not limited to grazoprevir, danoprevir, simeprevir, asunaprevir, ciluprevir, boceprevir, sovaprevir, paritaprevir, ombitasvir, paritaprevir, ritonavir, dasabuvir, and telaprevir. Additional non-limiting examples of NS3 protease inhibitors are listed in Table 12 (see e.g., McCauley and Rudd, Hepatitis C virus NS3/4a protease inhibitors, Current Opinion in Pharmacology 2016, 30:84-92; the content of which is incorporated herein by reference in its entirety).

TABLE 12

Exemplary NS3/NS4A protease inhibitors

| Description or Name(s) | Structure |
| --- | --- |
| The N-terminal hexapeptide product of substrate cleavage (e.g., DDIVPC-OH, SEQ ID NO: 352) | 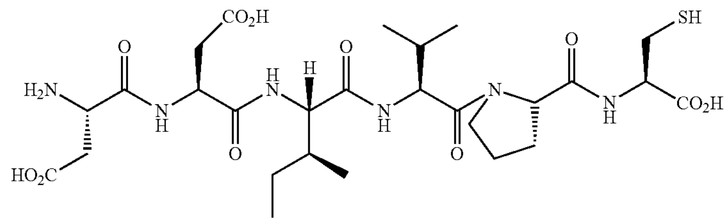 1 |
| One of the products of cleavage of the NS4a-NS4b peptide (e.g., Ac-DEMEEC-OH, SEQ ID NO: 353; or Ac-DEMEFC-OH, SEQ ID NO: 354) | 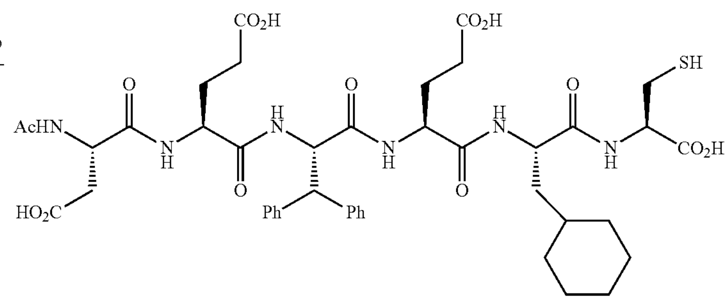 2 |
| VICTRELIS ™ boceprevir SCH503034 | 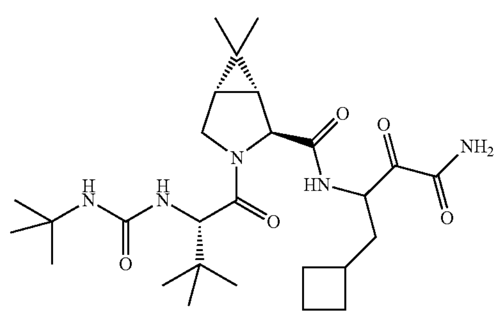 [SMILES: CC(C)(C)NC(=O)N[C@H](C(=O)N1C[C@H]2[C@@H]([C@H]1C(=O)NC(CC1CCC1)C(=O)C(N)=O)C2(C)C)C(C)(C)C] |
| INCIVEK ™, INCIVIO ™, telaprevir, VX-950 | 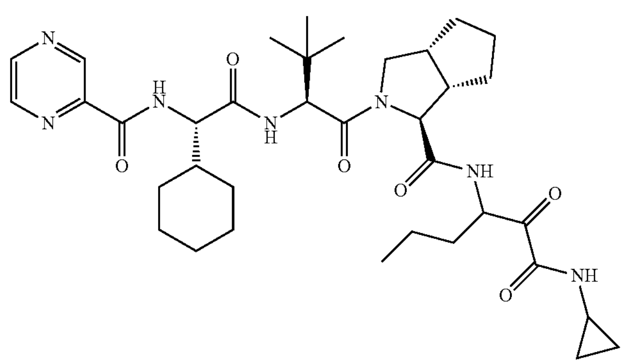 [SMILES: CCCC(NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1] |

TABLE 12-continued
| Exemplary NS3/NS4A protease inhibitors | |
|---|---|
| Description or Name(s) | Structure |
| Ciluprevir; BILN-2061 | 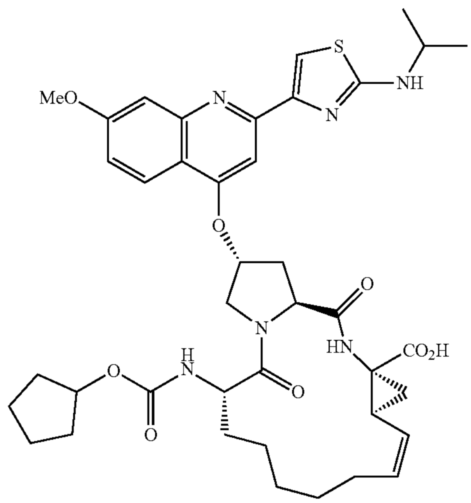 [SMILES: COc1ccc2c(O[C@@H]3C[C@H]4C(=O)N[C@]5(C(=O)O)C[C@H]5/C=C\CCCCC[C@H](NC(=O)OC5CCCC5)C(=O)N4C3)cc(-c3csc(NC(C)C)n3)nc2c1] |
| BMS-605339 | 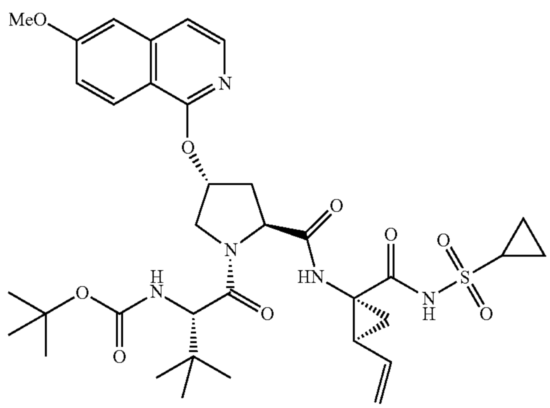 |
| MK-4519 | 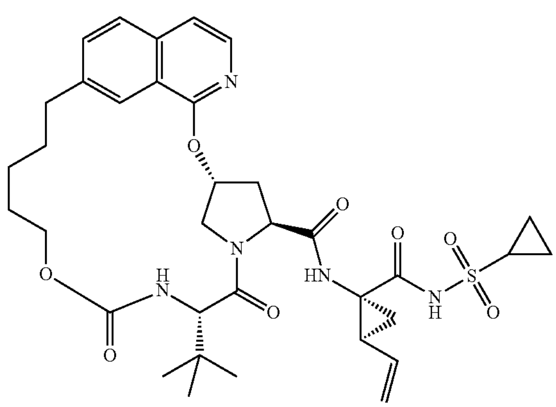 [SMILES: C=C[C@@H]1C[C@]1(NC(=O)[C@@H]1C[C@@H]2CN1C(=O)[C@H](C(C)(C)C)NC(=O)OCCCCCc1ccc3ccnc(c3c1)O2)C(=O)NS(=O)(=O)C1CC1] |

TABLE 12-continued
| Exemplary NS3/NS4A protease inhibitors | |
|---|---|
| Description or Name(s) | Structure |
| faldaprevir, BI-201335 | 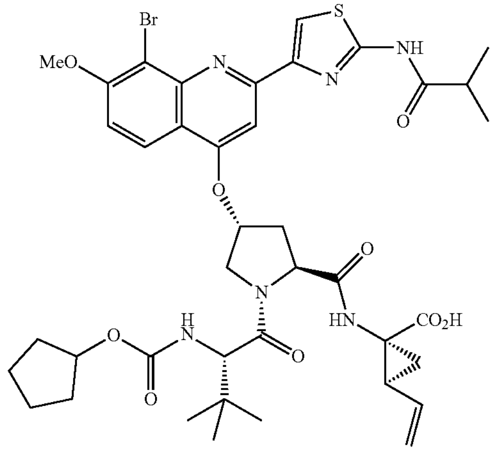 |
| Danoprevir, ITMN-191, R7227 | 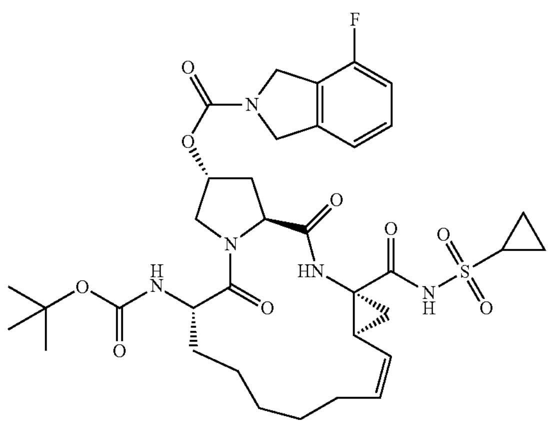 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@@H](OC(=O)N3Cc4cccc(F)c4C3)CN2C1=O] |
| SUNVEPRA ™, asunaprevir, BMS-650032 | 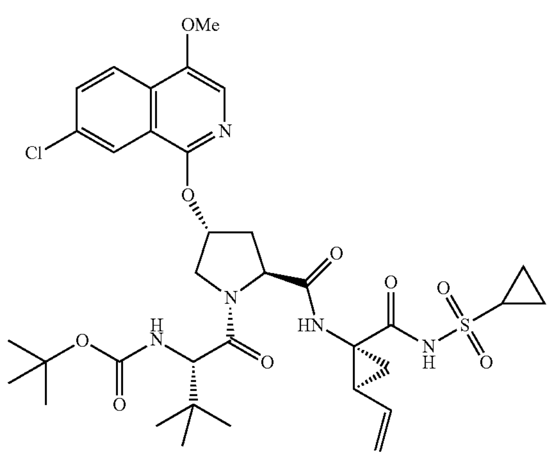 |

TABLE 12-continued
| Exemplary NS3/NS4A protease inhibitors | |
|---|---|
| Description or Name(s) | Structure |
| VANIHEP ™, vaniprevir, MK-7009 | 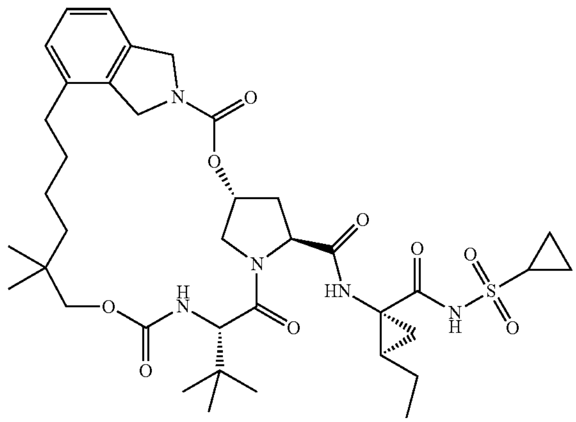 [SMILES: CC[C@@H]1C[C@]1(NC(=O)[C@@H]1C[C@@H]2CN1C(=O)[C@H](C(C)(C)C)NC(=O)OCC(C)(C)CCCCc1cccc3c1CN(C3)C(=O)O2)C(=O)NS(=O)(=O)C1CC1] |
| OLYSIO ™, simeprevir, TMC-435350 | 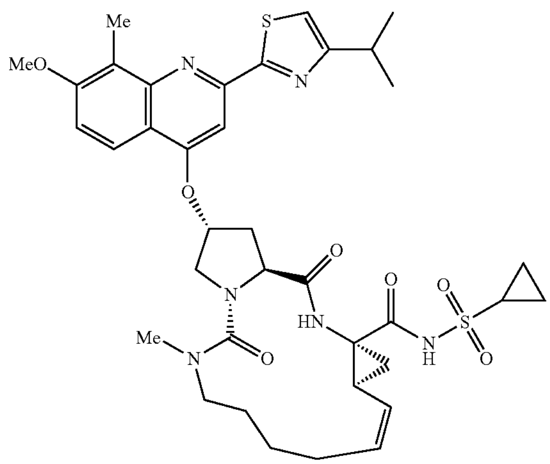 |
| Sovaprevir, ACH-1625 | 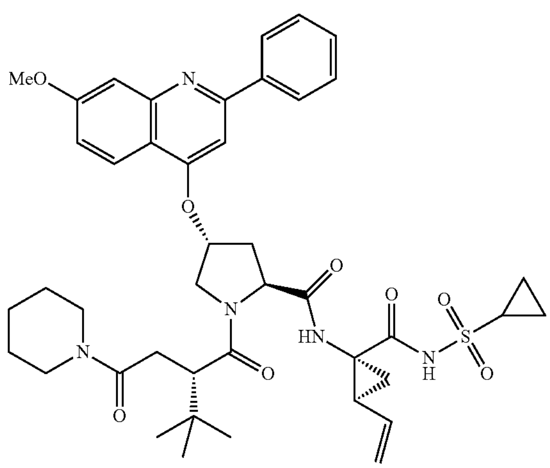 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] |

TABLE 12-continued
| Exemplary NS3/NS4A protease inhibitors | |
|---|---|
| Description or Name(s) | Structure |
| Deldeprevir/neceprevir, ACH-2684 | 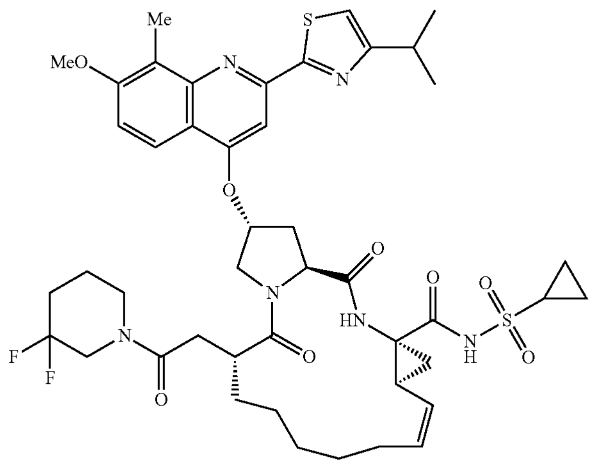 [SMILES: COc1ccc2c(O[C@@H]3C[C@H]4C(=O)N[C@]5(C(=O)NS(=O)(=O)C6CC6)C[C@H]5/C=C\CCCCC[C@H](CC(=O)N5CCCC(F)(F)C5)C(=O)N4C3)cc(-c3nc(C(C)C)cs3)nc2c1C] |
| IDX320 | 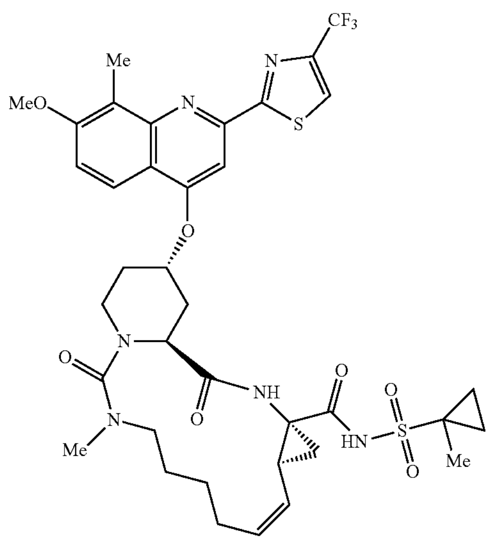 [SMILES: COc1ccc2c(O[C@H]3CCN4C(=O)N(C)CCCC/C=C\[C@@H]5C[C@@]5(C(=O)NS(=O)(=O)C5(C)CC5)NC(=O)[C@@H]4C3)cc(-c3nc(C(F)(F)F)cs3)nc2c1C] |
| GS-9256 | 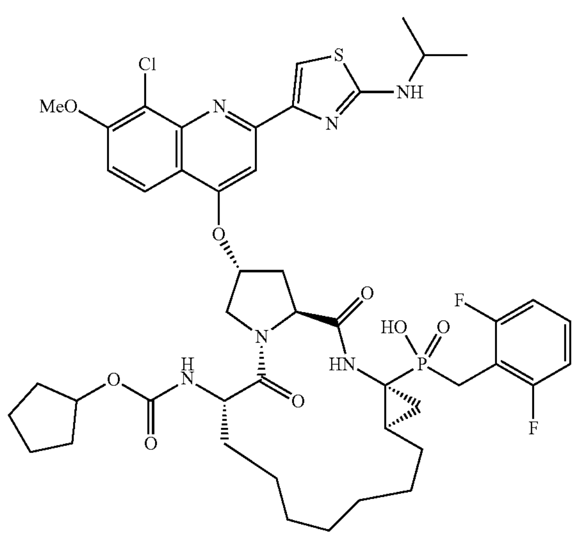 |

TABLE 12-continued
| Exemplary NS3/NS4A protease inhibitors | |
|---|---|
| Description or Name(s) | Structure |
| PHX1766 | 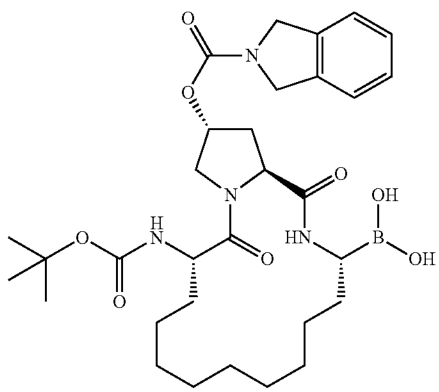 [SMILES: CC(C)(C)OC(=O)N[C@H]1CCCCCCCCC[C@@H](B(O)O)NC(=O)[C@@H]2C[C@@H](OC(=O)N3Cc4ccccc4C3)CN2C1=O] |
| MK-2748 | 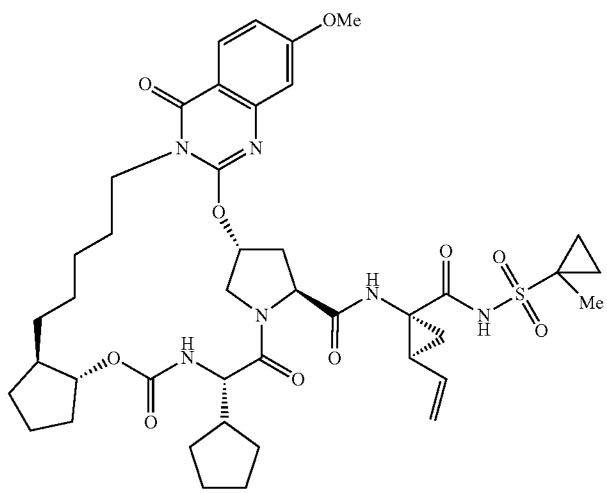 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3cc(OC)ccc3c1=O)O2)C(=O)NS(=O)(=O)C1(C)CC1] |
| Vedrorevir, GS-9451, GS-9451 | 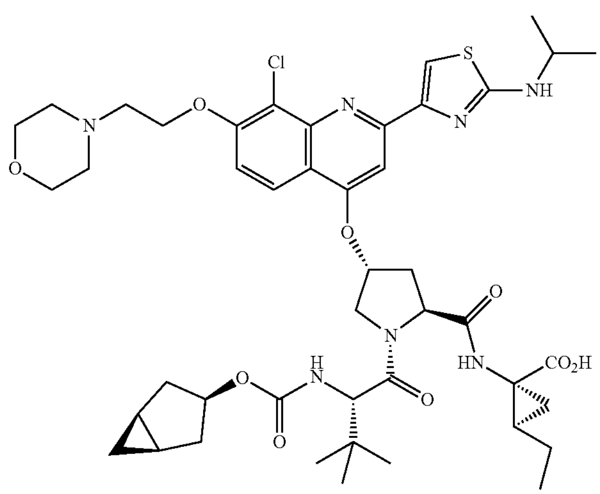 |

TABLE 12-continued
| Exemplary NS3/NS4A protease inhibitors | |
|---|---|
| Description or Name(s) | Structure |
| MK-6325 | 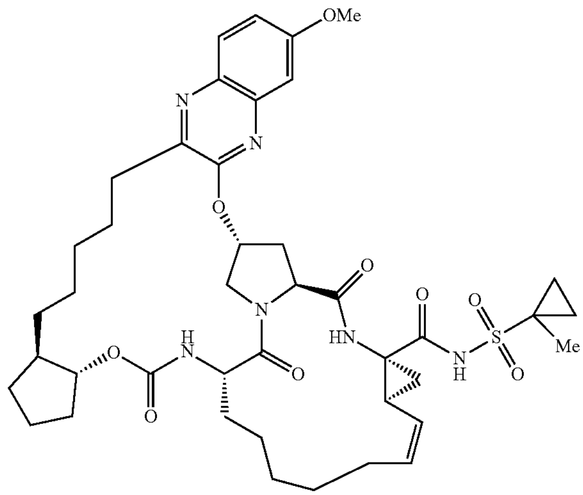 [SMILES: COc1ccc2nc3c(nc2c1)O[C@@H]1C[C@H]2C(=O)N[C@]4(C(=O)NS(=O)(=O)C5(C)CC5)C[C@H]4/C=C\CCCCC[C@H](NC(=O)O[C@@H]4CCC[C@H]4CCCCC3)C(=O)N2C1] |
| MK-8831 | 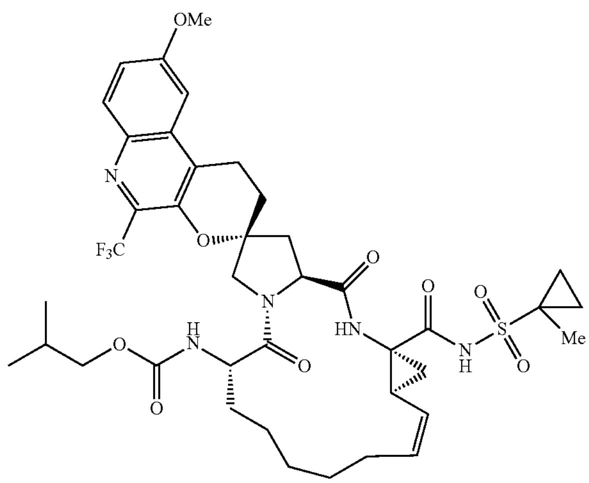 |
| VIKERA PAK ™, paritaprevir, ABT-450 | 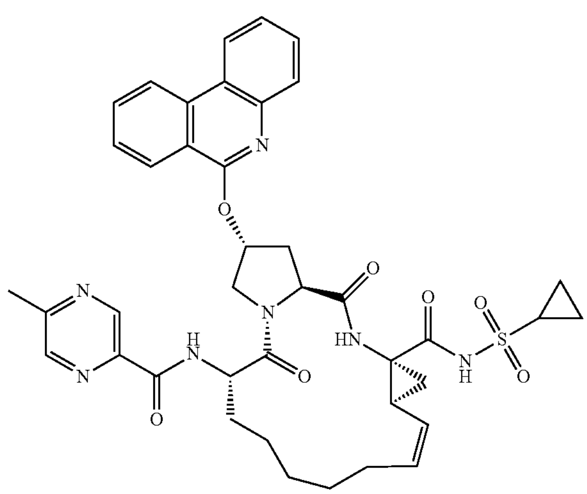 |

TABLE 12-continued

| Exemplary NS3/NS4A protease inhibitors | |
|---|---|
| Description or Name(s) | Structure |
| ZEPATIER ™, grazoprevir, MK-5172 | 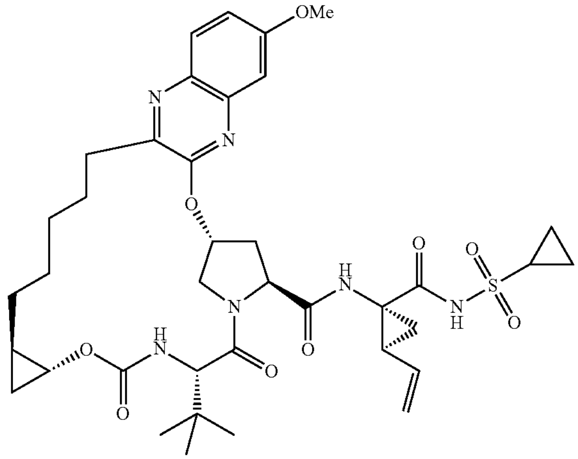 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1nc3ccc(OC)cc3nc1O2)C(=O)NS(=O)(=O)C1CC1] |
| Glecaprevir, ABT-493 | 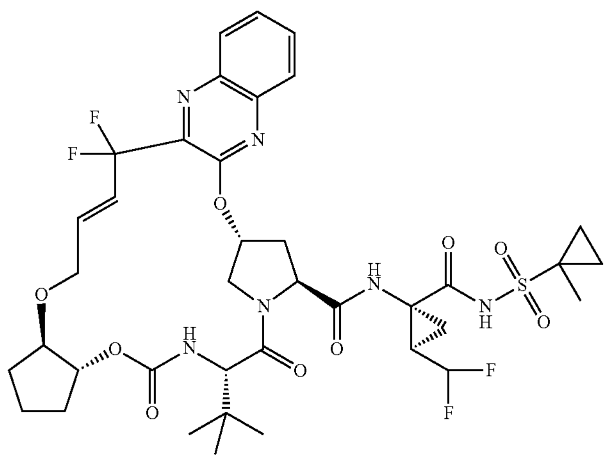 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)N[C@]3(C(=O)NS(=O)(=O)C4(C)CC4)C[C@H]3C(F)F)N(C2)C1=O] |
| Voxilaprevir, GS-9857 | 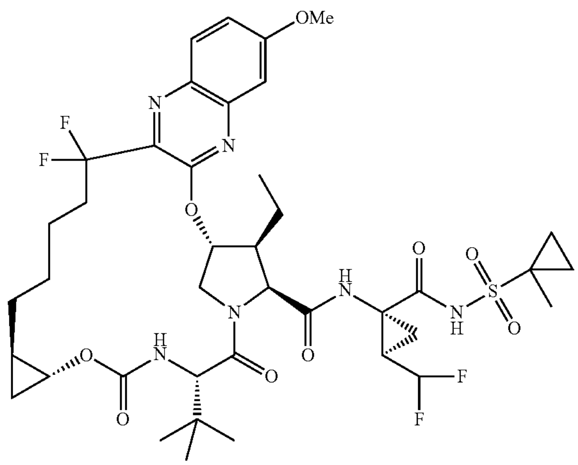 [SMILES: CC[C@@H]1[C@@H]2CN(C(=O)[C@H](C(C)(C)C)NC(=O)O[C@@H]3C[C@H]3CCCCC(F)(F)c3nc4ccc(OC)cc4nc3O2)[C@@H]1C(=O)N[C@]1(C(=O)NS(=O)(=O)C2(C)CC2)C[C@H]1C(F)F] |

Degron Domain

In several aspects, described herein are synTF polypeptides comprising a degron domain. As used herein, the term "degron domain" refers to a sequence that promotes degradation of an attached protein, e.g., through the proteasome or autophagy-lysosome pathways; in some embodiments of any of the aspects, the terms "degron", "degradation domain" and "degradation domain" can be used interchangeably with "degron domain". In some embodiments, a degron domain is a polypeptide that destabilize a protein such that half-life of the protein is reduced at least two-fold, when fused to the protein. In some embodiments of any of the aspects, a synTF polypeptide as described herein (or a synTF polypeptide system collectively) comprises 1, 2, 3, 4, 5, or more degron domains. In some embodiments of any of the aspects, the synTF polypeptide or system comprises one degron domain. In embodiments comprising multiple degron domains, the multiple degron domains can be different individual degron domains or multiple copies of the same degron domain, or a combination of the foregoing.

Many different degron sequences/signals (e.g., of the ubiquitin-proteasome system) have been described, any of which can be used as provided herein. A degron domain may be operably linked to a cell receptor, but need not be contiguous or immediately adjacent with it as long as the degron domain still functions to direct degradation of the cell receptor. In some embodiments, the degron domain induces rapid degradation of the cell receptor. For a discussion of degron domains and their function in protein degradation, see, e.g., Kanemaki et al. (2013) Pflugers Arch. 465(3):419-425, Erales et al. (2014) Biochim Biophys Acta 1843(1):216-221, Schrader et al. (2009) Nat. Chem. Biol. 5(11): 815-822, Ravid et al. (2008) Nat. Rev. Mol. Cell. Biol. 9(9):679-690, Tasaki et al. (2007) Trends Biochem Sci. 32(1 1):520-528, Meinnel et al. (2006) Biol. Chem. 387(7): 839-851, Kim et al. (2013) Autophagy 9(7): 1100-1103, Varshavsky (2012) Methods Mol. Biol. 832: 1-11, and Fayadat et al. (2003) Mol Biol Cell. 14(3): 1268-1278; Chassin et al., Nature Communications volume 10, Article number: 2013 (2019); Natsume and Kanemaki Annu Rev Genet. 2017 Nov. 27, 51:83-102; the contents of each of which is incorporated herein by reference in its entirety.

In some embodiments of any of the aspects, the degron domain comprises a ubiquitin tag, including but not limited to: UbR, UbP, UbW, UbH, UbI, UbK, UbQ, UbV, UbL, UbD, UbN, UbG, UbY, UbT, UbS, UbF, UbA, UbC, UbE, UbM, 3×UbVR, 3×UbVV, 2×UbVR, 2×UbVV, UbAR, UbVV, UbVR, UbAV, 2×UbAR, 2×UbAV. In some embodiments of any of the aspects, the degron domain comprises a self-excising degron, which refers to a complex comprising a repressible protease, a protease cleavage site, and a degron domain. In some embodiments of any of the aspects, the degron domain is a conditional degron domain, wherein the degradation is induced by ligands (e.g., a degron stabilizer) or another input such as temperature shift or a specific wave length of light. Non-limiting examples of conditional degron domains include the eDHFR degron (e.g., TMP inducer); FKBP12 (e.g., rapamycin analog inducer); temperature-sensitive dihydrofolate reductase (R-DHFRts, or ts-DHFR); an HCV NS3/NS4A degron; a modified version of R-DHFRts termed the low-temperature degron (lt-degron); auxin-inducible degradation (AID); HaloTag-Hydrophobic Tag, HaloPROTAC, and dTAG system (e.g., HyT13 or HyT36 inducer); photosensitive degron (PSD); blue-light-inducible degron (B-LID); tobacco etch virus (TEV) protease-induced protein inactivation (TIPI)-degron system; deGradFP (degrade green fluorescent protein; e.g., induced by NSlmb-vhhGFP expression); or split ubiquitin for the rescue of function (SURF; e.g., induced by rapamycin).

In some embodiments of any of the aspects, the degron domain is the *E. coli* dihydrofolate reductase (eDHFR) degron. The eDHFR degron permits extensive depletion of exogenously expressed proteins in mammalian cells and *C. elegans*. The eDHFR degron is stabilized by tight binding to the antibiotic and degron stabilizer trimethoprim (TMP), shown below, which is innocuous in eukaryotic cells.

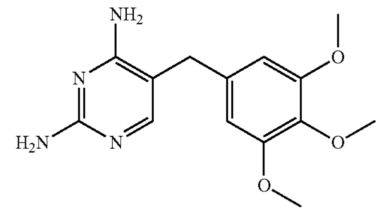 [SMILES: COc1cc(Cc2cnc(N)nc2N)cc(OC)c1OC]

Proteins tagged with eDHFR are constitutively degraded unless the cells are exposed to TMP. The level of tagged protein can be directly controlled by modulating the TMP concentration in the growth medium. Unlike shRNA methods this degron-based strategy is advantageous since depletion kinetics are not limited by the natural protein half-life, which allows for more rapid knockdown of stable proteins. TMP stabilizes the DD-target protein fusion in a dose-dependent manner up to 100-fold, which gives the system a substantial dynamic range. The ligand TMP works by itself and does not require dimerization with a second protein. This system is so effective that it can control the levels of transmembrane proteins, such as the synTF polypeptides described herein; see e.g., Schrader et al., Chem Biol. 2010 Sep. 24, 17(9): 917-918; Ryan M. Sheridan and David L. Bentley, Biotechniques. 2016, 60(2): 69-74; Iwamoto et al., Chem Biol. 2010 Sep. 24; 17(9):981-8.

In some embodiments of any of the aspects, the degron domain comprises an amino acid sequence derived from an FK506- and rapamycin-binding protein (FKBP12) (UniProtKB—P62942 (FKB1A_HUMAN), incorporated herein by reference), or a variant thereof. In some embodiments of any of the aspects, the FKBP12 derived amino acid sequence comprises a mutation of the phenylalanine (F) at amino acid position 36 (as counted without the methionine) to valine (V) (F36V) (also referred to as FKBP12* or FKBP*). In some embodiments of any of the aspects, the degron stabilizer is a rapamycin analog, such as Sheild-1, shown below. See e.g., Banaszynski et al., Cell. 2006 Sep. 8; 126(5): 995-1004; US Patent Application US20180179522; U.S. Pat. No. 10,137,180; the content of each of which is incorporated herein by reference in its entirety.

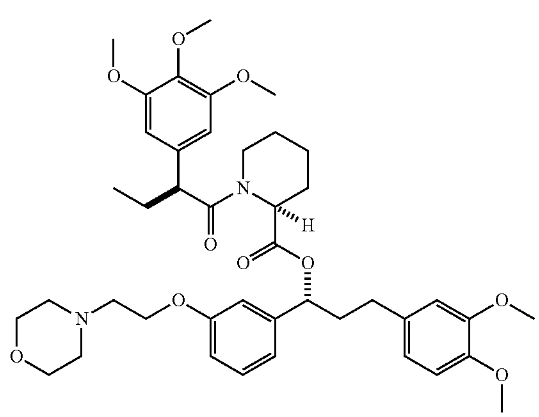

In some embodiments of any of the aspects, the degron domain of a synTF polypeptide as described herein comprises SEQ ID NOs: 270 or 271, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NOs: 270 or 271 that maintains the same function (e.g., degradation, binding to TMP or Shield-1).

```
DHFR (V19A), 158 aa,
                                                      SEQ ID NO: 270
ISLIAALAVDYVIGMENAMPWNLPADLAWFKRNTLNKPVIMGRHTWESIGRPLPGRKNIILSSQP

STDDRVTWVKSVDEAIAACGDVPEIMVIGGGRVIEQFLPKAQKLYLTHIDAEVEGDTHFPDYEPD

DWESVFSEFHDADAQNSHSYCFEILERR,

FK506- and rapamycin-binding protein (FKBP), 107 aa
                                                      SEQ ID NO: 271
GVQVETISPGDGRTFPKRGQTCVVHYTGMLEDGKKFDSSRDRNKPFKFMLGKQEVIRGWEEGV

AQMSVGQRAKLTISPDYAYGATGHPGIIPPHATLVFDVELLKLE,
```

In some embodiments of any of the aspects, the destabilizing degron domain comprises at least one mutation that causes almost complete removal or degradation of the synTF polypeptide. Non-limiting examples of DHFR (e.g., SEQ ID NO: 270) mutations include: V19A, Y100I, G121V, H12Y, H12L, R98H, F103S, M42T, H114R, I61F, T68S, H12Y/Y100I, H12L/Y100I, R98H/F103S, M42T/H114R, and I61F/T68S, or any combinations thereof; see e.g., U.S. Pat. No. 8,173,792, the content of which is incorporated herein by reference in its entirety.

In some embodiments of any of the aspects, the degron domain comprises a ligand-induced degradation (LID) domain. Proteins comprising a LID domain are destabilized and degraded in the presence of a degron destabilizer. In some embodiments of any of the aspects, the LID domain of a degron domain can bind to a degron destabilizer, promoting the degradation of the attached protein. The system is reversible and when the degron destabilizer is withdrawn, the protein is not destabilized and/or not degraded. In some embodiments of any of the aspects, a synTF polypeptide is bound to a degron destabilizer bound to the degron domain. In some embodiments of any of the aspects, the synTF polypeptide is bound specifically to a degron destabilizer bound to the degron domain.

In some embodiments of any of the aspects, the synTF polypeptide is in combination with 1, 2, 3, 4, 5, or more degron destabilizers. In some embodiments of any of the aspects, the synTF polypeptide is in combination with one degron destabilizer. In embodiments comprising multiple degron destabilizers, the multiple degron destabilizers can be different individual degron destabilizers or multiple copies of the same degron stabilizer, or a combination of the foregoing.

In some embodiments of any of the aspects, the LID degron domain comprises the FK506- and rapamycin-binding protein (FKBP), further comprising a degron fused to the C terminus of FKBP, e.g., with an intervening linker such as the 10-amino acid linker (Gly4SerGly4Ser (SEQ ID NO: 357)) or another linker as described herein. In some embodiments of any of the aspects, the degron fused to the C terminus of FKBP (e.g., SEQ ID NO: 271) comprises the 19 amino acid sequence: TRGVEEVAEGVVLLRRRGN (SEQ ID NO: 272), or a sequence that is at least 95% identical that maintains the same function. In the absence of the small molecule Shield-1, the 19-aa degron is bound to the FKBP fusion protein, and the protein is stable. When present, Shield-1 binds tightly to FKBP, displacing the 19-aa degron and inducing rapid and processive degradation of the LID domain and any fused partner protein. In some embodiments of any of the aspects, the degron destabilizer is Sheild-1, shown above, or an analog thereof; see e.g., Bonger et al., Nat Chem Biol. 2011 Jul. 3; 7(8):531-7.

In some embodiments of any of the aspects, the degron domain comprises an auxin-inducible degradation (AID). Proteins fused to AID (also known as indole-3-acetic acid inducible 17 or AUX/IAA transcriptional regulator family protein) are rapidly degraded. Degradation requires the ectopic expression of the plant F-Box protein TIR1, which recruits proteins tagged with AID in an auxin-dependent manner to the SKP1-CUL1-F-Box (SCF) ubiquitin E3 ligases resulting in their ubiquitylation and proteasomal degradation. In some embodiments of any of the aspects, the degron domain comprises residues 65-133, 65-130, 70-130, or 70-120 of SEQ ID NO: 273. In some embodiments of any of the aspects, the degron domain of a synTF polypeptide as described herein comprises SEQ ID NOs: 273 or 274, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NOs: 273 or 274 that maintains the same function. See e.g., Daniel et al., Nat Commun. 2018 Aug. 17; 9(1):3297; the content of which is incorporated herein by reference in its entirety.

```
AUX/IAA transcriptional regulator family protein [Arabidopsis
thaliana], NCBI Reference Sequence: NP_171921.1, 229 aa
                                                      SEQ ID NO: 273
MMGSVELNLRETELCLGLPGGDTVAPVTGNKRGFSETVDLKLNLNNEPANKEGSTTHDVVTFD

SKEKSACPKDPAKPPAKAQVVGWPPVRSYRKNVMVSCQKSSGGPEAAAFVKVSMDGAPYLRKI

DLRMYKSYDELSNALSNMFSSFTMGKHGGEEGMIDFMNERKLMDLVNSWDYVPSYEDKDGD

WMLVGDVPWPMFVDTCKRLRLMKGSDAIGLAPRAMEKCKSRA,
```

-continued

```
mAID (minimal AID), 68 aa
                                                         SEQ ID NO: 274
KEKSACPKDPAKPPAKAQVVGWPPVRSYRKNVMVSCQKSSGGPEAAAFVKVSMDGAPYLRKI

DLRMYK,
```

In some embodiments of any of the aspects, the degron domain comprises a modified portion of the NS3 helicase and NS4A. The arrangement of NS3pro and NS4A sequences in the construct creates a functional degron. During HCV replication, the free NS4A N-terminus forms a hydrophobic α-helix that is inserted into the endoplasmic reticulum membrane. This N-terminus is created by cleavage of the HCV nonstructural polypeptide at the NS3/4A junction due to its positioning in the protease active site by the NS3 helicase domain. The engineered construct lacks the helicase domain, so NS3/4A cleavage does not occur. The hydrophobic sequences of NS4A, unable to insert into the membrane without a free N-terminus, then exhibit degron-like activity. See e.g., U.S. Pat. No. 10,550,379; Chung et al., Nat Chem Biol. 2015 September; 11(9): 713-720; the contents of which are incorporated herein by reference in their entireties.

In some embodiments of any of the aspects, the degron domain comprises SEQ ID NO: 275, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 275 that maintains the same function.

```
HCV NS3/NS4A degron domain (42 aa)
                                            SEQ ID NO: 275
PITKIDTKYIMTCMSADLEVVTSTWVLVGGVLAALAAYCLST,
```

Induced Degradation Domain

In several aspects, described herein are synTF polypeptides comprising an induced degradation domain, also referred to herein as a self-excising degron or a small molecule-assisted shutoff (SMASh) domain. In some embodiments of any of the aspects, the SMASh domain comprises a repressible protease, at least one protease cleavage site, and a degron domain. In the absence of the protease inhibitor, the repressible protease cleaves the degron from the synTF, and the synTF is not degraded. In the presence of the protease inhibitor, the repressible protease does not cleave the degron from the synTF, and the degron domain leads to the degradation of the synTF.

In some embodiments of any of the aspects, a synTF polypeptide as described herein (or a synTF polypeptide system collectively) comprises 1, 2, 3, 4, 5, or more induced degradation domain(s). In some embodiments of any of the aspects, the synTF polypeptide or system comprises one induced degradation domain. In embodiments comprising multiple induced degradation domains, the multiple induced degradation domains can be different individual induced degradation domains or multiple copies of the same induced degradation domain, or a combination of the foregoing.

In some embodiments of any of the aspects, degron domain (e.g., of the SMASh domain) is selected from the group consisting of: a ubiquitin tag; eDHFR degron (e.g., TMP inducer); FKBP12 (e.g., rapamycin analog inducer); temperature-sensitive dihydrofolate reductase (R-DHFRts, or ts-DHFR); an HCV NS3/NS4A degron; a modified version of R-DHFRts termed the low-temperature degron (lt-degron); auxin-inducible degradation (AID); HaloTag-Hydrophobic Tag, HaloPROTAC, and dTAG system (e.g., HyT13 or HyT36 inducer); photosensitive degron (PSD); blue-light-inducible degron (B-LID); tobacco etch virus (TEV) protease-induced protein inactivation (TIPI)-degron system; deGradFP (degrade green fluorescent protein; e.g., induced by NSlmb-vhhGFP expression); or split ubiquitin for the rescue of function (SURF; e.g., induced by rapamycin).

In some embodiments of any of the aspects, the degron domain (e.g., of the SMASh domain) comprises a modified portion of the NS3 helicase and NS4A. In some embodiments of any of the aspects, the degron domain (e.g., of the SMASh domain) comprises SEQ ID NO: 275, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 275 that maintains the same function.

In some embodiments of any of the aspects, the SMASh tag comprises a repressible protease, a partial protease helical domain, and a cofactor domain. In some embodiments of any of the aspects, the SMASh tag comprises a repressible protease, a partial protease helical domain, a cofactor domain, and at least one protease cleavage site. In some embodiments of any of the aspects, the SMASh tag comprises an NS3 repressible protease, an NS3 partial protease helical domain, an NS3 cofactor domain (i.e., NS4A), and at least one protease cleavage site of the NS3 repressible protease.

In some embodiments of any of the aspects, the SMASh tag is a C-terminal SMASh tag, e.g., the tag is engineered to be attached to the C-terminus of the synTF. In some embodiments of any of the aspects, the C-terminal SMASh tag comprises a protease cleavage site at the N-terminus of the tag. In some embodiments of any of the aspects, the C-terminal SMASh tag comprises in a N-terminal to C-terminal order: a NS3 cleavage site, at least one linker, a NS3 domain, a NS3 partial helicase, a NS4A domain. In some embodiments of any of the aspects, the C-terminal SMASh tag is fused to the C-terminus of the transcriptional effector domain of the synTF. In some embodiments of any of the aspects, the C-terminal SMASh tag is fused to the C-terminus of the DNA-binding domain of the synTF.

In some embodiments of any of the aspects, the C-terminal SMASh tag comprises one of SEQ ID NOs: 276-278 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 276-278 that maintains the same function.

C-terminal SMASh domain (304 aa); bold text indicates NS3 Cleavage Site; *italicized double underlined text* indicates a Linker; *bold italicized text* indicates the FLAG tag; *italicized text* indicates the NS3 Protease Domain; unformatted text indicates NS3 Partial Helicase; *bold italicized double underlined text* indicates NS4A Domain:

SEQ ID NO: 276

DEMEECSQHL*PGAGSSGDIM**DYKDDDDK**GSSGTGSGSGTS APITAYAQQTRGLLGCIITSLTGRDKN*

*QVEGEVQIVSTATQTFLATCINGVCWAVYHGAGTRTIASPKGPVIQMYTNVDQDLVGWPAPQGSRSLT*

*PCTCGSSDLYLVTRHADVIPVRRRGDSRGSLLSPRPISYLKGSSGGPLLCPAGHAVGLFRAAVCTRGVAK*

*AVDFIPVENLETTMRSPVFTD*NSSPPAVTLTHPITKIDTKYIMTCMSADLEVVT*STWVLVGGVLAA*

*LAAYCLSTGCVVIVGRIVLSGKPAIIPDREVLY*

In some embodiments of any of the aspects, the SMASh tag is a N-terminal SMASh tag, e.g., the tag is engineered to be attached to the N-terminus of the synTF. In some embodiments of any of the aspects, the N-terminal SMASh tag comprises a protease cleavage site at the C-terminus of the tag. In some embodiments of any of the aspects, the N-terminal SMASh tag comprises in a N-terminal to C-terminal order at least one Linker, a NS3 domain, a NS3 partial helicase, a NS4 domain, and a NS3 cleavage site. In some embodiments of any of the aspects, the N-terminal SMASh tag is fused to the N-terminus of the transcriptional effector domain of the synTF. In some embodiments of any of the aspects, the N-terminal SMASh tag is fused to the N-terminus of the DNA-binding domain of the synTF.

In some embodiments of any of the aspects, the N-terminal SMASh tag comprises SEQ ID NOs: 279 to 284, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 279 to 284, that maintains the same function.

N-terminal SMASh domain (297 aa), *italicized double underlined text* indicates a Linker; bold italicized text indicates the FLAG tag (; italicized text indicates the NS3 Protease Domain; unformatted text indicates NS3 Partial Helicase; *bold italicized double underlined text* indicates NS4A Domain; bold text indicates NS3 Cleavage Site:

SEQ ID NO: 279

*DYKDDDDK**GSSGTGSGSGTS APITAYAQQTRGLLGCIITSLTGRDKNQVEGEVQIVSTATQTFLATCING*

*VCWAVYHGAGTRTIASPKGPVIQMYTNVDQDLVGWPAPQGSRSLTPCTCGSSDLYLVTRHADVIPVRR*

*RGDSRGSLLSPRPISYLKGSSGGPLLCPAGHAVGLFRAAVCTRGVAKAVDFIPVENLETTMRSPVFTD*N

SSPPAVTLTHPITKIDTKYIMTCMSADLEVVT*STWVLVGGVLAALAAYCLSTGCVVIVGRIVLSGK*

*PAIIPDREVLY* QEFEDVVPCSMGS,

N-terminal SMASh domain (303 aa, with GSSGSS (SEQ ID NO: 285) L6 domain in NS4A), *italicized double underlined text* indicates a Linker; *bold italicized text* indicates the FLAG tag; *italicized text* indicates the NS3 Protease Domain; unformatted text indicates NS3 Partial Helicase; *bold italicized double underlined text* indicates NS4A Domain; bold text indicates NS3 Cleavage Site.

SEQ ID NO: 280

*DYKDDDDK**GSSGTGSGSGTS APITAYAQQTRGLLGCIITSLTGRDKNQVEGEVQIVSTATQTFLATCING*

*VCWAVYHGAGTRTIASPKGPVIQMYTNVDQDLVGWPAPQGSRSLTPCTCGSSDLYLVTRHADVIPVRR*

RGDSRGSLLSPRPISYLKGSSGGPLLCPAGHAVGLFRAAVCTRGVAKAVDFIPVENLETTMRSPVFTDN

SSPPAVTLTHPITKIDTKYIMTCMSADLEVVT*STWVLVGGVLAALAAYCLSTGCVVIVGRIVLSGK*

*PAGSSGSSIIPDREVLY* QEFEDVVPCSMGS,

In some embodiments of any of the aspects, SMASh domain comprises a repressible protease that comprises at least one mutation that increases its sensitivity to at least one protease inhibitor. In some embodiments of any of the aspects, the NS3 protease (e.g., of the SMASh domain) comprises at least one of the following mutations: V36M, T54A, S122G, F43L, Q80K, S122R, D168Y, or any combination thereof. In some embodiments of any of the aspects, the NS3 protease (e.g., of the SMASh domain) comprises at least one of the following mutations: V36M, T54A, S122G, or any combination thereof; such a SMASh is also referred to herein as $SMASh^{AI}$, as these mutations increase its sensitivity to asunaprevir (see e.g., SEQ ID NOs: 197, 277, 281, 282). In some embodiments of any of the aspects, the NS3 protease (e.g., of the SMASh domain) comprises at least one of the following mutations: F43L, Q80K, S122R, D168Y, or any combination thereof; such a protease is also referred to herein as $SMASh^{TI}$, as these mutations increase its sensitivity to telaprevir (see e.g., SEQ ID NOs: 198, 278, 283, 284).

C-terminal SMASh$^{AI}$ domain with (304 aa); bold text indicates NS3 Cleavage Site; *italicized double underlined text* text indicates a Linker; *bold italicized text* indicates the FLAG tag; italicized text indicates the NS3 Protease Domain; unformatted text indicates NS3 Partial Helicase; *bold italicized double underlined text* indicates NS4A Domain; the V36M, T54A, S122G mutations are shown in bold double underlined text, respectively.

SEQ ID NO: 277

DEMEECSQHL*PGAGSSGDIM**DYKDDDDK**GSSGTGSGSGTS APITAYAQQTRGLLGCIITSLTGRDKN*

*QVEGEVQI*M*STATQTFLATCINGVCW*A*VYHGAGTRTIASPKGPVIQMYTNVDQDLVGWPAPQGSRSLT*

*PCTCGSSDLYLVTRHADVIPVRRRGD*G*RGSLLSPRPISYLKGSSGGPLLCPAGHAVGLFRAAVCTRGVA*

*KAVDFIPVENLETTMRSPVFTD*NSSPPAVTLTHPITKIDTKYIMTCMSADLEVVT*STWVLVGGVLA*

*ALAAYCLSTGCVVIVGRIVLSGKPAIIPDREVLY*

N-terminal SMASh$^{AI}$ domain (297 aa), *italicized double underlined text* indicates a Linker; *bold italicized text* text indicates the FLAG tag; italicized text indicates the NS3 Protease Domain; unformatted text indicates NS3 Partial Helicase; *bold italicized double underlined text* indicates NS4A Domain; bold text indicates NS3 Cleavage Site; the bold double underlined text, respectively.

SEQ ID NO: 281

*DYKDDDDKGSSGTGSGSGTS APITAYAQQTRGLLGCIITSLTGRDKNQVEGEVQI*M***STATQTFLATCIN*

*GVCW*A*VYHGAGTRTIASPKGPVIQMYTNVDQDLVGWPAPQGSRSLTPCTCGSSDLYLVTRHADVIPVR*

*RRGD*G*RGSLLSPRPISYLKGSSGGPLLCPAGHAVGLFRAAVCTRGVAKAVDFIPVENLETTMRSPVFTD*

NSSPPAVTLTHPITKIDTKYIMTCMSADLEVVT*STWVLVGGVLAALAAYCLSTGCVVIVGRIVLSG*

*KPAIIPDREVLY* QEFEDVVPCSMGS,

N-terminal SMASh$^{AI}$ domain (303 aa, with L6 domain in NS4A), italicized *italicized double underlined text* indicates a Linker; *bold italicized text* indicates the FLAG tag; italicized text indicates the NS3 Protease Domain; unformatted text indicates NS3 Partial Helicase; *bold italicized double underlined text* indicates NS4A Domain; bold text indicates NS3 Cleavage Site; the V36M, T54A, S122G mutations are shown in bold double underlined text , respectively.

SEQ ID NO: 282

*DYKDDDDKGSSGTGSGSGTS APITAYAQQTRGLLGCIITSLTGRDKNQVEGEVQI*M***TATQTFLATCIN*

*GVCW*A*VYHGAGTRTIASPKGPVIQMYTNVDQDLVGWPAPQGSRSLTPCTCGSSDLYLVTRHADVIPVR*

*RRGD*G*RGSLLSPRPISYLKGSSGGPLLCPAGHAVGLFRAAVCTRGVAKAVDFIPVENLETTMRSPVFTD*

NSSPPAVTLTHPITKIDTKYIMTCMSADLEVVT*STWVLVGGVLAALAAYCLSTGCVVIVGRIVLSG*

*KPAGSSGSSIIPDREVLY* QEFEDVVPCSMGS,

C-terminal SMASh$^{TI}$ domain with (304 aa); bold text indicates NS3 Cleavage Site; *italicized double underlined text* indicates a Linker; *bold italicized text* indicates the FLAG tag; italicized text indicates the NS3 Protease Domain; unformatted text indicates NS3 Partial Hlicase; *bold italicized double underlined text* indicates NS4A Domain; the F43L, Q80K, S122R, D168Y mutations are shown in bold double underlined text, respectively.

SEQ ID NO: 278

DEMEECSQHL*PGAGSSGDIM**DYKDDDDK**GSSGTGSGSGTS APITAYAQQTRGLLGCIITSLTGRDKN*

*QVEGEVQIVSTATQT*L *LATCINGVCWAVYHGAGTRTIASPKGPVIQMYTNVI*K *DLVGWPAPQGSRSLT*

*PCTCGSSDLYLVTRHADVIPVRRRGD*R *RGSLLSPRPISYLKGSSGGPLLCPAGHAVGLFRAAVCTRGVA*

*KAV*Y *FIPVENLETTMRSPVFTD*NSSPPAVTLTHPITKIDTKYIMTCMSADLEVVT*STWVLVGGVLA*

*ALAAYCLSTGCVVIVGRIVLSGKPAIIPDREVLY*

-continued

N-terminal SMASh$^{II}$ domain (297 aa), *italicized double underlined text* indicates a Linker; *bold italicized text* indicates the FLAG tag; italicized text indicates the NS3 Protease Domain; unformatted text indicates NS3 Partial Helicase; *bold italicized double underlined text* indicates NS4A Domain; bold text indicates NS3 Cleavage Site; the F43L, Q80K, S122R, D168Y mutations are shown in bold double underlined text , respectively.

SEQ ID NO: 283

*DYKDDDDK**GSSGTGSGSGTS* *APITAYAQQTRGLLGCIITSLTGRDKNQVEGEVQIVSTATQT**L* *LATCING*

*VCWAVYHGAGTRTIASPKGPVIQMYTNVD**K* *DLVGWPAPQGSRSLTPCTCGSSDLYLVTRHADVIPVRR*

*RGD**R* *RGSLLSPRPISYLKGSSGGPLLCPAGHAVGLFRAAVCTRGVAKAV**Y* *FIPVENLETTMRSPVFTDN*

SSPPAVTLTHPITKIDTKYIMTCMSADLEVVT*STWVLVGGVLAALAAYCLSTGCVVIVGRIVLSGK*

*PAIIPDREVLY* QEFEDVVPCSMGS,

N-terminal SMASh$^{II}$ domain (303 aa, with L6 domain in NS4A), *italicized double underlined text* indicates a Linker; *bold italicized text* indicates the FLAG tag; italicized text indicates the NS3 Protease Domain; unformatted text indicates NS3 Partial Helicase; *bold italicized double underlined text* indicates NS4A Domain; bold text indicates NS3 Cleavage Site; the F43L, Q80K, S122R, D168Y mutations are shown in bold double underlined text , respectively.

SEQ ID NO: 284

*DYKDDDDK**GSSGTGSGSGTS* *APITAYAQQTRGLLGCIITSLTGRDKNQVEGEVQIVSTATQT**L* *LATCING*

*VCWAVYHGAGTRTIASPKGPVIQMYTNVD**K* *DLVGWPAPQGSRSLTPCTCGSSDLYLVTRHADVIPVRR*

*RGD**R* *GSLLSPRPISYLKGSSGGPLLCPAGHAVGLFRAAVCTRGVAKAV**Y* *IPVENLETTMRSPVFTDN*

*SSPPAVTLTHPITKIDTKYIMTCMSADLEVVT**STWVLVGGVLAALAAYCLSTGCVVIVGRIVLSGK*

*PAGSSGSSIIPDREVLY* QEFEDVVPCSMGS,

In some embodiments of any of the aspects, the SMASh domain of the synTF polypeptide is in combination with 1, 2, 3, 4, 5, or more protease inhibitors. In some embodiments of any of the aspects, the SMASh domain of the synTF polypeptide is in combination with one protease inhibitor. In embodiments comprising multiple protease inhibitors, the multiple protease inhibitors can be different individual protease inhibitors or multiple copies of the same protease inhibitor, or a combination of the foregoing.

In some embodiments of any of the aspects, the protease inhibitor is grazoprevir (abbreviated as GZV or GZP; see e.g., PubChem CID: 44603531). In some embodiments of any of the aspects, the protease inhibitor is danoprevir (DNV; see e.g., PubChem CID: 11285588). In some embodiments of any of the aspects, the protease inhibitor is an approved NS3 protease inhibitor, such as but not limited to grazoprevir, danoprevir, simeprevir, asunaprevir, ciluprevir, boceprevir, sovaprevir, paritaprevir, ombitasvir, paritaprevir, ritonavir, dasabuvir, and telaprevir. Additional non-limiting examples of NS3 protease inhibitors are listed in Table 12 (see e.g., McCauley and Rudd, Hepatitis C virus NS3/4a protease inhibitors, Current Opinion in Pharmacology 2016, 30:84-92; the content of which is incorporated herein by reference in its entirety).

Induced Proximity Domains

In several aspects, described herein are synTF polypeptides comprising at least two induced proximity domains, also referred to herein as heterodimerization domains. As used herein the term "induced proximity domains" refers to at least two domains that are induced to dimerize or come into close proximity in the presence of a stimulus (e.g., chemical inducer, light, etc.). In some embodiments of any of the aspects, the induced proximity domain pair comprises a first induced proximity domain ($IPD^A$) and at least a second induced proximity domain ($IPD^B$), wherein in the presence of an inducer agent or inducer signal, the $IPD^A$ and $IPD^B$ come together. In some embodiments of any of the aspects, the synTF effector domain is linked to $IPD^A$ (or $IPD^B$) in a first polypeptide, and the synTF DBD is linked to $IPD^B$(or $IPD^A$) in a second polypeptide. Thus, in the presence of an inducer agent or inducer signal, the $IPD^A$ and $IPD^B$ come together linked to resulting in the linkage of the TA to the DBD of the synthetic TF. In the absence of an inducer agent or inducer signal, the TA is uncoupled or unlinked to the DBD of the synthetic TF.

In some embodiments of any of the aspects, a synTF polypeptide as described herein (or a synTF polypeptide system collectively) comprises 1, 2, 3, 4, 5, or more induced proximity domain(s). In some embodiments of any of the aspects, the synTF polypeptide or system comprises one induced proximity domain. In embodiments comprising multiple induced proximity domains, the multiple induced proximity domains can be different individual induced proximity domains or multiple copies of the same induced proximity domain, or a combination of the foregoing.

In some embodiments of any of the aspects, the induced proximity domain pair (IPD pair) comprises a $IPD^A$ and $IPD^B$ selected from any one or more of: (1) a $IPD^A$ comprising a GID1 domain or a fragment thereof, and a $IPD^B$ comprising a GAI domain, wherein the GID1 domain and GAI domain bind to the inducer agent Gibberellin Ester (GIB); (2) a $IPD^A$ comprising a FKBP domain or a fragment thereof, and a $IPD^B$ comprising a FRB domain, wherein the FKBP domain and FRB domain bind to the inducer agent Rapalog (RAP); (3) a $IPD^A$ comprising a PYL domain or a fragment thereof, and a $IPD^B$ comprising a ABI domain, wherein the PYL domain and ABI domain bind to the inducer agent Abscisic acid (ABA); (4) a $IPD^A$ comprising a Light-inducible dimerization domain (LIDD), wherein a LIDD dimerizes with a complementary LIDD ($IPD^B$) upon exposure to a light inducer signal of an appropriate wavelength.

In some embodiments of any of the aspects, the synTF polypeptide is in combination with 1, 2, 3, 4, 5, or more inducer agents, i.e., that induce dimerization or proximity of the IPDs. In some embodiments of any of the aspects, the synTF polypeptides are in combination with one inducer agent. In embodiments comprising multiple inducer agents, the multiple inducer agents can be different individual inducer agents or multiple copies of the same inducer agent, or a combination of the foregoing.

In some embodiments of any of the aspects, the IPD pair comprises a ABI (ABA insensitive) domain and a PYL (pyrabactin resistance-like) domain, derived from components of the Abscisic acid (ABA) signaling pathway from *Arabidopsis thaliana*. In some embodiments of any of the aspects, the IPD pair comprises the interacting complementary surfaces (CSs) of PYL1 (PYLcs, amino acids 33 to 209) and AB11 (ABIcs, amino acids 126 to 423). In some embodiments of any of the aspects, the ABI domain (e.g., SEQ ID NO: 286 or 287) comprises mutations A18D and E108G. In some embodiments of any of the aspects, the ABI domain further comprises a detectable marker (e.g., a FLAG tag). In some embodiments of any of the aspects, the PYL domain further comprises a detectable marker (e.g., an HA tag).

In some embodiments of any of the aspects, the ABI domain comprises SEQ ID NOs: 286 or 287 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 286 or 287, that maintains the same function.

In some embodiments of any of the aspects, the PYL domain comprises SEQ ID NOs: 288 or 289 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 288 or 289, that maintains the same function.

SEQ ID NO: 286, ABI cs CO1 (298 aa)
VPLYGFTSICGRRPEMEAAVSTIPRFLQSSSGSMLDGRFDPQSAAHFFGVYDGHGGSQVANYCRE

RMHLALAEEIAKEKPMLCDGDTWLEKWKKALFNSFLRVDSEIESVAPETVGSTSVVAVVFPSHIF

VANCGDSRAVLCRGKTALPLSVDHKPDREDEAARIEAAGGKVIQWNGARVFGVLAMSRSIGDR

YLKPSIIPDPEVTAVKRVKEDDCLILASDGVWDVMTDEEACEMARKRILLWHKKNAVAGDASL

LADERRKEGKDPAAMSAAEYLSKLAIQRGSKDNISVVVVDLK

SEQ ID NO: 288, PYL1cs Domain (177 aa)
TQDEFTQLSQSIAEFHTYQLGNGRCSSLLAQRIHAPPETVWSVVRRFDRPQIYKHFIKSCNVSEDF

EMRVGCTRDVNVISGLPANTSRERLDLLDDDRRVTGFSITGGEHRLRNYKSVTTVHRFEKEEEEE

RIWTVVLESYVVDVPEGNSEEDTRLFADTVIRLNLQKLASITEAMN

SEQ ID NO: 287, Alternative ABI binding motif
PLYGFTSICGRRPEMEDAVSTIPRFLQSSSGSMLDGRFDPQSAAHFFGVYDGHGGSQVANYCRER

MHLALAEEIAKEKPMLCDGDTWLEKWKKALFNSFLRVDSEIGSVAPETVGSTSVVAVVFPSHIF

VANCGDSRAVLCRGKTALPLSVDHKPDREDEAARIEAAGGKVIQWNGARVFGVLAMSRSIGDR

YLKPSIIPDPEVTAVKRVKEDDCLILASDGVWDVMTDEEACEMARKRILLWHKKNAVAGDASL

LADERRKEGKDPAAMSAAEYLSKLAIQRGSKDNISVVVVDLKDYKDDDDK

SEQ ID NO: 289, Alternative PYL binding motif
APTQDEFTQLSQSIAEFHTYQLGNGRCSSLLAQRIHAPPETVWSVVRRFDRPQIYKHFIKSCNVSE

DFEMRVGCTRDVNVISGLPANTSRERLDLLDDDRRVTGFSITGGEHRLRNYKSVTTVHRFEKEEE

EERIWTVVLESYVVDVPEGNSEEDTRLFADTVIRLNLQKLASITEAMNYPYDVPDYA

In some embodiments of any of the aspects, the proximity inducer agent (e.g., for ABI and PYL domains) is abscisic acid (ABA):

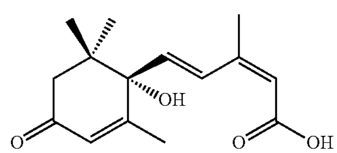

In some embodiments, the IPD pair are FKBP (FK506- and rapamycin-binding protein) and FKBP12-rapamycin-binding protein (FRB) proteins, which come together and dimerize in the presence of a rapalog. In some embodiments of any of the aspects, the FKBP domain comprises SEQ ID NOs: 290 or 271 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 290 or 271, that maintains the same function. In some embodiments of any of the aspects, the FRB domain comprises SEQ ID NO: 291 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 291, that maintains the same function.

```
SEQ ID NO: 290, FKBP aa binding motif:
SRGVQVETISPGDGRTFPKRGQTCVVHYTGMLEDGKKFDSSRDRNKPFK

FMLGKQEVIRGWEEGVAQMSVGQRAKLTISPDYAYGATGHPGIIPPHAT

LVFDVELLKLE
```

```
SEQ ID NO: 291, FRB binding motif,
ILWHEMWHEGLEEASRLYFGERNVKGMFEVLEPLHAMMERGPQTLKETS

FNQAYGRDLMEAQEWCRKYMKSGNVKDLLQAWDLYYHVFRRIS
```

In some embodiments of any of the aspects, the proximity inducer agent (e.g., for FKBP and FRB domains) is rapamycin shown below. In some embodiments of any of the aspects, the proximity inducer agent (e.g., for FKBP and FRB domains) is a rapalog, i.e., a rapamycin analog. In some embodiments of any of the aspects, the rapalog is Sheild-1, as described further herein.

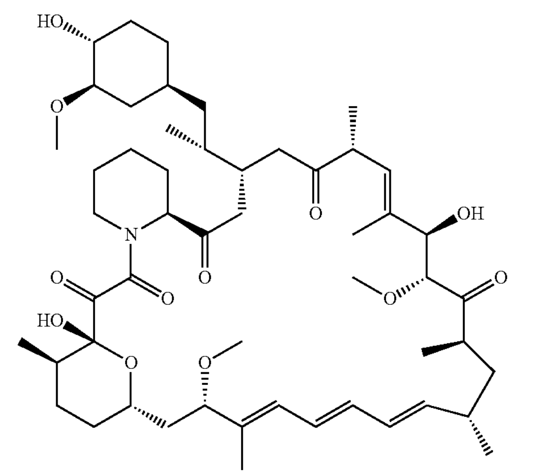 [SMILES: CO[C@H]1C[C@@H]2CC[C@@H](C)[C@@](O)(O2)C(=O)C(=O)N2CCCC[C@H]2C(=O)C[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

In other embodiments, the IPD pair are GAI (Gibberellin insensitive) and GID1 (Gibberellin insensitive dwarf1) proteins, derived from, *Arabidopsis thaliana*, which come together in the presence of Gibberellin Ester (GE). In some embodiments of any of the aspects, the GAI domain comprises SEQ ID NO: 292 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 292, that maintains the same function. In some embodiments of any of the aspects, the GAI domain comprises the amino-terminal DELLA domain of GAL. In some embodiments of any of the aspects, the GID domain comprises SEQ ID NO: 293 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 293, that maintains the same function.

```
SEQ ID NO: 292, GAI binding motif,
MKRDHHHHHHQDKKTMMMNEEDDGNGMDELLAVLGYKVRSSEMAD

VAQKLEQLEVMMSNVQEDDLSQLATETVHYNPAELYTWLDSMLTD

LN
```

-continued

```
SEQ ID NO: 293, GID1 binding motif
MAASDEVNLIESRTVVPLNTWVLISNFKVAYNILRRPDGTFNRHL

AEYLDRKVTANANPVDGVFSFDVLIDRRINLLSRVYRPAYADQEQ

PPSILDLEKPVDGDIVPVILFFHGGSFAHSSANSAIYDTLCRRLV

GLCKCVVVSVNYRRAPENPYPCAYDDGWIALNWVNSRSWLKSKKD

SKVHIFLAGDSSGGNIAHNVALRAGESGIDVLGNILLNPMFGGNE

RTESEKSLDGKYFVTVRDRDWYWKAFLPEGEDREHPACNPFSPRG

KSLEGVSFPKSLVVVAGLDLIRDWQLAYAEGLKKAGQEVKLMHLE

KATVGFYLLPNNNHFHNVMDEISAFVNAEC
```

In some embodiments of any of the aspects, the proximity inducer agent (e.g., for GAI and GID1 domains) is a bioactive gibberellin (shown below), a Gibberellin Ester (GE), or another gibberellin analog.

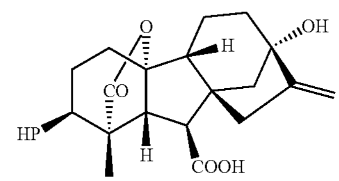

In some embodiments, the IPD pair comprises a caffeine-induced dimerization system, such as a VHH camelid antibody (referred to as aCaffVHH) that has high affinity (Kd=500 nM) and homodimerizes in the presence of caffeine. In some embodiments, the IPD pair is selected from a combinatorial binders-enabled selection of chemically induced dimerization systems (COMBINES-CID), using a specific chemical ligand. As a non-limiting example, the ligand can be CBD (cannabidiol). In some embodiments, the IPD pair comprises human antibody-based chemically induced dimerizes (AbCIDs), which are derived from known small-molecule-protein complexes by selecting for synthetic antibodies that recognize the chemical epitope created by the small molecule bound to the protein (e.g., ABT-737). In some embodiments, the IPD pair comprises Calcineurin and FKBP, which come together in the presence of FK506. In some embodiments, the IPD pair comprises Calcineurin and prolyl isomerase CyP, which come together in the presence of Cyclosporine A. In some embodiments, the IPD pair comprises CyP and FKBP, which come together in the presence of FKCsA, a fusion of FK506 and Cyclosprin A. In some embodiments, the IPD pair comprises two copies of FKBP, which come together in the presence of FK2012, a fusion of two FK506 molecules. See e.g., Franco et al., Journal of Chromatography B, Volume 878, Issue 2, 15 Jan. 2010, Pages 177-186; Liang et al. Sci Signal 2011 Mar. 15; 4(164):rs2; Laura A. Banaszynski et al. JACS 2005 Apr. 6; 127(13):4715-21; Miyamoto et al. Nat Chem Biol Nature Chemical Biology volume 8, pages 465-470(2012); Bojar et al. Nature Communications volume 9, Article number: 2318 (2018); Kang et al. JACS 2019 Jul. 17; 141(28): 10948-10952; Hill et al. Nat ChemBio 2018 February; 14(2):112-117; Stanton et al. Science 2018 Mar. 9; 359(6380): eaao5902; Weinberg et al. Nat Biotech 2017 May; 35(5): 453-462; Matthew J Kennedy, Nature Methods volume 7, pages 973-975(2010); US Patent Applications US20180163195 and US20170183654; U.S. Pat. No. 8,735, 096; the contents of each of which are incorporated herein by reference in their entireties.

In some embodiments, the IPD pair comprises a light-inducible dimerization domain (LIDD) pair, non-limiting examples of which include nMag/nMag, CRY2/CIBN, and photochromic proteins. In some embodiments, the IPD pair comprises a light-inducible dimerization domain (LIDD) pair, such as nMag and pMag proteins, which come together and dimerize in a blue light signal, e.g., after a blue light pulse signal, or pulse of a light of an appropriate wavelength. In some embodiments of any of the aspects, the nMag domain comprises SEQ ID NO: 294 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 294, that maintains the same function. In some embodiments of any of the aspects, the pMag domain comprises SEQ ID NO: 295 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 295, that maintains the same function.

```
SEQ ID NO: 294, nMag binding motif
HTLYAPGGYDIMGYLDQIGNRPNPQVELGPVDTSCALILCDLKQK

DTPIVYASEAFLYMTGYSNAEVLGRNCRFLQSPDGMVKPKSTRKY

VDSNTINTMRKAIDRNAEVQVEVVNFKKNGQRFVNFLTMIPVRDE

TGEYRYSMGFQCETE

SEQ ID NO: 295, pMag binding motif
HTLYAPGGYDIMGYLRQIRNRPNPQVELGPVDTSCALILCDLKQK

DTPIVYASEAFLYMTGYSNAEVLGRNCRFLQSPDGMVKPKSTRKY

VDSNTINTMRKAIDRNAEVQVEVVNFKKNGQRFVNFLTMIPVRDE

TGEYRYSMGFQCETE,
```

In some embodiments, the IPD pair comprises a light-inducible dimerization domain (LIDD) pair, such as cryptochrome 2 (CRY2) and CIBN (a truncated version of CIB1 (Calcium And Integrin-Binding Protein 1; CRY2 interacting basic-helix-loop-helix 1)) and proteins, derived from *Arabidopsis thaliana*, which come together and dimerize in a blue light signal, e.g., after a blue light pulse signal, or pulse of a light of an appropriate wavelength. In some embodiments of any of the aspects, the CIBN domain comprises SEQ ID NO: 296 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 296, that maintains the same function. In some embodiments of any of the aspects, the CRY2 domain comprises SEQ ID NO: 297 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 297, that maintains the same function.

```
SEQ ID NO: 296, CIBN LIDD
MNGAIGGDLLLNFPDMSVLERQRAHLKYLNPTFDSPLAGFFADSS

MITGGEMDSYLSTAGLNLPMMYGETTVEGDSRLSISPETTLGTGN

FKKRKFDTETKDCNEKKKKMTMNRDDLVEEGEEEKSKITEQNNGS

TKSIKKMKHKAKKEENNFSNDSSKVTKELEKTDYIH

SEQ ID NO: 297, CRY2 LIDD
MKMDKKTIVWFRRDLRIEDNPALAAAAHEGSVFPVFIWCPEEEGQ

FYPGRASRWWMKQSLAHLSQSLKALGSDLTLIKTHNTISAILDCI

RVTGATKVVFNHLYDPVSLVRDHTVKEKLVERGISVQSYNGDLLY

EPWEIYCEKGKPFTSFNSYWKKCLDMSIESVMLPPPWRLMPITAA

AEAIWACSIEELGLENEAEKPSNALLTRAWSPGWSNADKLLNEFI

EKQLIDYAKNSKKVVGNSTSLLSPYLHFGEISVRHVFQCARMKQI

IWARDKNSEGEESADLFLRGIGLREYSRYICFNFPFTHEQSLLSH

LRFFPWDADVDKFKAWRQGRTGYPLVDAGMRELWATGWMHNRIRV

IVSSFAVKFLLLPWKWGMKYFWDTLLDADLECDILGWQYISGSIP

DGHELDRLDNPALQGAKYDPEGEYIRQWLPELARLPTEWIHHPWD

APLTVLKASGVELGTNYAKPIVDIDTARELLAKAISRTREAQIMI

GAAPDEIVADSFEALGANTIKEPGLCPSVSSNDQQVPSAVRYNGS

KRVKPEEEEERDMKKSRGFDERELFSTAESSSSSSVFFVSQSCSL

ASEGKNLEGIQDSSDQITTSLGKNGCK
```

In some embodiments, the IPD pair comprises a light-inducible dimerization domain (LIDD) pair, such as photochromic protein domains including, but not limited to Dronpa, Padron, rsTagRFP, and mApple, or a variant or polypeptide fragment thereof having fluorescence characteristics (e.g., Dronpa-145N, Padron-145N, or mApple-162H-164A). Such photochromic protein domains dimerize in the presence of a specific wavelength (e.g., blue light). In some embodiments of any of the aspects, the photochromic protein domain comprises one of SEQ ID NOs: 298-301 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 298-301, that maintains the same function.

```
SEQ ID NO: 298, Dropna-145K (224 aa)
MSVIKPDMKIKLRMEGAVNGHPFAIEGVGLGKPFEGKQSMDLKVK

EGGPLPFAYDILTTVFCYGNRVFAKYPENIVDYFKQSFPEGYSWE

RSMNYEDGGICNATNDITLDGDCYIYEIRFDGVNFPANGPVMQKR

TVKWEPSTEKLYVRDGVLKGDVNMALSLEGGGHYRCDFKTTYKAK

KVVQLPDYHFVDHHIEIKSHDKDYSNVNLHEHAEAHSELPRQAK

SEQ ID NO: 299, Dropna-145N (224 aa)
MSVIKPDMKIKLRMEGAVNGHPFAIEGVGLGKPFEGKQSMDLKVK

EGGPLPFAYDILTTVFCYGNRVFAKYPENIVDYFKQSFPEGYSWE

RSMNYEDGGICNATNDITLDGDCYIYEIRFDGVNFPANGPVMQKR

TVKWEPSTENLYVRDGVLKGDVNMALSLEGGGHYRCDFKTTYKAK

KVVQLPDYHFVDHHIEIKSHDKDYSNVNLHEHAEAHSELPRQAK
```

-continued

SEQ ID NO: 300, Padron-145N (224 aa)
MSVIKPDMKIKLRMEGAVNGHPFAIEGVGLGKPFEGKQSMDLKVK
EGGPLPFAYDILTMAFCYGNRVFAKYPENIVDYFKQSFPEGYSWE
RSMHYEDGGSCNATNDITLDGDCYIYEIRFDGVNFPANGPVMQKR
TVKWERSTENLYVRDGVLKSDGNYALSLEGGGHYRCDFKTTYKAK
KVVQLPDYHSVDHHIEIKSHDKDYSNVNLHEHAEAHSELPRQAN SEQ ID NO: 301, mApple-162H-164A (236 aa)
MVSKGEENNMAIIKEFMRFKVHMEGSVNGHEFEIEGEGEGRPYEA
FQTAKLKVTKGGPLPFAWDILSPQFMYGSKVYIKHPADIPDYFKL
SFPEGFRWERVMNFEDGGIIHVNQDSSLQDGVFIYKVKLRGTNFP
SDGPVMQKKTMGWEASEERMYPEDGAHKAEIKKRLKLKDGGHYAA
EVKTTYKAKKPVQLPGAYIVDIKLDIVSHNEDYTIVEQYERAEGR
HSTGGMDELYK Cytosolic Sequestering Domain In several aspects, described herein are synTF polypeptides comprising a cytosolic sequestering domain or protein, also referred to herein as a translocation domain. As used herein, the term "cytosolic sequestering domain" refers to a domain that influences the subcellular location of the synTF to which it is linked, e.g., through the binding of a ligand.

In some embodiments of any of the aspects, a synTF polypeptide as described herein (or a synTF polypeptide system collectively) comprises 1, 2, 3, 4, 5, or more cytosolic sequestering domain(s). In some embodiments of any of the aspects, the synTF polypeptide or system comprises one cytosolic sequestering domain. In embodiments comprising multiple cytosolic sequestering domains, the multiple cytosolic sequestering domains can be different individual cytosolic sequestering domains or multiple copies of the same cytosolic sequestering domain, or a combination of the foregoing.

In some embodiments of any of the aspects, the cytosolic sequestering protein comprises a ligand binding domain (LBD), wherein in the presence of the ligand, the sequestering of the protein to the cytosol is inhibited. In some embodiments of any of the aspects, cytosolic sequestering protein further comprises a nuclear localization signal (NLS), wherein in the absence of the ligand the NLS is inhibited thereby preventing translocation of the sequestering protein to the nucleus, and wherein in the presence of the ligand the nuclear localization signal is exposed enabling translocation of the sequestering protein to the nucleus. Accordingly, when the ligand is absent, the synTF is sequestered to the cytosol. When the ligand is absent, the synTF is translocated to the nucleus.

In some embodiments of any of the aspects, the sequestering protein comprises at least a portion of the estrogen receptor (ER). The ER naturally associates with cytoplasmic factors in the cell in the absence of cognate ligands, effectively sequestering itself in the cytoplasm. Binding of cognate ligands, such as estrogen or other steroid hormone derivatives, cause a conformational change to the receptor that allow dissociation from the cytoplasmic complexes and expose a nuclear localization signal, permitting translocation into the nucleus.

In some embodiments of any of the aspects, the sequestering protein comprises SEQ ID NO: 302 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 302 that maintains the same function. In some embodiments of any of the aspects, the sequestering protein comprises a portion of the ER (e.g., SEQ ID NO: 302), e.g., the C-terminal ligand-binding and nuclear localization domains of ER. In some embodiments of any of the aspects, the sequestering protein comprises residues 282-595 of SEQ ID NO: 302 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to residues 282-595 of SEQ ID NO: 302.

SEQ ID NO: 302, estrogen receptor isoform 1 [*Homo sapiens*]; NCBI Reference Sequence: NP_000116.2 (595 aa)
MTMTLHTKASGMALLHQIQGNELEPLNRPQLKIPLERPLGEVYLD
SSKPAVYNYPEGAAYEFNAAAAANAQVYGQTGLPYGPGSEAAAFG
SNGLGGFPPLNSVSPSPLMLLHPPPQLSPFLQPHGQQVPYYLENE
PSGYTVREAGPPAFYRPNSDNRRQGGRERLASTNDKGSMAMESAK
ETRYCAVCNDYASGYHYGVWSCEGCKAFFKRSIQGHNDYMCPATN
QCTIDKNRRKSCQACRLRKCYEVGMMKGGIRKDRRGGRMLKHKRQ
RDDGEGRGEVGSAGDMRAANLWPSPLMIKRSKKNSLALSLTADQM
VSALLDAEPPILYSEYDPTRPFSEASMMGLLTNLADRELVHMINW
AKRVPGFVDLTLHDQVHLLECAWLEILMIGLVWRSMEHPGKLLFA
PNLLLDRNQGKCVEGMVEIFDMLLATSSRFRMMNLQGEEFVCLKS
IILLNSGVYTFLSSTLKSLEEKDHIHRVLDKITDTLIHLMAKAGL
TLQQQHQRLAQLLLILSHIRHMSNKGMEHLYSMKCKNVVPLYDLL
LEMLDAHRLHAPTSRGGASVEETDQSHLATAGSTSSHSLQKYYIT
GEAEGFPATV In some embodiments of any of the aspects, the estrogen receptor comprises at least one mutation that decreases its ability to bind to its natural ligands (e.g., estradiol) but maintains the ability to bind to synthetic ligands such as tamoxifen and analogs thereof. In some embodiments of any of the aspects, the estrogen receptor comprises at least one of the following mutations: G400V, G521R, L539A, L540A, M543A, L544A, V595A or any combination thereof. In some embodiments of any of the aspects, a triple G400V/MS43A/L544A ER mutant is referred to herein as ERT2. In some embodiments of any of the aspects, the sequestering protein further comprises a V595A mutation from ER (e.g., SEQ ID NO: 302). In some embodiments of any of the aspects, the sequestering protein comprises an estrogen ligand binding domain (ERT2) or a variant thereof. In some embodiments of any of the aspects, the sequestering protein comprises ERT, ERT2, ERT3, or a variant thereof. In some embodiments of any of the aspects, the sequestering protein comprises one of SEQ ID NOs: 43, 304-306 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 43, 304-306, that maintains the same function. See e.g., U.S. Pat. No. 7,112,715; Feil et al., Biochemical and Biophysical Research Communications, Volume 237, Issue 3, 28 Aug. 1997, Pages 752-757; Felker et al., PLoS One. 2016 Apr. 14; 11(4):e0152989; the contents of each of which are incorporated herein by reference in their entireties.

SEQ ID NO: 43, ERT2 (314 aa), G400V, M543A, L544A, and V595A mutations from ER (e.g., SEQ ID NO: 302) shown in bold, double underlined text

```
SAGDMRAANLWPSPLMIKRSKKNSLALSLTADQMVSALLDAEPPI

LYSEYDPTRPFSEASMMGLLTNLADRELVHMINWAKRVPGFVDLT

LHDQVHLLECAWLEILMIGLVWRSMEHP KLLFAPNLLLDRNQGK

CVEGMVEIFDMLLATSSRFRMMNLQGEEFVCLKSIILLNSGVYTF

LSSTLKSLEEKDHIHRVLDKITDTLIHLMAKAGLTLQQQHQRLAQ

LLLILSHIRHMSNKGMEHLYSMKCKNVVPLYDLLLEAA DAHRLHA

PTSRGGASVEETDQSHLATAGSTSSHSLQKYYITGEAEGFPATA
```

SEQ ID NO: 304, ERT (314 aa), G521R mutation from ER (e.g., SEQ ID NO: 302) shown in bold, double underlined text

```
SAGDMRAANLWPSPLMIKRSKKNSLALSLTADQMVSALLDAEPPI

LYSEYDPTRPFSEASMMGLLTNLADRELVHMINWAKRVPGFVDLT

LHDQVHLLECAWLEILMIGLVWRSMEHPGKLLFAPNLLLDRNQGK

CVEGMVEIFDMLLATSSRFRMMNLQGEEFVCLKSIILLNSGVYTF

LSSTLKSLEEKDHIHRVLDKITDTLIHLMAKAGLTLQQQHQRLAQ

LLLILSHIRHMSNKR MEHLYSMKCKNVVPLYDLLLEMLDAHRLH

APTSRGGASVEETDQSHLATAGSTSSHSLQKYYITGEAEGFPATV
```

SEQ ID NO: 305, ERT3 (314 aa), M543A, L544A, and V595A mutations from ER (e.g., SEQ ID NO: 302) shown in bold, double underlined text

```
SAGDMRAANLWPSPLMIKRSKKNSLALSLTADQMVSALLDAEPPI

LYSEYDPTRPFSEASMMGLLTNLADRELVHMINWAKRVPGFVDLT

LHDQVHLLECAWLEILMIGLVWRSMEHPGKLLFAPNLLLDRNQGK

CVEGMVEIFDMLLATSSRFRMMNLQGEEFVCLKSIILLNSGVYTF

LSSTLKSLEEKDHIHRVLDKITDTLIHLMAKAGLTLQQQHQRLAQ

LLLILSHIRHMSNKGMEHLYSMKCKNVVPLYDLLLEAA DAHRLHA

PTSRGGASVEETDQSHLATAGSTSSHSLQKYYITGEAEGFPATA
```

SEQ ID NO: 306, ERT (314 aa), G400V, L539A, L540A mutations from ER (e.g., SEQ ID NO: 302) shown in bold, double underlined text

```
SAGDMRAANLWPSPLMIKRSKKNSLALSLTADQMVSALLDAEPPI

LYSEYDPTRPFSEASMMGLLTNLADRELVHMINWAKRVPGFVDLT

LHDQVHLLECAWLEILMIGLVWRSMEHP KLLFAPNLLLDRNQGK

CVEGMVEIFDMLLATSSRFRMMNLQGEEFVCLKSIILLNSGVYTF

LSSTLKSLEEKDHIHRVLDKITDTLIHLMAKAGLTLQQQHQRLAQ

LLLILSHIRHMSNKGMEHLYSMKCKNVVPLYDAA LEMLDAHRLHA

PTSRGGASVEETDQSHLATAGSTSSHSLQKYYITGEAEGFPATV
```

In some embodiments of any of the aspects, the sequestering protein of the synTF polypeptide is in combination with 1, 2, 3, 4, 5, or more ligands. In some embodiments of any of the aspects, the sequestering protein of the synTF polypeptide is in combination with one ligand. In embodiments comprising multiple ligands, the multiple ligands can be different individual ligands or multiple copies of the same ligands, or a combination of the foregoing.

In some embodiments of any of the aspects, the ligand is estradiol (PubChem CID: 5757), or an analog thereof. In some embodiments of any of the aspects, the ligand is a synthetic ligand of the estrogen receptor, such as tamoxifen or a derivative thereof the ligand is selected from: tamoxifen, 4-hydroxytamoxifen (4OHT), endoxifen, and Fulvestrant, wherein binding of the ligand to the ERT (e.g., ERT2) exposes the NLS and results in nuclear translocation of the ERT. In some embodiments of any of the aspects, the ligand is 4-hydroxytamoxifen (4-OHT), shown below (PubChem CID: 449459), which can also be referred to as afimoxifene. In some embodiments of any of the aspects, the ligand is 4-Hydroxy-N-desmethyltamoxifen, shown below (PubChem CID: 10090750), which can also be referred to as endoxifen. In some embodiments of any of the aspects, the ligand is Fulvestrant shown below (PubChem CID 104741), which can also be referred to as ICI 182,780.

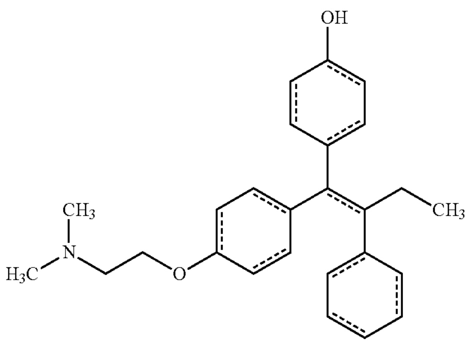

trans-4-OHT

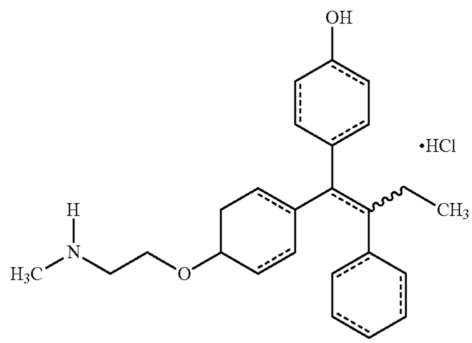

Endoxifen

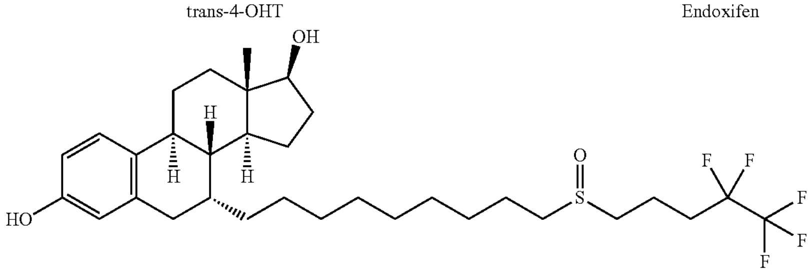

Fulvestrant

In some embodiments of any of the aspects, the sequestering protein of the synTF is a transmembrane receptor sequestering protein, and the DNA-binding domain (DBD) and transcriptional activator (TA) domain and transcriptional effector domain (TED) of the synTF are linked to the cytosolic side of the transmembrane domain of the receptor. In the absence of a specific ligand for the transmembrane protein, the DBD, TED, and TA of the synTF are sequestered to the cellular membrane. In the presence of a specific ligand for the transmembrane protein, the transmembrane protein cleaves itself such that the DBD, TED, and TA of the synTF are released into the cytosol to be transported to the nucleus. Non-limiting examples of transmembrane receptor sequestering protein include a synthetic notch receptor or first and second exogenous extracellular sensors, described further herein.

In some embodiments of any of the aspects, the cytosolic sequestering protein comprises a Notch receptor or a variant of endogenous Notch receptor, such as a synthetic Notch (synNotch) receptor. In some embodiments of any of the aspects, the synTF comprising a synNotch comprises: (a) an extracellular domain comprising a first member of a specific binding pair that is heterologous to the Notch receptor; (b) a Notch receptor regulatory region; and (c) an intracellular domain comprising the DNA binding domain, transcriptional activator (TA) domain, and transcriptional effector domain (TED) of the synTF. In the presence of a second member of the specific binding pair, binding of the first member of the specific binding pair to the second member of the specific binding pair induces cleavage of the binding-induced proteolytic cleavage site to activate the intracellular domain, thereby permitting the synTF to translocate to the nucleus. In the absence of a second member of the specific binding pair, the synTF remains sequestered at the cellular membrane. In some embodiments of any of the aspects, the sequestering protein comprises one of SEQ ID NOs: 307-308 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 307-308, that maintains the same function. See e.g., U.S. Pat. No. 10,590,182; Morsut et al., Cell. 2016 Feb. 11; 164(4):780-91; the contents of which are incorporated herein by reference in their entireties. In some embodiments of any of the aspects, the Notch receptor regulatory region comprises Lin-12 Notch repeats A-C, heterodimerization domains HD-N and HD-C, a binding-induced proteolytic cleavage site, and a transmembrane domain. In some embodiments of any of the aspects, the Notch variant is a Notch receptor where the Notch extracellular subunit (NEC) (which includes the negative regulatory region (NRR)) is partially or completely removed. In some embodiments of any of the aspects, the Notch receptor regulatory region is a truncated or modified variant of synNotch, e.g., lacking one or more of the following domains: Lin-12 Notch repeats A-C, heterodimerization domains HD-N and HD-C, a binding-induced proteolytic cleavage site, the Notch extracellular domain (NEC), the negative regulatory region (NRR), or a transmembrane domain.

```
SEQ ID NO: 307, synNotch (306 aa)
PPQIEEACELPECQVDAGNKVCNLQCNNHACGWDGGDCSLNFNDP

WKNCTQSLQCWKYFSDGHCDSQCNSAGCLFDGFDCQLTEGQCNPL
```

-continued

```
YDQYCKDHFSDGHCDQGCNSAECEWDGLDCAEHVPERLAAGTLVL

VVLLPPDQLRNNSFHFLRELSHVLHTNVVFKRDAQGQQMIFPYYG

HEEELRKHPIKRSTVGWATSSLLPGTSGGRQRRELDPMDIRGSIV

YLEIDNRQCVQSSSQCFQSATDVAAFLGALASLGSLNIPYKIEAV

KSEPVEPPLPSQLHLMYVAAAAFVLLFFVGCGVLLS

SEQ ID NO: 308, synNotch (358 aa)
PCVGSNPCYNQGTCEPTSENPFYRCLCPAKFNGLLCHILDYSFTG

GAGRDIPPPQIEEACELPECQVDAGNKVCNLQCNNHACGWDGGDC

SLNFNDPWKNCTQSLQCWKYFSDGHCDSQCNSAGCLFDGFDCQLT

EGQCNPLYDQYCKDHFSDGHCDQGCNSAECEWDGLDCAEHVPERL

AAGTLVLVVLLPPDQLRNNSFHFLRELSHVLHTNVVFKRDAQGQQ

MIFPYYGHEEELRKHPIKRSTVGWATSSLLPGTSGGRQRRELDPM

DIRGSIVYLEIDNRQCVQSSSQCFQSATDVAAFLGALASLGSLNI

PYKIEAVKSEPVEPPLPSQLHLMYVAAAAFVLLFFVGCGVLLS
```

Suitable first members of a specific binding pairs (e.g., of the synNotch) include, but are not limited to, antibody-based recognition scaffolds; antibodies (i.e., an antibody-based recognition scaffold, including antigen-binding antibody fragments); non-antibody-based recognition scaffolds; antigens (e.g., endogenous antigens; exogenous antigens; etc.); a ligand for a receptor; a receptor; a target of a non-antibody-based recognition scaffold; an Fc receptor (e.g., FcγRIIIa; FcγRIIIb; etc.); an extracellular matrix component; and the like.

Specific binding pairs (e.g., of the synNotch) include, e.g., antigen-antibody specific binding pairs, where the first member is an antibody (or antibody-based recognition scaffold) that binds specifically to the second member, which is an antigen, or where the first member is an antigen and the second member is an antibody (or antibody-based recognition scaffold) that binds specifically to the antigen; ligand-receptor specific binding pairs, where the first member is a ligand and the second member is a receptor to which the ligand binds, or where the first member is a receptor, and the second member is a ligand that binds to the receptor; non-antibody-based recognition scaffold-target specific binding pairs, where the first member is a non-antibody-based recognition scaffold and the second member is a target that binds to the non-antibody-based recognition scaffold, or where the first member is a target and the second member is a non-antibody-based recognition scaffold that binds to the target; adhesion molecule-extracellular matrix binding pairs; Fc receptor-Fc binding pairs, where the first member comprises an immunoglobulin Fc that binds to the second member, which is an Fc receptor, or where the first member is an Fc receptor that binds to the second member which comprises an immunoglobulin Fc; and receptor-co-receptor binding pairs, where the first member is a receptor that binds specifically to the second member which is a co-receptor, or where the first member is a co-receptor that binds specifically to the second member which is a receptor.

In some embodiments of any of the aspects, the transmembrane receptor sequestering protein comprises first and second exogenous extracellular sensors, wherein said first exogenous extracellular sensor comprises: (a) a ligand binding domain, (b) a transmembrane domain, (c) a protease cleavage site, and (d) the DBD, TED, and TA of the synTF; and wherein said second exogenous extracellular sensor comprises: (e) a ligand binding domain, (f) a transmembrane domain, and (g) a protease domain. Such a system can also be referred to as a modular extracellular sensor architecture (MESA) system. In the presence of a ligand for the first and second exogenous extracellular sensors, the two receptors are brought into proximity, permitting the protease to cleave the protease cleavage site and release the DBD, TED, and TA of the synTF into the cytosol to be translocated to the nucleus. In the absence of a ligand for the first and second exogenous extracellular sensors, the DBD, TED, and TA of the synTF remains sequestered at the cell membrane. In some embodiments of any of the aspects, the protease comprises any protease as described herein (e.g., NS3), and the protease cleavage site comprises an NS3 protease cleavage site as described herein. See e.g., US Patent Application 2014/0234851; Daringer et al., ACS Synth. Biol. 2014, 3, 12, 892-902.

Any type of suitable ligand binding domain (LB) can be employed with transmembrane receptor sequestering protein. Ligand binding domains can, for example, be derived from either an existing receptor ligand-binding domain or from an engineered ligand binding domain. Existing ligand-binding domains could come, for example, from cytokine receptors, chemokine receptors, innate immune receptors (TLRs, etc.), olfactory receptors, steroid and hormone receptors, growth factor receptors, mutant receptors that occur in cancer, neurotransmitter receptors. Engineered ligand-binding domains can be, for example, single-chain antibodies (see scFv constructs discussion below), engineered fibronectin based binding proteins, and engineered consensus-derived binding proteins (e.g., based upon leucine-rich repeats or ankyrin-rich repeats, such as DARPins). The ligand can be any cognate ligand of such ligand-binding domains.

Linker Peptide

In several aspects, described herein are synTF polypeptides comprising at least one linker peptide. As used herein "linker peptide" (used interchangeably with "peptide linker") refers to an oligo- or polypeptide region from about 2 to 100 amino acids in length, which links together any of the sequences of the polypeptides as described herein. In some embodiment, linkers can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable.

In some embodiments of any of the aspects, a synTF polypeptide as described herein (or a synTF polypeptide system collectively) comprises 1, 2, 3, 4, 5, or more linker peptide(s). In some embodiments of any of the aspects, the synTF polypeptide or system comprises one linker peptide. In embodiments comprising multiple linker peptides, the multiple linker peptides can be different individual linker peptides or multiple copies of the same linker peptide, or a combination of the foregoing. In some embodiments of any of the aspects, the linker peptide can be positioned anywhere, between any two domains as described herein: e.g., between the DBD and the RP; between the RP and TA; between the DBD and TA; between the TED and TA; between the TED and DBD; between the TED and RP; within the DBD, TA, TED, or regulator protein; or any combination thereof. In some embodiments of any of the aspects, the linker peptide can be positioned within the DBD, TA, TED, or RP, e.g., to link constituents of the domains.

In some embodiments of any one aspects described herein, the linkers connect several ZFs to each other in tandem to form a ZF array. In some embodiments of any one aspects described herein, the linker connects a first ZFA with a second ZFA. In some embodiments of any one aspects described herein, the linkers connect several ZFAs to each other to in tandem to form a ZF-containing ZF protein domain. Non-limiting examples of peptide linker molecules useful in the polypeptides described herein include glycine-rich peptide linkers (see, e.g., U.S. Pat. No. 5,908,626), wherein more than half of the amino acid residues are glycine. Preferably, such glycine-rich peptide linkers consist of about 20 or fewer amino acids. A linker molecule may also include non-peptide or partial peptide molecules. For instance, the peptides can be linked to peptides or other molecules using well known cross-linking molecules such as glutaraldehyde or EDC (Pierce, Rockford, Illinois). In some embodiments of the engineered synTFs described herein, the ZF arrays (ZFAs) in the ZF protein domain of the synTF are joined together in the respective fusion protein with a linker peptide.

```
Non-limiting examples of linker peptide include,
but are not limited to:
                                      (SEQ ID NO: 309)
PGER,

                                      (SEQ ID NO: 310)
TGSQK,

                                      (SEQ ID NO: 311)
TGEKP,

                                      (SEQ ID NO: 312)
THLR,

                                      (SEQ ID NO: 313)
TGGGEKP,

                                      (SEQ ID NO: 314)
FHYDRNNIAVGADESVVKEAHREVINSS

TEGLLLNIDKDIRKILSGYIVEIEDTE;

                                      (SEQ ID NO: 315)
VEIEDTE,

                                      (SEQ ID NO: 316)
KDIRKILSGYIVEIEDTE;

                                      (SEQ ID NO: 317)
STEGLLLNIDKDIRKILSGYIVEIEDTE,

                                      (SEQ ID NO: 318)
EVKQENRLLNESES;

                                      (SEQ ID NO: 319)
VGADESVVKEAHREVINSSTEGLLLNID

KDIRKILSGYIVEIEDTE;

                                      (SEQ ID NO: 320)
GGSGG;

                                      (SEQ ID NO: 321)
GGGSG;

                                      (SEQ ID NO: 322)
CVRGS,

                                      (SEQ ID NO: 323)
GGGGSG,

                                      (SEQ ID NO: 324)
GGSGSGSAC,
```

-continued

```
                                      (SEQ ID NO: 325)
LEGGGGSGG,

                                      (SEQ ID NO: 326)
GGGGSGGT,

                                      (SEQ ID NO: 327)
SGGGSGGSGSS;

                                      (SEQ ID NO: 328)
PGAGSSGDIM

                                      (SEQ ID NO: 329)
GSSGTGSGSGTS;

                                      (SEQ ID NO: 224)
SGTS;

                                      (SEQ ID NO: 225)
GSGS,

                                      (SEQ ID NO: 330)
GGSGGS,
and

                                      (SEQ ID NO: 285)
GSSGSS.
```

As non-limiting examples, TGSQK (SEQ ID NO: 310) or TGEKP (SEQ ID NO: 311) or TGGGEKP (SEQ ID NO: 313) can be used as linker between ZFAs; VEIEDTE (SEQ ID NO: 315), GGSGGS (SEQ ID NO: 330), GGSGG (SEQ ID NO: 320), GGGSG (SEQ ID NO: 321), CVRGS (SEQ ID NO: 322), GGGGSG (SEQ ID NO: 323), GGSGSGSAC (SEQ ID NO: 324), LEGGGGSGG (SEQ ID NO: 325), GGGGSGGT (SEQ ID NO: 326), or SGGGSGGSGSS (SEQ ID NO: 327) can be used to link ZF domains and effector domains together; PGAGSSGDIM (SEQ ID NO: 328) GSSGTGSGSGTS (SEQ ID NO: 329); SGTS (SEQ ID NO: 224); GSGS (SEQ ID NO: 225), or GSSGSS (SEQ ID NO: 285) can be used to link regions of a SMASh domain, a StaPL domain, or an NS3/NS4a domain, described further herein.

Flexible linkers are generally composed of small, non-polar or polar residues such as Gly, Ser and Thr. In one embodiment of any fusion protein described herein that includes a linker, the linker peptide comprises at least one amino acid that is Gly or Ser. In one embodiment of a fusion protein described herein that includes a linker, the linker is a flexible polypeptide between 1 and 25 residues in length. Common examples of flexible peptide linkers include (GGS)n, where n=1 to 8 (SEQ ID NO: 358) (SEQ ID NO: 331, GGSGGSGGSGGSGGSGGSGGSGGS), or $(Gly_4Ser)n$ repeat where n=1-8 (SEQ ID NO: 359) (SEQ ID NO: 332, GGGGSGGGGSGGGGSGGGGSGGGGSGGGGSGGGGSGGGGS), preferably, n=3, 4, 5, or 6, that is (Gly-Gly-Gly-Gly-Ser)n (SEQ ID NO: 333), GGGGS (SEQ ID NO: 333), where n indicates the number of repeats of the motif. For example, the flexible linker is $(GGS)_2$ (SEQ ID NO: 334, GGSGGS). Alternatively, flexible peptide linkers include Gly-Ser repeats $(Gly\text{-}Ser)_p$ where p indicates the number of Gly-Ser repeats of the motif, p=1-8 (SEQ ID NO: 360) (SEQ ID NO: 335 GSGSGSGSGSGSGSGS), preferably, n=3, 4, 5, or 6. Another example of a flexible linker is TGSQK (SEQ ID NO: 310).

In one embodiment of the engineered synTFs described herein, wherein the ZF protein domains and effector domains are joined together with a linker peptide, the linker peptide is about 1-20 amino acids long. In one embodiment, the linker peptide does not comprise Lys, or does not comprise Arg, or does not comprise both Lys and Arg.

In some embodiments of the engineered synTFs described herein, the ZF protein domains and effector domains are joined together chemical cross-linking agents. Bifunctional cross-linking molecules are linker molecules that possess two distinct reactive sites. For example, one of the reactive sites of a bifunctional linker molecule may be reacted with a functional group on a peptide to form a covalent linkage and the other reactive site may be reacted with a functional group on another molecule to form a covalent linkage. General methods for cross-linking molecules have been reviewed (see, e.g., Means and Feeney, Bioconjugate Chem., 1: 2-12 (1990)).

Homobifunctional cross-linker molecules have two reactive sites which are chemically the same. Non-limiting examples of homobifunctional cross-linker molecules include, without limitation, glutaraldehyde; N,N'-bis(3-maleimido-propionyl)-2-hydroxy-1,3-propanediol (a sulfhydryl-specific homobifunctional cross-linker); certain N-succinimide esters (e.g., disuccinimidyl suberate, dithiobis (succinimidyl propionate), and soluble bis-sulfonic acid and salt thereof (see, e.g., Pierce Chemicals, Rockford, Illinois; SIGMA-ALDRICH CORP., St. Louis, Missouri).

A bifunctional cross-linker molecule is a heterobifunctional linker molecule, meaning that the linker has at least two different reactive sites, each of which can be separately linked to a peptide or other molecule. Use of such heterobifunctional linkers permits chemically separate and stepwise addition (vectorial conjunction) of each of the reactive sites to a selected peptide sequence. Heterobifunctional linker molecules useful in the disclosure include, without limitation, m-maleimidobenzoyl-N-hydroxysuccinimide ester (see, Green et al., Cell, 28: 477-487 (1982); Palker et al., Proc. Natl. Acad. Sci (USA), 84: 2479-2483 (1987)); m-maleimido-benzoylsulfosuccinimide ester; maleimidobutyric acid N-hydroxysuccinimide ester; and N-succinimidyl 3-(2-pyridyl-dithio)propionate (see, e.g., Carlos et al., Biochem. J., 173: 723-737 (1978); SIGMA-ALDRICH CORP., St. Louis, Missouri).

In some embodiments of any aspect described herein, in the synTF described or the ZF-containing fusion protein described herein, all the helices within a ZFA are linked by peptide linkers ($L_2$) having four to six amino acid residues.

In some embodiments of any aspect described herein, in the synTF described or the ZF-containing fusion protein described herein, all the helices within an individual ZFA are linked by rigid peptide linkers such as TGEKP (SEQ ID NO: 311) or TGSKP (SEQ ID NO: 336) or TGQKP (SEQ ID NO: 337) or TGGKP (SEQ ID NO: 338). The rigid linker aids in conferring synergistic binding of the ZF motifs to its target DNA sequence.

In one embodiment of any aspect described herein, in the synTF described or the ZF containing fusion protein described herein, the ($L_1$) or ($L_2$) is a flexible linker. Non-limiting examples include: TGSQKP (SEQ ID NO: 339) and TGGGEKP (SEQ ID NO: 313). In one embodiment, the linker flexible peptide is 1-20 amino acids long. The flexible linker aid in weakening cooperativity between adjacent ZF motifs.

In one embodiment of any aspect described herein, in the synTF described or the ZF containing fusion protein described herein, the (L1) or (L2) is a rigid linker. Non-limiting examples include: TGEKP (SEQ ID NO: 311), TGSKP (SEQ ID NO: 336), TGQKP (SEQ ID NO: 337) and TGGKP (SEQ ID NO: 338).

In some embodiments of any aspect described herein, in the synTF described or the ZF containing fusion protein described herein, where there are two or more ZFAs, the individual ZFAs are linked by flexible peptide linkers, such as TGSQKP (SEQ ID NO: 339). In another embodiment, the ZFAs are linked by chemical crosslinkers. Chemical cross-linkers are known in the art.

In some embodiments of any aspect described herein, in the synTF described or the ZF containing fusion protein described herein, all the helices within an individual ZFA are linked by a combination of rigid peptide linkers and flexible peptide linkers. In some embodiments of any of the aspects, the rigid peptide linkers and flexible peptide linkers are used alternatingly to connect the fingers.

Self-Cleaving Peptide

In several aspects, described herein are synTF polypeptides comprising a self-cleaving peptide. As used herein, the term "self-cleaving peptide" refers to a short amino acid sequence (e.g., approximately 18-22 aa-long peptides) that can catalyze its own cleavage. In some embodiments of any of the aspects, a multi-component synTF system as described herein (e.g., induced proximity synTF system) comprises at least two polypeptides that are physically linked to one another through a self-cleaving peptide domain. The self-cleaving peptide allows the nucleic acids of the first polypeptide and second polypeptide (and/or third polypeptide, etc.) to be present in the same vector, but after translation the self-cleaving peptide cleaves the translated polypeptide into the multiple separate polypeptides.

In some embodiments of any of the aspects, a synTF polypeptide as described herein (or a synTF polypeptide system collectively) comprises 1, 2, 3, 4, 5, or more self-cleaving peptides, e.g., in between each synTF polypeptide. In some embodiments of any of the aspects, the synTF polypeptide or system comprises one self-cleaving peptide, e.g., in between a first polypeptide and a second polypeptide of a synTF polypeptide system. In embodiments comprising multiple self-cleaving peptides, the multiple self-cleaving peptides can be different individual self-cleaving peptides or multiple copies of the same self-cleaving peptide, or a combination of the foregoing.

In some embodiments, self-cleaving peptides are used, for example, in heterodimerization domain synTFs. As a non-limiting example, a 2A self-cleaving peptide can be in between a first polypeptide region comprising [ABI]-[ZF] and a second polypeptide region comprising [TA]-[TED]-[PYL]. Following translation of the polypeptide, the 2A sequence, which is a self-cleaving peptide, cleaves the polypeptide into two polypeptides: [ABI]-[ZF] and [TA]-[TED]-[PYL], which in the presence of ABA can form a [TA]-[TED]-[PYL]-ABA-[ABI]-[ZF] complex, thus coupling the DBD (ZF), TA (e.g., p65), and TED (e.g., IWS1 TIMs domain).

In some embodiments of any of the aspects, the self-cleaving peptide belongs to the 2A peptide family, which can also be referred to as a 2A Ribosomal Skip Sequence. Non-limiting examples of 2A peptides include P2A, E2A, F2A and T2A (see e.g., Table 13). F2A is derived from foot-and-mouth disease virus 18; E2A is derived from equine rhinitis A virus; P2A is derived from porcine teschovirus-1 2A; T2A is derived from those a asigna virus 2A. In some embodiments of any of the aspects, the N-terminal of the 2A peptide comprises the sequence "GSG" (Gly-Ser-Gly). In some embodiments of any of the aspects, the N-terminal of the 2A peptide does not comprise the sequence "GSG" (Gly-Ser-Gly).

TABLE 13

| Exemplary Self-Cleaving Peptides | | |
|---|---|---|
| SEQ ID NO: | Name | Sequence |
| 340 | T2A | (GSG) EGRGSLLTCGDVEENPGP |
| 341 | P2A | (GSG) ATNFSLLKQAGDVEENPGP |
| 342 | E2A | (GSG) QCTNYALLKLAGDVESNPGP |
| 343 | F2A | (GSG) VKQTLNFDLLKLAGDVESNPGP |

The 2A-peptide-mediated cleavage commences after protein translation. The cleavage is triggered by breaking of peptide bond between the Proline (P) and Glycine (G) in the C-terminal of the 2A peptide. The molecular mechanism of 2A-peptide-mediated cleavage involves ribosomal "skipping" of glycyl-prolyl peptide bond formation rather than true proteolytic cleavage. Different 2A peptides have different efficiencies of self-cleaving, with P2A being the most efficient and F2A the least efficient. Therefore, up to 50% of F2A-linked proteins can remain in the cell as a fusion protein.

In some embodiments of any of the aspects, the self-cleaving peptide of a synTF polypeptide system as described herein comprises SEQ ID NOs: 340-343, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 340-343, that maintains the same function (e.g., self-cleavage).

In some embodiments of any of the aspects, providing the multiple polypeptides of the synTF systems as described herein in a 1:1 (or 1:1:1, etc.) stoichiometric ratio is advantageous (e.g., this stoichiometric ratio results in optimal functionality). In embodiments where a 1:1 (or 1:1:1, etc.) ratio of the first and second (and third etc.) polypeptides of a synTF system is advantageous, then the first and second polypeptides can be provided in a single vector, flanking a self-cleaving peptide(s) as described herein. In embodiments where a 1:1 (or 1:1:1, etc.) ratio of the first and second (and third etc.) polypeptides of a synTF system is not advantageous (e.g., this stoichiometric ratio results in suboptimal functionality, and other ratios result in optimal functionality) then the first and second polypeptides can be provided in multiple separate vectors, e.g., at the desired stoichiometric ratios.

Detectable Marker

In several aspects, described herein are synTF polypeptides comprising at least one detectable marker. As used herein, the term "detectable marker" refers to a moiety that, when attached to the synTF polypeptide, confers detectability upon that polypeptide or another molecule to which the polypeptide binds. In some embodiments of any of the aspects, the synTF polypeptide (or the synTF polypeptide system collectively) comprises 1, 2, 3, 4, 5, or more detectable markers. In some embodiments of any of the aspects, the synTF polypeptide or system comprises one detectable marker. In embodiments comprising multiple detectable markers, the multiple detectable markers can be different individual detectable markers or multiple copies of the same detectable markers, or a combination of the foregoing.

In some embodiments of any of the aspects, fluorescent moieties can be used as detectable markers, but detectable markers also include, for example, isotopes, fluorescent proteins and peptides, enzymes, components of a specific binding pair, chromophores, affinity tags as defined herein, antibodies, colloidal metals (i.e. gold) and quantum dots. Detectable markers can be either directly or indirectly detectable. Directly detectable markers do not require additional reagents or substrates in order to generate detectable signal. Examples include isotopes and fluorophores. Indirectly detectable markers require the presence or action of one or more co-factors or substrates. Examples include enzymes such as β-galactosidase which is detectable by generation of colored reaction products upon cleavage of substrates such as the chromogen X-gal (5-bromo-4-chloro-3-indoyl-β-D-galactopyranoside), horseradish peroxidase which is detectable by generation of a colored reaction product in the presence of the substrate diaminobenzidine and alkaline phosphatase which is detectable by generation of colored reaction product in the presence of nitroblue tetrazolium and 5-bromo-4-chloro-3-indolyl phosphate, and affinity tags. Non-limiting examples of affinity tags include Strep-tags, chitin binding proteins (CBP), maltose binding proteins (MBP), glutathione-S-transferase (GST), FLAG-tags, HA-tags, Myc-tags, poly(His)-tags as well as derivatives thereof. In some embodiments of any of the aspects, the detectable marker is selected from GFP, V5, HA1, Myc, VSV-G, HSV, FLAG, HIS, mCherry, AU1, and biotin.

```
SEQ ID NO: 344, NLS,
PKKKRKV

SEQ ID NO: 345, 3X FLAG Tag + Nuclear
Localization Sequence (in bold text)
DYKDHDGDYKDHDIDYKDDDDKMAPKKKRKVGIHGVPGG

SEQ ID NO: 346, AU1 tag,
DTYRYI

SEQ ID NO: 347, HA tag,
YPYDVPDYA

SEQ ID NO: 348, FLAG Tag,
DYKDDDDK

SEQ ID NO: 349, mCherry:
VSKGEEDNMAIIKEFMRFKVHMEGSVNGHEFEIEGEGEGRPYEGT

QTAKLKVTKGGPLPFAWDILSPQFMYGSKAYVKHPADIPDYLKLS

FPEGFKWERVMNFEDGGVVTVTQDSSLQDGEFIYKVKLRGTNFPS

DGPVMQKKTMGWQASSERMYPEDGALKGEIKQRLKLKDGGHYDAE

VKTTYKAKKPVQLPGAYNVNIKLDITSHNEDYTIVEQYERAEGRH

STGGMDELYK

SEQ ID NO: 350, huEGFRt
(a truncated human EGFR polypeptide)
RKVCNGIGIGEFKDSLSINATNIKHFKNCTSISGDLHILPVAFRG

DSFTHTPPLDPQELDILKTVKEITGFLLIQAWPENRTDLHAFENL

EIIRGRTKQHGQFSLAVVSLNITSLGLRSLKEISDGDVIISGNKN

LCYANTINWKKLFGTSGQKTKIISNRGENSCKATGQVCHALCSPE

GCWGPEPRDCVSCRNVSRGRECVDKCNLLEGEPREFVENSECIQC

HPECLPQAMNITCTGRGPDNCIQCAHYIDGPHCVKTCPAGVMGEN

NTLVWKYADAGHVCHLCHPNCTYGCTGPGLEGCPTNGPKIPSIAT

GMVGALLLLLVVALGIGLFM
```

In some embodiments of any of the aspects, the detectable marker of a synTF polypeptide as described herein comprises SEQ ID NOs: 40-41 or SEQ ID NOs: 344-350, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 40-41 or SEQ ID NOs: 344 to 350, that maintains the same function (e.g., detection of the synTF polypeptide or cleaved fragments of the synTF polypeptide).

In some embodiments of any of the aspects, the detectable marker can be located anywhere within a synTF polypeptide as described herein. In one embodiment, the detectable marker is located between any domain of a synTF polypeptide as described herein, but is not found within a functional domain or does not disrupt the function of a domain. In some embodiments of any of the aspects, the detectable marker is located adjacent to and C terminal of the extracellular binding domain. Such a marker can be used to detect the expression of the synTF polypeptide, including cytosolic expression or nuclear translocation.

In some embodiments of any of the aspects, the detectable marker is located between the repressible protease and a protease cleavage site; such a marker can be used to detect the cleavage and/or expression of the synTF polypeptide. In some embodiments of any of the aspects, the detectable marker that is located between the repressible protease and a protease cleavage site comprises the AU1 tag, the HA1 tag, or any other marker as described herein.

In some embodiments of any of the aspects, the detectable marker is located adjacent and N-terminal to the repressible protease. In some embodiments of any of the aspects, the detectable marker is located adjacent and N-terminal to the repressible protease and C-terminal to a first protease cleavage site. In some embodiments of any of the aspects, the detectable marker is located adjacent to and C terminal to the repressible protease. In some embodiments of any of the aspects, the detectable marker is located adjacent to and C terminal to the repressible protease and N-terminal to a second protease cleavage site.

In some embodiments of any of the aspects, the detectable marker is located at the C-terminal end of the polypeptide. Such a marker can be used to detect the intracellular expression of the synTF polypeptide. In some embodiments of any of the aspects, the detectable marker located at the C-terminal end of the polypeptide comprises mCherry or another marker as described herein.

In some embodiments of any of the aspects, synTF polypeptides as described herein, especially those that are administered to a subject or those that are part of a pharmaceutical composition, do not comprise detectable markers that are immunogenic. In some embodiments of any of the aspects, synTF polypeptides as described herein do not comprise GFP, mCherry, HA1, or any other immunogenic markers.

II. Synthetic Transcription Factors

In multiple aspects described herein are synthetic transcription factors comprising: (a) at least one DNA binding domain (DBD), (b) a transcriptional activator (TA) domain; (c) a transcriptional effector domain (TED), and (d) at least one regulator protein (RP). In some embodiments of any of the aspects, the TA is directly coupled or linked to the DBD; as used herein the terms "directly coupled" or "directly linked" indicate that there are no other domain (other than a linker) found between the TA and DBD in the synTF or other construct. In some embodiments of any of the aspects, the TA is indirectly coupled or linked to the DBD; as used herein the terms "indirectly coupled" or "indirectly linked" indicate that at least one other domain is found between the TA and DBD in the synTF or other construct. In some embodiments of any of the aspects, the coupling of the TA to the DBD is regulated by the at least one RP. In some embodiments of any of the aspects, the cellular localization of the TA is regulated by the at least one regulator protein. In some embodiments of any of the aspects, at least one regulator protein is selected from the group consisting of repressible protease, induced degradation domain, induced proximity domain, and cytosolic sequestering domain.

In some embodiments of any of the aspects, the domains of the synTF can be in order, e.g., from N-terminus to C-terminus: DBD-ED-RP; DBD-RP-ED; ED-DBD-RP; ED-RP-DBD; RP-DBD-ED; or RP-ED-DBD; where "ED" designates the combination of the TA and TED (e.g., TA-TED or TED-TA). See also Tables 3-4. In embodiments comprising two regulator proteins (i.e., RP1 and RP2), the domains of the synTF can be in order, e.g., from N-terminus to C-terminus: DBD-ED-RP1-RP2; ED-DBD-RP1-RP2; RP1-DBD-ED-RP2; DBD-RP1-ED-RP2; ED-RPP1-DBD-RP2; RP1-ED-DBD-RP2; RP1-ED-RP2-DBD; ED-RP1-RP2-DBD; RP2-RP1-ED-DBD; RP1-RP2-ED-DBD; ED-RP2-RP1-DBD; RP2-ED-RP1-DBD; RP2-DBD-RP1-ED; DBD-RP2-RP1-ED; RP1-RP2-DBD-ED; RP2-RP1-DBD-ED; DBD-RP1-RP2-ED; RP1-DBD-RP2-ED; ED-DBD-RP2-RP1; DBD-ED-RP2-RP1; RP2-ED-DBD-RP1; ED-RP2-DBD-RP1; DBD-RP2-ED-RP1; and RP2-DBD-ED-RP1, where "ED" designates the combination of the TA and TED (e.g., TA-TED or TED-TA).

In some embodiments and by way of an example only, an exemplary RP1 is selected from an induced proximity domain (IPD), or cytosolic sequestering domain (CS), and the RP2 is selected from the induced degradation domain (comprising a SMASh domain), as disclosed herein. In another embodiment, an exemplary RP1 is an induced degradation domain (comprising a SMASh domain) and the PR2 is selected from an induced proximity domain (IPD) or a cytosolic sequestering domain (IPD).

A. Repressible Protease SynTF

In some embodiments of any of the aspects, the regulator protein is a repressible protease. Accordingly, in one aspect described herein is a synTF comprising: (a) a DBD; (b) a TA; (c) a TED; and (d) a repressible protease domain (referred to herein as a PRO or RPD). In some embodiments of any of the aspects, the domains of the synTF can be in order, e.g., from N-terminus to C-terminus: DBD-ED-PRO; DBD-PRO-ED; ED-DBD-PRO; ED-PRO-DBD; PRO-DBD-ED; or PRO-ED-DBD, where "ED" designates the combination of the TA and TED (e.g., TA-TED or TED-TA) (see e.g., Table 3).

In some embodiments of any of the aspects, the repressible protease synTF further comprises at least one protease cleavage site (PC), as described further herein. In a preferred embodiment, the at least one protease cleavage site is located in between the DBD and TA, such that when the protease cleaves at the protease cleavage site, the DBD and TA are uncoupled. Accordingly, in some embodiments, the repressible protease synTF comprises from N-terminus to C-terminus: PRO-ED-PC-DBD; ED-PRO-PC-DBD; ED-PC-PRO-DBD; DBD-PC-PRO-ED; DBD-PRO-PC-ED; PRO-DBD-PC-ED; ED-PC-DBD-PRO; and DBD-PC-ED-PRO, where "ED" designates the combination of the TA and TED (e.g., TA-TED or TED-TA).

In some embodiments of any of the aspects, the repressible protease synTF comprises two protease cleavage sites (PC). In some embodiments of any of the aspects, the two protease cleavage sites are located directly N terminal and C terminal of the repressible protease domain, e.g., from N-terminus to C-terminus: PC1-PRO-PC2. In some embodiments of any of the aspects, the repressible protease synTF comprises from N-terminus to C-terminus: DBD-PC1-PRO-PC2-ED, or ED-PC1-PRO-PC2-DBD, where "ED" designates the combination of the TA and TED (e.g., TA-TED or TED-TA).

In some embodiments of any of the aspects, the repressible protease synTF further comprises a cofactor for the repressible protease (CO), as described further herein. In some embodiments of any of the aspects, the cofactor for the repressible protease is directly linked to the repressible protease, e.g., from N-terminus to C-terminus: CO—PRO or PRO-CO. In some embodiments of any of the aspects, the repressible protease synTF comprises from N-terminus to C-terminus: DBD-ED-PRO-CO; DBD-PRO-CO-ED; ED-DBD-PRO-CO; ED-PRO-CO-DBD; PRO-CO-DBD-ED; PRO-CO-ED-DBD; DBD-ED-CO-PRO; DBD-CO-PRO-ED; ED-DBD-CO-PRO; ED-CO-PRO-DBD; CO-PRO-DBD-ED; CO-PRO-ED-DBD; DBD-PC1-PRO-CO-PC2-ED; ED-PC1-PRO-CO-PC2-DBD; DBD-PC1-CO—PRO-PC2-ED; or ED-PC1-CO-PRO-PC2-DBD, where "ED" designates the combination of the TA and TED (e.g., TA-TED or TED-TA).

In some embodiments of any of the aspects, the DBD of the repressible protease synTF comprises ZF10-1. In some embodiments of any of the aspects, the DBD of the repressible protease synTF comprises SEQ ID NO: 36 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the SEQ ID NO: 36, that maintains the same function.

B. Induced Degradation Domain SynTF

In some embodiments of any of the aspects, the regulator protein is an induced degradation domain. Accordingly, in one aspect described herein is a synTF comprising: (a) a DBD; (b) a TA; (c) a TED; and (d) induced degradation domain (SMASh). As described herein, the SMASh domain can be a C-terminal SMASh domain or an N-terminal SMASh domain. In some embodiments of any of the aspects, the domains of the synTF can be in order, e.g., from N-terminus to C-terminus: DBD-ED-SMASh; ED-DBD-SMASh; SMASh-DBD-ED; or SMASh-ED-DBD; where "ED" designates the combination of the TA and TED (e.g., TA-TED or TED-TA) (see e.g., Table 3).

In some embodiments of any of the aspects, the DBD of the SMASh synTF comprises ZF10-1. In some embodiments of any of the aspects, the DBD of the SMASh synTF comprises SEQ ID NO: 36 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the SEQ ID NO: 36, that maintains the same function.

In some embodiments of the aspects, the induced degradation domain synTF further comprises a second regulator protein, e.g., a cytosolic sequestering domain (CS). Accordingly, in one aspect described herein is a synTF comprising: (a) a DBD; (b) a TA; (c) a TED; (d) an induced degradation domain (SMASh); and (e) a cytosolic sequestering domain (CS). In some embodiments of any of the aspects, the synTF comprises from N-terminus to C-terminus: DBD-ED-SMASh-CS; ED-DBD-SMASh-CS; SMASh-DBD-ED-CS; DBD-SMASh-ED-CS; ED-SMASh-DBD-CS; SMASh-ED-DBD-CS; SMASh-ED-CS-DBD; ED-SMASh-CS-DBD; CS-SMASh-ED-DBD; SMASh-CS-ED-DBD; ED-CS-SMASh-DBD; CS-ED-SMASh-DBD; CS-DBD-SMASh-ED; DBD-CS-SMASh-ED; SMASh-CS-DBD-ED; CS-SMASh-DBD-ED; DBD-SMASh-CS-ED; SMASh-DBD-CS-ED; ED-DBD-CS-SMASh; DBD-ED-CS-SMASh; CS-ED-DBD-SMASh; ED-CS-DBD-SMASh; DBD-CS-ED-SMASh; and CS-DBD-ED-SMASh, where "ED" designates the combination of the TA and TED (e.g., TA-TED or TED-TA). In some embodiments, the SMASh domain is at the C-terminus or N-terminus: e.g., SMASh-DBD-ED-CS; SMASh-ED-DBD-CS; SMASh-ED-CS-DBD; SMASh-CS-ED-DBD; SMASh-CS-DBD-ED; SMASh-DBD-CS-ED; ED-DBD-CS-SMASh; DBD-ED-CS-SMASh; CS-ED-DBD-SMASh; ED-CS-DBD-SMASh; DBD-CS-ED-SMASh; and CS-DBD-ED-SMASh, where "ED" designates the combination of the TA and TED (e.g., TA-TED or TED-TA).

In some embodiments of any of the aspects, the DBD of the SMASh/cytosolic sequestering synTF comprises ZF3-5. In some embodiments of any of the aspects, the DBD of the SMASh/cytosolic sequestering synTF comprises SEQ ID NO: 45 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the SEQ ID NO: 45, that maintains the same function.

In some embodiments of the aspects, the induced degradation domain synTF further comprises a second regulator protein, e.g., a repressible protease domain (PRO). Accordingly, in one aspect described herein is a synTF comprising: (a) a DBD; (b) a TA; (c) a TED; (d) induced degradation domain (SMASh); and (e) a repressible protease domain (PRO). In some embodiments of any of the aspects, the synTF comprises from N-terminus to C-terminus: DBD-ED-SMASh-PRO; ED-DBD-SMASh-PRO; SMASh-DBD-ED-PRO; DBD-SMASh-ED-PRO; ED-SMASh-DBD-PRO; SMASh-ED-DBD-PRO; SMASh-ED-PRO-DBD; ED-SMASh-PRO-DBD; PRO-SMASh-ED-DBD; SMASh-PRO-ED-DBD; ED-PRO-SMASh-DBD; PRO-ED-SMASh-DBD; PRO-DBD-SMASh-ED; DBD-PRO-SMASh-ED; SMASh-PRO-DBD-ED; PRO-SMASh-DBD-ED; DBD-SMASh-PRO-ED; SMASh-DBD-PRO-ED; ED-DBD-PRO-SMASh; DBD-ED-PRO-SMASh; PRO-ED-DBD-SMASh; ED-PRO-DBD-SMASh; DBD-PRO-ED-SMASh; and PRO-DBD-ED-SMASh, where "ED" designates the combination of the TA and TED (e.g., TA-TED or TED-TA). In some embodiments, the SMASh domain is at the C-terminus or N-terminus and the PRO domain is in between the DBD and ED domains: e.g., SMASh-ED-PRO-DBD; SMASh-DBD-PRO-ED; ED-PRO-DBD-SMASh; and DBD-PRO-ED-SMASh, where "ED" designates the combination of the TA and TED (e.g., TA-TED or TED-TA).

In some embodiments, the sequence of each domain is selected from exemplary domain sequences as described herein. When a protease inhibitor for the PRO domain is present, the TA and DBD are coupled and the synTF is ON, and when protease inhibitor for the PRO domain is absent, the TA and DBD are uncoupled and the synTF is OFF. When an inducer of the induced degradation pair is present (e.g., a protease inhibitor), the PRO/SMASh synTF system is degraded. When an inducer of the induced degradation pair is absent (e.g., a protease inhibitor), the SMASh tag is degraded and the PRO/SMASh synTF system is not degraded. In some embodiments of any of the aspects, the repressible protease domain and the induced degradation domain each comprise a different protease or each comprise an NS3 protease with sensitivities to different NS3 protease inhibitors, such that a separate protease inhibitor can be used to separately regulate the PRO domain and the SMASh domain.

In some embodiments of the aspects, the induced degradation domain synTF further comprises a second regulator protein, e.g., an induced proximity pair (IPD). Accordingly, in one aspect described herein is a synTF system comprising: (a) a DBD; (b) a TA; (c) a TED; (d) induced degradation domain (SMASh); and (e) an induced proximity pair (IPD). The induced degradation domain can be linked to either polypeptide of the IPD synTF system. In one aspect described herein is a synTF system comprising: (a) first polypeptide comprising: (i) a DBD, (ii) a first member of an induced proximity pair (IP1), and (iii) an induced degradation domain (SMASh); and (b) a second polypeptide comprising: (i) a TA; (ii) a TED; and (iii) a second member of an induced proximity pair (IP2). In another aspect described herein is a synTF system comprising: (a) first polypeptide comprising: (i) a DBD and (ii) a first member of an induced proximity pair (IP1); and (b) a second polypeptide comprising: (i) a TA; (ii) a TED, (iii) a second member of an induced proximity pair (IP2), and (iv) an induced degradation domain (SMASh). In another aspect described herein is a synTF system comprising: (a) first polypeptide comprising: (i) a DBD, (ii) a first member of an induced proximity pair (IP1), and (iii) an induced degradation domain (SMASh); and (b) a second polypeptide comprising: (i) a TA; (ii) a TED, (ii) a second member of an induced proximity pair (IP2), and (iii) an induced degradation domain (SMASh). The SMASh is linked such that it does not impede binding of IPD1 and IPD2 in the presence of an inducer agent, e.g., through the use of a flexible linker peptide. Non-limiting examples of 1$^{st}$ and 2$^{nd}$ IPD/SMASh synTF systems are shown in Table 14.

TABLE 14

Exemplary Pairs of 1$^{st}$ and 2$^{nd}$ IPD/SMASh synTF systems, with each polypeptide shown from N-terminus to C-terminus, where "ED" designates the combination of the TA and TED (e.g., TA-TED or TED-TA).

| 1st | 2nd | 1st | 2nd | 1st | 2nd |
|---|---|---|---|---|---|
| DBD-IP1 | ED-IP2<br>IP2-ED<br>SMASh-ED-IP2<br>SMASh-IP2-ED<br>ED-IP2-SMASh<br>IP2-ED-SMASh | SMASh-DBD-IP1 | ED-IP2<br>IP2-ED<br>SMASh-ED-IP2<br>SMASh-IP2-ED<br>ED-IP2-SMASh<br>IP2-ED-SMASh | DBD-IP1-SMASh | ED-IP2<br>IP2-ED<br>SMASh-ED-IP2<br>SMASh-IP2-ED<br>ED-IP2-SMASh<br>IP2-ED-SMASh |
| IP1-DBD | ED-IP2<br>IP2-ED<br>SMASh-ED-IP2<br>SMASh-IP2-ED<br>ED-IP2-SMASh<br>IP2-ED-SMASh | SMASh-IP1-DBD | ED-IP2<br>IP2-ED<br>SMASh-ED-IP2<br>SMASh-IP2-ED<br>ED-IP2-SMASh<br>IP2-ED-SMASh | IP1-DBD-SMASh | ED-IP2<br>IP2-ED<br>SMASh-ED-IP2<br>SMASh-IP2-ED<br>ED-IP2-SMASh<br>IP2-ED-SMASh |

In some embodiments, the sequence of each domain is selected from exemplary domain sequences as described herein. When an inducer of the induced proximity pair is present, the IP1 and IP2 bind to the inducer resulting in formation of a protein complex comprising both polypeptides of the IPD/SMASh system, and when the inducer is absent, the polypeptides of the IPD/SMASh system do not form a complex. When an inducer of the induced degradation pair is present (e.g., a protease inhibitor), the IPD/SMASh synTF system is degraded. When an inducer of the induced degradation pair is absent (e.g., a protease inhibitor), the SMASh tag is degraded and the IPD/SMASh synTF system is not degraded.

C. Induced Proximity Domain SynTF

In some embodiments of any of the aspects, the regulator protein is a pair of induced proximity domains. Each of two members of the induced proximity pair is directly linked to the DBD or TA. Accordingly, in one aspect described herein is a synTF system comprising: (a) first polypeptide comprising: (i) a DBD and (ii) a first member of an induced proximity pair (IP1); and (b) a second polypeptide comprising: (i) a TA; (ii) a TED and (iii) a second member of an induced proximity pair (IP2). In some embodiments of any of the aspects, the domains of the synTF can be in order, e.g., from N-terminus to C-terminus: DBD-IP1 and ED-IP2; DBD-IP1 and IP2-ED; IP1-DBD and ED-IP2; or IP1-DBD and IP2-ED, where "ED" designates the combination of the TA and TED (e.g., TA-TED or TED-TA). That is, the DBD is attached to one member of the induced proximity pair (i.e., IP1), and the TA is attached to the other member or cognate member of the induced proximity pair (i.e., IP2), such that when an inducer of the induced proximity pair is present, the IP1 and IP2 bind to the inducer resulting in formation of a protein complex comprising DBD-IP1:IP2-TED-TA, and when the inducer is absent, the DBD-IP1 and TA-TED-IP2 do not form a complex.

In another aspect described herein is a synTF system comprising: (a) first polypeptide comprising: (i) a DBD; (ii) a TED; and (iii) a first member of an induced proximity pair (IP1); and (b) a second polypeptide comprising: (i) a TA; and (iii) a second member of an induced proximity pair (IP2).

In some embodiments of any of the aspects, the two polypeptides of the induced proximity synTF are linked by a self-cleaving peptide (SCP), such that the synTF system is expressed by one vector and the two polypeptides are cleaved from each following translation. Accordingly, the induced proximity synTF system can comprise from N-terminus to C-terminus: DBD-IP1-SCP-ED-IP2; DBD-IP1-SCP-IP2-ED; IP1-DBD-SCP-ED-IP2; or IP1-DBD-SCP-IP2-ED, where "ED" designates the combination of the TA and TED (e.g., TA-TED or TED-TA).

In some embodiments of any of the aspects, the DBD of the induced proximity synTF comprises ZF1-3. In some embodiments of any of the aspects, the DBD of the induced proximity synTF comprises SEQ ID NO: 86 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the SEQ ID NO: 86, that maintains the same function.

D. Cytosolic Sequestering Domain SynTF

In some embodiments of any of the aspects, the regulator protein is a cytosolic sequestering protein. Accordingly, in one aspect described herein is a synTF comprising: (a) a DBD; (b) a TA; (c) a TED; and (d) a cytosolic sequestering protein (CS). In some embodiments of any of the aspects, the domains of the synTF can be in order, e.g., from N-terminus to C-terminus: DBD-ED-CS; DBD-CS-ED; ED-DBD-CS; ED-CS-DBD; CS-DBD-ED; or CS-ED-DBD, where "ED" designates the combination of the TA and TED (e.g., TA-TED or TED-TA).

In some embodiments of any of the aspects, the DBD of the cytosolic sequestering synTF comprises ZF3-5. In some embodiments of any of the aspects, the DBD of the cytosolic sequestering synTF comprises SEQ ID NO: 45 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the SEQ ID NO: 45, that maintains the same function.

III. Polynucleotides and Vectors

In multiple aspects, described herein are polynucleotides that encode for synTFs. In some embodiments of any of the aspects, a synTF polynucleotide comprises one of SEQ ID NOs: 17-47, or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 17-47, that as a polypeptide maintains the same function (e.g., inducible transcription factor).

In some embodiments, the synTF polynucleotide comprises a codon-optimized version, e.g., of SEQ ID NOs: 17-47. In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

In some embodiments, one or more of the genes described herein (e.g., synTF, gene of interest) is expressed in a recombinant expression vector or plasmid. As used herein, the term "vector" refers to a polynucleotide sequence suitable for transferring transgenes into a host cell. The term "vector" includes plasmids, mini-chromosomes, phage, naked DNA and the like. See, for example, U.S. Pat. Nos. 4,980,285; 5,631,150; 5,707,828; 5,759,828; 5,888,783 and, 5,919,670, and, Sambrook et al, Molecular Cloning: A Laboratory Manual, 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A cloning vector is one which is able to replicate autonomously or integrated in the genome in a host cell, and which is further characterized by one or more endonuclease restriction sites at which the vector may be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence can be inserted by restriction and ligation such that it is operably joined to regulatory sequences, comprising DNA-binding domains as described herein, and can be expressed as an RNA transcript. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds, genes which encode enzymes whose activities are detectable by standard assays known in the art (e.g., 0-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the polypeptides described herein is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression can vary between species or cell types, but in general can include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences can also include enhancer sequences or upstream activator sequences as desired. The vectors of the invention may optionally include 5' leader or signal sequences. The choice and design of an appropriate vector is within the ability and discretion of one of ordinary skill in the art.

In some embodiments of any of the aspects, the promoter is a eukaryotic or human constitutive promoter, including but not limited to: a human elongation factor-1 alpha (EF-1alpha, EF1a) promoter; a silencing-prone spleen focus forming virus (SFFV); cytomegalovirus (CMV) promoter; a ubiquitin C (UbiC, pUb, UbC) promoter; phosphoglycerate kinase 1 (PGK, pGK) promoter; cytomegalovirus (CMV) enhancer fused to the chicken beta-actin promoter (CAG/CAGG); Simian virus 40 (SV40) enhancer and early promoter; beta actin (ACTB) promoter; and the like. In some embodiments of any of the aspects, the promoter is a minimal promoter or a core promoter. The minimal or core promoter, by definition, is the sequence located between the −35 to +35 region with respect to transcription start site; the minimal promoter is typically shorter than full promoters, and does not comprise additional elements such as enhancers or silencers. Non-limiting examples of minimal promoters include minCMV; CMV53 (minCMV with the addition of an upstream GC box); minSV40 (minimal simian virus 40 promoter); miniTK (the −33 to +32 region of the Herpes simplex thymidine kinase promoter); MLP (the −38 to +6 region of the adenovirus major late promoter); pJB42CAT5 (a minimal promoter derived from the human junB gene); ybTATA (a synthetic minimal promoter), and the TATA box alone. See e.g., Ede et al., ACS Synth Biol. 2016 May 20, 5(5): 395-404; Qin et al., PLoS One. 2010, 5(5): e10611; Norman et al., PLoS One. 2010 Aug. 26, 5(8):e12413; the contents of each of which are incorporated herein by reference in their entireties.

In some embodiments of any of the aspects, the vector comprises a SFFV promoter (e.g., SEQ ID NO: 17). In some embodiments of any of the aspects, the vector comprises a CMV promoter (e.g., SEQ ID NO: 34). In some embodiments of any of the aspects, the vector comprises a minCMV promoter. In some embodiments of any of the aspects, the vector comprises a minTK promoter. In some embodiments of any of the aspects, the vector comprises a Kozak sequence (e.g., GCCGCCACC), which is a nucleic acid motif that functions as the protein translation initiation site in eukaryotic mRNA transcripts.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell.

In some embodiments, the vector is a pHR vector. In some embodiments, the vector is a lentiviral vector. The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

In some embodiments of any of the aspects, the lentiviral vector comprises a central polypurine tract (cPPT). A central polypurine tract/central termination sequence creates a "DNA flap" that increases nuclear importation of the viral genome during target-cell infection. The cPPT/CTS element improves vector integration and transduction efficiency. In some embodiments of any of the aspects, the lentiviral vector comprises a woodchuck hepatitis virus posttranscriptional regulatory element (WPRE), which prevents poly(A) site read-through, promotes RNA processing and maturation, and increases nuclear export of RNA. In genomic transcripts, it enhances vector packaging and increases titer. In transduced target cells, the WPRE boosts transgene expression by facilitating mRNA transcript maturation. In some embodiments of any of the aspects, the lentiviral vector comprises long terminal repeats (LTRs). LTRs are identical sequences of DNA that repeat hundreds or thousands of times found at either end of retrotransposons or proviral DNA formed by reverse transcription of retroviral RNA; they are used by viruses to insert their genetic material into the host genomes. In some embodiments of any of the aspects, the lentiviral vector comprises Rev response elements (RRE), which is required for producing high titer vectors.

Without limitations, the genes described herein can be included in one vector or separate vectors. For example, a polynucleotide encoding a synTF and a polynucleotide encoding a gene of interest can be included in the same vector. In some embodiments of any of the aspects, a polynucleotide encoding a synTF and a polynucleotide encoding a gene of interest can be included in different vectors. In some embodiments of any of the aspects, a single vector can comprise at least one polynucleotide encoding a synTF. In some embodiments of any of the aspects, a single vector can comprise at least one polynucleotide encoding a gene of interest. In some embodiments of any of the aspects, a single vector can comprise at least one polynucleotide encoding a synTF and at least one polynucleotide encoding a gene of interest.

In one aspect, described herein are synTF lentiviral expression vectors. In some embodiments, the synTF lentiviral expression vector comprises a polynucleotide encoding a synTF that is operably linked to a promoter (e.g., SFFV). In another aspect, described herein are lentiviral reporter vectors. In some embodiments, the lentiviral reporter vector comprises: (i) at least one (e.g., 1, 2, 3, 4, or more) DNA-binding motif (DBM) for the DBD of a synTF; (ii) a promoter sequence located 3' of the at least one DBM; and (iii) a detectable marker (i.e., a reporter; e.g., mCherry) that is operably linked to the promoter sequence. In some embodiments, the lentiviral reporter vector is an activation reporter for a synTF comprising a transcriptional activation domain, such that when the inducible synTF is ON, the DBD of the synTF binds to the DBM of the reporter and, the transcriptional activation domain and TED activate transcription of the detectable marker; when the DBD of the inducible synTF is OFF and not bound to the DBM of the reporter, the detectable marker is not produced as it is operably linked to only a core or minimal promoter (e.g., minCMV).

In one aspect, described herein are gene of interest (GOI) lentiviral expression vectors. In some embodiments, the GOI vector comprises a gene of interest that is operably linked to at least one (e.g., 1, 2, 3, 4, or more) DNA-binding motif (DBM) for the DBD of a synTF and a minimal promoter. In some embodiments, the GOI vector comprises a reporter vector as described herein, wherein the detectable marker is replaced with or fused to a gene of interest; as such the synTF can induce the expression of the gene of interest in the presence or absence of the regulator protein inducer.

In some embodiments, the polypeptide encoded by the gene of interest is selected from the group consisting of: a chemokine, a chemokine receptor, a chimeric antigen receptor (CAR), a cytokine, a cytokine receptor, a differentiation factor, a growth factor, a growth factor receptor, a hormone, a metabolic enzyme, a pathogen derived protein, a proliferation inducer, a receptor, a RNA guided nuclease, a site-specific nuclease, a small molecule 2nd messenger synthesis enzyme, a T cell receptor, a toxin derived protein, a transcription activator, a transcription repressor, a transcriptional activator, a transcriptional repressor, a translation regulator, a translational activator, a translational repressor, an activating immunoreceptor, an antibody, an apoptosis inhibitor, an apoptosis inducer, an engineered T cell receptor, an immunoactivator, an immunoinhibitor, an inhibiting immunoreceptor, and an RNA guided DNA binding protein. In some embodiments, the polypeptide encoded by the gene of interest would benefit a subject in need of treatment, e.g., a subject with cancer, autoimmunity, or need of regenerative medicine.

In some embodiments, the polypeptide encoded by the gene of interest is a CD19 CAR (e.g., SEQ ID NOs: 39), e.g., linked to a detectable marker such as mCherry (e.g., SEQ ID NO: 40). In some embodiments, the polypeptide encoded by the gene of interest is IL2 (e.g., SEQ ID NO: 44), which can be linked to a detectable marker, (e.g., huEGFRt), using a self-cleaving peptide. In some embodiments, the polypeptide encoded by the gene of interest is IL10. In some embodiments, the polypeptide encoded by the gene of interest is STAT1 or STAT6 (see e.g., SEQ ID NOs: 28 or 35).

In one aspect described herein is a lentiviral vector that comprises both a synTF operably linked to a constitutive promoter and a gene of interest operably linked to at least one (e.g., 1, 2, 3, 4, or more) DNA-binding motif (DBM) for the DBD of a synTF and a minimal promoter. Accordingly, described herein is a nucleic acid construct comprising in the 5' to 3' direction: (a) a nucleic acid sequence encoding a gene of interest (GOI) in the inverse orientation; (b) a first promoter sequence in the inverse orientation and operatively linked to the nucleic acid encoding the GOI; (c) a nucleic acid sequence comprising at least one target DNA binding motif (DBM) comprising a target nucleic acid for binding of the at least one DBD of a synTF, wherein binding of the DBD of the synTF places the transcriptional activator (TA) domain and transcriptional effector domain (TED) in the proximity of the promoter sequence operatively linked to the GOI; (d) a second promoter sequence; and (e) a nucleic acid sequence encoding the synthetic transcription factor (synTF), operatively linked to the second promoter sequence, wherein the encoded synTF comprises at least one DBD that binds to the at least one DBM of the nucleic acid sequence of (c).

In some embodiments of any of the aspects, the promoter sequence operatively linked to the GOI is selected from any of: miniCMV promoter, miniTK promoter, ybTATA promoter, minSV40 promoter, CMV53 promoter, pJB42CAT5 promoter, MLP promoter, and TATA promoter. In some embodiments of any of the aspects, wherein the promoter sequence operatively linked to the nucleic acid encoding the synTF is a pSFFV promoter, CMV promoter, pUb/UbC promoter, EF1a promoter, PGK/pGK promoter, CAG/CAGG promoter, SV40 promoter, and beta actin/ACTB promoter.

In some embodiments, the polynucleotide encoding the synTF is operatively linked to an inducible promoter, which is active in the presence of the promoter activator or the absence of the promoter repressor, and inactive in the absence of the promoter inducer or the presence of the promoter repressor. Non-limiting examples of inducible promoters include: a doxycycline-inducible promoter, the lac promoter, the lacUV5 promoter, the tac promoter, the trc promoter, the T5 promoter, the T7 promoter, the T7-lac promoter, the araBAD promoter, the rha promoter, the tet promoter, an isopropyl β-D-1-thiogalactopyranoside (IPTG)-dependent promoter, an AlcA promoter, a LexA promoter, a temperature inducible promoter (e.g., Hsp70 or Hsp90-derived promoters), or a light inducible promoter (e.g., pDawn/YFI/FixK2 promoter/CI/pR promoter system).

In some embodiments, the vector comprises a selectable marker, e.g., for selectively amplifying the vector in bacteria. Non-limiting examples of selectable marker genes for use in bacteria include antibiotic resistance genes conferring resistance to ampicillin, tetracycline and kanamycin. The tetracycline (tet) and ampicillin (amp) resistance marker genes can be obtained from any of a number of commercially available vectors including pBR322 (available from New England BioLabs, Beverly, Mass., cat. no. 303-3s). The tet coding sequence is contained within nucleotides 86-476; the amp gene is contained within nucleotides 3295-4155. The nucleotide sequence of the kanamycin (kan) gene is available from vector pACYC 177, from New England BioLabs, Cat no. 401-L, GenBank accession No. X06402.

In some embodiments, one or more of the recombinantly expressed genes can be integrated into the genome of the cell.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

IV. synTF Systems

Another aspect of the technology relates to synTF system for controlling gene expression of a gene of interest (GOI), where the system comprises a synTF described herein and a nucleic acid construct comprising the elements that the synTF binds to regulate gene expression. In one aspect described herein is a system for controlling gene expression, comprising: (a) at least one synthetic transcription factor (synTF) as described herein; and (b) at least one nucleic acid construct as described herein, e.g., a nucleic acid construct comprising: (i) at least one target DNA binding motif (DBM) comprising a target nucleic acid for binding of the at least one DBD of the synTF; (ii) a promoter sequence located 3' of the at least one DBM, and (iii) a gene of interest operatively linked to the promoter sequence.

Exemplary systems are shown in FIG. 1B, 2B, 4B, or 5B, showing the synTF and the nucleic acid sequence construct comprising the gene of interest (e.g., mCherry, CD19 CAR, etc.). In synTF embodiments where the synTF is a protease synTF or induced proximity domain synTF, (i.e., where the coupling of the TA to the DBD is regulated by the at least one protease RP or at least one induced proximity pair), in the presence of the RP inducer, the coupling of the TA to the DBD of the synTF is maintained, such that when the DBD binds to the DNA binding motif (DBM) it permits the TA to be in proximity to the promoter sequence and promotes initiation or inhibition of gene expression of the gene of interest ("TA-on", transcription on). Alternatively, in the absence of the RP inducer, the coupling of the TA to the DBD of the synTF is severed, preventing the TA from being in proximity to the promoter sequence when the DBD binds to the DNA binding motif (DBM), preventing the TA from regulating the expression of the gene of interest ("TA-off", transcription off). A summary of the effect of each regulator promoter inducer on the ultimate gene expression depending on the different synTF is summarized in Table 15 herein.

Similarly, and by way of example only, in a synTF embodiment where the synTF is a cytosolic sequestering domain synTF, (i.e., where the cellular localization of the TA-DBD fusion protein is regulated by the at least one cytosolic sequestering regulator protein), in the presence of the RP inducer, the TA-DBD is not sequestered in the cytosol, permitting the DBD to bind to the DNA binding motif (DBM) and placing the transcriptional activator domain (TA) to be in proximity to the promoter sequence to control the expression of the gene of interest ("TA-on", transcription-on). Alternatively, in the absence of the RP inducer, the TA coupled to the DBD of the synTF is sequestered in the cytosol, preventing the DBD of the synTF from binding to the DBM, and preventing the TA from being in proximity to the promoter sequence, preventing expression of the gene of interest ("TA-off", transcription off).

In some embodiments of any of the aspect described herein, the synTF is an induced degradation domain synTF or further comprises a N-terminal or C-terminal Small molecule-Assisted Shutoff (SMASh) domain. As described herein, the SMASh domain comprises a self-cleaving SMASh protease, a partial protease helical domain and a cofactor domain. In some embodiments of any of the aspects, in the presence of an inhibitor to the SMASh protease (referred to as a "SMASh inhibitor"), the SMASh protease activity is inhibited resulting in the synTF being degraded, which prevents the DBD binding to the DBM and controlling the expression of the gene of interest ("synTF-degradation"; TA-off). In some embodiments of any of the aspects, in the absence of an inhibitor to the SMASh protease, the SMASh protease is active and self cleaves/uncouples from the synTF, resulting the SMASh domain being targeted for degradation and allowing the DBD of the synTF to bind to the DBM and the TA of synTF to increase the expression of the gene of interest ("SMASh-degradation, TA-on (yes-expression)).

TABLE 15

Table summarizing the effect of the presence or absence of regulator protein inducers on the ultimate expression of the gene of interest.

| SynTF | Presence or absence of RP inducer → effect on the SynTF → effect on binding to the DBM | Gene expression ON or OFF |
|---|---|---|
| Protease domain synTF | Present → DBD-TA is coupled → "TA-On"<br>Absent → DBD-TA is uncoupled → TA-Off | ON<br>OFF |
| Induced proximity domain synTF | Present → DBD-TA is coupled → TA-On<br>Absent → DBD-TA is uncoupled → TA-Off | ON<br>OFF |
| Translocation domain syn TF | Present → SynTF translocates to nucleus (sequestering is inhibited) → TA-On<br>Absent → SynTF is sequestered in cytosol → TA-Off | ON<br>OFF |
| Induced degradation domain synTF | Present → SynTF-degradation → TA-Off<br>Absent → SMASh degradation, TA available → TA-On | OFF<br>ON |

Accordingly, the expression of the GOI is dependent on 3 levels of control, including but not limited to; (i) the type of regulator protein in the synTF, (ii) the presence or absence of a regulator protein inducer (RP inducer), and (iii) the type of effector domain (e.g., presence or absence of TED in combination with the TA). In some embodiments, if the synTF comprises an induced degradation domain or SMASh domain, it can also provide an additional level of control on the expression of the GOI. The ultimate expression of the GOI of synTF comprising a SMASh domain are shown in Table 16.

TABLE 16

| SynTF | SMASh inhibitor | Effect of SMASh inhibitor | Regulator Protein inducer | Effect of RP inducer | Effector domain | Gene expression |
|---|---|---|---|---|---|---|
| Protease domain syn TF: PD-SynTF:SMASh | Present | SynTF degradation (TA-OFF) | n/a | n/a | TA (TA-off) | OFF |
| | Absent | SMASh degradation | Protease inhibitor Present | "TA on" (DBD-TA coupled) | TA (TA-on) | ON |
| | | | Protease inhibitor Absent | "TA off" (DBD and TA uncoupled) | TA (TA-off) | OFF |

TABLE 16-continued

| SynTF | SMASh inhibitor | Effect of SMASh inhibitor | Regulator Protein inducer | Effect of RP inducer | Effector domain | Gene expression |
|---|---|---|---|---|---|---|
| Induced proximity domain | Present | SynTF degradation (TA-OFF) | n/a | n/a | TA (TA-off) | OFF |
| synTF: IPD-SynTF:SMASh | Absent | SMASh degradation | IPD inducer Present | "TA on" (DBD-TA coupled) | TA (TA-on) | ON |
| | | | IPD inducer Absent | "TA off" (DBD and TA uncoupled) | TA (TA-off) | OFF |
| Cytosolic sequestering: CS- | Present | SynTF degradation (TA-OFF) | n/a | n/a | TA (TA-off) | OFF |
| synTF:SMASh | Absent | SMASh degradation | Cytosolic sequestering ligand Present | "TA on" (CS-synTF translocates to nucleus (sequestering is inhibited)) | TA (TA-on) | ON |
| | | | Cytosolic sequestering ligand Absent | "TA off" (CS-SynTF sequestered in cytosol) | TA (TA-off) | OFF |

As indicated in Table 16, if the SMASh inhibitor is present, then even in the absence or presence of the regulator protein inducer (e.g., protease inhibitor, IPD inducer agent or ligand for CS-SynTF), the synTF is degraded and there is no expression of the GOI. However, in the absence of the SMASh inhibitor, the expression of the GOI is dependent on the presence or absence of the regulator protein inducer, as shown in Table 16.

Accordingly, in one aspect, described herein is a system for controlling gene expression, comprising: (a) at least one synthetic transcription factor (synTF) comprising at least one DNA binding domain (DBD), a transcriptional activator (TA) domain, a transcriptional effector domain (TED), and at least one regulator protein (RP), wherein the TA is directly or indirectly coupled or linked to the DBD, and wherein the coupling is regulated by the at least one RP, or wherein the cellular localization of the TA linked to the DBD is regulated by the at least one RP, wherein the at least one RP is regulated by an RP inducer, wherein the DBD can bind to a target DNA binding motif (DBM) located upstream of a promoter operatively linked to a gene; (b) a nucleic acid construct comprising: (i) at least one target DNA binding motif (DBM) comprising a target nucleic acid for binding of the at least one DBD of the synTF, and (ii) a promoter sequence located 3' of the at least one DBM, and (iii) a gene of interest operatively linked to the promoter sequence; wherein for synTFs where the coupling of the TA to the DBD is regulated by the at least one RP; in the presence of the RP inducer, the coupling of the TA to the DBD of the synTF is maintained, permitting the TA to be in proximity to the promoter sequence when the DBD binds to the DNA binding motif (DBM), where the TA controls the expression of the gene of interest ("TA-on"), or in the absence of the RP inducer, the coupling of the TA to the DBD of the synTF is severed, preventing the TA from being in proximity to the promoter sequence when the DBD binds to the DNA binding motif (DBM), preventing gene expression of the gene of interest ("TA-off"); and wherein for synTFs where the cellular localization of the TA linked to the DBD is regulated by the at least one regulator protein; in the presence of the RP inducer, the TA coupled to the DBD of the synTF is not sequestered in the cytosol, permitting the DBD to bind to the DNA binding motif (DBM) and permitting the TA to be in proximity to the promoter sequence to control the expression of the gene of interest ("TA-on"), or in the absence of the RP inducer, the TA coupled to the DBD of the synTF is sequestered in the cytosol, preventing the DBD of the synTF from binding to the DBM, and preventing the TA from being in proximity to the promoter sequence, preventing expression of the gene of interest ("TA-off").

Nucleic Acid Constructs Encoding the GOI for Regulation by the synTF

As described herein, in some aspects, the system comprises a synTF as described herein and a nucleic acid construct comprising the GOI. In some embodiments, the nucleic acid construct comprises in the 5' to 3' direction, (i) a DNA binding motif (DBM) that permits binding of the DBD of the synTF, (ii) a promoter sequence, and (iii) a nucleic acid encoding the GOI, where the nucleic acid encoding the GOI is operatively linked to the promoter sequence. An exemplary system is shown in FIG. 1B, 2B, 4B, or 5B.

In some embodiments, the system further comprises a nucleic acid sequence encoding the synTF, operatively linked to a promoter, for example, where the promoter is an inducible promoter or a constitutive promoter. In such an embodiment, when the inducer to the inducible promoter is present, the synTF can be expressed, and the activity of the synTF on controlling gene expression of the GOI is dependent on the presence or absence of the regulator protein inducer and/or SMASh inducer if a SMASh domain is attached to the synTF.

In some embodiments, the nucleic acid construct comprises (a) a first nucleic acid encoding the synTF under a promoter; and (b) a second nucleic acid construct comprising (i) a DNA binding motif (DBM) that permits binding of the DBD of the expressed synTF, (ii) a promoter sequence, and (iii) a nucleic acid encoding the GOI, where the nucleic acid encoding the GOI is operatively linked to the promoter sequence. Accordingly, the nucleic acid encoding the inducible synTF and the GOI are present on the same nucleic acid construct, which is also referred to herein as a "single vector" or "single lentiviral vector".

In some embodiments, the nucleic acid construct comprises (i) a first promoter operatively linked to a nucleic acid encoding the synTF, and (ii) a nucleic acid encoding a GOI, operatively linked to a second promoter, where 5' to the second promoter is the DBM for the synTF protein which is expressed under control of the first promoter. In some embodiments, the construct comprises the following in a 5' to 3' orientation: (i) a nucleic acid encoding a GOI in the antisense orientation, (ii) a first promoter in the antisense orientation which is operatively linked to the GOI, (iii) a DBD in the antisense orientation, (iv) a second promoter in the sense orientation, and (v) a nucleic acid encoding a synTF in the sense orientation which is operatively linked to the second promoter. Such a system allows the expression of the synTF, where the expressed synTF can be used to regulate the expression of the GOI in the presence or absence of inducers for the synTF.

In some embodiments of any of the aspects, the promoter which is operatively linked to the GOI or to the synTF is selected from any of miniCMV promoter, miniTK promoter, ybTATA promoter, minSV40 promoter, CMV53 promoter, pJB42CAT5 promoter, MLP promoter, TATA promoter, pSFFV promoter, CMV promoter, pUb/UbC promoter, EF1a promoter, PGK/pGK promoter, CAG/CAGG promoter, SV40 promoter, and beta actin/ACTB promoter.

In some embodiments of any of the aspects, the at least one synTF expressed by the system is selected from any of those described herein. In some embodiments of any of the aspects, a synTF system can comprise any combination of at least two synTF polypeptides as described herein, controlling the same or different GOIs. As a non-limiting example a system can comprise two synTFs each with a separate regulator protein and GOI: e.g., a repressible protease synTF that controls CD19 CAR expression and a cytosolic sequestering domain synTF that controls IL4 expression. Table 17 below shows non-limiting examples of such synTF system combinations. In some embodiments of any of the aspects, the examples shown in Table 17 can be in combination with at least one regulator protein inducer (e.g., a small molecule drug such as grazoprevir, ABA, and/or 4OHT).

TABLE 17 synTF systems. "PRO" indicates the repressible protease synTF polypeptides and systems as described herein. "ID" indicates the induced degradation synTF polypeptides and systems as described herein. "IPD" indicates the induced proximity synTF polypeptides and systems as described herein. "CS" indicates the cytosolic sequestering domain synTF polypeptides and systems as described herein.

| PRO | ID | IPD | CS |
|---|---|---|---|
| X | | | |
| | X | | |
| | | X | |
| | | | X |
| X | X | | |
| X | | X | |
| X | | | X |
| | X | X | |
| | X | | X |
| | | X | X |
| X | X | X | |
| X | X | | X |
| X | | X | X |
| | X | X | X |
| X | X | X | X |

V. Cells

In one aspect, described herein is a cell or population thereof comprising the at least one synTF polypeptide, synTF system, synTF polynucleotide, or synTF vector as described herein. In some embodiments of any of the aspects, the cell or population thereof can comprise any combination of synTF polypeptides or systems (see e.g., Table 17).

In one aspect, the invention provides a cell (e.g., T cell) engineered to express a synTF, wherein the activity of the synTF cell can be controlled by a small molecule. In one aspect, a cell is transformed with the synTF, and the synTF is expressed on the cell surface. In some embodiments, the cell (e.g., T cell) is transduced with a viral vector encoding a synTF. In some embodiments, the viral vector is a retroviral vector. In some embodiments, the viral vector is a lentiviral vector. In some such embodiments, the cell can stably express the synTF. In another embodiment, the cell (e.g., T cell) is transfected with a nucleic acid, e.g., mRNA, cDNA, DNA, encoding a synTF. In some embodiments, the cell can transiently express the synTF.

In one aspect described herein is a cell comprising: a nucleic acid sequence comprising at least one target DNA binding motif (DBM) comprising a target nucleic acid for binding of the at least one DBD of a synTF, a promoter sequence located 3' of the at least one DBM, and a nucleic acid encoding a gene of interest (GOI) operatively linked to the promoter sequence.

In one aspect described herein is a cell comprising: (a) a first nucleic acid sequence comprising at least one target DNA binding motif (DBM) comprising a target nucleic acid for binding of the at least one DBD of a synTF, a promoter sequence located 3' of the at least one DBM, and a nucleic acid encoding a gene of interest (GOI) operatively linked to the promoter sequence, and (b) a second nucleic acid sequence comprising a nucleic acid encoding a synthetic transcription factor (synTF) as described herein, operatively linked to an inducible or constitutive promoter.

In some embodiments of any of the aspects, the cell comprises a nucleic acid construct comprising in the 5' to 3' direction: (a) a nucleic acid sequence encoding a gene of interest (GOI) in the inverse orientation; (b) a first promoter sequence in the inverse orientation and operatively linked to the nucleic acid encoding the GOI; (c) a nucleic acid sequence comprising at least one target DNA binding motif (DBM) comprising a target nucleic acid for binding of the at least one DBD of a synTF, wherein binding of the DBD of the synTF places the TA in the proximity of the promoter sequence operatively linked to the GOI; (d) a second promoter sequence; and (e) a nucleic acid sequence encoding the synthetic transcription factor (synTF), operatively linked to the second promoter sequence, wherein the encoded synTF comprises at least one DBD that binds to the at least one DBM of the nucleic acid sequence of (c).

In some embodiments of any of the aspects, the promoter sequence operatively linked to the GOI is selected from any of: miniCMV promoter, miniTK promoter, ybTATA promoter, minSV40 promoter, CMV53 promoter, pJB42CAT5 promoter, MLP promoter, and TATA promoter. In some embodiments of any of the aspects, wherein the promoter sequence operatively linked to the nucleic acid encoding the synTF is a pSFFV promoter, CMV promoter, pUb/UbC promoter, EF1a promoter, PGK/pGK promoter, CAG/CAGG promoter, SV40 promoter, and beta actin/ACTB promoter.

In some embodiments of any of the aspects, the cell comprises an immune cell. In some embodiments of any of the aspects, the immune cell comprises a CD4+ T cell, a CD8+ T cell, a regulatory T cell (Treg), or a natural killer (NK) cell. In some embodiments of any of the aspects, the immune cell comprises a monocyte or macrophage. In one embodiment, the cell comprises a T cell. In one embodiment, the cell comprises a CD4+ T cell. In one embodiment, the cell comprises a CD8+ T cell. In other embodiments, the cell comprises a B cell.

In some embodiments of any of the aspects, the cells are isolated from a subject. The term "isolated" as used herein signifies that the cells are placed into conditions other than their natural environment. The term "isolated" does not preclude the later use of these cells thereafter in combinations or mixtures with other cells. In some embodiments of any of the aspects, an immune cell (e.g., T cell) is: (a) isolated from the subject; (b) genetically modified to express a synTF or synTF system as described herein; and (c) administered to the subject. In some embodiments of any of the aspects, the cells are isolated from a first subject and administered to a second subject. In some embodiments of any of the aspects, the immune cells are first differentiated from a somatic cell sample from the subject and then genetically modified to express a synTF or synTF system as described herein.

In some embodiments of any of the aspects, the cell comprises an inactivating modification of at least one HLA Class I gene in the cell. In some embodiments, an endogenous HLA (e.g., class I and/or class II major histocompatibility complexes) can be edited or removed, e.g., to reduce immunogenicity. In some embodiments, the genetic modification can comprise introduction and expression of non-canonical HLA-G and HLA-E to prevent NK cell-mediated lysis (see e.g., Riolobos L et al. 2013), which can provide a source of universal T cells for immunotherapy, e.g., cancer immune therapy.

In some embodiments, methods of genetically modifying a cell to express a synTF system can comprise but are not limited to: transfection or electroporation of a cell with a vector encoding a synTF; transduction with a viral vector (e.g., retrovirus, lentivirus) encoding a synTF system; gene editing using zinc finger nucleases (ZFNs), transcription activator-like effector nucleases (TALENs), meganuclease-TALENs, or CRISPR-Cas; or any other methods known in the art of genetically modifying a cell to express a synTF system.

VI. Pharmaceutical Compositions and Administration

In some embodiments, the methods described herein relate to treating a subject having or diagnosed as having a disease or disorder (e.g., cancer or autoimmunity) with a synTF system as described herein. Subjects having such a disease or disorder can be identified by a physician using current methods of diagnosis for cancer or autoimmunity. Symptoms and/or complications which characterize these conditions and aid in diagnosis are known in the art. A family history of cancer or autoimmunity, or exposure to risk factors for cancer or autoimmunity can also aid in determining if a subject is likely to have such a disease or disorder, or in making a diagnosis of cancer or autoimmunity.

The compositions described herein can be administered to a subject having or diagnosed as having cancer or autoimmunity. In some embodiments, the methods described herein comprise administering an effective amount of compositions described herein, e.g., a synTF or a synTF system as described herein to a subject in order to alleviate a symptom of cancer or autoimmunity. As used herein, "alleviating a symptom" is ameliorating any condition or symptom associated with the cancer or autoimmunity. As compared with an equivalent untreated control, such reduction is by at least 5%, 10%, 20%, 40%, 50%, 60%, 80%, 90%, 95%, 99% or more as measured by any standard technique.

A variety of means for administering the compositions described herein to subjects are known to those of skill in the art. An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, intratumorally, and can be delivered by peristaltic means, if desired, or by other means known by those skilled in the art. In some embodiments of any of the aspects, the compositions used herein are administered orally, intravenously or intramuscularly. Administration can be local or systemic. Local administration, e.g., directly to the site of an organ or tissue transplant is specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

In embodiments where the subject is administered a synTF cell and at least one regulator protein inducer to modulate the activity of the synTF polypeptide(s) (e.g., grazoprevir, ABA, and/or 4OHT), the cells and drug(s) can be administered together or separately. In embodiments where the subject is separately administered a synTF cell and at least one drug to modulate the activity of the synTF polypeptide(s), each of the compositions can be administered, separately, according to any of the dosages and administration routes/routines described herein.

The term "effective amount" as used herein refers to the amount of a synTF or a synTF system as described herein and/or a regulator protein inducer (e.g., grazoprevir, ABA, and/or 4OHT) needed to alleviate at least one or more symptom of the disease or disorder, and relates to a sufficient amount of a pharmacological composition to provide the desired effect. The term "therapeutically effective amount" therefore refers to an amount of a synTF or a synTF system as described herein and/or a regulator protein inducer (e.g., grazoprevir, ABA, and/or 4OHT) that is sufficient to provide a particular effect (e.g., anti-tumor or anti-autoimmune effect) when administered to a typical subject. An effective amount as used herein, in various contexts, would also include an amount sufficient to delay the development of a symptom of the disease, alter the course of a symptom of the disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the ED50 (the dose therapeutically effective in 50% of the population). The dosage can vary depending upon the dosage form employed and the route of administration utilized. A therapeutically effective dose can be estimated initially from cell culture assays. Also, a dose can be formulated in animal models to achieve a circulating plasma concentration range that includes the IC50 (e.g., the concentration of a regulator protein inducer (e.g., grazoprevir, ABA, and/or 4OHT)), which achieves a half-maximal inhibition of symptoms) as determined in cell culture, or in an appropriate animal model. Levels in plasma can be measured, for example, by high performance liquid chromatography for the regulator protein inducer or flow cytometry for synTF cells. The effects of any particular dosage can be monitored by a suitable bioassay. The dosage can be determined by a physician and adjusted, as necessary, to suit observed effects of the treatment.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the route of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay, e.g., assay for tumor growth and/or size among others. The dosage can be determined by a physician and adjusted, as necessary, to suit observed effects of the treatment.

It can generally be stated that a pharmaceutical composition comprising the synTF-expressing cells or the synTF-system-expressing cells described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. SynTF-expressing cell compositions or SynTF-system-expressing cell compositions may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response. In some embodiments, the dosage can be from about $1\times10^5$ cells to about $1\times10^8$ cells per kg of body weight. In some embodiments, the dosage can be from about $1\times10^6$ cells to about $1\times10^7$ cells per kg of body weight. In some embodiments, the dosage can be about $1\times10^6$ cells per kg of body weight. In some embodiments, one dose of cells can be administered. In some embodiments, the dose of cells can be repeated, e.g., once, twice, or more. In some embodiments, the dose of cells can be administered on, e.g., a daily, weekly, or monthly basis.

In certain embodiments, an effective dose of a regulatory protein inducer (e.g., grazoprevir, ABA, and/or 4OHT; also referred to herein as an inducer agent) that regulates the activity of a synTF as described herein can be administered to a patient once. In certain embodiments, an effective dose of a regulatory protein inducer can be administered to a patient repeatedly. In some embodiments of any of the aspects, the effective dose of ABA is about 1 mM. In some embodiments of any of the aspects, the effective dose of 4OHT is about 4 μM. In some embodiments of any of the aspects, the effective dose of grazoprevir is about 4 μM. In some embodiments of any of the aspects, the effective dose of 4OHT or grazoprevir is about 1 μM.

In some embodiments of any of the aspects, the effective dose of a regulatory protein inducer (e.g., ABA) is at least 0.05 mM, at least 0.1 mM, at least 0.15 mM, at least 0.2 mM, at least 0.25 mM, at least 0.3 mM, at least 0.35 mM, at least 0.4 mM, at least 0.45 mM, at least 0.5 mM, at least 0.55 mM, at least 0.6 mM, at least 0.65 mM, at least 0.7 mM, at least 0.75 mM, at least 0.8 mM, at least 0.85 mM, at least 0.9 mM, at least 0.95 mM, at least 1 mM, at least 1.05 mM, at least 1.1 mM, at least 1.15 mM, at least 1.2 mM, at least 1.25 mM, at least 1.3 mM, at least 1.35 mM, at least 1.4 mM, at least 1.45 mM, at least 1.5 mM, at least 1.55 mM, at least 1.6 mM, at least 1.65 mM, at least 1.7 mM, at least 1.75 mM, at least 1.8 mM, at least 1.85 mM, at least 1.9 mM, at least 1.95 mM, at least 2 mM, at least 2.05 mM, at least 2.1 mM, at least 2.15 mM, at least 2.2 mM, at least 2.25 mM, at least 2.3 mM, at least 2.35 mM, at least 2.4 mM, at least 2.45 mM, at least 2.5 mM, at least 2.55 mM, at least 2.6 mM, at least 2.65 mM, at least 2.7 mM, at least 2.75 mM, at least 2.8 mM, at least 2.85 mM, at least 2.9 mM, at least 2.95 mM, at least 3 mM, at least 3.05 mM, at least 3.1 mM, at least 3.15 mM, at least 3.2 mM, at least 3.25 mM, at least 3.3 mM, at least 3.35 mM, at least 3.4 mM, at least 3.45 mM, at least 3.5 mM, at least 3.55 mM, at least 3.6 mM, at least 3.65 mM, at least 3.7 mM, at least 3.75 mM, at least 3.8 mM, at least 3.85 mM, at least 3.9 mM, at least 3.95 mM, at least 4 mM, at least 4.05 mM, at least 4.1 mM, at least 4.15 mM, at least 4.2 mM, at least 4.25 mM, at least 4.3 mM, at least 4.35 mM, at least 4.4 mM, at least 4.45 mM, at least 4.5 mM, at least 4.55 mM, at least 4.6 mM, at least 4.65 mM, at least 4.7 mM, at least 4.75 mM, at least 4.8 mM, at least 4.85 mM, at least 4.9 mM, at least 4.95 mM, or at least 5 mM.

In some embodiments of any of the aspects, the effective dose of a regulatory protein inducer (e.g., grazoprevir, 4OHT) is at least 0.05 μM, at least 0.1 μM, at least 0.15 μM, at least 0.2 μM, at least 0.25 μM, at least 0.3 μM, at least 0.35 μM, at least 0.4 μM, at least 0.45 μM, at least 0.5 μM, at least 0.55 μM, at least 0.6 μM, at least 0.65 μM, at least 0.7 μM, at least 0.75 μM, at least 0.8 μM, at least 0.85 μM, at least 0.9 μM, at least 0.95 μM, at least 1 μM, at least 1.05 μM, at least 1.1 μM, at least 1.15 μM, at least 1.2 μM, at least 1.25 μM, at least 1.3 μM, at least 1.35 μM, at least 1.4 μM, at least 1.45 μM, at least 1.5 μM, at least 1.55 μM, at least 1.6 μM, at least 1.65 μM, at least 1.7 μM, at least 1.75 μM, at least 1.8 μM, at least 1.85 μM, at least 1.9 μM, at least 1.95 μM, at least 2 μM, at least 2.05 μM, at least 2.1 μM, at least 2.15 μM, at least 2.2 μM, at least 2.25 μM, at least 2.3 μM, at least 2.35 μM, at least 2.4 μM, at least 2.45 μM, at least 2.5 μM, at least 2.55 μM, at least 2.6 μM, at least 2.65 μM, at least 2.7 μM, at least 2.75 μM, at least 2.8 μM, at least 2.85 μM, at least 2.9 μM, at least 2.95 μM, at least 3 μM, at least 3.05 μM, at least 3.1 μM, at least 3.15 μM, at least 3.2 μM, at least 3.25 μM, at least 3.3 μM, at least 3.35 μM, at least 3.4 μM, at least 3.45 μM, at least 3.5 μM, at least 3.55 μM, at least 3.6 μM, at least 3.65 μM, at least 3.7 μM, at least 3.75 μM, at least 3.8 μM, at least 3.85 μM, at least 3.9 μM, at least 3.95 μM, at least 4 μM, at least 4.05 μM, at least 4.1 μM, at least 4.15 μM, at least 4.2 μM, at least 4.25 μM, at least 4.3 μM, at least 4.35 μM, at least 4.4 μM, at least 4.45 μM, at least 4.5 μM, at least 4.55 μM, at least 4.6 μM, at least 4.65 μM, at least 4.7 μM, at least 4.75 μM, at least 4.8 μM, at least 4.85 μM, at least 4.9 μM, at least 4.95 μM, or at least 5 μM.

For systemic administration, subjects can be administered a therapeutic amount of a regulatory protein inducer (e.g., grazoprevir, ABA, and/or 4OHT), such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, the regulatory protein inducer (e.g., grazoprevir, ABA, and/or 4OHT) dose can be from about 2 mg/kg to about 15 mg/kg. In some embodiments, the regulatory protein inducer dose can be about 2 mg/kg. In some embodiments, the regulatory protein inducer dose can be about 4 mg/kg. In some embodiments, the regulatory protein inducer dose can be about 5 mg/kg. In some embodiments, the regulatory protein inducer dose can be about 6 mg/kg. In some embodiments, the regulatory protein inducer dose can be about 8 mg/kg. In some embodiments, the regulatory protein inducer dose can be about 10 mg/kg. In some embodiments, the regulatory protein inducer dose can be about 15 mg/kg. In some embodiments, the regulatory protein inducer dose can be from about 100 $mg/m^2$ to about 700 $mg/m^2$. In some embodiments, the regulatory protein inducer dose can be about 250 $mg/m^2$. In some embodiments, the regulatory protein inducer dose can be about 375 $mg/m^2$. In some embodiments, the regulatory protein inducer dose can be about 400 $mg/m^2$. In some embodiments, the regulatory protein inducer dose can be about 500 $mg/m^2$.

In some embodiments, the regulatory protein inducer (e.g., grazoprevir, ABA, and/or 4OHT) dose can be administered intravenously. In some embodiments, the intravenous administration can be an infusion occurring over a period of from about 10 minute to about 3 hours. In some embodiments, the intravenous administration can be an infusion occurring over a period of from about 30 minutes to about 90 minutes.

In some embodiments the SynTF-expressing cell compositions or SynTF-system-expressing cell compositions and/or regulatory protein inducer (e.g., grazoprevir, ABA, and/or 4OHT) dose(s) can be administered about weekly. In some embodiments, the dose(s) can be administered weekly. In some embodiments, the dose(s) can be administered weekly for from about 12 weeks to about 18 weeks. In some embodiments, the dose(s) can be administered about every 2 weeks. In some embodiments, the dose(s) can be administered about every 3 weeks. In some embodiments, a total of from about 2 to about 10 doses are administered. In some embodiments, a total of 4 doses are administered. In some embodiments, a total of 5 doses are administered. In some embodiments, a total of 6 doses are administered. In some embodiments, a total of 7 doses are administered. In some embodiments, a total of 8 doses are administered. In some embodiments, the administration occurs for a total of from about 4 weeks to about 12 weeks. In some embodiments, the administration occurs for a total of about 6 weeks. In some embodiments, the administration occurs for a total of about 8 weeks. In some embodiments, the administration occurs for a total of about 12 weeks. In some embodiments, the initial dose can be from about 1.5 to about 2.5 fold greater than subsequent doses.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a synTF cell and/or regulatory protein inducer as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the synTF system and/or the regulatory protein inducer. The desired dose or amount can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising a synTF or synTF system as described herein can be administered over a period of time, such as over a 5 minute, 10 minute, 15 minute, 20 minute, or 25 minute period.

The dosage ranges for the administration of a synTF or a synTF system, according to the methods described herein depend upon, for example, the form of the synTF or synTF system, its potency, and the extent to which symptoms, markers, or indicators of a condition described herein are desired to be reduced, for example the percentage reduction desired for the disease or disorder (e.g., cancer or autoimmunity). The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a synTF or a synTF system in, e.g. the treatment of a condition described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor size. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. tumor size). It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. tumor size.

In vitro and animal model assays are provided herein which allow the assessment of a given dose of a synTF or a synTF system. The efficacy of a given dosage combination can also be assessed in an animal model, e.g. a specific cancer animal model.

In one aspect, described herein is a pharmaceutical composition comprising at least one synTF polypeptide, at least one synTF system, at least one synTF polynucleotide, at least one synTF nucleic acid construct, at least one synTF vector, or at least one synTF-comprising cell as described herein, which are collectively referred to as a "synTF composition". In some embodiments of any of the aspects, the pharmaceutical composition can comprise any combination of synTF polypeptides or systems (see e.g., Table 17). In some embodiments of any of the aspects, the pharmaceutical composition can further comprise a regulator protein inducer (e.g., grazoprevir, ABA, and/or 4OHT).

In some embodiments, the technology described herein relates to a pharmaceutical composition comprising a synTF composition and/or regulator protein inducer as described herein, and optionally a pharmaceutically acceptable carrier. In some embodiments, the active ingredients of the pharmaceutical composition comprise the synTF, the synTF system, and/or the regulator protein inducer as described herein. In some embodiments, the active ingredients of the pharmaceutical composition consist essentially of the synTF, the synTF system, and/or the regulator protein inducer as described herein. In some embodiments, the active ingredients of the pharmaceutical composition consist of the synTF, synTF system, and/or the regulator protein inducer as described herein.

Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids; (23) serum component, such as serum albumin, HDL and LDL; (24) $C_2$-$C_{12}$ alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. the synTF polypeptide, the synTF system, and/or the regulator protein inducer as described herein.

In some embodiments, the pharmaceutical composition comprising a synTF composition and/or a regulator protein inducer as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of synTF compositions and/or a regulator protein inducer as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Pharmaceutical compositions comprising synTF compositions and/or a regulator protein inducer can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the synTF composition and/or regulator protein inducer described herein is administered as a monotherapy, e.g., another treatment for the disease or disorder (e.g., cancer) is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include radiation therapy, surgery, gemcitabine, cisplatin, paclitaxel, carboplatin, bortezomib, AMG479, vorinostat, rituximab, temozolomide, rapamycin, ABT-737, PI-103; alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylmelamines including altretamine, triethylenemelamine, trietylenephosphoramide, triethylenethiophosphoramide and trimethylol melamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomycins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylomithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

VII. Treatment Methods

The synTF compositions described herein can be administered to a subject in need thereof, in particular the treatment of cancer or autoimmunity. In some embodiments of any of the aspects, the subject has a genetic disorder in need of regenerative medicine and/or immunotherapy.

In some embodiments, the synTF system expresses a gene of interest (e.g., a therapeutic protein, analyte), which is controlled by at least one inducible synTF, that is itself regulated by at least one regulator protein and its corresponding regulator protein inducer. As such, the expression of the gene of interest can be specifically regulated by the presence, absence, or increased or decreased level of the regulator protein inducer (e.g., an FDA-approved small molecule such as grazoprevir, ABA, or 4OHT) for the treatment of a disease such as cancer, autoimmunity, or a genetic disorder.

By way of example only, an exemplary system to treat cancer includes a CAR (e.g., CD19-CAR) regulated by a synTF as described herein (e.g., a repressible protease synTF). As another non-limiting example, an exemplary system to treat cancer includes a CAR (e.g., CD19-CAR) and a cytokine (e.g., IL4), which are each regulated by a separate synTF, e.g., a repressible protease synTF and a cytosolic sequestering synTF, respectively. As another non-limiting example, an exemplary system to treat autoimmune disease includes a cytokine (e.g., IL10) regulated by a synTF as described herein (e.g., a repressible protease synTF), which can be expressed from a single vector system or a double vector system.

In some embodiments, the method of treatment can comprise first diagnosing a subject or patient who can benefit from treatment by a composition described herein. In some embodiments, such diagnosis comprises detecting or measuring an abnormal level of a marker (e.g., the tumor) in a sample from the subject or patient. In some embodiments, the method further comprises administering to the patient a synTF composition as described herein.

In some embodiments, the subject has previously been determined to have an abnormal level of an analyte described herein relative to a reference. In some embodiments, the reference level can be the level in a sample of similar cell type, sample type, sample processing, and/or obtained from a subject of similar age, sex and other demographic parameters as the sample/subject. In some embodiments, the test sample and control reference sample are of the same type, that is, obtained from the same biological source, and comprising the same composition, e.g. the same number and type of cells.

The term "sample" or "test sample" as used herein denotes a sample taken or isolated from a biological organism, e.g., a blood or plasma sample from a subject. In some embodiments of any of the aspects, the technology described herein encompasses several examples of a biological sample. In some embodiments of any of the aspects, the biological sample is cells, or tissue, or peripheral blood, or bodily fluid. Exemplary biological samples include, but are not limited to, a biopsy, a tumor sample, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject.

In some embodiments of any of the aspects, the step of determining if the subject has an abnormal level of an analyte described herein can comprise i) obtaining or having obtained a sample from the subject and ii) performing or having performed an assay on the sample obtained from the subject to determine/measure the level of the analyte in the subject. In some embodiments of any of the aspects, the step of determining if the subject has an abnormal level of an analyte described herein can comprise performing or having performed an assay on a sample obtained from the subject to determine/measure the level of analyte in the subject. In some embodiments of any of the aspects, the step of determining if the subject has an abnormal level of an analyte described herein can comprise ordering or requesting an assay on a sample obtained from the subject to determine/measure the level of the analyte in the subject. In some embodiments of any of the aspects, the step of determining if the subject has an abnormal level of an analyte described herein can comprise receiving the results of an assay on a sample obtained from the subject to determine/measure the level of the analyte in the subject. In some embodiments of any of the aspects, the step of determining if the subject has an abnormal level of an analyte described herein can comprise receiving a report, results, or other means of identifying the subject as a subject with a decreased level of the analyte.

In one aspect of any of the embodiments, described herein is a method of treating cancer (or autoimmunity or another disease or disorder as described herein) in a subject in need thereof, the method comprising: a) determining if the subject has an abnormal level of an analyte described herein; and b) instructing or directing that the subject be administered a synTF composition as described herein if the level of the analyte is increased or otherwise abnormal relative to a reference. In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

In one aspect, described herein is a method of regulating the activity of a synTF, comprising the steps of: (a) providing a population of cells comprising a synTF or a synTF system as described herein; and (b) contacting the population of cells with an effective amount of at least one regulator protein inducer.

In one aspect, described herein is a method of regulating the expression of a gene of interest, comprising the steps of: (a) providing a population of cells comprising a synTF or a synTF system as described herein; and (b) contacting the population of cells with an effective amount of at least one regulator protein inducer.

In one aspect, described herein is a method of treating a subject in need of a cell-based therapy. In some embodiments of any of the aspects, a subject in need of a cell-based therapy comprises any subject that would benefit from regulated expression of a gene of interest. In some embodiments of any of the aspects, a subject in need of a cell-based therapy comprises a subject with cancer, autoimmunity, or another disease or disorder. In some embodiments of any of the aspects, the subject has a genetic disorder in need of regenerative medicine and/or immunotherapy. Accordingly, the method comprises the steps of: (a) administering to the subject a population of cells comprising a synTF or a synTF system as described herein; and (b) administering to the subject an effective amount of at least one regulator protein inducer.

In embodiments wherein the synTF comprises a transcriptional activator, a TED, and a repressible protease, induced proximity domain, and/or cytosolic sequestering domain, in the presence of the regulator protein inducer, the synTF is ON and the transcription of the gene of interest is ON; and in the absence of the regulator protein inducer, the synTF is OFF and the transcription of the gene of interest is OFF.

In embodiments wherein the synTF comprises a transcriptional activator, a TED, and an induced degradation domain (e.g., SMASh), in the presence of the regulator protein inducer, the synTF is OFF and the transcription of the gene of interest is OFF; and in the absence of the regulator protein inducer, the synTF is ON and the transcription of the gene of interest is ON.

In some embodiments of any of the aspects, the population of cells comprises immune cells. In some embodiments of any of the aspects, the population of immune cells comprises CD4+ T cells, CD8+ T cells, Tregs, or NK cells. In some embodiments of any of the aspects, the population of immune cells comprises macrophages or monocytes.

In some embodiments of any of the aspects, the regulator protein inducer is administered at the same time the population of cells is administered. In some embodiments of any of the aspects, the regulator protein inducer is administered after the population of cells is administered. As a non-limiting example, the regulator protein inducer is administered at least 1 minute, at least 2 minutes, at least 3 minutes, at least 4 minutes, at least 5 minutes, at least 10 minutes, at least 20 minutes, at least 30 minutes, at least 1 hour, at least 2 hours, at least 3 hours, at least 6 hours, at least 12 hours, at least 24 hours, at least 2 days, at least 3 days, at least 4 days, at least 5 days, at least 6 days, at least 7 days, at least 1.5 weeks, at least 2 weeks, at least 3 weeks, at least 4 weeks, at least 5 weeks, at least 6 weeks, at least 7 weeks, at least 8 weeks, at least 9 weeks, at least 10 weeks, at least 1 month, at least 2 months, at least 3 months, at least 4 months, at least 5 months, at least 6 months, at least 7 months, at least 8 months, at least 9 months, at least 10 months, at least 11 months, or at least 1 year after the population of cells is administered. In some embodiments of any of the aspects, the regulator protein inducer is administered continuously, e.g., using an IV.

Cancer

In various embodiments, a cell comprising a synTF or a synTF system as described herein can be used to treat a cancer. In some embodiments, an immune cell (e.g., T cell) comprises a synTF system expressing an anti-cancer gene of interest under the control of the synTF can be used to treat a cancer.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastases. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

Autoimmune Diseases

In various embodiments, a cell comprising a synTF or a synTF system as described herein can be used to treat an autoimmune disease. In some embodiments, an immune cell (e.g., T cell) comprises a synTF system expressing a gene of interest directed against an autoimmune disease-specific antigen under the control of the synTF can be used to treat an autoimmune disease. Autoimmunity is the system of immune responses of an organism against its own healthy cells and tissues. Any disease that results from such an aberrant immune response is termed an "autoimmune disease". "Autoimmune disease" refers to a class of diseases in which a subject's own antibodies react with host tissue and/or in which immune effector T cells are autoreactive to endogenous self-peptides and cause destruction of tissue. Thus, an immune response is mounted against a subject's own antigens, referred to as self-antigens. A "self-antigen" as used herein refers to an antigen of a normal host tissue. Normal host tissue does not include neoplastic cells.

Autoantigens, as used herein, are endogenous proteins or fragments thereof that elicit this pathogenic immune response. Autoantigen can be any substance or a portion thereof normally found within a mammal that, in an autoimmune disease, becomes the primary (or a primary) target of attack by the immune system. The term also includes antigenic substances that induce conditions having the characteristics of an autoimmune disease when administered to mammals. Additionally, the term includes peptic subclasses consisting essentially of immunodominant epitopes or immunodominant epitope regions of autoantigens. Immunodominant epitopes or regions in induced autoimmune conditions are fragments of an autoantigen that can be used instead of the entire autoantigen to induce the disease. In humans afflicted with an autoimmune disease, immunodominant epitopes or regions are fragments of antigens specific to the tissue or organ under autoimmune attack and recognized by a substantial percentage (e.g. a majority though not necessarily an absolute majority) of autoimmune attack T-cells.

Autoantigens that are known to be associated with autoimmune disease include myelin proteins with demyelinating diseases, e.g. multiple sclerosis and experimental autoimmune myelitis; collagens and rheumatoid arthritis; insulin, proinsulin, glutamic acid decarboxylase 65 (GAD65); islet cell antigen (ICA512; ICA12) with insulin dependent diabetes.

A common feature in a number of autoimmune related diseases and inflammatory conditions is the involvement of pro-inflammatory CD4+ T cells. These T cells are responsible for the release of inflammatory, Th1 type cytokines. Cytokines characterized as Th1 type include interleukin 2 (IL-2), y-interferon, TNF$\alpha$ and IL-12. Such pro-inflammatory cytokines act to stimulate the immune response, in many cases resulting in the destruction of autologous tissue. Cytokines associated with suppression of T cell response are the Th2 type, and include IL-10, IL-4 and TGF-$\beta$. It has been found that Th1 and Th2 type T cells may use the identical antigen receptor in response to an immunogen; in the former producing a stimulatory response and in the latter a suppressive response.

Provided herein is a method of treating an autoimmune disease, which comprises administering an effective amount of a synTF composition to a patient in need thereof. In one embodiment of any one of the methods described, the autoimmune disorder is selected from the group consisting of thyroiditis, type 1 diabetes mellitus, Hashimoto's thyroidits, Graves' disease, celiac disease, multiple sclerosis, Guillain-Barre syndrome, Addison's disease, and Raynaud's phenomenon, Goodpasture's disease, arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, guttate psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritus scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, erythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, diabetic retinopathy, diabetic nephropathy, diabetic large-artery disorder, immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, an immune complex disorder such as immune complex nephritis, antibody-mediated nephritis, polyneuropathies, chronic neuropathy such as IgM polyneuropathies or IgM-mediated neuropathy, and autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, lupoid hepatitis, giant-cell hepatitis, autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcomeal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amyotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies including channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to antispermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, Sampter's syndrome, Caplan's syndrome, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic fasciitis, Shulman's syndrome, Felty's syndrome, cyclitis such as chronic cyclitis, heterochromic cyclitis, iridocyclitis (acute or chronic), or Fuch's cyclitis, Henoch-Schonlein purpura, SCID, sepsis, endotoxemia, post-vaccination syndromes, Evan's syndrome, autoimmune gonadal failure, Sydenham's chorea, post-streptococcal nephritis, thromboangitis obliterans, thyrotoxicosis, tabes dorsalis, chorioiditis, giant-cell polymyalgia, chronic hypersensitivity pneumonitis, keratoconjunctivitis sicca, idiopathic nephritic syndrome, minimal change nephropathy, benign familial and ischemia-reperfusion injury, transplant organ reperfusion, retinal autoimmunity, aphthae, aphthous stomatitis, arteriosclerotic disorders, aspermiogenesis, autoimmune hemolysis, Boeck's disease, enteritis allergica, erythema nodosum leprosum, idiopathic facial paralysis, chronic fatigue syndrome, febris rheumatica, Hamman-Rich's disease, sensoneural hearing loss, ileitis regionalis, leucopenia, transverse myelitis, primary idiopathic myxedema, ophthalmia symphatica, polyradiculitis acuta, pyoderma gangrenosum, acquired splenic atrophy, vitiligo, toxic-shock syndrome, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, rheumatic diseases, mixed connective tissue disease, nephrotic syndrome, insulitis, polyendocrine failure, autoimmune polyglandular syndrome type I, adult-onset idiopathic hypoparathyroidism (AOIH), myocarditis, nephrotic syndrome, primary sclerosing cholangitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, granulomas containing eosinophils, seronegative spondyloarthritides, polyendocrine autoimmune disease, sclerosing cholangitis, sclera, episclera, Bruton's syndrome, transient hypogammaglobulinemia of infancy, Wiskott-Aldrich syndrome, ataxia telangiectasia syndrome, angiectasis, autoimmune disorders associated with collagen disease, rheumatism, allergic hypersensitivity disorders, glomerulonephritides, reperfusion injury, ischemic reperfusion disorder, lymphomatous tracheobronchitis, inflammatory dermatoses, dermatoses with acute inflammatory components, and autoimmune uveoretinitis (AUR).

Genetic Disorders

In various embodiments, a cell comprising a synTF or a synTF system described herein can be used to treat a genetic disorder. In some embodiments, a cell comprises a synTF system expressing a gene of interest that replaces a defective gene under the control of the synTF can be used to treat a genetic disorder. In some embodiments, the cell is a stem cell.

Non-limiting examples of genetic disorders that can be treated using a synTF, a synTF system, or a synTF cell as described herein include: hemoglobinopathies; b-Thalassemia major; a-Thalassemia major; Sickle cell anemia; Immunodeficiency Diseases; Severe combined immunodeficiency syndrome; Bare lymphocyte syndrome; Chronic granulomatous disease; Wiskott-Aldrich syndrome; Infantile agranulocytosis (Kostman's syndrome); Lazy leukocyte syndrome (neutrophil actin deficiency); Neutrophil membrane GP-180 deficiency; Agammaglobulinemia; X-linked lymphoproliferative syndrome; X-linked hyper-IgM syndrome; inborn errors of metabolism; Mucopolysaccharidoses; Hurler's disease (MPS-1) (a-iduronidase deficiency); Hurler-Scheie syndrome; Hunter disease (MPS-II) (iduronate sulfatase deficiency); Sanfillippo B (MPS-IIIB) (a-glycosaminidase deficiency); Morquio (MPS-IV) (hexosamine-6-sulfatase deficiency); Maroteaux-Lamy syndrome (MPS-VI) (arylsulfatase B deficiency); Sly syndrome (MPS-VII) (b-glucuronidase deficiency); Mucolipidoses; Fabry disease (a-galactosidase A deficiency); Gaucher disease (glucocerebrosidase deficiency); Krabbe disease (galactosylceramidase deficiency); Metachromatic leukodystrophy (arylsulfatase A deficiency); Niemann-Pick disease (sphingomyelinase deficiency); Adrenal leukodystrophy; I-cell mucolipidosis II; hematopoietic diseases; Osteopetrosis; Diamond-Blackfan syndrome; and Fanconi anemia.

VII. Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, the terms "reporter gene", "reporter construct", "reporter", "engineered responsive reporter" or "engineered transcription unit" refer to a nucleic acid construct containing an engineered promoter that is operably linked to a reporter gene, and the expression of the reporter gene is controlled by upstream regulatory elements such orthogonal DNA target sequence(s) in the engineered promoter. A reporter gene is typically one where the gene product, the transcribed protein, is easily detected and monitored, e.g., the green fluorescent protein.

As used herein, the term "promoter" as used in the art, is a region of DNA that initiates transcription of a particular gene and is at which RNA polymerase binds and initiates transcription. Promoters are located near the transcription start sites of genes, on the same strand and upstream on the DNA As used herein, the term "orthogonal" when used in DNA sequences and genome biology "orthogonal" means DNA sequences that are so dissimilar from that which is naturally occurring in nature in the eukaryotic system.

As used herein, the term "derived from" refers to the origin or source, and can include naturally occurring, recombinant, truncated, unpurified, or purified molecules. For example, domain sequences and truncations thereof described herein can be derived from the full-length naturally occurring polypeptide sequences.

As used herein, the term "responsive" in the context of an engineered promoter or engineered transcription unit or engineered responsive reporter, the term refers to whether gene transcription initiation from the promoter is enhanced when upstream nearby orthogonal DNA target sequences are bound by their respective ZF-containing synthetic transcription factors.

As used herein, the term "operably linked" when used in context of the orthogonal DNA target sequences described herein or the promoter sequence (RNA polymerase binding site) in a nucleic acid construct, an engineered responsive reporter, and in an engineered transcription unit means that the orthogonal DNA target sequences and the promoters are in-frame and in proper spatial and distance away from a nucleic acid coding for a protein or peptide or an RNA to permit the effects of the respective binding by transcription factors or RNA polymerase on transcription.

The terms "nucleic acid", "polynucleotide", "nucleic acid sequence", and "oligonucleotide" are used interchangeably and refer to a deoxyribonucleotide (DNA) or ribonucleotide (RNA) polymer, in linear or circular conformation, and in either single- or double-stranded form. For the purposes of the present disclosure such DNA or RNA polymers may include natural nucleotides, non-natural or synthetic nucleotides, and mixtures thereof. Non-natural nucleotides may include analogues of natural nucleotides, as well as nucleotides that are modified in the base, sugar and/or phosphate moieties (e.g. phosphorothioate backbones). Non-limiting examples of modified nucleic acids are PNAs and morpholino nucleic acids. Generally an analogue of a particular nucleotide has the same base-pairing specificity, i.e. an analogue of G will base-pair with C. For the purposes of the disclosure, these terms are not to be considered limiting with respect to the length of a polymer. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA, cDNA, or vector DNA. Suitable RNA can include, e.g., mRNA.

A "gene", as used herein, is the segment of nucleic acid (typically DNA) that is involved in producing a polypeptide or ribonucleic acid gene product. It includes regions preceding and following the coding region (leader and trailer) as well as intervening sequences (introns) between individual coding segments (exons). Conveniently, this term also includes the necessary control sequences for gene expression (e.g. enhancers, silencers, promoters, terminators etc.), which may be adjacent to or distant to the relevant coding sequence, as well as the coding and/or transcribed regions encoding the gene product.

As used herein the term "modulation", in relation to the expression of a gene refers to a change in the gene's activity. Modulation includes both activation (i.e. increase in activity or expression level) and repression or inhibition of gene activity. In preferred embodiments of the disclosure, the therapeutic molecules (e.g. peptides) of the disclosure are activators of gene expression or activity.

A nucleic acid "target", "target site" or "target sequence" or "DNA target sequence", as used herein, is a nucleic acid sequence to which a ZFA in a synTF of the disclosure will bind, provided that conditions of the binding reaction are not prohibitive. A target site may be a nucleic acid molecule or a portion of a larger polynucleotide. In accordance with the disclosure, a target sequence for a ZFA in a synTF of the disclosure may comprise a single contiguous nucleic acid sequence. These terms may also be substituted or supplemented with the terms "binding site", "binding sequence", "recognition site" or "recognition sequence", which are used interchangeably.

As used herein, "binding" refers to a non-covalent interaction between macromolecules (e.g. between a ZF-array containing protein and a nucleic acid target site). In some cases binding will be sequence-specific, such as between one or more specific nucleotides (or base pairs) and one or more specific amino acids. It will be appreciated, however, that not all components of a binding interaction need be sequence-specific (e.g. non-covalent interactions with phosphate residues in a DNA backbone). Binding interactions between a nucleic acid sequence and a ZF peptide of the disclosure may be characterized by binding affinity and/or dissociation constant (Kd). A suitable dissociation constant for a ZF peptide of the disclosure binding to its target site may be in the order of 1 μM or lower, 1 nM or lower, or 1 pM or lower. "Affinity" refers to the strength of binding, such that increased binding affinity correlates with a lower Kd value. ZF synTF of the disclosure may have DNA-binding activity, RNA-binding activity, and/or even protein-binding activity. In some embodiments, the ZF synTF of the disclosure are designed or selected to have sequence specific dsDNA-binding activity. For example, the target site for a particular ZF array or protein is a sequence to which the ZF concerned is capable of nucleotide-specific binding. It will be appreciated, however, that depending on the amino acid sequence of a ZF array or protein it may bind to or recognize more than one target sequence, although typically one sequence will be bound in preference to any other recognized sequences, depending on the relative specificity of the individual non-covalent interactions. Generally, specific binding is preferably achieved with a dissociation constant (Kd) of 1 nM or lower, 100 pM or lower; or 10 pM or lower. In some embodiments, a ZF synTF of the disclosure binds to a specific target sequence with a dissociation constant of 1 nM or lower, or 1 pM or lower, or 0.1 pM or lower, or even 10 fM or lower.

By "non-target" it is meant that the nucleic acid sequence concerned is not appreciably bound by the relevant ZF peptide. In some embodiments it may be considered that, where a ZF peptide described herein has a known sequence-specific target sequence, all other nucleic acid sequences may be considered to be non-target. From a practical perspective it can be convenient to define an interaction between a non-target sequence and a particular ZF peptide as being sub-physiological (i.e. not capable of creating a physiological response under physiological target sequence/ZF peptide concentrations). For example, if any binding can be measured between the ZF peptide and the non-target sequence, the dissociation constant (Kd) is typically weaker than 1 μM, such as 10 μM or weaker, 100 μM or weaker, or at least 1 mM.

As used herein, the term "interaction" when used in the context of a receptor and its ligand refers to the binding between the receptor and its ligand as a result of the non-covalent bonds between the ligand-binding site (or fragment) of the receptor and the receptor-binding site (or fragment) of the ligand. In the context of two entities, e.g., molecules or proteins, having some binding affinity for each other, the term "interaction" refers to the binding of the two entities as a result of the non-covalent bonds between the two entities. A term "interaction", "complexing" and "bonding" are used interchangeably when used in the context of a receptor and its ligand and in the context of two binding entities.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal, e.g., for an individual without a given disorder.

The terms "increased", "increase", "enhance", or "activate" are all used herein to mean an increase by a statistically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10%-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually, the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer, autoimmunity, genetic disorder, etc.) or one or more complications related to such a condition, and optionally, have already undergone treatment for the disease or disorder (e.g., cancer, autoimmunity, genetic disorder, etc.) or the one or more complications related to the disease or disorder (e.g., cancer, autoimmunity, genetic disorder, etc.). Alternatively, a subject can also be one who has not been previously diagnosed as having the disease or disorder (e.g., cancer, autoimmunity, genetic disorder, etc.) or one or more complications related to the disease or disorder (e.g., cancer, autoimmunity, genetic disorder, etc.). For example, a subject can be one who exhibits one or more risk factors for the disease or disorder (e.g., cancer, autoimmunity, genetic disorder, etc.) or one or more complications related to the disease or disorder (e.g., cancer, autoimmunity, genetic disorder, etc.) or a subject who does not exhibit risk factors.

A "subject in need" of treatment for a particular condition can be a subject having that condition, diagnosed as having that condition, or at risk of developing that condition (e.g., cancer, autoimmunity, genetic disorder, etc.).

As used herein, the terms "protein" and "polypeptide" are used interchangeably to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. function and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wild-type reference polypeptide's activity according to the assays described below herein. A functional fragment can comprise conservative substitutions of the sequences disclosed herein. In some embodiments of any of the aspects, a polypeptide can comprise the first N-terminal amino acid methionine. In embodiments where a polypeptide does not comprise a first N-terminal methionine, it is understood that a variant of the polypeptide does comprise a first N-terminal methionine.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 70%, at least 75%, at least 80%, at least 85%, at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (e.g., mRNA) or antisense RNA derived from a nucleic acid fragment or fragments and/or to the translation of mRNA into a polypeptide.

As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

As used herein, the term "humanized" refers to a nucleic acid or polypeptide that has been modified to increase its similarity to variants produced naturally in humans. In some embodiments, a humanized nucleic acid or humanized polypeptide has at least 90%, at least 91%, at least 92%, at least 93%, at least 94%, at least 95%, at least 96%, at least 97%, at least 98%, at least 99%, or more, sequence identity to the corresponding human nucleic acid or human polypeptide.

In some embodiments of any of the aspects, a polypeptide, nucleic acid, or cell as described herein can be engineered. As used herein, "engineered" refers to the aspect of having been manipulated by the hand of man. For example, a polypeptide or nucleic acid is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the synTF polypeptide or synTF system described herein is exogenous. In some embodiments of any of the aspects, the synTF polypeptide or synTF system described herein is ectopic. In some embodiments of any of the aspects, the synTF polypeptide or synTF system described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

As described herein, an "antigen" is a molecule that is bound by a binding site on an antibody agent (e.g., extracellular binding domain). Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

In some embodiments, a nucleic acid encoding a polypeptide as described herein (e.g. a synTF polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art. Non-limiting examples of a viral vector of this invention include an AAV vector, an adenovirus vector, a lentivirus vector, a retrovirus vector, a herpesvirus vector, an alphavirus vector, a poxvirus vector, a baculovirus vector, and a chimeric virus vector.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with the disease or disorder (e.g., cancer, autoimmunity, genetic disorder, etc.). Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in or within nature.

As used herein, the term "administering," refers to the placement of a composition as disclosed herein into a subject by a method or route which results in at least partial delivery of the agent at a desired site. Pharmaceutical compositions comprising the synTF polypeptides, synTF systems, synTF nucleic acids, synTF vectors, and/or synTF cells disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, transfection, transduction, perfusion, injection, or other delivery method known to one skilled in the art. In some embodiments, contacting comprises physical human activity, e.g., an injection; an act of dispensing, mixing, and/or decanting; and/or manipulation of a delivery device or machine.

As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149×); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338×, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A synthetic transcription factor (synTF) comprising:
(a) at least one DNA binding domain (DBD),
(b) a transcriptional activator domain (TA),
(c) a transcriptional effector domain (TED), and
(d) at least one regulator protein (RP), and
wherein the TED increases the transcriptional activation of the synTF compared to an otherwise identical synTF lacking the TED,
wherein the TA is directly or indirectly coupled to the DBD, and
wherein the coupling is regulated by the at least one RP, or
wherein cellular localization of the TA is regulated by the at least one RP.

2. The synTF of paragraph 1, wherein the TED comprises an elongation domain, an activator domain, or a domain with pioneer ability.

3. The synTF of paragraph 2, wherein the elongation domain is derived from a polypeptide selected from the group consisting of: Interacts with Suppressor Of Ty 6 (Spt6) Homolog (IWS1); Suppressor Of Ty 5 (Spt5) Homolog (SUPT5H); Bromodomain-containing protein 4 (BRD4); and cellular Myelocytomatosis (cMyc).

4. The synTF of paragraph 2, wherein the elongation domain is derived from IWS1.

5. The synTF of paragraph 2, wherein the elongation domain is derived from human IWS1.

6. The synTF of paragraph 2, wherein the elongation domain comprises at least one TFIIS N-terminal domains (TND)-interacting motif (TIM) domain of IWS1.

7. The synTF of paragraph 2, wherein the elongation domain comprises at least one TIM1, TIM2, and/or TIM3 domain from IWS1.

8. The synTF of paragraph 2, wherein the elongation domain comprises one of SEQ ID NOs: 5-9 or an amino acid sequence with at least 80% sequence identity to one of SEQ ID NOs: 5-9.

9. The synTF of paragraph 2, wherein the activator domain is derived from a polypeptide selected from the group consisting of: Heat Shock Factor 1 (HSF1), Glucocorticoid Receptor (GR), and MLX interacting protein like (MLXIPL).

10. The synTF of paragraph 2, wherein the domain with pioneer ability is derived from a polypeptide selected from the group consisting of Fused in Sarcoma (FUS) and Ewing Sarcoma Breakpoint Region (EWSR).

11. The synTF of any one of paragraphs 1-10, wherein the TA is selected from the group consisting of: p65; Rta; miniVPR; full VPR; VP16; VP64; NFZ; 3Z; p300; p300 HAT Core; and a CBP HAT domain; or a variant thereof.

12. The synTF of any one of paragraphs 1-11, wherein the TA is p65, or a variant thereof.

13. The synTF of paragraph 12, wherein the p65 comprises one of SEQ ID NOs: 38, 58-67 or an amino acid sequence with at least 80% sequence identity to one of SEQ ID NOs: 38, 58-67.

14. The synTF of any one of paragraphs 1-13, wherein the at least one DBD is an engineered zinc finger (ZF)-binding domain.

15. The synTF of paragraph 14, wherein the engineered ZF-binding domain comprises 2 or more ZF motifs.

16. The synTF of paragraph 15, wherein the engineered ZF-binding domain comprises 3, 4, 5, 6, 7, 8, 9, 10, 11, 12, 13, 14, 15, 16, 17, 18, or more ZF motifs arranged adjacent to each other in tandem to form a ZF array (ZFA).

17. The synTF of any one of paragraphs 14-16, wherein the engineered ZF binding domain comprises a sequence selected from the group consisting of: ZF 1-1, ZF 1-2, ZF 1-3, ZF 1-4, ZF 1-5, ZF 1-6, ZF 1-7, ZF 1-8, ZF 2-1, ZF 2-2, ZF 2-3, ZF 2-4, ZF 2-5, ZF 2-6, ZF 2-7, ZF 2-8, ZF 3-1, ZF 3-2, ZF 3-3, ZF 3-4, ZF 3-5, ZF 3-6, ZF 3-7, ZF 3-8, ZF 4-1, ZF 4-2, ZF 4-3, ZF 4-4, ZF 4-5, ZF 4-6, ZF 4-7, ZF 4-8, ZF 5-1, ZF 5-2, ZF 5-3, ZF 5-4, ZF 5-5, ZF 5-6, ZF 5-7, ZF 5-8, ZF 6-1, ZF 6-2, ZF 6-3, ZF 6-4, ZF 6-5, ZF 6-6, ZF 6-7, ZF 6-8, ZF 7-1, ZF 7-2, ZF 7-3, ZF 7-4, ZF 7-5, ZF 7-6, ZF 7-7, ZF 7-8, ZF 8-1, ZF 8-2, ZF 8-3, ZF 8-4, ZF 9-1, ZF 9-2, ZF 9-3, ZF 9-4, ZF 10-1, and ZF 11-1.

18. The synTF of any one of paragraphs 14-17, wherein the engineered ZF-binding domain comprises one of SEQ ID NO: 36 (ZF10-1), SEQ ID NO: 45 (ZF3-5), or SEQ ID NO: 86 (ZF1-3).

19. The synTF of any one of paragraphs 14-18, wherein the engineered ZF-binding domain comprises ZF 10-1.

20. The synTF of any one of paragraphs 14-19, wherein the engineered ZF-binding domain specifically binds to a nucleic acid with a sequence comprising at least one of SEQ ID NO: 100 (ZF10 binding site (BS)), SEQ ID NO: 93 (ZF3 BS), or SEQ ID NO: 91 (ZF1 BS).

21. The synTF of any one of paragraphs 14-20, wherein the engineered ZF-binding domain comprises SEQ ID NO: 48 and specifically binds endogenous VEGF gene (VEGF ZF).

22. The synTF of any one of paragraphs 1-21, wherein the at least one RP comprises a polypeptide selected from the group consisting of: a repressible protease; a pair of induced proximity domains (IPD pair); a cytosolic sequestering protein; and combinations thereof.

23. The synTF of any one of paragraphs 1-22, wherein the at least one RP comprises a repressible protease.

24. The synTF of any one of paragraphs 1-23, wherein the at least one RP comprises a NS3 protease protein.

25. The synTF of any one of paragraphs 1-24, wherein the at least one RP comprises the amino acid sequence of SEQ ID NOs: 182-198, or a homologue with at least 80% sequence identity to one of SEQ ID NOs: 182-198.

26. The synTF of any one of paragraphs 24-25, wherein in the presence of a protease inhibitor, or an inhibitor of NS3, the protease protein is inhibited, thereby maintaining the coupling of the DBD to the TA.

27. The synTF of any one of paragraphs 24-26, wherein in the absence of a protease inhibitor, or an inhibitor of NS3, the protease protein is active, and the TA is excised from the DBD, thereby uncoupling the DBD and the TA.

28. The synTF of paragraph 26 or 27, wherein the inhibitor of NS3 is selected from the group consisting of: grazoprevir (GRZ/GZV), danoprevir, simeprevir, asunaprevir, ciluprevir, boceprevir, sovaprevir, paritaprevir, ombitasvir, paritaprevir, ritonavir, dasabuvir, and telaprevir.

29. The synTF of any one of paragraphs 1-28, wherein the at least one RP is a pair of induced proximity domains (IPD pair), wherein the IPD pair comprises:

a first induced proximity domain ($IPD^A$) and at least a second complementary IPD ($IPD^B$), wherein in the presence of an inducer agent or signal, the $IPD^A$ and $IPD^B$ specifically bind together resulting in the coupling of the TA to the DBD, and wherein in the absence of an inducer agent or signal, the TA is uncoupled from the DBD.

30. The synTF of paragraph 29, wherein the IPD pair comprises:

(a) a $IPD^A$ comprising a GID1 domain or a fragment thereof, and a $IPD^B$ comprising a GAI domain, wherein the GID1 domain and GAI domain bind to the inducer agent Gibberellin Ester (GIB);

(b) a $IPD^A$ comprising a FKBP domain or a fragment thereof, and a $IPD^B$ comprising a FRB domain, wherein the FKBP domain and FRB domain bind to the inducer agent Rapalog (RAP);

(c) a $IPD^A$ comprising a PYL domain or a fragment thereof, and a $IPD^B$ comprising an ABI domain, wherein the PYL domain and ABI domain bind to the inducer agent Abscisic acid (ABA); and/or (d) a $IPD^A$ comprising a Light-inducible dimerization domain (LIDD), wherein a LIDD dimerizes with a complementary LIDD ($IPD^B$) upon exposure to a light inducer signal of an appropriate wavelength.

31. The synTF of paragraph 30, wherein the LIDD is nMag, Calcium And Integrin-Binding Protein 1 truncation (CIBN), or a photochromic protein domain; wherein nMag can dimerize with a complementary LIDD pMag upon exposure to a blue light inducer signal; or wherein CIBN can dimerize with a complementary cryptochrome 2 (CRY2) upon exposure to a blue inducer light signal; or wherein the photochromic protein domains can dimerize upon exposure to a blue inducer light signal.

32. The synTF of paragraph 30 or 31, wherein the light inducer signal is a pulse light signal.

33. The synTF of any one of paragraphs 1-32, wherein the at least one RP comprises a cytosolic sequestering protein.

34. The synTF of paragraph 33, wherein the cytosolic sequestering protein comprises a ligand binding domain (LBD), wherein in the presence of a ligand to which the LBD binds, sequestering of the synTF to the cytosol is inhibited.

35. The synTF of paragraph 33 or 34, wherein the cytosolic sequestering protein comprises a LBD and a nuclear localization signal (NLS); wherein in the absence of a ligand to which the LBD binds, the NLS is inhibited thereby preventing translocation of the synTF to the nucleus; and wherein in the presence of the ligand, the NLS is exposed permitting translocation of the synTF to the nucleus.

36. The synTF of any one of paragraphs 33-35, wherein the cytosolic sequestering protein comprises at least a portion of an estrogen receptor (ER).

37. The synTF of any one of paragraphs 33-36, wherein the cytosolic sequestering protein comprises an estrogen ligand binding domain (ERT) or a variant thereof, selected from the group consisting of: SEQ ID NO: 43 (ERT2), SEQ ID NO: 304, and SEQ ID NO: 305 (ERT3).

38. The synTF of paragraph 37, wherein the ERT binds to one or more ligands selected from the group consisting of: tamoxifen, 4-hydroxytamoxifen (4OHT), endoxifen, and Fulvestrant; wherein binding of the ligand to the ERT exposes the NLS and results in nuclear translocation of the ERT.

39. The synTF of any one of paragraphs 33-38, wherein the cytosolic sequestering protein comprises a transmembrane receptor sequestering protein.

40. The synTF of any one of paragraphs 24-39, wherein the NS3 protease protein is part of a Small molecule-Assisted Shutoff (SMASh) domain, wherein the SMASh domain comprises the NS3 protease protein, a partial protease helical domain and a NS4A domain.

41. The synTF of any one of paragraphs 1-40, further comprising a Small molecule-Assisted Shutoff (SMASh) domain, wherein the SMASh domain is a N-terminal or C-terminal SMASh domain comprising a repressible protease, a partial protease helical domain and a cofactor domain.

42. The synTF of paragraph 41, wherein the SMASh domain is a C-terminal SMASh domain comprising, in N-terminal to C-terminal order: a NS3 cleavage site, at least one linker, a NS3 domain, a NS3 partial helicase, and a NS4A domain, wherein the SMASh domain is fused to the C-terminus of the synTF.

43. The synTF of paragraph 41, wherein the SMASh domain is a N-terminal SMASh domain comprising in N-terminal to C-terminal order: at least one Linker, a NS3 domain, a NS3 partial helicase, a NS4 domain, and a NS3 cleavage site, wherein the SMASh domain is fused to the N-terminus of the synTF.

44. The synTF of any one of paragraphs 40-43, wherein in the absence of an inhibitor for the NS3 protease, the NS3 protease is active and self cleaves/uncouples from the synTF, thereby resulting in the SMASh domain targeted for degradation ("SMASh-degradation", synTF-on/TA-on), and
wherein in the presence of an inhibitor for the NS3 protease, NS3 protease activity is inhibited thereby resulting in the SMASh-comprising synTF targeted for degradation ("synTF-degradation", synTF-OFF/TA-off").

45. The synTF of paragraph 44, wherein the inhibitor for the NS3 protease is selected from the group consisting of: grazoprevir (GRZ/GZV), danoprevir, simeprevir, asunaprevir, ciluprevir, boceprevir, sovaprevir, paritaprevir, ombitasvir, paritaprevir, ritonavir, dasabuvir, and telaprevir.

46. The synTF of any one of paragraphs 1-45, wherein the synTF comprises a SMASh domain and a cytosolic sequestering protein.

47. The synTF of paragraph 46, wherein the synTF is active in the presence of the ligand for the cytosolic sequestering protein and in the absence of the inhibitor for the NS3 protease; and wherein the synTF is inactive in the absence of the ligand for the cytosolic sequestering protein and/or in the presence of the inhibitor for the NS3 protease.

48. The synTF of any of paragraphs 1-47, further comprising a linker peptide, wherein the linker peptide can be positioned anywhere from: between the DBD and the RP; between the RP and TA; between the DBD and TA; between the TED and TA; between the TED and DBD; between the TED and RP; within the DBD, TA, TED, or regulator protein; or any combination thereof.

49. The synTF of any one of paragraphs 1-48, wherein the DBD, TA, TED, and/or RP are human domains or humanized domains.

50. The synTF of any one of paragraphs 1-49, wherein the DBD, TA, TED, and RP are human domains or humanized domains.

51. A synthetic transcription factor (synTF) comprising:
(a) at least one DNA binding domain (DBD),
(b) a transcriptional activator domain (TA), and
(c) a transcriptional effector domain (TED),
wherein the TED increases the transcriptional activation of the synTF compared to an otherwise identical synTF lacking the TED.

52. A hybrid transcription activator domain (hTAD), comprising:
(a) a transcriptional activator domain (TA), and
(b) a transcriptional effector domain (TED),
wherein the TED increases the transcriptional activation of the TA compared to an otherwise identical hTAD lacking the TED.

53. The hTAD of paragraph 52, wherein the TA and/or TED are human domains or humanized domains.

54. A synthetic transcription factor (synTF) comprising the hTAD of paragraph 52 or 53 and at least one DNA binding domain (DBD).

55. The synTF of paragraph 54, further comprising at least one regulator protein (RP).

56. A humanized hybrid transcription activator domain (hhTAD), comprising:
(a) a transcriptional activator domain (TA), and
(b) a transcriptional effector domain (TED),
wherein the TED increases the transcriptional activation of the TA compared to an otherwise identical hhTAD lacking the TED; and
wherein the TA and TED are human domains or humanized domains.

57. A synthetic transcription factor (synTF) comprising the hhTAD of paragraph 56 and at least one DNA binding domain (DBD).

58. The synTF of paragraph 57, further comprising at least one regulator protein (RP).

59. A system for controlling gene expression, comprising:
(a) at least one synthetic transcription factor (synTF) of any one of paragraphs 1-51, 54-55, 57 and 58,
wherein the at least one DBD of the synTF can bind to a target DNA binding motif (DBM) located upstream of a promoter operatively linked to a gene; and
(b) a nucleic acid construct comprising:
(i) at least one target DNA binding motif (DBM) comprising a target nucleic acid for binding of the at least one DBD of the synTF;

(ii) a promoter sequence located 3' of the at least one DBM; and (iii) a gene of interest operatively linked to the promoter sequence.

60. The system of paragraph 59, wherein the synTF comprises at least one RP regulated by an RP inducer.

61. The system of paragraph 59 or 60, wherein the coupling of the TA to the DBD is regulated by the at least one RP.

62. The system of paragraph 61, wherein the RP comprises a repressible protease or an IPD pair.

63. The system of any one of paragraphs 61-62, wherein in the presence of the RP inducer, the coupling of the TA to the DBD of the synTF is maintained, permitting the TA to be in proximity to the promoter sequence when the DBD binds to the DBM, and wherein the TA turns on expression of the gene of interest ("TA-on").

64. The system of paragraph 61-63, wherein in the absence of the RP inducer, the coupling of the TA to the DBD of the synTF is severed, preventing the TA from being in proximity to the promoter sequence when the DBD binds to the DBM, preventing expression of the gene of interest ("TA-off").

65. The system of any one of paragraphs 59-64, wherein cellular localization of the TA linked to the DBD is regulated by the at least one RP.

66. The system of paragraph 65, wherein the RP comprises a cytosolic sequestering protein.

67. The system of any one of paragraphs 65-66, wherein in the presence of the RP inducer, the TA coupled to the DBD of the synTF is not sequestered in the cytosol, permitting the DBD to bind to the DNA binding motif (DBM) and permitting the TA domain to be in proximity to the promoter sequence to thereby turn on expression of the gene of interest ("TA-on").

68. The system of any one of paragraphs 65-67, wherein in the absence of the RP inducer, the TA coupled to the DBD of the synTF is sequestered in the cytosol, preventing the DBD from binding to the DBM, and preventing the TA domain from being in proximity to the promoter sequence, thereby preventing expression of the gene of interest ("TA-off").

69. The system of any one of paragraphs 59-68, wherein the at least one synTF further comprises a N-terminal or C-terminal Small molecule-Assisted Shutoff (SMASh) domain, wherein SMASh domain comprises a self-cleaving SMASh protease, a partial protease helical domain and a cofactor domain.

70. The system of paragraph 69, wherein in the presence of an inhibitor to the SMASh protease, the SMASh protease activity is inhibited, resulting in the synTF being degraded and preventing the DBD of the synTF binding to the DBM and controlling the expression of the gene of interest ("synTF-degradation"; TA-off (no expression)).

71. The system of paragraph 69 or 70, wherein in the absence of an inhibitor to the SMASh protease, the SMASh protease is active and self cleaves/uncouples from the synTF, resulting the SMASh domain being targeted for degradation and allowing the DBD of the synTF to bind to the DBM and the TA of synTF to control the expression of the gene of interest ("SMASh-degradation, TA-on (yes-expression)).

72. The system of any of paragraphs 59-71, wherein the promoter is selected from the group consisting of: miniCMV promoter, miniTK promoter, ybTATA promoter, minSV40 promoter, CMV53 promoter, pJB42CAT5 promoter, MLP promoter, TATA promoter, pSFFV promoter, CMV promoter, pUb/UbC promoter, EF1a promoter, PGK/pGK promoter, CAG/CAGG promoter, SV40 promoter, and beta actin/ACTB promoter.

73. A system comprising:

(a) a first nucleic acid sequence comprising at least one target DNA binding motif (DBM) comprising a target nucleic acid for binding of at least one DBD of a synTF, a promoter sequence located 3' of the at least one DBM, and a nucleic acid encoding a gene of interest (GOI) operatively linked to the promoter sequence; and (b) a second nucleic acid sequence comprising a nucleic acid encoding a synthetic transcription factor (synTF) according to any one of paragraphs 1-51, 54-55, 57 and 58, operatively linked to an inducible or constitutive promoter.

74. The system of paragraph 73, wherein the promoter sequence operatively linked to the GOI is selected from the group consisting of: miniCMV promoter, miniTK promoter, ybTATA promoter, minSV40 promoter, CMV53 promoter, pJB42CAT5 promoter, MLP promoter, and TATA promoter.

75. The system of paragraph 73 or 74, wherein the promoter sequence operatively linked to the nucleic acid encoding the synTF is selected from the group consisting of pSFFV promoter, CMV promoter, pUb/UbC promoter, EF1a promoter, PGK/pGK promoter, CAG/CAGG promoter, SV40 promoter, and beta actin/ACTB promoter.

76. A polynucleotide encoding the synTF of any one of paragraphs 1-51, 54-55, 57, and 58; the hTAD of paragraph 52 or 53; the hhTAD of paragraph 56; or the system of any one of paragraphs 59-75; or portion thereof.

77. A nucleic acid construct, comprising in the 5' to 3' direction:

(a) a nucleic acid sequence encoding a gene of interest (GOI) in the inverse orientation, (b) a first promoter sequence in the inverse orientation and operatively linked to the nucleic acid encoding the GOI, (c) a nucleic acid sequence comprising at least one target DNA binding motif (DBM) comprising a target nucleic acid for binding of at least one DBD of a synthetic transcription factor (synTF), wherein binding of the DBD places a TA of the synTF in the proximity of the promoter sequence operatively linked to the GOI, (d) a second promoter sequence, and (e) a nucleic acid sequence encoding the synTF, operatively linked to the second promoter sequence, wherein the encoded synTF comprises at least one DBD that binds to the at least one DBM of the nucleic acid sequence of (c).

78. The nucleic acid construct of paragraph 77, wherein the promoter sequence operatively linked to the GOI is selected from the group consisting of: miniCMV promoter, miniTK promoter, ybTATA promoter, minSV40 promoter, CMV53 promoter, pJB42CAT5 promoter, MLP promoter, and TATA promoter.

79. The nucleic acid construct of paragraph 77 or 78, wherein the promoter sequence operatively linked to the nucleic acid encoding the synTF is selected from the group consisting of a pSFFV promoter, CMV promoter, pUb/UbC promoter, EF1a promoter, PGK/pGK promoter, CAG/CAGG promoter, SV40 promoter, and beta actin/ACTB promoter.

80. A vector comprising the system of any one of paragraphs 59-75; the polynucleotide of paragraph 76; or the nucleic acid construct of any one of paragraphs 77-79; or portion thereof.

81. The vector of paragraph 80, wherein the vector is a lentiviral vector.

82. A cell comprising the synTF of any one of paragraphs 1-51, 54-55, 57, and 58; the hTAD of paragraph 52 or 53; the hhTAD of paragraph 56; the system of any one of paragraphs 59-75; the polynucleotide of paragraph 76; the nucleic acid construct of any one of paragraphs 77-79; or the vector of paragraph 80 or 81; or portion thereof.

83. The cell of paragraph 82, wherein the cell is an immune cell.

84. The cell of paragraph 83, wherein the immune cell is selected from the group consisting of: a CD4+ T cell, a CD8+ T cell, a Treg, an NK cell, a monocyte, and a macrophage.

85. A composition comprising the synTF of any one of paragraphs 1-51, 54-55, 57, and 58; the hTAD of paragraph 52 or 53; the hhTAD of paragraph 56; the system of any one of paragraphs 59-75; the polynucleotide of paragraph 76; the nucleic acid construct of any one of paragraphs 77-79; the vector of paragraph 80 or 81; or the cell of any one of paragraphs 82-84; or portion thereof.

86. A pharmaceutical composition comprising the synTF of any one of paragraphs 1-51, 54-55, 57, and 58; the hTAD of paragraph 52 or 53; the hhTAD of paragraph 56; the system of any one of paragraphs 59-75; the polynucleotide of paragraph 76; the nucleic acid construct of any one of paragraphs 77-79; the vector of paragraph 80 or 81; or the cell of any one of paragraphs 82-84; or portion thereof; and a pharmaceutically acceptable carrier.

87. A method of regulating the activity of a synTF, comprising the steps of:
- (a) providing a population of cells of paragraph 82-84; and
- (b) contacting the population of cells with an effective amount of at least one RP inducer.

88. A method of regulating the expression of a gene of interest, comprising the steps of:
- (a) providing a population of cells of paragraph 82-84; and
- (b) contacting the population of cells with an effective amount of at least one RP inducer.

89. A method of treating a subject in need of a cell-based therapy, comprising the steps of:
- (a) administering to the subject a population of cells of paragraph 82-84; and
- (b) administering to the subject an effective amount of at least one RP inducer.

90. The method of any one of paragraphs 87-89, wherein the population of cells comprises immune cells.

91. The method of paragraph 90, wherein the population of immune cells comprises CD4+ T cells, CD8+ T cells, Tregs, NK cells, monocytes, or macrophages.

92. The method of any one of paragraphs 87-91, wherein the at least one RP inducer is administered at the same time the population of cells is administered.

93. The method of any one of paragraphs 87-92, wherein the at least one RP inducer is administered after the population of cells is administered.

Some embodiments of the technology described herein can be defined according to any of the following numbered paragraphs:

1. A synthetic transcription factor (synTF) comprising:
- (a) at least one DNA binding domain (DBD),
- (b) a transcriptional activator domain (TA),
- (c) a transcriptional effector domain (TED), and
- (d) at least one regulator protein (RP), and wherein the TED increases the transcriptional activation of the synTF compared to an otherwise identical synTF lacking the TED, wherein the TA is directly or indirectly coupled to the DBD, and wherein the coupling is regulated by the at least one RP, or wherein cellular localization of the TA is regulated by the at least one RP.

2. The synTF of paragraph 1, wherein the TED comprises an elongation domain, an activator domain, or a domain with pioneer ability.

3. The synTF of paragraph 2, wherein the elongation domain is derived from a polypeptide selected from the group consisting of: Interacts with Suppressor Of Ty 6 (Spt6) Homolog (IWS1); Suppressor Of Ty 5 (Spt5) Homolog (SUPT5H); Bromodomain-containing protein 4 (BRD4); and cellular Myelocytomatosis (cMyc); or wherein the activator domain is derived from a polypeptide selected from the group consisting of: Heat Shock Factor 1 (HSF1), Glucocorticoid Receptor (GR), and MLX interacting protein like (MLXIPL); or wherein the domain with pioneer ability is derived from a polypeptide selected from the group consisting of Fused in Sarcoma (FUS) and Ewing Sarcoma Breakpoint Region (EWSR).

4. The synTF of paragraph 2, wherein the elongation domain: is derived from human IWS1; comprises at least one TFIIS N-terminal domains (TND)-interacting motif (TIM) domain of IWS1; comprises at least one TIM1, TIM2, and/or TIM3 domain from IWS1; and/or comprises one of SEQ ID NOs: 5-9 or an amino acid sequence with at least 80% sequence identity to one of SEQ ID NOs: 5-9.

5. The synTF of paragraph 1, wherein the TA is selected from the group consisting of: p65; Rta; miniVPR; full VPR; VP16; VP64; NFZ; 3Z; p300; p300 HAT Core; and a CBP HAT domain; or a variant thereof.

6. The synTF of paragraph 1, wherein the at least one DBD is an engineered zinc finger (ZF)-binding domain.

7. The synTF of paragraph 6, wherein the engineered ZF binding domain comprises a sequence selected from the group consisting of ZF 1-1, ZF 1-2, ZF 1-3, ZF 1-4, ZF 1-5, ZF 1-6, ZF 1-7, ZF 1-8, ZF 2-1, ZF 2-2, ZF 2-3, ZF 2-4, ZF 2-5, ZF 2-6, ZF 2-7, ZF 2-8, ZF 3-1, ZF 3-2, ZF 3-3, ZF 3-4, ZF 3-5, ZF 3-6, ZF 3-7, ZF 3-8, ZF 4-1, ZF 4-2, ZF 4-3, ZF 4-4, ZF 4-5, ZF 4-6, ZF 4-7, ZF 4-8, ZF 5-1, ZF 5-2, ZF 5-3, ZF 5-4, ZF 5-5, ZF 5-6, ZF 5-7, ZF 5-8, ZF 6-1, ZF 6-2, ZF 6-3, ZF 6-4, ZF 6-5, ZF 6-6, ZF 6-7, ZF 6-8, ZF 7-1, ZF 7-2, ZF 7-3, ZF 7-4, ZF 7-5, ZF 7-6, ZF 7-7, ZF 7-8, ZF 8-1, ZF 8-2, ZF 8-3, ZF 8-4, ZF 9-1, ZF 9-2, ZF 9-3, ZF 9-4, ZF 10-1, and ZF 11-1; or wherein the engineered ZF-binding domain specifically binds an endogenous VEGF gene (VEGF ZF).

8. The synTF of paragraph 1, wherein the at least one RP comprises a polypeptide selected from the group consisting of a repressible protease; a pair of induced proximity domains (IPD pair); a cytosolic sequestering protein; and combinations thereof.

9. The synTF of paragraph 1, wherein the at least one RP comprises a repressible protease or an NS3 protease.

10. The synTF of paragraph 9, wherein in the presence of a protease inhibitor, or an inhibitor of NS3, the protease protein is inhibited, thereby maintaining the coupling of the DBD to the TA; or wherein in the absence of a protease inhibitor, or an inhibitor of NS3, the protease protein is active, and the TA is excised from the DBD, thereby uncoupling the DBD and the TA.

11. The synTF of paragraph 10, wherein the inhibitor of NS3 is selected from the group consisting of: grazoprevir (GRZ/GZV), danoprevir, simeprevir, asunaprevir, ciluprevir, boceprevir, sovaprevir, paritaprevir, ombitasvir, paritaprevir, ritonavir, dasabuvir, and telaprevir.

12. The synTF of paragraph 1, wherein the at least one RP is a pair of induced proximity domains (IPD pair), wherein the IPD pair comprises:

a first induced proximity domain ($IPD^A$) and at least a second complementary IPD ($IPD^B$), wherein in the presence of an inducer agent or signal, the $IPD^A$ and $IPD^B$ specifically bind together resulting in the coupling of the TA to the DBD, and wherein in the absence of an inducer agent or signal, the TA is uncoupled from the DBD.

13. The synTF of paragraph 12, wherein the IPD pair comprises:

(a) a $IPD^A$ comprising a GID1 domain or a fragment thereof, and a $IPD^B$ comprising a GAI domain, wherein the GID1 domain and GAI domain bind to the inducer agent Gibberellin Ester (GIB);

(b) a $IPD^A$ comprising a FKBP domain or a fragment thereof, and a $IPD^B$ comprising a FRB domain, wherein the FKBP domain and FRB domain bind to the inducer agent Rapalog (RAP);

(c) a $IPD^A$ comprising a PYL domain or a fragment thereof, and a $IPD^B$ comprising an ABI domain, wherein the PYL domain and ABI domain bind to the inducer agent Abscisic acid (ABA); and/or (d) a $IPD^A$ comprising a Light-inducible dimerization domain (LIDD), wherein a LIDD dimerizes with a complementary LIDD ($IPD^B$) upon exposure to a light inducer signal of an appropriate wavelength.

14. The synTF of paragraph 13, wherein the LIDD is nMag, Calcium And Integrin-Binding Protein 1 truncation (CIBN), or a photochromic protein domain; wherein nMag can dimerize with a complementary LIDD pMag upon exposure to a blue light inducer signal; or wherein CIBN can dimerize with a complementary cryptochrome 2 (CRY2) upon exposure to a blue inducer light signal; or wherein the photochromic protein domains can dimerize upon exposure to a blue inducer light signal.

15. The synTF of paragraph 1, wherein the at least one RP comprises a cytosolic sequestering protein.

16. The synTF of paragraph 15, wherein the cytosolic sequestering protein comprises a ligand binding domain (LBD), wherein in the presence of a ligand to which the LBD binds, sequestering of the synTF to the cytosol is inhibited.

17. The synTF of paragraph 15, wherein the cytosolic sequestering protein comprises a LBD and a nuclear localization signal (NLS); wherein in the absence of a ligand to which the LBD binds, the NLS is inhibited thereby preventing translocation of the synTF to the nucleus; and wherein in the presence of the ligand, the NLS is exposed permitting translocation of the synTF to the nucleus.

18. The synTF of paragraph 15, wherein the cytosolic sequestering protein comprises at least a portion of an estrogen receptor (ER), an estrogen ligand binding domain (ERT), or a variant thereof.

19. The synTF of paragraph 18, wherein the ERT binds to one or more ligands selected from the group consisting of: tamoxifen, 4-hydroxytamoxifen (4OHT), endoxifen, and Fulvestrant; wherein binding of the ligand to the ERT exposes the NLS and results in nuclear translocation of the ERT.

20. The synTF of paragraph 15, wherein the cytosolic sequestering protein comprises a transmembrane receptor sequestering protein.

21. The synTF of paragraph 9, wherein the NS3 protease protein is part of a Small molecule-Assisted Shutoff (SMASh) domain, wherein the SMASh domain comprises the NS3 protease protein, a partial protease helical domain and a NS4A domain.

22. The synTF of paragraph 1, further comprising a Small molecule-Assisted Shutoff (SMASh) domain, wherein the SMASh domain is a N-terminal or C-terminal SMASh domain comprising a repressible protease, a partial protease helical domain and a cofactor domain.

23. The synTF of paragraph 22, wherein the SMASh domain is a C-terminal SMASh domain comprising, in N-terminal to C-terminal order: a NS3 cleavage site, at least one linker, a NS3 domain, a NS3 partial helicase, and a NS4A domain, wherein the SMASh domain is fused to the C-terminus of the synTF.

24. The synTF of paragraph 22, wherein the SMASh domain is a N-terminal SMASh domain comprising in N-terminal to C-terminal order: at least one Linker, a NS3 domain, a NS3 partial helicase, a NS4 domain, and a NS3 cleavage site, wherein the SMASh domain is fused to the N-terminus of the synTF.

25. The synTF of paragraph 22, wherein in the absence of an inhibitor for the NS3 protease, the NS3 protease is active and self cleaves/uncouples from the synTF, thereby resulting in the SMASh domain targeted for degradation ("SMASh-degradation", synTF-on/TA-on), and wherein in the presence of an inhibitor for the NS3 protease, NS3 protease activity is inhibited thereby resulting in the SMASh-comprising synTF targeted for degradation ("synTF-degradation", synTF-OFF/TA-off").

26. The synTF of paragraph 44, wherein the inhibitor for the NS3 protease is selected from the group consisting of: grazoprevir (GRZ/GZV), danoprevir, simeprevir, asunaprevir, ciluprevir, boceprevir, sovaprevir, paritaprevir, ombitasvir, paritaprevir, ritonavir, dasabuvir, and telaprevir.

27. The synTF of paragraph 1, wherein the DBD, TA, TED, and/or RP are human domains or humanized domains.

28. A synthetic transcription factor (synTF) comprising:

(a) at least one DNA binding domain (DBD), (b) a transcriptional activator domain (TA), and (c) a transcriptional effector domain (TED), wherein the TED increases the transcriptional activation of the synTF compared to an otherwise identical synTF lacking the TED.

29. A humanized hybrid transcription activator domain (hhTAD), comprising:

(a) a transcriptional activator domain (TA), and (b) a transcriptional effector domain (TED), wherein the TED increases the transcriptional activation of the TA compared to an otherwise identical hhTAD lacking the TED; and wherein the TA and TED are human domains or humanized domains.

30. A system for controlling gene expression, comprising:

(a) at least one synthetic transcription factor (synTF) of paragraph 1, wherein the at least one DBD of the synTF can bind to a target DNA binding motif (DBM) located upstream of a promoter operatively linked to a gene; and (b) a nucleic acid construct comprising:

(i) at least one target DNA binding motif (DBM) comprising a target nucleic acid for binding of the at least one DBD of the synTF;

(ii) a promoter sequence located 3' of the at least one DBM; and (iii) a gene of interest operatively linked to the promoter sequence.

The technology described herein is further illustrated by the following examples which in no way should be construed as being further limiting.

EXAMPLES

Example 1: synZiFTR2.0: The Development of Improved Synthetic Human Transcription Activation Factors The advent of synthetic transcriptional regulators built mainly on human-derived proteins, namely synthetic Zinc Finger Transcription Regulators (synZiFTRs), has permitted fine-tuned control of therapeutically significant genes in primary T cells. Their clinical relevance can be enhanced by amplifying synthetic gene circuit activation and expanding the synZiFTR toolkit with standardized components for the construction of more complex circuits. This study describes the development of the next iteration of synZiFTR, the synZiFTR2.0, incorporating the human-derived transcription elongation domain, IWS1. Described herein is an engineered version 2.0 of GZV- and 4OHT/TMX-regulated gene switches, exhibiting a robust increase in transcriptional output upon drug induction. Furthermore, the synZiFTR toolkit was expanded and utilized to examine the feasibility of constructing a two-input AND logic gate. The integration of IWS1 unveiled a role of PP1-NUTS phosphatase in enhancing synthetic circuit output. The introduction of synZiFTR2.0 boosts its clinical applicability, particularly in settings where circuit output strength is contingent on disease context that is often uncertain.

TABLE 1

List of exemplary abbreviations

| Abbreviation | Definition |
|---|---|
| 4OHT | 4-hydroxytamoxifen |
| A2AR | A2 adenosine receptor |
| ADs | activator domains |
| AP-1 | Activator protein 1 |
| BBB | blood brain barrier |
| BET | bromodomain and extra-terminal domain |
| BiTE | bispecific T cell engager |
| bHLH-LZ | basic helix-loop-helix leucine zipper |
| BRD4 | Bromodomain-containing protein 4 |
| CAR | Chimeric Antigen Receptor |
| CBP | CREB-binding protein |
| CDC2 | cyclin-dependent kinase 1 |
| CDC7 | cell division cycle 7 |
| CEM | chemical epigenetic modifier |
| CHOP | C/EBP homologous protein |
| ChIP-Seq | Chromatin Immunoprecipitation Sequencing |
| CTD | C-terminal domain |
| DBD | DNA binding domain |
| DHD | designed protein heterodimers |
| DNA | deoxyRibonucleic acid |
| DMSO | Dimethylsulfoxide |
| Dox | Doxycycline |
| DSIF | DRB Sensitivity-Inducing Factor |
| dCas | "dead" Cas |
| DPF3 | Double PHD Fingers 3 |
| *E. coli* | *Escherichia coli* |

TABLE 1-continued

List of exemplary abbreviations

| Abbreviation | Definition |
|---|---|
| EDs | elongation domains |
| EGFP | Enhanced green fluorescent protein |
| EloA | Elongin A |
| Ert2 | human estrogen receptor T2 |
| ERG | ETS-related gene |
| EWSR1 | Ewing Sarcoma Breakpoint Region 1 |
| FDA | Food and Drug Administration |
| FKBP | FK506 binding protein |
| FL1 | Follicular Lymphomal |
| FOXO3 | Forkhead box O3 |
| FUS | Fused in Sarcoma |
| GOI | gene of interest |
| GvHD | graft-versus-host disease |
| GZV | grazoprevir |
| HER | human epidermal growth factor receptor |
| HCV | hepatitis C virus |
| HLA | histocompatibility leukocyte antigen |
| HRP2 | H3K36me2/3 binding protein HDGFL2 |
| HSF1 | Heat Shock Factor 1 |
| HSEs | heat shock elements |
| HSPs | heat shock proteins |
| HSCTs | hematopoietic stem cell transplants |
| IWS1 | Interacts with Spt6 |
| ICT | immune cell therapy |
| IDRs | intrinsically disordered regions |
| IL | interleukin |
| iCasp9 | inducible caspase 9 |
| IMC | inducible MyD88/CD40 |
| IPTG | Isopropyl-beta-D-1-thiogalactopyranoside |
| LEDGF | lens epithelium-derived growth factor |
| M2H | mammalian two-hybrid assay |
| MAGE | melanoma-associated antigen |
| MED1 | Mediator Complex Subunit 1 |
| MFI | median fluorescence intensity |
| MLXIPL | MLX interacting protein like |
| NCOA3 | Nuclear Receptor Coactivator 3 |
| NELF | Negative Elongation Factor |
| NFAT | nuclear factor of activated T |
| NF-kB | nuclear factor kB |
| NCoR | nuclear receptor corepressor |
| NIR | near-infrared |
| NK | natural killer |
| NS3 | non-structural 3 |
| NY-ESO-1 | New York esophageal squamous cell carcinoma 1 |
| ODD | oxygen-dependent degradation |
| P-TEFb | Positive Transcription Elongation Factor b |
| PA-CXCR4 | photoactivatable chemokine receptor |
| pSFFV | Spleen Focus-Forming Virus promoter |
| PICS | pre-initiation complexes |
| Pol II | RNA polymerase II |
| PRO-seq | precision nuclear run-on sequencing |
| PSCA | prostate stem cell antigen |
| pybTATA | synthetic YB_TATA promoter |
| R2A | Arginine to alanine |
| RNA | Ribonucleic acid |
| RTA | reverse tetracycline transactivator |
| SAM | synergistic activation mediator |
| scFv | single-chain variable fragment |
| SMRT | silencing mediator of retinoic acid and thyroid hormone receptor |
| SNR | signal-to-noise ratio |
| SRC-1 | steroid receptor coactivator-1 |
| SUPRA | split, universal, and programmable |
| synZiFTRs | Synthetic zinc finger transcription regulators |
| TAM | tumor-associated macrophage |
| TCR | T cell receptors |
| TED | transcription effector domain |
| TGF-β | transforming growth factor β |
| TIMs | TFIIS N-terminal domains-interacting motifs |
| TMX | tamoxifen |
| TME | tumor microenvironment |
| TND | TFIIS N-terminal domains |
| TF | transcription factor |
| TRE3G | tetracycline-responsive promoter |
| VIPER | versatile protease-regulatable |

TABLE 1-continued

| List of exemplary abbreviations | |
|---|---|
| Abbreviation | Definition |
| VPR | VP64-p65-Rta |
| ZF | zinc-finger |
| ZNF473 | Zinc Finger Protein 473 |

Described herein is the utilization of bioengineered immune cells in cancer therapy, including both their clinical uses and limitations. Synthetic biology has offered various strategies and tools to augment this therapy's safety and effectiveness. Described herein is the emergent utilization of small molecules for transcriptional control over therapeutic payloads. Small molecule-regulated transcriptional circuits and their development are also discussed. This discussion leads to the following objective: to enhance a synthetic transcription factor toolkit tailored for clinical application. The various stages of the transcriptional process are then investigated to identify enhancement factors for this toolkit.

Synthetic transcription circuits have advanced the capabilities and safety of cell-based therapeutics. In order to advance the robust application of these circuits, described herein is a humanized hybrid transcription activator domain (hhTAD) that can be used in a synthetic transcription factor. When fused to a human genome orthogonal zinc-finger array and a drug-inducible translocation system, the hhTAD allows one to achieve robust and significantly stronger activation of a transgene.

Figure 5A:
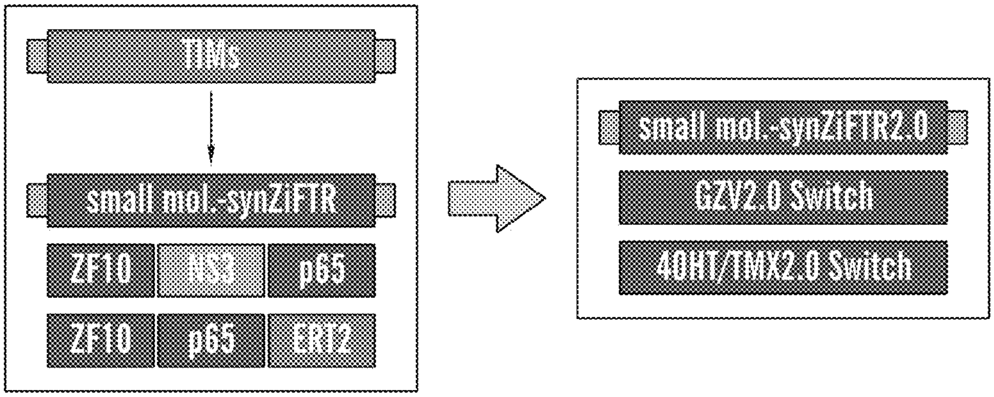
FIG. 5A-5D shows examples of the hhTAD synTFs.
Figure 5B:
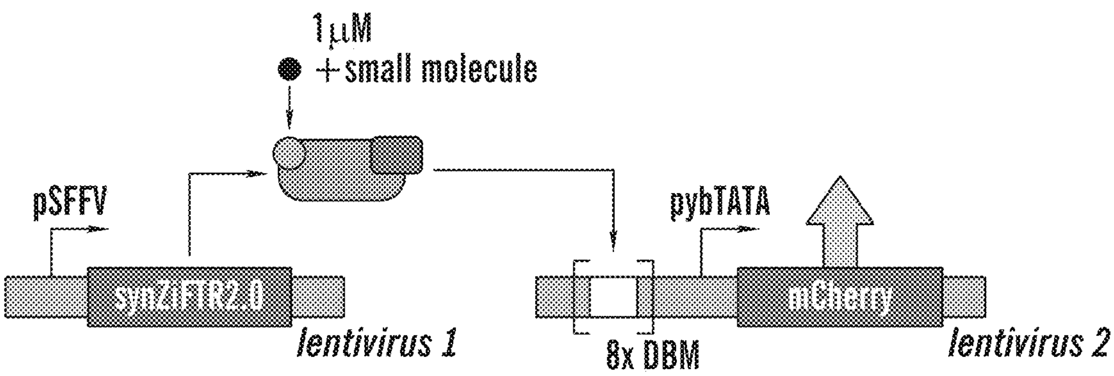

The humanized hybrid transcription activator domain (see e.g., SEQ ID NOs: 15-16) when integrated into small-molecule inducible transcriptional activation systems is able to robustly and strongly induce transgene expression in mammalian cells. The humanized hybrid transcription activation domain (hhTAD) was attached to an artificial zinc finger proteins (see e.g., U.S. Pat. No. 10,138,493 B2 and US Patent Publication No. 2020/0377564 A1; the contents of each of which are incorporated herein by reference in their entirety) to either a NS3 or ERT2 domain (see e.g., FIG. 5A). To report transcriptional activation, described herein is a constitutively expressed mCherry fluorescent reporter (see e.g., FIG. 5B).

Figure 5C:
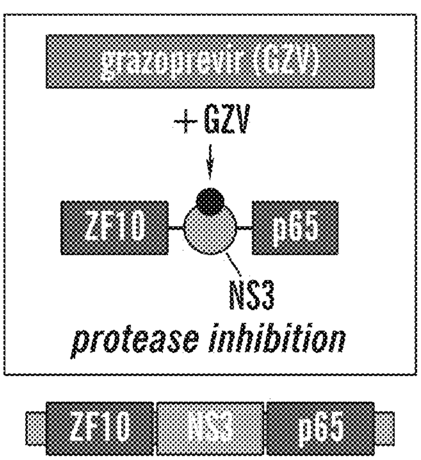
Figure 5D:
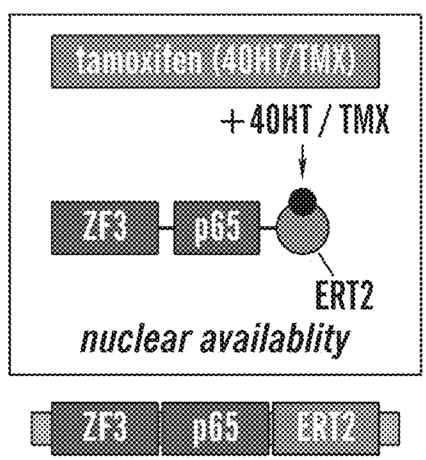

The system works as follows:

1) In the absence of the inducer molecule GZV, the NS3 protease self-cleaves to prevent the formation of an effective transcription activator (see e.g., FIG. 5C). However, in the presence of GZV, the transcription activator is stabilized and can bind to the zinc finger binding domain (ZF BD) and induces transcription of gene of interest (GOI) (see e.g., FIG. 5C).
2) In the absence of the inducer molecule 4-OHT, the ERT2 keeps the transcription activator in the cytoplasm (see e.g., FIG. 5D). However, in the presence of 4-OHT, the ERT2 domain shuttles the transcription activator to the nucleus where it binds to the zinc finger binding domain (ZF BD) and induces transcription of the gene of interest (GOI) (see e.g., FIG. 5D).

Figure 6A:
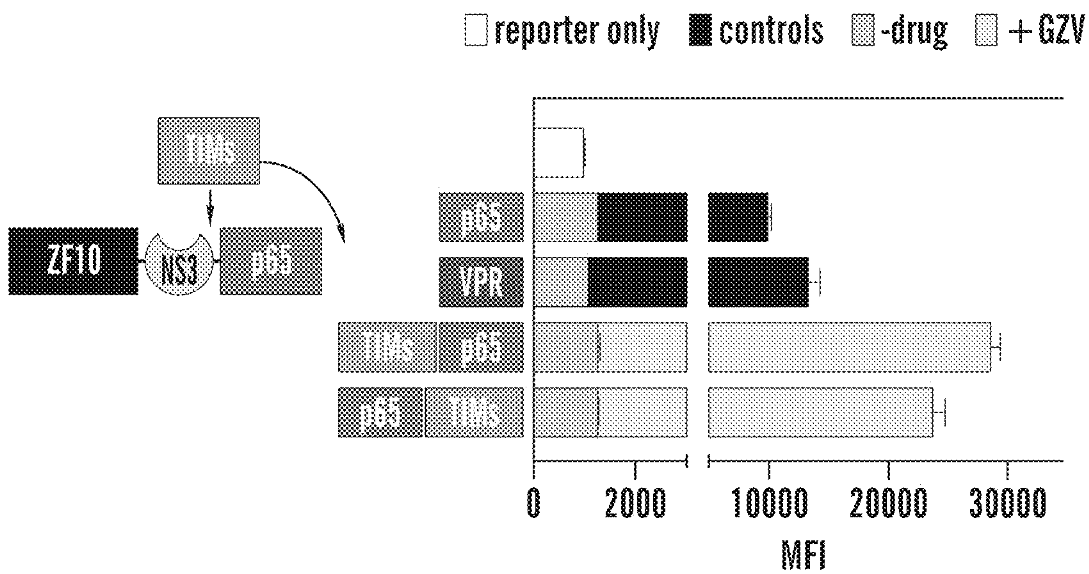
FIG. 6A-6B shows that incorporation of the IWS1 TIMs domain into synTFs increases their transcriptional activation.
Figure 6B:
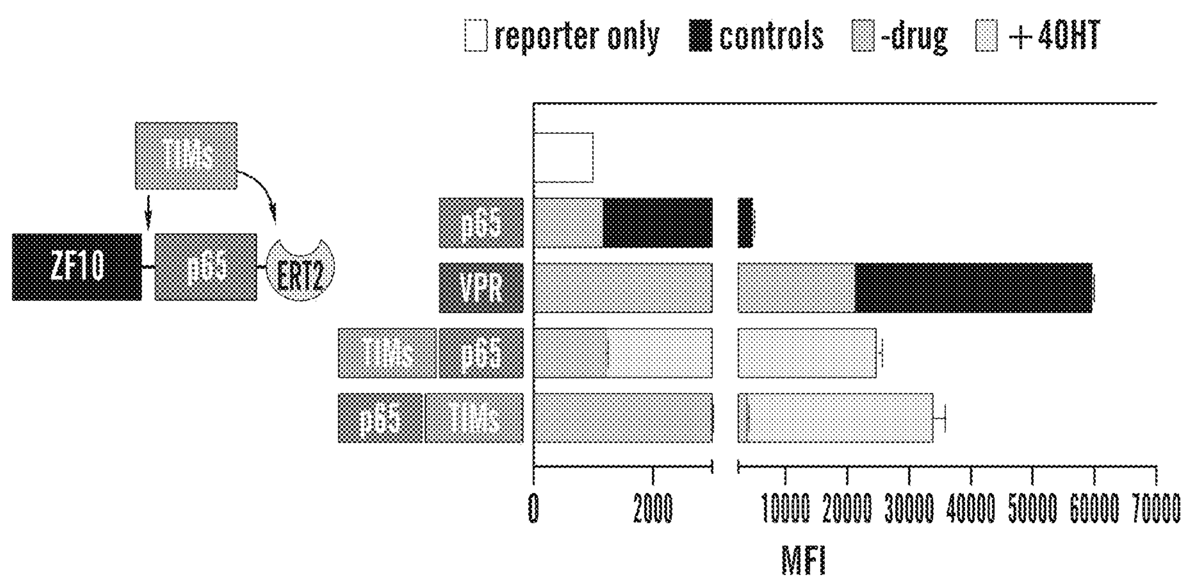
Figure 7:
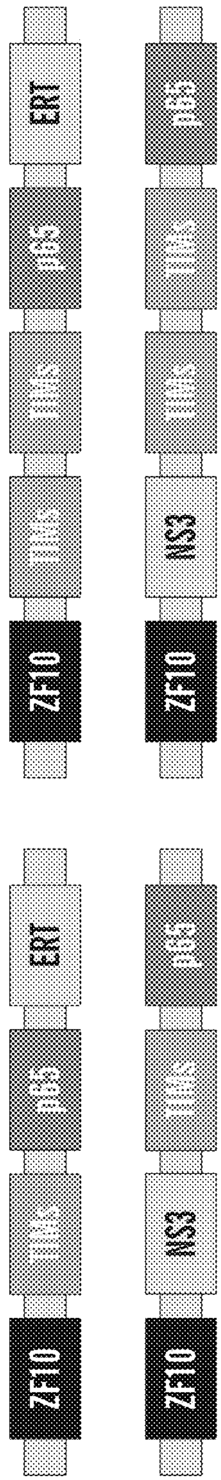
FIG. 7 is a series of schematics showing one (left) or two (right) copies of IWS1 TND-interacting motifs (TIMs), a small scaffolding domain involved in assembling transcriptional elongation complexes, fused to the N terminus of the p65 transcriptional activator domain in the synZiFTR technologies to generate synZiFTR 2.0 systems. Top: 4OHT-inducible synZiFTR 2.0. Bottom: GZV-inducible synZiFTR 2.0.

To evaluate the strength of this hhTAD, Jurkat T cells were generated stably expressing both the transcription activator(s) modified with the hhTAD and fluorescent reporter. In order to determine whether the activator switch is able to strongly induce GOIs compared to previous iterations of TADs, expressed transcription activator(s) were also with the p65 and VPR TADs. Reporter cells with were treated 1 uM GZV or 4-OHT, and mCherry reporter fluorescence was measured at 72h (see e.g., FIG. 6A-6B). Reporter fluorescence expression was partially significantly higher without substantial increase in basal output (no drug) when comparing hhTAD transcription activators with the p65 and VPR counterparts, validating the hhTAD as a robust and significant improvement to the activator systems.

There are many variants which can be developed from this initial design, such as alterations to the transcriptional machinery, genetic payload and induction system. For the transcriptional machinery, variants can encompass use of stronger or weaker constitutive promoters (e.g., hPGK, CAG, SFFV), and DNA binding domain variants (e.g., Zinc Fingers, Gal4, Tetracycline Responsive Element, dCas9). For the genetic payload, variants can include, for example, secreted cytokines (e.g., IL-2, IL-12, IL-18, Interferon Gamma), antibodies (e.g., anti-CD19, anti-CD47, anti-PD1), or additional genetic switches (e.g., Transcription Factors). For the induction system, additional small molecule inducers (e.g., Tetracycline, Caffeine, Abscisic Acid), light gated activation (e.g., Optogenetic CRY2/CIB1), cellular environment factor induction (e.g., HIF1a, NFkB, ARG1), GPCR activation induced (e.g., TANGO), and surface receptor activation (TCR activation, SynNotch) can be tailored to induce stronger transcription mediated activation of the genetic payload.

1.1 Engineered Immune Cells and their Use in Cancer Treatment.

Engineered immune cells, acting as living medications, have made significant progress since the 1980s when T cells infiltrating tumors were extracted from cancer patients and utilized to treat metastatic melanoma. The initial success of these clinical trials spurred further research into immune cell therapy (ICT) using various immune cell types and extending its application to a wide range of cancers and pathologies, from infectious diseases to autoimmunity. Nevertheless, certain challenges became apparent, especially concerning T cells. Isolating and preparing large quantities of functional tumor-specific T cells is difficult for numerous cancer types, natural T cells can lose functionality over time due to high tumor antigen load (referred to as exhaustion), and tumors develop multiple strategies to evade attacks from native lymphocytes. Despite these obstacles, ICT has demonstrated effectiveness for patients who have not responded well to radiation and chemotherapy. Following the early trials, the field of immune cell engineering has made significant progress.

1.1.1 Redirecting T Cell Activity by Introducing Tumor-Targeting Receptors Through Genetic Engineering.

1.1.1.1 T Cell Receptors

Cellular immunotherapy has concentrated on redirecting T cell activity by incorporating tumor-targeting receptors through genetic engineering, such as T cell receptors (TCRs). The identification of suitable receptors involves screening and directed evolution of native TCRs. For instance, T cells engineered to express the cancer-testis antigen (NY-ESO-1)-specific TCRS have exhibited clinical responses in 80% of patients with advanced diseases.

1.1.1.2 Chimeric Antigen Receptors (CARs)

To improve the efficacy of immune cells in cancer treatment, the single-chain variable fragment (scFv) of an antibody targeting cancer antigens is combined with intracellular signaling domains from the TCR and other immune costimulatory pathways. The resulting fusion receptors are known as chimeric antigen receptors (CARs). CAR T cells have demonstrated remarkable success against lymphoid leukemia, especially in pediatric patients who did not respond to or relapsed after other therapies. Notably, over 90% of these patients achieved complete remission, which is double the rate observed with standard chemotherapy alone.

Initial clinical trials employed CARs made of scFVs joined to CD3ζ (native TCR signaling domain), but these were unsuccessful in targeting ovarian cancer via the folate receptor, as they did not reduce tumor burden. The point of failure was that the engineered T cells could not proliferate and remain in circulation long enough to be effective. However, one study showed that incorporating the CD28 costimulatory domain into CD3ζ resulted in enhanced T cell proliferation and antitumor effects. As a result, adding costimulatory domains became a common practice in developing the next generation of CARs to boost immune response and extend the engineered cells' persistence.

Third-generation CARs feature multiple costimulatory domains in addition to CD3ζ, exhibiting even greater effectiveness against tumor cells in vivo. These synthetic agents have been proven successful in numerous clinical trials, indicating that genetic engineering possesses significant ability for cellular immunotherapies. T cells genetically modified with a chimeric antigen receptor (CAR) have displayed powerful anticancer cytotoxicity in clinical settings, resulting in five Food and Drug Administration (FDA)-approved treatments for B cell malignancies. These progresses highlight the capacity of engineered immune cells to transform cancer treatment and other pathologies.

1.2 Challenges Facing CAR T Therapies

CAR T therapy, although a promising avenue for cancer treatment, faces multiple challenges. Specifically, both safety and efficacy. Safety concerns arise from toxicity issues caused by overactivation and off-tumor targeting of the engineered immune cells. As for efficacy, disease heterogeneity and continuous evolution call for a dynamic intervention rather than a single, static treatment. Additionally, patients receiving CAR T cell therapy might experience relapse due to antigenic escape if the targeted destruction is not effective enough. Finally, a significant challenge lies in the effectiveness of CAR T therapies against solid tumors, which necessitates further research and refinement.

1.2.1 Safety

Safety issues in CAR T therapy encompass potentially life-threatening, aberrant activation due to overstimulation or hypersensitivity of the immune system. This may result in hypoxia, neurological disorders, and even fatalities. In conditions characterized by high cell proliferation rates, such as cancer, the overactivity of engineered immune cells can cause an excessive production of cytokines, leading to a systemic hyperinflammatory state known as cytokine release syndrome (CRS). T cell overactivation continues to be a major complication in clinical trials. In one phase I trial, patients with acute and chronic lymphocytic leukemia as well as B cell lymphomas were treated with anti-CD19 CARs. CRS was observed in 16 out of 21 patients, with three patients experiencing grade 4 CRS. In extreme cases, CRS may lead to systemic organ failure, neurotoxicity, and B cell aplasia.

Another hurdle involves comprehending the exact mechanisms and antigens related to on-target, off-tumor autoreactivity, which requires accurate target identification. In cancer immunotherapy, engineered cells might recognize normal cells that express low levels of antigen. For example, Mural cells lining the blood-brain barrier (BBB) express CD19, and their destruction can compromise the integrity of the BBB, leading to CAR T-related encephalopathy syndrome and even death. In a separate phase I/II clinical trial, two metastatic cancer patients treated with anti-MAGE-A3 (melanoma-associated antigen 3) TCR-engineered T cells suffered severe neurotoxicity and ultimately died. It was later determined that one of the targeted antigens, MAGE-A12, is also expressed in the brain. This underscores the necessity of selecting the appropriate target antigen and performing thorough screening to ascertain the antigen's specificity to the target cell type and whether it is expressed in healthy tissue.

1.2.2 Efficacy

Cancer arises in diverse environments, and each type presents unique challenges. Although T cells expressing anti-CD19 CAR have achieved up to 90% complete response rates, addressing solid tumors with adoptive immunotherapy remains complex due to multiple factors. Deformed vasculature in solid tumors obstructs T cell penetration, and the presence of adhesion molecules on endothelial cells, such as intercellular adhesion molecule 1 and vascular cell adhesion molecule 1, further complicates the issue.

Moreover, deformed vasculature results in insufficient oxygen supply, creating a hypoxic tumor microenvironment (TME). Hypoxia stimulates the upregulation of hypoxia-inducible factor 1a, which promotes glycolysis and inhibits oxidative phosphorylation. When combined with high tumor cell consumption and growth rates, a TME lacking essential nutrients for cytokine production arises, leading to tumor-infiltrating T-cytotoxic cells becoming anergic, unable to undergo glycolysis, and metabolically exhausted. Hypoxia-induced extracellular adenosine accumulation hampers immune response through the A2 adenosine receptor (A2AR), while A2AR deletion boosts growth inhibition and metastasis destruction in in vivo tumor models. The TME can also induce metabolic exhaustion in effector T cells due to the progressive decline of peroxisome proliferator-activated receptor γ coactivator 1α.

Additionally, solid tumors frequently display inflammation, which attracts leukocytes with immunosuppressive properties, thereby promoting tumor cell proliferation, survival, and migration. Besides, tumor-associated macrophages (TAMs) not only contribute to cytotoxic T cell immunosuppression but also upregulate inhibitory molecules such as interleukin (IL)-10 and transforming growth factor β (TGF-β). Inhibiting macrophage tumor infiltration enhances survival in tumor-bearing mice, and reprogramming macrophages toward an antitumor phenotype using histidine-rich glycoprotein reduces tumor growth and metastasis, enhancing the efficacy of conventional chemotherapy.

Lastly, Foxp3+ Tregs, found in many solid tumors, create an immunosuppressive environment that hinders the efficacy of tumor-infiltrating lymphocytes and are directly associated with breast cancer progression, helping to identify high-risk patients.

1.3 Synthetic Biology

The modular nature of synthetic biology components permits the development of groundbreaking systems that offer genetically encoded computation and spatiotemporal control. This is achieved by utilizing high-performance elements and expertly assembling them into a cohesive, functional unit. By capitalizing on synthetic biology's potential, one can significantly advance the creation of accurate and effective immune cell treatments for cancer.

1.4 General Tools Used in Synthetic Biology

Synthetic biology presents a range of general tools that can be applied to cellular immunotherapy. One such as method involve controlling protein activity and degradation. Degron domains, which impact protein degradation regulation, have been used to control degradation kinetics and protein levels within cells. Furthermore, ligand-inducible domains offer a way to manage the degradation or dimerization of specific proteins in a tunable fashion. For instance, CARs have been designed that can be regulated by small molecules, functioning like an ON switch, utilizing heterodimerization domains. Another approach involves light-inducible dimerization domains, which allow for spatiotemporal control over cell activity.

Similarly, various strategies have been developed for transcription level control, such as combining natural transcription factors (TetR/Gal4) with transcriptional activator or repressor domains. Synthetic transcription factors can also be engineered to regulate endogenous transcription using techniques like zinc fingers (ZFs), transcription activator-like effectors, or the CRISPR/Cas system. These tools facilitate highly specific and efficient genome editing at predetermined genomic loci and have already shown ability to enhance cellular immunotherapies. For example, CD19 CARs were precisely integrated at the endogenous T cell receptor α-constant (TRAC) locus using CRISPR/Cas9, resulting in consistent CAR expression and improved T cell potency. By utilizing these synthetic biology tools, researchers can make significant progress in the development of cellular immunotherapies and ultimately enhance treatment outcomes.

1.5 Synthetic Biology Applications for CAR T Safety and Efficacy

Cell therapy can be enhanced with complex circuits to increase targeting, specificity, safety, and effectiveness. Both cell-autonomous and exogenous circuits can be employed concurrently. In this context, both types of circuits have been utilized to improve engineered T cells for cancer treatment.

1.5.1 Cell-Autonomous Gene Circuits

Cell-autonomous gene circuits represent an aspect of advancing cellular immunotherapies. These circuits rely on signals within the engineered immune cells or the native environment, allowing them to operate autonomously when necessary, such as when precisely locating a tumor based on molecular markers. However, cell-autonomous gene circuits can be unpredictable in their behavior, presenting challenges for researchers.

Progress in this area has been made by developing circuits designed to sense various factors, including the combination of antigens from both target and healthy cells, intracellular cell states, and the tumor microenvironment. By incorporating logic and feedback control mechanisms, these circuits can achieve more precise temporal and contextual responses, further enhancing the targeting, specificity, safety, and efficacy of cellular immunotherapies.

1.5.1.1 Receptor Logic Circuits

Cell therapy can be improved by employing receptor logic circuits, which tackle the need for combinatorial antigen recognition, as no single antigen uniquely characterizes cancer cells. These circuits enhance CAR T cell specificity by detecting and reacting to antigen combinations, ultimately preventing antigen escape, and avoiding ON-target/OFF-tissue toxicities. The primary aim of a multi-input CAR logic circuit design is to generate distinct and separate CARs targeting various antigens and subsequently combine their signals through the endogenous signaling network.

When a single, sufficient tumor-specific antigen is absent, genetic logic circuits such as AND, OR, or NOT gates can be applied to integrate multiple input signals, enhancing specificity, and killing efficiency. For AND-gates, dual CAR systems have been developed for combinatorial antigen detection, increasing the specificity of engineered T cells. One CAR contains the CD3ζ signaling domain, while the other incorporates the CD28/4-1BB costimulatory domains, permitting T cells to respond only to tumor cells expressing both antigens. This strategy helps avoid ON-target/OFF-tissue toxicities observed in CAR T cell therapy.

NOT gates can mitigate safety concerns. In the case of inhibitory CARs (iCARs), researchers have utilized intracellular signaling domains from inhibitory receptors to counteract the signals from traditional activating CARs (aCARs). By harnessing the intrinsic properties of inhibitory receptors, iCARs provide an additional layer of control over T cell activation, enhancing the precision and safety of CAR-based immunotherapies.

The development of NOT AND (NAND) gate CARs, also known as NIMPLY (A AND NOT B) gate CARs, presents a compelling direction in bioengineering. These designs are activated exclusively when target A is present, and target B is absent. This strategy has been trialed across a variety of cancer forms. The operating principle not only facilitates accurate cancer cell targeting but also ensures an additional safety measure by averting unintended effects on healthy cells that express target B.

OR gates can aid in preventing tumor antigen escape. Bispecific OR-gate CARs feature two distinct scFv fragments on the outer surface of modified immune cells (see e.g., FIG. 3A) and can be activated by multiple antigens. Although two orthogonal, full-length CARs can also be employed, bispecific CARs provide comparable effectiveness while minimizing genetic payload size, enhancing CAR T production efficiency. These CARS have been tested in cancer treatment. Utilizing the OR logic gate, CAR T cells are activated upon the recognition of either one of two separate antigen targets. This enhances the probability of cancer cell detection and eradication, while simultaneously reducing the risk of tumor evasion due to antigen loss or alteration.

A bispecific tandem CAR (TanCAR) targeting human epidermal growth factor 2 (HER2) and CD19 showed that two scFvs connected by a short, flexible linker can target both antigens. Later research using bispecific CD19/CD20 CARs revealed that adjusting the order of scFvs and utilizing a more rigid peptide linker can improve CAR activation, facilitate targeting of CD19+/CD20+ cells in vitro, and prevent CD19 antigenic escape in mouse CD19+ tumor models. Phase I clinical trials displayed maximum response rates of 82% for relapsed, refractory, CD19+/CD20+ non-Hodgkin's lymphoma, with relapsed patients maintaining expression of either CD19 or CD20151. These results highlight the capacity for logic processing in cell-based therapies.

1.5.1.2 Split CARs

A new generation of receptor design has emerged, offering advancements. One of these developments is the split CAR design, which has the ability to provide greater control over T cell activation. These designs split the receptor into two separate components: a universal CAR, comprising an intracellular signaling component and an extracellular docking domain, and modular docking adapters, which are employed for selecting different targets and titrating specific activation degrees. Adaptor antibodies facilitate the interaction between the antigen and the CAR, allowing for more precise temporal regulation of T cell activity. These split designs enhance the flexibility of the therapy by permitting T cells to target multiple antigens without the need for reengineering receptors.

To achieve a complete T cell response, one can consider the roles of split TCR signaling and costimulatory receptor domains. By incorporating these components into the receptor designs, researchers can optimize T cell activation and responsiveness. Immune cells engineered to express universal CARs cannot bind target antigens directly. Instead, they bind to adaptor molecules composed of an antigen-specific scFv connected to a docking ligand recognized by the CAR. Examples include leucine zippers, unique epitopes, and chemical tags. Universal CARs permit continuous adjustments in adaptor molecules administered to patients in response to evolving or heterogeneous disease states, and they allow for control over immune-cell activation through varying adaptor concentrations or binding strengths. The split, universal, and programmable (SUPRA) CAR system is one such example, utilizing an orthogonal set of leucine-zipper universal CAR receptors (zipCARs) and leucine-zipper "adaptor" domains that bridge zipCAR receptors to various antigens specified by a single-chained variable fragment (scFv) domain (zipFv). CAR activation can be tuned via zipFv titration and antigen-specific activation. While highly modular, this approach is limited by tissue permeability, short half-life, and unknown immune responses.

Clinical evidence highlights the benefits of a platform that enables the use of any antibody for controlling antigen targeting. In clinical trials of ACTR087 (see e.g., NCT02776813) and ACTR707 (see e.g., NCT03189836), up to 50% of patients exhibited a complete response following cotreatment with CAR T cells and the CD20 monoclonal antibody (mAb) rituximab. Despite safety concerns, a third phase I clinical trial using HER2 mAb trastuzumab (see e.g., NCT03680560) has successfully concluded, with results pending.

A similar platform has been developed with the switchable CAR (sCAR), which contains an extracellular scFv specific for a peptide neo-epitope (PNE) that can be conjugated to a second scFv or antibody targeting cancer cells. In mice bearing CD19+ tumors, cotreatment with sCAR T cells and PNE adapters led to survival up to five months. Moreover, providing sCAR T cells with rest periods by temporarily removing PNE adapters was essential for their expansion and memory induction.

1.5.1.3 Synthetic Notch Receptors

In addition to CARs, a class of receptors has emerged, known as synthetic Notch (synNotch) receptors. These receptors comprise an extracellular antigen-binding domain, a proteolytic transmembrane core from the Notch receptor, and a programmable transcription factor targeting the gene promoter. This programmable surface ligand-inducible gene expression system functions by activating transcription upon ligand binding to the synNotch receptor. SynNotch receptors have been utilized for reprogramming immune cells and designing complex tissue patterns. SynNotch-based logic, characterized by its "IF-THEN" structure, results in the expression of a CAR or an apoptotic gene to achieve AND or NOT logic, respectively.

SynNotch and CAR can each target different antigens, giving rise to multi-input logic circuits. The AND logic derived from synNotch-based circuits can enhance specificity, even against glioblastoma. However, a potential drawback of this approach is that once CAR expression is triggered by synNotch activation, the antigen for synNotch is no longer necessary. This can similarly lead to off targeting of healthy cells expressing the antigen for the CAR. This underscores the need for further refinement and optimization of these receptor systems to ensure the safety and efficacy of future immunotherapies. As an effort to humanize synNotch, one group has developed new proteolytic-based receptors like synNotch, primarily using human components to minimize immunogenicity and facilitate clinical transition.

1.5.1.4 Co-LOCKR

Another group developed an alternative method for implementing logical operations using a single receptor. This approach is based on a set of computationally designed adaptor proteins that interact with one another, modulating the binding of adaptor proteins to the CAR in the presence of target antigens.

At the heart of this system are the "cage" and "key" proteins, both of which contain antigen-binding domains. The cage protein features a peptide capable of binding and activating CAR T cells, which is sequestered by a latch domain. When the key protein binds to the cage protein, a conformational change occurs, exposing the latch domain and leading to CAR activation.

The cage and key proteins do not interact in solution. Instead, they only interact when colocalized to the cell surface by antigen-binding proteins, where the equilibrium favors the formation of cage-key complexes. This approach has been applied to CAR designs targeting up to three different antigens on cancer cells and can function with AND, OR, and advanced logic operations such as A AND B NOT C.

An advantage of this system is that it does not require balancing of intracellular signaling domains; it only requires the "key" protein to open the "cage." The primary challenge arises when employing NOT logic, where the abundance of decoy "key" proteins becomes a critical factor.

1.5.2 Cell-State-Based Control

In addition to direct interaction with cell surface receptors, immune cells can be engineered to respond to disease signals based on cell states. In cancer, the tumor microenvironment (TME) contains numerous immunosuppressive cues and metabolites that limit cytotoxic immune function, such as inhibitory cytokines (IL-4, TGF-β) and cell surface markers (PD-L1), which hinder the antitumor activity of engineered T cells.

Various strategies have been employed to counteract these inhibitory effects. One approach involves blocking TGF-β signaling by overexpressing a nonfunctional TGF-β receptor, which has been shown to mitigate inhibitory effects. Another strategy is to convert immunosuppressive cues into immunostimulatory responses. For example, fusing the inhibitory cytokine receptor IL-4 exodomain to the IL-7 receptor endodomain transforms the tumor-derived IL-4 inhibitory pathway into IL-7 immune stimulation.

Engineered T cells have also been designed to express receptors that combine the PD-1 exodomain and CD28 endodomain, allowing them to bind to PD-L1+ tumor cells, secrete cytokines, and exhibit increased proliferative capacity. Furthermore, tumor-specific T cells have been engineered to conditionally secrete immunostimulatory cytokines, such as IL-12, within the TME to enhance the efficacy of engineered T cells. However, clinical trials indicate that better control of IL-12 secretion is needed through improved genetic circuit design, as IL-12 has shown severe toxicity in clinical settings. Feedback control has also been employed to regulate the duration and dynamics of the T cell response, ensuring an optimal balance between efficacy and safety in immunotherapies.

Outlined below are the efforts made by researchers to develop engineered T cells that can overcome the TME beyond the challenges posed by inhibitory cytokines:

1.5.2.1 Hypoxia

Hypoxia, marked by low oxygen levels, is a prevalent characteristic in the tumor microenvironment (TME) due to abnormal vasculature and a high density of cells. In response, researchers have developed a hypoxia-inducible CAR by attaching an oxygen-dependent degradation (ODD)

domain to a CAR, which stabilizes the CAR only under hypoxic conditions. This method showed in vitro cancer cell elimination under hypoxia, although it also revealed considerable basal killing at standard oxygen levels. An alternative approach uses the ODD-fused CAR together with a synthetic hypoxia-inducible promoter to control ODD-CAR (HypoxiCAR) transcription, offering a dual-layer regulation of CAR activity. HypoxiCAR T cells have demonstrated their ability to infiltrate tumors and partially clear them without inducing CRS, a well-known problem associated with specific CARs, like anti-Her2.

1.5.2.2 Tumor-Secreted Protease

Tumors secrete proteases to promote invasion and facilitate various stages of tumor development. In response, researchers have designed a masked anti-EGFP CAR T cell by adding a masking peptide with a proteolytic site before the scFv domain. This masking peptide blocks the antigen-binding site, thereby inhibiting CAR activation. Upon cleavage of the masking peptide by tumor-specific proteases, the scFv is revealed, permitting antigen binding and subsequent activation of CAR T cells. Masked CAR T cells displayed decreased activity without proteases in the presence of target antigens in vitro. In a subcutaneous human lung cancer xenograft model, their activity was comparable to unmasked CAR T cells, indicating that the masking peptide is successfully cleaved.

1.5.2.3 Managing Overactivated Cell State in CAR T Cell Therapy

Cytokines serve as crucial immune modulatory factors that help maintain immune balance and fight tumors and infections. In the realm of cancer immunotherapy, cytokines like IL-2 and IL-12 have been widely examined both as individual treatments and in conjunction with CAR therapy. Nonetheless, systemic administration of cytokines can result in serious side effects. To mitigate systemic toxicity, it has been suggested that CAR T cells should produce cytokines exclusively within the TME. This selective cytokine production can be accomplished by making it dependent on CAR activation. The nuclear factor of activated T cells (NFATs)/IL-2 composite promoter, previously employed as an indicator of T cell activation, can be adapted to regulate cytokine production in CAR T cells. Various cytokines, such as IL-12, IL-18, and IL-21, have been explored for controlled production in CAR T cells. These investigations offer perspectives on the advantages and obstacles of employing specific cytokines in CAR T cell therapy.

1.5.2.4 Overcoming T Cell Migration Challenges in Solid Tumors

A major challenge in cancer immunotherapy is the restricted capacity of T cells to infiltrate solid tumors. To tackle this problem, T cells have been engineered to express the chemokine receptor CXCR2, which augments their localization to tumors expressing the chemokine CXCL1 in vivo. This enhanced trafficking has been demonstrated to significantly improve antitumor efficacy in vivo.

An alternative method to ameliorate T cell migration within solid tumors involves the restoration of heparanase expression. T cells expanded ex vivo typically exhibit low heparanase levels, an enzyme that facilitates the degradation of the extracellular matrix. Modifying T cells to express heparinase, scientists enhanced tumor penetration and antitumor activity.

1.5.3 Exogenous Control of Engineered Immune Cells

Exogenous control employs external agents like small molecules, light, or ultrasound to regulate the activity of engineered immune cells. The choice of control input hinges on the specific application; systemic control can be achieved with small molecules, while light and ultrasound provide more localized control. Exogenous control can enhance the safety of engineered immune cells by limiting T cell activity to prevent adverse side effects and increase tumor-targeting specificity.

While small molecules are easy to administer, their potential toxicity or suboptimal pharmacokinetics can be considered. Designing an inducible system dependent on small molecules requires attention to the inducer's pharmacokinetics and safety profile. Light and ultrasound provide non-invasive and precise targeting, but maintaining sustained input for cell function with these methods is challenging.

The aim for clinical use is to develop a safe, clinically approved inducer and promote the development of CARs with improved safety profiles. Inducible switches can also enhance durability; temporarily stopping tonic receptor signaling through a drug-gated CAR can save T cells from exhaustion, boosting their in vivo persistence and anti-tumor activity.

Exogenous inducers can control ON or OFF states, but most systems lack memory except for kill switch or recombinase-based systems. This requires a continuous presence of the inducer, considering delivery and toxicity. When creating an ON switch, meticulous regulation and fine-tuning are necessary if the controlled output may become toxic at high levels (e.g., pleiotropic cytokines or overactive CARs). On the other hand, an OFF switch is appropriate for outputs that are relatively safe (e.g., well-regulated CARs) and only need to be deactivated in case of severe side effects. The ON switch is advantageous when the output is no longer required.

1.5.3.1 Small Molecules 1.5.3.1.1 Regulation of CAR Activity Through Drug-Triggered Assembly or Receptor Stabilization Assembly: CARs can be divided into antigen recognition and signaling domains, with small molecules either facilitating (ON) or interfering with (OFF) the assembly of these components.

Stabilization: By fusing a small molecule-regulated degradation domain (degron) to the CAR, inducers can stabilize the degron or inhibit proteolysis (ON), while others engage endogenous proteolysis machinery in the presence of a small molecule (OFF).

The hepatitis C virus (HCV) non-structural (NS3) protease has been utilized to develop an inducible CAR system, regulated by a clinically approved protease inhibitor with a positive safety profile. The versatile protease-regulatable CAR (VIPER CAR) and the lenalidomide system can leverage both assembly and stabilization systems to create ON and OFF switches with the same inducer. The NS3-based system can be combined with other CAR designs, such as SUPRA or the lenalidomide system, for multiplexed control circuits that enhance CAR T cell therapy safety and specificity.

1.5.3.1.2 Regulation CAR or Therapeutic Gene Expression

The Tet-on transcription system permits CAR transcription in the presence of doxycycline, although some leaky expression has been reported. High TetR levels can be toxic due to off-target genome binding. Synthetic zinc finger transcription regulators (synZiFTRs), designed to be orthogonal to the human genome, have been used to develop multiple inducible synZiFTR systems with clinically approved drugs as inducers, resulting in the first dual inducible gene expression control system in human primary T cells for regulating CAR and cytokine expression.

Besides drugs, natural products such as resveratrol, found in red wine, grapes, and berries, have been employed to suppress or induce CAR expression, demonstrating their effectiveness in primary T cells both in vitro and in vivo with a high dynamic range. Furthermore, a recombinase-based gene circuit employing the FlpO-ERT2 fusion protein can be deployed to permit drug-inducible CAR expression to achieve memory. This way, long-term gene expression changes can be achieved with temporary drug exposure, reducing the need for continuous drug inducer administration.

1.5.3.1.3 Safety Switches

Safety switches have become an aspect of CAR T cell therapies, allowing better control over cell activity, and providing an additional layer of safety. Small-molecule-mediated dimerization of split functional proteins can be used to achieve user-defined activation of cell circuits, including drug-inducible cell-death circuits as safety switches.

One example is the drug-inducible caspase 9 (iCasp9) kill switch, which has been used in over 20 clinical trials for CAR T cell and histocompatibility leukocyte antigen (HLA)-mismatched hematopoietic stem cell transplants (HSCTs). The iCasp9 switch comprises two parts: (1) a genetically encoded split caspase-9 protein fused to a chemically inducible dimerization system based on mutated FKBP12 (F36V) homodimerization domains, and (2) the dimerization-inducing small molecule AP1903. Native caspase-9 is activated by cytochrome c-mediated dimerization to trigger apoptosis. Fusing caspase-9 to FKBP12 (F36V) in engineered cells permits the induction of apoptosis after AP1903 administration. In a phase I clinical trial (see e.g., NCT00710892) using T cells carrying iCasp9, four patients given AP1903 after the onset of acute graft-versus-host disease (GvHD) experienced a 90% reduction in iCasp9+ cells within 30 minutes of administration and complete reversal of GvHD. Pediatric patients receiving HLA-mismatched HSCT and donor T cells expressing iCasp9 (BPX-501) showed successful engraftment in a phase I clinical trial (see e.g., NCT03301168, NCT02065869). Two of the four patients who developed GvHD symptoms improved after two administrations of AP1903.

Utilizing the FKBP12/AP1903 dimerization system and non-caspase effectors, small molecules have been employed in the development of activity switches to control activation and avoid overactivity. One strategy involves combining an inducible MyD88/CD40 (iMC) costimulatory domain with a first-generation CAR targeting prostate stem cell antigen (PSCA), which has produced promising results in a combined phase I/II clinical trial (see e.g., NCT02744287). Native homodimerization of MyD88, a Toll-like receptor adaptor molecule, and CD40, a tumor necrosis factor family member, functions to stimulate nuclear factor kB (NF-kB), Activator protein 1 (AP-1), and other immune activating and anti-apoptotic proteins. By fusing MyD88 and CD40 to two copies of FKBP12 (F36V), an inducible costimulatory domain is created through AP1903 binding, which enhances T and natural killer (NK) cell residence time by promoting cell proliferation and CAR activation in murine models. Cells co-transduced with iMC and a first-generation CAR that lack co-stimulatory domains show limited activation without concurrent CAR/iMC activation. T cells expressing a first-generation PSCA-specific CAR and the iMC go-switch have exhibited prolonged T cell residence time in patients, with 8 out of 11 (66%) demonstrating stable disease 9.8 weeks after infusion.

1.5.3.2 Light

Using light-inducible dimerization domains, researchers have developed photoactivatable CARs in immune cells. A blue-light-inducible system has been employed to engineer T cells with localized CAR expression, and the same system has been used to trigger cytokine production in T cells, leading to the elimination of cancer cells.

Light-based control methods offer advantages such as precise spatiotemporal control and minimal side effects. However, one significant limitation is the minimal tissue penetration depth of blue light (less than 1 um). To overcome this issue, a nanoplate technology has been developed to convert more penetrative near-infrared (NIR) light into blue light. By injecting nanoplates along with blue light-inducible CAR T cells into tumor-bearing mice, researchers achieved reversible and real-time control of CAR activation, reducing the risk of cytokine storms.

Finally, T cells have been engineered to express a photoactivatable chemokine receptor (PA-CXCR4), resulting in enhanced directional migration to tumor sites and a significant improvement in antitumor efficacy in vivo.

1.5.3.3 Ultrasound

Ultrasound is a safe technique with excellent penetration depth, making it an attractive option for controlling CAR T cell activity. Researchers have explored a mechanically sensitive Piezol calcium channel that can be activated by ultrasound. Ultrasound generates microbubbles that activate the Piezo 1 channel, allowing calcium to enter the cell. Calcium influx activates calcineurin, which in turn leads to the downstream dephosphorylation of an NFAT transcription factor. NFAT binds to an NFAT-responsive promoter to induce CAR transcription upon ultrasound exposure. However, the requirement for microbubbles limits the technique's in vivo applicability.

To overcome the issue with microbubbles, one group developed a heat-induced CAR that responds to ultrasound. Focused ultrasound waves increase local temperature, and a heat shock protein promoter encoding Cre recombinase initiates and maintains CAR expression. Another study used plasmonic gold nanorods to convert NIR light into heat, inducing the expression of an IL-15 superagonist to enhance CAR activity in vivo and the expression of a bispecific T cell engager (BiTE) to counteract tumor outgrowth due to antigen escape.

1.6 Small Molecule Regulated Synthetic Transcription Factors

Described herein are the numerous tools available to enhance the safety and efficacy of immune cell therapy. Discussed below is the ability of conventional transcriptional tools to regulate gene expression. Specifically, described herein are small molecule regulated synthetic transcription factors, which exhibit at least the following benefits:

- Precision control: small molecules can provide precise and tunable control over the expression of specific genes. This allows researchers and clinicians to modulate immune cell activity in a controlled manner, reducing side effects and improving therapeutic outcomes.
- Reversible regulation: Many small molecules can be administered in a dose-dependent manner, and their effects can be reversed by removing the small molecule or administering an antagonist. This reversibility allows for the fine-tuning of immune cell activity and can help minimize adverse events, such as CRS and neurotoxicity.
- Temporal control: small molecules can be administered at specific time points, permitting temporal control of gene expression. This can be useful in immune cell therapy, as it allows for the activation or suppression of immune cells at specific moments during treatment.

Combinatorial control: small molecules can be used in combination to regulate multiple genes simultaneously or sequentially, permitting the design of complex and sophisticated gene expression programs.

Clinical applicability: small molecules are generally easier to manufacture, and store. In addition, small molecules are simpler to administer thus lowering the threshold for medication compliance.

The next four sections delve deeper into this topic, examining the field of synthetic transcription factors and their applications. Furthermore, discussed are areas where further investigation and development can contribute to the advancement of immune cell therapy, paving the way for effective treatments.

1.6.1 Anatomy of Small Molecule Gene Regulatory Systems

Small molecule inducible gene regulatory systems in mammalian cells have the capacity to provide exacting control over gene activation through transcription. This mechanism permits nuanced adjustment of protein levels and temporal regulation of cellular output states.

A conventional inducible system encompasses two key elements: 1) a ligand-binding domain that identifies the inducer, and 2) an effector domain that effects a modification on the genetic target. This study's focus on small molecules in this process is motivated by their bioavailability, their ability to permeate membranes, and their ease of production. Described herein is the role of effectors that influence RNA activity, thereby contributing to the protein output of these systems.

A central player in this mechanism is the transcription factor (TF) that governs the expression of the gene of interest (GOI). Various facets of TFs, such as dimerization domains, destabilization domains, and localization tags, require consideration. Transcription regulation-based systems lean on the modularity of TFs, which are usually composed of a DNA binding domain, a transcription regulatory domain, and an optional ligand-binding domain. This architecture and the principles underpinning it permit effective control over gene expression.

1.6.2 Synthetic Transcription Factors

One exemplary TF is the Tet-On/Tet-Off tetracycline-inducible system, often referred to as TET. Its role in the design of multilayer circuits has been a contribution to the progression of genetic engineering. This system has been harnessed for the differentiation of human induced pluripotent stem cells (hiPSC) into dopaminergic neurons, exemplifying its capacity in the realm of cellular programming.

Another potent small molecule playing a role in gene regulation is Isopropyl-beta-D-1-thiogalactopyranoside (IPTG). IPTG has been the focus of research, aiming at design modifications to mitigate leakiness and augment inducible fold change. Both the IPTG-binding lacI repressor and the reverse tetracycline-controlled transactivator, rtTA, can be deployed. However, given their bacterial origins, they pose potential immunogenicity concerns when introduced into mammalian systems, leading to challenges for their therapeutic use.

One approach involves the fusion of "dead" Cas proteins (dCas) with TFs. For instance, dCas9 has been fused with FK506 binding protein (FKBP), permitting transcriptional activation in the presence of chemical epigenetic modifier (CEM) small molecules. The CRISPR/Cas systems offer the capacity for simultaneous control of multiple genes, featuring tunability and orthogonal guide RNAs for different orthologs, thereby adding an additional level of precision to these gene regulatory tools.

1.63 Small Molecule-Inducible Genetic Circuit

A small molecule-inducible genetic circuit can encompass several fundamental characteristics:

(1) Strong fold induction: This is defined as the ratio of average activity when the inducer is present to the average basal activity without the inducer. Basal expression, often referred to as leakiness, poses an obstacle in the successful construction of inducible promoter-based genetic circuits. By minimizing leakiness, one can enhance fold induction metrics since the comparison is drawn between induced expression levels and basal expression levels. For therapeutic applications, low leakiness can be maintained, as high basal expression could jeopardize the safety of a genetic switch.

(2) Increased signal-to-noise ratio (SNR): This measure considers both the variance and the amplitude of data from single-cell flow cytometry. Here, the signal represents the differences between on/off populations, whereas the noise includes the standard deviation among populations and the discrepancy from the ideal performance of the circuit due to the overlap of on and off states. By adapting the SNR to inducible genetic circuits, one can better evaluate and enhance the distinction between on/off output states. The characterization of SNR is useful in the context of multilayered genetic circuits.

(3) Minimal toxicity: This attribute relates to the origins of the proteins used to build these circuits, and safety of the small molecules utilized as inducers. Generally, proteins that are not of human origin can trigger an immune response in cells. Small molecules such as tamoxifen and grazoprevir, which have received FDA approval and have been rigorously tested to show a lack of toxicity in mammalian cells at effective doses for activating synthetic genetic circuits, can be used.

(4) Orthogonal effectors for multiplexed control: The use of orthogonal chemical-inducible effectors allows for a capacity to regulate multiple variables within a genetic circuit with minimal interference. This feature contributes to the sophistication and adaptability of synthetic circuits, broadening their possible applications.

1.6.4 Synthetic Zinc Finger Transcriptional Regulators (synZiFTR)

In the development of gene regulatory toolkits, the introduction of TFs necessitates thorough characterization of their DNA binding affinity and regulatory dynamics. This preliminary step can be carried out in model systems before the TFs can be integrated into gene circuit designs. Such evaluation ensures their functionality, stability, and reliability, ultimately enhancing the efficacy and predictability of the genetic circuits in which they are implemented.

Described herein are the synZiFTRs; see e.g., Li et al. Science 378, 1227-1234 (2022); U.S. Pat. No. 11,530,246 B2; the contents of each of which are incorporated herein by reference in their entireties. These regulators are characterized by several features that make them useful in gene circuit regulation. They utilize FDA-approved small molecules, ensuring safety and compatibility with human physiology. In terms of design, synZiFTRs are compact, permitting efficient integration into genetic circuits. They offer orthogonal regulation, providing an additional layer of control and minimizing potential interference with other regulatory elements.

Another feature of synZiFTRs is their tunable activity, allowing for precise, context-dependent control over gene expression. These regulators are derived from human-based origins, enhancing their compatibility with mammalian cells, and reducing potential immunogenicity. Moreover, synZiFTRs harness natural inducible pathways to regulate synthetic programmable circuits. This strategy of co-opting existing cellular mechanisms can facilitate the integration of synthetic circuits into the broader cellular context, enhancing their robustness and functionality. As such, the design and implementation of synZiFTRs contribute to the field of small molecule inducible gene regulatory systems.

While synZiFTRs carry immense potential in regulating gene expression, achieving the desired level of control presents a challenge. This difficulty stems from the complexities of cellular contexts and diverse therapeutic requirements associated with different diseases.

The cellular context is a crucial element that significantly influences the efficacy of synZiFTRs in the domain of synthetic biology. Considerations such as chromatin structure, the presence of competing factors, and variations in transcriptional and translational machinery across distinct cell types can affect the performance of synZiFTRs when regulating target genes. Consequently, maintaining a consistent level of control in disparate cellular environments is a challenge.

Moreover, the therapeutic needs for various diseases can differ, necessitating distinct responses from gene regulatory systems. Depending on the specific disease context, the required degree of gene activation, the precise timing of gene regulation, and the duration of gene expression can vary. Furthermore, in the administration of therapeutic agents in humans, it is useful to consider the drug's pharmacokinetics, including when utilizing small-molecule inducers in the engineering of immune cells, as this not only involves an effective drug inducer but also monitoring of the circuit output. Catering to these diverse requirements adds another layer of complexity to the design and implementation of synZiFTRs.

Given these challenges, the primary objective of this study is to build the synZiFTR2.0 toolkit via enhancing and expanding the synZiFTR toolkit towards stronger fold induction and a higher signal-to-noise ratio. The goal is to ensure efficacy across varying contexts, permitting the delivery of therapeutic payloads at the necessary doses. Additionally, described herein is the incorporation of an extra layer of regulation using these synZiFTR2.0.

To achieve the primary objective, described herein are the multifaceted processes of transcription (discussed in Section 1.7, Organization and regulation of gene transcription), from the initial identification of motifs through to the elongation phase, with the purpose of finding a transcription effector domain (TED) to augment the strength of synZiFTRs. Transcriptional synergy can be achieved by integrating transcription domains from both viral and human origins.

By fusing transcriptional effectors with p65, a transcription factor ubiquitously employed in numerous biological processes, the performance of synZiFTRs can be enhanced. Hence, the first aim of this project is to identify a compatible p65 fusion partner that bolsters the capabilities of the two small molecule-regulated synZiFTRs.

The second aim of this study capitalizes on heterodimerization domains to establish AND logic gates for gene regulation. Dimerization domains have been utilized to create logic gates for receptors, resulting in enhanced safety and efficacy within immune cells. Heterodimerization domains can be used to construct split synZiFTR2.0. The application of clamp-mediated cooperativity is an approach to building an AND gate.

In the final aim, the biological mechanism is explored concerning how the identified TED aids in the generation of the synZiFTR2.0 toolkit. This research advances understanding of transcriptional processes and further improves the precision and control of gene regulation techniques.

1.7 Organization and Regulation of Gene Transcription

The process of gene transcription into RNA constitutes a locus of regulation for gene expression. This process, catalysed by RNA polymerase enzymes, is a DNA-dependent synthesis that is modulated at several stages, affording the cell a dynamic mechanism to respond to various cues and demands. The transcription process commences with initiation, where the RNA polymerase recognizes the promoter region at the start of the gene. This enzyme opens the DNA duplex, allowing it to synthesize RNA. Subsequently, the RNA polymerase escapes from the promoter, marking the transition to the next stage of the process.

The elongation phase ensues, wherein the elongation complex extends the nascent RNA chain. This process continues until the complex encounters a termination signal, which triggers the release of both DNA and RNA. This sequential orchestration ensures the accurate transcription of genetic information, a prerequisite for effective gene expression.

The steps during transcription of genes into RNA serve as knobs where intricate regulation of gene expression can happen to regulate cellular phenotype.

1.7.1 Enhancer and Promoter Recognition

The initiation process begins when the polymerase gains access to enhancers and the promoter region at the beginning of a gene. However, this access can be obstructed by chromatin, as nucleosomes have been shown to inhibit initiation. To circumvent this, nucleosomes can be removed or shifted for effective transcription to occur. Active promoters are typically situated within nucleosome-depleted regions, which are characteristically bordered by specialized +1 and −1 nucleosomes on the downstream and upstream sides of these regions, respectively.

Different classes of promoters demonstrate distinct regulatory patterns in relation to chromatin opening. For instance, promoters with CpG islands, typically found at housekeeping genes, exhibit one form of regulation, while promoters with a TATA element upstream of the transcription start site, often found at genes that are cell-type specific and regulated during differentiation, demonstrate another form of regulation.

TFs, of which approximately 1600 are known in humans, bind to DNA elements in a sequence-specific manner and guide polymerases to their target promoters. These factors utilize intrinsically disordered "transactivation" regions composed of low-complexity amino acid sequences, which help recruit proteins that regulate promoter accessibility and transcription initiation. While most TFs bind to free DNA, some can bind to nucleosomal DNA. These specialized TFs, known as "pioneer" factors, can open chromatin to facilitate transcription. They accomplish this by recruiting histone acetyltransferase and chromatin remodeling complexes that render promoters accessible to Pol II.

Enhancers further add to this regulatory landscape. These distant DNA elements, which contain binding sites for multiple cooperating transcription factors, exert their influence on transcription via their target gene promoters. This complex interplay between promoters, enhancers, and transcription factors, along with the spatial organization of transcription, contributes to the intricacy of gene expression regulation and the resulting cellular phenotypes.

1.7.2 Transcription Initiation

The regulation of transcription initiation in eukaryotes is a process that involves the concerted action of several molecular components. Central to this process is the formation of specific pre-initiation complexes (PICs) on promoter DNA. These complexes are assembled when eukaryotic polymerases interact with their corresponding initiation factors, permitting the correct positioning and priming of the polymerase for transcription initiation.

Regulation of Pol II initiation is influenced by the co-activator complex known as Mediator. This complex has been shown to stabilize the PIC in vitro, although in vivo, the PIC-Mediator complex is relatively short-lived. The Mediator complex is composed of a conserved core that includes two key modules, referred to as the 'head' and 'middle'. These modules interact with Pol II and the initiation factors TFIIB and TFIIH, establishing a platform for transcription initiation.

The periphery of the Mediator complex varies across species, adding another layer of complexity to its regulatory function. The 'tail' module of Mediator, for instance, is known to bind activating transcription factors, while the detachable kinase module is implicated in repression. One of the roles of Mediator is to stimulate the phosphorylation of Pol II by the TFIIH kinase subunit cyclin dependent kinase 7 (CDK7). This kinase targets the C-terminal domain (CTD)—a tail-like extension of Pol II- and phosphorylates it, a modification that facilitates the transition from the initiation to the elongation phase of transcription.

1.7.3 Transcription Elongation

Elongation, the next phase following transcription initiation, is also finely regulated to ensure accurate and efficient gene transcription. The formation of an elongation complex occurs when the RNA strand reaches a critical length, permitting the RNA chain to extend in a processive manner. To add a nucleotide to the growing RNA, the polymerase closes the active site, catalyzes the formation of a phosphodiester bond, and subsequently moves to the next template position.

However, some DNA sequences can interrupt this nucleotide-addition cycle, inducing transcriptional pausing that could lead to polymerase backtracking, arrest, and termination. Pol II, for instance, can arrest in front of nucleosomes but can be rescued by the elongation factor TF IS. This factor binds to the Pol II funnel and pore, aligns the DNA-RNA hybrid with the active site, and triggers the cleavage of backtracked RNA to restart transcription.

In metazoan cells, the elongation phase of Pol II transcription is tightly regulated. For example, Pol II often pauses approximately 50 base pairs downstream of the transcription start site—a phenomenon known as promoter-proximal pausing, which is also highly regulated. The stability of this pausing is maintained by the factors DRB Sensitivity-Inducing Factor (DSIF) and Negative Elongation Factor (NELF). DSIF binds around the exiting DNA and RNA, while NELF impairs the binding of TFIIS to the funnel and restricts Pol II mobility, thereby suppressing the release of pausing.

The release of paused Pol II into gene bodies is regulated by the Positive Transcription Elongation Factor b (P-TEFb), which phosphorylates DSIF, NELF, and the Pol II CTD. This triggers the formation of an activated elongation complex. Within this complex, the elongation factor SPT6 binds the phosphorylated linker to the CTD, and the PAF complex binds to the funnel, competing with NELF.

Promoter-proximal pausing can limit the frequency of transcription initiation and thus gene expression by changing the amount of RNA synthesized per unit time. Some transcription factors can target both initiation and elongation phases. The oncogenic transcription factor MYC, for instance, promotes Pol II release from pausing, while factors from the BET family, such as BRD4, can bind enhancers and recruit P-TEFb. P-TEFb can also be recruited as part of the Super Elongation Complex, which contains fusion partner proteins of the mixed-lineage leukemia protein. Phosphorylation of the Pol II CTD recruits factors required for Pol II elongation and for co-transcriptional events such as RNA processing, histone modification, and chromatin remodeling. The CDK7 initiates phosphorylation by targeting serine-5 residues in the CTD's heptapeptide repeats, leading to the recruitment of the capping enzyme to protect the nascent RNA's 5' end. The regulatory process continues as the cyclin dependent kinase 9 (CDK9) subunit of P-TEFb conducts further phosphorylation, recruiting positive elongation factors including SET1 and SET2. These factors are involved in chromatin configuration and transcription regulation, permitting precise gene expression control.

In conclusion, the intricacies of transcription regulation, ranging from the formation of the preinitiation complex to the elongation phase, demonstrate the complexity inherent in controlling gene expression and cellular phenotype. Each step of the process, including initiation, promoter access, elongation, and pausing, involves a multitude of molecular interactions and modifications, all of which contribute to the fine-tuning of gene expression.

Moreover, these stages of transcription include co-factors that can be recruited in synthetic transcription factors. These recruited co-factors can then synergize with the human transcription factor p65 to amplify transcriptional expression. The recruitment of such co-factors can result in enhanced gene regulation, demonstrating the ability to modify these complex mechanisms for desired outcomes. Taken together, this intricate dance of molecular machinery not only ensures the accurate and precise expression of genes, but also opens avenues for therapeutic interventions and innovations in synthetic biology.

Example 2: Materials and Methods 2.1 Plasmid Design and Construction

Plasmids were constructed using established molecular biology methods and Gibson isothermal assembly. Engineered cassettes were subcloned into vectors containing Ampicillin resistance as a bacterial selection marker. All plasmids were sequence-verified and archived in competent *E. coli* TG1 (GOLDBIO CC-205-A). Donor plasmids for lentiviral integration were constructed by subcloning cassettes into the pHR'SIN vector backbone digested with EcoRI/NotI. SynZiFTR expression cassettes contained a constitutive promoter (pSFFV) driving expression synZiFTR. Minimal synZiFTRs contained a SV40 nuclear localization signal. Bicistronic cassettes used for doxycycline induced minimal synZiFTRs contained (5'-3') pGK regulated constitutive TetON expression in the reverse orientation, followed by pTreg promoter regulated synZiFTR expression cassettes in the forward orientation. All inducible synZiFTRs contained a SV40 NLS, except for ERT2 fusions.

2.2 Mammalian Cell Culture

All cells were maintained in 10 cm treated dishes (adherent) or 75 mL flasks (suspension) at 37 C and 5% $CO_2$. Cells were passaged every 3-4 days when they reached 70-80% confluency or ~2 million cells/mL. Cell lines were not used for experiments beyond 40 passages.

HEK293FT cell lines (THERMO FISHER SCIENTIFIC R700-07) were cultured in DULBECCO'S MODIFIED EAGLE'S MEDIUM (CORNING 10-013-CV) supplemented with 10% Fetal Bovine Serum (TAKARA BIO 631367), 1% GLUTAMAX (THERMO SCIENTIFIC 35050061), 1% Non-Essential Amino Acids (THERMO SCIENTIFIC 11140050), and 1% Penicillin-Streptomycin (THERMO SCIENTIFIC 15140122).

Jurkat cell lines (ATCC TIP-152) were cultured in RPMI 1640 Medium (CORNING 10-040-CV) supplemented with 10% FBS, 1% GLUTAMAX, and 1% Pen-Strep.

2.3 Lentiviral Transduction of Jurkat Cell Lines

Cassettes cloned into lentiviral donor plasmids were integrated into Jurkat cell lines using lentiviral infection. Lentivirus was harvested from transfected HEK293FT cells. 500,000 HEK293FT cells were seeded into 6-well treated plates for 24 hours and subsequently transfected with 2 ug total DNA in a NaCl-PEI solution. All constructs were diluted to 100 ng/uL in deionized water prior to being added to the transfection mix. 1 ug of the donor plasmid was co-transfected with 700 ng of the pCMVR8.74 plasmid (ADDGENE #22036), 100 ng of the pAdVantage plasmid (PROMEGA), and 200 ng of the pMD2.G VSVG plasmid (ADDGENE #12259). Upon transfection, cells were incubated for 72 hours prior to harvesting media containing lentiviral supernatant. Lentiviral media was centrifuged for 5 minutes at 300 g. 500,000 Jurkat cells were seeded into 12-well treated plates in 1 mL media. 1 mL of each lentiviral media was added to the cells (approximate multiplicity of infection (MOI)=30). Infected cells were incubated for 24-48 hours prior to removal of lentivirus. Cells were collected and centrifuged for 5 minutes at 300 g. Lentiviral media was removed and fresh media was added. Transduced cells were subsequently used for downstream induction measurements.

2.4 Flow Cytometry

All flow cytometry measurements were performed on an ATTUNE NxT Flow Cytometer (THERMO FISHER SCIENTIFIC). Cell samples were suspended in 200 uL fresh culture media and measured on the flow cytometer in biological triplicate. Live cells were gated by forward scatter (FSC) and side scatter (SSC). Fluorescence data was collected for GFP (excitation laser: 488 nm, emission filter: 530/30 nm), and mCherry (excitation laser: 561 nm, emission filter: 620/15 nm). A minimum of 10,000 live cells were collected for each sample. Flow cytometry data was analyzed using FLOWJO (TREESTAR Software). Live cells were gated by forward scatter and side scatter. Median of fluorescence distributions were calculated by FLOWJO. Data was further analyzed using the PRISM 9 software (GRAPHPAD).

2.5 Small Molecule Induction

Stock solutions of Doxycycline hydrochloride (SIGMA ALDRICH, 50 mg/mL in DMSO), 4-hydroxytamoxifen (SIGMA ALDRICH, 1 mM in ethanol), and grazoprevir (MEDCHEMEXPRESS, 1 mM in DMSO) were stored at −80° C. 50,000 Jurkat cells were seeded into 96-well untreated round-bottom plates in 100 uL fresh media. 100 μL of media containing 2× concentrated amounts of the small molecule inducer was added to each well on day 0 of induction. For longer time course experiments, cells were passaged in refreshed induction media every 2-4 days. All inductions were performed in biological triplicate.

2.6 Quantification and Statistical Analysis

Data between two groups was compared using an unpaired two-tailed t-test as indicated; data between three or more groups was compared using one-way ANOVA with Dunnett's Multiple Comparisons post-hoc test or two-way ANOVA with Tukey's Multiple Comparisons post-hoc test as indicated. All statistical analyses were performed with Prism 9 (GraphPad) and p values are reported (not significant (ns): $p>0.05$, *: $p<0.05$, : $p<0.01$, *: $p<0.001$, ****: $p<0.0001$). All error bars are represented either SEM or SD.

Example 3: Screening Transcription Effector Domains (TEDs) and Development of synZiFTR2.0

Described herein is the identification and incorporation of a TED into synZiFTR to develop synZiFTR2.0.

Li et al., in 2022, supra, identified two distinctive of small molecules, Grazoprevir (GZV) and 4-Hydroxytamoxifen/tamoxifen (4OHT/TMX), that can control synZiFTR activity via distinct mechanisms. This dualistic approach paves the way for the expansion of gene expression control strategies. GZV, an FDA-sanctioned antiviral drug, stabilizes synZiFTRs by inhibiting the NS3 self-cleaving protease domain, enabling gene transcription. 4OHT/TMX, an FDA-approved breast cancer medication, selectively modulates the nuclear availability of ERT2-linked molecules. The GZV switch allows for safe regulation with an approved drug that does not target native cellular proteins, while the TMX switch offers an entirely human-derived option.

These two molecules were deployed in a two-switch system that sequentially controlled circuits. TMX followed by GZV treatment reduced tumor load in mice injected with HER2+ Nalm6 tumor cells. The TMX-inducible synZiFTR regulates dose-dependent control over super IL-2 production, resulting in engineered cell proliferation and maintenance. The GZV switch, on the other hand, regulates the anti-Her2 CAR expression, which triggers efficient killing of Her2-overexpressing (HER2+) NALM6 leukemia cells. The properties of these constructs were defined. The TMX-inducible synZiFTR plasmid designs were used to express various super IL-2 mutants and their capacity to sustain T cell populations was assessed in vitro in the absence of IL-2 media supplement. Given their effectiveness in controlling therapeutic genes, the GZV and 4OHT/TMX regulated synZiFTRs were selected for further development.

3.1 Introduction 3.1.1 Small Molecule-Mediated synZiFTRs and Application of Transcriptional Synergy Studies to improve the potency of Cas9-mediated gene activation were influenced by the observations of transcriptional activation in natural contexts. Endogenous transcription factors generally act in synergy with co-factors. To achieve this transcriptional synergy, the synergistic activation mediator (SAM) comprising multiple heterotypic transcription activators (VP64, p65, HSF1) was developed. SAM recruited to a dCas9 drives higher endogenous gene expression when compared to the recruitment of homotypic transcription factors. In a similar study, a hybrid VP64-p65-Rta (VPR) transcription activation domain (TAD) was generated where the dCas-VPR transcription factor exhibited stronger gene regulation when compared to dCas9-VP64, dCas9-p65, and dCas9-Rta respectively.

The TAD used to build synZiFTRs is the NF-κB transactivating subunit p65. p65 recruits a distinct subset of transcription factors and chromatin remodeling complexes to positively regulate mRNA transcription. Given that hybrid TADs have been shown to enhance transcriptional activity, fusing effectors involve in various transcription stages to p65 can increase transcription output by enhancing transcription mechanisms beyond initiation. Specifically, a subset of transcriptional effectors from these categories were tested: 1) pioneer/condensate forming factors, 2) transcription activators, and 3) transcription elongation factors. Described below are the protein domains chosen for the screen.

3.1.1.1 Pioneer Transcription Factors

Pioneer transcription factors are distinctive proteins that interact with heterochromatin-which are usually not accessible to other proteins. During these interactions, the compacted chromatin structure is loosened to be available to the transcriptional machinery and other transcription factors, thus triggering gene expression. Pioneer factors are involved in various cellular activities, including cell differentiation, embryonic growth, and adaptation to environmental shifts. They can however contribute to the abnormal activation or deactivation of specific genes in cancer.

The domains selected for this category are intrinsically disordered regions (IDRs) from the EWSR1 (Ewing Sarcoma Breakpoint Region 1) and FUS (Fused in Sarcoma) proteins. They are RNA-binding proteins with associations with cancer, due to their role in chromosomal translocations. While they do not fit into the classical definition of pioneer transcription factors, IDRs from EWSR1 and FUS are part of gene fusions that produce aberrant transcription factors with pioneering capabilities.

EWS-FLI rearrangement in Ewing's Sarcoma recruits an IDR to oncogenes at inaccessible GGAA repeat sites, resulting in malignant transformation. IDR from EWS mediates a transition from closed to open chromatin and establishing an active enhancer state. IDR from FUS functions as the transcriptional activator domain of FUS-CHOP and FUS-ERG fusion proteins observed in cancer, via targeting the SWI/SNF chromatin remodeling complex. In addition, these IDRs are shown to form phase-separated hydrogels and interact with the RNA polymerase II C-terminal domain (CTD). The involvement of both IDRs in inducing gene expression particularly in closed chromatin regions makes them candidates for the screen.

3.1.1.2 Transcription Activators

Domains were selected from transcription factors known to be involved in positive transcription regulation. MLXIPL (MLX interacting protein like) encodes a basic helix-loop-helix leucine zipper (bHLH-LZ) transcription factor of the MYC/MAX/MAD superfamily that have been shown to be effective in driving active transcription. Heat Shock Factor 1 (HSF1) is a transcription factor that responds to heat shock and other forms of stress. During stress, activated HSF1 binds to heat shock elements (HSEs) in the promoter regions of target genes, leading to the transcription of heat shock proteins (HSPs). Beyond its canonical role, HSF1 upregulates expression of proteins involved in cell cycle progression, inhibition of apoptosis, and protein synthesis. Furthermore, HSF1 has also been described to stimulate pause-release activity. The glucocorticoid receptor (GR) is a type of nuclear receptor that is activated by binding to glucocorticoid hormones, such as cortisol. Once activated, it translocates to the nucleus, where it regulates the transcription of various genes involved in processes like inflammation, metabolism, and apoptosis via interaction with various proteins. Some of these proteins are coactivators, such as steroid receptor coactivator-1 (SRC-1), p300, and CREB-binding protein (CBP) that enhance GR's transcriptional activity.

3.1.1.3 Elongation Factors

Elongation factors participate in the elongation phase of DNA transcription, contributing to the precision and effectiveness of these biological processes. The selected domains are from proteins involved in the elongation process. cMyc interacts with the elongation factor Spt5 to mediate pause-release. Bromodomain-containing protein 4 (BRD4) positively regulates elongation through the interaction with pTEF-b. Its colocalization with condensates at super-enhancers further indicates that it can be involved in other steps in the transcription cycle. From the Spt5 elongation factor, the Kow5 domain binds to Pol II and is involved in stabilizing the elongation complex. Interacts with Spt6 (IWS1) is a scaffold protein that interacts with multiple elongation factors. Specifically, an IDR in IWS1 was selected which harbors a series of three unique TFIIS N-terminal domains (TND)-interacting motifs (TIMs) that selectively and discretely interact with different TND-containing factors.

3.2 Results 3.2.1 Screening Transcription Effector Domains for synZiFTR2.0

To select the TED-p65 hybrid TAD, each TEDs was integrated in the minimal synZiFTRs, to reduce confounding factors from ligand interaction regions. The minimal synZiFTRs comprises: (1) zinc-finger (ZF) based-DNA binding domain (DBD) generated by linking 2F units to construct functional six-finger (6F) arrays fused to (2) the p65 activation domain.

The TEDs were fused in between the DBD and p65. Activity was measured in Jurkat T reporter line by measuring the mCherry fluorescence activity (see e.g., FIG. 1A). The expression of these synZiFTRs is regulated by a TetON circuit, where they are expressed in the presence of Doxycycline (Dox) (see e.g., FIG. 1B).

Figure 1C:
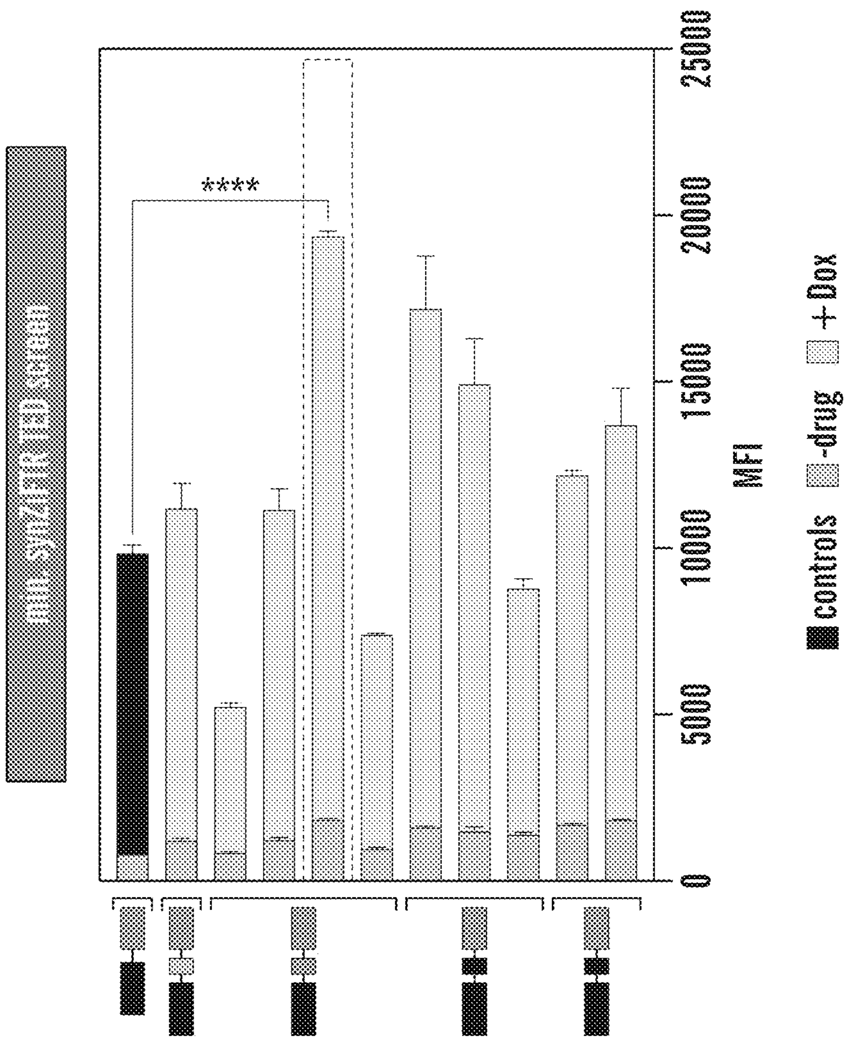

5 out of the 9 TED-p65 fusions activated stronger mCherry output when compared to the ZF-p65 synZiFTR (see e.g., FIG. 1C). Out of the 5, the IWS1 IDR domain-p65 fusion showed the strongest activity.

The work that generated the VPR transcription activation domain demonstrated the importance of domain ordering. Hence, to evaluate domain order, the positions of the three domains (ZF, p65, and TIMs) were shuffled, generating all possible TIMs integrated-synZiFTR arrangements. Ordering of the domains can impact the mCherry output, depending on the location TIMs is inserted (see e.g., FIG. 1D).

Figure 1E:
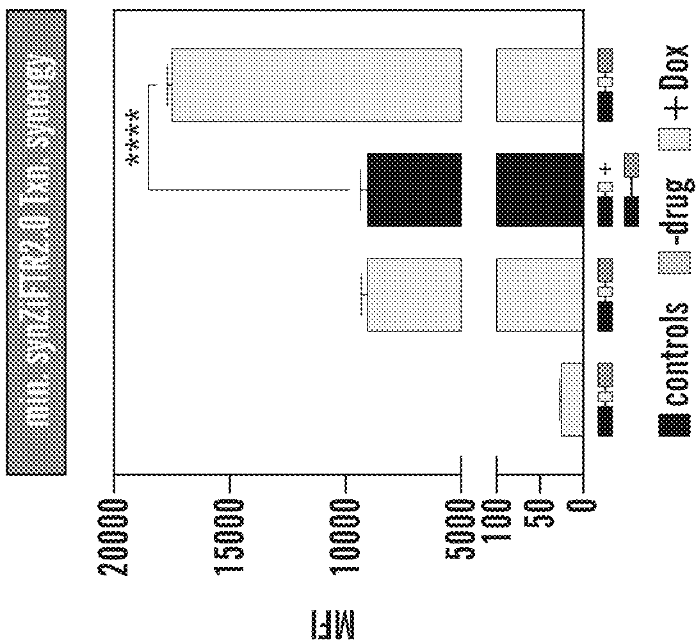

While the TIMs integrated-synZiFTR's regulated transcription activation is stronger than the original minimal synZiFTR (ZF-p65), it was also investigated whether there is transcription synergy. Transcription synergy is defined as the greater-than-additive transcriptional effect of multiple activators on a promoter or enhancer. To achieve this, p65 from the original minimal synZiFTR was replaced with TIMs (ZF-TIMs), and its ability to regulate mCherry output was measured in a Jurkat T reporter line. mCherry expression under the regulation of TIMs integrated-synZiFTR was significantly higher than the addition of the mCherry output of ZF-p65 and ZF-TIMs (see e.g., FIG. 1E). These results identified TIMs as a TED that can be integrated into synZiFTRs for improved gene expression output and synthetic circuit design in human cells. TIMs integrated-synZiFTRs will be herein referred to as synZiFTR2.0.

3.2.2 Small Molecule-Inducible synZiFTR2.0

Figure 2A:
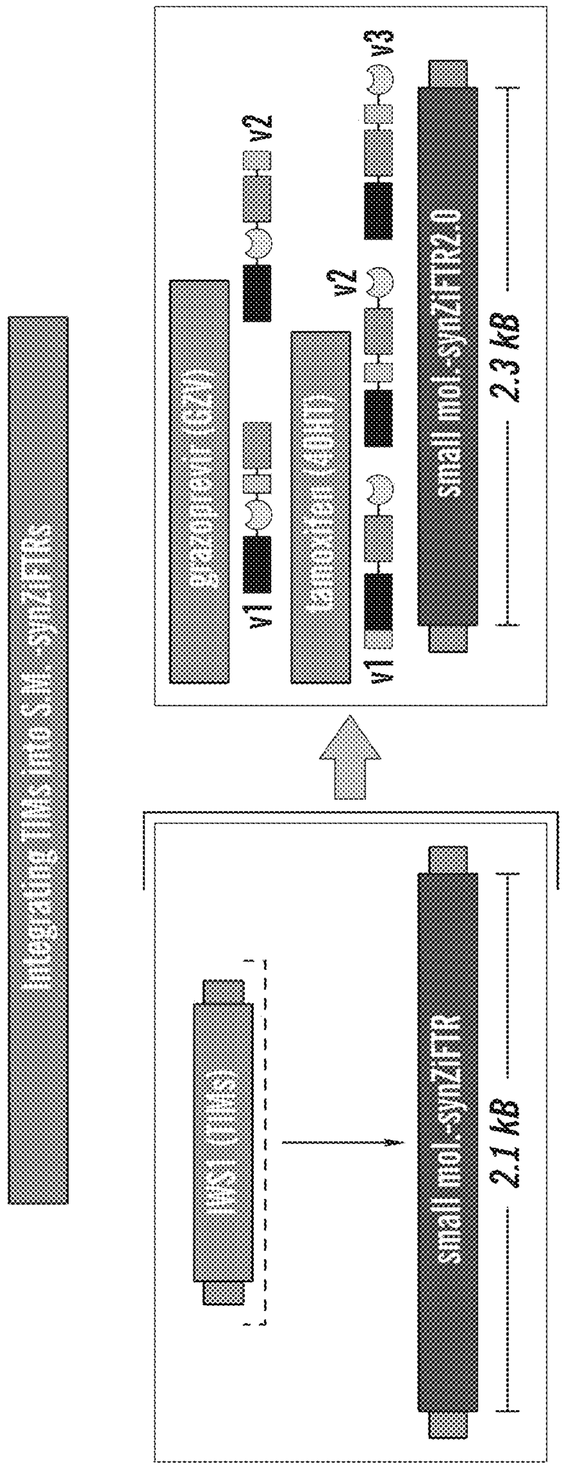
FIG. 2A-2E. Small molecule regulated synZiFTR2.0.
Figure 2B:
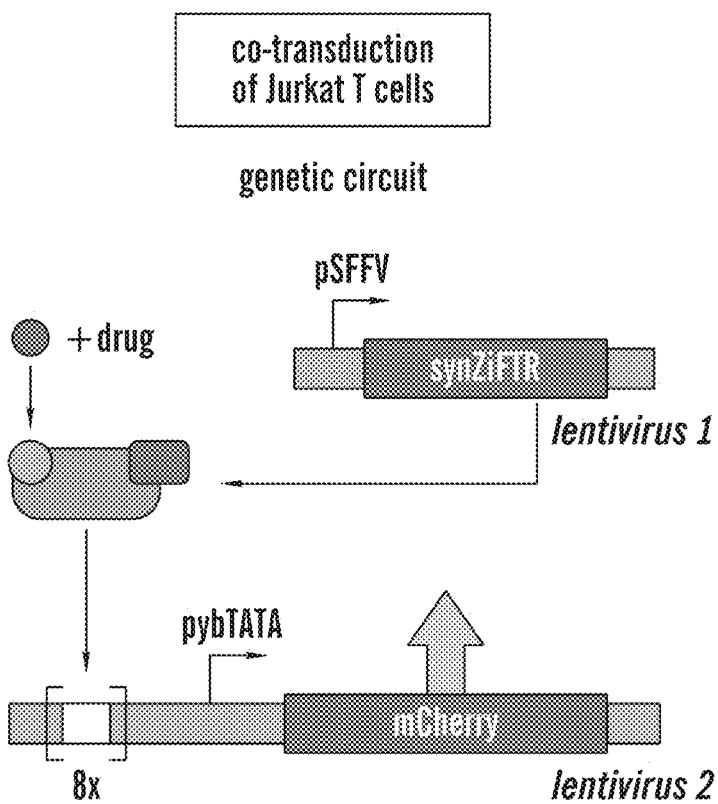

Besides strongly activating the circuit output amongst the TEDs when fused to p65, TIMs also has the advantage of being a small domain. Only 44 amino acids long, inclusion of TIMs increases the sequence length of synZiFTRs by 132 base pairs (see e.g., FIG. 2A). This adheres to the goal of synZiFTRs as being compact gene cassettes for efficient delivery into primary human cells and tissues.

Figure 1D:
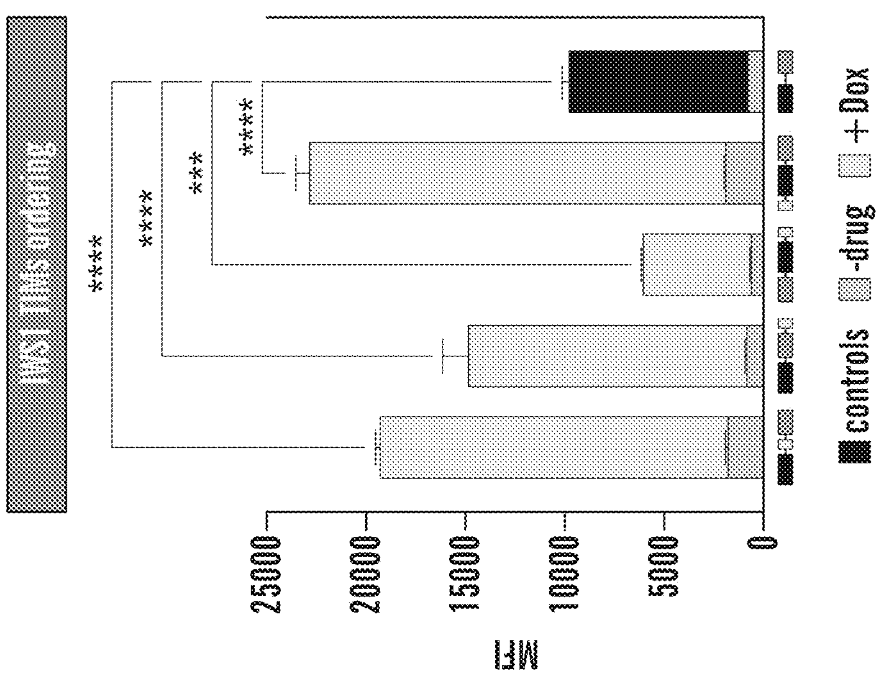

As such, TIMs were inserted into the GZV- and 4OHT-synZiFTRs to determine if there would be similar improvement in their transcription potency shown in FIG. 1C. Results from FIG. 1D showed the important of domain ordering when designing synZiFTR2.0. Hence, TIMs were fused to various positions for both synZiFTRs. TIMs was fused into two different positions into the GZV-synZiFTR, and three different positions into the 4OHT-synZiFTR to generate the 2.0 variants. For GZV-synZiFTR, TIMs was fused in between the NS3 and p65 domain (variant 1), or by extending the C-terminal by fusing it after p65 (variant 2). As for 4OHT-synZiFTR, TIMs was fused via N-terminal extension by fusing it upstream of the ZF (variant 1), in between ZF and p65 (variant 2), and finally in between p65 and the Ert2 domain (variant 3) (see e.g., FIG. 2A).

Figure 2C:
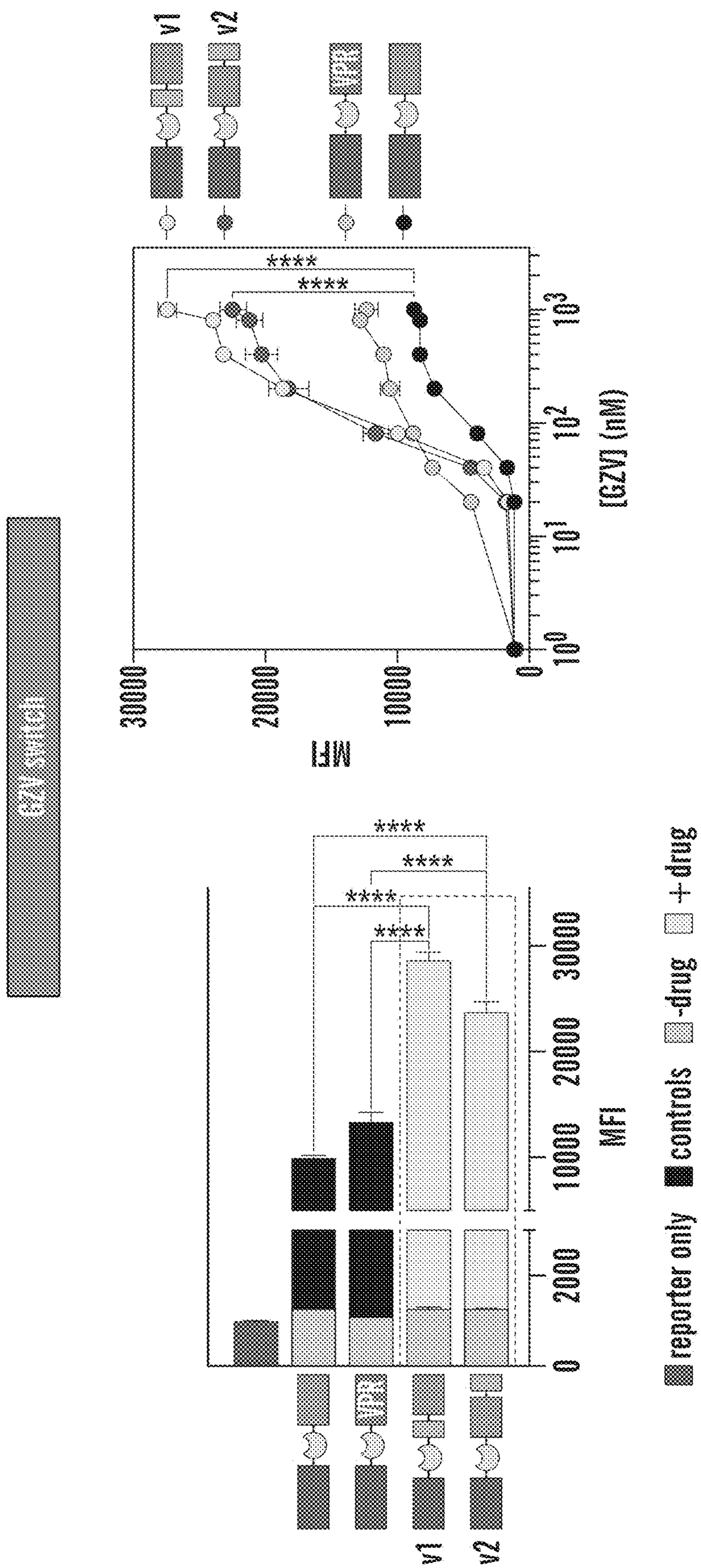

All NS3-synZiFTR2.0 variants exhibited increase in mCherry fluorescence output compared to the NS3-synZiFTR. Variant 1 demonstrated with significantly stronger mCherry output with negligible increase in leakage (+20 MFI). Variant 2 exhibited slightly weaker mCherry output compared to variant 1 without penalty in leakage. They also exhibited titratable control of reporter output (see e.g., FIG. 2B, FIG. 2C).

Figure 2D:
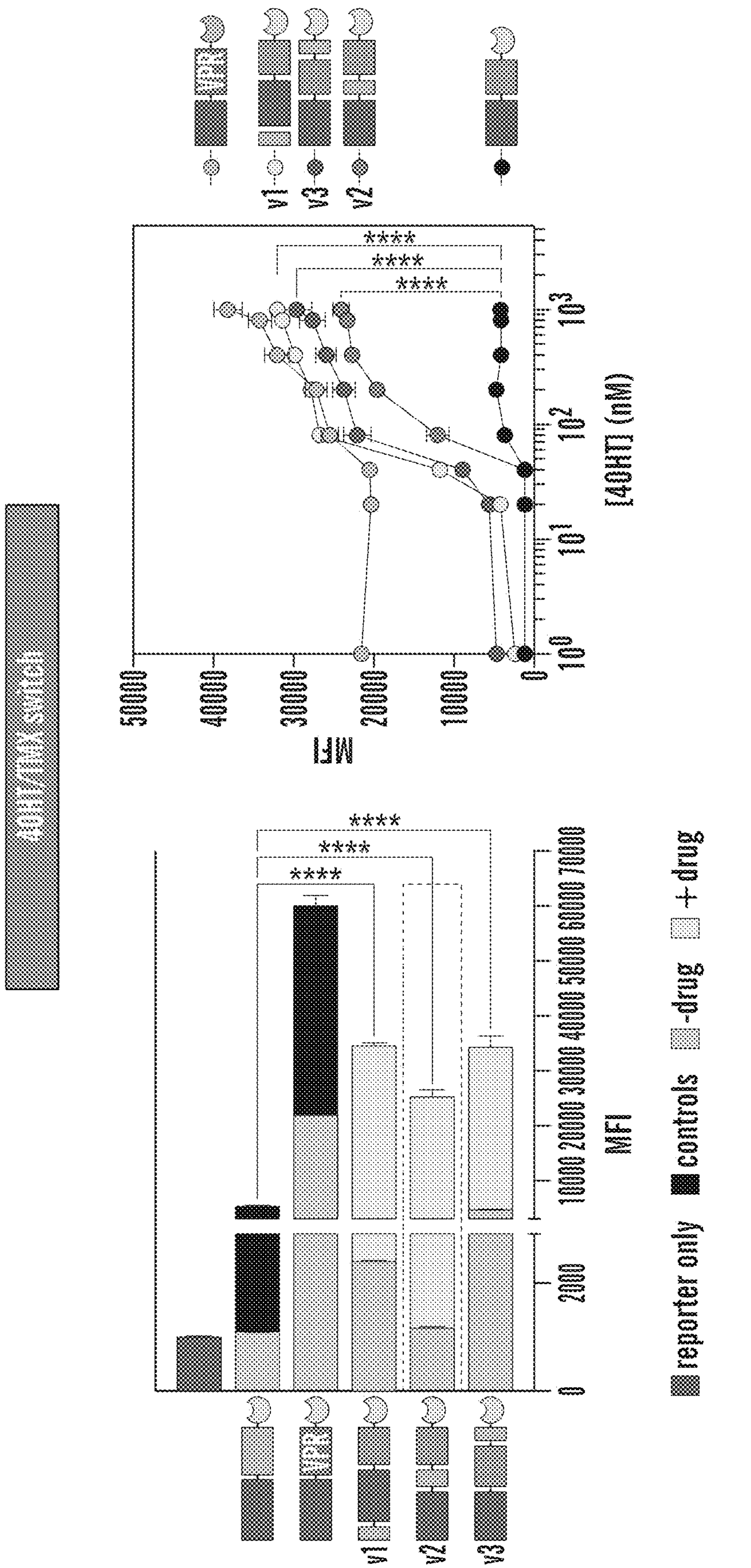

All 4OHT-synZiFTR2.0 variants exhibited increase in mCherry fluorescence output compared to the 4OHT-synZiFTR. Variant 2 was the best 4OHT-synZiFTR2.0 due to its negligible penalty in leakage, while both variant 1 and variant 3 displayed significant penalty in leakage. Like the GZV-synZiFTR2.0 variants, 4OHT-synZiFTR2.0 variant 2 exhibited titratable control of reporter output similar 4OHT-synZiFTR (see e.g., FIG. 2B, FIG. 2D). They both outperformed VPR fused synZiFTRs, In the case of GZV-synZiFTR2.0, the maximum output surpasses VPR while replacement of p65 with VPR in the 4OHT-synZiFTR demonstrated significant leakage (see e.g., FIG. 2C, FIG. 2D).

Figure 2E:
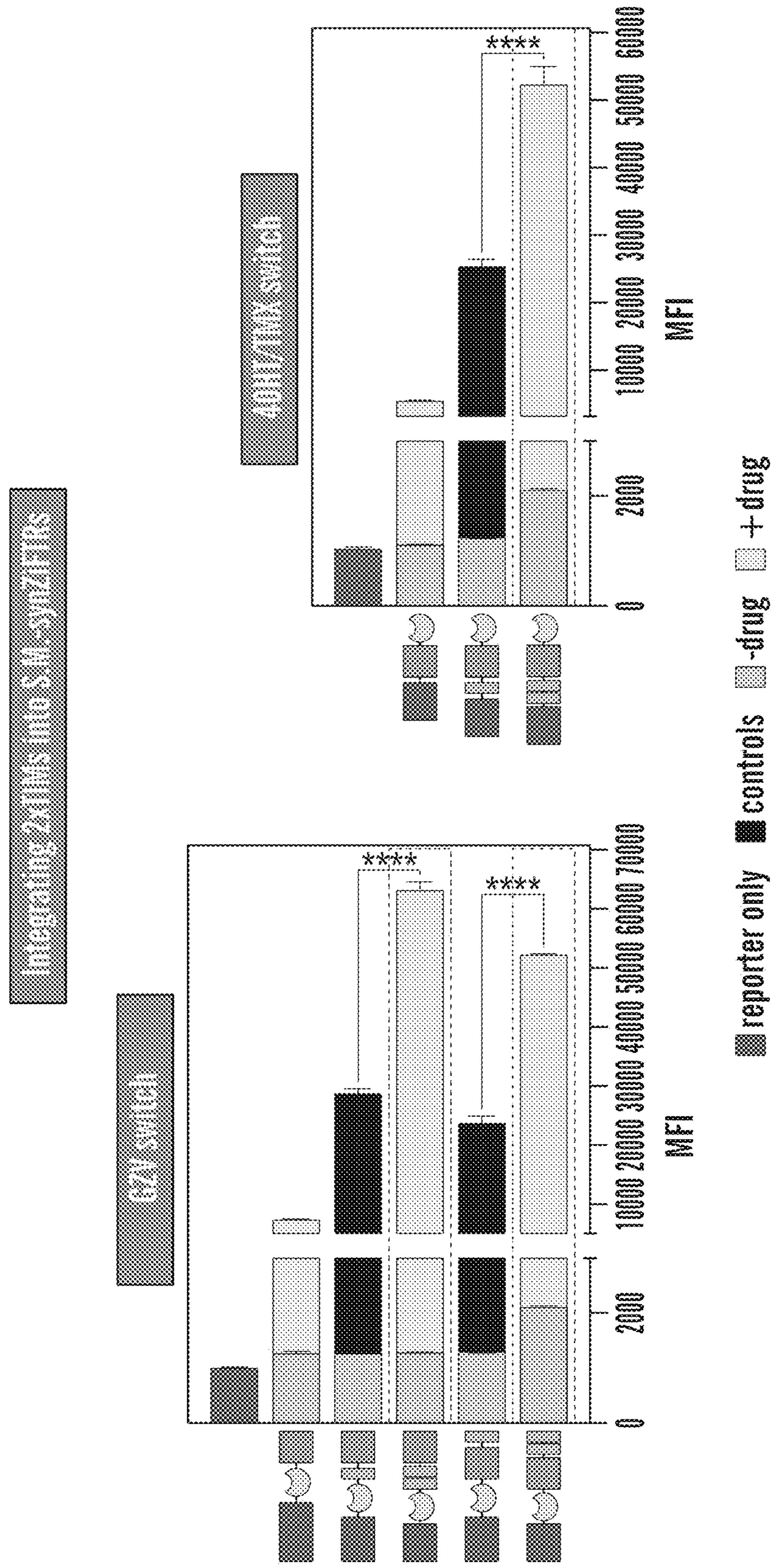

3.2.3 Increasing Small Molecule-synZiFTR2.0's Potency Via Fusion of Two TIMs Domains Having demonstrated the compatibility of TIMs in small molecule-synZiFTRs, its ability to further improve circuit output when two TIMs are inserted into the synZiFTRs was assessed. Two TIMs were fused upstream of p65 in both GZV- and 4OHT-synZiFTRs. Fusion of two TIMs produced a circuit that surpassed a single TIMs fusion for small molecule induced circuits (see e.g., FIG. 2B, FIG. 2E).

3.3 Conclusion

Described herein is a targeted screen that identified TIMs as a domain that can confer transcription synergy when fused to p65. When compared with previously generated hybrid transcription activators, this study with TIMs similarly highlighted the influence of domain ordering. Using TIMs, the transcription output of GZV- and 4OHT/TMX-synZiFTRs were significantly improved, without taking significant penalty in leakage. This result indicates that small molecule synZiFTR2.0s can be deployed in therapeutic contexts.

3.4 Discussion

One aspect of CAR T-cell therapy involves maintaining a fine equilibrium between enhanced safety controls and the incorporation of more effective therapeutic payloads beyond CAR. A multitude of CAR T cell therapies have been engineered to bolster anti-tumor activity by simultaneously generating factors like checkpoint inhibitors, or immunomodulatory factors. For instance, one study highlighted the engineering of CAR T cells to produce checkpoint inhibitors. This tactic aims to counteract the immunosuppressive tumor milieu and bolster T cell responses. In addition, the generation of immunomodulatory factors by CAR T cells provides an alternative avenue for amplifying their anti-tumor activity. These factors can reshape the tumor environment, making it more susceptible to CAR T cell actions, and can also directly stimulate the activation and proliferation of these cells.

The 4OHT-inducible synZiFTR have been used to successfully induce the expression of super IL-2 in vitro in primary T cells. Downstream proliferation studies using this switch showed maintenance of primary T cell population when induced in a temporal-dependent manner. However, compared to cells that constitutively expressed super IL-2, 4OHT induced super IL-2 did not increase the cell population over time in vitro. This indicates a capacity for improving temporal and amplitude regulation of super IL-2 expression in the switch. To address this, the 4OHT-synZiFTR2.0 is used to evaluate if this switch can induce higher IL-2 secretion and thus induce cell proliferation.

The ubiquitously used transcriptional activator, VP64 consists of four tandem repeats of the herpes simplex virus early transcriptional activator VP16. Fusing two tandem repeats on TIMs into synZiFTRs produced even stronger transcriptional outputs than VP64. There was no leakage penalty for the GZV switch.

Example 4: Constructing the synZiFTR Based Two-Input AND Logic Gate

Described herein is the expansion of the synZiFTR toolkit towards developing a two-input AND logic gate.

The synZiFTRs is a synthetic toolbox of standardized components that can be integrated into gene circuit designs of further complexity. Two-input AND-gates are useful for immune cell engineering because they offer a more nuanced and precise means of controlling cellular behavior. The safety of immune cell engineering can be substantially elevated with the use of two-input AND-gates. The engineered cell would only activate when both the inputs are present, allowing for more controlled manipulation of the engineered cells and reducing the risk of unintended side effects. In this example, components for AND-Gate circuits were developed and characterize using synZiFTR2.0s via cooperativity and split transcription factors. The viability of using these to develop components in constructing AND-Gate circuits was also evaluated.

4.1 Introduction 4.1.1 Cooperativity in Eukaryotic Transcription

In eukaryotic transcription, cooperativity refers to the phenomenon where the binding of one transcription factor to a specific DNA sequence increases the likelihood of additional transcription factors binding to nearby sequences. Based on studies of bacterial gene regulation, cooperativity of TF binding can increase the nonlinearity of gene expression. Nonlinear (or switch-like) regulation of transcription allows a gene to switch decisively "on" in an all-or-none manner, at a precise and narrow concentration range of its inducer. Switch-like gene regulation is involved in many biological processes, including in developmental contexts. Cooperativity in eukaryotic transcription regulation can occur through recruitment of coactivators by transcription factors. Coactivators do not bind to DNA directly but help enhance the transcriptional activity. In addition to configurational cooperativity, cells make use of allosteric cooperativity. During transcription, allosteric cooperativity would stabilize a modified conformation of a transcriptional regulator or DNA after a binding event, therefore altering binding of additional molecules. Both types may be involved in the formation of large multisubunit transcriptional complexes that involve interactions between the DNA and its structural components, the general transcriptional machinery, and coactivator or co-repressor molecules. One example of this observation is the interferon-β enhanceosome formation in response to viral infection. In this structure, cooperativity transforms weak interactions between individual molecules into a tight and functional assembly to regulate gene expression.

In synthetic biology, cooperativity can be harnessed to create gene circuits with sharp switch-like responses or to amplify the response to a particular signal. This is achieved by designing synthetic transcription factors that can bind to each other and to the DNA, creating a cooperative binding effect.

One demonstration of synthetic cooperative response is by Bashor et al. Science 364, 593-597 (2019); see e.g., U.S. Pat. No. 11,781,149 B2; the contents of each of which are incorporated herein by reference in their entireties. They used a scaffold of covalently linked protein domains (called PDZ domains) that bind to a PDZ domain-interacting ligand fused to a particular synthetic transcription factor (synTF) to imbue transcriptional synergy to the circuit. In the presence of the PDZ scaffold, binding of a single synTF-PDZ ligand fusion to DNA increases the probability that another synTF-PDZ ligand fusion will bind to an adjacent DNA binding motif, forming a complex of synthetic transcriptional activators. The formation of this cooperative assembly is highly tunable. By varying the number of DNA binding motifs in the promoter and the number of PDZ domains, as well as the affinity of the PDZ ligand and the affinity of the DNA binding domain, they demonstrated programmable dose responses with customizable shape and sharpness characteristics. This scaffold-mediated cooperative complex assembly provides a framework for an AND-gate construction.

4.1.2 Split Transcription Factors

Split transcription factors are the transcription factor proteins divided into two separate parts, each of which is unable to bind to the DNA and initiate transcription on its own. These two parts can be engineered so that they only express and assemble to form the functional transcription factor in the presence of designated signals.

Split TFs using small molecules have been used to study the transcriptional activation kinetics in yeast, flies, and mammals. In the CRISPR-Cas9 system, the use of enzymatically dead Cas9 (dCas9) with small molecules induced dimerization have allowed for combinatorial and ordered recruitment of activators and repressor to regulate gene expression. Furthermore, split transcription factors based on ZFs and tetracycline repressor (TetR) variants have been used to build transcriptional AND-gates in mammalian cells as a proof of concept.

4.2 Results 4.2.1 Screening of Heterodimers for synZiFTR2.0s Cooperativity and Split synZiFTR2.0s Both the development of cooperative synZiFTR2.0 assemblies and split synZiFTR2.0s include a heterotypic protein-protein interaction pair. 2 mutually orthogonal de novo designed protein heterodimers (DHDs, hereafter referred to by numbers, e.g., 1 and 1' form one cognate pair) with hydrogen bond network-mediated specificity (Programmable design of orthogonal protein heterodimers) were obtained. To evaluate if each DHD can interact in a mammalian cell context, a mammalian two-hybrid assay (M2H) was conducted with monomers from either heterodimer fused to the ZF10 DBD and p65 TAD.

Figure 3A:
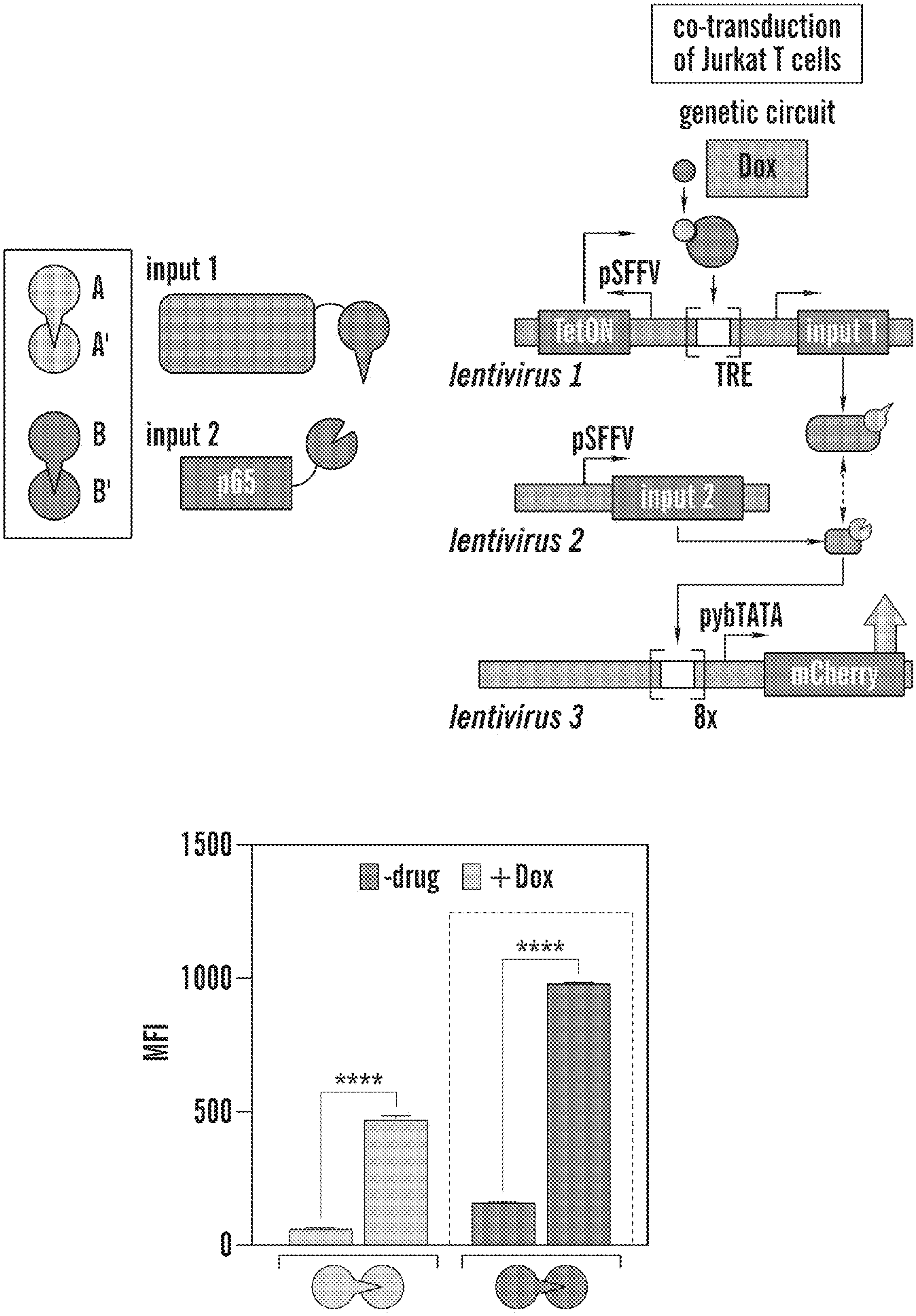
FIG. 3A-3D. Expansion of the synZiFTR toolkit for two-input AND gate.
Figure 3B:
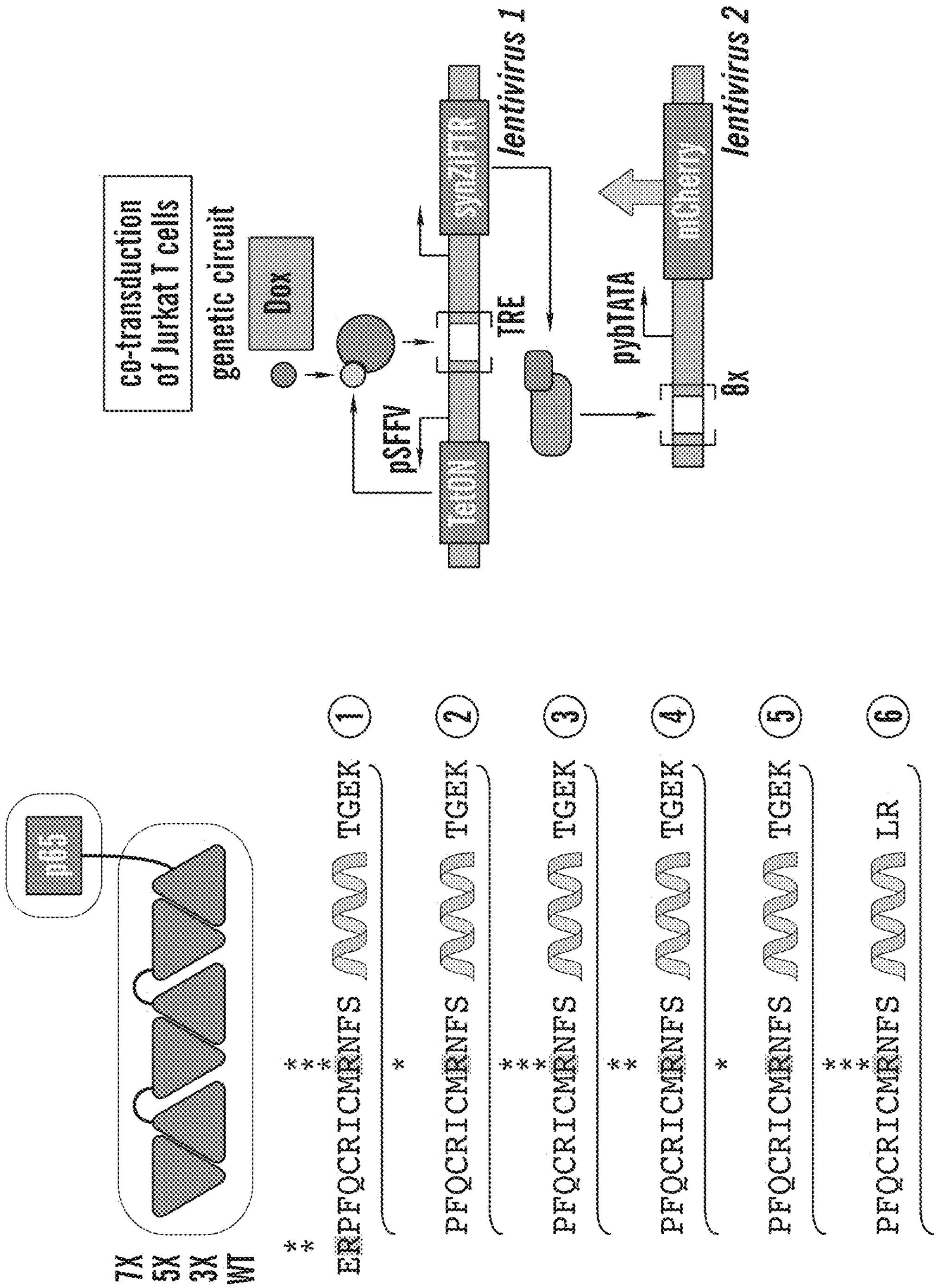
Figure 3B:
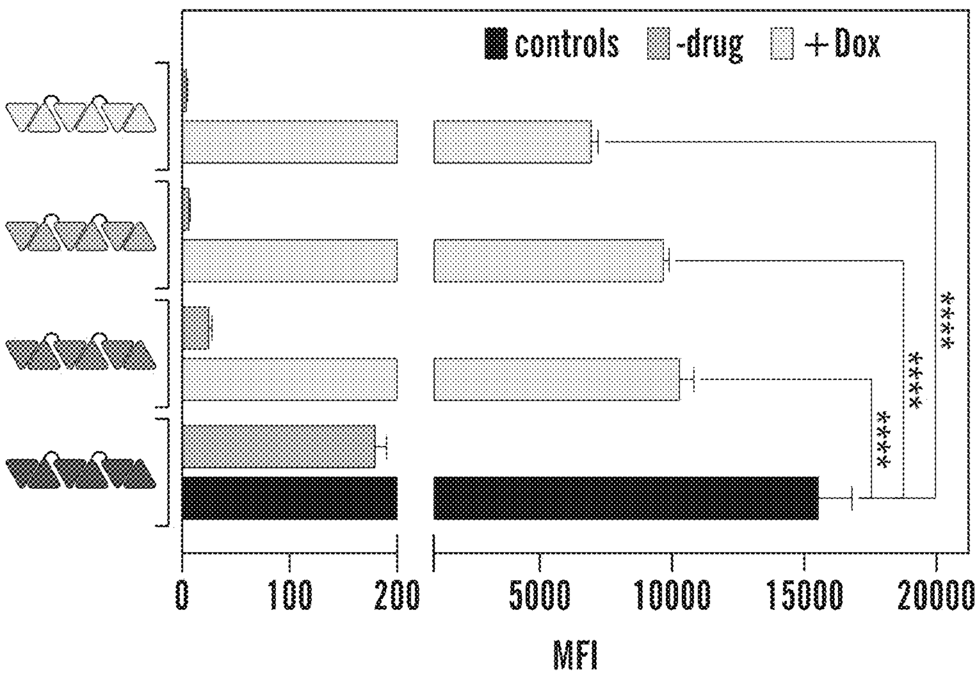
Figure 3C:
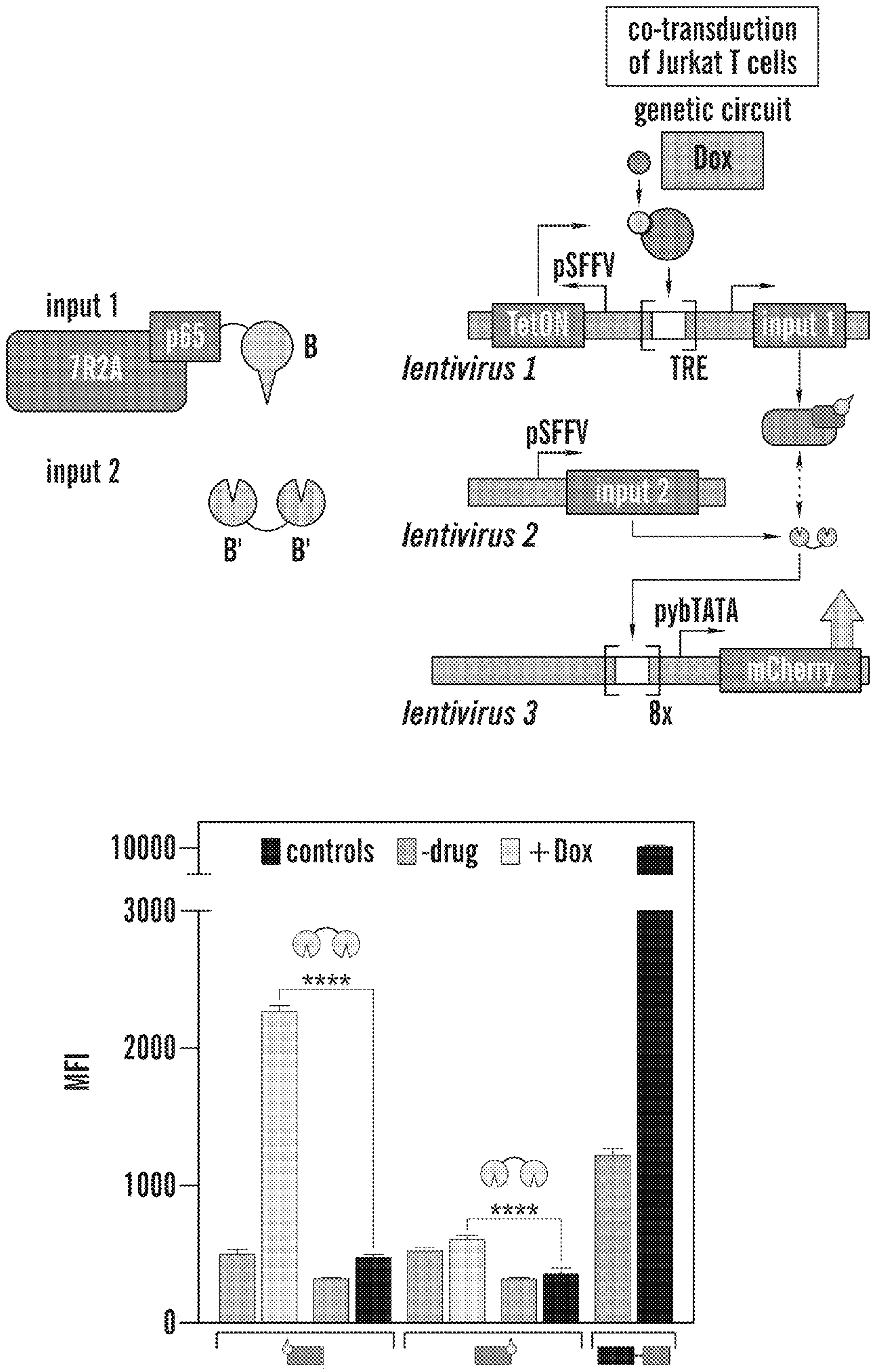
Figure 3D:
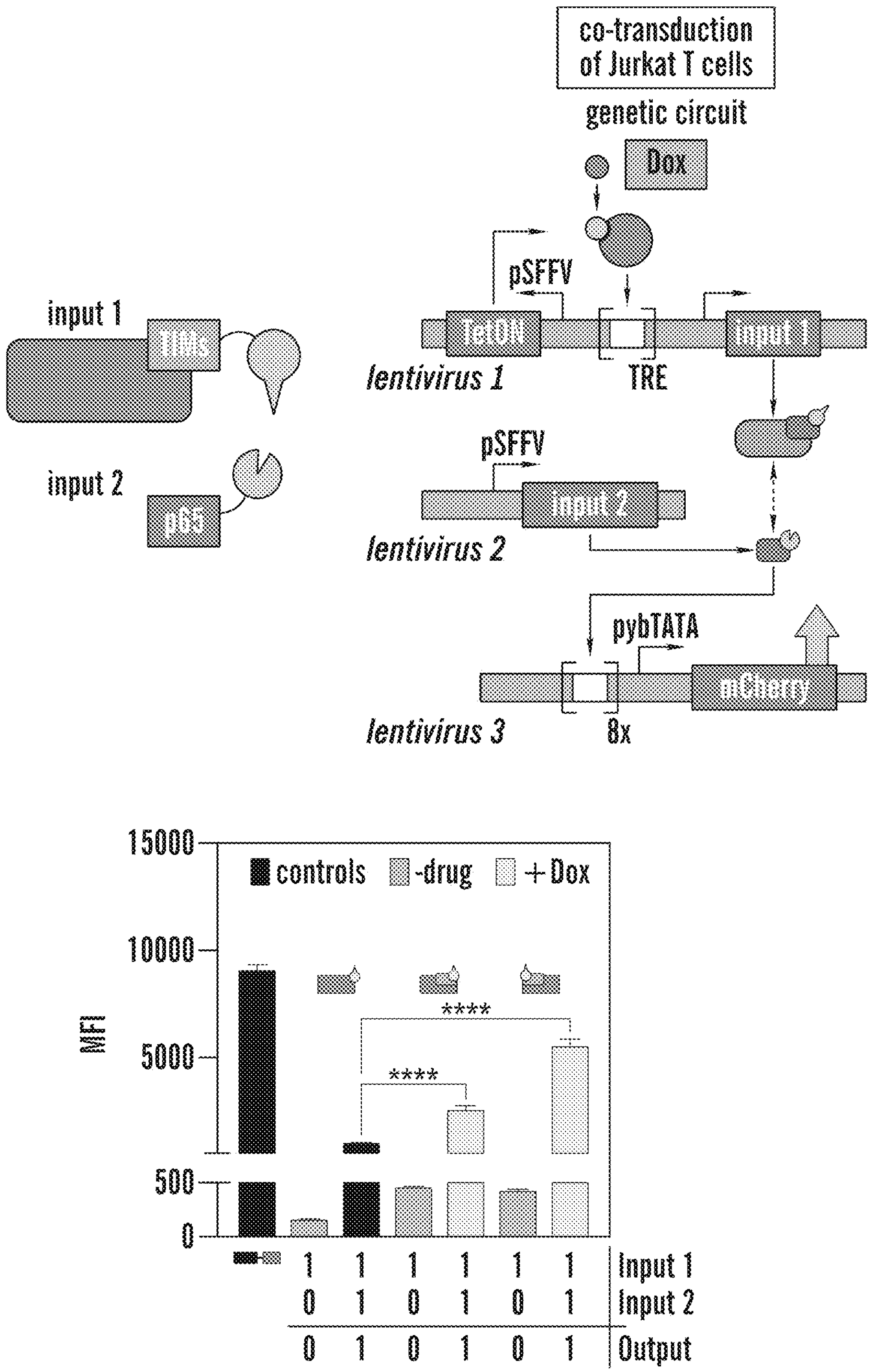

Coexpression of the heterodimer fusions as separate polypeptide chains increased signal significantly over background albeit with different levels of output (see e.g., FIG. 3A). The [B B'] pair demonstrated the strongest mCherry signal and was chosen for further testing.

4.2.2 Characterizing Transcription Output of ZF10 Affinity Variants Using the Minimal synZiFTR Khalil et al. Cell 150, 647-658, 2012, demonstrated that mutating key arginine residues on residues outside of the DNA recognition helices on zinc finger arrays can lower ZF binding affinity to its cognate DNA binding site. Based on structural studies, these arginine residues mediate nonspecific interactions array with the DNA phosphate backbone partly through their positive charge. They increased the amount of arginine to alanine mutations of these residues in a three ZF array and observed a stepwise decrease in DNA-binding activity. This is reflected in their capability to drive transcriptional activity where transcriptional output in yeast could be analogously tuned down as the number of mutations was increased from zero to three. Effectively, creating weaker-activating transcription factor variants from the lower-affinity variants.

It was hypothesized that this method of downregulating transcriptional output could be applied to the humanized six finger-array ZF DBD. A stepwise decrease in transcriptional output was similarly observed in Jurkat T cells in the synthetic eukaryotic system as number of mutations was increased from zero to seven (see e.g., FIG. 3B).

4.2.3 Validating Cooperativity in Jurkat T Cells

Bashor et al. 2019, supra, demonstrated that a scaffold mediated-cooperative assembly is a robust and flexible strategy for engineering nonlinear circuit behavior. A two input-AND logic gate includes an all-or-none circuit output when both inputs are present. Thus, cooperative assembly can be incorporated to create an AND logic gate. The cooperative assembly design that exhibited the most switch-like (high Hill coefficient, $n_H$) behavior were high-valency configurations (scaffold with more covalently linked monomers from a heterodimer, $n_c$) with low transcription factor binding affinity. The goal of the final design is to govern the expression of both synZiFTR2.0 engineered to interact with the scaffold and the scaffold protein by two separate inputs.

One signifier of scaffold-mediated cooperativity assembly is the observation of increased transcription output in the presence of the scaffold protein in the circuit. To test whether the synZiFTR-scaffold-DBM module can support cooperative assembly in Jurkat T cells, a transcriptional circuit was constructed in which a $n_c$=2 synZiFTR(7R2A) assembly drives the mCherry reporter, with synZiFTR(7R2A) levels controlled via the Dox-inducible expression systems while the scaffold is constitutively expressed via the pSFFV promoter. Here, the synZiFTR-scaffold protein-protein interaction is mediated by the B B' heterodimer. The B monomer is fused to the ZF10 minimal synZiFTR whereas the B' monomer is covalently linked to generate the scaffold. The presence of a two-B' scaffold increased mCherry output compared to the circuit where a non-interacting $n_c$=2 scaffold is coexpressed (see e.g., FIG. 3C). This demonstrates that synZiFTR-scaffold-DBM can serve as a framework to build an AND logic gate.

4.2.4 Characterizing Split synZiFTR2.0 Using the Minimal synZiFTR2.0

The split TF design where the DBD and TAD are separated is a straightforward method to build AND logic gates. However, recapitulation of the single molecule TF upon assembly at the reporter site often does not induce an equivalent transcriptional output (see e.g., FIG. 3D). As the transcriptional output driven by synZiFTR2.0 was significantly stronger than synZiFTR, further tests asked whether split synZiFTR2.0 is viable as a strategy to build AND logic gates. The minimal synZiFTR2.0 was split into ZF-TIMs and p65, where B is fused to either the N- or C-terminal of ZF-TIMs, and B' was fused to the N-terminal of p65.

To test whether split synZiFTR2.0 can drive gene expression in Jurkat T cells, a transcriptional circuit was constructed in which reconstitution of the synZiFTR2.0 drives the mCherry reporter, with ZF-TIMs-B/B-ZF-TIMs levels controlled via the Dox-inducible expression systems while the B' only (negative control)/B'-p65 is constitutively expressed via the pSFFV promoter. Split minimal synZiFTR2.0 indeed drove higher compared to split minimal synZiFTR.

4.3 Conclusion

Described herein is a set of standardized components for the synZiFTR toolkit. These components can be used to build more complex circuits, particularly the AND logic gate described here. While the B B' heterodimer resulted in stronger transcriptional output in the M2H assay, the weaker A A' can be applied in circuits where weaker binding is required.

The ZF10 arginine to alanine variants represent another dimension in which transcriptional output could be downregulated. This provides the ability for further expansion of complex circuit architecture, such as the application of cooperativity.

Finally, by splitting synZiFTR2.0s it was demonstrated that they have the capacity as a strategy to build AND logic gates.

4.4 Discussion

The change in transcriptional output from the circuit consisting of a $n_c$=2 synZiFTR(7R2A) assembly demonstrated a starting point for engineering cooperativity in mammalian cells. From there onwards, further parameters can be tested to obtain an output that is sufficiently high and sharp in its dose response. The valency of the cooperative complex can be increased, e.g., up to $n_c$=4 synZiFTR (7R2A). Further optimization of the assembly can involve testing the cooperative assembly output using ZFs affinity variants, and protein-protein interactors of different binding strength e.g., the A A' heterodimer.

A cooperative transcriptional circuit can include TIMs to build cooperativity 2.0. This can be applied in at least two ways: (1) similar to synZiFTR2.0, TIMs can be fused to the synTF component with a weak DBD-DNA binding affinity, and (2) TIMs is fused to the scaffold.

As for the split synZiFTR2.0, strategies can improve its transcriptional circuit output. For the first strategy, a study showed recruitment of multiple VP64 using the dCas9-SunTag multimerization system to the CXCR4 loci exhibited a vast (10-50) fold change in CXCR4 gene expression compared to dCas9-VP64. Recruitment of two p65s on each ZF DBD instead of one can improve the efficacy of the split synZiFTR when reconstituted. To test this, two covalently linked B monomers are fused to obtain ZF-TIMs-(B-B)/(B-B)-ZF-TIMs.

Next, synZiFTR2.0 can be split into ZF and TIMs-p65. Similarly, ZF-B/B-ZF levels can be controlled via the Doxycycline-inducible expression systems while the A' only/A'-TIMs-p65 is constitutively expressed via the pSFFV promoter.

Finally, it has been shown that performance of transiently transfected synthetic circuits in mammalian cells could be affected due to limited cellular resources. As the pSFFV is one of the strongest promoters, transcriptional circuit outputs can be characterized for both cooperativity and split TF systems when using a weaker constitutive promoters.

Example 5: Mechanisms of TIMs-Mediated Enhanced Expression of synZiFTR2.0

Figure 4A:
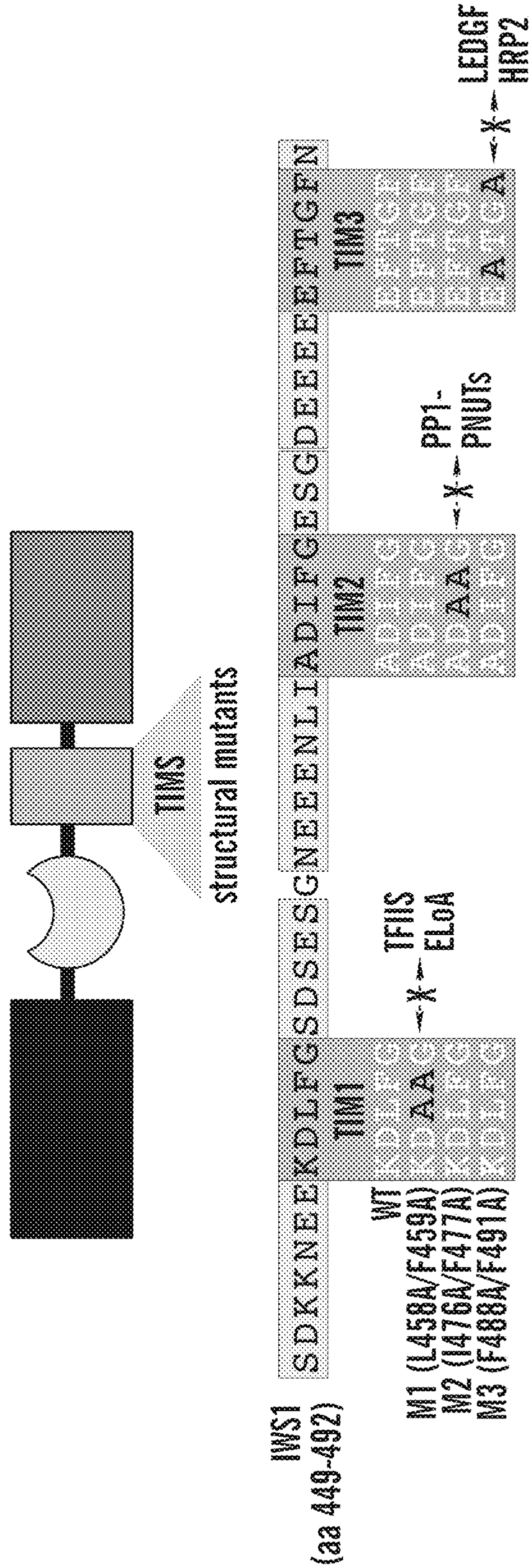
FIG. 4A-4B. IWS1 TIMs mechanism of action.
Figure 4B:
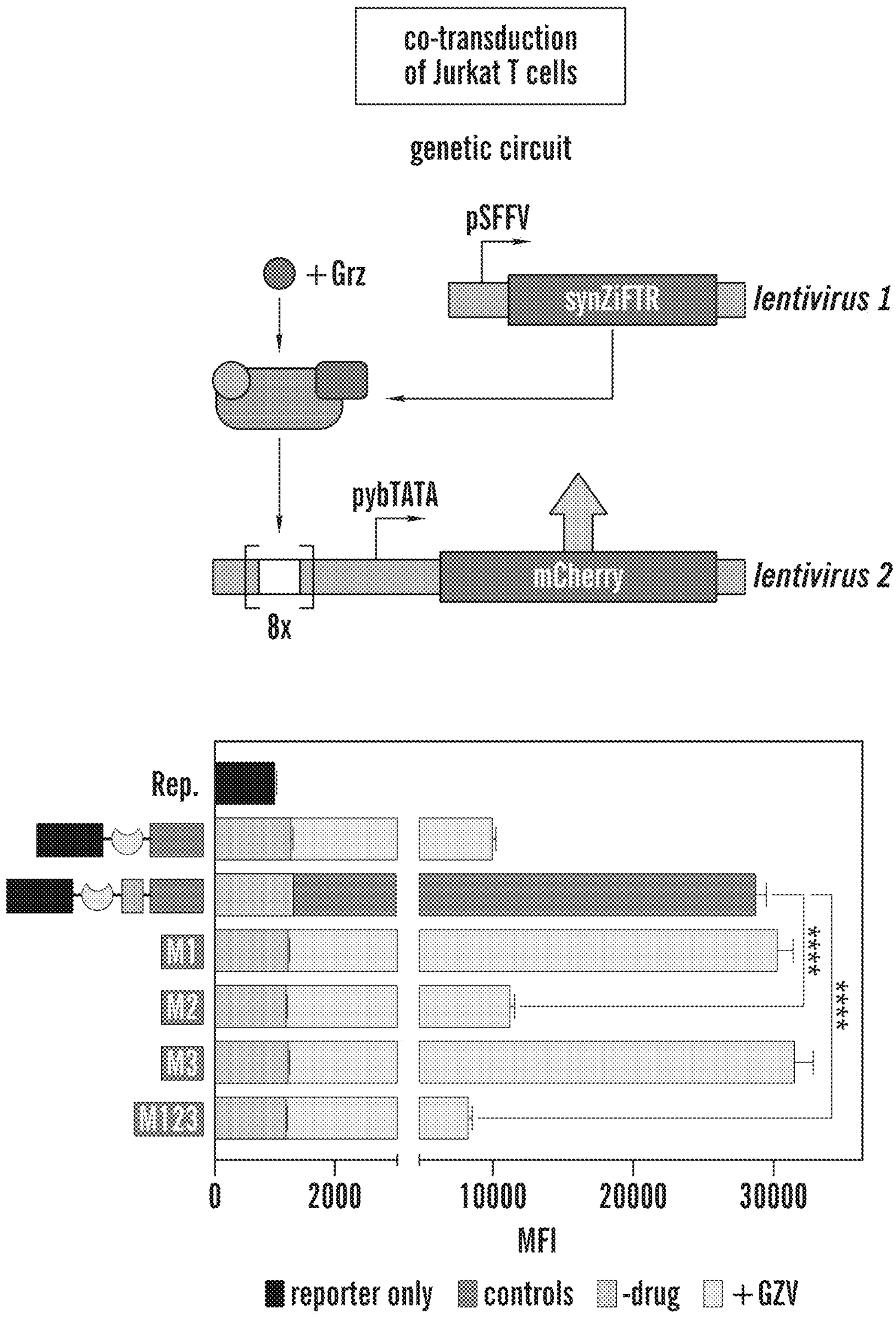

The TIMs domain contains a series of three unique TIMs that selectively interact with different TND-containing factors. TIM1 interacts with Transcription Factor IIS (TFIIS) and Elongin A (EloA), TIM2 is recognized by the PP1-PNUTS phosphatase, and finally the H3K36me3 readers, lens epithelium-derived growth factor (LEDGF), and H3K36me2/3 binding protein HDGFL2 (HRP2) bind to TIM3. Here, it was investigated which direct interactions between each TIMs and their protein partner is involved in the enhanced transcriptional output by synZiFTR2.0s. The involvement of each of these interactions was interrogated by introducing a structure-guided mutation of each individual TIM (M1, M2, M3) and for all three TIMs (M123) (see e.g., FIG. 4A). GZV-synZiFTR2.0 variant 1 was used as the synTF backbone for this study.

5.1 Introduction 5.1.1 TIM1 Interacting Protein(s)

TFIIS is a transcription factor that plays a role in resolving transcriptional arrest. During transcription, stalling of Pol II creates a roadblock. TFIIS helps restart the transcription process by binding to Pol II and inducing a conformational change that allows the enzyme to cleave the 3' end of the nascent RNA. This permits Pol II to resume transcription from the new 3' end, effectively resolving the transcriptional arrest. TFIIS stimulates transcription elongation by shortening the durations of transcriptional pauses, without affecting the pause-free velocity.

EloA is a component of the Elongin complex, including Elongin B and Elongin C. This complex increases the processivity of Pol II by suppressing transient pausing of Pol II during elongation. The Elongin complex suppresses Pol II pausing by DSIF. This suppression helps Pol II maintain a steady elongation rate during transcription. Separately, EloA forms phase-separated condensates in vitro. It associates broadly with actively transcribed genes but does not appear to affect RNAPII elongation significantly, indicating a role in fine-tuning transcription.

5.1.2 TIM2 Interacting Protein(s)

PP1-PNUTS complex could interact with the chromatin-associated enzyme CDC2 (cyclin-dependent kinase 1), which is involved in cell cycle progression and transcription regulation. This interaction indicates a role for the PP1-PNUTS complex in transcription elongation through its association with chromatin and transcription-related proteins. PP1-PNUTS complex is involved in the regulation of transcription elongation by interacting with the transcription elongation factor SPT5. This interaction could allow direct dephosphorylation of SPT5 which could affect the SPT5-Pol II interaction. In addition, there is evidence of direct Pol II regulation as knockdown of the PP1-PNUTS complex is correlated with Pol II CTD hyperphosphorylation.

5.1.3 TIM3 Interacting Protein(s)

LEDGF and HRP2 are chromatin readers that recognize H3K36me2/3 methylated histone tails. They share some functional redundancy. Both proteins influence RNAP2 transcription elongation by functioning as histone chaperones and directly interact with transcription regulators. They include the KMT2A histone methyltransferase, IWS1 or JPO2. Separately, LEDGF also directly interacts with MED1 and CDC7-ASK. HRP2 additionally interacts with DPF3a, a subunit of SWI/SNF chromatin remodeling complexes. They contribute towards pause release near the +1 nucleosome in part through their interaction with IWS1.

5.2 Results

Loss of function mutations at all 3 TIMs (TIM123) ablated the increase in transcription imbued by TIMs-p65 fusion. Indeed, the mCherry fluorescence output was equivalent to GZV-synZiFTR. M1 and M3 mutants did not affect GZV-synZiFTR2.0 output. The M2 mutant ablated the mCherry fluorescence output by TIMs-p65 fusion (see e.g., FIG. 4B). This indicates that PP1-Nuts phosphatase recruitment to the reporter loci is involved in the increase in transcriptional activity.

5.3 Conclusion

Cermakova et al., Science 374, 1113-1121, 2021 found a natively unstructured region of IWS1 facilitated the recruitment of transcription elongation factors. Each TIM in this region interacts with different factors in a binary manner. TIM2 is identified herein as the TIM that prescribed transcriptional synergy to the TIMs-p65 hybrid TAD.

5.4 Discussion

Based on Cermakova et al., 2021, the impact of the M2 mutant in ablating the transcriptional synergy indicates that PP1-PNUTS phosphatase plays a role in this observation. To ask whether PP1-PNUTS phosphatase recruitment is directly responsible for the increase in reporter activity, the transcriptional output GZV-synZiFTR2.0 can be compared in the presence or absence of the PP1-PNUTS phosphatase. siRNA can be used to knockdown PP1-PNUTS phosphatase, and mCherry levels are measured following GZV induction.

PP1-PNUTS phosphatase have been shown to dephosphorylate SPT5, and its knockdown is correlated with Pol II CTD hyperphosphorylation. Dephosphorylation of SPT5 has been shown to directly impact Pol II elongation. There are however several functional consequences that can arise due to the phosphorylation state of the Pol II CTD. Hyperphosphorylated Pol II is often referred to as Pol IIo (the "o" denotes the phosphorylated form), and it carries out productive transcription elongation. Pol IIo also recruits various proteins involved in transcription, mRNA processing, and chromatin remodeling. These interactions facilitate co-transcriptional processes such as capping, splicing, and polyadenylation of nascent transcripts. Finally, towards the end of the transcription process, the CTD is dephosphorylated, which is involved in proper transcription termination and Pol II recycling. The PP1-PNUTS phosphatase could fine tune these processes via regulating elongation speed affected by splicing delays, or speeding up Pol II turnover by accelerating Pol II's termination. These mechanisms can be elucidated using precision nuclear run-on sequencing (PRO-seq) to measure pause-release dynamics, and Chromatin Immunoprecipitation Sequencing (ChIP-Seq) to measure Pol II occupancy on the synthetic reporter loci.

Example 6

The objective of this work is to enhance the synZiFTR toolkit, which is useful due to its compact, humanized design, with proven capability in regulating therapeutic payloads. Leveraging the small molecules GZV and 4OHT, which are FDA approved and recognized for their safety as drugs, the synZiFTR2.0 toolkit was designed to improve circuit output and complexity without compromising basal activity.

Eukaryotic transcription processes led to the identification of IWS1 TIMs as a region that offers maximal transcriptional synergy when fused to p65, giving rise to synZiFTR2.0. These results show that both GZV- and 4OHT-synZiFTR2.0 deliver a marked increase in transcriptional circuit output compared to their predecessors. Interestingly, the addition of another TIMs (2 versus 1) further amplifies this output. the viability of synZiFTR2.0 can be investigated across various cell types.

In addition, this study expanded the synZiFTR toolkit through the creation of standardized components, including in the process of developing a two-input AND logic gate. Both cooperativity and split synZiFTR2.0 were demonstrated as frameworks for this task.

The studies herein also provided insights into the mechanisms of transcription. While previous work focused on multimerizing homo- and heterotypic transcriptional activators in the formation of hybrid TADs, this research indicates that transcription elongation factors present another resource. For designing transcription repressors, factors that promote elongation pausing can be explored.

While the current model is minimalistic, lacking splicing and other elements found in an endogenous environment, it offers a starting point for dissecting the complex transcriptional components, modules, and circuitry that underpin eukaryotic cell development and function. These findings suggest that a protein that suppresses elongation activity might unexpectedly aid in activation, due to its effect in transcription kinetics and unknown protein interactions.

Taken together, this work contributes to the improvement of synthetic circuit components to be applied to therapeutic contexts, whilst also shedding light on mechanisms of transcription.

6.1 Discussion

The field of synthetic biology has witnessed advancements with the development of synthetic transcription factors, particularly the synZiFTRs. This work focused on enhancing these components by fusing the TIMs domain to p65, and expansion of the synZiFTR toolkit, yielding synZiFTR2.0. The screen also identified other transcriptional activation domains (TADs) that demonstrated transcriptional synergy with p65.

This observation presents an opportunity for further embodiments, by combining these TADs in various permutations to create additional TADs. One goal would be to engineer a hybrid TAD, smaller than p65 but maintaining the same transcriptional output. The reduced size of such hybrid TADs could minimize the genetic footprint during therapeutic delivery, thereby improving integration into the genome and ensuring greater efficiency in induction. This is of particular utility given the size constraints imposed by most viral vectors used in gene delivery. This approach could permit the inducible expression of longer therapeutic payloads, as exemplified by the NFZ domain, which combined domains from NCOA3, FOXO3, and ZNF473 to create a construct significantly smaller than the VPR.

In the context of synthetic transcription circuits, synZiFTR2.0 has shown effective results. Another goal is to examine whether the TIMs-p65 hybrid TAD can also be effective in regulating endogenous gene expression. A comparison with the leading TADs on dCas9-activators provides a robust testing platform for this purpose.

The synZiFTR circuits assessed in this study necessitated dual lentivectors, carrying the synTF(s) and the reporter separately. Combining these elements into a single vector can improve the consistency of therapeutic delivery. Without wishing to be bound by theory, it is contemplated herein that synZiFTR2.0 can be utilized in a single vector system, owing to its improved circuit output.

A two-input AND gate can also be tested to confirm the compatibility of the inputs with sensor units, for instance, integrating both inputs with the small molecule sensors. Moreover, environmental sensors could be utilized to transcriptionally regulate the inputs, thereby permitting circuit activation through various modalities (e.g., cell state, and small molecules)

Finally, the intrinsic disorder in the TIMs domain, which has the potential to form condensates, can be considered. Models indicate that these condensates play a role in transcriptional regulation by maintaining the separation between initiation and elongation compartments. In addition to the direct interaction with PP1-PNUTS phosphatase and other transcription elongation factors, this indicates yet another layer of control that can be used.

The formation and dynamics of condensates play a role in transcription regulation, providing an effective mechanism through which cells can rapidly alter their gene-expression program. These largely unstructured entities rapidly form highly organized, functional transcription complexes on DNA, referred to as promoter condensates, or on nascent RNA, termed gene-body condensates. The reactions within these structured complexes drive Pol II shuttling between condensates, further illustrating the dynamic nature of this process. These condensate dynamics can be modulated by post-translational modifications such as phosphorylation, methylation, acetylation, or ubiquitination, thus altering the phase-separation properties of their substrate proteins. Furthermore, the sharing of condensates by multiple active genes provides an explanation for how a single enhancer can activate multiple target genes.

Promoter condensates, comprised of transcription factors, co-factors, unphosphorylated Pol II enzymes, and initiation factors, play a role in supporting PIC assembly, transcription initiation, RNA synthesis, and Pol II phosphorylation. These factors drive the formation of a dynamic promoter condensate, which subsequently gives rise to gene-body condensates. The short-lived, dynamic nature of promoter condensates can be attributed to nuclear self-organization, contingent upon transcription factor concentrations. This provides insights into how different transcription factors recruit the same general Pol II machinery to promoters, considering the capacity of promoter condensates to grow, shrink, and reform at alternative sites in the nucleus.

Conversely, gene-body condensates encompass phosphorylated Pol II enzymes, nascent RNA, elongation factors, RNA processing factors, and elongation-specific co-activators. They play a role in RNA elongation and processing within chromatin, supporting elongation and co-transcriptional RNA processing. As the polymerase reaches the gene end, polymerase dephosphorylation liberates Pol II from the gene-body condensate. Subsequently, the CTD may be transferred back to the promoter condensate, allowing for Pol II recycling upon transcription termination. Unlike promoter condensates, gene-body condensates are transient structures formed by transcribing polymerases and serve as downstream consequences of promoter activity.

The intrinsic dynamics and intricate interplay between promoter and gene-body condensates present a useful aspect of transcription regulation. The role of condensates, particularly in relation to TFs and the pol II CTD, has been investigated. Evidence indicates that TFs undergoing phase separation can recruit the intrinsically disordered CTD of Pol II, which is capable of phase separation under the influence of a crowding agent. This provides a model where CTD acts as a client of promoter condensates, facilitating the recruitment of Pol II to active genes. Furthermore, the CTD is also considered as a client for gene-body condensates, which are distinguishable from promoter condensates. The phosphorylation of the CTD by CDK7 counters the self-association and phase separation of the CTD. In turn, the phosphorylated CTD gets incorporated into phase-separated droplets formed by the disordered region in P-TEFb. Given that PP1-PNUTS phosphatase can remove phosphate groups from the Pol II CTD, there several areas to investigate. Without wishing to be bound by theory, it is contemplated herein that PP1-PNUTS can mediate Pol II's shuttling between different condensates. Studies can be performed to determine how such shuttling affects transcription kinetics or changes the dynamics between the two condensates.

Example 7

(1) Dual Lentiviral Vectors: GZV-Inducible Systems in Jurkat Cells

Figure 8A:
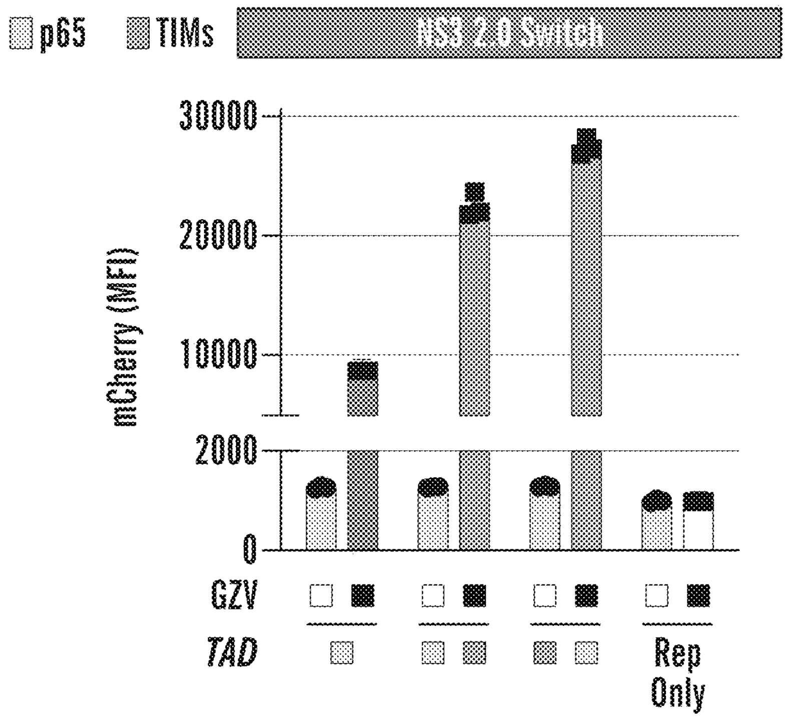
FIG. 8A-8B shows testing of dual lentiviral vectors for GZV inducible systems driving mCherry reporter in Jurkat cells (benchmarked against VPR and minVPR).
Figure 8B:
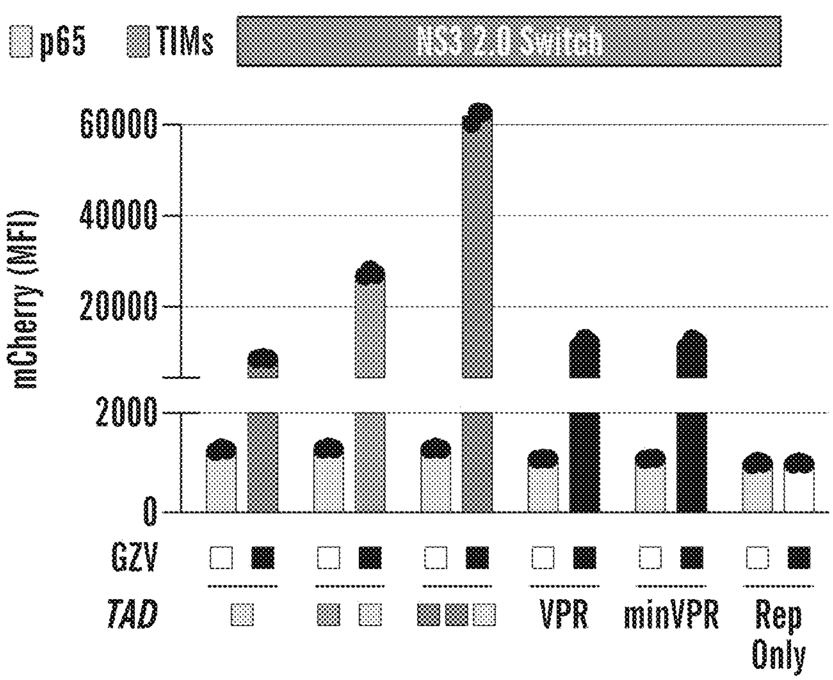

Jurkat cells were co-transduced with different TIMs-incorporated synZiFTR variants and a minimally expressed mCherry reporter. Upon addition of GZV, synZiFTR constructs activated mCherry, expression which was measured on a flow cytometer (see e.g., FIG. 8A-8B).

(2) Dual Lentiviral Vectors: 4OHT-inducible systems in Jurkat cells

Figure 9A:
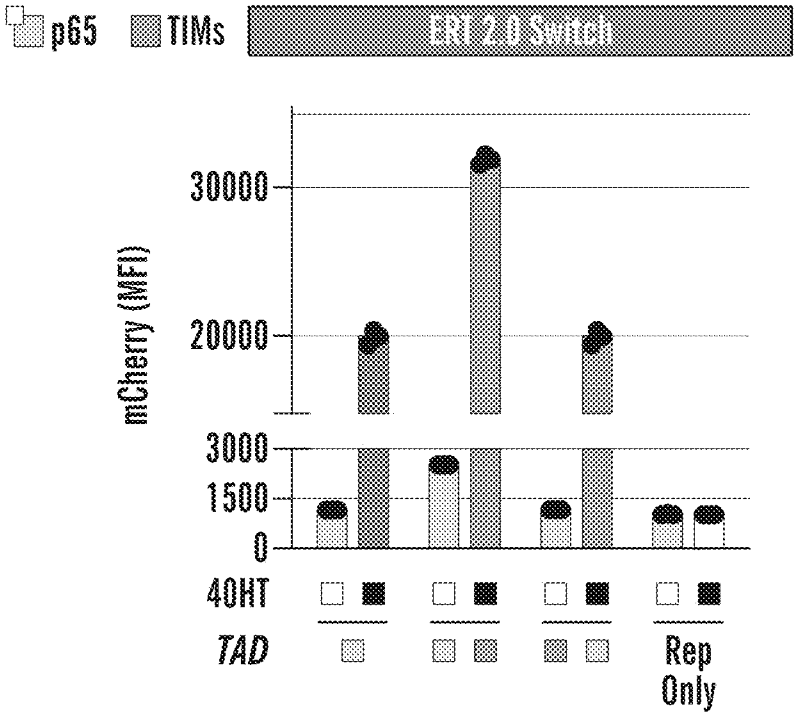
FIG. 9A-9B shows testing of dual lentiviral vectors for 4OHT inducible systems driving mCherry reporter in Jurkat cells (benchmarked against VPR and minVPR).
Figure 9B:
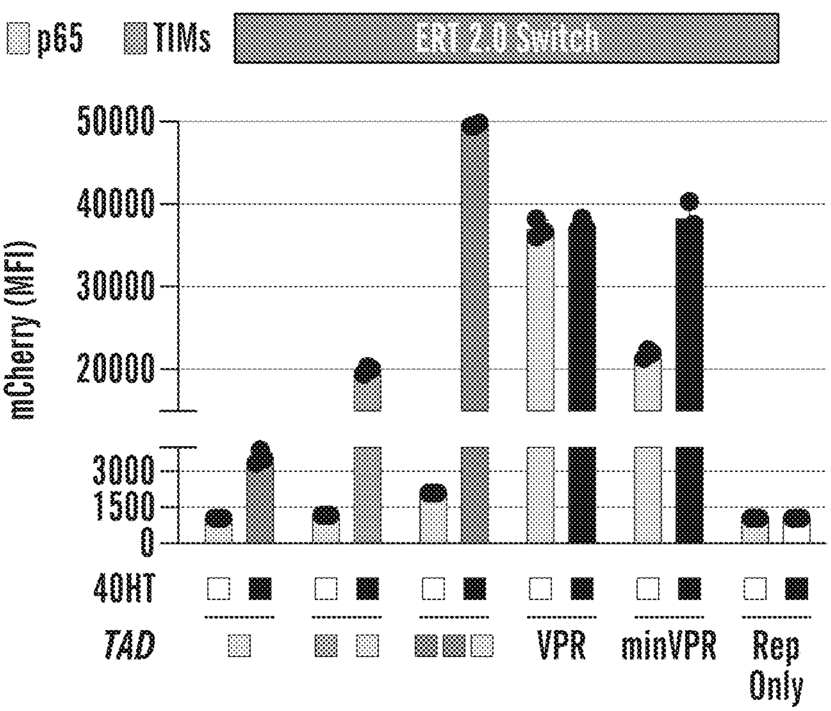

Jurkat cells were co-transduced with different TIMs-incorporated synZiFTR variants and a minimally expressed mCherry reporter. Upon addition of 4OHT, synZiFTR constructs activated mCherry expression, which was measured on a flow cytometer (see e.g., FIG. 9A-9B).

(3) Dual Lentiviral Vectors: GZV-inducible systems in primary T cells

Figure 10:
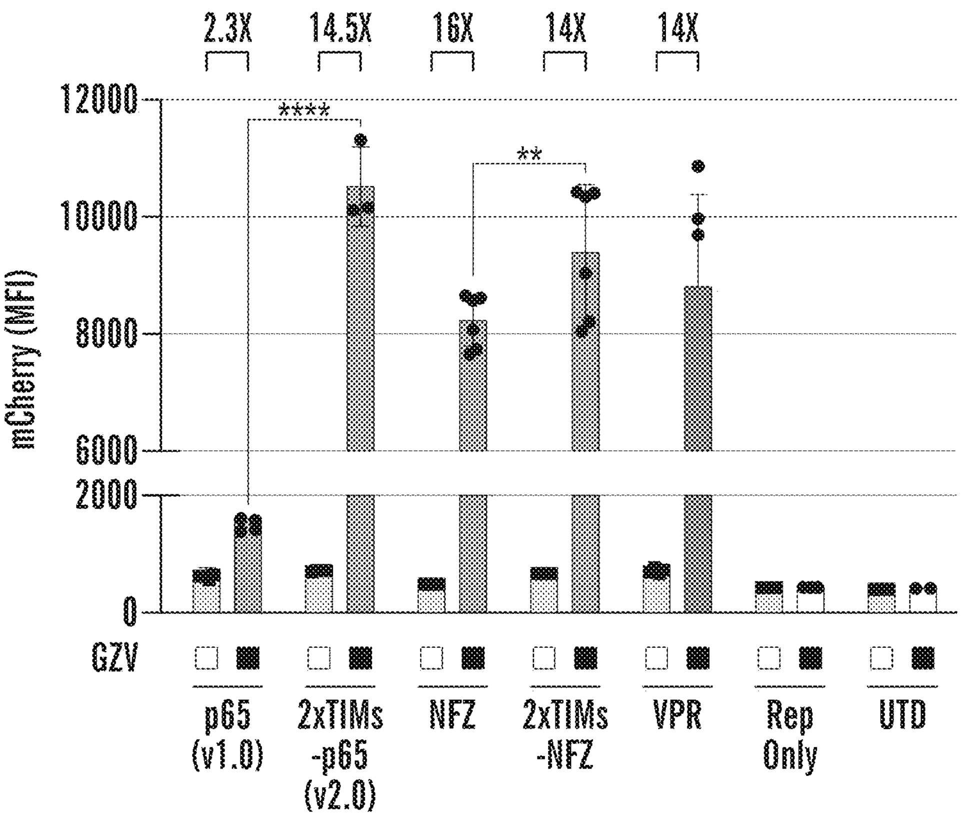
FIG. 10 shows testing of dual lentiviral vectors for GZV inducible systems driving mCherry reporter in Primary T cells (benchmarked against VPR). synZiFTR 2.0 drove a high output level compared to the VPR domain. In addition, fusing TIMs domains on the N terminus also enhanced activation potency of the NFZ transcriptional activator.

Primary T cells were co-transduced with synZiFTR 2.0 and a minimally expressed mCherry reporter. Upon addition of GZV, the synZiFTR construct activated mCherry expression, which was measured on a flow cytometer (see e.g., FIG. 10).

(4) Dual Lentiviral Vectors: 4OHT-inducible systems in primary T cells

Figure 11:
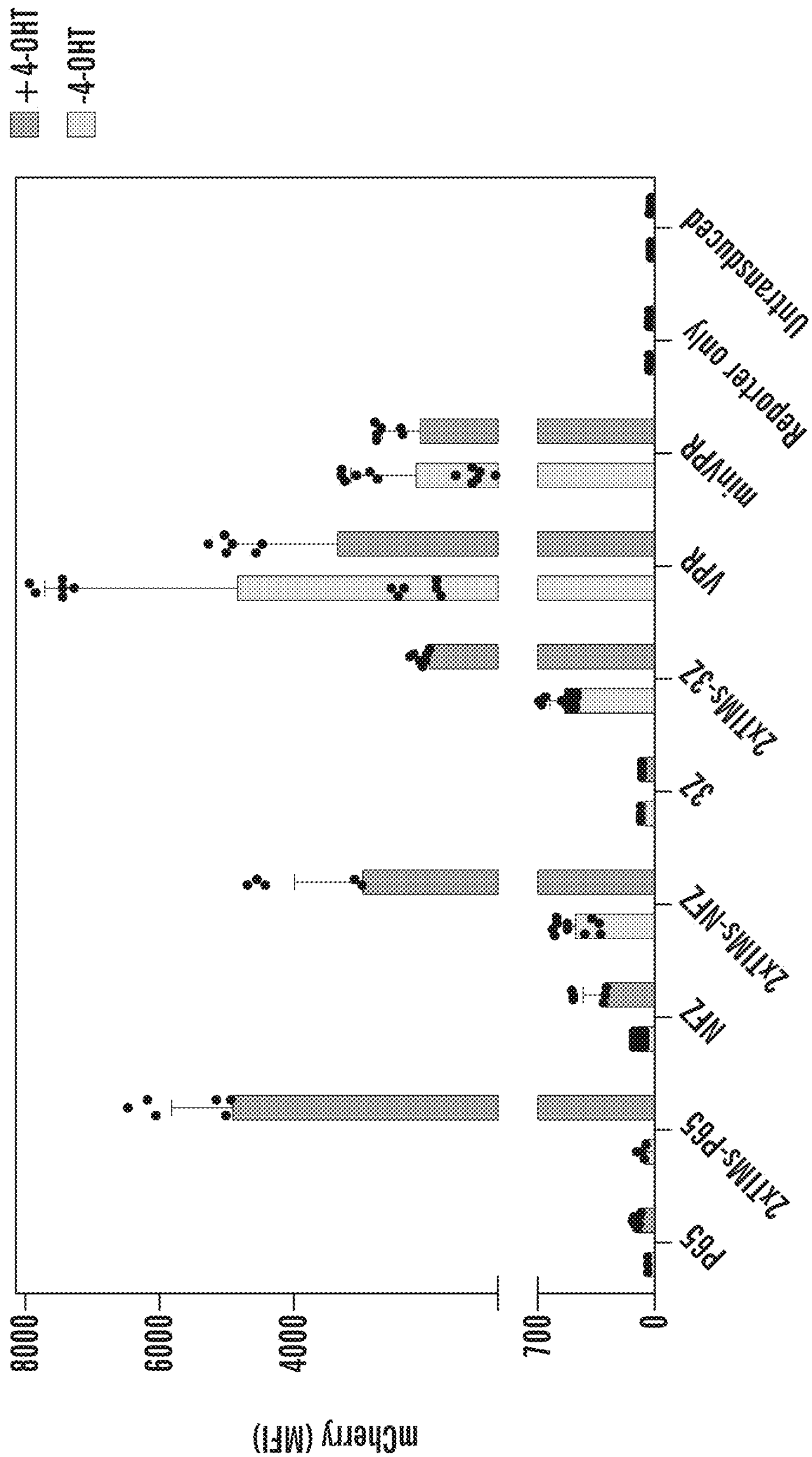
FIG. 11 shows testing of dual lentiviral vectors for 4OHT inducible systems driving mCherry reporter in Primary T cells (benchmarked against VPR and minVPR).

Primary T cells were co-transduced with synZiFTR 2.0 and a minimally expressed mCherry reporter. Upon addition of 4OHT, the synZiFTR construct activated mCherry, expression which was measured on a flow cytometer (72 hr). synZiFTR 2.0 drove high reporter expression comparable to VPR and minVPR domains. synZiFTR 2.0 exhibited less expression of the reporter when no 4OHT is added (less leak) compared to constructs with VPR and minVPR domains. In addition, fusing TIMs domains on the N terminus also enhanced activation potency of NFZ and 3Z transcriptional activators (see e.g., FIG. 11).

(5) Single Lentiviral Vectors: 4OHT-Inducible Systems in HEK Cells

HEK293T cells were transduced with a single lentiviral vector containing the synZiFTR 2.0 architecture and a minimally expressed mCherry reporter. Two types of promoters, SFFV and CMV, were used to drive synZiFTR 2.0 expression, and an iRFP reporter was used to gate cells transduced with the construct. Upon addition of 4OHT, the synZiFTR construct activated mCherry expression which was measured on a flow cytometer (96 hr). This data demonstrates that the addition of the TIM domains in the synZiFTR 2.0 architecture resulted in higher reporter expression than the p65 domain alone. While both the CMV and SFFV promoters resulted in similar reporter expression, the constructs with the CMV promoter exhibited less expression of the reporter when no 4OHT is added (less leak) compared to constructs with the SFFV promoter (see e.g., FIG. 12).

Figure 13:
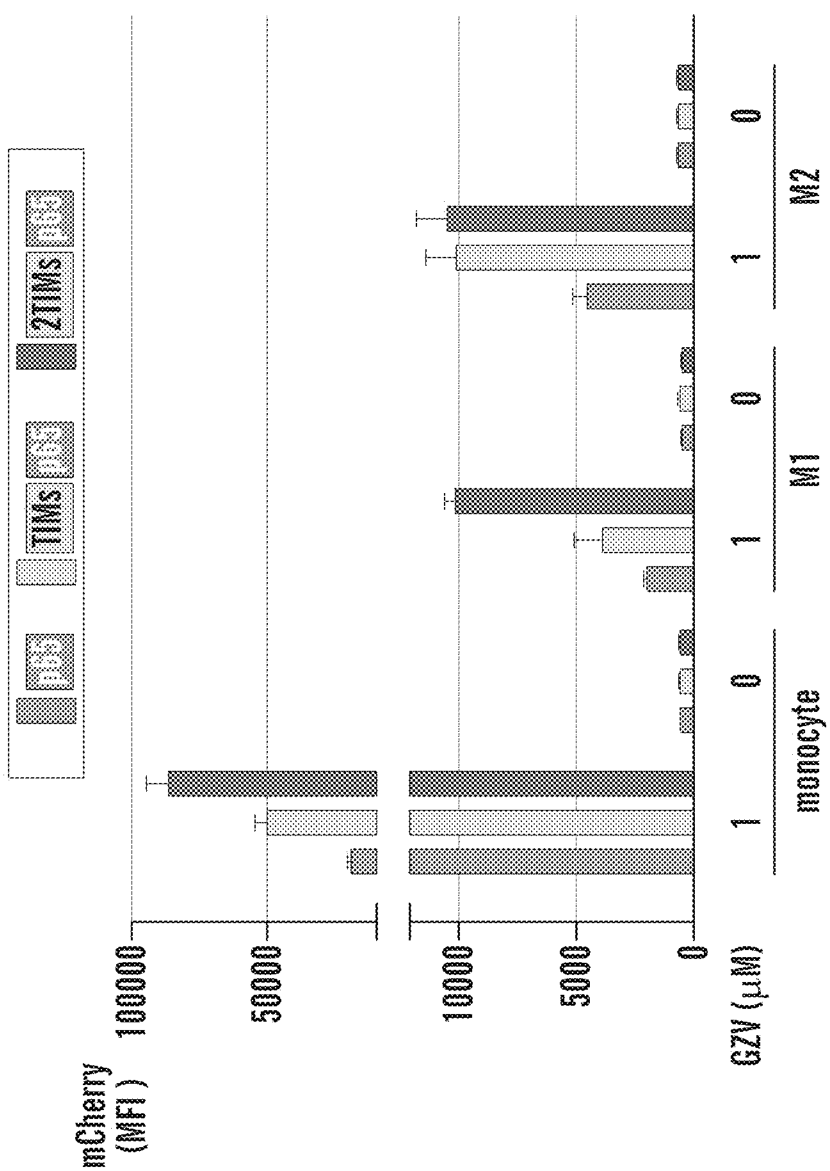
FIG. 13 shows testing of dual lentiviral vectors for GZV inducible systems driving mCherry reporter in THP1 monocytes/macrophages.

(6) Dual Lentiviral Vectors: GZV-Inducible Systems in THP1 Monocytes and Macrophages THP1 monocytes were co-transduced with synZiFTR 2.0 and a minimally expressed mCherry reporter. Upon addition of GZV, the synZiFTR construct activated mCherry expression, which was measured on a flow cytometer. Fusing two copies of TIMs on N terminus of p65 drove higher output than fusing a single copy of TIMs at the same loci. The increased output was observed in monocytes, IFN gamma-induced M1 macrophages, and IL10-induced M2 macrophages (see e.g., FIG. 13).

Figure 14:
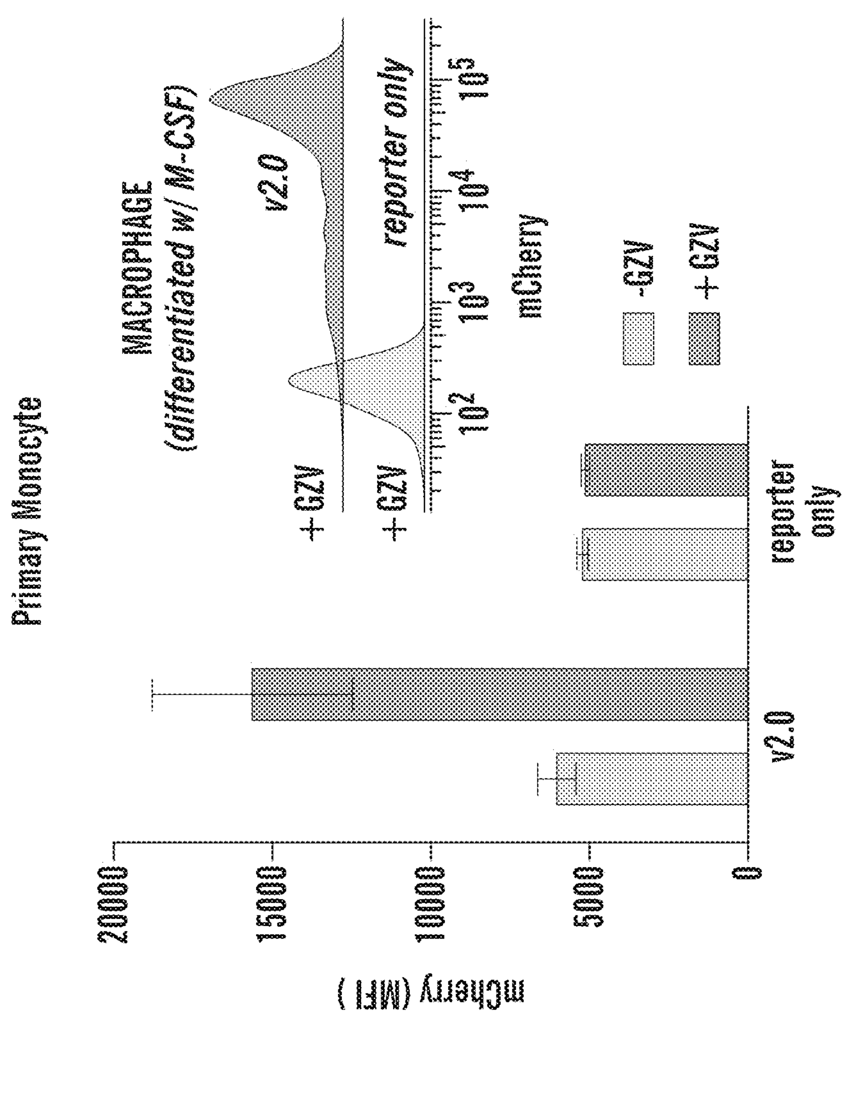
FIG. 14 shows testing of dual lentiviral vectors for GZV inducible systems driving mCherry reporter in Primary monocytes/macrophages.

(7) Dual Lentiviral Vectors: GZV-Inducible Systems in Primary Monocytes and Macrophages Primary monocytes were co-transduced with synZiFTR 2.0 and a minimally expressed mCherry reporter. Upon addition of GZV, the synZiFTR construct activated mCherry expression, which was measured on a flow cytometer. Primary monocytes were then differentiated to macrophages by M-CSF (see e.g., FIG. 14).

(8) Dual Lentiviral Vectors: GZV-Inducible Systems Driving GFP-STAT1 in THP1 Monocytes Primary monocytes were co-transduced with synZiFTR 2.0 and a minimally expressed GFP-STAT1 fusion. Upon addition of GZV, the synZiFTR construct activated GFP-STAT1, expression which was measured on a flow cytometer. GFP-STAT1 fusion is much larger in size (3.2 kb) than other tested constructs. While the synZiFTR and single TIMs-fused synZiFTR were unable to drive high expression level of this fusion protein, synZiFTR 2.0 significantly boosted the output level, showcasing its robust activation potency across diverse cell types and payloads (see e.g., FIG. 15).

(9) Single Lentiviral Vectors: GZV-Inducible Systems in THP1 Monocytes

THP1 monocytes were co-transduced with a single vector comprised of both synZiFTR 2.0 and a minimally expressed GFP-STAT fusion. Upon addition of GZV, the synZiFTR construct activated GFP-STAT expression, which was measured on a flow cytometer (see e.g., FIG. 16).

Example 8: VEGF synZiFTRs

Figure 17:
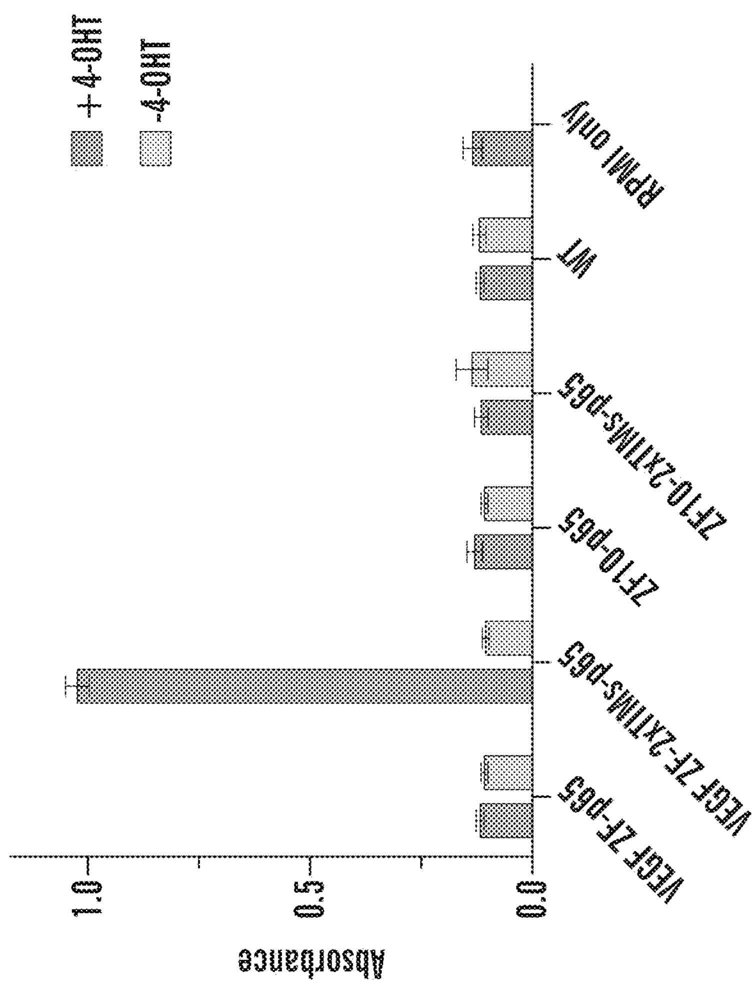
FIG. 17 shows testing of VEGF synTFs. The bar graph shows the 450 nm absorbance readout from the ELISA assay, indicating the relative level of VEGF. Only VEGF-targeting synZiFTR 2.0 successfully drove VEGF production upon addition of 4OHT, in a ZF dependent manner.

A zinc finger targeting the endogenous VEGF gene (VEGF ZF) replaced ZF10 in the ERT-synZiFTR (1.0 and 2.0) to generate VEGF synZiFTR. Jurkat cells were transduced with different synZiFTR constructs and treated with 4OHT or methanol for 72 h. The cumulative VEGF secreted in the supernatant was collected and quantified with an ELISA kit (see e.g., FIG. 17).

Example 9: Exemplary Sequences

SEQ ID NO: 15, hhTAD DNA, 714 nucleotides (nt)
TCAGACAAGAAAAACGAAGAAAAGGATTTGTTCGGAAGTGATTCC
GAGAGCGGGAACGAAGAGGAGAATCTGATTGCCGACATTTTTGGT
GAGAGCGGCGATGAGGAAGAAGAAGAGTTCACTGGGTTTAATgga
agcggcGATGAGTTTCCCACCATGGTGTTTCCTTCTGGGCAGATC
AGCCAGGCCTCGGCCTTGGCCCCGGCCCCTCCCCAAGTCCTGCCC
CAGGCTCCAGCCCCTGCCCCTGCTCCAGCCATGGTATCAGCTCTG
GCCCAGGCCCCAGCCCCTGTCCCAGTCCTAGCCCCAGGCCCTCCT
CAGGCTGTGGCCCCACCTGCCCCCAAGCCCACCCAGGCTGGGGAA
GGAACGCTGTCAGAGGCCCTGCTGCAGCTGCAGTTTGATGATGAA
GACCTGGGGGCCTTGCTTGGCAACAGCACAGACCCAGCTGTGTTC
ACAGACCTGGCATCCGTCGACAACTCCGAGTTTCAGCAGCTGCTG
AACCAGGGCATACCTGTGGCCCCCCACACAACTGAGCCCATGCTG
ATGGAGTACCCTGAGGCTATAACTCGCCTAGTGACAGGGGCCCAG
AGGCCCCCCGACCCAGCTCCTGCTCCACTGGGGGCCCCGGGGCTC
CCCAATGGCCTCCTTTCAGGAGATGAAGACTTCTCCTCCATTGCG
GACATGGACTTCTCAGCCCTGCTGAGTCAGATCAGCTCC SEQ ID NO: 16, hhTAD polypeptide, 238 amino acids (aa); IWS TIMs domain bolded (aa 1-44 of SEQ ID NO: 16; see e.g., SEQ ID NO: 5); p65 domain italicized (aa 48-238 of SEQ ID NO: 16; see e.g., SEQ ID NO: 38).
SDKKNEEKDLFGSDSESGNEEENLIADIFGESGDEEEEEFTGFNG
*SGDEFPTMVFPSGQISQASALAPAPPQVLPQAPAPAPAPAMVSAL*
*AQAPAPVPVLAPGPPQAVAPPAPKPTQAGEGTLSEALLQLQFDDE*
*DLGALLGNSTDPAVFTDLASVDNSEFQQLLNQGIPVAPHTTEPML*
*MEYPEAITRLVTGAQRPPDPAPAPLGAPGLPNGLLSGDEDFSSIA*
*DMDFSALLSQISS*

Exemplary Constructs

Provided below are exemplary constructs of the synTFs described herein. Domains are shown left-to-right in 5' to 3' for nucleic acids and N-terminus to C-terminus for amino acids. Nucleic acid and amino acid sequences for the corresponding domains are provided below (see e.g., SEQ ID NOs: 5, 17-46).

I. GZV synZiFTR 2.0

(1) Dual lentiviral vectors for GZV inducible systems: ZF inducer:

(a) pSA767: pSFFV-ZF10-NS3-TIMs-p65;

(b) pSA771: pSFFV-ZF10-NS3-p65-TIMs;

(c) pSA917: pSFFV-ZF10-NS3-2×TIMs-p65;

(d) pSA936: pSFFV-ZF10-NS3-2×TIMs-NFZ.

(2) Single lentiviral vectors for GZV inducible systems driving CD19 CAR: pSA938: inverted[8×ZF10 binding site (BS)-ybTATA-CD19CAR-mCherry]-pSFFV-ZF10-NS3-2×TIMs-p65.

(3) Single lentiviral vectors for GZV inducible systems driving STAT1: pO1sv-210-TT: inverted[8×ZF10 BS-ybTATA-GFP-STAT1]-pSFFV-ZF10-NS3-2×TIMs-p65

II. 4-OHT synZiFTR 2.0

(4) Dual lentiviral vectors for 4OHT inducible systems: ZF inducer (a) pSA782 pSFFV-ZF10-p65-TIMs-wtERT2;

(b) pSA786 pSFFV-ZF10-TIMs-p65-wtERT2;

(c) pSA919 pSFFV-ZF10-2×TIMs-p65-wtERT2;

(d) pSA937 pSFFV-ZF10-2×TIMs-NFZ-wtERT2.

(5) Single lentiviral vectors for 4OHT inducible systems driving IL2: pSA942: inverted[8× ZF10 BS-ybTATA-mCherry-SUPER2]-pSFFV-ZF10-2×TIMs-p65-wtERT2.

(6) Single lentiviral vectors for Tamoxifen/4-OHT inducible system driving mCherry reporter:

(a) pNV048: inverted[8×ZF3 BS-ybTATA-mCherry-bovine growth hormone polyadenylation signal (BgHpA)]-pSFFV-ZF3-5-p65-wtERT2;

(b) pNV049: inverted[8×ZF3 BS-ybTATA-mCherry-BgHpA-pSFFV-ZF3-5-TIMs-p65 wtERT2;

(c) pNV050: inverted[8×ZF3 BS-ybTATA-mCherry-BgHpA]-pSFFV-ZF3-5-2×TIMs-p65-wtERT2;

(d) pNV058: inverted[8×ZF3 BS-ybTATA-mCherry-BgHpA]-pCMV-ZF3-5-p65-wtERT2;

(e) pNV059: inverted[8×ZF3 BS-ybTATA-mCherry-BgHpA]-pCMV-ZF3-5-1×TIM-p65-wtERT2;

(f) pNV060: inverted[8×ZF3 BS-ybTATA-mCherry-BgHpA]-pCMV-ZF3-5-2×TIM-p65-wtERT2.

III. Payloads (7) Dual lentiviral vectors for T cells (primary/cell lines):

(a) pSC145: 8×ZF10BS-ybTATA-CD19CAR-mCherry;

(b) pSC146: 8×ZF10BS-ybTATA-mCherry;

(c) pSC147: 8×ZF10BS-ybTATA-SUPER2.

(8) Dual lentiviral vectors for monocytes/macrophages (primary/cell lines):

(a) pO1z-210: 8×ZF10BS-ybTATA-GFP-STAT1;

(b) pO6z-210: 8×ZF10BS-ybTATA-GFP-STAT6.

IV. VEGF synZiFTRs (9) VEGF synZiFTR constructs:

(a) pSFFV-VEGF ZF-p65-ERT-P2A-puro;

(b) pSFFV-VEGF ZF-TIMs-TIMs-p65-ERT-P2A-puro.

Exemplary Domains—Nucleic Acid Sequences

SEQ ID NO: 17, [pSFFV]

```
gtaacgccattttgcaaggcatggaaaaataccaaaccaagaata

gagaagttcagatcaagggcgggtacatgaaaatagctaacgttg

ggccaaacaggatatctgcggtgagcagtttcggccccggcccgg

ggccaagaacagatggtcaccgcagtttcggccccggcccgaggc

caagaacagatggtccccagatatggcccaaccctcagcagtttc
```

-continued

```
ttaagacccatcagatgtttccaggctcccccaaggacctgaaat

gaccctgcgccttatttgaattaaccaatcagcctgcttctcgct

tctgttcgcgcgcttctgcttcccgagctctataaaagagctcac

aacccctcacteggegcgccagtcctccgacagactgagtcgccc

ggg
```

SEQ ID NO: 18, [ZF10](for amino acid sequence, see e.g., SEQ ID NO: 36)

```
TCTAGACCCGGAGAGCGCCCATTCCAGTGTCGGATTTGCATGCGG

AACTTTTCGAGAAGACACGGCCTGGACAGACATACCCGTACTCAT

ACAGGTGAAAAACCCTTTCAGTGTCGGATCTGTATGCGAAATTTC

TCCGACCACAGCAGCCTGAAGAGACATCTACGTACCCACACCGGC

AGCCAGAAGCCATTTCAGTGTCGGATCTGTATGCGGAACTTCTCC

GTGAGACACAACCTGACCAGACATCTACGTACGCACACCGGAGAG

AAGCCATTCCAATGCCGAATATGCATGCGCAACTTCAGTGACCAC

AGCAACCTGAGCAGACACCTAAAAACCCACACCGGTTCCCAGAAG

CCATTTCAGTGTCGGATCTGTATGCGGAACTTCTCCCAGCGCAGC

AGCCTGGTGAGACATCTACGTACGCACACCGGAGAGAAGCCATTC

CAATGCCGAATATGCATGCGCAACTTCAGTGAGAGCGGCCACCTG

AAGAGACACCTGCGTACGCACCTGAGGGGATCC
```

SEQ ID NO: 19, [NS3](for amino acid sequence, see e.g., SEQ ID NO: 37)

```
GGCTGCGTGGTCATAGTGGGCAGGATCGTCTTGTCCGGATCCGGC

ACTAGTGCGCCCATCACGGCGTACGCCCAGCAGACGAGAGGCCTC

CTAGGGTGTATAATCACCAGCCTGACTGGCCGGGACAAAAACCAA

GTGGAGGGTGAGGTCCAGATCGTGTCAACTGCTACCCAAACCTTC

CTGGCAACGTGCATCAATGGGGTATGCTGGGCAGTCTACCACGGG

GCCGGAACGAGGACCATCGCATCACCCAAGGGTCCTGTCATCCAG

ATGTATACCAATGTGGACCAAGACCTTGTGGGCTGGCCCGCTCCT

CAAGGTTCCCGCTCATTGACACCCTGTACCTGCGGCTCCTCGGAC

CTTTACCTGGTCACGAGGCACGCCGATGTCATTCCCGTGCGCCGG

CGAGGTGATAGCAGGGGTAGCCTGCTTTCGCCCCGGCCCATTTCC

TACTTGAAAGGCTCCTCGGGGGGTCCGCTGTTGTGCCCCGCGGGA

CACGCCGTGGGCCTATTCAGGGCCGCGGTGTGCACCCGTGGAGTG

GCTAAAGCGGTGGACTTTATCCCTGTGGAGAACCTAGAGACAACC

ATGAGATCCCCGGTGTTCACGGACAACTCCTCTCCACCAGCAGTC

ACCCTGACGCACCCAATCACCAAAATCGATAGGGAGGTTCTCTAC

CAGGAGTTCGATGAGATGGAAGAGTGCTCTCAGCAC
```

SEQ ID NO: 20, TIMs (for amino acid sequence, see e.g., SEQ ID NO: 5)

```
tcagacaagaaaaacgaagaaaaggatttgttcggaagtgattcc

gagagcgggaacgaagaggagaatctgattgccgacatttttggt

gagagcggcgatgaggaagaagaagagttcactgggtttaat
```

SEQ ID NO: 21, [p65](for amino acid sequence, see e.g., SEQ ID NO: 38)
gatgagtttcccaccatggtgtttccttctgggcagatcagccag
gcctcggccttggccccggcccctccccaagtcctgccccaggct
ccagcccctgcccctgctccagccatggtatcagctctggcccag
gccccagcccctgtcccagtcctagccccaggccctcctcaggct
gtggccccacctgcccccaagcccacccaggctggggaaggaacg
ctgtcagaggccctgctgcagctgcagtttgatgatgaagacctg
ggggccttgcttggcaacagcacagacccagctgtgttcacagac
ctggcatccgtcgacaactccgagtttcagcagctgctgaaccag
ggcatacctgtggcccccacacaactgagcccatgctgatggag
taccctgaggctataactcgcctagtgacaggggcccagaggccc
cccgacccagctcctgctccactgggggccccggggctccccaat
ggcctcctttcaggagatgaagacttctcctccattgcggacatg
gacttctcagccctgctgagtcagatcagctcc SEQ ID NO: 22, [NFZ](for amino acid sequence, see e.g., SEQ ID NO: 57)
GAGGGCCAGAGCGACGAGAGAGCCCTGCTGGACCAGCTGCACACC
CTGCTGAGCAACACCGACGCCACCGGCCTGGAGGAGATCGACAGA
GCCCTGGGCATCCCCGAGCTGGTGAACCAGGGCCAGGCCCTGGAG
CCCAAGCAGGGAGGAGGAGGTAGCggaCACGAGAAGTTCCCCAGC
GACCTGGACCTGGACATGTTCAACGGCAGCCTGGAGTGCGACATG
GAGAGCATCATCAGAAGCGAGCTGATGGACGCCGACGGCCTGGAC
TTCAACTTCGACAGCGGAGGAGGAGGTAGCggaTTCGTGACCCTG
AAGGACGTGGGCATGGACTTCACCCTGGGCGACTGGGAGCAGCTG
GGCCTGGAGCAGGGCGACACCTTCTGGGACACCGCCCTGGACAAC
TGCCAGGACCTGTTCCTGCTGGACCCCCCC SEQ ID NO: 23, [8X ZF10 BS]
acgattgagtaacactgtatctagtctacctacagggctcGGCGT
AGCCGATGTCGCGcggatagcgtcaacctcttcGGCGTAGCCGAT
GTCGCGcaatcagttctcccgaggtcGGCGTAGCCGATGTCGCGc
agagccgtgcttccaatacGGCGTAGCCGATGTCGCGccgggttt
cgtaacaatcgcatgaggattcgcaacgccttcGGCGTAGCCGAT
GTCGCGctcccgtctcagtaaaggtcGGCGTAGCCGATGTCGCGc
aatcggactgccttcgtacGGCGTAGCCGATGTCGCGcgtatcag
tcgcctoggaacGGCGTAGCCGATGTCGCGcattcgtaagaggct
cactctcccttacacggagtggata SEQ ID NO: 24, [ybTATA]
tggcccccattatataccctctaga SEQ ID NO: 25, [CD19CAR](for amino acid sequence, see e.g., SEQ ID NO: 39)
GCCTTACCAGTGACCGCCTTGCTCCTGCCGCTGGCCTTGCTGCTC
CACGCCGCCAGGCCGGACATCCAGATGACACAGACTACATCCTCC
CTGTCTGCCTCTCTGGGAGACAGAGTCACCATCAGTTGCAGGGCA
AGTCAGGACATTAGTAAATATTTAAATTGGTATCAGCAGAAACCA GATGGAACTGTTAAACTCCTGATCTACCATACATCAAGATTACAC
TCAGGAGTCCCATCAAGGTTCAGTGGCAGTGGGTCTGGAACAGAT
TATTCTCTCACCATTAGCAACCTGGAGCAAGAAGATATTGCCACT
TACTTTTGCCAACAGGGTAATACGCTTCCGTACACGTTCGGAGGC
GGCACCAAGCTGGAGATCACAGGTGGCGGTGGCTCGGGCGGTGGT
GGGTCGGGTGGCGGCGGATCTGAGGTGAAACTGCAGGAGTCAGGA
CCTGGCCTGGTGGCGCCCTCACAGAGCCTGTCCGTCACATGCACT
GTCTCAGGGGTCTCATTACCCGACTATGGTGTAAGCTGGATTCGC
CAGCCTCCACGAAAGGGTCTGGAGTGGCTGGGAGTAATATGGGGT
AGTGAAACCACATACTATAATTCAGCTCTCAAATCCAGACTGACC
ATCATCAAGGACAACTCCAAGAGCCAAGTTTTCTTAAAAATGAAC
AGTCTGCAAACTGATGACACAGCCATTTACTACTGTGCCAAACAT
TATTACTACGGTGGTAGCTATGCTATGGACTACTGGGGCCAAGGA
ACCTCAGTCACCGTCTCCTCAGAACAAAAACTCATCTCAGAAGAA
GATCTGAATGGGGCCGCAACCACGACGCCAGCGCCGCGACCACCA
ACACCGGCGCCCACCATCGCGTTGCAGCCCCTGTCCCTGCGCCCA
GAGGCGTGCCGGCCAGCGGCGGGGGGCGCAGTGCACACGAGGGGG
CTGGACTTCGCCTGTGATTTTTGGGTGCTGGTGGTGGTTGGTGGA
GTCCTGGCTTGCTATAGCTTGCTAGTAACAGTGGCCTTTATTATT
TTCTGGGTGAGGAGTAAGAGGAGCAGGCTCCTGCACAGTGACTAC
ATGAACATGACTCCCCGCCGCCCCGGGCCCACCCGCAAGCATTAC
CAGCCCTATGCCCCACCACGCGACTTCGCAGCCTATCGCTCCAAA
CGGGGCAGAAAGAAACTCCTGTATATATTCAAACAACCATTTATG
AGACCAGTACAAACTACTCAAGAGGAAGATGGCTGTAGCTGCCGA
TTTCCAGAAGAAGAAGAAGGAGGATGTGAACTGAGAGTGAAGTTC
AGCAGGAGCGCAGACGCCCCCGCGTACAAGCAGGGCCAGAACCAG
CTCTATAACGAGCTCAATCTAGGACGAAGAGAGGAGTACGATGTT
TTGGACAAGAGACGTGGCCGGGACCCTGAGATGGGGGGAAAGCCG
AGAAGGAAGAACCCTCAGGAAGGCCTGTACAATGAACTGCAGAAA
GATAAGATGGCGGAGGCCTACAGTGAGATTGGGATGAAAGGCGAG
CGCCGGAGGGGCAAGGGGCACGATGGCCTTTACCAGGGTCTCAGT
ACAGCCACCAAGGACACCTACGACGCCCTTCACATGCAGGCCCTG
CCCCCTCGCGGC SEQ ID NO: 26, [mCherry](for amino acid sequence, see e.g., SEQ ID NO: 40)
ttacttgtacagctcgtccatgccgccggtggagtggcggccctc
ggcgcgttcgtactgttccacgatggtgtagtcctcgttgtggga
ggtgatgtccaacttgatgttgacgttgtaggcgccgggcagctg
cacgggcttcttggccttgtaggtggtcttgacctcagcgtcgta
gtggccgccgtccttcagcttcagcctctgcttgatctcgccctt
cagggcgccgtcctcggggtacatccgctcggaggaggcctgcca -continued gcccatggtcttcttctgcattacggggccgtcggaggggaagtt ggtgccgcgcagcttcaccttgtagatgaactcgccgtcctgcag ggaggagtcctgggtcacggtcaccacgccgccgtcctcgaagtt catcacgcgctcccacttgaagccctcggggaaggacagcttcaa gtagtcggggatgtcggcggggtgcttcacgtaggccttggagcc gtacatgaactgaggggacaggatgtcccaggcgaagggcagggg gccacccttggtcaccttcagcttggcggtctgggtgccctcgta ggggggccctcgccctcgccctcgatctcgaactcgtggccgttc acggagccctccatgtgcaccttgaagcgcatgaactccttgatg atggccatgttatcctcctogcccttgctcaccat SEQ ID NO: 27, 717 nt, [GFP](for amino acid sequence, see e.g., SEQ ID NO: 41)

CTTGTACAGCTCGTCCATGCCGAGAGTGATCCCGGCGGCGGTCAC

GAACTCCAGCAGGACCATGTGATCGCGCTTCTCGTTGGGGTCTTT

GCTCAGGGCGGACTGGGTGCTCAGGTAGTGGTTGTCGGGCAGCAG

CACGGGGCCGTCGCCGATGGGGGTGTTCTGCTGGTAGTGGTCGGC

GAGCTGCACGCTGCCGTCCTCGATGTTGTGGCGGATCTTGAAGTT

CgCCTTGATGCCGTTCTTCTGCTTGTCGGCCATGATATAGACGTT

GTGGCTGTTGTAGTTGTACTCCAGCTTGTGCCCCAGGATGTTGCC

GTCCTCCTTGAAGTCGATGCCCTTCAGCTCGATGCGGTTCACCAG

GGTGTCGCCCTCGAACTTCACCTCGGCGCGGGTCTTGTAGTTGCC

GTCGTCCTTGAAGAAGATGGTGCGCTCCTGGACGTAGCCTTCGGG

CATGGCGGACTTGAAGAAGTCGTGCTGCTTCATGTGGTCGGGGTA

GCGGCTGAAGCACTGCACGCCGTAGGTCAGGGTGGTCACGAGGGT

GGGCCAGGGCACGGGCAGCTTGCCGGTGGTGCAGATGAACTTCAG

GGTCAGCTTGCCGTAGGTGGCATCGCCCTCGCCCTCGCCaGACAC

GCTGAACTTGTGGCCGTTTACGTCGCCGTCCAGCTCGACCAGGAT

GGGCACCACCCCGGTGAACAGCTCCTCGCCCTTGCTCACCAT

SEQ ID NO: 28, [STAT1](reverse complement) (for amino acid sequence, see e.g., SEQ ID NO: 42), 2250 nt tactgtgttcatcatactgtcgaactctacagagcccactatccg agacacctcgtcaaactcctcaggagacatggggagcaggttgtc tgtggtctgaagtctagaagggtgaacttcagacacagaaatcaa ctcagtcttgatatatccagttcctttagggccatcaagttccat tggctctggtgcttcctttggcctggagtaatactttccaaaggc atggtctttgtcaatatttggatacagatacttcaggggattctc aggaatGCActcGCAagccatgactttgtaattgcgaatgatgtc agggaaagtaacagcagaaagttctttcttcgtgtagggttcaac cgcatggaagtcaggttcgcctccgttctgggaccgctccaccca tgtgaatgtgatggccccttcccgggagctctcactgaaccgcag caggaaggtccccggctgctggtccttcaacagggcacgctctcg ctccttgctgatgaagcccatgatgcacccatcattccagagagg -continued gagcaggtgtttttaatgagttctaggatgctttcaatccaaag ccagaagggaaaatttttatcatttatattttccttacaaaacct cgtccacggaatgagaccatcggggctggcgttaggaccaagaag cttctctcccaacatgttcagctggtccacattgagacctctttt ggtgacagaagaaaactgccaactcagcacttctgaaagctgagc ccatcgtgcacatggtggagtcaggaagaaggacagattcctggg ttccgccaccagcatgttgtaccaaaggatggaggcccaaccgct cgggagctggctgacgttggagatcaccacaacgggcagagaggt cgtctcgaggtcaattaccaaaccaggctggcacaattgggtttc aaaactaagggagtgaagctcttcagtaacgatgagaggaccctc attcgttctggtgccagcatttttctgttctttcaattgcaggtg ccgaaattcagccgccagactgccattggtggactcctccatgtt catcacttttgtgtgcgtgcccaaaatgttgaacttcctaaatcc ttttactgtatctctctcattcacatctttatcaaataagacttt gactttcaaattataattcagctcttgcaatttcaccaacagtct caacttcacagtgaactggacccctgtcttcaagaccagcggcct ctgagggtgcgttggcatgcagggctgtctttccaccacaaacga gctctgaatgagctgctggaaaagactgaaggtgcggtcccataa cacttgtttgtttttttgtgatagggtcatgttcgtaggtgtattt ctgttccaattcctccaactttttaagctgctgccgaacttgctg cagactctccgcaactatagtgaaccagttctgcagctgatccaa gcaagcattgggggcccccccaatacaggcgctctgctgtctccgc ttccactccactagttcatcattaatcagggcattctgggtaagt tcagtgacattcagcaactctattattttgtgaactacttccttt ctcttattgtcaagcattaaatacatcttcttgagtaacagctgt tcttgtttctgatcactctttgccacaccattggtctcgtgttct ctgttctgcaaggttttgcatttgaagtcatattcatcttgtaaa tcttccaggctcttgatttcatgctctatacacataaccttgtcc ttcacatttctgactttactgtcaagctctttctgtttgtctaac atcactgtgctctgaatattccccgactgagcctgattaaatctc tgggcgttttccagaattttcctttcttccttcagacagctgtaa atgatcatagacatctggattgggtcttcctgaaaattatcctga agattacgcttgcttttccttatgttatgctgtagcaagaagtta ttctccaaagaaaagcgactatattgatcatccagctgtgacagg aggtcatgaaaacggatggtggcaaatgaaacatcattggcagcg tgctcccagtcttgcttttctaaccactgtgccaggtactgtctg atttccatgggaaaactgtcatcataaagctggtgaacctgctcc aggaattttgagtcaagctgctgaagttcgtaccactgagacat SEQ ID NO: 29, wtERT2 (for amino acid sequence, see e.g., SEQ ID NO: 43)

tctgctggagacatgagagctgccaacctttggccaagcccgctc atgatcaaacgctctaagaagaacagcctggccttgtccctgacg -continued gccgaccagatggtcagtgccttgttggatgctgagccccccata
ctctattccgagtatgatcctaccagacccttcagtgaagcttcg
atgatgggcttactgaccaacctggcagacagggagctggttcac
atgatcaactgggcgaagagggtgccaggctttgtggatttgacc
ctccatgatcaggtccaccttctagaatgtgcctggctagagatc
ctgatgattggtctcgtctggcgctccatggagcacccagtgaag
ctactgtttgctcctaacttgctcttggacaggaaccagggaaaa
tgtgtagagggcatggtggagatcttcgacatgctgctggctaca
tcatctcggttccgcatgatgaatctgcagggagaggagtttgtg
tgcctcaaatctattatttgcttaattctggagtgtacacattt
ctgtccagcaccctgaagtctctggaagagaaggaccatatccac
cgagtcctggacaagatcacagacactttgatccacctgatggcc
aaggcaggcctgaccctgcagcagcagcaccagcggctggcccag
ctcctcctcatcctctcccacatcaggcacatgagtaacaaaggc
atggagcatctgtacagcatgaagtgcaagaacgtggtgcccctc
tatgacctgctgctggaggcggcggacgcccaccgcctacatgcg
cccactagccgtggaggggcatccgtggaggagacggaccaaagc
cacttggccactgcgggctctacttcatcgcattccttgcaaaag
tattacatcacgggggaggcagagggtttccctgccacagct SEQ ID NO: 30, [SUPER2]
(for amino acid sequence, see e.g.,
SEQ ID NO: 44)
gcggatcccgcacctacttcaagttctacaaagaaaacacagcta
caactggagcatttacttctggatttacagatgattttgaatgga
attaataattacaagaatcccaaactcaccaggatgctcacagca
aagttttacatgcccaagaaggccacagaactgaaacatcttcag
tgtctagaagaagaactcaaacctctggaggaagtgctaaattta
gctcagagcaaaaactttcacttcgatcccagggacgtcgtcagc
aatatcaacgtattcgtcctggaactaaagggatctgaaacaaca
ttcatgtgtgaatatgctgatgagacagcaaccattgtagaattt
ctgaacagatggattaccttttgtcaaagcatcatctcaacacta
actggcggc SEQ ID NO: 31, [8X ZF3 BS]
tatccactccgtgtaagggagagtgagcctcttacgaatctacgg
ctacttcgacgtctttccgaggcgactgatacctacggctacttc
gacgtcttacgaaggcagtccgattctacggctacttcgacgtct
acctttactgagacgggactacggctacttcgacgtctaaggcgt
tgcgaatcctcatgcgattgttacgaaacccgctacggctacttc
gacgtcttattggaagcacggctctctacggctacttcgacgtct
acctcgggagaactgattctacggctacttcgacgtctaagaggt
tgacgctatccctacggctacttcgacgtctagccctgtaggtag
actagatacagtgttactcaatcgt -continued SEQ ID NO: 32, [BgHpA]
cgctacagggcgcgtggggataccccctagagccccagctggttc
tttccgcctcagaagccatagagcccaccgcatccccagcatgcc
tgctattgtcttcccaatcctcccccttgctgtcctgccccaccc
cacccccagaatagaatgacacctactcagacaatgcgatgcaa
tttcctcattttattaggaaaggacagtgggagtggcaccttcca
gggtcaaggaaggcacgggggagggggcaaacaacagatggctggc
aactagaaggcacag SEQ ID NO: 33, [ZF3-5](for amino acid sequence,
see e.g., SEQ ID NO: 45)
tctagaccaggcgaacgaccgtttcaatgccggatatgtatgagg
aacttctcccagaggtccagcttggtacggcacacccgaacacat
acaggagaaaagccattccaatgtcgaatttgtatgcgcaatttt
tcagacaagtctgtgttggctcgacacctccgcacacatactggt
tcacagaagccctttcagtgcaggatttgtatgcgcaactttagc
caacgctcatccctggtaaggcacactagaacgcatacaggtgag
aagcctttccagtgtcgcatctgtatgcggaacttcagccagcgg
aataacttgggcaggcatttgcgaactcacaccggttctcaaaaa
ccttttcagtgccgaatttgtatgcgcaacttcagcacccacgcc
gtattgacacgacacacgcgcacgcacaccggggaaaaaccgttt
caatgtcgaatctgcatgcgcaattttagcgatagagggaacctc
actcgacatctgcgcacacacttgcggggatcc SEQ ID NO: 34, [pCMV]
gacattgattattgactagttattaatagtaatcaattacggggt
cattagttcatagcccatatatggagttccgcgttacataactta
cggtaaatggcccgcctggctgaccgcccaacgacccccgcccat
tgacgtcaataatgacgtatgttcccatagtaacgccaataggga
ctttccattgacgtcaatgggtggagtatttacggtaaactgccc
acttggcagtacatcaagtgtatcatatgccaagtacgcccccta
ttgacgtcaatgacggtaaatggcccgcctggcattatgcccagt
acatgaccttatgggactttcctacttggcagtacatctacgtat
tagtcatcgctattaccatggtgatgcggttttggcagtacatca
atgggcgtggatagcggtttgactcacggggatttccaagtctcc
accccattgacgtcaatgggagtttgttttggcaccaaaatcaac
gggactttccaaaatgtcgtaacaactccgccccattgacgcaaa
tgggcggtaggcgtgtacggtgggaggtctatataagcagagct SEQ ID NO: 35, [STAT6], 2544 nt, (for amino
acid sequence, see e.g., SEQ ID NO: 46)
atgtctctgtggggtctggtctccaagatgcccccagaaaaagtg
cagcggctctatgtcgactttccccaacacctgcggcatcttctg
ggtgactggctggagagccagccctgggagttcctggtcggctcc
gacgccttctgctgcaacttggctagtgccctactttcagacact
gtccagcaccttcaggcctcggtgggagagcaggggggaggggagc
accatcttgcaacacatcagcacccttgagagcatatatcagagg -continued gacccccctgaagctggtggccactttcagacaaatacttcaagga
gagaaaaaagctgttatggaacagttccgccacttgccaatgcct
ttccactggaagcaggaagaactcaagtttaagacaggcttgcgg
aggctgcagcaccgagtaggggagatccaccttctccgagaagcc
ctgcagaaggggggctgaggctggccaagtgtctctgcacagcttg
atagaaactcctgctaatgggactgggccaagtgaggccctggcc
atgctactgcaggagaccactggagagctagaggcagccaaagcc
ctagtgctgaagaggatccagatttggaaacggcagcagcagctg
gcagggaatggcgcaccgtttgaggagagcctggccccactccag
gagaggtgtgaaagcctggtggacatttattcccagctacagcag
gaggtaggggcggctggtggggagcttgagcccaagacccgggca
tcgctgactggccggctggatgaagtcctgagaaccctcgtcacc
agttgcttcctggtggagaagcagcccccccaggtactgaagact
cagaccaagttccaggctggagttcgattcctgttgggcttgagg
ttcctgggggccccagccaagcctccgctggtcagggccgacatg
gtgacagagaagcaggcgcgggagctgagtgtgcctcagggtcct
ggggctggagcagaaagcactggagaaatcatcaacaacactgtg
cccttggagaacagcattcctgggaactgctgctctgccctgttc
aagaacctgcttctcaagaagatcaagcggtgtgagcggaagggc
actgagtctgtcacagaggagaagtgcgctgtgctcttctctgcc
agcttcacacttggccccggcaaactccccatccagctccaggcc
ctgtctctgcccctggtggtcatcgtccatggcaaccaagacaac
aatgccaaagccactatcctgtgggacaatgccttctctgagatg
gaccgcgtgccctttgtggtggctgagcgggtgccctgggagaag
atgtgtgaaactctgaacctgaagttcatggctgaggtggggacc
aaccgggggctgctcccagagcacttcctcttcctggcccagaag
atcttcaatgacaacagcctcagtatggaggccttccagcaccgt
tctgtgtcctggtcgcagttcaacaaggagatcctgctgggccgt
ggcttcaccttttggcagtggtttgatggtgtcctggacctcacc
aaacgctgtctccggagctactggtctgaccggctgatcattggc
ttcatcagcaaacagtacgctgctagccttcttctcaatgagccc
gacggaacctttctcctccgcttcagcgactcagagattgggggc
atcaccattgcccatgtcatccggggccaggatggctctccacag
atagagaacatccagccattctctgccaaagacctgtccattcgc
tcactgggggaccgaatccgggatcttgcacagctcaaaaatctc
tatcccaagaagcccaaggatgaggctttccggagccactacaag
cctgaacagatgggtaaggatggcaggggttatgtcccagctacc
atcaagatgaccgtggaaagggaccaaccacttcctaccccagag
ctccagatgcctaccatggtgccttcttatgaccttggaatggcc
cctgattcctccatgagcatgcagcttggcccagatatggtgccc -continued caggtgtacccaccacactctcactccatccccccgtatcaaggc
ctctccccagaagaatcagtcaacgtgttgtcagccttccaggag
cctcacctgcagatgccccccagcctgggccagatgagcctgccc
tttgaccagcctcacccccagggcctgctgccgtgccagcctcag
gagcatgctgtgtccagccctgacccccctgctctgctcagatgtg
accatggtggaagacagctgcctgagccagccagtgacagcgttt
cctcagggcacttggattggtgaagacatattccctcctctgctg
cctcccactgaacaggacctcactaagcttctcctggaggggcaa
ggggagtcgggggggagggtccttgggggcacagcccctcctgcag
ccctcccactatgggcaatctgggatctcaatgtcccacatggac
ctaagggccaaccccagttggtga SEQ ID NO: 47, VEGF ZF sequence (for amino acid sequence, see e.g., SEQ ID NO: 48)
Ggcaaaaagaagcagcacatctgccacatccagggctgcggcaag
gtgtacggcgacaggagcaacctgaccaggcaccttaggtggcac
accggggagaggcccttcatgtgcacctggagctactgcggaaaa
aggttcaccatgagccatcacttgagcaggcacaagaggacccac
acaggcgagaagaagttcgcctgccccgagtgccccaagaggttt
atgaggagcgaccatctgagcaggcacatcaagacccaccagaac
aagaaaggcgggggcagtggcgggagcgggcgggccGAA SEQ ID NO: 351, 3Z (for amino acid sequence, see e.g., SEQ ID NO: 303)
ATGGCGGAAGAGTTTGTAACGCTCAAGGATGTAGGAATGGATTTT
ACATTGGGTGACTGGGAACAGCTTGGTTTGGAACAGGGTGATACG
TTCTGGGATACTGCATTGGATAACTGCCAAGATCTGTTCCTGCTG
GATCCCCCGAGGCCAAATCTTACCTCACATCCCGATGGCAGTGAG
GATCTTGAACCTCTGGCAGGAGGAAGTCCCGAAGCAACTAGTATG
GCAGAAGAATTTGTGACATTGAAGGACGTGGGAATGGACTTTACA
TTGGGGGACTGGGAACAATTGGGTCTTGAGCAGGGTGATACATTT
TGGGACACAGCTCTCGACAATTGCCAAGATCTTTTCTTGCTGGAT
CCACCCCGCCCTAACCTGACATCACATCCAGACGGTAGCGAGGAT
TTGGAACCCCTGGCCGGAGGTAGTCCTGAGGCAACCTCCATGGCG
GAGGAATTTGTGACTCTGAAGGATGTAGGGATGGACTTCACGCTC
GGAGATTGGGAGCAGCTCGGATTGGAGCAAGGTGACACATTCTGG
GACACCGCACTTGACAACTGCCAAGATCTTTTTCTTCTCGACCCA
CCGCGGCCGAACTTGACTAGCCACCCCGATGGCTCTGAAGATCTT
GAACCACTCGCCGGGGGATCACCTGAAGCCACGAGC Exemplary Domains - Amino Acid Sequences SEQ ID NO: 36, [ZF10]
SRPGERPFQCRICMRNFSRRHGLDRHTRTHTGEKPFQCRICMRNF
SDHSSLKRHLRTHTGSQKPFQCRICMRNFSVRHNLTRHLRTHTGE
KPFQCRICMRNFSDHSNLSRHLKTHTGSQKPFQCRICMRNFSQRS
SLVRHLRTHTGEKPFQCRICMRNFSESGHLKRHLRTHLRGS -continued

SEQ ID NO: 37, [NS3]
GCVVIVGRIVLSGSGTSAPITAYAQQTRGLLGCIITSLTGRDKNQ

VEGEVQIVSTATQTFLATCINGVCWAVYHGAGTRTIASPKGPVIQ

MYTNVDQDLVGWPAPQGSRSLTPCTCGSSDLYLVTRHADVIPVRR

RGDSRGSLLSPRPISYLKGSSGGPLLCPAGHAVGLFRAAVCTRGV

AKAVDFIPVENLETTMRSPVFTDNSSPPAVTLTHPITKIDREVLY

QEFDEMEECSQH

SEQ ID NO: 5, TIMs
SDKKNEEKDLFGSDSESGNEEENLIADIFGESGDEEEEEFTGFN

SEQ ID NO: 38, [p65]
DEFPTMVFPSGQISQASALAPAPPQVLPQAPAPAPAPAMVSALAQ

APAPVPVLAPGPPQAVAPPAPKPTQAGEGTLSEALLQLQFDDEDL

GALLGNSTDPAVFTDLASVDNSEFQQLLNQGIPVAPHTTEPMLME

YPEAITRLVTGAQRPPDPAPAPLGAPGLPNGLLSGDEDFSSIADM

DFSALLSQISS

SEQ ID NO: 57, NFZ
EGQSDERALLDQLHTLLSNTDATGLEEIDRALGIPELVNQGQALE

PKQGGGGSGHEKFPSDLDLDMFNGSLECDMESIIRSELMDADGLD

FNFDSGGGGSGFVTLKDVGMDFTLGDWEQLGLEQGDTFWDTALDN

CQDLFLLDPP

SEQ ID NO: 39, [CD19CAR]
ALPVTALLLPLALLLHAARPDIQMTQTTSSLSASLGDRVTISCRA

SQDISKYLNWYQQKPDGTVKLLIYHTSRLHSGVPSRFSGSGSGTD

YSLTISNLEQEDIATYFCQQGNTLPYTFGGGTKLEITGGGGSGGG

GSGGGGSEVKLQESGPGLVAPSQSLSVTCTVSGVSLPDYGVSWIR

QPPRKGLEWLGVIWGSETTYYNSALKSRLTIIKDNSKSQVFLKMN

SLQTDDTAIYYCAKHYYYGGSYAMDYWGQGTSVTVSSEQKLISEE

DLNGAATTTPAPRPPTPAPTIALQPLSLRPEACRPAAGGAVHTRG

LDFACDFWVLVVVGGVLACYSLLVTVAFIIFWVRSKRSRLLHSDY

MNMTPRRPGPTRKHYQPYAPPRDFAAYRSKRGRKKLLYIFKQPFM

RPVQTTQEEDGCSCRFPEEEEGGCELRVKFSRSADAPAYKQGQNQ

LYNELNLGRREEYDVLDKRRGRDPEMGGKPRRKNPQEGLYNELQK

DKMAEAYSEIGMKGERRRGKGHDGLYQGLSTATKDTYDALHMQAL

PPRG

SEQ ID NO: 40, [mCherry]
LLVQLVHAAGGVAALGAFVLFHDGVVLVVGGDVQLDVDVVGAGQL

HGLLGLVGGLDLSVVVAAVLQLQPLLDLALQGAVLGVHPLGGGLP

AHGLLLHYGAVGGEVGAAQLHLVDELAVLQGGVLGHGHHAAVLEV

HHALPLEALGEGQLQVVGDVGGVLHVGLGAVHELRGQDVPGEGQG

ATLGHLQLGGLGALVGAALALALDLELVAVHGALHVHLEAHELLD

DGHVILLALAHH

SEQ ID NO: 41, [GFP]
LVQLVHAESDPGGGHELQQDHVIALLVGVFAQGGLGAQVVVVGQQ

HGAVADGGVLLVVVGELHAAVLDVVADLEVRLDAVLLLVGHDIDV

-continued

VAVVVVLQLVPQDVAVLLEVDALQLDAVHQGVALELHLGAGLVVA

VVLEEDGALLDVAFGHGGLEEVVLLHVVGVAAEALHAVGQGGHEG

GPGHGQLAGGADELQGQLAVGGIALALARHAELVAVYVAVQLDQD

GHHPGEQLLALAHH

SEQ ID NO: 42, [STATI]
MSQWYELQQLDSKFLEQVHQLYDDSFPMEIRQYLAQWLEKQDWEH

AANDVSFATIRFHDLLSQLDDQYSRFSLENNFLLQHNIRKSKRNL

QDNFQEDPIQMSMIIYSCLKEERKILENAQRFNQAQSGNIQSTVM

LDKQKELDSKVRNVKDKVMCIEHEIKSLEDLQDEYDFKCKTLQNR

EHETNGVAKSDQKQEQLLLKKMYLMLDNKRKEVVHKIIELLNVTE

LTQNALINDELVEWKRRQQSACIGGPPNACLDQLQNWFTIVAESL

QQVRQQLKKLEELEQKYTYEHDPITKNKQVLWDRTFSLFQQLIQS

SFVVERQPCMPTHPQRPLVLKTGVQFTVKLRLLVKLQELNYNLKV

KVLFDKDVNERDTVKGFRKFNILGTHTKVMNMEESTNGSLAAEFR

HLQLKEQKNAGTRTNEGPLIVTEELHSLSFETQLCQPGLVIDLET

TSLPVVVISNVSQLPSGWASILWYNMLVAEPRNLSFFLTPPCARW

AQLSEVLSWQFSSVTKRGLNVDQLNMLGEKLLGPNASPDGLIPWT

RFCKENINDKNFPFWLWIESILELIKKHLLPLWNDGCIMGFISKE

RERALLKDQQPGTFLLRFSESSREGAITFTWVERSQNGGEPDFHA

VEPYTKKELSAVTFPDIIRNYKVMACECIPENPLKYLYPNIDKDH

AFGKYYSRPKEAPEPMELDGPKGTGYIKTELISVSEVHPSRLQTT

DNLLPMSPEEFDEVSRIVGSVEFDSMMNTV

SEQ ID NO: 43, wtERT2
SAGDMRAANLWPSPLMIKRSKKNSLALSLTADQMVSALLDAEPPI

LYSEYDPTRPFSEASMMGLLTNLADRELVHMINWAKRVPGFVDLT

LHDQVHLLECAWLEILMIGLVWRSMEHPVKLLFAPNLLLDRNQGK

CVEGMVEIFDMLLATSSRFRMMNLQGEEFVCLKSIILLNSGVYTF

LSSTLKSLEEKDHIHRVLDKITDTLIHLMAKAGLTLQQQHQRLAQ

LLLILSHIRHMSNKGMEHLYSMKCKNVVPLYDLLLEAADAHRLHA

PTSRGGASVEETDQSHLATAGSTSSHSLQKYYITGEAEGFPATA

SEQ ID NO: 44, [SUPER2]
ADPAPTSSSTKKTQLQLEHLLLDLQMILNGINNYKNPKLTRMLTA

KFYMPKKATELKHLQCLEEELKPLEEVLNLAQSKNFHFDPRDVVS

NINVFVLELKGSETTFMCEYADETATIVEFLNRWITFCQSIISTL

TGG

SEQ ID NO: 45, [ZF3-5]
SRPGERPFQCRICMRNFSQRSSLVRHTRTHTGEKPFQCRICMRNF

SDKSVLARHLRTHTGSQKPFQCRICMRNFSQRSSLVRHTRTHTGE

KPFQCRICMRNFSQRNNLGRHLRTHTGSQKPFQCRICMRNFSTHA

VLTRHTRTHTGEKPFQCRICMRNFSDRGNLTRHLRTHLRGS

SEQ ID NO: 46, [STAT6]
MSLWGLVSKMPPEKVQRLYVDFPQHLRHLLGDWLESQPWEFLVGS

DAFCCNLASALLSDTVQHLQASVGEQGEGSTILQHISTLESIYQR

-continued

DPLKLVATFRQILQGEKKAVMEQFRHLPMPFHWKQEELKFKTGLR

RLQHRVGEIHLLREALQKGAEAGQVSLHSLIETPANGTGPSEALA

MLLQETTGELEAAKALVLKRIQIWKRQQQLAGNGAPFEESLAPLQ

ERCESLVDIYSQLQQEVGAAGGELEPKTRASLTGRLDEVLRTLVT

SCFLVEKQPPQVLKTQTKFQAGVRFLLGLRFLGAPAKPPLVRADM

VTEKQARELSVPQGPGAGAESTGEIINNTVPLENSIPGNCCSALF

KNLLLKKIKRCERKGTESVTEEKCAVLFSASFTLGPGKLPIQLQA

LSLPLVVIVHGNQDNNAKATILWDNAFSEMDRVPFVVAERVPWEK

MCETLNLKFMAEVGTNRGLLPEHFLFLAQKIFNDNSLSMEAFQHR

SVSWSQFNKEILLGRGFTFWQWFDGVLDLTKRCLRSYWSDRLIIG

FISKQYAASLLLNEPDGTFLLRFSDSEIGGITIAHVIRGQDGSPQ

IENIQPFSAKDLSIRSLGDRIRDLAQLKNLYPKKPKDEAFRSHYK

PEQMGKDGRGYVPATIKMTVERDQPLPTPELQMPTMVPSYDLGMA

-continued

PDSSMSMQLGPDMVPQVYPPHSHSIPPYQGLSPEESVNVLSAFQE

PHLQMPPSLGQMSLPFDQPHPQGLLPCQPQEHAVSSPDPLLCSDV

TMVEDSCLSQPVTAFPQGTWIGEDIFPPLLPPTEQDLTKLLLEGQ

GESGGGSLGAQPLLQPSHYGQSGISMSHMDLRANPSW

SEQ ID NO: 48, VEGF ZF sequence
GKKKQHICHIQGCGKVYGDRSNLTRHLRWHTGERPFMCTWSYCGK

RFTMSHHLSRHKRTHTGEKKFACPECPKRFMRSDHLSRHIKTHQN

KKGGGSGGSGRAE

SEQ ID NO: 303, 3Z
MAEEFVTLKDVGMDFTLGDWEQLGLEQGDTFWDTALDNCQDLFLL

DPPRPNLTSHPDGSEDLEPLAGGSPEATSMAEEFVTLKDVGMDFT

LGDWEQLGLEQGDTFWDTALDNCQDLFLLDPPRPNLTSHPDGSED

LEPLAGGSPEATSMAEEFVTLKDVGMDFTLGDWEQLGLEQGDTFW

DTALDNCQDLFLLDPPRPNLTSHPDGSEDLEPLAGGSPEATS

What is claimed herein is:

1. A synthetic transcription factor (synTF) comprising:

(a) at least one DNA binding domain (DBD), (b) a transcriptional activator domain (TA), (c) a transcriptional effector domain (TED), which comprises an elongation domain derived from Interacts with Suppressor Of Ty 6 (Spt6) Homolog (IWS1), and (d) at least one regulator protein (RP); and wherein the TED increases the transcriptional activation of the synTF compared to an otherwise identical synTF lacking the TED, wherein the TA is directly or indirectly coupled to the DBD, and wherein the coupling is regulated by the at least one RP, or wherein cellular localization of the TA is regulated by the at least one RP.

2. The synTF of claim 1, wherein the elongation domain: is derived from human IWS1; comprises at least one TFIIS N-terminal domains (TND)-interacting motif (TIM) domain of IWS1; comprises at least one TIM1, TIM2, and/or TIM3 domain from IWS1; and/or comprises one of SEQ ID NOs: 5-9 or an amino acid sequence with at least 80% sequence identity to one of SEQ ID NOs: 5-9.

3. The synTF of claim 1, wherein the TA is selected from the group consisting of: p65; Rta; miniVPR; full VPR; VP16; VP64; NFZ; 3Z; p300; p300 HAT Core; and a CBP HAT domain; or a variant thereof.

4. The synTF of claim 1, wherein the at least one DBD is an engineered zinc finger (ZF)-binding domain.

5. The synTF of claim 4, wherein the engineered ZF binding domain comprises a sequence selected from the group consisting of: ZF 1-1, ZF 1-2, ZF 1-3, ZF 1-4, ZF 1-5, ZF 1-6, ZF 1-7, ZF 1-8, ZF 2-1, ZF 2-2, ZF 2-3, ZF 2-4, ZF 2-5, ZF 2-6, ZF 2-7, ZF 2-8, ZF 3-1, ZF 3-2, ZF 3-3, ZF 3-4, ZF 3-5, ZF 3-6, ZF 3-7, ZF 3-8, ZF 4-1, ZF 4-2, ZF 4-3, ZF 4-4, ZF 4-5, ZF 4-6, ZF 4-7, ZF 4-8, ZF 5-1, ZF 5-2, ZF 5-3, ZF 5-4, ZF 5-5, ZF 5-6, ZF 5-7, ZF 5-8, ZF 6-1, ZF 6-2, ZF 6-3, ZF 6-4, ZF 6-5, ZF 6-6, ZF 6-7, ZF 6-8, ZF 7-1, ZF 7-2, ZF 7-3, ZF 7-4, ZF 7-5, ZF 7-6, ZF 7-7, ZF 7-8, ZF 8-1, ZF 8-2, ZF 8-3, ZF 8-4, ZF 9-1, ZF 9-2, ZF 9-3, ZF 9-4, ZF 10-1, and ZF 11-1; or wherein the engineered ZF-binding domain specifically binds an endogenous VEGF gene (VEGF ZF).

6. The synTF of claim 1, wherein the at least one RP comprises a polypeptide selected from the group consisting of: a repressible protease; a pair of induced proximity domains (IPD pair); a cytosolic sequestering protein; and combinations thereof.

7. The synTF of claim 1, wherein the at least one RP comprises a repressible protease or an NS3 protease.

8. The synTF of claim 7, wherein in the presence of a protease inhibitor, or an inhibitor of NS3, the protease protein is inhibited, thereby maintaining the coupling of the DBD to the TA; or wherein in the absence of a protease inhibitor, or an inhibitor of NS3, the protease protein is active, and the TA is excised from the DBD, thereby uncoupling the DBD and the TA.

9. The synTF of claim 8, wherein the inhibitor of NS3 is selected from the group consisting of: grazoprevir (GRZ/GZV), danoprevir, simeprevir, asunaprevir, ciluprevir, boceprevir, sovaprevir, paritaprevir, ombitasvir, paritaprevir, ritonavir, dasabuvir, and telaprevir.

10. The synTF of claim 1, wherein the at least one RP is a pair of induced proximity domains (IPD pair), wherein the IPD pair comprises:

a first induced proximity domain ($IPD^A$) and at least a second complementary IPD ($IPD^B$), wherein in the presence of an inducer agent or signal, the $IPD^A$ and $IPD^B$ specifically bind together resulting in the coupling of the TA to the DBD, and wherein in the absence of an inducer agent or signal, the TA is uncoupled from the DBD.

11. The synTF of claim 10, wherein the IPD pair comprises:

(a) a $IPD^A$ comprising a GID1 domain or a fragment thereof, and a $IPD^B$ comprising a GAI domain, wherein the GID1 domain and GAI domain bind to the inducer agent Gibberellin Ester (GIB);

(b) a $IPD^A$ comprising a FKBP domain or a fragment thereof, and a $IPD^B$ comprising a FRB domain, wherein the FKBP domain and FRB domain bind to the inducer agent Rapalog (RAP);

(c) a $IPD^A$ comprising a PYL domain or a fragment thereof, and a $IPD^B$ comprising an ABI domain, wherein the PYL domain and ABI domain bind to the inducer agent Abscisic acid (ABA); and/or (d) a $IPD^A$ comprising a Light-inducible dimerization domain (LIDD), wherein a LIDD dimerizes with a complementary LIDD ($IPD^B$) upon exposure to a light inducer signal of an appropriate wavelength.

12. The synTF of claim 11, wherein the LIDD is nMag, Calcium And Integrin-Binding Protein 1 truncation (CIBN), or a photochromic protein domain; wherein nMag can dimerize with a complementary LIDD pMag upon exposure to a blue light inducer signal; or wherein CIBN can dimerize with a complementary cryptochrome 2 (CRY2) upon exposure to a blue inducer light signal; or wherein the photochromic protein domains can dimerize upon exposure to a blue inducer light signal.

13. The synTF of claim 1, wherein the at least one RP comprises a cytosolic sequestering protein.

14. The synTF of claim 13, wherein the cytosolic sequestering protein comprises a LBD and a nuclear localization signal (NLS); wherein in the absence of a ligand to which the LBD binds, the NLS is inhibited thereby preventing translocation of the synTF to the nucleus; and wherein in the presence of the ligand to which the LBD binds, the NLS is exposed permitting translocation of the synTF to the nucleus and sequestering of the synTF to the cytosol is inhibited.

15. The synTF of claim 13, wherein the cytosolic sequestering protein comprises at least a portion of an estrogen receptor (ER), an estrogen ligand binding domain (ERT), or a variant thereof, selected from the group consisting of: SEQ ID NO: 43 (ERT2), SEQ ID NO: 304, and SEQ ID NO: 305 (ERT3).

16. The synTF of claim 15, wherein the ERT binds to one or more ligands selected from the group consisting of: tamoxifen, 4-hydroxytamoxifen (4OHT), endoxifen, and Fulvestrant; wherein binding of the ligand to the ERT exposes the NLS and results in nuclear translocation of the ERT.

17. The synTF of claim 13, wherein the cytosolic sequestering protein comprises a transmembrane receptor sequestering protein.

18. The synTF of claim 7, wherein the NS3 protease protein is part of a Small molecule-Assisted Shutoff (SMASh) domain, wherein the SMASh domain comprises the NS3 protease protein, a partial protease helical domain and a NS4A domain.

19. The synTF of claim 1, further comprising a Small molecule-Assisted Shutoff (SMASh) domain, wherein the SMASh domain is a N-terminal or C-terminal SMASh domain comprising a repressible protease, a partial protease helical domain and a cofactor domain.

20. The synTF of claim 18, wherein the SMASh domain is a C-terminal SMASh domain comprising, in N-terminal to C-terminal order: a NS3 cleavage site, at least one linker, a NS3 domain, a NS3 partial helicase, and a NS4A domain, wherein the SMASh domain is fused to the C-terminus of the synTF.

21. The synTF of claim 18, wherein the SMASh domain is a N-terminal SMASh domain comprising in N-terminal to C-terminal order: at least one Linker, a NS3 domain, a NS3 partial helicase, a NS4 domain, and a NS3 cleavage site, wherein the SMASh domain is fused to the N-terminus of the synTF.

22. The synTF of claim 18, wherein in the absence of an inhibitor for the NS3 protease, the NS3 protease is active and self cleaves/uncouples from the synTF, thereby resulting in the SMASh domain targeted for degradation ("SMASh-degradation", synTF-on/TA-on), and wherein in the presence of an inhibitor for the NS3 protease, NS3 protease activity is inhibited thereby resulting in the SMASh-comprising synTF targeted for degradation ("synTF-degradation", synTF-OFF/TA-off").

23. The synTF of claim 22, wherein the inhibitor for the NS3 protease is selected from the group consisting of: grazoprevir (GRZ/GZV), danoprevir, simeprevir, asunaprevir, ciluprevir, boceprevir, sovaprevir, paritaprevir, ombitasvir, paritaprevir, ritonavir, dasabuvir, and telaprevir.

24. The synTF of claim 1, wherein the DBD, TA, TED, and/or RP are human domains or humanized domains.

25. A synthetic transcription factor (synTF) comprising:

(a) at least one DNA binding domain (DBD), (b) a transcriptional activator domain (TA), and (c) a transcriptional effector domain (TED), which comprises an elongation domain derived from Interacts with Suppressor Of Ty 6 (Spt6) Homolog (IWS1), wherein the TED increases the transcriptional activation of the synTF compared to an otherwise identical synTF lacking the TED.

26. A humanized hybrid transcription activator domain (hhTAD), comprising:

(a) a transcriptional activator domain (TA), and (b) a transcriptional effector domain (TED), which comprises an elongation domain derived from Interacts with Suppressor Of Ty 6 (Spt6) Homolog (IWS1), wherein the TED increases the transcriptional activation of the TA compared to an otherwise identical hhTAD lacking the TED; and wherein the TA and TED are human domains or humanized domains.

27. A system for controlling gene expression, comprising:

(a) at least one synthetic transcription factor (synTF) of claim 1, wherein the at least one DBD of the synTF can bind to a target DNA binding motif (DBM) located upstream of a promoter operatively linked to a gene; and (b) a nucleic acid construct comprising:

(i) at least one target DNA binding motif (DBM) comprising a target nucleic acid for binding of the at least one DBD of the synTF;

(ii) a promoter sequence located 3' of the at least one DBM; and (iii) a gene of interest operatively linked to the promoter sequence.

28. The synTF of claim 1, wherein the at least one DBD comprises an engineered zinc finger (ZF)-binding domain, Gal4, TetR, a Transcription Activator-Like Effector (TALE), or a Cas protein;

wherein the TA is selected from the group consisting of: p65; Rta; miniVPR; full VPR; VP16; VP64; NFZ; 3Z; p300; p300 HAT Core; and CBP HAT domain; and wherein the at least one RP comprises a polypeptide selected from the group consisting of: a repressible protease; a pair of induced proximity domains (IPD pair); a cytosolic sequestering protein; a Small molecule-Assisted Shutoff (SMASh) domain; and combinations thereof.

* * * * *